United States Patent
Cole et al.

(10) Patent No.: US 11,098,010 B2
(45) Date of Patent: Aug. 24, 2021

(54) SUBSTITUTED DIHYDROINDENE-4-CARBOXAMIDES AND ANALOGS THEREOF, AND METHODS USING SAME

(71) Applicant: ARBUTUS BIOPHARMA CORPORATION, Burnaby (CA)

(72) Inventors: Andrew G. Cole, Cranbury, NJ (US); Bruce D. Dorsey, Ambler, PA (US); Ramesh Kakarla, Doylestown, PA (US); Steven Kultgen, Hamilton, NJ (US); Jorge Quintero, Sayreville, NJ (US)

(73) Assignee: Arbutus Biopharma Corporation, Burnaby (CA)

( * ) Notice: Subject to any disclaimer, the term of this patent is extended or adjusted under 35 U.S.C. 154(b) by 0 days.

(21) Appl. No.: 16/495,794

(22) PCT Filed: Mar. 20, 2018

(86) PCT No.: PCT/IB2018/000387
§ 371 (c)(1),
(2) Date: Sep. 19, 2019

(87) PCT Pub. No.: WO2018/172852
PCT Pub. Date: Sep. 27, 2018

(65) Prior Publication Data
US 2020/0024226 A1    Jan. 23, 2020

Related U.S. Application Data

(60) Provisional application No. 62/588,711, filed on Nov. 20, 2017, provisional application No. 62/474,263, filed on Mar. 21, 2017.

(51) Int. Cl.
| | | |
|---|---|---|
| *C07C 271/24* | (2006.01) |
| *A61K 31/27* | (2006.01) |
| *A61K 45/06* | (2006.01) |
| *A61K 31/16* | (2006.01) |
| *C07C 237/48* | (2006.01) |
| *A61K 31/167* | (2006.01) |
| *C07D 213/55* | (2006.01) |
| *A61K 31/4402* | (2006.01) |
| *C07D 207/267* | (2006.01) |

(Continued)

(52) U.S. Cl.
CPC ............ *C07C 271/24* (2013.01); *A61K 31/16* (2013.01); *A61K 31/167* (2013.01); *A61K 31/18* (2013.01); *A61K 31/27* (2013.01); *A61K 31/397* (2013.01); *A61K 31/40* (2013.01); *A61K 31/4015* (2013.01); *A61K 31/415* (2013.01); *A61K 31/4184* (2013.01); *A61K 31/4196* (2013.01); *A61K 31/42* (2013.01); *A61K 31/426* (2013.01); *A61K 31/437* (2013.01); *A61K 31/44* (2013.01); *A61K 31/4402* (2013.01); *A61K 31/445* (2013.01); *A61K 31/4436* (2013.01); *A61K 31/47* (2013.01); *A61K 31/4965* (2013.01); *A61K 31/505* (2013.01); *A61K 31/519* (2013.01); *A61K 31/5375* (2013.01); *A61K 31/5377* (2013.01); *A61K 31/54* (2013.01); *A61K 45/06* (2013.01); *C07C 237/48* (2013.01); *C07C 311/10* (2013.01); *C07C 313/06* (2013.01); *C07D 205/08* (2013.01); *C07D 207/06* (2013.01); *C07D 207/267* (2013.01); *C07D 207/27* (2013.01); *C07D 211/34* (2013.01); *C07D 213/55* (2013.01); *C07D 213/643* (2013.01); *C07D 213/73* (2013.01); *C07D 213/89* (2013.01); *C07D 215/14* (2013.01); *C07D 231/20* (2013.01); *C07D 235/02* (2013.01); *C07D 239/26* (2013.01); *C07D 241/12* (2013.01); *C07D 249/08* (2013.01); *C07D 263/32* (2013.01); *C07D 265/30* (2013.01); *C07D 277/24* (2013.01); *C07D 279/12* (2013.01); *C07D 409/12* (2013.01); *C07D 471/04* (2013.01); *C07D 487/04* (2013.01)

(58) Field of Classification Search
None
See application file for complete search history.

(56) References Cited

U.S. PATENT DOCUMENTS 3,968,163 A * 7/1976 Solomons .................. C07C 1/22
568/436
7,034,049 B1    4/2006 Pevarello et al.
(Continued)

FOREIGN PATENT DOCUMENTS

AU    2008245082 A1    11/2008
CA    2896554 A1    7/2014
(Continued)

OTHER PUBLICATIONS

Ballell, et al., "Fueling Open-Source Drug Discovery: 177 Small-Molecule Leads Against Tuberculosis", ChemMedChem, vol. 8, No. 2, 2013, pp. 313-321.
(Continued)

*Primary Examiner* — Kristin A Vajda
(74) *Attorney, Agent, or Firm* — Saul Ewing Arnstein & Lehr LLP; Kathryn Doyle; Domingos J. Silva

(57) ABSTRACT

The present invention includes novel substituted bicyclic compounds, and compositions comprising the same, that can be used to treat or prevent hepatitis B virus (HBV) infections in a patient. In certain embodiments, the compounds and compositions of the invention are capsid inhibitors.

32 Claims, No Drawings

(51) Int. Cl.

| | |
|---|---|
| C07C 313/06 | (2006.01) |
| A61K 31/4015 | (2006.01) |
| C07D 207/27 | (2006.01) |
| C07D 207/06 | (2006.01) |
| A61K 31/40 | (2006.01) |
| C07D 213/643 | (2006.01) |
| A61K 31/44 | (2006.01) |
| C07D 213/73 | (2006.01) |
| A61K 31/5377 | (2006.01) |
| C07D 211/34 | (2006.01) |
| A61K 31/445 | (2006.01) |
| C07D 471/04 | (2006.01) |
| A61K 31/437 | (2006.01) |
| C07D 231/20 | (2006.01) |
| A61K 31/415 | (2006.01) |
| C07D 213/89 | (2006.01) |
| C07D 277/24 | (2006.01) |
| A61K 31/426 | (2006.01) |
| C07D 263/32 | (2006.01) |
| A61K 31/42 | (2006.01) |
| C07D 215/14 | (2006.01) |
| A61K 31/47 | (2006.01) |
| C07D 241/12 | (2006.01) |
| A61K 31/4965 | (2006.01) |
| C07D 239/26 | (2006.01) |
| A61K 31/505 | (2006.01) |
| C07D 249/08 | (2006.01) |
| A61K 31/4196 | (2006.01) |
| C07D 265/30 | (2006.01) |
| A61K 31/5375 | (2006.01) |
| C07D 205/08 | (2006.01) |
| A61K 31/397 | (2006.01) |
| C07D 279/12 | (2006.01) |
| A61K 31/54 | (2006.01) |
| C07C 311/10 | (2006.01) |
| A61K 31/18 | (2006.01) |
| C07D 487/04 | (2006.01) |
| A61K 31/519 | (2006.01) |
| C07D 409/12 | (2006.01) |
| A61K 31/4436 | (2006.01) |
| C07D 235/02 | (2006.01) |
| A61K 31/4184 | (2006.01) |

(56) References Cited

U.S. PATENT DOCUMENTS

| | | | |
|---|---|---|---|
| 7,776,869 B2 | 8/2010 | Chaffee et al. | |
| 8,106,068 B2 * | 1/2012 | Liu | A61P 37/00 514/300 |
| 8,703,771 B2 | 4/2014 | Yang et al. | |
| 9,615,579 B2 | 4/2017 | Walston et al. | |
| 2014/0275013 A1 | 9/2014 | Chatterjee et al. | |
| 2017/0000124 A1 | 1/2017 | Corbin, Jr. | |

FOREIGN PATENT DOCUMENTS

| | | |
|---|---|---|
| EP | 0291245 A2 | 11/1988 |
| JP | 2002161084 A | 6/2002 |
| WO | 9631511 A1 | 10/1996 |
| WO | 0103644 A2 | 1/2001 |
| WO | 03030937 A1 | 4/2003 |
| WO | 03084949 A1 | 10/2003 |
| WO | 2005030702 A1 | 4/2005 |
| WO | 2006039356 A2 | 4/2006 |
| WO | 2006039718 A2 | 4/2006 |
| WO | 2006070202 A1 | 7/2006 |
| WO | 2006120178 A1 | 11/2006 |
| WO | 2007036733 A1 | 4/2007 |
| WO | 2007051810 A2 | 5/2007 |
| WO | 2007076474 A1 | 7/2007 |
| WO | 2008011557 A2 | 1/2008 |
| WO | 2008051757 A1 | 5/2008 |
| WO | 2008078196 A2 | 7/2008 |
| WO | 2008155666 A2 | 12/2008 |
| WO | 2009072581 A1 | 6/2009 |
| WO | 2009108670 A1 | 9/2009 |
| WO | 2010092489 A1 | 8/2010 |
| WO | 2011079102 A1 | 6/2011 |
| WO | 2012024179 A1 | 2/2012 |
| WO | 2012120398 A1 | 9/2012 |
| WO | 2012166951 A1 | 12/2012 |
| WO | 2013161312 A1 | 10/2013 |
| WO | 2014008214 A1 | 1/2014 |
| WO | 2014089296 A2 | 6/2014 |
| WO | 2014102378 A1 | 7/2014 |
| WO | 2014155301 A1 | 10/2014 |
| WO | 2014165128 A2 | 10/2014 |
| WO | 2015134334 A1 | 9/2015 |
| WO | 2017015451 A1 | 1/2017 |

OTHER PUBLICATIONS

Bonafoux, et al., "Fragment-based Discovery of Dual JC Virus and BK Virus Helicase Inhibitors", J Med Chem, vol. 59, No. 15, 2016, pp. 7138-7151.

Daydé-Cazals, et al., "Rational Design, Synthesis, and Biological Evaluation of 7-Azaindole Derivatives as Potent Focused Multi-Targeted Kinase Inhibitors", J Med Chem, vol. 59, No. 8, 2016, pp. 3886-3905.

Dong, et al., "trans-Cyclohexane-1,2-diamine is a Weak Director of Absolute Helicity in Chiral Nickel-Salen Complexes", J Am Chem Soc, vol. 129, No. 38, 2007, pp. 11850-11853.

Kim, et al., "Synthesis and Phosphodiesterase 5 Inhibitory Activity of Novel Phenyl Ring Modified Sildenafil Analogues", Bioorganic Med Chem, vol. 9, No. 6, 2001, pp. 1609-1616.

Meshram, et al., "Zirconium(IV) Chloride Catalyzed Cyclization of ortho-allylphenols: Synthesis of 2-Methyl-2,3-dihydrobenzofurans", Synthetic Communications, vol. 34, No. 17, 2004, pp. 3091-3097.

Smirnova, et al., "Synthesis and Pharmacological Activity of Substituted Amides of 2-Chloro- and 2-Arylamino-5,6-Tri(tetra)methyleneisonicotinic Acids", Pharmaceutical Chemistry Journal, vol. 33, No. 3, 1999, pp. 21-23.

Stanetty, et al., "Synthase neuer 7-Benzofuranmethanamine als heterocyclische Analoga des Squalenepoxidasehemmers Butenafine", Archiv der Pharmazie, vol. 326, No. 6, 1993, pp. 351-358.

Tester, et al., "Amide-based Inhibitors of p38alpha MAP Kinase. Part 2: Design, Synthesis and Sar of Potent N-Pyrimidyl Amides", Bioorganic & Med Chem Lett, vol. 20, No. 8, 2010, pp. 2560-2563.

Voelter, et al., "Synthesis and Properties of Biagra. A 5-(2,3-dihydro-7-benzofuryl) analog of Viagra", Zeitschrift fuer Naturforschung, B: Chemical Sciences, vol. 54, No. 11, 1999, pp. 1469-1473.

International Search Report and Written Opinion for corresponding International Application No. PCT/IB2018/000387 dated Jul. 18, 2018.

Kemnitzer, et al., "Discovery of N-aryl-9-oxo-9H-fluorene-1-carboxamides as a new series of apoptosis inducers using a cell- and caspase-based high-throughput screening assay. 2. Structure-activity relationships of the 9-oxo-9H-fluorene ring", Bioorganic & Medicinal Chemistry Letters, vol. 20, No. 3, Feb. 1, 2010, pp. 1288-1292.

Supplementary European Search Report dated Dec. 8, 2020 for corresponding European Application No. 18771245.0.

* cited by examiner

SUBSTITUTED DIHYDROINDENE-4-CARBOXAMIDES AND ANALOGS THEREOF, AND METHODS USING SAME

CROSS-REFERENCE TO RELATED APPLICATIONS

The present application is a 35 U.S.C. § 371 national phase application of, and claims priority to, International Application No. PCT/IB2018/000367, filed Mar. 20, 2018, which claims priority under 35 U.S.C. § 119(e) to 62/474,263, filed Mar. 21, 2017, and U.S. Provisional Application No. 62/588,711, filed Nov. 20, 2017, all of which applications are hereby incorporated herein by reference in their entireties.

BACKGROUND OF THE INVENTION

Hepatitis B is one of the world's most prevalent diseases, being listed by National Institute of Allergy and Infectious Diseases (NIAID) as a High Priority Area of Interest. Although most individuals resolve the infection following acute symptoms, approximately 30% of cases become chronic. 350-400 million people worldwide are estimated to have chronic hepatitis B, leading to 0.5-1 million deaths per year, due largely to the development of hepatocellular carcinoma, cirrhosis and/or other complications.

A limited number of drugs are currently approved for the management of chronic hepatitis B, including two formulations of alpha-interferon (standard and pegylated) and five nucleoside/nucleotide analogues (lamivudine, adefovir, entecavir, telbivudine, and tenofovir) that inhibit hepatitis B virus (HBV) DNA polymerase. At present, the first-line treatment choices are entecavir, tenofovir and/or peg-interferon alfa-2a. However, peg-interferon alfa-2a achieves desirable serological milestones in only one third of treated patients, and is frequently associated with severe side effects. Entecavir and tenofovir are potent HBV inhibitors, but require long-term or possibly lifetime administration to continuously suppress HBV replication, and may eventually fail due to emergence of drug-resistant viruses. There is thus a pressing need for the introduction of novel, safe, and effective therapies for chronic hepatitis B.

HBV is a noncytopathic, liver tropic DNA virus belonging to Hepadnaviridae family. Pregenomic (pg) RNA is the template for reverse transcriptional replication of HBV DNA. The encapsidation of pg RNA, together with viral DNA polymerase, into a nucleocapsid is essential for the subsequent viral DNA synthesis. Inhibition of pg RNA encapsidation may block HBV replication and provide a new therapeutic approach to HBV treatment. A capsid inhibitor acts by inhibiting the expression and/or function of a capsid protein either directly or indirectly: for example, it may inhibit capsid assembly, induce formation of non-capsid polymers, promote excess capsid assembly or misdirected capsid assembly, affect capsid stabilization, and/or inhibit RNA encapsidation. A capsid inhibitor may also act by inhibiting capsid function in one or more downstream events within the replication process, such as, but not limited to, viral DNA synthesis, transport of relaxed circular DNA (rcDNA) into the nucleus, covalently closed circular DNA (cccDNA) formation, virus maturation, budding and/or release.

Clinically, inhibition of pg RNA encapsidation, or more generally inhibition of nucleocapsid assembly, may offer certain therapeutic advantages. In one aspect, inhibition of pg RNA encapsidation may complement the current medications by providing an option for a subpopulation of patients that do not tolerate or benefit from the current medications. In another aspect, based on their distinct antiviral mechanism, inhibition of pg RNA encapsidation may be effective against HBV variants resistant to the currently available DNA polymerase inhibitors. In yet another aspect, combination therapy of the pg RNA encapsidation inhibitors with DNA polymerase inhibitors may synergistically suppress HBV replication and prevent drug resistance emergence, thus offering a more effective treatment for chronic hepatitis B infection.

There is thus a need in the art for the identification of novel compounds that can be used to treat and/or prevent HBV infection in a subject. In certain embodiments, the novel compounds inhibit HBV nucleocapsid assembly. In other embodiments, the novel compounds can be used in patients that are HBV infected, patients who are at risk of becoming HBV infected, and/or patients that are infected with drug-resistant HBV. The present invention addresses this need.

BRIEF SUMMARY OF THE INVENTION

The invention provides a compound of formula (I), or a salt, solvate, prodrug, stereoisomer, tautomer, or isotopically labelled derivative thereof, or any mixtures thereof:

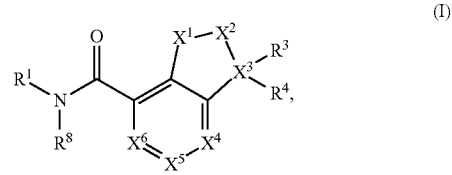

wherein in (I):

—$X^1$—$X^2$— is selected from the group consisting of —$CH_2CH_2$—*, —$CH_2CH(CH_3)$—*, —$CH_2C(CH_3)_2$—*, —$CH(CH_3)CH_2$—*, —$C(CH_3)_2CH_2$—*, —$CH_2CHF$—*, —$CH_2CF_2$—*, —$OCH_2$—*, —$SCH_2$—*, —$CH_2NR^{6a}$—*, and —$CH_2CH(OR^{6a})$—*, wherein the single bond marked as "*" is between —$X^1$—$X^2$— and $X^3$;

$X^3$ is C, or $X^3$ combines with $R^3$ and $R^4$ to form —$S(=O)_2$—;

$X^4$ is N or $C(R^{5a})$, $X^5$ is N or $C(R^{5b})$, $X^6$ is N or $C(R^{5c})$, wherein 0-1 of $X^4$, $X^5$, and $X^6$ is N;

$R^1$ is selected from the group consisting of optionally substituted phenyl, optionally substituted benzyl, optionally substituted heteroaryl, and —$(CH_2)$(optionally substituted heteroaryl);

each occurrence of $R^2$ is independently selected from the group consisting of H and $C_1$-$C_6$ alkyl;

$R^3$ is selected from the group consisting of —$N(R^2)C(=O)OR^6$, H, —OH, —$OR^6$, —$NH_2$, —$NHR^6$, —$NR^6R^6$, —$OC(=O)OR^6$, —$OC(=O)N(R^2)R^6$, —$NR^7C(=O)N(R^6)(R^7)$, —$N(R^2)C(=O)R^6$, —$NR^2S(=O)_{1-2}R^6$, optionally substituted aryl, optionally substituted heteroaryl, —$CH_2C(=O)OH$, —$CH_2C(=O)NR^6R^6$, —$N(R^2)C(=O)(CH_2)_{1-2}R^6$, $NR^2S(=O)_2N(R^6)(R^7)$, and —$NR^2C(=O)C(=O)N(R^6)(R^7)$;

$R^4$ is H or $C_1$-$C_6$ alkyl, or $R^3$ and $R^4$ combine to form =O or —$C(=O)NR^{6a}$—$C(=O)$—$NR^{6a}$—;

$R^{5a}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

$R^{5b}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

$R^{5c}$ is independently selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

each occurrence of $R^6$ is independently selected from the group consisting of optionally substituted $C_1$-$C_6$ alkyl, optionally substituted $C_3$-$C_8$ cycloalkyl, optionally substituted phenyl, and optionally substituted hetereoaryl;

each occurrence of $R^{6a}$ is independently selected from the group consisting of H, optionally substituted $C_1$-$C_6$ alkyl, optionally substituted $C_3$-$C_8$ cycloalkyl, optionally substituted phenyl, and optionally substituted hetereoaryl;

each occurrence of $R^7$ is independently selected from the group consisting of H and optionally substituted $C_1$-$C_6$ alkyl; or, if $R^6$ and $R^7$ are bound to the same N atom, $R^6$ and $R^7$ optionally combine with the N atom to which both are bound to form an optionally substituted 3-7 membered heterocycle;

$R^8$ is selected from the group consisting of H and $C_1$-$C_6$ alkyl.

The invention further provides a compound of formula (I'):

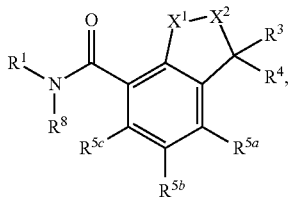

wherein in (I'):

—$X^1$—$X^2$— is selected from the group consisting of —$CH_2CH_2$—*, —$CH_2CH(CH_3)$—*, —$CH_2C(CH_3)_2$—*, —$CH(CH_3)CH_2$—*, —$C(CH_3)_2CH_2$—*, —$CH_2CHF$—*, —$CH_2CF_2$—*, —$OCH_2$—*, —$SCH_2$—*, and —$CH_2CH(OR^2)$—*, wherein the single bond marked as "*" is between —$X^1$—$X^2$— and —$CR^3R^4$—;

$R^1$ is selected from the group consisting of optionally substituted phenyl, optionally substituted benzyl, optionally substituted heteroaryl, and —($CH_2$)(optionally substituted heteroaryl);

each occurrence of $R^2$ is independently selected from the group consisting of H and $C_1$-$C_6$ alkyl;

$R^3$ is selected from the group consisting of H, —OH, —$OR^6$, —$NH_2$, —$NHR^6$, —$NR^6R^6$, —$OC(=O)OR^6$, —$OC(=O)N(R^2)R^6$, —$N(R^2)C(=O)OR^6$ —$NR^7C(=O)N(R^6)(R^7)$, —$N(R^2)C(=O)R^6$, —$NR^2S(=O)_2R^6$, optionally substituted aryl, optionally substituted heteroaryl, —$CH_2C(=O)OH$, —$CH_2C(=O)NR^6R^6$, —$N(R^2)C(=O)(CH_2)_{0-2}R^6$, $NR^2S(=O)_2N(R^6)(R^7)$, and —$NR^2C(=O)C(=O)N(R^6)(R^7)$;

$R^4$ is H or $C_1$-$C_6$ alkyl, or $R^3$ and $R^4$ combine to form =O;

$R^{5a}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

$R^{5b}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

$R^{5c}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

each occurrence of $R^6$ is independently selected from the group consisting of optionally substituted $C_1$-$C_6$ alkyl, optionally substituted $C_3$-$C_8$ cycloalkyl, optionally substituted phenyl, and optionally substituted hetereoaryl;

each occurrence of $R^7$ is independently selected from the group consisting of H and optionally substituted $C_1$-$C_6$ alkyl; or, if $R^6$ and $R^7$ are bound to the same N atom, $R^6$ and $R^7$ optionally combine with the N atom to which both are bound to form an optionally substituted 3-7 membered heterocycle;

$R^8$ is selected from the group consisting of H and $C_1$-$C_6$ alkyl.

In certain embodiments, at least one of $R^{5a}$, $R^{5b}$, and $R^{5c}$ is H.

In certain embodiments, the compound is a compound of formula (Ie):

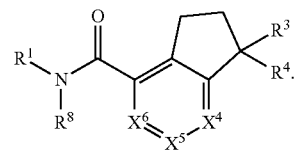

In certain embodiments, the compound is selected from the group consisting of:

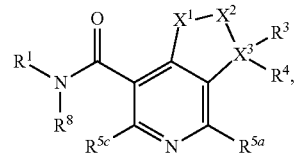

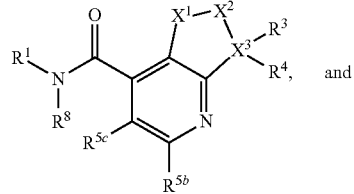

and

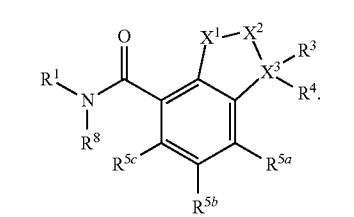

The invention further provides a compound of formula (Is), or a salt, solvate, prodrug, stereoisomer, tautomer, or isotopically labelled derivative thereof, or any mixtures thereof:

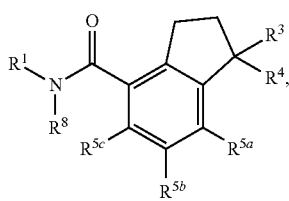

(Is)

wherein in (Is):

R$^1$ is selected from the group consisting of optionally substituted phenyl, optionally substituted benzyl, optionally substituted heteroaryl, and —(CH$_2$)(optionally substituted heteroaryl);

each occurrence of R$^2$ is independently selected from the group consisting of H and C$_1$-C$_6$ alkyl;

R$^3$ is selected from the group consisting of —N(R$^2$)C(=O)OR$^6$, H, —OH, —OR$^6$, —NH$_2$, —NHR$^6$, —NR$^6$R$^6$, —OC(=O)OR$^6$, —OC(=O)N(R$^2$)R$^6$, —NR$^7$C(=O)N(R$^6$)(R$^7$), —N(R$^2$)C(=O)R$^6$, —NR$^2$S(=O)$_{1-2}$R$^6$, optionally substituted aryl, optionally substituted heteroaryl, —CH$_2$C(=O)OH, —CH$_2$C(=O)NR$^6$R$^6$, —N(R$^2$)C(=O)(CH$_2$)$_{1-2}$R$^6$, NR$^2$S(=O)$_2$N(R$^6$)(R$^7$), and —NR$^2$C(=O)C(=O)N(R$^6$)(R$^7$);

R$^4$ is H or C$_1$-C$_6$ alkyl, or R$^3$ and R$^4$ combine to form =O or —C(=O)NR$^{6a}$—C(=O)—NR$^{6a}$—;

R$^{5a}$ is selected from the group consisting of H, halo, C$_1$-C$_6$ alkyl, C$_1$-C$_6$ alkoxy, C$_1$-C$_6$ aminoalkyl, C$_1$-C$_6$ haloalkoxy, and C$_1$-C$_6$ haloalkyl;

R$^{5b}$ is selected from the group consisting of H, halo, C$_1$-C$_6$ alkyl, C$_1$-C$_6$ alkoxy, C$_1$-C$_6$ aminoalkyl, C$_1$-C$_6$ haloalkoxy, and C$_1$-C$_6$ haloalkyl;

R$^{5c}$ is independently selected from the group consisting of H, halo, C$_1$-C$_6$ alkyl, C$_1$-C$_6$ alkoxy, C$_1$-C$_6$ aminoalkyl, C$_1$-C$_6$ haloalkoxy, and C$_1$-C$_6$ haloalkyl;

each occurrence of R$^6$ is independently selected from the group consisting of optionally substituted C$_1$-C$_6$ alkyl, optionally substituted C$_3$-C$_8$ cycloalkyl, optionally substituted phenyl, and optionally substituted hetereoaryl;

each occurrence of R$^{6a}$ is independently selected from the group consisting of H, optionally substituted C$_1$-C$_6$ alkyl, optionally substituted C$_3$-C$_8$ cycloalkyl, optionally substituted phenyl, and optionally substituted hetereoaryl;

each occurrence of R$^7$ is independently selected from the group consisting of H and optionally substituted C$_1$-C$_6$ alkyl;

or, if R$^6$ and R$^7$ are bound to the same N atom, R$^6$ and R$^7$ optionally combine with the N atom to which both are bound to form optionally substituted 3-7 membered heterocyclyl; and R$^8$ is selected from the group consisting of H and C$_1$-C$_6$ alkyl.

In certain embodiments, wherein each occurrence of R$^6$ or R$^{6a}$ is independently selected from the group consisting of —(CH$_2$)$_{1-3}$-(optionally substituted heteroaryl), —(CH$_2$)$_{1-3}$-(optionally substituted heterocyclyl), and —(CH$_2$)$_{1-3}$-(optionally substituted aryl).

In certain embodiments, each occurrence of optionally substituted alkyl, optionally substituted heterocyclyl, or optionally substituted cycloalkyl is independently optionally substituted with at least one substituent selected from the group consisting of C$_1$-C$_6$ alkyl, halo, —OR$^a$, optionally substituted phenyl, optionally substituted heteroaryl, optionally substituted heterocyclyl, —N(R$^a$)C(=O)R$^a$, —C(=O)NR$^a$R$^a$, and —N(R$^a$)(R$^a$), wherein each occurrence of R$^a$ is independently H, optionally substituted C$_1$-C$_6$ alkyl, optionally substituted C$_3$-C$_8$ cycloalkyl, optionally substituted aryl, or optionally substituted heteroaryl, or two R$^a$ groups combine with the N to which they are bound to form a heterocycle.

In certain embodiments, each occurrence of optionally substituted aryl or optionally substituted heteroaryl is independently optionally substituted with at least one substituent selected from the group consisting of C$_1$-C$_6$ alkyl, C$_1$-C$_6$ haloalkyl, C$_1$-C$_6$ haloalkoxy, halo, —CN, —OR$^b$, —N(R$^b$)(R$^b$), —NO$_2$, —S(=O)$_2$N(R$^b$)(R$^b$), acyl, and C$_1$-C$_6$ alkoxycarbonyl, wherein each occurrence of R$^b$ is independently H, C$_1$-C$_6$ alkyl, or C$_3$-C$_8$ cycloalkyl.

In certain embodiments, each occurrence of optionally substituted aryl or optionally substituted heteroaryl is independently optionally substituted with at least one substituent selected from the group consisting of C$_1$-C$_6$ alkyl, C$_1$-C$_6$ haloalkyl, C$_1$-C$_6$ haloalkoxy, halo, —CN, —OR$^c$, —N(R$^c$)(R$^c$), and C$_1$-C$_6$ alkoxycarbonyl, wherein each occurrence of R$^c$ is independently H, C$_1$-C$_6$ alkyl, or C$_3$-C$_8$ cycloalkyl.

In certain embodiments, R$^1$ is selected from the group consisting of optionally substituted phenyl, optionally substituted benzyl, and —(CH$_2$)(optionally substituted heteroaryl), wherein the phenyl, benzyl, or heteroaryl is optionally substituted with at least one substituent selected from the group consisting of C$_1$-C$_6$ alkyl, halo, C$_1$-C$_3$ haloalkyl, and —CN.

In certain embodiments, R$^1$ is selected from the group consisting of 3,4-difluorophenyl, 3,5-difluorophenyl, 2,4,5-trifluorophenyl, 3,4,5-trifluorophenyl, 3,4-dichlorophenyl, 3-chloro-4-fluorophenyl, 4-chloro-3-fluorophenyl, 4-chloro-3-methylphenyl, 3-chloro-4-methylphenyl, 4-fluoro-3-methylphenyl, 3-fluoro-4-methylphenyl, 4-chloro-3-methoxyphenyl, 3-chloro-4-methoxyphenyl, 4-fluoro-3-methoxyphenyl, 3-fluoro-4-methoxyphenyl, phenyl, 3-chlorophenyl, 4-chlorophenyl, 3-fluorophenyl, 4-fluorophenyl, 3-trifluoromethylphenyl, 4-trifluoromethylphenyl, 3-trifluoromethyl-4-fluorophenyl, 4-trifluoromethyl-3-fluorophenyl, 3-cyanophenyl, 4-cyanophenyl, 3-cyano-4-fluorophenyl, 4-cyano-3-fluorophenyl, 3-difluoromethyl-4-fluorophenyl, 4-difluoromethyl-3-fluorophenyl, benzo[d][1,3]dioxol-5-yl, 2,3-dihydrobenzo[b][1,4]dioxin-6-yl, benzyl, 3-fluorobenzyl, 4-fluorobenzyl, 3-chlorobenzyl, 4-chlorobenzyl, 2-pyridyl, 4-methyl-2-pyridyl, 5-methyl-2-pyridyl, 6-methyl-2-pyridyl, 3-pyridyl, 2-methyl-3-pyridyl, 3-methyl-3-pyridyl, 4-pyridyl, 2-methyl-4-pyridyl, and 6-methyl-4-pyridyl.

In certain embodiments, each occurrence of R$^2$ is independently selected from the group consisting of H and methyl.

In certain embodiments, R$^3$ is selected from the group consisting of: H; Ph; pyridin-2-yl; pyridin-3-yl; pyridin-4-yl; —CH$_2$C(=O)OH; —CH$_2$C(=O)NHCH$_3$; —CH$_2$C(=O)N(CH$_3$)$_2$; —OH; C$_1$-C$_6$ alkoxy; ((R)-1-pyrid-4-yl)ethoxy; ((S)-1-pyridin-4-yl)ethoxy; —OC(=O)O(C$_1$-C$_6$ alkyl); —OC(=O)NH(C$_1$-C$_6$ alkyl); —NH$_2$; —NH(C$_1$-C$_6$ alkyl); —N(C$_1$-C$_6$ alkyl)(C$_1$-C$_6$ alkyl); pyrimidin-2-yl-amino; pyrimidin-4-yl-amino; pyrimidin-5-yl-amino; 4-methyl-pyrimidin-2-yl-amino; 5-methyl-pyrimidin-2-yl-amino; 4-methoxy-pyrimidin-2-yl-amino; 5-methoxy-pyrimidin-2-yl-amino; 4-(pyridin-2-yl)-pyrimidin-2-yl-amino; 4-aminocarbonyl-pyrimidin-2-yl-amino; pyrazin-2-yl-amino; oxazol-2-yl-amino; —NHCH$_2$-(1H-pyrazol-5-yl); —NHC(=O)(C$_1$-C$_6$ alkyl); —NHC(=O)(C$_1$-C$_6$ haloalkyl), —NHC(=O)CH$_2$OCH$_3$; —NHC(=O)Ph; —NHC(=O)-[thiazol-2-yl]; —NHC(=O)-[thiazol-4-yl]; —NHC(=O)-[thiazol-5-yl]; —NHC(=O)-[pyridin-2-yl]; —NHC(=O)-[pyridin-3-yl]; —NHC(=O)-[pyridin-4-yl]; —NHC(=O)-

[1-methyl-1H-pyrazol-3-yl]; —NHC(=O)-[1-methyl-1H-pyrazol-5-yl]; —NH(C(=O)-thiazol-5-yl; —NH(C(=O)-oxazol-5-yl; —NHC(=O)CH$_2$—(N-morpholinyl); —NHC(=O)(CH$_2$)$_{1-6}$NH$_2$; —NHC(=O)(CH$_2$)$_{1-6}$NH(CH$_3$); —NHC(=O)(CH$_2$)$_{1-6}$N(CH$_3$)$_2$; —NHC(=O)O(tetrahydro-2H-pyran-4-yl); —NHC(=O)O(optionally substituted C$_1$-C$_6$ alkyl); —N(CH$_3$)C(=O)O(C$_1$-C$_6$ alkyl)]; —N(CH$_3$)C(=O)O(C$_3$-C$_8$ cycloalkyl)]; —NHC(=O)O(CH$_2$)$_{1-6}$O(CH$_2$)$_{0-3}$CH$_3$; —NHC(=O)O-benzyl; —NHC(=O)O-(1-(R)-phenyl-ethyl); —NHC(=O)O-(1-(S)-phenyl-ethyl); —NHC(=O)O—((R)-5-oxopyrrolidin-3-yl); —NHC(=O)O(CH$_2$)$_2$O(optionally substituted phenyl); —NHC(=O)OCH$_2$(1-methyl-1H-imidazol-2-yl); —NHC(=O)OCH$_2$-(thiazol-2-yl); —NHC(=O)OCH$_2$-(thiazol-4-yl); —NHC(=O)OCH$_2$-(thiazol-5-yl); —NHC(=O)OCH$_2$CH$_2$-(4-methyl-thiazol-5-yl); —NHC(=O)OCH$_2$-(isoxazol-3-yl); —NHC(=O)OCH$_2$-(oxazol-2-yl); —NHC(=O)OCH$_2$-(oxazol-4-yl); —NHC(=O)OCH$_2$-(oxazol-5-yl); —NHC(=O)OCH$_2$-(2-oxo-oxazolidin-5-yl); —NHC(=O)OCH$_2$-(2-oxo-oxazolidin-4-yl); —NHC(=O)OCH$_2$-(1-methyl-1H-1,2,4-triazol-3-yl); —NHC(=O)OCH$_2$-(1-(2-tetrahydropyranyl)-1H-1,2,4-triazol-3-yl); —NHC(=O)OCH$_2$-(pyridin-2-yl); —NHC(=O)OCH$_2$-(3-fluoro-pyridin-2-yl); —NHC(=O)OCH$_2$CH$_2$-(pyridin-2-yl); —NHC(=O)OCH$_2$—(N-oxide-pyridin-2-yl); —NHC(=O)OCH(CH$_3$)-(pyridin-2-yl); —NHC(=O)OCH(CH$_3$)—(N-oxide-pyridin-2-yl); —NHC(=O)O—(S-1-(pyridin-2-yl)ethyl); —NHC(=O)O—(R-1-(pyridin-2-yl)ethyl); —NHC(=O)OCH$_2$-(4-methoxy-pyridin-2-yl); —NHC(=O)OCH$_2$-(5-methoxy-pyridin-2-yl); —NHC(=O)OCH$_2$-(6-methoxy-pyridin-2-yl); —NHC(=O)OCH$_2$-(6-dimethylamino-pyridin-2-yl); —NHC(=O)OCH$_2$-(4-chloro-pyridin-2-yl); —NHC(=O)OCH$_2$-(5-chloro-pyridin-2-yl); —NHC(=O)OCH$_2$-(5-methyl-pyridin-2-yl); —NHC(=O)OCH$_2$-(6-methyl-pyridin-2-yl); —NHC(=O)OCH$_2$-(pyridin-3-yl); —NHC(=O)OCH$_2$-(pyridin-4-yl); —NHC(=O)OCH$_2$-(pyrimidin-2-yl); —NHC(=O)OCH$_2$-(1,3,4-oxadiazol-2-yl); —NHC(=O)OCH$_2$CH$_2$-phenoxy; —NHC(=O)OCH$_2$CH$_2$-(pyrimidin-2-yl); —NHC(=O)OCH$_2$-(pyrimidin-4-yl); —NHC(=O)OCH$_2$-(5-fluoro-pyrimidin-2-yl); —NHC(=O)OCH$_2$-(5-fluoro-pyridin-2-yl); —NHC(=O)OCH$_2$-(1-methyl-1H-pyrazol-3-yl); —NHC(=O)OCH$_2$-(1-methyl-1H-pyrazol-5-yl); —NHC(=O)OCH$_2$-(1-isopropyl-1H-pyrazol-3-yl); —NHC(=O)OCH$_2$-(1H-pyrazol-1l-yl); —NHC(=O)OCH$_2$CH$_2$-(1H-pyrazol-4-yl); —NHC(=O)OCH$_2$CH$_2$(1H-imidazol-1yl); —NHC(=O)OCH$_2$CH$_2$CH$_2$(1H-imidazol-1yl); —NHC(=O)OCH$_2$-(isoxazol-3-yl); —NHC(=O)OCH$_2$-(pyrrolidin-3-yl); —NHC(=O)OCH$_2$-(pyrrolidin-2-yl); —NHC(=O)OCH$_2$-(1-acetyl-4,4-difluoro-pyrrolidin-2-yl); —NHC(=O)OCH$_2$-(1-(tert-butoxycarbonyl)-4,4-difluoro-pyrrolidin-2-yl); —NHC(=O)OCH$_2$-(1H-4,4-difluoro-pyrrolidin-2-yl); —NHC(=O)OCH$_2$-(1-(2,2,2-trifluoroethyl)-pyrrolidin-2-yl); —NHC(=O)OCH$_2$-(piperidin-2-yl); —NHC(=O)OCH$_2$-(piperidin-3-yl); —NHC(=O)OCH$_2$-(1-(2,2,2-trifluoroethyl)-piperidin-4-yl); —NHC(=O)OCH$_2$-(1-methyl-piperidin-3-yl); —NHC(=O)OCH$_2$-(1-methyl-piperidin-4-yl); —NHC(=O)OCH$_2$—((S)-5-oxopyrrolidin-2-yl); —NHC(=O)OCH$_2$—((R)-5-oxopyrrolidin-2-yl); —NHC(=O)OCH$_2$—((S)-5-oxopyrrolidin-3-yl); —NHC(=O)OCH$_2$—((R)-5-oxopyrrolidin-3-yl); —NHC(=O)OCH$_2$-(1-methyl-(S)-5-oxopyrrolidin-2-yl); —NHC(=O)OCH$_2$-(1-methyl-(R)-5-oxopyrrolidin-2-yl); —NHC(=O)O(CH$_2$)$_{1-3}$(2-oxopyrrolidin-1-yl); —NHC(=O)OCH$_2$—(N-acetyl-pyrrolidin-2-yl); —NHC(=O)OCH$_2$—(N-acetyl-pyrrolidin-3-yl); —NHC(=O)OCH$_2$—(N-acetyl-piperidin-4-yl); —NHC(=O)OCH$_2$—(R-6-oxo-piperidin-2-yl); —NHC(=O)OCH$_2$—((S)-6-oxo-piperidin-2-yl); NHC(=O)OCH$_2$CH$_2$-(pyridin-2-yl); —NHC(=O)OCH$_2$CH$_2$-(2-oxo-pyrrolidin-1-yl); —NHC(=O)OCH$_2$C(=O)-(pyrrolidin-1-yl); —NHC(=O)O(tetrahydrofur-3-yl); —NHC(=O)OCH$_2$(tetrahydrofur-2-yl); —NHC(=O)OCH$_2$(tetrahydro-2H-pyran-4-yl); —NHC(=O)OCH$_2$(pyrazin-2-yl); —NHC(=O)OCH$_2$-(6-morpholinopyridin-2-yl); —NHC(=O)OCH$_2$-(imidazo[1,2-a]pyridin-2-yl); —NHC(=O)OCH$_2$-(8-methyl-imidazo[1,2-a]pyridin-2-yl); —NHC(=O)NH$_2$; —NHC(=O)NH(CH$_2$)$_{0-5}$CH$_3$; —N(CH$_3$)C(=O)NH(CH$_2$)$_{0-5}$CH$_3$; —N(CH$_3$)C(=O)N(CH$_3$)(CH$_2$)$_{0-5}$CH$_3$; —NHC(=O)-(pyrrolidin-1-yl); —NHC(=O)-(piperidin-1-yl); —NHC(=O)-(4-hydroxy-piperidin-1-yl); —NHC(=O)-(2-hydroxymethyl-piperidin-1-yl); —NHS(=O)$_2$(C$_1$-C$_6$ alkyl); —NHS(=O)$_2$(C$_3$-C$_8$ cycloalkyl); —NHS(=O)$_2$ (optionally substituted phenyl or heterocyclyl); —NHS(=O)$_2$heterocyclyl; —NHC(=O)C(=O)NH—(C$_1$-C$_6$ alkyl); —NHS(=O)$_2$NH—(C$_1$-C$_6$ alkyl))]; and —NHS(=O)$_2$NH—(C$_3$-C$_8$ cycloalkyl).

In certain embodiments, R$^3$ is selected from the group consisting of: —NH$_2$; —OH; —NH(pyridinyl); —NH(pyrimidinyl); —NH(piridinyl-pyrimidinyl); —NH(pyrrolo[2,3-d]pyrimidinyl); —NHS(=O)$_2$(C$_1$-C$_6$ alkyl); —NHS(=O)$_2$(C$_3$-C$_6$ cycloalkyl); —NHS(=O)$_2$(CH$_2$)$_{0-3}$pyridinyl; —NHS(=O)$_2$(benzyl); —NHS(=O)$_2$(pyrazolyl); —NHS(=O)$_2$(morpholinyl); —NHS(=O)$_2$NH(C$_1$-C$_6$ alkyl); —NHS(=O)$_2$NH(C$_3$-C$_6$ cycloalkyl); —NHS(=O)$_2$NH(CH$_2$)$_{0-3}$pyridinyl; —NHS(=O)$_2$NH(benzyl); —NHS(=O)$_2$NH(pyrazolyl); —NHS(=O)$_2$NH(morpholinyl); —NHC(=O)(C$_1$-C$_6$ alkyl); —NHC(=O)(C$_3$-C$_8$ cycloalkyl); —NHC(=O)(C$_1$-C$_6$ haloalkyl); —NHC(=O)(pyrazolyl); —NHC(=O)(thiazolyl); —NHC(=O)(oxazolyl); —NHC(=O)(pyridinyl); —NHC(=O)(CH$_2$)$_{1-3}$(pyridinyl); —NHC(=O)(CH$_2$)$_{1-3}$(pyrazinyl); —NHC(=O)(CH$_2$)$_{1-3}$(pyrimidinyl); —NHC(=O)(CH$_2$)$_{1-3}$(quinolinyl); —NHC(=O)(CH$_2$)$_{1-3}$(isoxazolyl); —NHC(=O)(CH$_2$)$_{1-3}$(oxazolyl); —NHC(=O)(CH$_2$)$_{1-3}$(oxadiazolyl); —NHC(=O)(CH$_2$)$_{1-3}$(triazolyl); —NHC(=O)(CH$_2$)$_{1-3}$(thiazolyl); —NHC(=O)(CH$_2$)$_{1-3}$(imidazolyl); —NHC(=O)(CH$_2$)$_{1-3}$(pyrazolyl); —NHC(=O)(CH$_2$)$_{1-3}$(piperidinyl); —NHC(=O)(CH$_2$)$_{1-3}$(oxopiperidinyl); —NHC(=O)(CH$_2$)$_{1-3}$(pyrrolidinyl); —NHC(=O)(CH$_2$)$_{1-3}$(oxopyrrolidinyl); —NHC(=O)(CH$_2$)$_{1-3}$(tetrahydrofuryl); —NHC(=O)(CH$_2$)$_{1-3}$(tetrahydropyranyl); —NHC(=O)(CH$_2$)$_{1-3}$(2-oxooxazolidinyl); —NHC(=O)(CH$_2$)$_{1-3}$(morpholinyl); —NHC(=O)(CH$_2$)$_{1-3}$(thiomorpholinyl); —NHC(=O)(CH$_2$)$_{1-3}$(1-oxido-thiomorpholinyl); —NHC(=O)(CH$_2$)$_{1-3}$(1,1-dioxido-thiomorpholinyl); —NHC(=O)(CH$_2$)$_{1-3}$(oxoazetidinyl); —NHC(=O)(CH$_2$)$_{1-3}$(imidazo[1,2-a]pyridin-2-yl); —NHC(=O)(CH$_2$)$_{1-3}$C(=O)-(pyrrolidin-1-yl); —NHC(=O)O(C$_1$-C$_6$ alkyl); —NHC(=O)O(C$_3$-C$_8$ cycloalkyl); —NHC(=O)O(C$_1$-C$_6$ haloalkyl); —NHC(=O)O(CH$_2$)$_{1-3}$(pyridinyl); —NHC(=O)O(CH$_2$)$_{1-3}$(pyrazinyl); —NHC(=O)O(CH$_2$)$_{1-3}$(pyrimidinyl); —NHC(=O)O(CH$_2$)$_{1-3}$(quinolinyl); —NHC(=O)O(CH$_2$)$_{1-3}$(isoxazolyl); —NHC(=O)O(CH$_2$)$_{1-3}$(oxazolyl); —NHC(=O)O(CH$_2$)$_{1-3}$(oxadiazolyl); —NHC(=O)O(CH$_2$)$_{1-3}$(triazolyl); —NHC(=O)O(CH$_2$)$_{1-3}$(thiazolyl); —NHC(=O)O(CH$_2$)$_{1-3}$(imidazolyl); —NHC(=O)O(CH$_2$)$_{1-3}$(pyrazolyl); —NHC(=O)O(CH$_2$)$_{1-3}$(piperidinyl); —NHC(=O)O(CH$_2$)$_{1-3}$(oxopiperidinyl); —NHC(=O)O(CH$_2$)$_{1-3}$(pyrrolidinyl); —NHC(=O)O(CH$_2$)$_{1-3}$(oxopyrrolidinyl); —NHC(=O)O(CH$_2$)$_{1-3}$(tetrahydrofuryl); —NHC(=O)O(CH$_2$)$_{1-3}$(tetrahydropyranyl); —NHC(=O)O(CH$_2$)$_{1-3}$(2-oxooxazolidinyl); —NHC(=O)O(CH$_2$)$_{1-3}$(morpholinyl); —NHC(=O)O(CH$_2$)$_{1-3}$(thiomorpholinyl); —NHC(=O)O (CH₂)₁₋₃(1-oxido-thiomorpholinyl); —NHC(=O)O(CH₂)₁₋₃(1,1-dioxido-thiomorpholinyl); —NHC(=O)O(CH₂)₁₋₃(oxoazetidinyl); —NHC(=O)O(CH₂)₁₋₃(imidazo[1,2-a]pyridin-2-yl); —NHC(=O)O(CH₂)₁₋₃C(=O)-(pyrrolidin-1-yl); —NHC(=O)NH(C₁-C₆ alkyl); —NHC(=O)NH(C₃-C₈ cycloalkyl); —NHC(=O)NH(C₁-C₆ haloalkyl); —NHC(=O)NH(CH₂)₁₋₃(pyridinyl); —NHC(=O)NH(CH₂)₁₋₃(pyrazinyl); —NHC(=O)NH(CH₂)₁₋₃(pyrimidinyl); —NHC(=O)NH(CH₂)₁₋₃(quinolinyl); —NHC(=O)NH(CH₂)₁₋₃(isoxazolyl); —NHC(=O)NH(CH₂)₁₋₃(oxazolyl); —NHC(=O)NH(CH₂)₁₋₃(oxadiazolyl); —NHC(=O)NH(CH₂)₁₋₃(triazolyl); —NHC(=O)NH(CH₂)₁₋₃(thiazolyl); —NHC(=O)NH(CH₂)₁₋₃(imidazolyl); —NHC(=O)NH(CH₂)₁₋₃(pyrazolyl); —NHC(=O)NH(CH₂)₁₋₃(piperidinyl); —NHC(=O)NH(CH₂)₁₋₃(oxopiperidinyl); —NHC(=O)NH(CH₂)₁₋₃(pyrrolidinyl); —NHC(=O)NH(CH₂)₁₋₃(oxopyrrolidinyl); —NHC(=O)NH(CH₂)₁₋₃(tetrahydrofuryl); —NHC(=O)NH(CH₂)₁₋₃(tetrahydropyranyl); —NHC(=O)NH(CH₂)₁₋₃(2-oxooxazolidinyl); —NHC(=O)NH(CH₂)₁₋₃(morpholinyl); —NHC(=O)NH(CH₂)₁₋₃(thiomorpholinyl); —NHC(=O)NH(CH₂)₁₋₃(1-oxido-thiomorpholinyl); —NHC(=O)NH(CH₂)₁₋₃(1,1-dioxido-thiomorpholinyl); —NHC(=O)NH(CH₂)₁₋₃(oxoazetidinyl); —NHC(=O)NH(CH₂)₁₋₃(imidazo[1,2-a]pyridin-2-yl); —NHC(=O)NH(CH₂)₁₋₃C(=O)-(pyrrolidin-1-yl); —C(=O)NHC(=O)NH—; —C(=O)N(C₁-C₆ alkyll)C(=O)NH—; —C(=O)N((CH₂)₁₋₃pyridinyl)CONH—; wherein the alkyl, cycloalkyl, heteroaryl, heterocyclyl, aryl, or benzyl group is optionally independently substituted with at least one group selected from the group consisting of C₁-C₆ alkyl; C₁-C₆ alkoxy; C₁-C₆ haloalkyl; C₁-C₆ haloalkoxy; —NH₂, —NH(C₁-C₆ alkyl), —N(C₁-C₆ alkyl)(C₁-C₆ alkyl), halogen, —OH; —CN; phenoxy, —NHC(=O)H, —NHC(=O)C₁-C₆ alkyl, —C(=O)NH₂, —C(=O)NHC₁-C₆ alkyl, —C(=O)N(C₁-C₆ alkyl)(C₁-C₆ alkyl), tetrahydropyranyl, morpholinyl, —C(=O)CH₃, —C(=O)CH₂OH, —C(=O)NHCH₃, —C(=O)CH₂OMe, or an N-oxide thereof.

In certain embodiments, R₄ is H or CH₃.

In certain embodiments, R⁵ᵃ, R⁵ᵇ, and R⁵ᶜ are independently selected from the group consisting of H, F, and Cl. In certain embodiments, one of R⁵ᵃ, R⁵ᵇ, and R⁵ᶜ is F, and the two remaining are H.

In certain embodiments, the compound is selected from the group consisting of:

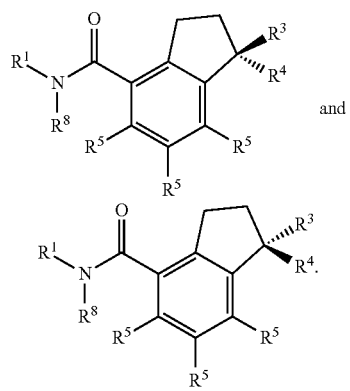

and

In certain embodiments, the compound is selected from the group consisting of:

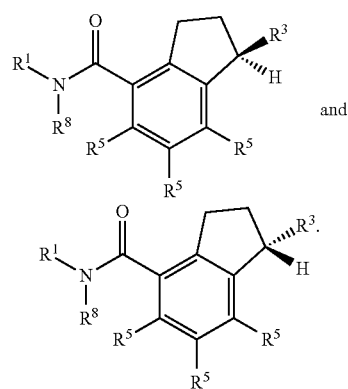

and

In certain embodiments, the compound is at least partially deuterated. In certain embodiments, the compound is a prodrug. In certain embodiments, the compound comprises a —(CRR)—O—P(=O)(OR)₂ group, or a salt thereof, which is attached to a heteroatom, wherein each occurrence of R is independently H and C₁-C₆ alkyl.

In certain embodiments, the compound is at least one selected from the group consisting of:

O-methyl, N—(S)-(4-((3,4-difluorophenyl)carbamoyl)-2,3-dihydro-1H-inden-1-yl) carbamate;

(S)—N-(3,4-difluorophenyl)-1-(3-methylureido)-2,3-dihydro-1H-indene-4-carboxamide;

O-pyridin-2-ylmethyl, N—(S)-(4-((3,4-difluorophenyl)carbamoyl)-2,3-dihydro-1H-inden-1-yl) carbamate;

O—((R)-5-oxopyrrolidin-2-yl)methyl, N—((S)-4-((3-chloro-4-fluorophenyl)carbamoyl)-7-fluoro-2,3-dihydro-1H-inden-1-yl) carbamate;

O-tert-butyl, N—(S)-(4-((3-chloro-4-fluorophenyl)carbamoyl)-7-fluoro-2,3-dihydro-1H-inden-1-yl) carbamate;

O-methyl, N—(S)-(7-fluoro-4-((4-fluoro-3-methylphenyl)carbamoyl)-2,3-dihydro-1H-inden-1-yl) carbamate;

(S)-7-fluoro-N-(4-fluoro-3-methylphenyl)-1-(3-methylureido)-2,3-dihydro-1H-indene-4-carboxamide;

(S)-1-amino-N-(3-chloro-4-fluorophenyl)-7-fluoro-2,3-dihydro-1H-indene-4-carboxamide;

O-2-(2-oxopyrrolidin-1-yl)ethyl, N—(S)-(4-((3-chloro-4-fluorophenyl)carbamoyl)-7-fluoro-2,3-dihydro-1H-inden-1-yl) carbamate;

O-pyridin-2-ylmethyl, N—(S)-(4-((3-chloro-4-fluorophenyl)carbamoyl)-2,3-dihydro-1H-inden-1-yl) carbamate;

O—((S)-5-oxopyrrolidin-2-yl)methyl, N—((S)-4-((3-chloro-4-fluorophenyl)carbamoyl)-7-fluoro-2,3-dihydro-1H-inden-1-yl) carbamate;

O-methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(3-methylureido)-2,3-dihydro-1H-indene-4-carboxamide;

O—((R)-5-oxopyrrolidin-2-yl)methyl, N—((S)-4-((3-chloro-4-fluorophenyl)carbamoyl)-2,3-dihydro-1H-inden-1-yl) carbamate;

O—((S)-5-oxopyrrolidin-2-yl)methyl, N—((S)-4-((3-chloro-4-fluorophenyl)carbamoyl)-2,3-dihydro-1H-inden-1-yl) carbamate;

O-pyridin-2-ylmethyl, N—(S)-(4-((4-fluoro-3-methylphenyl)carbamoyl)-2,3-dihydro-1H-inden-1-yl) carbamate;

O—((R)-5-oxopyrrolidin-2-yl)methyl, N—((S)-4-((4-fluoro-3-methylphenyl)carbamoyl)-2,3-dihydro-1H-inden-1-yl)carbamate;

O—((S)-5-oxopyrrolidin-2-yl)methyl, N—((S)-4-((4-fluoro-3-methylphenyl)carbamoyl)-2,3-dihydro-1H-inden-1-yl) carbamate;

O-2-oxo-2-(pyrrolidin-1-yl)ethyl, N—(S)-(4-((3-chloro-4-fluorophenyl)carbamoyl)-7-fluoro-2,3-dihydro-1H-inden-1-yl) carbamate;

O-pyridin-2-ylmethyl, N—(S)-(4-((3-chloro-4-fluorophenyl)carbamoyl)-7-fluoro-2,3-dihydro-1H-inden-1-yl) carbamate;

O—((S)-1-methyl-5-oxopyrrolidin-2-yl)methyl, N—((S)-4-((3-chloro-4-fluorophenyl)carbamoyl)-7-fluoro-2,3-dihydro-1H-inden-1-yl) carbamate;

O-pyridin-2-ylmethyl, N—(S)-(7-fluoro-4-((4-fluoro-3-methylphenyl)carbamoyl)-2,3-dihydro-1H-inden-1-yl) carbamate;

O-imidazo[1,2-a]pyridin-2-ylmethyl, N—(S)-(4-((3-chloro-4-fluorophenyl)carbamoyl)-7-fluoro-2,3-dihydro-1H-inden-1-yl) carbamate;

O-(6-morpholinopyridin-2-yl)methyl, N—(S)-(4-((3-chloro-4-fluorophenyl)carbamoyl)-7-fluoro-2,3-dihydro-1H-inden-1-yl) carbamate;

O—((R)-1-methyl-5-oxopyrrolidin-2-yl)methyl, N—((S)-4-((3-chloro-4-fluorophenyl)carbamoyl)-7-fluoro-2,3-dihydro-1H-inden-1-yl) carbamate;

O-(6-methoxypyridin-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(pyrimidin-2-ylamino)-2,3-dihydro-1H-indene-4-carboxamide;

O-(6-(dimethylamino) pyridin-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-((5-methoxypyrimidin-2-yl)amino)-2,3-dihydro-1H-indene-4-carboxamide;

(S)—N-(3-chloro-4-fluorophenyl)-7-fluoro-1-((4-(pyridin-2-yl)pyrimidin-2-yl)amino)-2,3-dihydro-1H-indene-4-carboxamide;

tert-butyl 2-(((((S)-4-((3-chloro-4-fluorophenyl)carbamoyl)-7-fluoro-2,3-dihydro-1H-inden-1-yl)carbamoyl)oxy)methyl)-4,4-difluoropyrrolidine-1-carboxylate;

O-(4,4-difluoropyrrolidin-2-yl)methyl, N—((S)-4-((3-chloro-4-fluorophenyl)carbamoyl)-7-fluoro-2,3-dihydro-1H-inden-1-yl) carbamate;

O-(1-acetyl-4,4-difluoropyrrolidin-2-yl)methyl, N—((S)-4-((3-chloro-4-fluorophenyl)carbamoyl)-7-fluoro-2,3-dihydro-1H-inden-1-yl) carbamate;

O-(1-(2,2,2-trifluoroethyl)piperidin-4-yl)methyl, N—(S)-(4-((3-chloro-4-fluorophenyl)carbamoyl)-7-fluoro-2,3-dihydro-1H-inden-1-yl) carbamate;

(S)-2-((((4-((3-chloro-4-fluorophenyl)carbamoyl)-7-fluoro-2,3-dihydro-1H-inden-1-yl)carbamoyl)oxy)methyl)pyridine 1-oxide;

O—(S)-1-(pyridin-2-yl)ethyl, N—((S)-4-((3-chloro-4-fluorophenyl)carbamoyl)-7-fluoro-2,3-dihydro-1H-inden-1-yl) carbamate;

O—(S)-pyrrolidin-2-ylmethyl, N—((S)-4-((3-chloro-4-fluorophenyl)carbamoyl)-7-fluoro-2,3-dihydro-1H-inden-1-yl) carbamate;

O-3,3,3-trifluoropropyl, N—(S)-(4-((3-chloro-4-fluorophenyl)carbamoyl)-7-fluoro-2,3-dihydro-1H-inden-1-yl) carbamate;

O-(1-methyl-1H-pyrazol-3-yl)methyl, N—(S)-(4-((3-chloro-4-fluorophenyl)carbamoyl)-7-fluoro-2,3-dihydro-1H-inden-1-yl) carbamate;

O—(R)-5-oxopyrrolidin-3-yl, N—((S)-4-((3-chloro-4-fluorophenyl)carbamoyl)-7-fluoro-2,3-dihydro-1H-inden-1-yl) carbamate;

O-(6-methylpyridin-2-yl)methyl, N—(S)-(4-((3-chloro-4-fluorophenyl)carbamoyl)-7-fluoro-2,3-dihydro-1H-inden-1-yl) carbamate;

N—(S)-4-((3-chloro-4-fluorophenyl)carbamoyl)-7-fluoro-2,3-dihydro-1H-inden-1-yl, O-(pyridin-2-ylmethyl) carbamate;

(S)—N-(3-chloro-4-fluorophenyl)-7-fluoro-1-(2-methoxyacetamido)-2,3-dihydro-1H-indene-4-carboxamide;

(S)—N-(3-chloro-4-fluorophenyl)-7-fluoro-1-(3-fluoropropanamido)-2,3-dihydro-1H-indene-4-carboxamide;

(S)-1-acetamido-N-(3-chloro-4-fluorophenyl)-7-fluoro-2,3-dihydro-1H-indene-4-carboxamide;

O-pyrazin-2-ylmethyl, N—(S)-(4-((3-chloro-4-fluorophenyl)carbamoyl)-7-fluoro-2,3-dihydro-1H-inden-1-yl) carbamate;

O-pyrimidin-2-ylmethyl, N—(S)-(4-((3-chloro-4-fluorophenyl)carbamoyl)-7-fluoro-2,3-dihydro-1H-inden-1-yl) carbamate;

O-(4-chloropyridin-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-hydroxy-2,3-dihydro-1H-indene-4-carboxamide;

O-isoxazol-3-ylmethyl, N—(S)-(4-((3-chloro-4-fluorophenyl)carbamoyl)-7-fluoro-2,3-dihydro-1H-inden-1-yl) carbamate;

O-2-(pyridin-2-yl)ethyl, N—(S)-(4-((3-chloro-4-fluorophenyl)carbamoyl)-7-fluoro-2,3-dihydro-1H-inden-1-yl) carbamate;

O-2,2-difluoroethyl, N—(S)-(4-((3-chloro-4-fluorophenyl)carbamoyl)-7-fluoro-2,3-dihydro-1H-inden-1-yl) carbamate;

O-pyrimidin-4-ylmethyl, N—(S)-(4-((3-chloro-4-fluorophenyl)carbamoyl)-7-fluoro-2,3-dihydro-1H-inden-1-yl) carbamate;

O-3-(2-oxopyrrolidin-1-yl)propyl, N—(S)-(4-((3-chloro-4-fluorophenyl)carbamoyl)-7-fluoro-2,3-dihydro-1H-inden-1-yl) carbamate;

O-(8-methylimidazo[1,2-a]pyridin-2-yl)methyl, N—(S)-(4-((3-chloro-4-fluorophenyl)carbamoyl)-7-fluoro-2,3-dihydro-1H-inden-1-yl) carbamate;

O-2,2,2-trifluoroethyl, N—(S)-(4-((3-chloro-4-fluorophenyl)carbamoyl)-7-fluoro-2,3-dihydro-1H-inden-1-yl) carbamate;

O—(S)-4-((3-chloro-4-fluorophenyl)carbamoyl)-7-fluoro-2,3-dihydro-1H-inden-1-yl, N-methylcarbamate;

N—(S)-4-((3-chloro-4-fluorophenyl)carbamoyl)-7-fluoro-2,3-dihydro-1H-inden-1-yl, O-(pyridin-2-ylmethyl) carbonate;

O-thiazol-5-ylmethyl, N—(S)-(4-((3-chloro-4-fluorophenyl)carbamoyl)-7-fluoro-2,3-dihydro-1H-inden-1-yl) carbamate;

O-thiazol-2-ylmethyl, N—(S)-(4-((3-chloro-4-fluorophenyl)carbamoyl)-7-fluoro-2,3-dihydro-1H-inden-1-yl) carbamate;

O-oxazol-4-ylmethyl, N—(S)-(4-((3-chloro-4-fluorophenyl)carbamoyl)-7-fluoro-2,3-dihydro-1H-inden-1-yl) carbamate;

O-oxazol-2-ylmethyl, N—(S)-(4-((3-chloro-4-fluorophenyl)carbamoyl)-7-fluoro-2,3-dihydro-1H-inden-1-yl) carbamate;

O-oxazol-5-ylmethyl, N—(S)-(4-((3-chloro-4-fluorophenyl)carbamoyl)-7-fluoro-2,3-dihydro-1H-inden-1-yl) carbamate;

O-2-(1H-imidazol-1-yl)ethyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-(pyridin-2-ylamino)-2,3-dihydro-1H-indene-4-carboxamide;
(S)—N-(4-((3-chloro-4-fluorophenyl)carbamoyl)-7-fluoro-2,3-dihydro-1H-inden-1-yl)-1-methyl-1H-pyrazole-3-carboxamide;
O-2-phenoxyethyl, N—(S)-(4-((3-chloro-4-fluorophenyl)carbamoyl)-7-fluoro-2,3-dihydro-1H-inden-1-yl) carbamate;
(S)—N-(4-((3-chloro-4-fluorophenyl)carbamoyl)-7-fluoro-2,3-dihydro-1H-inden-1-yl)-1-methyl-1H-pyrazole-5-carboxamide;
(S)—N-(3-chloro-4-fluorophenyl)-7-fluoro-1-((1-methyl-1H-pyrazole)-3-sulfonamido)-2,3-dihydro-1H-indene-4-carboxamide;
O-(1-methyl-1H-1,2,4-triazol-3-yl)methyl, N—(S)-(4-((3-chloro-4-fluorophenyl)carbamoyl)-7-fluoro-2,3-dihydro-1H-inden-1-yl) carbamate;
O-(1-methyl-1H-pyrazol-5-yl)methyl, N—(S)-(4-((3-chloro-4-fluorophenyl)carbamoyl)-7-fluoro-2,3-dihydro-1H-inden-1-yl) carbamate;
(S)-2-((4-((3-chloro-4-fluorophenyl)carbamoyl)-7-fluoro-2,3-dihydro-1H-inden-1-yl)amino)pyrimidine-4-carboxamide;
O-2-(4-methylthiazol-5-yl)ethyl, N—(S)-(4-((3-chloro-4-fluorophenyl)carbamoyl)-7-fluoro-2,3-dihydro-1H-inden-1-yl) carbamate;
O-(1-isopropyl-1H-pyrazol-3-yl)methyl, N—(S)-(4-((3-chloro-4-fluorophenyl)carbamoyl)-7-fluoro-2,3-dihydro-1H-inden-1-yl) carbamate;
O-(5-methoxypyridin-2-yl)methyl, N—(S)-(4-((3-chloro-4-fluorophenyl)carbamoyl)-7-fluoro-2,3-dihydro-1H-inden-1-yl) carbamate;
O—((S)-1-(2,2,2-trifluoroethyl)pyrrolidin-2-yl)methyl, N—((S)-4-((3-chloro-4-fluorophenyl)carbamoyl)-7-fluoro-2,3-dihydro-1H-inden-1-yl) carbamate;
O-(5-fluoropyridin-2-yl)methyl, N—(S)-(4-((3-chloro-4-fluorophenyl)carbamoyl)-7-fluoro-2,3-dihydro-1H-inden-1-yl) carbamate;
O-2-(1H-pyrazol-4-yl)ethyl, N—(S)-(4-((3-chloro-4-fluorophenyl)carbamoyl)-7-fluoro-2,3-dihydro-1H-inden-1-yl) carbamate;
O-2-methoxyethyl, N—(S)-(4-((3-chloro-4-fluorophenyl)carbamoyl)-7-fluoro-2,3-dihydro-1H-inden-1-yl) carbamate;
O—((R)-tetrahydrofuran-2-yl)methyl, N—((S)-4-((3-chloro-4-fluorophenyl)carbamoyl)-7-fluoro-2,3-dihydro-1H-inden-1-yl) carbamate;
O-tetrahydro-2H-pyran-4-yl, N—(S)-(4-((3-chloro-4-fluorophenyl)carbamoyl)-7-fluoro-2,3-dihydro-1H-inden-1-yl) carbamate;
O-3-methoxypropyl, N—(S)-(4-((3-chloro-4-fluorophenyl)carbamoyl)-7-fluoro-2,3-dihydro-1H-inden-1-yl) carbamate;
(S)—N-(4-((3-chloro-4-fluorophenyl)carbamoyl)-7-fluoro-2,3-dihydro-1H-inden-1-yl)picolinamide;
(S)—N-(4-((3-chloro-4-fluorophenyl)carbamoyl)-7-fluoro-2,3-dihydro-1H-inden-1-yl)thiazole-5-carboxamide;
(S)—N-(3-chloro-4-fluorophenyl)-7-fluoro-1-(methylsulfonamido)-2,3-dihydro-1H-indene-4-carboxamide;
(S)—N-(3-chloro-4-fluorophenyl)-7-fluoro-1-(2-morpholinoacetamido)-2,3-dihydro-1H-indene-4-carboxamide;
(S)—N-(4-((3-chloro-4-fluorophenyl)carbamoyl)-7-fluoro-2,3-dihydro-1H-inden-1-yl)nicotinamide;
(S)—N-(4-((3-chloro-4-fluorophenyl)carbamoyl)-7-fluoro-2,3-dihydro-1H-inden-1-yl)isonicotinamide;
(S)-4-((3-chloro-4-fluorophenyl)carbamoyl)-7-fluoro-2,3-dihydro-1H-inden-1-yl methyl carbonate;
O-thiazol-4-ylmethyl, N—(S)-(4-((3-chloro-4-fluorophenyl)carbamoyl)-7-fluoro-2,3-dihydro-1H-inden-1-yl) carbamate;
O-3-(1H-imidazol-1-yl)propyl, N—(S)-(4-((3-chloro-4-fluorophenyl)carbamoyl)-7-fluoro-2,3-dihydro-1H-inden-1-yl) carbamate;
O-pyridin-2-ylmethyl, N—(S)-(4-((3-cyano-4-fluorophenyl)carbamoyl)-7-fluoro-2,3-dihydro-1H-inden-1-yl) carbamate;
(S)—N-(4-((3-chloro-4-fluorophenyl)carbamoyl)-7-fluoro-2,3-dihydro-1H-inden-1-yl)thiazole-2-carboxamide;
(S)—N-(3-chloro-4-fluorophenyl)-1-(cyclopropanesulfonamido)-7-fluoro-2,3-dihydro-1H-indene-4-carboxamide;
(S)—N-(4-((3-chloro-4-fluorophenyl)carbamoyl)-7-fluoro-2,3-dihydro-1H-inden-1-yl)oxazole-5-carboxamide;
O-cyclopentyl, N—(S)-(4-((3-chloro-4-fluorophenyl)carbamoyl)-7-fluoro-2,3-dihydro-1H-inden-1-yl)carbamate;
O-(2-oxo-oxazolidin-5-yl)methyl, N—((S)-4-((3-chloro-4-fluorophenyl)carbamoyl)-7-fluoro-2,3-dihydro-1H-inden-1-yl) carbamate;
O-2-(1H-pyrazol-1-yl)ethyl, N—(S)-(4-((3-chloro-4-fluorophenyl)carbamoyl)-7-fluoro-2,3-dihydro-1H-inden-1-yl) carbamate;
O-(1-methyl-1H-imidazol-2-yl)methyl, N—(S)-(4-((3-chloro-4-fluorophenyl)carbamoyl)-7-fluoro-2,3-dihydro-1H-inden-1-yl) carbamate;
O-(3-fluoropyridin-2-yl)methyl, N—(S)-(4-((3-chloro-4-fluorophenyl)carbamoyl)-7-fluoro-2,3-dihydro-1H-inden-1-yl) carbamate;
O—((R)-morpholin-3-yl)methyl, N—((S)-4-((3-chloro-4-fluorophenyl)carbamoyl)-7-fluoro-2,3-dihydro-1H-inden-1-yl) carbamate;
O-(4-methoxypyridin-2-yl)methyl, N—(S)-(4-((3-chloro-4-fluorophenyl)carbamoyl)-7-fluoro-2,3-dihydro-1H-inden-1-yl) carbamate;
O-2-hydroxyethyl, N—(S)-(4-((3-chloro-4-fluorophenyl)carbamoyl)-7-fluoro-2,3-dihydro-1H-inden-1-yl) carbamate;
O—((S)-tetrahydrofuran-2-yl)methyl, N—((S)-4-((3-chloro-4-fluorophenyl)carbamoyl)-7-fluoro-2,3-dihydro-1H-inden-1-yl)carbamate;
(S)—N-(3-chloro-4-fluorophenyl)-7-fluoro-1-(2-hydroxyacetamido)-2,3-dihydro-1H-indene-4-carboxamide;
(S)—N-(3-chloro-4-fluorophenyl)-7-fluoro-1-(3-(pyridin-3-yl)ureido)-2,3-dihydro-1H-indene-4-carboxamide;
(S)—N-(3-chloro-4-fluorophenyl)-7-fluoro-1-(3-(pyridin-4-yl)ureido)-2,3-dihydro-1H-indene-4-carboxamide;
(S)—N-(3-chloro-4-fluorophenyl)-7-fluoro-1-(thiazol-2-ylamino)-2,3-dihydro-1H-indene-4-carboxamide;
O-2-(piperidin-1-yl)ethyl, N—(S)-(4-((3-chloro-4-fluorophenyl)carbamoyl)-7-fluoro-2,3-dihydro-1H-inden-1-yl) carbamate;
O-pyridin-2-ylmethyl, N—(S)-(4-((3-(difluoromethyl)-4-fluorophenyl)carbamoyl)-7-fluoro-2,3-dihydro-1H-inden-1-yl) carbamate;
(S)—N-(3-chloro-4-fluorophenyl)-7-fluoro-1-(3-(pyridin-2-ylmethyl)ureido)-2,3-dihydro-1H-indene-4-carboxamide;
O-(6-cyanopyridin-2-yl)methyl, N—(S)-(4-((3-chloro-4-fluorophenyl)carbamoyl)-7-fluoro-2,3-dihydro-1H-inden-1-yl) carbamate;
O-quinolin-2-ylmethyl, N—(S)-(4-((3-chloro-4-fluorophenyl)carbamoyl)-7-fluoro-2,3-dihydro-1H-inden-1-yl) carbamate;

O-(5-methylpyrazin-2-yl)methyl, N—(S)-(4-((3-chloro-4-fluorophenyl)carbamoyl)-7-fluoro-2,3-dihydro-1H-inden-1-yl) carbamate;
O-2-morpholinoethyl-N—(S)-(4-((3-chloro-4-fluorophenyl)carbamoyl)-7-fluoro-2,3-dihydro-1H-inden-1-yl) carbamate;
O-[cis-4-hydroxycyclohexyl]-N—((S)-4-((3-chloro-4-fluorophenyl)carbamoyl)-7-fluoro-2,3-dihydro-1H-inden-1-yl)carbamate;
O-3-hydroxypropyl, N—(S)-(4-((3-chloro-4-fluorophenyl)carbamoyl)-7-fluoro-2,3-dihydro-1H-inden-1-yl) carbamate;
O-[trans-4-hydroxycyclohexyl]-N—((S)-4-((3-chloro-4-fluorophenyl)carbamoyl)-7-fluoro-2,3-dihydro-1H-inden-1-yl) carbamate;
O-2-acetamidoethyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-propionamido-2,3-dihydro-1H-indene-4-carboxamide;
(S)—N-(3-chloro-4-fluorophenyl)-7-fluoro-1-((4-methoxypyrimidin-2-yl)amino)-2,3-dihydro-1H-indene-4-carboxamide;
(S)—N-(3-chloro-4-fluorophenyl)-7-fluoro-1-((4-methylpyrimidin-2-yl)amino)-2,3-dihydro-1H-indene-4-carboxamide;
(S)—N-(3-chloro-4-fluorophenyl)-7-fluoro-1-((2-methoxypyrimidin-4-yl)amino)-2,3-dihydro-1H-indene-4-carboxamide;
(S)—N-(3-chloro-4-fluorophenyl)-7-fluoro-1-((5-methylpyrimidin-2-yl)amino)-2,3-dihydro-1H-indene-4-carboxamide;
(S)—N-(3-chloro-4-fluorophenyl)-7-fluoro-1-((6-methoxypyrimidin-4-yl)amino)-2,3-dihydro-1H-indene-4-carboxamide;
(S)—N-(3-chloro-4-fluorophenyl)-1-((4,6-dimethylpyrimidin-2-yl)amino)-7-fluoro-2,3-dihydro-1H-indene-4-carboxamide;
O—(S)-5-oxopyrrolidin-3-yl, N—((S)-4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-((2-(pyridin-2-yl)ethyl)sulfonamido)-2,3-dihydro-1H-indene-4-carboxamide;
O-(6-(trifluoromethyl)pyridin-2-yl)methyl, N—(S)-(4-((3-chloro-4-fluorophenyl)carbamoyl)-7-fluoro-2,3-dihydro-1H-inden-1-yl) carbamate;
O-(5-(trifluoromethyl) pyridin-2-yl)methyl, N—(S)-(4-((3-chloro-4-fluorophenyl)carbamoyl)-7-fluoro-2,3-dihydro-1H-inden-1-yl) carbamate;
O—(R)-tetrahydrofuran-3-yl, N—((S)-4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-(3-(1-methyl-1H-pyrazol-3-yl)propanamido)-2,3-dihydro-1H-indene-4-carboxamide;
O-(5-cyanopyridin-2-yl)methyl, N—(S)-(4-((3-chloro-4-fluorophenyl)carbamoyl)-7-fluoro-2,3-dihydro-1H-inden-1-yl) carbamate;
O-(3-methylpyrazin-2-yl)methyl, N—(S)-(4-((3-chloro-4-fluorophenyl)carbamoyl)-7-fluoro-2,3-dihydro-1H-inden-1-yl) carbamate;
O-(1-acetylpiperidin-4-yl)methyl, N—(S)-(4-((3-chloro-4-fluorophenyl)carbamoyl)-7-fluoro-2,3-dihydro-1H-inden-1-yl) carbamate;
O-(1-(2-hydroxyacetyl)piperidin-4-yl)methyl, N—(S)-(4-((3-chloro-4-fluorophenyl)carbamoyl)-7-fluoro-2,3-dihydro-1H-inden-1-yl) carbamate;
O-(1-(methylcarbamoyl)piperidin-4-yl)methyl, N—(S)-(4-((3-chloro-4-fluorophenyl)carbamoyl)-7-fluoro-2,3-dihydro-1H-inden-1-yl) carbamate;
O-(1,1-dioxidothiomorpholin-3-yl)methyl-N—((S)-4-((3-chloro-4-fluorophenyl)carbamoyl)-7-fluoro-2,3-dihydro-1H-inden-1-yl) carbamate;
(S)—N-(3-chloro-4-fluorophenyl)-1-(cyclopropanecarboxamido)-7-fluoro-2,3-dihydro-1H-indene-4-carboxamide;
O—((S)-morpholin-3-yl)methyl, N—((S)-4-((3-chloro-4-fluorophenyl)carbamoyl)-7-fluoro-2,3-dihydro-1H-inden-1-yl) carbamate;
O—(S)-tetrahydrofuran-3-yl, N—((S)-4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-((2-methoxyethyl) sulfonamido)-2,3-dihydro-1H-indene-4-carboxamide;
(S)—N-(3-chloro-4-fluorophenyl)-7-fluoro-1-(phenylsulfonamido)-2,3-dihydro-1H-indene-4-carboxamide;
(S)—N-(3-chloro-4-fluorophenyl)-7-fluoro-1-(pyridine-2-sulfonamido)-2,3-dihydro-1H-indene-4-carboxamide;
O-(1-(2-methoxyacetyl) piperidin-4-yl)methyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-((5-hydroxypyrimidin-2-yl)amino)-2,3-dihydro-1H-indene-4-carboxamide
O-(1H-pyrazol-3-yl)methyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-(3-((1-methyl-1H-pyrazol-3-yl)methyl)ureido)-2,3-dihydro-1H-indene-4-carboxamide;
O-(1H-1,2,4-triazol-3-yl)methyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-(pyrimidin-4-ylamino)-2,3-dihydro-1H-indene-4-carboxamide;
(S)—N-(3-chloro-4-fluorophenyl)-7-fluoro-1-((7-(4-methoxybenzyl)-7H-pyrrolo[2,3-d]pyrimidin-2-yl)amino)-2,3-dihydro-1H-indene-4-carboxamide;
O—((R)-6-oxopiperidin-2-yl)methyl, N—((S)-4-((3-chloro-4-fluorophenyl)carbamoyl)-7-fluoro-2,3-dihydro-1H-inden-1-yl) carbamate;
O—(R)-6-oxopiperidin-3-yl, N—((S)-4-((3-chloro-4-fluorophenyl)carbamoyl)-7-fluoro-2,3-dihydro-1H-inden-1-yl) carbamate;
O—(S)-6-oxopiperidin-3-yl, N—((S)-4-((3-chloro-4-fluorophenyl)carbamoyl)-7-fluoro-2,3-dihydro-1H-inden-1-yl) carbamate;
(S)—N-(3-chloro-4-fluorophenyl)-1-(3-cyclopropylureido)-7-fluoro-2,3-dihydro-1H-indene-4-carboxamide;
O—((S)-6-oxopiperidin-2-yl)methyl, N—((S)-4-((3-chloro-4-fluorophenyl)carbamoyl)-7-fluoro-2,3-dihydro-1H-inden-1-yl) carbamate;
O-(4-oxoazetidin-2-yl)methyl, N—((S)-4-((3-chloro-4-fluorophenyl)carbamoyl)-7-fluoro-2,3-dihydro-1H-inden-1-yl) carbamate;
O-methyl, N-(4-((3-chloro-4-fluorophenyl)carbamoyl)-7-fluoro-1-methyl-2,3-dihydro-1H-inden-1-yl) carbamate;
N-(3-chloro-4-fluorophenyl)-7-fluoro-1-methyl-1-(3-methylureido)-2,3-dihydro-1H-indene-4-carboxamide;
(S)—N-(3-chloro-4-fluorophenyl)-1-(cyclopropanesulfonamido)-2,3-dihydro-1H-indene-4-carboxamide;

O-pyridin-2-ylmethyl, N-(4-((3-chloro-4-fluorophenyl)carbamoyl)-7-fluoro-1-methyl-2,3-dihydro-1H-inden-1-yl) carbamate;

(S)—N-(3-chloro-4-fluorophenyl)-1-((cyclopropylmethyl)sulfonamido)-7-fluoro-2,3-dihydro-1H-indene-4-carboxamide;

(S)—N-(3-chloro-4-fluorophenyl)-7-fluoro-1-((phenylmethyl)sulfonamido)-2,3-dihydro-1H-indene-4-carboxamide;

O-cyclopropyl, N—S)-(4-((3-chloro-4-fluorophenyl)carbamoyl)-7-fluoro-2,3-dihydro-1H-inden-1-yl)carbamate;

(S)—N-(3-chloro-4-fluorophenyl)-7-fluoro-1-((N-methylsulfamoyl)amino)-2,3-dihydro-1H-indene-4-carboxamide;

(S)—N-(3-chloro-4-fluorophenyl)-7-fluoro-1-(morpholine-4-sulfonamido)-2,3-dihydro-1H-indene-4-carboxamide;

O-cyclopropyl, N—S)-(4-((3-chloro-4-fluorophenyl)carbamoyl)-2,3-dihydro-1H-inden-1-yl) carbamate;

(S)—N-(3-chloro-4-fluorophenyl)-1-((N-methyl sulfamoyl)amino)-2,3-dihydro-1H-indene-4-carboxamide;

O-(1,3,4-oxadiazol-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-1-(ethylsulfonamido)-7-fluoro-2,3-dihydro-1H-indene-4-carboxamide;

(S)—N-(3-chloro-4-fluorophenyl)-7-fluoro-1-(propylsulfonamido)-2,3-dihydro-1H-indene-4-carboxamide;

(S)—N-(4-chloro-3-fluorophenyl)-7-fluoro-1-((2-methylpropyl)sulfonamido)-2,3-dihydro-1H-indene-4-carboxamide;

(S)—N-(3-chloro-4-fluorophenyl)-7-fluoro-1-((N-isopropylsulfamoyl)amino)-2,3-dihydro-1H-indene-4-carboxamide;

(S)—N-(3-chloro-4-fluorophenyl)-7-fluoro-1-((1-methylethyl)sulfonamido)-2,3-dihydro-1H-indene-4-carboxamide;

(S)—N-(3-chloro-4-fluorophenyl)-1-(cyclopentanesulfonamido)-7-fluoro-2,3-dihydro-1H-indene-4-carboxamide;

(S)—N-(3-chloro-4-fluorophenyl)-1-(cyclohexanesulfonamido)-7-fluoro-2,3-dihydro-1H-indene-4-carboxamide;

(S)—N-(3-chloro-4-fluorophenyl)-1-((N-cyclopropylsulfamoyl)amino)-2,3-dihydro-1H-indene-4-carboxamide;

(S)—N-(3-chloro-4-fluorophenyl)-1-((N-cyclopropylsulfamoyl)amino)-7-fluoro-2,3-dihydro-1H-indene-4-carboxamide;

O-(1-(tetrahydro-2H-pyran-2-yl)-1H-1,2,4-triazol-3-yl)methyl, N—((S)-4-((3-chloro-4-fluorophenyl)carbamoyl)-7-fluoro-2,3-dihydro-1H-inden-1-yl) carbamate;

N-(3-Chloro-4-fluorophenyl)-7-fluoro-1-oxo-2,3-dihydro-1H-indene-4-carboxamide;

((1-(methyl-d₃)-1H-1,2,4-triazol-3-yl)methyl-d₂ (S)-(4-((3-chloro-4-fluorophenyl)carbamoyl)-7-fluoro-2,3-dihydro-1H-inden-1-yl)carbamate;

(S)-(3-((((4-((3-chloro-4-fluorophenyl)carbamoyl)-7-fluoro-2,3-dihydro-1H-inden-1-yl)carbamoyl)oxy)methyl)-1H-1,2,4-triazol-1-yl)methyl phosphoric acid;

(S)-(3-((((4-((3-chloro-4-fluorophenyl)carbamoyl)-7-fluoro-2,3-dihydro-1H-inden-1-yl)carbamoyl)oxy)methyl)-1H-pyrazol-1-yl)methyl phosphoric acid;

O—(S)-2-cyanoethyl, N-4-(3-chloro-4-fluorophenylcarbamoyl)-7-fluoro-2,3-dihydro-1H-inden-1-yl carbamate;

O—(S)-3-cyanopropyl, N-4-(3-chloro-4-fluorophenylcarbamoyl)-7-fluoro-2,3-dihydro-1H-inden-1-yl carbamate;

N-(3-chloro-4-fluorophenyl)-7'-fluoro-2,5-dioxo-2',3'-dihydrospiro[imidazolidine-4,1'-indene]-4'-carboxamide;

N-(3-chloro-4-fluorophenyl)-7'-fluoro-2,5-dioxo-1-(pyridin-2-ylmethyl)-2',3'-dihydrospiro[imidazolidine-4,1'-indene]-4'-carboxamide;

N-(3-chloro-4-fluoro-phenyl)-7'-fluoro-1-methyl-2,5-dioxo-spiro[imidazolidine-4,1'-indane]-4'-carboxamide;

(S)-1-(((S)-tert-butylsulfinyl)amino)-N-(3-chloro-4-fluorophenyl)-7-fluoro-2,3-dihydro-1H-indene-4-carboxamide;

(S)-1-(((R)-tert-butylsulfinyl)amino)-N-(3-chloro-4-fluorophenyl)-7-fluoro-2,3-dihydro-1H-indene-4-carboxamide;

or a salt, solvate, prodrug, isotopically labelled derivative, stereoisomer, or tautomer thereof, or any mixtures thereof.

In certain embodiments, the compound is at least one selected from the group consisting of:

O-methyl, N—(S)-(4-((3,4-difluorophenyl)carbamoyl)-2,3-dihydro-1H-inden-1-yl) carbamate;

(S)—N-(3,4-difluorophenyl)-1-(3-methylureido)-2,3-dihydro-1H-indene-4-carboxamide;

O-pyridin-2-ylmethyl, N—(S)-(4-((3,4-difluorophenyl)carbamoyl)-2,3-dihydro-1H-inden-1-yl) carbamate;

O-methyl, N-(7-((3,4-difluorophenyl)carbamoyl)-2,3-dihydrobenzofuran-3-yl) carbamate;

N-(3,4-difluorophenyl)-3-(3-methylureido)-2,3-dihydrobenzofuran-7-carboxamide;

O—((R)-5-oxopyrrolidin-2-yl)methyl, N—((S)-4-((3-chloro-4-fluorophenyl)carbamoyl)-7-fluoro-2,3-dihydro-1H-inden-1-yl) carbamate;

O-tert-butyl, N—(S)-(4-((3-chloro-4-fluorophenyl)carbamoyl)-7-fluoro-2,3-dihydro-1H-inden-1-yl) carbamate;

O-methyl, N—(S)-(7-fluoro-4-((4-fluoro-3-methylphenyl)carbamoyl)-2,3-dihydro-1H-inden-1-yl) carbamate;

(S)-7-fluoro-N-(4-fluoro-3-methylphenyl)-1-(3-methylureido)-2,3-dihydro-1H-indene-4-carboxamide;

(S)-1-amino-N-(3-chloro-4-fluorophenyl)-7-fluoro-2,3-dihydro-1H-indene-4-carboxamide;

O-2-(2-oxopyrrolidin-1-yl)ethyl, N—(S)-(4-((3-chloro-4-fluorophenyl)carbamoyl)-7-fluoro-2,3-dihydro-1H-inden-1-yl) carbamate;

O-pyridin-2-ylmethyl, N-(7-((3,4-difluorophenyl)carbamoyl)-2,3-dihydrobenzofuran-3-yl) carbamate;

O-pyridin-2-ylmethyl, N—(S)-(4-((3-chloro-4-fluorophenyl)carbamoyl)-2,3-dihydro-1H-inden-1-yl) carbamate;

O—((S)-5-oxopyrrolidin-2-yl)methyl, N—((S)-4-((3-chloro-4-fluorophenyl)carbamoyl)-7-fluoro-2,3-dihydro-1H-inden-1-yl) carbamate;

O-methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(3-methylureido)-2,3-dihydro-1H-indene-4-carboxamide;

O—((R)-5-oxopyrrolidin-2-yl)methyl, N—((S)-4-((3-chloro-4-fluorophenyl)carbamoyl)-2,3-dihydro-1H-inden-1-yl) carbamate;

O—((S)-5-oxopyrrolidin-2-yl)methyl, N—((S)-4-((3-chloro-4-fluorophenyl)carbamoyl)-2,3-dihydro-1H-inden-1-yl) carbamate;

O-pyridin-2-ylmethyl, N—(S)-(4-((4-fluoro-3-methylphenyl)carbamoyl)-2,3-dihydro-1H-inden-1-yl) carbamate;

O—((R)-5-oxopyrrolidin-2-yl)methyl, N—((S)-4-((4-fluoro-3-methylphenyl)carbamoyl)-2,3-dihydro-1H-inden-1-yl)carbamate;

O—((S)-5-oxopyrrolidin-2-yl)methyl, N—((S)-4-((4-fluoro-3-methylphenyl)carbamoyl)-2,3-dihydro-1H-inden-1-yl) carbamate;

O-2-oxo-2-(pyrrolidin-1-yl)ethyl, N—(S)-(4-((3-chloro-4-fluorophenyl)carbamoyl)-7-fluoro-2,3-dihydro-1H-inden-1-yl) carbamate;

O-pyridin-2-ylmethyl, N-(7-((3,4-difluorophenyl)carbamoyl)-2,3-dihydrobenzo[b]thiophen-3-yl) carbamate;

O-pyridin-2-ylmethyl, N-(7-((3-chloro-4-fluorophenyl)carbamoyl)-2,3-dihydrobenzo[b]thiophen-3-yl) carbamate;

O-methyl, N-(7-((3-chloro-4-fluorophenyl)carbamoyl)-2,3-dihydrobenzo[b]thiophen-3-yl) carbamate;

O-methyl, N-(7-((3,4-difluorophenyl)carbamoyl)-2,3-dihydrobenzo[b]thiophen-3-yl) carbamate;

O-pyridin-2-ylmethyl, N—(S)-(4-((3-chloro-4-fluorophenyl)carbamoyl)-7-fluoro-2,3-dihydro-1H-inden-1-yl) carbamate;

O-methyl, N-(7-((3-chloro-4-fluorophenyl)carbamoyl)-2,3-dihydrobenzo[b]thiophen-3-yl) carbamate;

O—((S)-1-methyl-5-oxopyrrolidin-2-yl)methyl, N—((S)-4-((3-chloro-4-fluorophenyl)carbamoyl)-7-fluoro-2,3-dihydro-1H-inden-1-yl) carbamate;

O-pyridin-2-ylmethyl, N—(S)-(7-fluoro-4-((4-fluoro-3-methylphenyl)carbamoyl)-2,3-dihydro-1H-inden-1-yl) carbamate;

O-imidazo[1,2-a]pyridin-2-ylmethyl, N—(S)-(4-((3-chloro-4-fluorophenyl)carbamoyl)-7-fluoro-2,3-dihydro-1H-inden-1-yl) carbamate;

O-(6-morpholinopyridin-2-yl)methyl, N—(S)-(4-((3-chloro-4-fluorophenyl)carbamoyl)-7-fluoro-2,3-dihydro-1H-inden-1-yl) carbamate;

O—((R)-1-methyl-5-oxopyrrolidin-2-yl)methyl, N—((S)-4-((3-chloro-4-fluorophenyl)carbamoyl)-7-fluoro-2,3-dihydro-1H-inden-1-yl) carbamate;

O-(6-methoxypyridin-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(pyrimidin-2-ylamino)-2,3-dihydro-1H-indene-4-carboxamide;

O-methyl, N-((1R,2R)-4-((3-chloro-4-fluorophenyl)carbamoyl)-2-hydroxy-2,3-dihydro-1H-inden-1-yl) carbamate;

N-(3-chloro-4-fluorophenyl)-2-hydroxy-1-(3-methylureido)-2,3-dihydro-1H-indene-4-carboxamide;

O-(6-(dimethylamino) pyridin-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-((5-methoxypyrimidin-2-yl)amino)-2,3-dihydro-1H-indene-4-carboxamide;

(S)—N-(3-chloro-4-fluorophenyl)-7-fluoro-1-((4-(pyridin-2-yl)pyrimidin-2-yl)amino)-2,3-dihydro-1H-indene-4-carboxamide;

O-pyridin-2-ylmethyl, N-((1R,2R)-4-((3-chloro-4-fluorophenyl)carbamoyl)-2-hydroxy-2,3-dihydro-1H-inden-1-yl) carbamate;

O-methyl, N-(4-((3,4-difluorophenyl)carbamoyl)-2-hydroxy-2,3-dihydro-1H-inden-1-yl) carbamate;

N-(3,4-difluorophenyl)-2-hydroxy-1-(3-methylureido)-2,3-dihydro-1H-indene-4-carboxamide;

tert-butyl 2-(((((S)-4-((3-chloro-4-fluorophenyl)carbamoyl)-7-fluoro-2,3-dihydro-1H-inden-1-yl)carbamoyl)oxy)methyl)-4,4-difluoropyrrolidine-1-carboxylate;

O-methyl, N-(7-((3,4-difluorophenyl)carbamoyl)-4-fluoro-2,3-dihydrobenzo[b]thiophen-3-yl) carbamate;

O-(4,4-difluoropyrrolidin-2-yl)methyl, N—((S)-4-((3-chloro-4-fluorophenyl)carbamoyl)-7-fluoro-2,3-dihydro-1H-inden-1-yl) carbamate;

O-methyl, N-(7-((3-chloro-4-fluorophenyl)carbamoyl)-4-fluoro-2,3-dihydrobenzo[b]thiophen-3-yl) carbamate;

O-pyridin-2-ylmethyl, N-((1R,2R)-4-((3,4-difluorophenyl)carbamoyl)-2-hydroxy-2,3-dihydro-1H-inden-1-yl) carbamate;

O-(1-acetyl-4,4-difluoropyrrolidin-2-yl)methyl, N—((S)-4-((3-chloro-4-fluorophenyl)carbamoyl)-7-fluoro-2,3-dihydro-1H-inden-1-yl) carbamate;

O-(1-(2,2,2-trifluoroethyl)piperidin-4-yl)methyl, N—(S)-(4-((3-chloro-4-fluorophenyl)carbamoyl)-7-fluoro-2,3-dihydro-1H-inden-1-yl) carbamate;

O-pyridin-2-ylmethyl, N-(7-((3,4-difluorophenyl)carbamoyl)-4-fluoro-2,3-dihydrobenzo[b]thiophen-3-yl) carbamate;

O-pyridin-2-ylmethyl, N-(7-((3-chloro-4-fluorophenyl)carbamoyl)-4-fluoro-2,3-dihydrobenzo[b]thiophen-3-yl) carbamate;

(S)-2-((((4-((3-chloro-4-fluorophenyl)carbamoyl)-7-fluoro-2,3-dihydro-1H-inden-1-yl)carbamoyl)oxy)methyl)pyridine 1-oxide;

O—(S)-1-(pyridin-2-yl)ethyl, N—((S)-4-((3-chloro-4-fluorophenyl)carbamoyl)-7-fluoro-2,3-dihydro-1H-inden-1-yl) carbamate;

O—(S)-pyrrolidin-2-ylmethyl, N—((S)-4-((3-chloro-4-fluorophenyl)carbamoyl)-7-fluoro-2,3-dihydro-1H-inden-1-yl) carbamate;

O-3,3,3-trifluoropropyl, N—(S)-(4-((3-chloro-4-fluorophenyl)carbamoyl)-7-fluoro-2,3-dihydro-1H-inden-1-yl) carbamate;

O-(1-methyl-1H-pyrazol-3-yl)methyl, N—(S)-(4-((3-chloro-4-fluorophenyl)carbamoyl)-7-fluoro-2,3-dihydro-1H-inden-1-yl) carbamate;

O—(R)-5-oxopyrrolidin-3-yl, N—(S)-4-((3-chloro-4-fluorophenyl)carbamoyl)-7-fluoro-2,3-dihydro-1H-inden-1-yl) carbamate;

O-(6-methylpyridin-2-yl)methyl, N—(S)-(4-((3-chloro-4-fluorophenyl)carbamoyl)-7-fluoro-2,3-dihydro-1H-inden-1-yl) carbamate;

N—(S)-4-((3-chloro-4-fluorophenyl)carbamoyl)-7-fluoro-2,3-dihydro-1H-inden-1-yl, O-(pyridin-2-ylmethyl) carbamate;

(S)—N-(3-chloro-4-fluorophenyl)-7-fluoro-1-(2-methoxyacetamido)-2,3-dihydro-1H-indene-4-carboxamide;

(S)—N-(3-chloro-4-fluorophenyl)-7-fluoro-1-(3-fluoropropanamido)-2,3-dihydro-1H-indene-4-carboxamide;

(S)-1-acetamido-N-(3-chloro-4-fluorophenyl)-7-fluoro-2,3-dihydro-1H-indene-4-carboxamide;

O-pyrazin-2-ylmethyl, N—(S)-(4-((3-chloro-4-fluorophenyl)carbamoyl)-7-fluoro-2,3-dihydro-1H-inden-1-yl) carbamate;

O-pyrimidin-2-ylmethyl, N—(S)-(4-((3-chloro-4-fluorophenyl)carbamoyl)-7-fluoro-2,3-dihydro-1H-inden-1-yl) carbamate;

O-(4-chloropyridin-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-hydroxy-2,3-dihydro-1H-indene-4-carboxamide;

O-isoxazol-3-ylmethyl, N—(S)-(4-((3-chloro-4-fluorophenyl)carbamoyl)-7-fluoro-2,3-dihydro-1H-inden-1-yl) carbamate;

O-2-(pyridin-2-yl)ethyl, N—(S)-(4-((3-chloro-4-fluorophenyl)carbamoyl)-7-fluoro-2,3-dihydro-1H-inden-1-yl) carbamate;

O-2,2-difluoroethyl, N—(S)-(4-((3-chloro-4-fluorophenyl)carbamoyl)-7-fluoro-2,3-dihydro-1H-inden-1-yl) carbamate;

O-pyrimidin-4-ylmethyl, N—(S)-(4-((3-chloro-4-fluorophenyl)carbamoyl)-7-fluoro-2,3-dihydro-1H-inden-1-yl) carbamate;

O-3-(2-oxopyrrolidin-1-yl)propyl, N—(S)-(4-((3-chloro-4-fluorophenyl)carbamoyl)-7-fluoro-2,3-dihydro-1H-inden-1-yl) carbamate;

O-(8-methylimidazo[1,2-a]pyridin-2-yl)methyl, N—(S)-(4-((3-chloro-4-fluorophenyl)carbamoyl)-7-fluoro-2,3-dihydro-1H-inden-1-yl) carbamate;

O-2,2,2-trifluoroethyl, N—(S)-(4-((3-chloro-4-fluorophenyl)carbamoyl)-7-fluoro-2,3-dihydro-1H-inden-1-yl) carbamate;

O—(S)-4-((3-chloro-4-fluorophenyl)carbamoyl)-7-fluoro-2,3-dihydro-1H-inden-1-yl, N-methylcarbamate;

N—(S)-4-((3-chloro-4-fluorophenyl)carbamoyl)-7-fluoro-2,3-dihydro-1H-inden-1-yl, O-(pyridin-2-ylmethyl) carbonate;

O-thiazol-5-ylmethyl, N—(S)-(4-((3-chloro-4-fluorophenyl)carbamoyl)-7-fluoro-2,3-dihydro-1H-inden-1-yl) carbamate;

O-thiazol-2-ylmethyl, N—(S)-(4-((3-chloro-4-fluorophenyl)carbamoyl)-7-fluoro-2,3-dihydro-1H-inden-1-yl) carbamate;

O-oxazol-4-ylmethyl, N—(S)-(4-((3-chloro-4-fluorophenyl)carbamoyl)-7-fluoro-2,3-dihydro-1H-inden-1-yl) carbamate;

O-oxazol-2-ylmethyl, N—(S)-(4-((3-chloro-4-fluorophenyl)carbamoyl)-7-fluoro-2,3-dihydro-1H-inden-1-yl) carbamate;

O-oxazol-5-ylmethyl, N—(S)-(4-((3-chloro-4-fluorophenyl)carbamoyl)-7-fluoro-2,3-dihydro-1H-inden-1-yl) carbamate;

O-2-(1H-imidazol-1-yl)ethyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(pyridin-2-ylamino)-2,3-dihydro-1H-indene-4-carboxamide;

(S)—N-(4-((3-chloro-4-fluorophenyl)carbamoyl)-7-fluoro-2,3-dihydro-1H-inden-1-yl)-1-methyl-1H-pyrazole-3-carboxamide;

O-2-phenoxyethyl, N—(S)-(4-((3-chloro-4-fluorophenyl)carbamoyl)-7-fluoro-2,3-dihydro-1H-inden-1-yl) carbamate;

(S)—N-(4-((3-chloro-4-fluorophenyl)carbamoyl)-7-fluoro-2,3-dihydro-1H-inden-1-yl)-1-methyl-1H-pyrazole-5-carboxamide;

(S)—N-(3-chloro-4-fluorophenyl)-7-fluoro-1-((1-methyl-1H-pyrazole)-3-sulfonamido)-2,3-dihydro-1H-indene-4-carboxamide;

O-(1-methyl-1H-1,2,4-triazol-3-yl)methyl, N—(S)-(4-((3-chloro-4-fluorophenyl)carbamoyl)-7-fluoro-2,3-dihydro-1H-inden-1-yl) carbamate;

O-(1-methyl-1H-pyrazol-5-yl)methyl, N—(S)-(4-((3-chloro-4-fluorophenyl)carbamoyl)-7-fluoro-2,3-dihydro-1H-inden-1-yl) carbamate;

(S)-2-((4-((3-chloro-4-fluorophenyl)carbamoyl)-7-fluoro-2,3-dihydro-1H-inden-1-yl)amino)pyrimidine-4-carboxamide;

O-2-(4-methylthiazol-5-yl)ethyl, N—(S)-(4-((3-chloro-4-fluorophenyl)carbamoyl)-7-fluoro-2,3-dihydro-1H-inden-1-yl) carbamate;

O-(1-isopropyl-1H-pyrazol-3-yl)methyl, N—(S)-(4-((3-chloro-4-fluorophenyl)carbamoyl)-7-fluoro-2,3-dihydro-1H-inden-1-yl) carbamate;

O-(5-methoxypyridin-2-yl)methyl, N—(S)-(4-((3-chloro-4-fluorophenyl)carbamoyl)-7-fluoro-2,3-dihydro-1H-inden-1-yl) carbamate;

O—((S)-1-(2,2,2-trifluoroethyl)pyrrolidin-2-yl)methyl, N—((S)-4-((3-chloro-4-fluorophenyl)carbamoyl)-7-fluoro-2,3-dihydro-1H-inden-1-yl) carbamate;

O-(5-fluoropyridin-2-yl)methyl, N—(S)-(4-((3-chloro-4-fluorophenyl)carbamoyl)-7-fluoro-2,3-dihydro-1H-inden-1-yl) carbamate;

O-2-(1H-pyrazol-4-yl)ethyl, N—(S)-(4-((3-chloro-4-fluorophenyl)carbamoyl)-7-fluoro-2,3-dihydro-1H-inden-1-yl) carbamate;

O-2-methoxyethyl, N—(S)-(4-((3-chloro-4-fluorophenyl)carbamoyl)-7-fluoro-2,3-dihydro-1H-inden-1-yl) carbamate;

O—((R)-tetrahydrofuran-2-yl)methyl, N—((S)-4-((3-chloro-4-fluorophenyl)carbamoyl)-7-fluoro-2,3-dihydro-1H-inden-1-yl) carbamate;

O-tetrahydro-2H-pyran-4-yl, N—(S)-(4-((3-chloro-4-fluorophenyl)carbamoyl)-7-fluoro-2,3-dihydro-1H-inden-1-yl) carbamate;

O-3-methoxypropyl, N—(S)-(4-((3-chloro-4-fluorophenyl)carbamoyl)-7-fluoro-2,3-dihydro-1H-inden-1-yl) carbamate;

(S)—N-(4-((3-chloro-4-fluorophenyl)carbamoyl)-7-fluoro-2,3-dihydro-1H-inden-1-yl)picolinamide;

(S)—N-(4-((3-chloro-4-fluorophenyl)carbamoyl)-7-fluoro-2,3-dihydro-1H-inden-1-yl)thiazole-5-carboxamide;

(S)—N-(3-chloro-4-fluorophenyl)-7-fluoro-1-(methyl sulfonamido)-2,3-dihydro-1H-indene-4-carboxamide;

(S)—N-(3-chloro-4-fluorophenyl)-7-fluoro-1-(2-morpholinoacetamido)-2,3-dihydro-1H-indene-4-carboxamide;

(S)—N-(4-((3-chloro-4-fluorophenyl)carbamoyl)-7-fluoro-2,3-dihydro-1H-inden-1-yl)nicotinamide;

(S)—N-(4-((3-chloro-4-fluorophenyl)carbamoyl)-7-fluoro-2,3-dihydro-1H-inden-1-yl)isonicotinamide;

O-methyl, N-(4-((3-chloro-4-fluorophenyl)carbamoyl)-7-fluoro-2,2-dimethyl-2,3-dihydro-1H-inden-1-yl)carbamate;

(S)-4-((3-chloro-4-fluorophenyl)carbamoyl)-7-fluoro-2,3-dihydro-1H-inden-1-yl methyl carbonate;

O-thiazol-4-ylmethyl, N—(S)-(4-((3-chloro-4-fluorophenyl)carbamoyl)-7-fluoro-2,3-dihydro-1H-inden-1-yl) carbamate;

O-3-(1H-imidazol-1-yl)propyl, N—(S)-(4-((3-chloro-4-fluorophenyl)carbamoyl)-7-fluoro-2,3-dihydro-1H-inden-1-yl) carbamate;

O-pyridin-2-ylmethyl, N—(S)-(4-((3-cyano-4-fluorophenyl)carbamoyl)-7-fluoro-2,3-dihydro-1H-inden-1-yl) carbamate;

(S)—N-(4-((3-chloro-4-fluorophenyl)carbamoyl)-7-fluoro-2,3-dihydro-1H-inden-1-yl)thiazole-2-carboxamide;

(S)—N-(3-chloro-4-fluorophenyl)-1-(cyclopropanesulfonamido)-7-fluoro-2,3-dihydro-1H-indene-4-carboxamide;

(S)—N-(4-((3-chloro-4-fluorophenyl)carbamoyl)-7-fluoro-2,3-dihydro-1H-inden-1-yl)oxazole-5-carboxamide;

O-methyl, N-((1R,2R)-4-((3-chloro-4-fluorophenyl)carbamoyl)-7-fluoro-2-methoxy-2,3-dihydro-1H-inden-1-yl) carbamate;

O-cyclopentyl, N—(S)-(4-((3-chloro-4-fluorophenyl)carbamoyl)-7-fluoro-2,3-dihydro-1H-inden-1-yl)carbamate;

O-(2-oxo-oxazolidin-5-yl)methyl, N—((S)-4-((3-chloro-4-fluorophenyl)carbamoyl)-7-fluoro-2,3-dihydro-1H-inden-1-yl) carbamate;

O-2-(1H-pyrazol-1-yl)ethyl, N—(S)-(4-((3-chloro-4-fluorophenyl)carbamoyl)-7-fluoro-2,3-dihydro-1H-inden-1-yl) carbamate;

O-pyridin-2-ylmethyl, N-(4-((3-chloro-4-fluorophenyl)carbamoyl)-7-fluoro-2,2-dimethyl-2,3-dihydro-1H-inden-1-yl) carbamate;

O-(1-methyl-1H-imidazol-2-yl)methyl, N—(S)-(4-((3-chloro-4-fluorophenyl)carbamoyl)-7-fluoro-2,3-dihydro-1H-inden-1-yl) carbamate;

O-(3-fluoropyridin-2-yl)methyl, N—(S)-(4-((3-chloro-4-fluorophenyl)carbamoyl)-7-fluoro-2,3-dihydro-1H-inden-1-yl) carbamate;

O—((R)-morpholin-3-yl)methyl, N—(S)-4-((3-chloro-4-fluorophenyl)carbamoyl)-7-fluoro-2,3-dihydro-1H-inden-1-yl) carbamate;

O-(4-methoxypyridin-2-yl)methyl, N—(S)-(4-((3-chloro-4-fluorophenyl)carbamoyl)-7-fluoro-2,3-dihydro-1H-inden-1-yl) carbamate;

O-2-hydroxyethyl, N—(S)-(4-((3-chloro-4-fluorophenyl)carbamoyl)-7-fluoro-2,3-dihydro-1H-inden-1-yl) carbamate;

O—((S)-tetrahydrofuran-2-yl)methyl, N—((S)-4-((3-chloro-4-fluorophenyl)carbamoyl)-7-fluoro-2,3-dihydro-1H-inden-1-yl)carbamate;

(S)—N-(3-chloro-4-fluorophenyl)-7-fluoro-1-(2-hydroxyacetamido)-2,3-dihydro-1H-indene-4-carboxamide;

(S)—N-(3-chloro-4-fluorophenyl)-7-fluoro-1-(3-(pyridin-3-yl)ureido)-2,3-dihydro-1H-indene-4-carboxamide;

(S)—N-(3-chloro-4-fluorophenyl)-7-fluoro-1-(3-(pyridin-4-yl)ureido)-2,3-dihydro-1H-indene-4-carboxamide;

(S)—N-(3-chloro-4-fluorophenyl)-7-fluoro-1-(thiazol-2-ylamino)-2,3-dihydro-1H-indene-4-carboxamide;

O-2-(piperidin-1-yl)ethyl, N—(S)-(4-((3-chloro-4-fluorophenyl)carbamoyl)-7-fluoro-2,3-dihydro-1H-inden-1-yl) carbamate;

O-pyridin-2-ylmethyl, N—(S)-(4-((3-(difluoromethyl)-4-fluorophenyl)carbamoyl)-7-fluoro-2,3-dihydro-1H-inden-1-yl) carbamate;

(S)—N-(3-chloro-4-fluorophenyl)-7-fluoro-1-(3-(pyridin-2-ylmethyl)ureido)-2,3-dihydro-1H-indene-4-carboxamide;

O-(6-cyanopyridin-2-yl)methyl, N—(S)-(4-((3-chloro-4-fluorophenyl)carbamoyl)-7-fluoro-2,3-dihydro-1H-inden-1-yl) carbamate;

O-quinolin-2-ylmethyl, N—(S)-(4-((3-chloro-4-fluorophenyl)carbamoyl)-7-fluoro-2,3-dihydro-1H-inden-1-yl) carbamate;

O-(5-methylpyrazin-2-yl)methyl, N—(S)-(4-((3-chloro-4-fluorophenyl)carbamoyl)-7-fluoro-2,3-dihydro-1H-inden-1-yl) carbamate;

O-2-morpholinoethyl-N—(S)-(4-((3-chloro-4-fluorophenyl)carbamoyl)-7-fluoro-2,3-dihydro-1H-inden-1-yl) carbamate;

O-[cis-4-hydroxycyclohexyl]-N—((S)-4-((3-chloro-4-fluorophenyl)carbamoyl)-7-fluoro-2,3-dihydro-1H-inden-1-yl)carbamate;

O-3-hydroxypropyl, N—(S)-(4-((3-chloro-4-fluorophenyl)carbamoyl)-7-fluoro-2,3-dihydro-1H-inden-1-yl) carbamate;

O-[trans-4-hydroxycyclohexyl]-N—((S)-4-((3-chloro-4-fluorophenyl)carbamoyl)-7-fluoro-2,3-dihydro-1H-inden-1-yl) carbamate;

O-2-acetamidoethyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-propionamido-2,3-dihydro-1H-indene-4-carboxamide;

(S)—N-(3-chloro-4-fluorophenyl)-7-fluoro-1-((4-methoxypyrimidin-2-yl)amino)-2,3-dihydro-1H-indene-4-carboxamide;

(S)—N-(3-chloro-4-fluorophenyl)-7-fluoro-1-((4-methylpyrimidin-2-yl)amino)-2,3-dihydro-1H-indene-4-carboxamide;

(S)—N-(3-chloro-4-fluorophenyl)-7-fluoro-1-((2-methoxypyrimidin-4-yl)amino)-2,3-dihydro-1H-indene-4-carboxamide;

(S)—N-(3-chloro-4-fluorophenyl)-7-fluoro-1-((5-methylpyrimidin-2-yl)amino)-2,3-dihydro-1H-indene-4-carboxamide;

(S)—N-(3-chloro-4-fluorophenyl)-7-fluoro-1-((6-methoxypyrimidin-4-yl)amino)-2,3-dihydro-1H-indene-4-carboxamide;

(S)—N-(3-chloro-4-fluorophenyl)-1-((4,6-dimethylpyrimidin-2-yl)amino)-7-fluoro-2,3-dihydro-1H-indene-4-carboxamide;

(1R,2R)—N-(3-chloro-4-fluorophenyl)-2-methoxy-1-(3-methylureido)-2,3-dihydro-1H-indene-4-carboxamide;

O—(S)-5-oxopyrrolidin-3-yl, N—(S)-4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-((2-(pyridin-2-yl)ethyl)sulfonamido)-2,3-dihydro-1H-indene-4-carboxamide;

O-(6-(trifluoromethyl)pyridin-2-yl)methyl, N—(S)-(4-((3-chloro-4-fluorophenyl)carbamoyl)-7-fluoro-2,3-dihydro-1H-inden-1-yl) carbamate;

O-(5-(trifluoromethyl) pyridin-2-yl)methyl, N—(S)-(4-((3-chloro-4-fluorophenyl)carbamoyl)-7-fluoro-2,3-dihydro-1H-inden-1-yl) carbamate;

O—(R)-tetrahydrofuran-3-yl, N—((S)-4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(3-(1-methyl-1H-pyrazol-3-yl)propanamido)-2,3-dihydro-1H-indene-4-carboxamide;

O-(5-cyanopyridin-2-yl)methyl, N—(S)-(4-((3-chloro-4-fluorophenyl)carbamoyl)-7-fluoro-2,3-dihydro-1H-inden-1-yl) carbamate;

O-(3-methylpyrazin-2-yl)methyl, N—(S)-(4-((3-chloro-4-fluorophenyl)carbamoyl)-7-fluoro-2,3-dihydro-1H-inden-1-yl) carbamate;

O-(1-acetylpiperidin-4-yl)methyl, N—(S)-(4-((3-chloro-4-fluorophenyl)carbamoyl)-7-fluoro-2,3-dihydro-1H-inden-1-yl) carbamate;

O-(1-(2-hydroxyacetyl)piperidin-4-yl)methyl, N—(S)-(4-((3-chloro-4-fluorophenyl)carbamoyl)-7-fluoro-2,3-dihydro-1H-inden-1-yl) carbamate;

O-(1-(methylcarbamoyl)piperidin-4-yl)methyl, N—(S)-(4-((3-chloro-4-fluorophenyl)carbamoyl)-7-fluoro-2,3-dihydro-1H-inden-1-yl) carbamate;

O-(1,1-dioxidothiomorpholin-3-yl)methyl-N—((S)-4-((3-chloro-4-fluorophenyl)carbamoyl)-7-fluoro-2,3-dihydro-1H-inden-1-yl) carbamate;

O-pyridin-2-ylmethyl, N—((1R,2R)-4-((3-chloro-4-fluorophenyl)carbamoyl)-2-methoxy-2,3-dihydro-1H-inden-1-yl) carbamate;

(S)—N-(3-chloro-4-fluorophenyl)-1-(cyclopropanecarboxamido)-7-fluoro-2,3-dihydro-1H-indene-4-carboxamide;

O—((S)-morpholin-3-yl)methyl, N—((S)-4-((3-chloro-4-fluorophenyl)carbamoyl)-7-fluoro-2,3-dihydro-1H-inden-1-yl) carbamate;

O—(S)-tetrahydrofuran-3-yl, N—((S)-4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-((2-methoxyethyl) sulfonamido)-2,3-dihydro-1H-indene-4-carboxamide;

(S)—N-(3-chloro-4-fluorophenyl)-7-fluoro-1-(phenylsulfonamido)-2,3-dihydro-1H-indene-4-carboxamide;

(S)—N-(3-chloro-4-fluorophenyl)-7-fluoro-1-(pyridine-2-sulfonamido)-2,3-dihydro-1H-indene-4-carboxamide;

O-(1-(2-methoxyacetyl) piperidin-4-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-((5-hydroxypyrimidin-2-yl)amino)-2,3-dihydro-1H-indene-4-carboxamide O-methyl, N-(7-((3-chloro-4-fluorophenyl)carbamoyl)-4-fluoro-2,3-dihydrobenzofuran-3-yl) carbamate;

N-(3-chloro-4-fluorophenyl)-4-fluoro-3-(3-methylureido)-2,3-dihydrobenzofuran-7-carboxamide;

O-pyridin-2-ylmethyl, N-(7-((3-chloro-4-fluorophenyl)carbamoyl)-4-fluoro-2,3-dihydrobenzofuran-3-yl) carbamate;

O-(1H-pyrazol-3-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(3-((1-methyl-1H-pyrazol-3-yl)methyl)ureido)-2,3-dihydro-1H-indene-4-carboxamide;

O-(1H-1,2,4-triazol-3-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(pyrimidin-4-ylamino)-2,3-dihydro-1H-indene-4-carboxamide;

(S)—N-(3-chloro-4-fluorophenyl)-7-fluoro-1-((7-(4-methoxybenzyl)-7H-pyrrolo[2,3-d]pyrimidin-2-yl)amino)-2,3-dihydro-1H-indene-4-carboxamide;

O—((R)-6-oxopiperidin-2-yl)methyl, N—((S)-4-((3-chloro-4-fluorophenyl)carbamoyl)-7-fluoro-2,3-dihydro-1H-inden-1-yl) carbamate;

O—(R)-6-oxopiperidin-3-yl, N—((S)-4-((3-chloro-4-fluorophenyl)carbamoyl)-7-fluoro-2,3-dihydro-1H-inden-1-yl) carbamate;

O—(S)-6-oxopiperidin-3-yl, N—((S)-4-((3-chloro-4-fluorophenyl)carbamoyl)-7-fluoro-2,3-dihydro-1H-inden-1-yl) carbamate;

O-methyl, N-(4-fluoro-7-((4-fluoro-3-methylphenyl)carbamoyl)-2,3-dihydrobenzofuran-3-yl) carbamate;

4-fluoro-N-(4-fluoro-3-methylphenyl)-3-(3-methylureido)-2,3-dihydrobenzofuran-7-carboxamide;

O-pyridin-2-ylmethyl, N-(4-fluoro-7-((4-fluoro-3-methylphenyl)carbamoyl)-2,3-dihydrobenzofuran-3-yl) carbamate;

N-(3-chloro-4-fluorophenyl)-3-(cyclopropanesulfonamido)-4-fluoro-2,3-dihydrobenzofuran-7-carboxamide;

(S)—N-(3-chloro-4-fluorophenyl)-1-(3-cyclopropylureido)-7-fluoro-2,3-dihydro-1H-indene-4-carboxamide;

O-methyl, N-(4-((3-chloro-4-fluorophenyl)carbamoyl)-2,2,7-trifluoro-2,3-dihydro-1H-inden-1-yl) carbamate;

N-(3-chloro-4-fluorophenyl)-2,2,7-trifluoro-1-(3-methylureido)-2,3-dihydro-1H-indene-4-carboxamide;

O—((S)-6-oxopiperidin-2-yl)methyl, N—((S)-4-((3-chloro-4-fluorophenyl)carbamoyl)-7-fluoro-2,3-dihydro-1H-inden-1-yl) carbamate;

O-(4-oxoazetidin-2-yl)methyl, N—((S)-4-((3-chloro-4-fluorophenyl)carbamoyl)-7-fluoro-2,3-dihydro-1H-inden-1-yl) carbamate;

O-methyl, N-(4-((3-chloro-4-fluorophenyl)carbamoyl)-7-fluoro-1-methyl-2,3-dihydro-1H-inden-1-yl) carbamate;

N-(3-chloro-4-fluorophenyl)-7-fluoro-1-methyl-1-(3-methylureido)-2,3-dihydro-1H-indene-4-carboxamide;

(S)—N-(3-chloro-4-fluorophenyl)-1-(cyclopropanesulfonamido)-2,3-dihydro-1H-indene-4-carboxamide;

O-pyridin-2-ylmethyl, N-(4-((3-chloro-4-fluorophenyl)carbamoyl)-7-fluoro-1-methyl-2,3-dihydro-1H-inden-1-yl) carbamate;

O-pyridin-2-ylmethyl, N-(4-((3-chloro-4-fluorophenyl)carbamoyl)-2,2,7-trifluoro-2,3-dihydro-1H-inden-1-yl) carbamate;

(S)—N-(3-chloro-4-fluorophenyl)-1-((cyclopropylmethyl)sulfonamido)-7-fluoro-2,3-dihydro-1H-indene-4-carboxamide;

(S)—N-(3-chloro-4-fluorophenyl)-7-fluoro-1-((phenylmethyl)sulfonamido)-2,3-dihydro-1H-indene-4-carboxamide;

O-cyclopropyl, N—(S)-(4-((3-chloro-4-fluorophenyl)carbamoyl)-7-fluoro-2,3-dihydro-1H-inden-1-yl)carbamate;

(S)—N-(3-chloro-4-fluorophenyl)-7-fluoro-1-((N-methyl sulfamoyl)amino)-2,3-dihydro-1H-indene-4-carboxamide;

(S)—N-(3-chloro-4-fluorophenyl)-7-fluoro-1-(morpholine-4-sulfonamido)-2,3-dihydro-1H-indene-4-carboxamide;

O-cyclopropyl, N—(S)-(4-((3-chloro-4-fluorophenyl)carbamoyl)-2,3-dihydro-1H-inden-1-yl) carbamate;

(S)—N-(3-chloro-4-fluorophenyl)-1-((N-methyl sulfamoyl)amino)-2,3-dihydro-1H-indene-4-carboxamide;

O-(1,3,4-oxadiazol-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-1-(ethylsulfonamido)-7-fluoro-2,3-dihydro-1H-indene-4-carboxamide;

(S)—N-(3-chloro-4-fluorophenyl)-7-fluoro-1-(propylsulfonamido)-2,3-dihydro-1H-indene-4-carboxamide;

(S)—N-(4-chloro-3-fluorophenyl)-7-fluoro-1-((2-methylpropyl)sulfonamido)-2,3-dihydro-1H-indene-4-carboxamide;

N-(3-chloro-4-fluorophenyl)-7-fluoro-2-methoxy-1-(3-methylureido)-2,3-dihydro-1H-indene-4-carboxamide;

O-methyl, N-(4-((3-chloro-4-fluorophenyl)carbamoyl)-7-fluoro-2-methoxy-2,3-dihydro-1H-inden-1-yl)carbamate;

(S)—N-(3-chloro-4-fluorophenyl)-7-fluoro-1-((N-isopropylsulfamoyl)amino)-2,3-dihydro-1H-indene-4-carboxamide;

(S)—N-(3-chloro-4-fluorophenyl)-7-fluoro-1-((1-methylethyl)sulfonamido)-2,3-dihydro-1H-indene-4-carboxamide;

(S)—N-(3-chloro-4-fluorophenyl)-1-(cyclopentanesulfonamido)-7-fluoro-2,3-dihydro-1H-indene-4-carboxamide;

(S)—N-(3-chloro-4-fluorophenyl)-1-(cyclohexanesulfonamido)-7-fluoro-2,3-dihydro-1H-indene-4-carboxamide;

N-(3-chloro-4-fluorophenyl)-7-fluoro-3,3-dimethyl-1-(3-methylureido)-2,3-dihydro-1H-indene-4-carboxamide;

(S)—N-(3-chloro-4-fluorophenyl)-1-((N-cyclopropylsulfamoyl)amino)-2,3-dihydro-1H-indene-4-carboxamide;

(S)—N-(3-chloro-4-fluorophenyl)-1-((N-cyclopropylsulfamoyl)amino)-7-fluoro-2,3-dihydro-1H-indene-4-carboxamide;

O-methyl, N-(4-((3,4-difluorophenyl)carbamoyl)-7-fluoro-2-methoxy-2,3-dihydro-1H-inden-1-yl) carbamate;

N-(3,4-difluorophenyl)-7-fluoro-2-methoxy-1-(3-methylureido)-2,3-dihydro-1H-indene-4-carboxamide;

O-pyridin-2-ylmethyl, N-(4-((3,4-difluorophenyl)carbamoyl)-7-fluoro-2-methoxy-2,3-dihydro-1H-inden-1-yl)carbamate O-pyridin-2-ylmethyl, N-(4-((3-chloro-4-fluorophenyl)carbamoyl)-7-fluoro-2-methoxy-2,3-dihydro-1H-inden-1-yl)carbamate;

O-(1-(tetrahydro-2H-pyran-2-yl)-1H-1,2,4-triazol-3-yl)methyl, N—((S)-4-((3-chloro-4-fluorophenyl)carbamoyl)-7-fluoro-2,3-dihydro-1H-inden-1-yl) carbamate;

N-(3-chloro-4-fluorophenyl)-7-fluoro-2,2-dimethyl-1-(3-methylureido)-2,3-dihydro-1H-indene-4-carboxamide;
N-(3-Chloro-4-fluorophenyl)-7-fluoro-1-oxo-2,3-dihydro-1H-indene-4-carboxamide; ((1-(methyl-d₃)-1H-1,2,4-triazol-3-yl)methyl-d₂ (S)-(4-((3-chloro-4-fluorophenyl)carbamoyl)-7-fluoro-2,3-dihydro-1H-inden-1-yl) carbamate;
(S)-(3-((((4-((3-chloro-4-fluorophenyl)carbamoyl)-7-fluoro-2,3-dihydro-1H-inden-1-yl)carbamoyl)oxy)methyl)-1H-1,2,4-triazol-1-yl)methyl phosphoric acid;
(S)-(3-((((4-((3-chloro-4-fluorophenyl)carbamoyl)-7-fluoro-2,3-dihydro-1H-inden-1-yl)carbamoyl)oxy)methyl)-1H-pyrazol-1-yl)methyl phosphoric acid;
O—(S)-2-cyanoethyl, N-4-(3-chloro-4-fluorophenylcarbamoyl)-7-fluoro-2,3-dihydro-1H-inden-1-yl carbamate;
O—(S)-3-cyanopropyl, N-4-(3-chloro-4-fluorophenylcarbamoyl)-7-fluoro-2,3-dihydro-1H-inden-1-yl carbamate;
N-(3-chloro-4-fluorophenyl)-7'-fluoro-2,5-dioxo-2',3'-dihydrospiro[imidazolidine-4,1'-indene]-4'-carboxamide;
N-(3-chloro-4-fluorophenyl)-7'-fluoro-2,5-dioxo-1-(pyridin-2-ylmethyl)-2',3'-dihydrospiro[imidazolidine-4,1'-indene]-4'-carboxamide;
N-(3-chloro-4-fluoro-phenyl)-7'-fluoro-1-methyl-2,5-dioxo-spiro[imidazolidine-4,1'-indane]-4'-carboxamide;
N-(3-chloro-4-fluorophenyl)-7-(3-methylureido)-6,7-dihydro-5H-cyclopenta[b]pyridine-4-carboxamide;
O-methyl, N-(4-((3-chloro-4-fluorophenyl)carbamoyl)-6,7-dihydro-5H-cyclopenta[b]pyridin-7-yl)carbamate;
O-pyridin-2-ylmethyl, N-(4-((3-chloro-4-fluorophenyl)carbamoyl)-6,7-dihydro-5H-cyclopenta[b]pyridin-7-yl) carbamate;
N-(3-chloro-4-fluorophenyl)-7-(cyclopropanesulfonamido)-6,7-dihydro-5H-cyclopenta[c]pyridine-4-carboxamide;
O-(pyridin-2-ylmethyl)-N-[(4-((3-chloro-4-fluorophenyl)carbamoyl)-6,7-dihydro-5H-cyclopenta[c]pyridin-7-yl)] carbamate;
N-(3-chloro-4-fluorophenyl)-7-fluoro-2,3-dihydrobenzo[b]thiophene-4-carboxamide 1,1-dioxide;
N-(3-chloro-4-fluorophenyl)-2,3-dihydrobenzo[b]thiophene-4-carboxamide 1,1-dioxide; 2-(tert-butyl)-N-(3-chloro-4-fluorophenyl)-2,3-dihydrobenzo[d]isothiazole-4-carboxamide 1,1-dioxide;
N-(3-chloro-4-fluorophenyl)-2,3-dihydrobenzo[d]isothiazole-4-carboxamide-1,1-dioxide;
N-(3-chloro-4-fluorophenyl)-2-(2-hydroxyethyl)-2,3-dihydrobenzo[d]isothiazole-4-carboxamide 1,1-dioxide;
N-(3-chloro-4-fluorophenyl)-2-methyl-2,3-dihydrobenzo[d]isothiazole-4-carboxamide 1,1-dioxide;
N-(3-chloro-4-fluorophenyl)-2-isopropyl-2,3-dihydrobenzo[d]isothiazole-4-carboxamide 1,1-dioxide;
N-(3-chloro-4-fluorophenyl)-2-cyclopropyl-2,3-dihydrobenzo[d]isothiazole-4-carboxamide 1,1-dioxide;
(S)-1-(((S)-tert-butylsulfinyl)amino)-N-(3-chloro-4-fluorophenyl)-7-fluoro-2,3-dihydro-1H-indene-4-carboxamide;
(S)-1-(((R)-tert-butylsulfinyl)amino)-N-(3-chloro-4-fluorophenyl)-7-fluoro-2,3-dihydro-1H-indene-4-carboxamide;
O-methyl, N-(4-((3-chloro-4-fluorophenyl)carbamoyl)-7-fluoro-3,3-dimethyl-2,3-dihydro-1H-inden-1-yl) carbamate;

The invention further provides a pharmaceutical composition comprising at least one compound of the invention and a pharmaceutically acceptable carrier. In certain embodiments, the composition further comprises at least one additional agent useful for treating hepatitis infection. In certain embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator.

The invention further provides a method of treating or preventing hepatitis virus infection in a subject, the method comprising administering to the subject in need thereof a therapeutically effective amount of at least one compound of the invention.

The invention further provides a method of inhibiting expression and/or function of a viral capsid protein directly or indirectly in a virus-infected subject, the method comprising administering to the subject in need thereof a therapeutically effective amount of at least one compound of the invention.

In certain embodiments, the at least one compound is administered to the subject in a pharmaceutically acceptable composition. In certain embodiments, the subject is further administered at least one additional agent useful for treating the viral or hepatitis infection. In certain embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In certain embodiments, the subject is co-administered the at least one compound and the at least one additional agent. In certain embodiments, the at least one compound and the at least one additional agent are coformulated. In certain embodiments, the virus comprises hepatitis B virus (HBV). In certain embodiments, the subject is a mammal. In certain embodiments, the mammal is a human.

DETAILED DESCRIPTION OF THE INVENTION

The invention relates, in certain aspects, to the discovery of certain substituted bicyclic compounds that are useful to treat and/or prevent hepatitis B virus (HBV) infection and related conditions in a subject. In certain embodiments, the compounds of the invention are viral capsid inhibitors.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science, and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —CH$_2$—CH═CH$_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is (C$_1$-C$_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., C$_1$-C$_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is (C$_1$-C$_6$)alkyl, such as, but not limited to, ethyl, methyl, isopropyl, isobutyl, n-pentyl, n-hexyl, and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH.

As used herein, the term "aromatic" refers to a carbocycle or heterocycle with one or more polyunsaturated rings and having aromatic character, i.e., having (4n+2) delocalized π (pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-(C$_1$-C$_6$)alkyl" refers to a functional group wherein a one-to-six carbon alkylene chain is attached to an aryl group, e.g., —CH$_2$CH$_2$-phenyl or —CH$_2$-phenyl (or benzyl). Specific examples are aryl-CH$_2$— and aryl-CH(CH$_3$)—. The term "substituted aryl-(C$_1$-C$_6$)alkyl" refers to an aryl-(C$_1$-C$_6$)alkyl functional group in which the aryl group is substituted. A specific example is substituted aryl(CH$_2$)—. Similarly, the term "heteroaryl-(C$_1$-C$_6$)alkyl" refers to a functional group wherein a one-to-three carbon alkylene chain is attached to a heteroaryl group, e.g., —CH$_2$CH$_2$-pyridyl. A specific example is heteroaryl-(CH$_2$)—. The term "substituted heteroaryl-(C$_1$-C$_6$)alkyl" refers to a heteroaryl-(C$_1$-C$_6$)alkyl functional group in which the heteroaryl group is substituted. A specific example is substituted heteroaryl-(CH$_2$)—.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "cycloalkyl" by itself or as part of another substituent refers to, unless otherwise stated, a cyclic chain hydrocarbon having the number of carbon atoms designated (i.e., C$_3$-C$_6$ refers to a cyclic group comprising a ring group consisting of three to six carbon atoms) and includes straight, branched chain or cyclic substituent groups.

Examples of (C$_3$-C$_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "halide" refers to a halogen atom bearing a negative charge. The halide anions are fluoride (F$^-$), chloride (Cl$^-$), bromide (Br$^-$), and iodide (I$^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—CH$_3$, —CH═CH—CH$_2$—OH, —CH$_2$—CH═N—OCH$_3$, —CH═CH—N(CH$_3$)—CH$_3$, and —CH$_2$—CH═CH—CH$_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: $-OCH_2CH_2CH_3$, $-CH_2CH_2CH_2OH$, $-CH_2CH_2NHCH_3$, $-CH_2SCH_2CH_3$, and $-CH_2CH_2S(=O)CH_3$. Up to two heteroatoms may be consecutive, such as, for example, $-CH_2NH-OCH_3$, or $-CH_2CH_2SSCH_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl, and 1,3,4-oxadiazolyl.

Examples of polycyclic heterocycles include indolyl (such as, but not limited to, 3-, 4-5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, a "pharmaceutically effective amount," "therapeutically effective amount," or "effective amount" of a compound is that amount of compound that is sufficient to provide a beneficial effect to the subject to which the compound is administered.

The term "prevent," "preventing," or "prevention" as used herein means avoiding or delaying the onset of symptoms associated with a disease or condition in a subject that has not developed such symptoms at the time the administering of an agent or compound commences. Disease, condition and disorder are used interchangeably herein.

As used herein, the term "RT" refers to retention time.

By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "substituted" refers to that an atom or group of atoms has replaced hydrogen as the substituent attached to another group.

As used herein, the term "substituted alkyl," "substituted cycloalkyl," "substituted alkenyl," or "substituted alkynyl" refers to alkyl, cycloalkyl, alkenyl, or alkynyl, as defined elsewhere herein, substituted by one, two or three substituents independently selected from the group consisting of halogen, —OH, alkoxy, tetrahydro-2-H-pyranyl, —$NH_2$, —NH($C_1$-$C_6$ alkyl), —N($C_1$-$C_6$ alkyl)$_2$, 1-methyl-imidazol-2-yl, pyridin-2-yl, pyridin-3-yl, pyridin-4-yl, —C(=O)OH, —C(=O)O($C_1$-$C_6$)alkyl, trifluoromethyl, —C≡N, —C(=O)$NH_2$, —C(=O)NH($C_1$-$C_6$)alkyl, —C(=O)N(($C_1$-$C_6$)alkyl)$_2$, —$SO_2NH_2$, —$SO_2$NH($C_1$-$C_6$ alkyl), —$SO_2$N($C_1$-$C_6$ alkyl)$_2$, —C(=NH)$NH_2$, and —$NO_2$, in certain embodiments containing one or two substituents independently selected from halogen, —OH, alkoxy, —$NH_2$, trifluoromethyl, —N($CH_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., $R^2$ and $R^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_8$, $C_3$-$C_4$, $C_4$-$C_6$, $C_4$-$C_5$, and $C_5$-$C_6$ alkyl.

The terms "treat," "treating" and "treatment," as used herein, means reducing the frequency or severity with which symptoms of a disease or condition are experienced by a subject by virtue of administering an agent or compound to the subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Compounds

The invention includes a compound of formula (I), or a salt, solvate, prodrug, isotopically labelled derivative (such as, for example, at least partially deuterated), stereoisomer (such as, in a non-limiting example, an enantiomer or diastereoisomer, and/or any mixtures thereof, such as, in a non-limiting example, mixtures in any proportions of enantiomers and/or diastereoisomers thereof), tautomer and any mixtures thereof, and/or geometric isomer and any mixtures thereof:

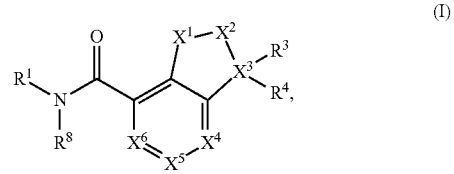

(I)

wherein in (I):

—$X^1$—$X^2$— is selected from the group consisting of —$CH_2CH_2$—*, —$CH_2CH(CH_3)$—*, —$CH_2C(CH_3)_2$—*, —$CH(CH_3)CH_2$—*, —$C(CH_3)_2CH_2$—*, —$CH_2CHF$—*, —$CH_2CF_2$—*, —$OCH_2$—*, —$SCH_2$—*, —$CH_2NR^{6a}$—*, and —$CH_2CH(OR^{6a})$—*, wherein the single bond marked as "*" is between —$X^1$—$X^2$— and $X^3$;

$X^3$ is C, or $X^3$ combines with $R^3$ and $R^4$ to form —S(=O)$_2$—;

$X^4$ is N or C($R^{5a}$), $X^5$ is N or C($R^{5b}$), $X^6$ is N or C($R^{5c}$), wherein 0-1 of $X^4$, $X^5$, and $X^6$ is N;

$R^1$ is selected from the group consisting of optionally substituted phenyl, optionally substituted benzyl, optionally substituted heteroaryl, and —($CH_2$)(optionally substituted heteroaryl);

each occurrence of $R^2$ is independently selected from the group consisting of H and $C_1$-$C_6$ alkyl;

R³ is selected from the group consisting of H, —OH, —OR⁶, —NH₂, —NHR⁶, —NR⁶R⁶, —OC(=O)OR⁶, —OC(=O)N(R²)R⁶, —N(R²)C(=O)OR⁶ [such as but not limited to N(R²)C(=O)O(optionally substituted $C_1$-$C_6$ alkyl), such as, for example, —N(R²)C(=O)O-(optionally substituted benzyl), —N(R²)C(=O)O(CH₂)$_{1-3}$ (optionally substituted pyridinyl), —N(R²)C(=O)O(CH₂)$_{1-3}$ (optionally substituted pyrimidinyl), —N(R²)C(=O)O(CH₂)$_{1-3}$ (optionally substituted azolyl, such as but not limited to optionally substituted isoxazolyl or optionally substituted oxazolyl], —NR⁷C(=O)N(R⁶)(R⁷), —N(R²)C(=O)R⁶, —NR²S(=O)$_{1-2}$R⁶, optionally substituted aryl, optionally substituted heteroaryl, —CH₂C(=O)OH, —CH₂C(=O)NR⁶R⁶, —N(R²)C(=O)(CH₂)$_{1-2}$R⁶, NR²S(=O)₂N(R⁶)(R⁷), and —NR²C(=O)C(=O)N(R⁶)(R⁷);

R⁴ is H or $C_1$-$C_6$ alkyl,
or R³ and R⁴ combine to form =O or —C(=O)NR$^{6a}$—C(=O)—NR$^{6a}$—;

R$^{5a}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

R$^{5b}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

R$^{5c}$ is independently selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

each occurrence of R⁶ is independently selected from the group consisting of optionally substituted $C_1$-$C_6$ alkyl, optionally substituted $C_3$-$C_8$ cycloalkyl, optionally substituted phenyl, and optionally substituted hetereoaryl;

each occurrence of R$^{6a}$ is independently selected from the group consisting of H, optionally substituted $C_1$-$C_6$ alkyl, optionally substituted $C_3$-$C_8$ cycloalkyl, optionally substituted phenyl, and optionally substituted hetereoaryl;

each occurrence of R⁷ is independently selected from the group consisting of H and optionally substituted $C_1$-$C_6$ alkyl;
or, if R⁶ and R⁷ are bound to the same N atom, R⁶ and R⁷ optionally combine with the N atom to which both are bound to form an optionally substituted 3-7 membered heterocycle;

R⁸ is selected from the group consisting of H and $C_1$-$C_6$ alkyl.

In certain embodiments, the compound of formula (I) is a compound of formula (I'):

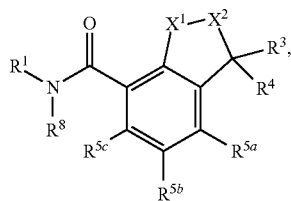

(I')

wherein:
—X¹—X²— is selected from the group consisting of —CH₂CH₂—*, —CH₂CH(CH₃)—*, —CH₂C(CH₃)₂—*, —CH(CH₃)CH₂—*, —C(CH₃)₂CH₂—*, —CH₂CHF—*, —CH₂CF₂—*, —OCH₂—*, —SCH₂—*, and —CH₂CH(OR²)—*, wherein the single bond marked as "*" is between —X¹—X²— and —CR³R⁴—;

R¹ is selected from the group consisting of optionally substituted phenyl, optionally substituted benzyl, optionally substituted heteroaryl, and —(CH₂)(optionally substituted heteroaryl);

each occurrence of R² is independently selected from the group consisting of H and $C_1$-$C_6$ alkyl;

R³ is selected from the group consisting of H, —OH, —OR⁶, —NH₂, —NHR⁶, —NR⁶R⁶, —OC(=O)OR⁶, —OC(=O)N(R²)R⁶, —N(R²)C(=O)OR⁶—NR⁷C(=O)N(R⁶)(R), —N(R²)C(=O)R⁶, —NR²S(=O)₂R⁶, optionally substituted aryl, optionally substituted heteroaryl, —CH₂C(=O)OH, —CH₂C(=O)NR⁶R⁶, —N(R²)C(=O)(CH₂)$_{1-2}$R⁶, NR²S(=O)₂N(R⁶)(R⁷), and —NR²C(=O)C(=O)N(R⁶)(R⁷);

R⁴ is H or $C_1$-$C_6$ alkyl, or R³ and R⁴ combine to form =O;

R$^{5a}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

R$^{5b}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

R$^{5c}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;

each occurrence of R⁶ is independently selected from the group consisting of optionally substituted $C_1$-$C_6$ alkyl, optionally substituted $C_3$-$C_8$ cycloalkyl, optionally substituted phenyl, and optionally substituted hetereoaryl;

each occurrence of R⁷ is independently selected from the group consisting of H and optionally substituted $C_1$-$C_6$ alkyl;
or, if R⁶ and R⁷ are bound to the same N atom, R⁶ and R⁷ optionally combine with the N atom to which both are bound to form an optionally substituted 3-7 membered heterocycle;

R⁸ is selected from the group consisting of H and $C_1$-$C_6$ alkyl.

In certain embodiments, each occurrence of alkyl or cycloalkyl is independently optionally substituted with at least one substituent selected from the group consisting of $C_1$-$C_6$ alkyl, halo, —OR$^a$, optionally substituted phenyl (thus yielding, in non-limiting examples, optionally substituted phenyl-($C_1$-$C_3$ alkyl), such as, but not limited to, benzyl or substituted benzyl), optionally substituted heteroaryl, optionally substituted heterocyclyl, —N(R$^a$)C(=O)R$^a$, —C(=O)NR$^a$R$^a$, and —N(R$^a$)(R$^a$), wherein each occurrence of R$^a$ is independently H, optionally substituted $C_1$-$C_6$ alkyl, optionally substituted $C_3$-$C_8$ cycloalkyl, optionally substituted aryl, or optionally substituted heteroaryl, or two R$^a$ groups combine with the N to which they are bound to form a heterocycle.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR$^b$, —N(R$^b$)(R$^b$), —NO₂, —S(=O)₂N(R$^b$)(R$^b$), acyl, and $C_1$-$C_6$ alkoxycarbonyl, wherein each occurrence of R$^b$ is independently H, $C_1$-$C_6$ alkyl or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR$^c$, —N(R$^c$)(R$^c$), and $C_1$-$C_6$ alkoxycarbonyl, wherein each occurrence of R$^c$ is independently H, $C_1$-$C_6$ alkyl or $C_3$-$C_8$ cycloalkyl.

In certain embodiments, R¹ is selected from the group consisting of optionally substituted phenyl, optionally substituted benzyl, and —(CH$_2$)(optionally substituted heteroaryl), wherein the phenyl, benzyl, or heteroaryl is optionally substituted with at least one selected from the group consisting of C$_1$-C$_6$ alkyl (such as, for example, methyl, ethyl, and isopropyl), halo (such as, for example, F, Cl, Br, and I), C$_1$-C$_3$ haloalkyl (such as, for example, monofluoromethyl, difluoromethyl, and trifluoromethyl), and —CN.

In certain embodiments, R$^1$ is selected from the group consisting of: phenyl, 3-chlorophenyl, 4-chlorophenyl, 3-fluorophenyl, 4-fluorophenyl, 3,4-difluorophenyl, 3,5-difluorophenyl, 2,4,5-trifluorophenyl, 3,4,5-trifluorophenyl, 3,4-dichlorophenyl, 3-chloro-4-fluorophenyl, 4-chloro-3-fluorophenyl, 4-chloro-3-methylphenyl, 3-chloro-4-methylphenyl, 4-fluoro-3-methylphenyl, 3-fluoro-4-methylphenyl, 4-chloro-3-methoxyphenyl, 3-chloro-4-methoxyphenyl, 4-fluoro-3-methoxyphenyl, 3-fluoro-4-methoxyphenyl, 3-trifluoromethylphenyl, 4-trifluoromethylphenyl, 3-trifluoromethyl-4-fluorophenyl, 4-trifluoromethyl-3-fluorophenyl, 3-cyanophenyl, 4-cyanophenyl, 3-cyano-4-fluorophenyl, 4-cyano-3-fluorophenyl, 3-difluoromethyl-4-fluorophenyl, 4-difluoromethyl-3-fluorophenyl, benzo[d][1,3]dioxol-5-yl, 2,3-dihydrobenzo[b][1,4]dioxin-6-yl, benzyl, 3-fluorobenzyl, 4-fluorobenzyl, 3-chlorobenzyl, 4-chlorobenzyl, 2-pyridyl, 4-methyl-2-pyridyl, 5-methyl-2-pyridyl, 6-methyl-2-pyridyl, 3-pyridyl, 2-methyl-3-pyridyl, 3-methyl-3-pyridyl, 4-pyridyl, 2-methyl-4-pyridyl, and 6-methyl-4-pyridyl. In other embodiments, R$^1$ is 3,4-difluorophenyl. In yet other embodiments, R$^1$ is 3-chloro-4-fluorophenyl. In yet other embodiments, R$^1$ is 4-chloro-3-fluorophenyl. In yet other embodiments, R$^1$ is 3-fluoro-4-methylphenyl. In yet other embodiments, R$^1$ is 4-fluoro-3-methylphenyl. In yet other embodiments, R$^1$ is 3-cyano-4-fluorophenyl. In yet other embodiments, R$^1$ is 3-difluoromethyl-4-fluorophenyl.

In certain embodiments, each occurrence of R$^2$ is independently selected from the group consisting of H and methyl. In other embodiments, R$^2$ is H. In yet other embodiments, R$^2$ is methyl.

In certain embodiments, R$^3$ is selected from the group consisting of: H; Ph; pyridin-2-yl; pyridin-3-yl; pyridin-4-yl; —CH$_2$C(=O)OH; —CH$_2$C(=O)NHCH$_3$; —CH$_2$C(=O)N(CH$_3$)$_2$; —OH; C$_1$-C$_6$ alkoxy [such as, for example, methoxy, ethoxy, prop-1-oxy, 2(R)-butoxy and 2(S)-butoxy]; ((R)-1-pyrid-4-yl)ethoxy; ((S)-1-pyridin-4-yl)ethoxy; —OC(=O)O(C$_1$-C$_6$ alkyl) [such as, for example, —OC(=O)OCH$_3$, —OC(=O)OCH$_2$CH$_3$ and —OC(=O)OCH(CH$_3$)$_2$]; —OC(=O)NH(C$_1$-C$_6$ alkyl) [such as, for example, —OC(=O)NHCH$_3$, —OC(=O)NHCH$_2$CH$_3$ and —OC(=O)NHCH(CH$_3$)$_2$]; —NH$_2$; —NH(C$_1$-C$_6$ alkyl) [such as, for example, —NH(CH$_3$), —NH-(2(R)-butyl)) and —NH-(2(S)-butyl)]; —N(C$_1$-C$_6$ alkyl)(C$_1$-C$_6$ alkyl) [such as, for example, —N(CH$_3$)$_2$]; pyrimidin-2-yl-amino; pyrimidin-4-yl-amino; pyrimidin-5-yl-amino; 4-methyl-pyrimidin-2-yl-amino; 5-methyl-pyrimidin-2-yl-amino; 4-methoxy-pyrimidin-2-yl-amino; 5-methoxy-pyrimidin-2-yl-amino; 4-(pyridin-2-yl)-pyrimidin-2-yl-amino; 4-aminocarbonyl-pyrimidin-2-yl-amino; pyrazin-2-yl-amino; oxazol-2-yl-amino; —NHCH$_2$-(1H-pyrazol-5-yl); —NHC(=O)(C$_1$-C$_6$ alkyl) [such as, for example, —NHC(=O)CH$_3$, —NHC(=O)CH$_2$CH$_3$ and —NHC(=O)CH(CH$_3$)CH$_3$]; —NHC(=O)(C$_1$-C$_6$ haloalkyl) [such as, for example, —NHC(=O)CH$_2$CH$_2$F and —NHC(=O)CH$_2$CHF$_2$], —NHC(=O)CH$_2$OCH$_3$; —NHC(=O)Ph; —NHC(=O)-[thiazol-2-yl]; —NHC(=O)-[thiazol-4-yl]; —NHC(=O)-[thiazol-5-yl]; —NHC(=O)-[pyridin-2-yl]; —NHC(=O)-[pyridin-3-yl]; —NHC(=O)-[pyridin-4-yl]; —NHC(=O)-[1-methyl-1H-pyrazol-3-yl]; —NHC(=O)-[1-methyl-1H-pyrazol-5-yl]; —NHC(=O)-thiazol-5-yl]; —NHC(=O)-oxazol-5-yl]; —NHC(=O)CH$_2$—(N-morpholinyl); —NHC(=O)(CH$_2$)$_{1-6}$NH$_2$ [such as, for example, —NHC(=O)CH$_2$NH$_2$]; —NHC(=O)(CH$_2$)$_{1-6}$NH(CH$_3$) [such as, for example, —NHC(=O)CH$_2$NHCH$_3$]; —NHC(=O)(CH$_2$)$_{1-6}$N(CH$_3$)$_2$ [such as, for example, —NHC(=O)CH$_2$N(CH$_3$)$_2$]; —NHC(=O)O(tetrahydro-2H-pyran-4-yl); —NHC(=O)O(optionally substituted C$_1$-C$_6$ alkyl) [such as, for example, —NHC(=O)OCH$_3$, —NHC(=O)OCH$_2$CH$_3$, —NHC(=O)CH(CH$_3$)$_2$, —NHC(=O)O(CH$_2$)$_2$CH$_3$, —NHC(=O)OCH$_2$CHF$_2$, —NHC(=O)O(CH$_2$)$_{1-2}$CF$_3$, —NHC(=O)CH(CH$_3$)$_2$, —NHC(=O)OC(CH$_3$)$_3$, —NHC(=O)O-(2(R)-butyl), and —NHC(=O)O-(2(S)-butyl)]; —N(CH$_3$)C(=O)O(C$_1$-C$_6$ alkyl) [such as, for example, —N(CH$_3$)C(=O)OCH$_3$]; —N(CH$_3$)C(=O)O(C$_3$-C$_8$ cycloalkyl) [such as, for example, —N(CH$_3$)C(=O)O-cyclopropyl, —N(CH$_3$)C(=O)O-cyclopentyl]; —NHC(=O)O(CH$_2$)$_{1-6}$O(CH$_2$)$_{0-3}$CH$_3$ [such as, for example, —NHC(=O)O(CH$_2$)$_2$OCH$_3$, and —NHC(=O)O(CH$_2$)$_3$OCH$_3$]; —NHC(=O)O-benzyl; —NHC(=O)O-(1(R)-phenyl-ethyl); —NHC(=O)O-1(S)-phenyl-ethyl); —NHC(=O)O—((R)-5-oxopyrrolidin-3-yl); —NHC(=O)O(CH$_2$)$_2$O (optionally substituted phenyl); —NHC(=O)OCH$_2$(1-methyl-1H-imidazol-2-yl); —NHC(=O)OCH$_2$-(thiazol-2-yl); —NHC(=O)OCH$_2$-(thiazol-4-yl); —NHC(=O)OCH$_2$-(thiazol-5-yl); —NHC(=O)OCH$_2$CH$_2$-(4-methyl-thiazol-5-yl); —NHC(=O)OCH$_2$-(isoxazol-3-yl); —NHC(=O)OCH$_2$-(oxazol-2-yl); —NHC(=O)OCH$_2$-(oxazol-4-yl); —NHC(=O)OCH$_2$-(oxazol-5-yl); —NHC(=O)OCH$_2$-(2-oxo-oxazolidin-5-yl); —NHC(=O)OCH$_2$-(2-oxo-oxazolidin-4-yl); —NHC(=O)OCH$_2$-(1-methyl-1H-1,2,4-triazol-3-yl); —NHC(=O)OCH$_2$-(1-(2-tetrahydropyranyl)-1H-1,2,4-triazol-3-yl); —NHC(=O)OCH$_2$-(pyridin-2-yl); —NHC(=O)OCH$_2$-(3-fluoro-pyridin-2-yl); —NHC(=O)OCH$_2$CH$_2$-(pyridin-2-yl); —NHC(=O)OCH$_2$—(N-oxide-pyridin-2-yl); —NHC(=O)OCH(CH$_3$)-(pyridin-2-yl); —NHC(=O)OCH(CH$_3$)—(N-oxide-pyridin-2-yl); —NHC(=O)O—((S)-1-(pyridin-2-yl)ethyl); —NHC(=O)O—((R)-1-(pyridin-2-yl)ethyl); —NHC(=O)OCH$_2$-(4-methoxy-pyridin-2-yl); —NHC(=O)OCH$_2$-(5-methoxy-pyridin-2-yl); —NHC(=O)OCH$_2$-(6-methoxy-pyridin-2-yl); —NHC(=O)OCH$_2$-(6-dimethylamino-pyridin-2-yl); —NHC(=O)OCH$_2$-(4-chloro-pyridin-2-yl); —NHC(=O)OCH$_2$-(5-chloro-pyridin-2-yl); —NHC(=O)OCH$_2$-(5-methyl-pyridin-2-yl); —NHC(=O)OCH$_2$-(6-methyl-pyridin-2-yl); —NHC(=O)OCH$_2$-(pyridin-3-yl); —NHC(=O)OCH$_2$-(pyridin-4-yl); —NHC(=O)OCH$_2$-(pyrimidin-2-yl); —NHC(=O)OCH$_2$-(1,3,4-oxadiazol-2-yl); —NHC(=O)OCH$_2$CH$_2$-phenoxy; —NHC(=O)OCH$_2$CH$_2$-(pyrimidin-2-yl); —NHC(=O)OCH$_2$-(pyrimidin-4-yl); —NHC(=O)OCH$_2$-(5-fluoro-pyrimidin-2-yl); —NHC(=O)OCH$_2$-(5-fluoro-pyridin-2-yl); —NHC(=O)OCH$_2$-(1-methyl-1H-pyrazol-3-yl); —NHC(=O)OCH$_2$-(1-methyl-1H-pyrazol-5-yl); —NHC(=O)OCH$_2$-(1-isopropyl-1H-pyrazol-3-yl); —NHC(=O)OCH$_2$CH$_2$-(1H-pyrazol-1-yl); NHC(=O)OCH$_2$CH$_2$-(1H-pyrazol-4-yl); —NHC(=O)OCH$_2$CH$_2$(1H-imidazol-1yl); —NHC(=O)OCH$_2$CH$_2$CH$_2$(1H-imidazol-1yl); —NHC(=O)OCH$_2$-(isoxazol-3-yl); —NHC(=O)OCH$_2$-(pyrrolidin-3-yl); —NHC(=O)OCH$_2$-(pyrrolidin-2-yl); —NHC(=O)OCH$_2$-(1-acetyl-4,4-difluoro-pyrrolidin-2-yl); —NHC(=O)OCH$_2$-(1-(tert-butoxycarbonyl)-4,4-difluoro-pyrrolidin-2-yl); —NHC(=O)OCH$_2$-(1H-4,4-difluoro-pyrrolidin-2-yl); —NHC(=O)OCH$_2$-(1-(2,2,2-trifluoroethyl)-pyrrolidin-2-yl); —NHC(=O)OCH$_2$-(piperidin-2-yl); —NHC(=O)OCH$_2$-(piperidin-3-yl); —NHC(=O)OCH$_2$-(1-(2,2,2-trifluoroethyl)-piperidin-4-yl); —NHC(=O)OCH$_2$-(1-methyl-piperidin-3-yl); —NHC (=O)OCH₂-(1-methyl-piperidin-4-yl); —NHC(=O)OCH₂—((S)-5-oxopyrrolidin-2-yl); —NHC(=O)OCH₂—((R)-5-oxopyrrolidin-2-yl); —NHC(=O)OCH₂—((S)-5-oxopyrrolidin-3-yl); —NHC(=O)OCH₂—((R)-5-oxopyrrolidin-3-yl); —NHC(=O)OCH₂-(1-methyl-((S)(-5-oxopyrrolidin-2-yl); —NHC(=O)OCH₂-(1-methyl-(R)-5-oxopyrrolidin-2-yl); —NHC(=O)O(CH₂)₁₋₃(2-oxopyrrolidin-1-yl); —NHC(=O)OCH₂—(N-acetyl-pyrrolidin-2-yl); —NHC(=O)OCH₂—(N-acetyl-pyrrolidin-3-yl); —NHC(=O)OCH₂—(N-acetyl-piperidin-4-yl); —NHC(=O)OCH₂—((R)-6-oxo-piperidin-2-yl); —NHC(=O)OCH₂—(S-6-oxo-piperidin-2-yl); NHC(=O)OCH₂CH₂-(pyridin-2-yl); —NHC(=O)OCH₂CH₂-(2-oxo-pyrrolidin-1-yl); —NHC(=O)OCH₂C(=O)-(pyrrolidin-1-yl); —NHC(=O)O(tetrahydrofur-3-yl); —NHC(=O)OCH₂(tetrahydrofur-2-yl); —NHC(=O)OCH₂(tetrahydro-2H-pyran-4-yl); —NHC(=O)OCH₂(pyrazin-2-yl); —NHC(=O)OCH₂-(6-morpholinopyridin-2-yl); —NHC(=O)OCH₂-(imidazo[1,2-a]pyridin-2-yl); —NHC(=O)OCH₂-(8-methyl-imidazo[1,2-a]pyridin-2-yl); —NHC(=O)NH₂; —NHC(=O)NH(CH₂)₀₋₅CH₃ [such as, for example, —NHC(=O)NHCH₃]; —N(CH₃)C(=O)NH(CH₂)₀₋₅CH₃ [such as, for example, —N(CH₃)C(=O)NHCH₃]; —N(CH₃)C(=O)N(CH₃)(CH₂)₀₋₅CH₃ [such as, for example, —N(CH₃)C(=O)N(CH₃)₂]; —NHC(=O)-(pyrrolidin-1-yl); —NHC(=O)-(piperidin-1-yl); —NHC(=O)-(4-hydroxy-piperidin-1-yl); —NHC(=O)-(2-hydroxymethyl-piperidin-1-yl); —NHS(=O)₂(C₁-C₆ alkyl) [such as, for example, —NHS(=O)₂CH₃, —NHS(=O)₂ethyl, —NHS(=O)₂isopropyl, —NHS(=O)₂n-propyl, or —NHS(=O)₂isobutyl]; —NHS(=O)₂(C₃—C cycloalkyl) [such as, for example, —NHS(=O)₂cyclopropyl, —NHS(=O)₂cyclopentyl, or —NHS(=O)₂cyclohexyl]; —NHS(=O)₂ (optionally substituted phenyl or heterocyclyl) [such as for example —NHS(=O)₂(1-methyl-1H-pyrazol-3-yl]; —NHS(=O)₂heterocyclyl [such as for example —NHS(=O)₂-morpholinyl]; —NHC(=O)C(=O)NH—(C₁-C₆ alkyl); —NHS(=O)₂NH—(C₁-C₆ alkyl) [such as for example —NHS(=O)₂NH-(isopropyl)]; and —NHS(=O)₂NH—(C₃—C cycloalkyl) [such as for example —NHS(=O)₂NH-(cyclopropyl)].

In certain embodiments, R³ is selected from the group consisting of —NH₂; —OH; —NH(pyridinyl); —NH(pyrimidinyl); —NH(piridinyl-pyrimidinyl); and —NH(pyrrolo[2,3-d]pyrimidinyl).

In certain embodiments, R³ is selected from the group consisting of —NHS(=O)₂(C₁-C₆ alkyl); —NHS(=O)₂(C₃-C₆ cycloalkyl); —NHS(=O)₂(CH₂)₀₋₃pyridinyl; —NHS(=O)₂(benzyl); —NHS(=O)₂(pyrazolyl); —NHS(=O)₂(morpholinyl); —NHS(=O)₂NH(C₁-C₆ alkyl); —NHS(=O)₂NH(C₃-C₆ cycloalkyl); —NHS(=O)₂NH(CH₂)₀₋₃pyridinyl; —NHS(=O)₂NH(benzyl); —NHS(=O)₂NH(pyrazolyl); and —NHS(=O)₂NH(morpholinyl).

In certain embodiments, R³ is selected from the group consisting of —NHC(=O)(C₁-C₆ alkyl); —NHC(=O)(C₃-C₈ cycloalkyl); —NHC(=O)(C₁-C₆ haloalkyl); —NHC(=O)(pyrazolyl); —NHC(=O)(thiazolyl); —NHC(=O)(oxazolyl); —NHC(=O)(pyridinyl); —NHC(=O)(CH₂)₁₋₃(pyridinyl); —NHC(=O)(CH₂)₁₋₃(pyrazinyl); —NHC(=O)(CH₂)₁₋₃(pyrimidinyl); —NHC(=O)(CH₂)₁₋₃(quinolinyl); —NHC(=O)(CH₂)₁₋₃(isoxazolyl); —NHC(=O)(CH₂)₁₋₃(oxazolyl); —NHC(=O)(CH₂)₁₋₃(oxadiazolyl); —NHC(=O)(CH₂)₁₋₃(triazolyl); —NHC(=O)(CH₂)₁₋₃(thiazolyl); —NHC(=O)(CH₂)₁₋₃(imidazolyl); —NHC(=O)(CH₂)₁₋₃(pyrazolyl); —NHC(=O)(CH₂)₁₋₃(piperidinyl); —NHC(=O)(CH₂)₁₋₃(oxopiperidinyl); —NHC(=O)(CH₂)₁₋₃(pyrrolidinyl); —NHC(=O)(CH₂)₁₋₃(oxopyrrolidinyl); —NHC(=O)(CH₂)₁₋₃(tetrahydrofuryl); —NHC(=O)(CH₂)₁₋₃(tetrahydropyranyl); —NHC(=O)(CH₂)₁₋₃(2-oxooxazolidinyl); —NHC(=O)(CH₂)₁₋₃(morpholinyl); —NHC(=O)(CH₂)₁₋₃(thiomorpholinyl); —NHC(=O)(CH₂)₁₋₃(1-oxido-thiomorpholinyl); —NHC(=O)(CH₂)₁₋₃(1,1-dioxido-thiomorpholinyl); —NHC(=O)(CH₂)₁₋₃(oxoazetidinyl); —NHC(=O)(CH₂)₁₋₃(imidazo[1,2-a]pyridin-2-yl); and —NHC(=O)(CH₂)₁₋₃C(=O)-(pyrrolidin-1-yl).

In certain embodiments, R³ is selected from the group consisting of —NHC(=O)O(C₁-C₆ alkyl); —NHC(=O)O(C₃-C₈ cycloalkyl); —NHC(=O)O(C₁-C₆ haloalkyl); —NHC(=O)O(CH₂)₁₋₃(pyridinyl); —NHC(=O)O(CH₂)₁₋₃(pyrazinyl); —NHC(=O)O(CH₂)₁₋₃(pyrimidinyl); —NHC(=O)O(CH₂)₁₋₃(quinolinyl); —NHC(=O)O(CH₂)₁₋₃(isoxazolyl); —NHC(=O)O(CH₂)₁₋₃(oxazolyl); —NHC(=O)O(CH₂)₁₋₃(oxadiazolyl); —NHC(=O)O(CH₂)₁₋₃(triazolyl); —NHC(=O)O(CH₂)₁₋₃(thiazolyl); —NHC(=O)O(CH₂)₁₋₃(imidazolyl); —NHC(=O)O(CH₂)₁₋₃(pyrazolyl); —NHC(=O)O(CH₂)₁₋₃(piperidinyl); —NHC(=O)O(CH₂)₁₋₃(oxopiperidinyl); —NHC(=O)O(CH₂)₁₋₃(pyrrolidinyl); —NHC(=O)O(CH₂)₁₋₃(oxopyrrolidinyl); —NHC(=O)O(CH₂)₁₋₃(tetrahydrofuryl); —NHC(=O)O(CH₂)₁₋₃(tetrahydropyranyl); —NHC(=O)O(CH₂)₁₋₃(2-oxooxazolidinyl); —NHC(=O)O(CH₂)₁₋₃(morpholinyl); —NHC(=O)O(CH₂)₁₋₃(thiomorpholinyl); —NHC(=O)O(CH₂)₁₋₃(1-oxido-thiomorpholinyl); —NHC(=O)O(CH₂)₁₋₃(1,1-dioxido-thiomorpholinyl); —NHC(=O)O(CH₂)₁₋₃(oxoazetidinyl); —NHC(=O)O(CH₂)₁₋₃(imidazo[1,2-a]pyridin-2-yl); and —NHC(=O)O(CH₂)₁₋₃C(=O)-(pyrrolidin-1-yl).

In certain embodiments, R³ is selected from the group consisting of —NHC(=O)NH(C₁-C₆ alkyl); —NHC(=O)NH(C₃-C₈ cycloalkyl); —NHC(=O)NH(C₁-C₆ haloalkyl); —NHC(=O)NH(CH₂)₁₋₃(pyridinyl); —NHC(=O)NH(CH₂)₁₋₃(pyrazinyl); —NHC(=O)NH(CH₂)₁₋₃(pyrimidinyl); —NHC(=O)NH(CH₂)₁₋₃(quinolinyl); —NHC(=O)NH(CH₂)₁₋₃(isoxazolyl); —NHC(=O)NH(CH₂)₁₋₃(oxazolyl); —NHC(=O)NH(CH₂)₁₋₃(oxadiazolyl); —NHC(=O)NH(CH₂)₁₋₃(triazolyl); —NHC(=O)NH(CH₂)₁₋₃(thiazolyl); —NHC(=O)NH(CH₂)₁₋₃(imidazolyl); —NHC(=O)NH(CH₂)₁₋₃(pyrazolyl); —NHC(=O)NH(CH₂)₁₋₃(piperidinyl); —NHC(=O)NH(CH₂)₁₋₃(oxopiperidinyl); —NHC(=O)NH(CH₂)₁₋₃(pyrrolidinyl); —NHC(=O)NH(CH₂)₁₋₃(oxopyrrolidinyl); —NHC(=O)NH(CH₂)₁₋₃(tetrahydrofuryl); —NHC(=O)NH(CH₂)₁₋₃(tetrahydropyranyl); —NHC(=O)NH(CH₂)₁₋₃(2-oxooxazolidinyl); —NHC(=O)NH(CH₂)₁₋₃(morpholinyl); —NHC(=O)NH(CH₂)₁₋₃(thiomorpholinyl); —NHC(=O)NH(CH₂)₁₋₃(1-oxido-thiomorpholinyl); —NHC(=O)NH(CH₂)₁₋₃(1,1-dioxido-thiomorpholinyl); —NHC(=O)NH(CH₂)₁₋₃(oxoazetidinyl); —NHC(=O)NH(CH₂)₁₋₃(imidazo[1,2-a]pyridin-2-yl); —NHC(=O)NH(CH₂)₁₋₃C(=O)-(pyrrolidin-1-yl); —C(=O)NHC(=O)NH—; —C(=O)N(C₁-C₆ alkyl)C(=O)NH—; and —C(=O)N((CH₂)₁₋₃pyridinyl)CONH—.

In certain embodiments, the alkyl, cycloalkyl, heteroaryl, heterocyclyl, aryl, or benzyl group is optionally independently substituted with at least one group selected from the group consisting of C₁-C₆ alkyl; C₁-C₆ alkoxy; C₁-C₆ haloalkyl; C₁-C₆ haloalkoxy; —NH₂, —NH(C₁-C₆ alkyl), —N(C₁-C₆ alkyl)(C₁-C₆ alkyl), halogen, —OH; —CN; phenoxy, —NHC(=O)H, —NHC(=O)C₁-C₆ alkyl, —C(=O)NH₂, —C(=O)NHC₁-C₆ alkyl, —C(=O)N(C₁-C₆ alkyl)(C₁-C₆ alkyl), tetrahydropyranyl, morpholinyl, —C(=O)CH₃, —C(=O)CH₂OH, —C(=O)NHCH₃, —C(=O)CH₂OMe, or an N-oxide thereof.

In certain embodiments, at least one of $R^3$ and $R^4$ comprises a deuterium atom. In other embodiments, $R^3$ comprises at least one deuterium atom. In yet other embodiments, $R^4$ comprises at least one deuterium atom. In yet other embodiments, the at least deuterium atom replaces a non-exchangeable hydrogen atom (i.e., a hydrogen atom that is not significantly exchanged under neutral conditions, such as for example a hydrogen atom bound to a carbon atom). In yet other embodiments, at least one non-exchangeable hydrogen atom in at least one of $R^3$ and $R^4$ is replaced with a deuterium atom. In yet other embodiments, at least one non-exchangeable hydrogen atom in $R^3$ is replaced with a deuterium atom. In yet other embodiments, at least one non-exchangeable hydrogen atom in $R^4$ is replaced with a deuterium atom. In yet other embodiments, each non-exchangeable hydrogen atom in $R^3$ is replaced with a deuterium atom. In yet other embodiments, each non-exchangeable hydrogen atom in $R^4$ is replaced with a deuterium atom. In yet other embodiments, at least one C(H) group in $R^3$ is replaced with a C(D) group. In yet other embodiments, at least one C(H) group in $R^4$ is replaced with a C(D) group. In yet other embodiments, each C(H) group in $R^3$ is replaced with a C(D) group. In yet other embodiments, each C(H) group in $R^4$ is replaced with a C(D) group. In yet other embodiments, at least one —CH$_2$— group in $R^3$ is independently replaced with a —CHD- or —CD$_2$- group. In yet other embodiments, at least one —CH$_2$— group in $R^4$ is independently replaced with a —CHD- or —CD$_2$- group. In yet other embodiments, each —CH$_2$— group in $R^3$ is independently replaced with a —CHD- or —CD$_2$- group. In yet other embodiments, each —CH$_2$— group in $R^4$ is independently replaced with a —CHD- or —CD$_2$- group. In yet other embodiments, at least one —CH$_3$ group in $R^3$ is independently replaced with a —CH$_2$D, —CHD$_2$, or —CD$_3$ group. In yet other embodiments, at least one —CH$_3$ group in $R^4$ is independently replaced with a —CH$_2$D, —CHD$_2$, or —CD$_3$ group. In yet other embodiments, each —CH$_3$ group in $R^3$ is independently replaced with a —CH$_2$D, —CHD$_2$, or —CD$_3$ group. In yet other embodiments, each —CH$_3$ group in $R^4$ is independently replaced with a —CH$_2$D, —CHD$_2$, or —CD$_3$ group.

In certain embodiments, $R^4$ is H or CH$_3$. In other embodiments, $R^4$ is H. In yet other embodiments, $R^4$ is CH$_3$.

In certain embodiments, $R^{5a}$, $R^{5b}$, and $R^{5c}$ are independently selected from the group consisting of H, F, Cl, Br and I. In other embodiments, $R^{5a}$, $R^{5b}$, and $R^{5c}$ are independently selected from the group consisting of H, F, Cl, and Br. In yet other embodiments, $R^{5a}$, $R^{5b}$, and $R^{5c}$ are independently selected from the group consisting of H, F, and Cl. In yet other embodiments, $R^{5a}$, $R^{5b}$, and $R^{5c}$ are independently selected from the group consisting of H and F. In other embodiments, one of $R^{5a}$, $R^{5b}$, and $R^{5c}$ is F, and the two remaining are H. In yet other embodiments, one of $R^{5a}$, $R^{5b}$, and $R^{5c}$ is Cl, and the two remaining are H. In yet other embodiments, one of $R^{5a}$, $R^{5b}$, and $R^{5c}$ is Br, and the two remaining are H. In yet other embodiments, $R^{5a}$ is not H. In yet other embodiments, $R^{5a}$ is F, and $R^{5b}$ and $R^{5c}$ are H.

In certain embodiments, $R^{5a}$ is H. In other embodiments, $R^{5b}$ is H. In yet other embodiments, $R^{5c}$ is H. In yet other embodiments, $R^{5a}$ and $R^{5c}$ are H. In yet other embodiments, $R^{5a}$ and $R^{5b}$ are H. In yet other embodiments, $R^{5b}$ and $R^{5c}$ are H. In yet other embodiments, $R^{5a}$ is F. In yet other embodiments, $R^{5b}$ is F. In yet other embodiments, $R^{5c}$ is F.

In certain embodiments, $R^6$ is selected from the group consisting of C$_1$-C$_6$ alkyl optionally substituted with at least one selected from the group consisting of halogen, OH, C$_1$-C$_3$ alkoxy, and cyano; —(CH$_2$)$_{0-3}$ (optionally substituted heterocyclyl); —(CH$_2$)$_{0-3}$ (optionally substituted heteroaryl); and —(CH$_2$)$_{0-3}$ (optionally substituted heteroaryl).

In certain embodiments, each occurrence of the heteroaryl is independently selected from the group consisting of quinolinyl, imidazo[1,2-a]pyridyl, pyridyl, pyrimidyl, pyrazinyl, imidazolyl, thiazolyl, pyrazolyl, isoxazolyl, oxadiazolyl (including 1,2,3-, 1,2,4-, 1,2,5-, and 1,3,4-oxadiazole), and triazolyl (such as 1,2,4-triazolyl).

In certain embodiments, each occurrence of the heterocyclyl group is independently selected from the group consisting of tetrahydrofuranyl, tetrahydropyranyl, piperidinyl, piperazinyl, pyrrolidinyl, morpholinyl, thiomorpholinyl, 1-oxido-thiomorpholinyl, 1,1-dioxido-thiomorpholinyl, oxazolidinyl, azetidinyl, and the corresponding oxo analogues (where a methylene ring group is replaced with a carbonyl) thereof.

In certain embodiments, $R^8$ is selected from the group consisting of H and methyl. In other embodiments, $R^8$ is H. In yet other embodiments, $R^8$ is methyl.

In certain embodiments, the compound of the invention is any compound disclosed herein, or a salt, solvate, prodrug, isotopically labelled (such as for example at least partially deuterated), stereoisomer, any mixture of stereoisomers, tautomer, and/or any mixture of tautomers thereof.

In certain embodiments, the compound of formula (I) is

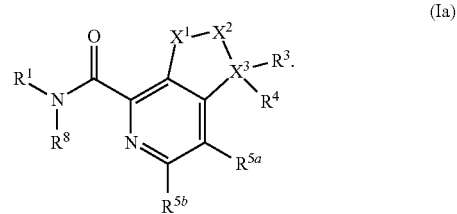

(Ia)

In certain embodiments, the compound of formula (I) is

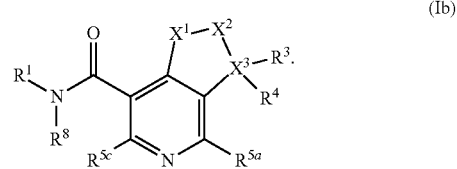

(Ib)

In certain embodiments, the compound of formula (I) is

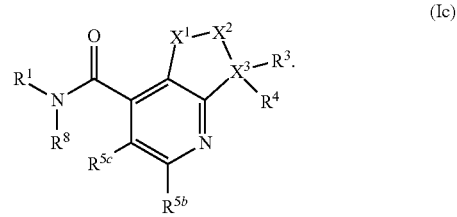

(Ic)

In certain embodiments, the compound of formula (I) is

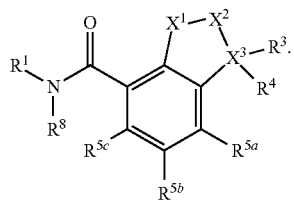
(Id)

In certain embodiments, the compound of formula (I) is

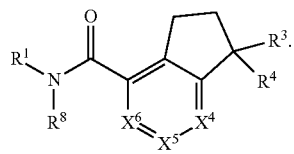
(Ie)

In certain embodiments, the compound of formula (I) is

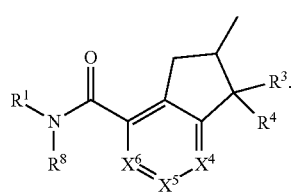
(If)

In certain embodiments, the compound of formula (I) is

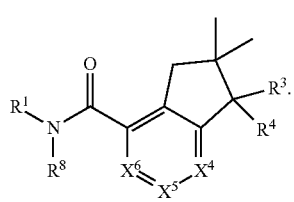
(Ig)

In certain embodiments, the compound of formula (I) is

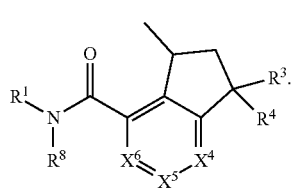
(Ih)

In certain embodiments, the compound of formula (I) is

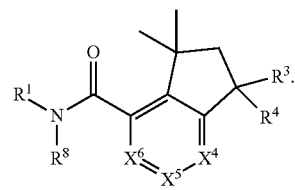
(Ii)

In certain embodiments, the compound of formula (I) is

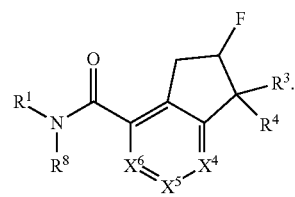
(Ij)

In certain embodiments, the compound of formula (I) is

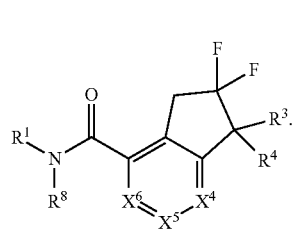
(Ik)

In certain embodiments, the compound of formula (I) is

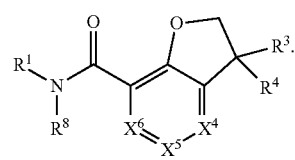
(Il)

In certain embodiments, the compound of formula (I) is

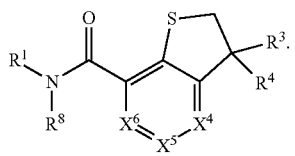
(Im)

In certain embodiments, the compound of formula (I) is

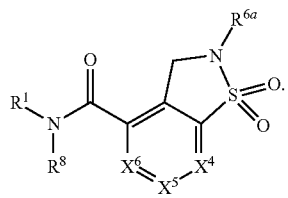
(In)

In certain embodiments, the compound of formula (I) is

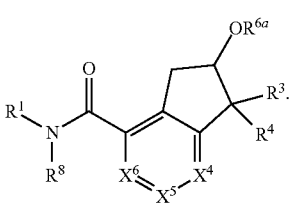
(Io)

In certain embodiments, the compound of formula (I) is

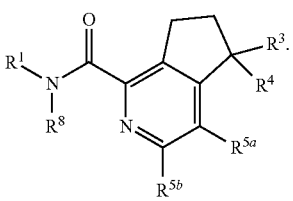
(Ip)

In certain embodiments, the compound of formula (I) is

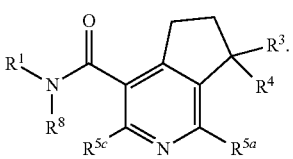
(Iq)

In certain embodiments, the compound of formula (I) is

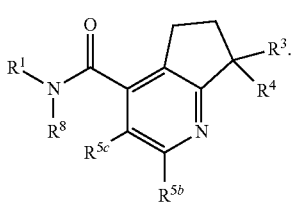
(Ir)

In certain embodiments, the compound of formula (I) is

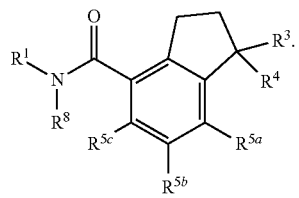
(Is)

In certain embodiments, the compound of formula (I) is

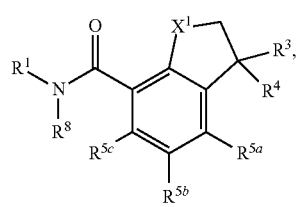
(It)

wherein $X^1$ is selected from the group consisting of $CH_2$, O, and S.

In certain embodiments, the compound of formula (I) is

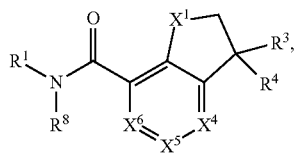
(Iu)

wherein $X^1$ is selected from the group consisting of $CH_2$, O, and S.

In certain embodiments, the compound of formula (I')

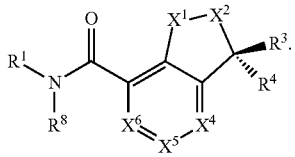
(Ia')

In certain embodiments, the compound of formula (I') is

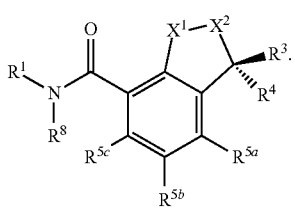
(Ib')

In certain embodiments, the compound of formula (I') is

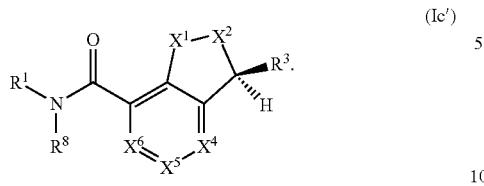
(Ic')

In certain embodiments, the compound of formula (I') is

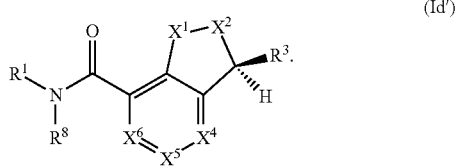
(Id')

In certain embodiments, the compound of formula (I') is

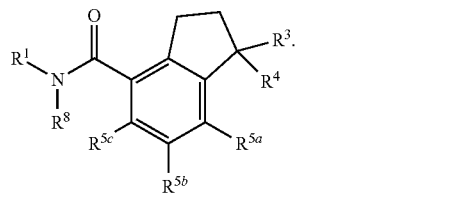

In certain embodiments, the compound of formula (I') is

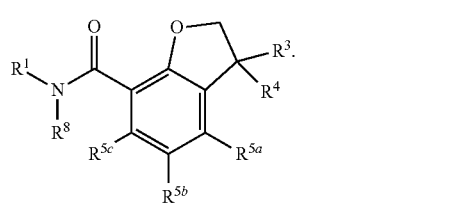

In certain embodiments, the compound of formula (I') is

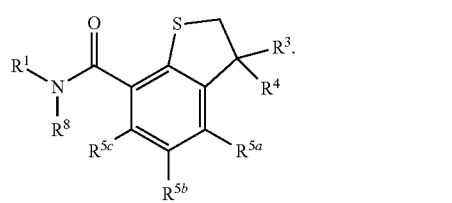

In certain embodiments, the compound of formula (I') is

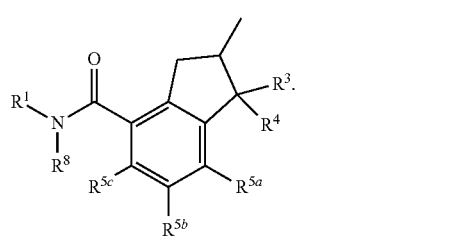

In certain embodiments, the compound of formula (I') is

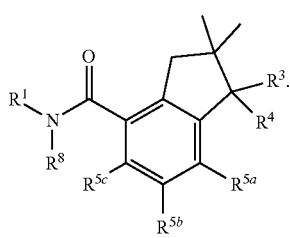

In certain embodiments, the compound of formula (I') is

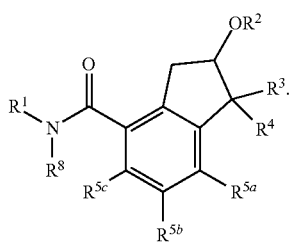

In certain embodiments, the compound of formula (I') is

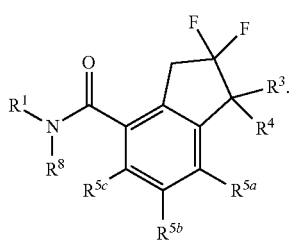

In certain embodiments, the compound of formula (I') is

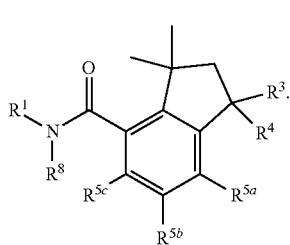

In certain embodiments, the compound of formula (I') is

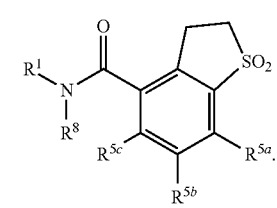

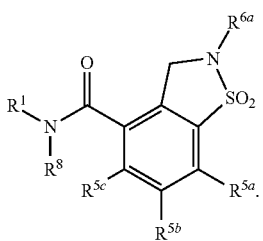

In certain embodiments, the compound of formula (I') is

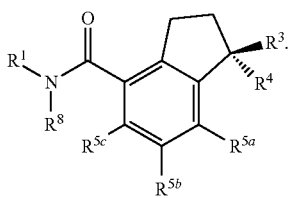

In certain embodiments, the compound of formula (I') is

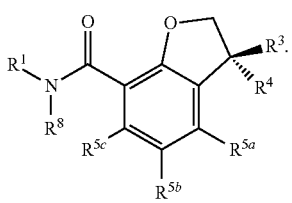

In certain embodiments, the compound of formula (I') is

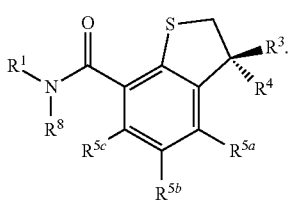

In certain embodiments, the compound of formula (I') is

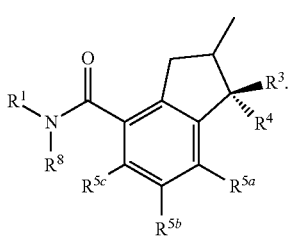

In certain embodiments, the compound of formula (I') is

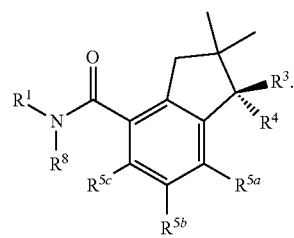

In certain embodiments, the compound of formula (I') is

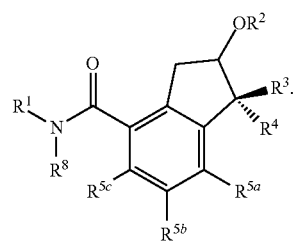

In certain embodiments, the compound of formula (I') is

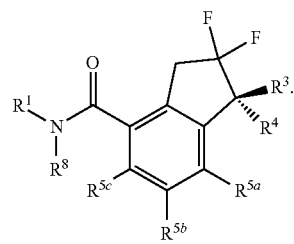

In certain embodiments, the compound of formula (I') is

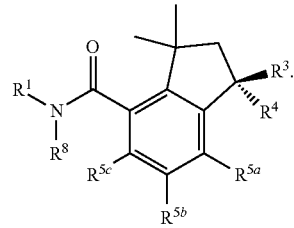

In certain embodiments, the compound of formula (I') is

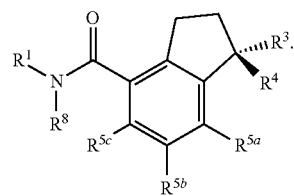

In certain embodiments, the compound of formula (I') is

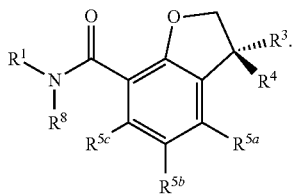

In certain embodiments, the compound of formula (I') is

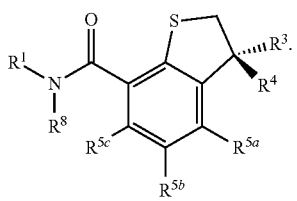

In certain embodiments, the compound of formula (I') is

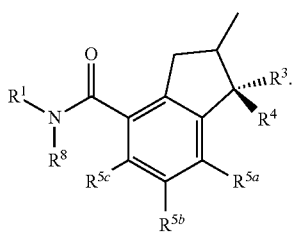

In certain embodiments, the compound of formula (I') is

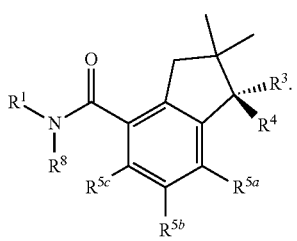

In certain embodiments, the compound of formula (I') is

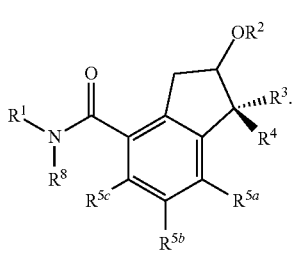

In certain embodiments, the compound of formula (I') is

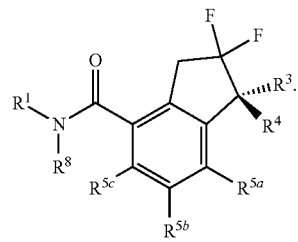

In certain embodiments, the compound of formula (I') is

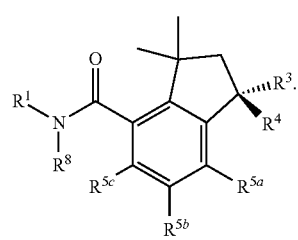

In certain embodiments, the compound of formula (I') is

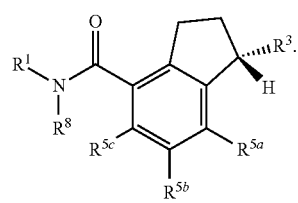

In certain embodiments, the compound of formula (I') is

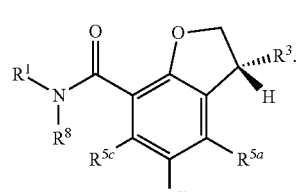

In certain embodiments, the compound of formula (I') is

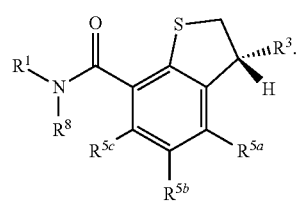

In certain embodiments, the compound of formula (I') is


In certain embodiments, the compound of formula (I') is

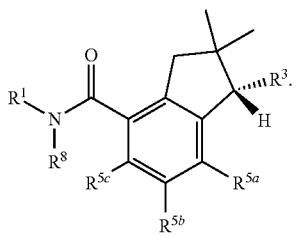

In certain embodiments, the compound of formula (I') is

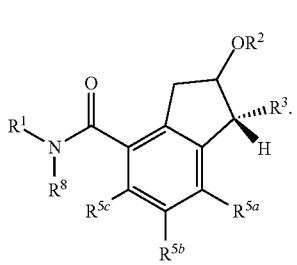

In certain embodiments, the compound of formula (I') is

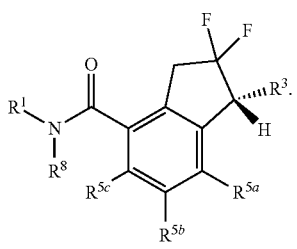

In certain embodiments, the compound of formula (I') is

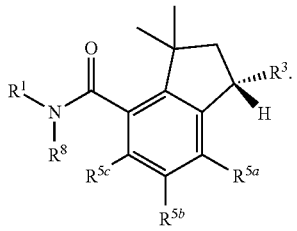

In certain embodiments, the compound of formula (I') is

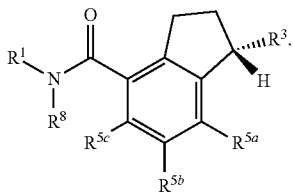

In certain embodiments, the compound of formula (I') is

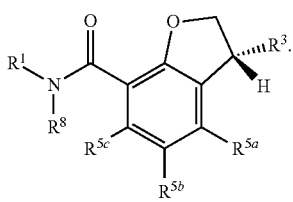

In certain embodiments, the compound of formula (I') is

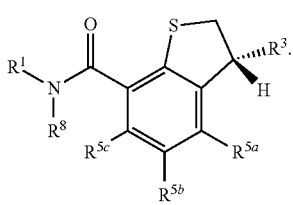

In certain embodiments, the compound of formula (I') is

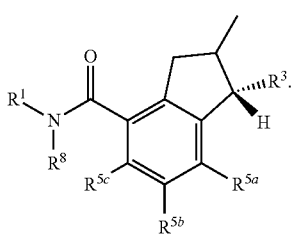

In certain embodiments, the compound of formula (I') is

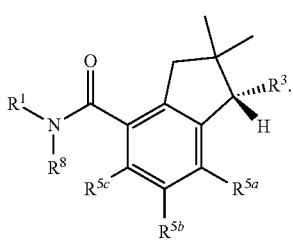

In certain embodiments, the compound of formula (I') is

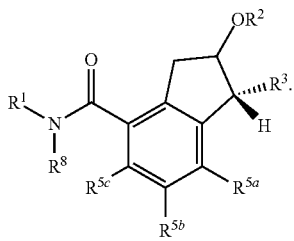

In certain embodiments, the compound of formula (I') is

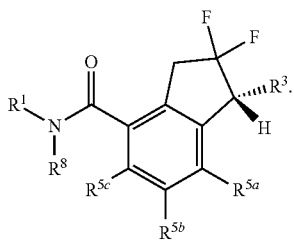

In certain embodiments, the compound of formula (I') is

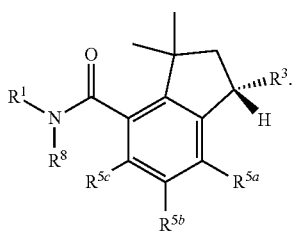

In certain embodiments, the compound of formula (I) is a prodrug, such as but not limited to a phosphate. In other embodiments, the phosphate group is present as a —(CRR)—O—P(=O)(OR)$_2$ group, or a salt thereof, which is attached to a heteroatom, wherein each occurrence of R is independently H and $C_1$-$C_6$ alkyl. In yet other embodiments, the —(CRR)—O—P(=O)(OR)$_2$ group, or a salt thereof, is attached to a group that is capable of acting as a leaving group under acidic conditions, such as but not limited to, —O— (giving rise to an alcohol upon hydrolysis of the prodrug), —NH— (giving rise to an amine or amide, for example, upon hydrolysis of the prodrug), 2-oxopyrrolidin-1-yl, pyrrolidin-1-yl, 1H-pyrazol-1-yl, 1H-1,2,4-triazol-1-yl, 1H-imidazol-1-yl, and/or other heterocyclic groups.

In certain embodiments, the compound is at least one selected from Table 1, or a salt, solvate, prodrug, isotopically labelled (such as for example at least partially deuterated), stereoisomer, any mixture of stereoisomers, tautomer, and/or any mixture of tautomers thereof.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein.

Preparation of optically active forms is achieved in any suitable manner, including, by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or any mixtures thereof, or in the case where two or more chiral centers are present, all diastereomers or any mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Combination Therapies

In one aspect, the compounds of the invention are useful within the methods of the invention in combination with one or more additional agents useful for treating HBV infections. These additional agents may comprise compounds or compositions identified herein, or compounds (e.g., commercially available compounds) known to treat, prevent, or reduce the symptoms of HBV infections.

Non-limiting examples of one or more additional agents useful for treating HBV infections include: (a) reverse transcriptase inhibitors; (b) capsid inhibitors; (c) cccDNA formation inhibitors; (d) sAg secretion inhibitors; (e) oligomeric nucleotides targeted to the Hepatitis B genome; and (f) immunostimulators.

(a) Reverse Transcriptase Inhibitors

In certain embodiments, the reverse transcriptase inhibitor is a reverse-transcriptase inhibitor (NARTI or NRTI). In other embodiments, the reverse transcriptase inhibitor is a nucleotide analog reverse-transcriptase inhibitor (NtARTI or NtRTI).

Reported reverse transcriptase inhibitors include, but are not limited to, entecavir, clevudine, telbivudine, lamivudine, adefovir, and tenofovir, tenofovir disoproxil, tenofovir alafenamide, adefovir dipovoxil, (1R,2R,3R,5R)-3-(6-amino-9H-9-purinyl)-2-fluoro-5-(hydroxymethyl)-4-methylenecyclopentan-1-ol (described in U.S. Pat. No. 8,816,074, incorporated herein in its entirety by reference), emtricitabine, abacavir, elvucitabine, ganciclovir, lobucavir, famciclovir, penciclovir, and amdoxovir.

Reported reverse transcriptase inhibitors further include, but are not limited to, entecavir, lamivudine, and (1R,2R,3R,5R)-3-(6-amino-9H-9-purinyl)-2-fluoro-5-(hydroxymethyl)-4-methylenecyclopentan-1-ol.

Reported reverse transcriptase inhibitors further include, but are not limited to, a covalently bound phosphoramidate or phosphonamidate moiety of the above-mentioned reverse transcriptase inhibitors, or as described in for example U.S. Pat. No. 8,816,074, US Patent Application Publications No. US 2011/0245484 A1, and US 2008/0286230A1, all of which incorporated herein in their entireties by reference.

Reported reverse transcriptase inhibitors further include, but are not limited to, nucleotide analogs that comprise a phosphoramidate moiety, such as, for example, methyl ((((1R,3R,4R,5R)-3-(6-amino-9H-purin-9-yl)-4-fluoro-5-hydroxy-2-methylenecyclopentyl) methoxy)(phenoxy) phosphoryl)-(D or L)-alaninate and methyl ((((1R,2R,3R,4R)-3-fluoro-2-hydroxy-5-methylene-4-(6-oxo-1,6-dihydro-9H-purin-9-yl)cyclopentyl)methoxy)(phenoxy) phosphoryl)-(D or L)-alaninate. Also included are the individual diastereomers thereof, which include, for example, methyl ((R)-(((1R,3R,4R,5R)-3-(6-amino-9H-purin-9-yl)-4-fluoro-5-hydroxy-2-methylenecyclopentyl)methoxy)(phenoxy) phosphoryl)-(D or L)-alaninate and methyl ((S)-(((1R,3R,4R,5R)-3-(6-amino-9H-purin-9-yl)-4-fluoro-5-hydroxy-2-methylenecyclopentyl) methoxy)(phenoxy)phosphoryl)-(D or L)-alaninate.

Reported reverse transcriptase inhibitors further include, but are not limited to, compounds comprising a phosphonamidate moiety, such as, for example, tenofovir alafenamide, as well as those described in U.S. Patent Application Publication No. US 2008/0286230 A1, incorporated herein in its entirety by reference. Methods for preparing stereoselective phosphoramidate or phosphonamidate containing actives are described in, for example, U.S. Pat. No. 8,816,074, as well as U.S. Patent Application Publications No. US 2011/0245484 A1 and US 2008/0286230 A1, all of which incorporated herein in their entireties by reference.

(b) Capsid Inhibitors

As described herein, the term "capsid inhibitor" includes compounds that are capable of inhibiting the expression and/or function of a capsid protein either directly or indirectly. For example, a capsid inhibitor may include, but is not limited to, any compound that inhibits capsid assembly, induces formation of non-capsid polymers, promotes excess capsid assembly or misdirected capsid assembly, affects capsid stabilization, and/or inhibits encapsidation of RNA (pgRNA). Capsid inhibitors also include any compound that inhibits capsid function in a downstream event(s) within the replication process (e.g., viral DNA synthesis, transport of relaxed circular DNA (rcDNA) into the nucleus, covalently closed circular DNA (cccDNA) formation, virus maturation, budding and/or release, and the like). For example, in certain embodiments, the inhibitor detectably inhibits the expression level or biological activity of the capsid protein as measured, e.g., using an assay described herein. In certain embodiments, the inhibitor inhibits the level of rcDNA and downstream products of viral life cycle by at least 5%, at least 10%, at least 20%, at least 50%, at least 75%, or at least 90%.

Reported capsid inhibitors include, but are not limited to, compounds described in International Patent Applications Publication Nos WO 2013006394, WO 2014106019, and WO2014089296, all of which incorporated herein in their entireties by reference.

Reported capsid inhibitors also include, but are not limited to, the following compounds and pharmaceutically acceptable salts and/or solvates thereof: Bay-41-4109 (see Int'l Patent Application Publication No. WO 2013144129), AT-61 (see Int'l Patent Application Publication No. WO 1998033501; and King, et al., 1998, Antimicrob. Agents Chemother. 42(12):3179-3186), DVR-01 and DVR-23 (see Int'l Patent Application Publication No. WO 2013006394; and Campagna, et al., 2013, J. Virol. 87(12):6931, all of which incorporated herein in their entireties by reference.

In addition, reported capsid inhibitors include, but are not limited to, those generally and specifically described in U.S. Patent Application Publication Nos. US 2015/0225355, US 2015/0132258, US 2016/0083383, US 2016/0052921 and Int'l Patent Application Publication Nos. WO 2013096744, WO 2014165128, WO 2014033170, WO 2014033167, WO 2014033176, WO 2014131847, WO 2014161888, WO 2014184350, WO 2014184365, WO 2015059212, WO 2015011281, WO 2015118057, WO 2015109130, WO 2015073774, WO 2015180631, WO 2015138895, WO 2016089990, WO 2017015451, WO 2016183266, WO 2017011552, WO 2017048950, WO2017048954, WO 2017048962, WO 2017064156 and are incorporated herein in their entirety by reference.

(c) cccDNA Formation Inhibitors

Covalently closed circular DNA (cccDNA) is generated in the cell nucleus from viral rcDNA and serves as the transcription template for viral mRNAs. As described herein, the term "cccDNA formation inhibitor" includes compounds that are capable of inhibiting the formation and/or stability of cccDNA either directly or indirectly. For example, a cccDNA formation inhibitor may include, but is not limited to, any compound that inhibits capsid disassembly, rcDNA entry into the nucleus, and/or the conversion of rcDNA into cccDNA. For example, in certain embodiments, the inhibitor detectably inhibits the formation and/or stability of the cccDNA as measured, e.g., using an assay described herein. In certain embodiments, the inhibitor inhibits the formation and/or stability of cccDNA by at least 5%, at least 10%, at least 20%, at least 50%, at least 75%, or at least 90%.

Reported cccDNA formation inhibitors include, but are not limited to, compounds described in Int'l Patent Application Publication No. WO 2013130703, and are incorporated herein in their entirety by reference.

In addition, reported cccDNA formation inhibitors include, but are not limited to, those generally and specifically described in U.S. Patent Application Publication No. US 2015/0038515 A1, and are incorporated herein in their entirety by reference.

(d) sAg Secretion Inhibitors

As described herein, the term "sAg secretion inhibitor" includes compounds that are capable of inhibiting, either directly or indirectly, the secretion of sAg (S, M and/or L surface antigens) bearing subviral particles and/or DNA containing viral particles from HBV-infected cells. For example, in certain embodiments, the inhibitor detectably inhibits the secretion of sAg as measured, e.g., using assays known in the art or described herein, e.g., ELISA assay or by Western Blot. In certain embodiments, the inhibitor inhibits the secretion of sAg by at least 5%, at least 10%, at least 20%, at least 50%, at least 75%, or at least 90%. In certain embodiments, the inhibitor reduces serum levels of sAg in a patient by at least 5%, at least 10%, at least 20%, at least 50%, at least 75%, or at least 90%.

Reported sAg secretion inhibitors include compounds described in U.S. Pat. No. 8,921,381, as well as compounds described in U.S. Patent Application Publication Nos. US 2015/0087659 and US 2013/0303552, all of which are incorporated herein in their entireties by reference.

In addition, reported sAg secretion inhibitors include, but are not limited to, those generally and specifically described in Int'l Patent Application Publication Nos. WO 2015113990, WO 2015173164, US 2016/0122344, WO 2016107832, WO 2016023877, WO 2016128335, WO 2016177655, WO 2016071215, WO 2017013046, WO 2017016921, WO 2017016960, WO 2017017042, WO 2017017043, WO 2017102648, WO 2017108630, WO 2017114812, WO 2017140821 and are incorporated herein in their entirety by reference.

(e) Immunostimulators

The term "immunostimulator" includes compounds that are capable of modulating an immune response (e.g., stimulate an immune response (e.g., an adjuvant)). Immunostimulators include, but are not limited to, polyinosinic:polycytidylic acid (poly I:C) and interferons.

Reported immunostimulators include, but are not limited to, agonists of stimulator of IFN genes (STING) and interleukins. Reported immunostimulators further include, but are not limited to, HBsAg release inhibitors, TLR-7 agonists (such as, but not limited to, GS-9620, RG-7795), T-cell stimulators (such as, but not limited to, GS-4774), RIG-1 inhibitors (such as, but not limited to, SB-9200), and SMAC-mimetics (such as, but not limited to, Birinapant).

(f) Oligomeric Nucleotides

Reported oligomeric nucleotides targeted to the Hepatitis B genome include, but are not limited to, Arrowhead-ARC-520 (see U.S. Pat. No. 8,809,293; and Wooddell et al., 2013, Molecular Therapy 21(5):973-985, all of which incorporated herein in their entireties by reference).

In certain embodiments, the oligomeric nucleotides can be designed to target one or more genes and/or transcripts of the HBV genome. Oligomeric nucleotide targeted to the Hepatitis B genome also include, but are not limited to, isolated, double stranded, siRNA molecules, that each include a sense strand and an antisense strand that is hybridized to the sense strand. In certain embodiments, the siRNA target one or more genes and/or transcripts of the HBV genome.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Synthesis

The present invention further provides methods of preparing compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high-performance liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

A compound of formula (I) can be prepared, for example, according to the synthetic methods outlined in Schemes I-V. It should be noted that the absolute stereochemistry of the chiral center(s) represented in Schemes I-V is merely illustrative, and the Schemes may be used to prepare any of the stereoisomers (or any mixtures thereof) of any compound of the invention. One skilled in the art would contemplate that the synthetic sequences illustrated in Schemes I-V can also be applied to starting materials comprising pyridine starting materials (i.e., analogs of II, XI, XV, XXV, and/or XXXII wherein the central phenyl ring (which is fused with the 5-membered ring) is replaced with a pyridinyl ring). Further, illustrative synthesis of compounds of the invention wherein the 6-membered central ring is a pyridinyl ring can be prepared according to the methodology illustrated in Examples 15-16, for example.

As illustrated in Scheme I, aryl bromide II can be converted to aryl ester III by, for example, a carbonylation reaction using carbon monoxide and an organometallic catalyst, such as but not limited to a Pd catalyst, such as but not limited to Pd(dppf)$_2$Cl$_2$, in the presence of a base, such as but not limited to a tertiary amine. Compound III can be reacted with a sulfinamide, and under reducing conditions, yield the sulfinylamino compound IV, which can be hydrolyzed to the corresponding carboxylic acid V, for example, by treatment with an aqueous hydroxide solution. Compound V can be converted to the corresponding amide using standard coupling reagents, such as but not limited to HATU or EDC-HOBt in the presence of a tertiary amine, and release of the sulfinylamino group under acidic conditions provides the free amine VII, which can be N-derivatized using an electrophilic reagent, such as but not limited to a reactive halide, mesylate, triflate, carboxylic acid (such as a reactive heteroaryl-carboxylate, such as but not limited to an 1H-imidazole-1-yl-carboxylate), acid anhydride, arylating agent, isocyanate, and/or any other electrophilic reagent exemplified herein and/or known in the art, to yield VIII.

Scheme I.

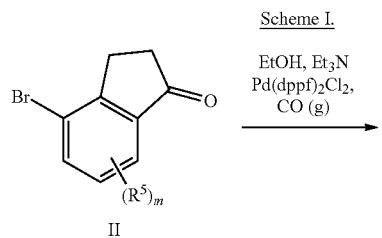

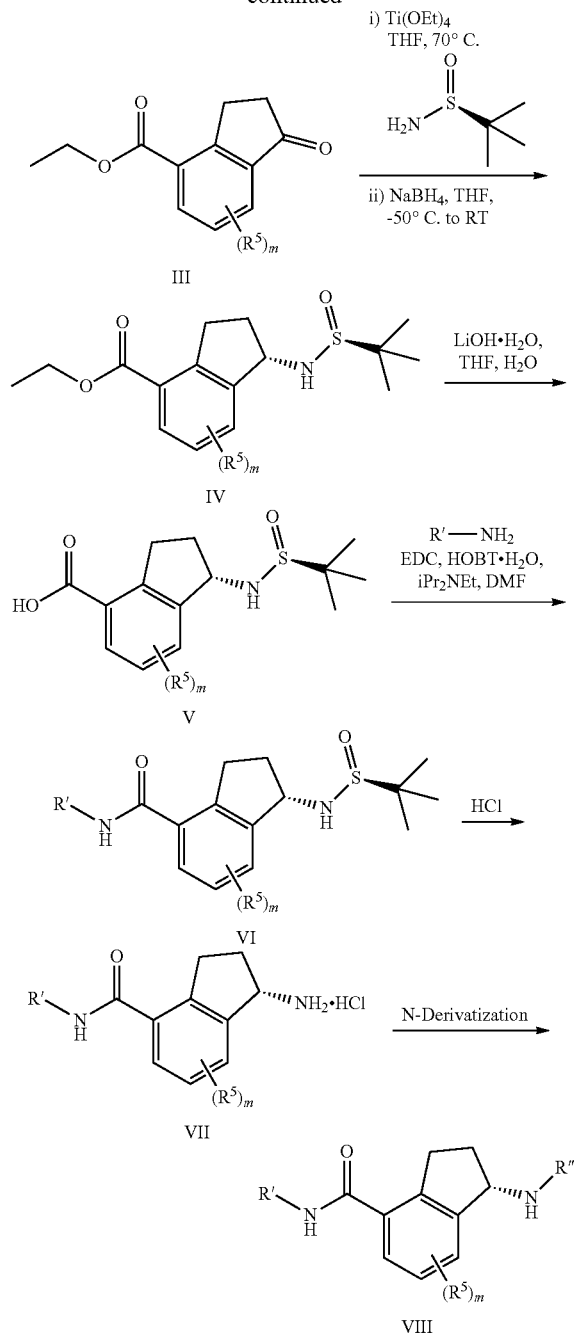

As illustrated in Scheme II, free amine XI can be protected with a base-stable group, such as but not limited to Boc (tert-butoxycarbonyl), to generate compound XII, which can be deprotected under basic hydrolytic conditions to provide the carboxylic acid XIII. The carboxylic acid in compound XIII can be converted to the corresponding amide XIV using standard amine coupling conditions, such as but not limited to HATU or EDC-HOBt in the presence of a tertiary amine, and removal of the amine protective group under acidic conditions provides the free amine VII, which can be N-derivatived using an electrophilic reagent, such as but not limited to a reactive halide, mesylate, triflate, carboxylic acid (such as a reactive heteroaryl-carboxylate, such as but not limited to an 1H-imidazole-1-yl-carboxylate), acid anhydride, arylating agent, isocyanate, and/or any other electrophilic reagent exemplified herein and/or known in the art, to yield VIII.

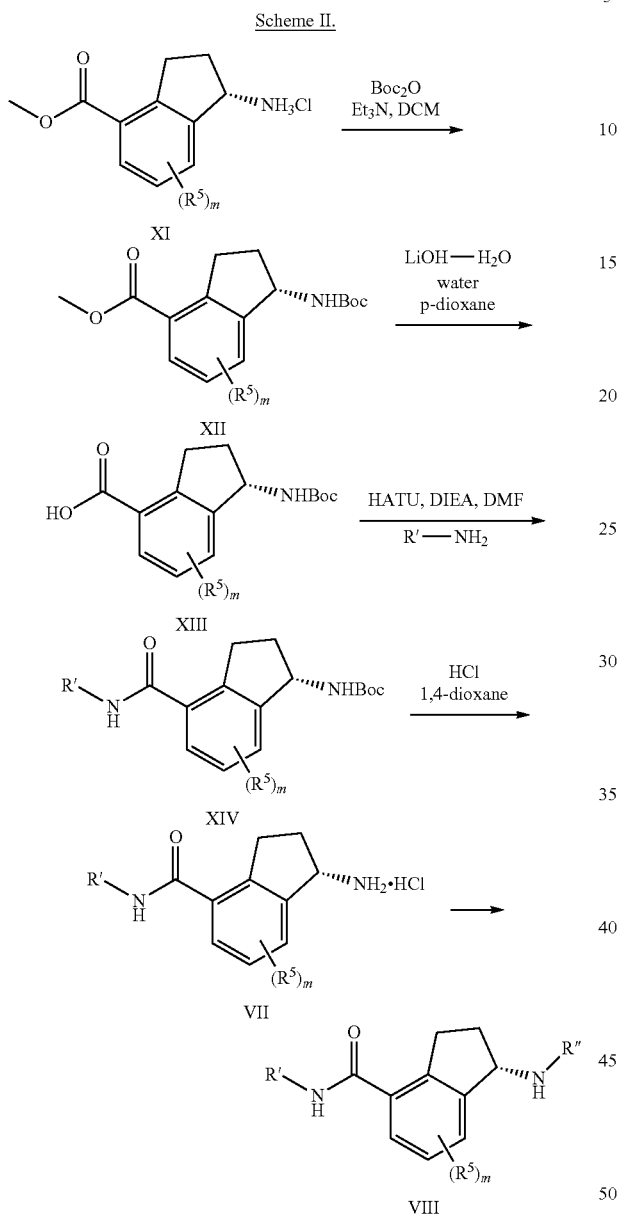

ketone group in XXII to an oxime (yielding compound XXIII), followed by reduction, using for example hydrogen gas in the presence of a metal catalyst or zinc metal in the presence of an acid (such as for example acetic acid), yields compound XXIV. The amine group in XXIV can be further N-derivatized using an electrophilic reagent, such as but not limited to a reactive halide, mesylate, triflate, carboxylic acid (such as a reactive heretoaryl-carboxylate, such as but not limited to an 1H-imidazole-1-yl-carboxylate), acid anhydride, arylating agent, isocyanate, and/or any other electrophilic reagent exemplified herein and/or known in the art.

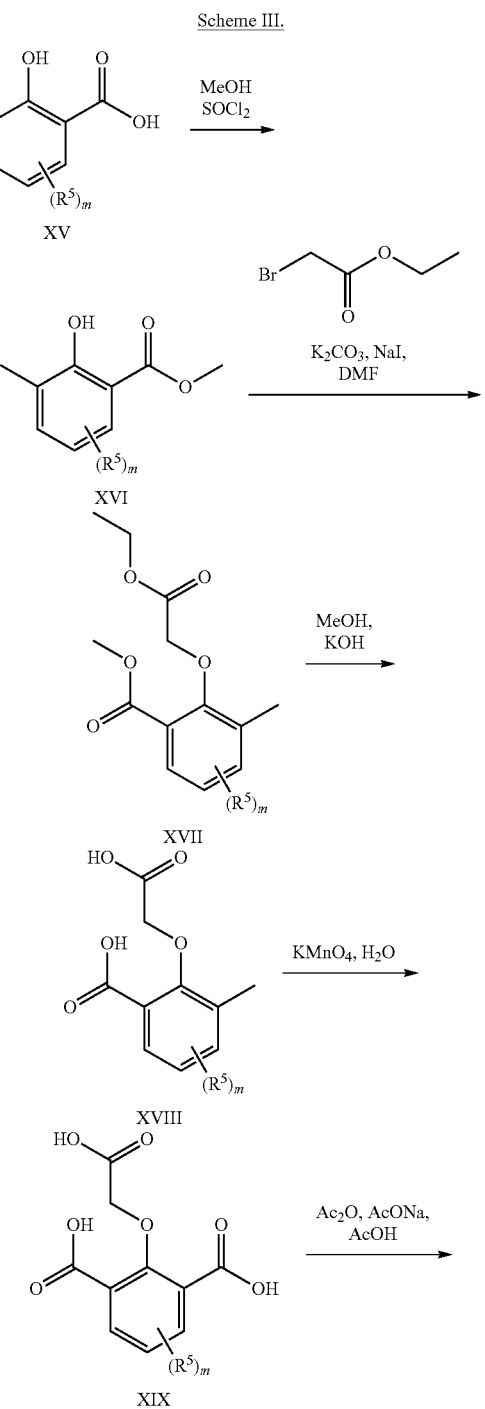

As illustrated in Scheme III, acid XV can be converted to the corresponding ester XVI, for example by treatment with an alcohol and thionyl chloride, and then coupled with a 2-bromo acetate under basic conditions to provide compound XVII, which can be hydrolyzed to provide the dicarboxylic acid XVIII, which upon oxidation yields the tricarboxylic acid XIX. Upon activation with an activating agent, such as but not limited to acetic anhydride, compound XIX can undergo cyclization to yield compound XX, which can be deprotected under acidic or basic conditions to yield compound XXI. The carboxylic acid group in XXI can be activated, in non-limiting examples by intermediate conversion to the corresponding aryl chloride or treatment with HATU or EDC-HOBt in the presence of a tertiary amine, to yield the corresponding amide XXII. Conversion of the

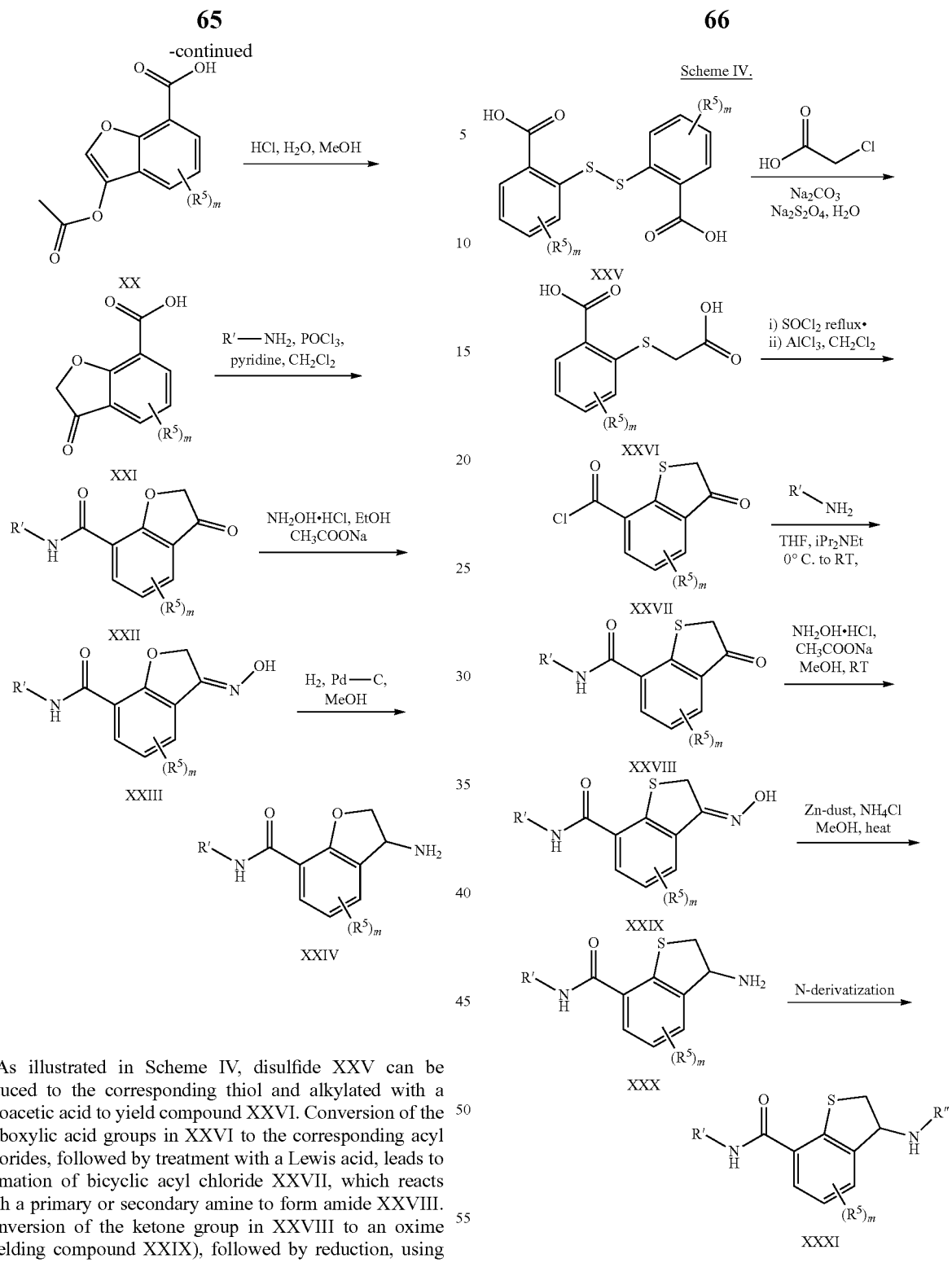

As illustrated in Scheme IV, disulfide XXV can be reduced to the corresponding thiol and alkylated with a haloacetic acid to yield compound XXVI. Conversion of the carboxylic acid groups in XXVI to the corresponding acyl chlorides, followed by treatment with a Lewis acid, leads to formation of bicyclic acyl chloride XXVII, which reacts with a primary or secondary amine to form amide XXVIII. Conversion of the ketone group in XXVIII to an oxime (yielding compound XXIX), followed by reduction, using for example hydrogen gas in the presence of a metal catalyst, or zinc metal in the presence of an acid (such as for example acetic acid), yields compound XXX. The amine group in XXX can be further N-derivatized using an electrophilic reagent, such as but not limited to a reactive halide, mesylate, triflate, carboxylic acid (such as a reactive heretoarylcarboxylate, such as but not limited to an 1H-imidazole-1-yl-carboxylate), acid anhydride, arylating agent, isocyanate, and/or any other electrophilic reagent exemplified herein and/or known in the art, to afford XXXI.

As illustrated in Scheme V, indene XXXII can be epoxidized under conditions known to those skilled in the art, including treatment with m-chloroperbenzoic acid, or Jacobsen's catalyst (N,N'-bis(3,5-di-tert-butylsalicylidene)-1,2-cyclohexanediaminomanganese(III) chloride) in the presence of an oxidant such as but not limited to sodium hypochloride (bleach), to yield compound XXXIII, which is optionally isolated as an enantiomerically enriched or pure form. Opening of the epoxide using an amine, such as but not limited to ammonia, yields amino alcohol XXXIV, wherein the amino group can be protected with a base-stable group, such as but not limited to Boc, to yield XXXV. The halo group in compound XXXV can be converted an ester group by, for example, a carbonylation reaction using carbon monoxide and an organometallic catalyst, such as but not limited to a Pd catalyst, such as but not limited to Pd(dppf)$_2$Cl$_2$, in the presence of a base, such as but not limited to a tertiary amine, thus yielding compound XXXVI. The ester group in compound XXXVI can be deprotected to the corresponding carboxylic acid XXXVII by treatment for example with an aqueous hydroxide solution. Compound XXXVII can be converted to the corresponding amide using standard coupling reagents, such as but not limited to HATU or EDC-HOBt in the presence of a tertiary amine. Removal of the amine-protecting group in compound XXXVIII provides the free amine XXXIX, which can be N-derivatised using an electrophilic reagent, such as but not limited to a reactive halide, mesylate, triflate, carboxylic acid (such as a reactive heteroaryl-carboxylate, such as but not limited to an 1H-imidazole-1-yl-carboxylate), acid anhydride, arylating agent, isocyanate, and/or any other electrophilic reagent exemplified herein and/or known in the art, to yield XL.

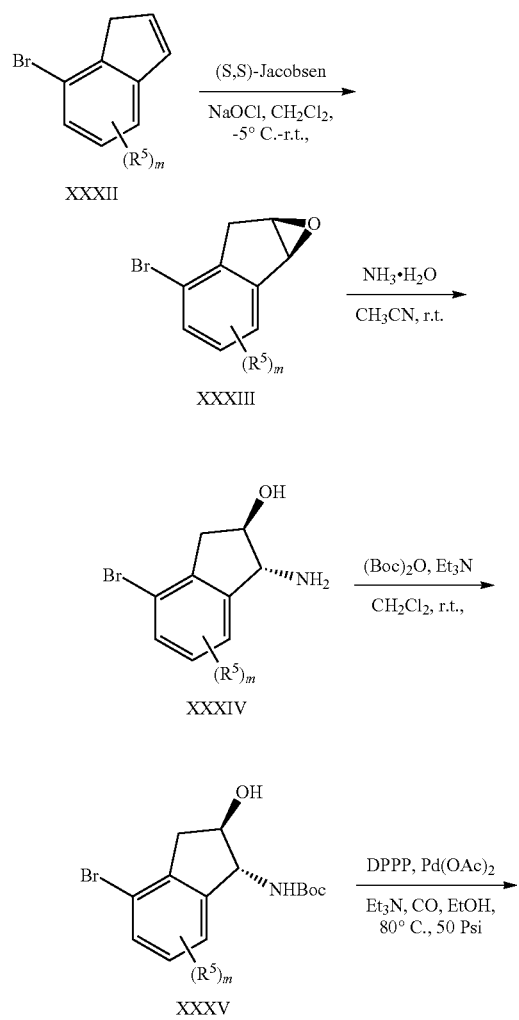

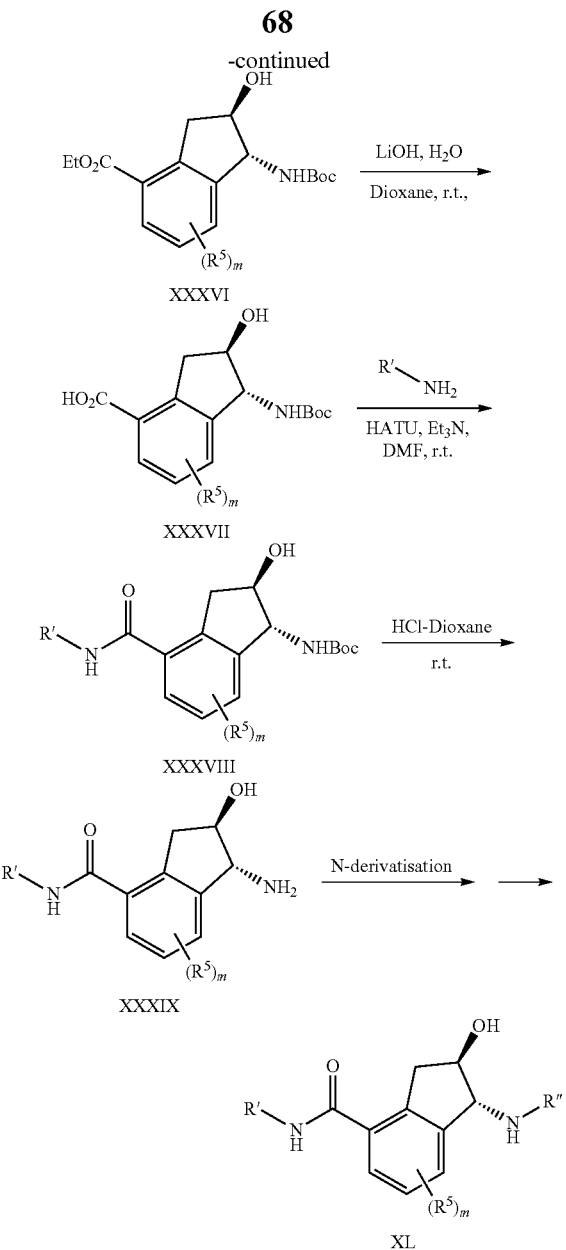

Methods

The invention provides a method of treating or preventing hepatitis virus infection in a subject. In certain embodiments, the infection comprises hepatitis B virus (HBV) infection. In other embodiments, the method comprises administering to the subject in need thereof a therapeutically effective amount of at least one compound of the invention. In yet other embodiments, the at least one compound of the invention is the only antiviral agent administered to the subject. In yet other embodiments, the at least one compound is administered to the subject in a pharmaceutically acceptable composition. In yet other embodiments, the subject is further administered at least one additional agent useful for treating the hepatitis infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In yet other embodiments, the subject is co-administered the at least one compound and the at least one additional agent. In yet other embodiments, the at least one compound and the at least one additional agent are coformulated.

The invention further provides a method of inhibiting expression and/or function of a viral capsid protein either directly or indirectly in a subject. In certain embodiments, the method comprises administering to the subject in need thereof a therapeutically effective amount of at least one compound of the invention. In other embodiments, the at least one compound is administered to the subject in a pharmaceutically acceptable composition. In yet other embodiments, the at least one compound of the invention is the only antiviral agent administered to the subject. In yet other embodiments, the subject is further administered at least one additional agent useful for treating HBV infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In yet other embodiments, the subject is co-administered the at least one compound and the at least one additional agent. In yet other embodiments, the at least one compound and the at least one additional agent are coformulated.

In certain embodiments, the subject is a mammal. In other embodiments, the mammal is a human.

The invention further provides methods of preparing compounds of the invention, using for examples synthetic transformations illustrated in Schemes I-V, and Schemes 1-17, or any experimental examples recited herein. For example, as an illustrative example, certain compounds of the invention can be prepared according to the procedure outlined in Scheme II. Compound VIII can be prepared by reacting free amine VII with an electrophilic reagent, such as but not limited to a reactive halide, mesylate, triflate, carboxylic acid, acid anhydride (such as a reactive heretoaryl-carboxylate, such as but not limited to an 1H-imidazole-1-yl-carboxylate), arylating agent, isocyanate, and/or any other electrophilic reagent exemplified herein and/or known in the art). Compound VII can be prepared by acidic deprotection of compound XIV. Compound XIV can be prepared by coupling the corresponding carboxylic acid XIII to an appropriate amine under amine coupling conditions, such as but not limited to HATU or EDC-HOBt in the presence of a tertiary amine. Compound XIII can be prepared by basic hydrolysis of the corresponding ester, such as but not limited to compound XII, which can be prepared from the corresponding amine XI by reaction with Boc (tert-butoxycarbonyl) anhydride or an equivalent reagent. It should be noted that the Boc group exemplified herein can be replaced by any other compatible based-stable, acid-sensitive group exemplified herein and/or known in the art.

Pharmaceutical Compositions and Formulations

The invention provides pharmaceutical compositions comprising at least one compound of the invention or a salt or solvate thereof, which are useful to practice methods of the invention. Such a pharmaceutical composition may consist of at least one compound of the invention or a salt or solvate thereof, in a form suitable for administration to a subject, or the pharmaceutical composition may comprise at least one compound of the invention or a salt or solvate thereof, and one or more pharmaceutically acceptable carriers, one or more additional ingredients, or any combinations of these. At least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous, or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring, and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and any combinations thereof. One such preservative is a combination of about 0.5% to 2.0% benzyl alcohol and 0.05-0.5% sorbic acid.

The composition may include an antioxidant and a chelating agent that inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non-ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 g to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as corn-starch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400). It is understood that similar type of film coating or polymeric products from other companies may be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (i.e., U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. For example, it should be present in an amount from about 0.0005% to about 5% of the composition; for example, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the compositions and/or formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods

The following procedures can be utilized in evaluating and selecting compounds that inhibit hepatitis B virus infection.

HepDE19 Assay with bDNA Quantitation of HBV rcDNA:

HepDE19 cell culture system is a HepG2 (human hepatocarcinoma) derived cell line that supports HBV DNA replication and cccDNA formation in a tetracycline (Tet)-regulated manner and produces HBV rcDNA and a detectable reporter molecule dependent on the production and maintenance of cccDNA (Guo, et al., 2007, J. Virol. 81:12472-12484).

HepDE19 (50,000 cells/well) were plated in 96-well collagen-coated tissue-culture treated microtiter plates in DMEM/F12 medium supplemented with 10% fetal bovine serum, 1% penicillin-streptomycin and 1 µg/mL tetracycline and incubated in a humidified incubator at 37° C. and 5% $CO_2$ overnight. Next day, the cells were switched to fresh medium without tetracycline and incubated for 4 hours at 37° C. and 5% $CO_2$. The cells were treated with fresh Tet-free medium with compounds at concentrations starting at 25 µM and a serial, ½ log, 8-point, titration series in duplicate. The final DMSO concentration in the assay was 0.5%. The plates were incubated for 7 days in a humidified incubator at 37° C. and 5% $CO_2$. Following a 7 day-incubation, the level of rcDNA present in the inhibitor-treated wells was measured using a Quantigene 2.0 bDNA assay kit (Affymetrix, Santa Clara, Calif.) with HBV specific custom probe set and manufacturers instructions. Concurrently, the effect of compounds on cell viability was assessed using replicate plates, plated at a density of 5,000 cells/well and incubated for 4 days, to determine the ATP content as a measure of cell viability using the cell-titer glo reagent (CTG; Promega Corporation, Madison, Wis.) as per manufacturer's instructions. The plates were read using a Victor luminescence plate reader (PerkinElmer Model 1420 Multilabel counter) and the relative luminescence units (RLU) data generated from each well was calculated as % inhibition of the untreated control wells and analyzed using XL-Fit module in Microsoft Excel to determine $EC_{50}$ and $EC_{90}$ (bDNA) and $CC_{50}$ (CTG) values using a 4-parameter curve fitting algorithm.

LCMS Methods:

LCMS Method A: Waters Acquity UPLC system employing a Waters Acquity UPLC BEH C18, 1.7 µm, 50×2.1 mm column with an aqueous acetonitrile based solvent gradient of 2-98% $CH_3CN/H_2O$ (0.05% TFA) over 9.5 mins. Flow rate=0.8 mL/min LCMS Method B: Waters Acquity UPLC system employing a Waters Acquity UPLC BEH C18, 1.7 µm, 50×2.1 mm column with an aqueous acetonitrile based solvent gradient of 2-98% $CH_3CN/H_2O$ (0.05% TFA) over 1.0 mins. Flow rate=0.8 mL/min LCMS Method C: Waters Acquity UPLC system employing a Waters Acquity UPLC BEH C18, 1.7 µm, 50×2.1 mm column with an aqueous component of 5 mM ammonium acetate in water containing 0.1% formic acid and an organic component of 0.1% formic acid in acetonitrile. Solvent events: 0-0.4 min, Isocratic 5% of (0.1% formic acid/acetonitrile); 0.4-0.8 min, Linear gradient of 5-35% of (0.1% formic acid/acetonitrile); 0.8-1.2 min, Linear gradient of 35-55% of (0.1% formic acid/acetonitrile); 1.2-2.5 min, Linear gradient of 55-100% of (0.1% formic acid/acetonitrile); 2.5-3.3 min, Isocratic 100% of (0.1% formic acid/acetonitrile). Flow rate=0.55 mL/min.

LCMS Method D: Waters Acquity UPLC system employing a Waters Acquity UPLC BEH C18, 1.7 µm, 50×2.1 mm column with an aqueous component of 2 mM ammonium acetate in water containing 0.1% formic acid and an organic component of 0.1% formic acid in acetonitrile. Solvent events: 0-0.4 min, Isocratic 5% of (0.1% formic acid/acetonitrile); 0.4-0.6 min, Linear gradient of 5-40% of (0.1% formic acid/acetonitrile); 0.6-1.2 min, Linear gradient of 40-60% of (0.1% formic acid/acetonitrile); 1.2-3 min, Linear gradient of 60-100% of (0.1% formic acid/acetonitrile); 2.5-3.0 min, Isocratic 100% of (0.1% formic acid/acetonitrile). Flow rate=0.55 mL/min.

LCMS Method H: Waters Acquity UPLC H class with Waters SQD 2 MS employing a Waters Acquity UPLC BEH C18, 1.7 µm, (50×2.1 mm) column with an aqueous component of 0.1% Formic acid in water and an organic component of 0.1% formic acid in acetonitrile. Solvent events: 0-0.3 min, Isocratic 3% (0.1% formic acid/acetonitrile); 0.3-2.2 min, Linear gradient of 3-98% (0.1% formic acid/acetonitrile); 2.2-3.2 min, Isocratic 98% of (0.1% formic acid/acetonitrile); 3.2-4.5 min, Isocratic 98% (0.1% formic acid/acetonitrile). Flow rate=0.6 mL/min.

LCMS Method I: Agilent 1200 series with 6130 Quadrupole LC/MS employing a XBridge C18 (4.6×100 mm) 3.5 µm column with an aqueous component of 10 mM Ammonium Bicarbonate in water and an organic component of acetonitrile. Solvent events: 0-2.0 min, Isocratic 10% (acetonitrile); 2.0-6.0 min, Linear gradient 10-98% (acetonitrile); 6.0-10.0 min, Isocratic 98% (acetonitrile); Flow rate=1.0 mL/min.

LCMS Method J: Agilent 1200 series with 6130 Quadrupole LC/MS employing a XBridge C18 (4.6×100 mm) 3.5 µm column with an aqueous component of 10 mM Ammonium Bicarbonate in water and an organic component of acetonitrile. Solvent events: 0-2.5 min, Isocratic 5% of (acetonitrile); 2.5-5.5 min, Linear gradient of 5-98% (acetonitrile); 5.5-10.0 min, Isocratic 98% (acetonitrile); Flow rate=1.0 mL/min.

HPLC Methods:

HPLC Method E: Waters 2695/2998 system employing a YMC Triart C18, 5 u, 150×4.6 mm column with an aqueous component of 0.1% formic acid in water and an organic component of 0.1% formic acid in acetonitrile. Solvent events: 0.4-7 min, Linear gradient of 10-90% of (0.1% formic acid/acetonitrile); 7-9 min, Linear gradient of 90-95% of (0.1% formic acid/acetonitrile); 9-13 kin, Isocratic 95% of (0.1% formic acid/acetonitrile). Flow rate=1 mL/min.

HPLC Method F: Waters 2695/2998 system employing a Xbridge C18, 5µ, 150×4.6 mm column with an aqueous component of 0.1% ammonia in water and an organic component of 0.1% ammonia in acetonitrile. Solvent events: 0.4-7 min, Linear gradient of 10-90% of (0.1% formic acid/acetonitrile); 7-9 min, Linear gradient of 90-95% of (0.1% formic acid/acetonitrile); 9-13 min, Isocratic 95% of (0.1% formic acid/acetonitrile). Flow rate=1 mL/min.

HPLC Method G: Shimadzu 20AB system employing a Luna C18, 5µ, 50×2 mm column with an aqueous component of 0.0375% TFA in water and an organic component of 0.0375% TFA in acetonitrile. Solvent events: 0.01-4 min, Linear gradient of 10-80% of (0.0375% TFA in acetonitrile); 4-4.9 min, isocratic 80% of (0.0375% TFA in acetonitrile); 4.90-4.92 min, Linear gradient of 80-10% of (0.0375% TFA in acetonitrile); 4.92-5.50 min, Isocratic 10% of (0.0375% TFA in acetonitrile). Flow rate=1 mL/min.

HPLC Method K: Waters alliance 2695/2996 system employing a XSelect CSH C18 (4.6×150 mm) 3.5 µm column with an aqueous component of 10 mM ammonium bicarbonate and an organic component of acetonitrile. Solvent events: 0-1.5 min, Isocratic 5% (acetonitrile); 1.5-3.0 min, Linear gradient of 5-15% (acetonitrile); 3.0-7.0 min, Linear gradient of 15-55% (acetonitrile); 7.0-10.0 min, Linear gradient of 55-95% (acetonitrile); 10.0-16.0 min, Linear gradient of 95-100% (acetonitrile). Flow rate=1.0 mL/min.

HPLC Method L: Waters alliance 2695/2996 system employing a XSelect C18 (4.6×150 mm) 3.5 µm column with an aqueous component of 10 mM ammonium bicarbonate in water and an organic component of acetonitrile. Solvent events: 0-1.5 min, Isocratic 5% (acetonitrile); 1.5-3.0 min, Linear gradient of 5-15% (acetonitrile); 3.0-7.0 min, Linear gradient of 15-55% (acetonitrile); 7.0-10.0 min, Linear gradient of 55-95% (acetonitrile); 10.0-16.0 min, Linear gradient of 95-100% (acetonitrile). Flow rate=1.0 mL/min.

HPLC Method M: Waters alliance 2695/2996 PDA employing an Atlantis T3 3.0 µm (4.6×150 mm) column with an aqueous component of 0.1% Formic acid in water and an organic component of acetonitrile. Solvent events: 0-1.5 min, Isocratic 5% (acetonitrile); 1.5-3.0 min, Linear gradient of 5-15% (acetonitrile); 3.0-7.0 min, Linear gradient of 15-55% (acetonitrile); 7.0-10.0 min, Linear gradient of 55-95% (acetonitrile); 10.0-16.0 min, Linear gradient of 95-100% (acetonitrile). Flow rate=1.0 mL/min.

HPLC Method N: Waters alliance HPLC 2695/2996 employing an Atlantis T3 3.0 µm (4.6×150 mm) column with an aqueous component of 10 mM ammonium acetate in water and an organic component of acetonitrile. Solvent events: 0-1.5 min, Isocratic 5% (acetonitrile); 1.5-3.0 min, Linear gradient of 5-15% (acetonitrile); 3.0-7.0 min, Linear gradient of 15-55% (acetonitrile); 7.0-10.0 min, Linear gradient of 55-95% (acetonitrile); 10.0-16.0 min, Linear gradient of 95-100% (acetonitrile). Flow rate=1.0 mL/min.

Example 1: Non-Limiting Synthesis of Selected 1-(Substituted Amino)-Dihydroindene-4-Carboxamides (Scheme 1)

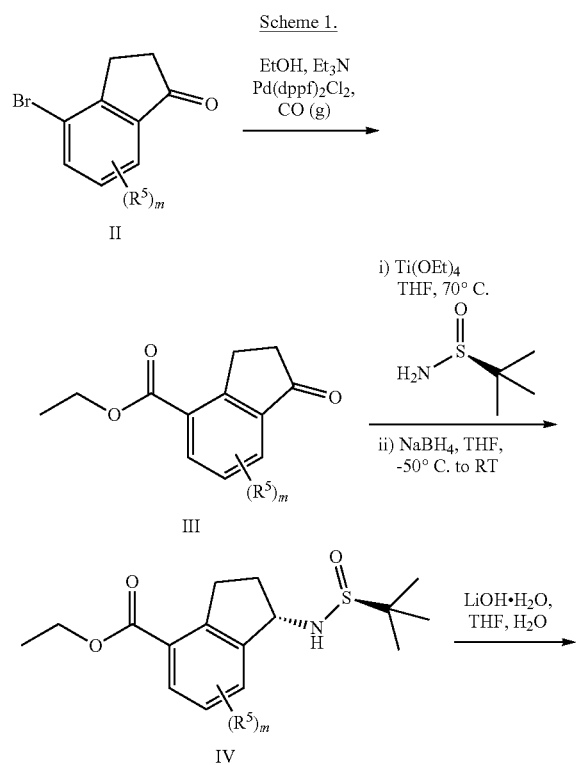

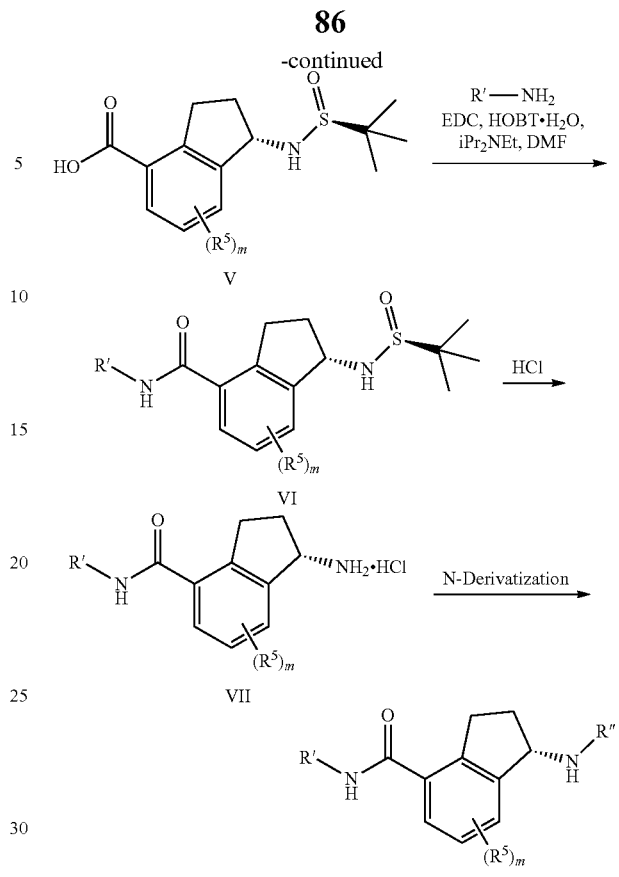

Non-Limiting Illustration of Scheme 1

Ethyl 1-oxo-2,3-dihydro-1H-indene-4-carboxylate (IIIa)

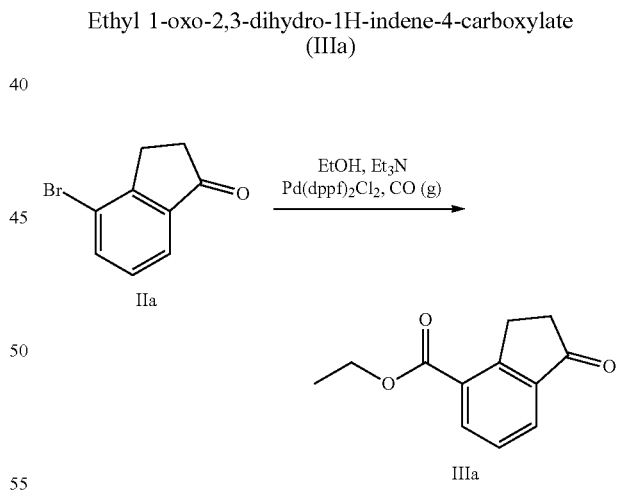

To a solution of 5.0 g (26.3 mmol. 1.0 eq.) of 4-bromo-2,3-dihydro-1H-inden-1-one (IIa) in 60 mL of ethanol in a pressure vessel was added 49.2 mL (355 mmol, 15 eq.) of trimethylamine. The mixture was degassed with argon for 15 minutes at room temperature and 2.9 g (3.55 mmol, 0.15 eq.) of 1,1-bis(diphenylphosphino) ferrocene] dichloropalladium (II) complex with dichloromethane was added. The mixture was degassed for 5 minutes further, and then purged with carbon monoxide gas. The reaction mixture was then heated at 100° C. under 50 psi pressure of carbon monoxide for 16 h. The reaction mixture was allowed to cool to room temperature and filtered through CELITE®. The filtrate was then concentrated and redissolved in 100 mL of ethyl acetate. The organic solution was washed with 2×50 mL of water, followed by 100 mL of brine. The organic phase was dried (Na$_2$SO$_4$) and the solvent was removed in vacuo. The residue was purified by flash chromatography (SiO$_2$, eluting with a linear gradient of 0-12% EtOAc/hexanes) to provide 3.6 g (17.6 mmol, 74%) ethyl 1-oxo-2,3-dihydro-1H-indene-4-carboxylate (IIIa).

Ethyl (S)-1-(((S)-tert-butylsulfinyl) amino)-2,3-dihydro-1H-indene-4-carboxylate (IVa)

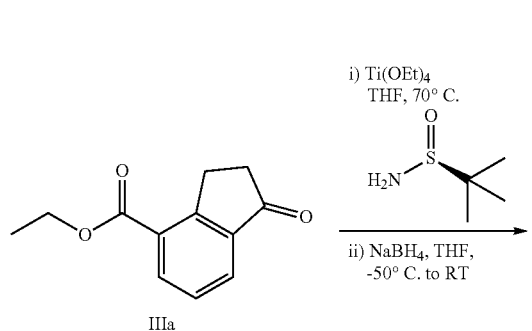

To a solution of 4.0 g (19.6 mmol, 1.0 eq.) of ethyl 1-oxo-2,3-dihydro-1H-indene-4-carboxylate (IIIa) and 7.14 g (58.0 mmol, 3.0 eq.) of (S)-2-methylpropane-2-sulfinamide in 100 mL of anhydrous THF at room temperature was added 15.6 g (68.6 mmol, 3.5 eq.) of titanium tetraethoxide. The reaction vessel was sealed and heated to 70° C. for 5 h. The mixture was allowed to cool to room temperature and then further cooled to −50° C. under an argon atmosphere, and 2.19 g (58 mmol, 3.0 eq) of sodium borohydride was then added portionwise. The reaction mixture was allowed to warm to room temperature over 3 h, and then stirred at room temperature for a further 2 h. The reaction mixture was quenched by the addition of 100 mL of 10% citric acid in water, and the mixture was extracted with 3×100 mL of ethyl acetate. The combined organic extracts were washed with 50 mL of water followed by 50 mL of brine. The organic phase was dried (Na$_2$SO$_4$), and the solvent was removed in vacuo to provide the crude mixture of diastereoisomers. The residue was purified by flash chromatography (SiO$_2$, eluting with a linear gradient of 0-7% EtOAc/hexanes) to provide 2.0 g (6.45 mmol, 33%) of ethyl (S)-1-(((S)-tert-butylsulfinyl) amino)-2,3-dihydro-1H-indene-4-carboxylate (IVa).

(S)-1-(((S)-tert-Butylsulfinyl)amino)-2,3-dihydro-1H-indene-4-carboxylic Acid (IVa)

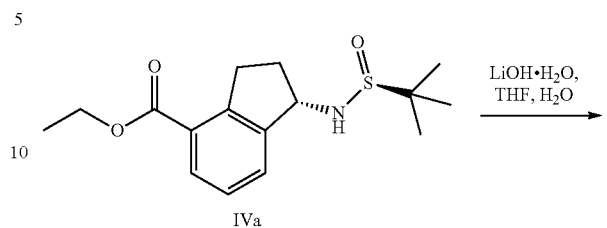

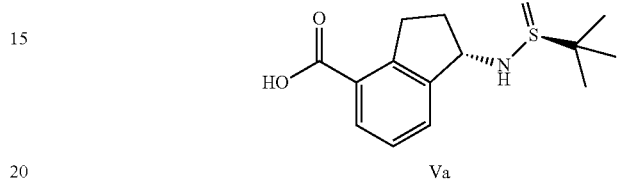

To a solution of 2.0 g (6.45 mmol, 1.0 eq.) of ethyl (S)-1-(((S)-tert-butylsulfinyl)amino)-2,3-dihydro-1H-indene-4-carboxylate in 10 mL of THF was added a solution of 1.08 g of lithium hydroxide monohydrate (25.7 mmol, 4.0 eq.) in 3 mL of water. The mixture was stirred at room temperature for 3 h. The solvent was removed in vacuo, and the residue was redissolved in water and cooled to 0° C. The aqueous solution was acidified with a 10% aqueous citric acid solution. The resulting precipitate was collected by filtration and dried under high vacuum to provide 1.2 g (3.14 mmol, 66%) of (S)-1-(((S)-tert-butylsulfinyl) amino)-2,3-dihydro-1H-indene-4-carboxylic acid (Va).

(S)-1-(((S)-tert-Butylsulfinyl)amino)-N-(3,4-difluorophenyl)-2,3-dihydro-1H-indene-4-carboxamide (VIa)

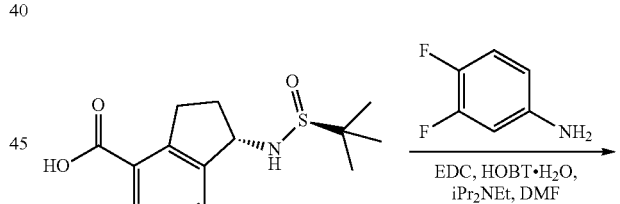

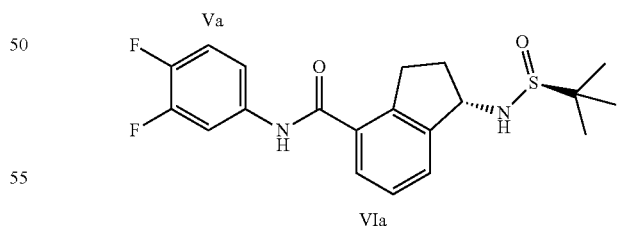

To a solution of 1.0 g (3.5 mmol, 1.0 eq.) of (S)-1-(((S)-tert-butylsulfinyl)amino)-2,3-dihydro-1H-indene-4-carboxylic acid in 10 mL of DMF at 0° C. were added 0.70 g (4.5 mmol, 1.3 eq.) of 1-hydroxybenzotriazole hydrate and 1.0 g (5.2 mmol, 1.5 eq.) of 1-ethyl-3-(3-dimethylamino propyl) carbodiimide hydrochloride. The resulting mixture was stirred at 0° C. for 30 min, and 1.8 mL (10.0 mmol, 3.0 eq.) of N,N-diisopropylethylamine and 0.55 g (4.2 mmol, 1.2 eq.) of 3,4-difluoroaniline were added. The reaction mixture was allowed to warm to room temperature and stirred for 10 h. The mixture was then poured into 100 mL of ice water and extracted with 3×100 mL of ethyl acetate. The combined organic extracts were dried (Na$_2$SO$_4$), and the solvent was removed in vacuo. The residue was purified by flash chromatography (SiO$_2$, eluting with a linear gradient of 0-17% EtOAc/hexanes) to provide 0.7 g (1.78 mmol, 50%) of (S)-1-(((S)-tert-butylsulfinyl)amino)-N-(3,4-difluorophenyl)-2,3-dihydro-1H-indene-4-carboxamide (VIa).

(S)-1-Amino-N-(3,4-difluorophenyl)-2,3-dihydro-1H-indene-4-carboxamide Hydrochloride (VIIa)

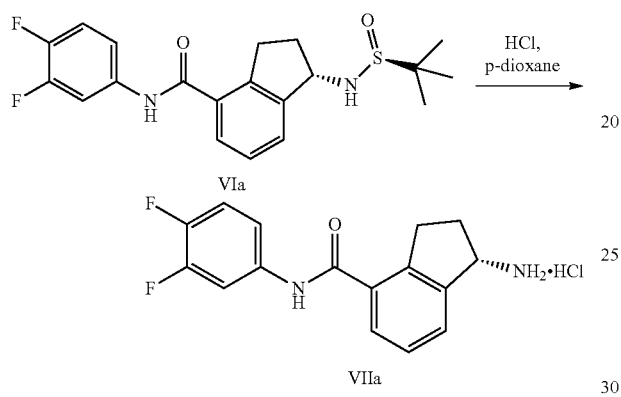

To a solution of 0.7 g (1.78 mmol, 1.0 eq.) of (S)-1-(((S)-tert-butylsulfinyl)amino)-N-(3,4-difluorophenyl)-2,3-dihydro-1H-indene-4-carboxamide (Via) in 10 mL of 1,4-dioxane was added 10 mL of a solution of 4 M HCl in 1,4-dioxane. The mixture was allowed to stir at room temperature for 30 minutes, and the solvent was removed in vacuo. The residue was triturated with diethyl ether to provide 0.43 g (1.32 mmol, 69%) of (S)-1-amino-N-(3,4-difluorophenyl)-2,3-dihydro-1H-indene-4-carboxamide hydrochloride (VIIa).

O-Methyl, N—S)-(4-((3,4-difluorophenyl)carbamoyl)-2,3-dihydro-1H-inden-1-yl) carbamate (1)

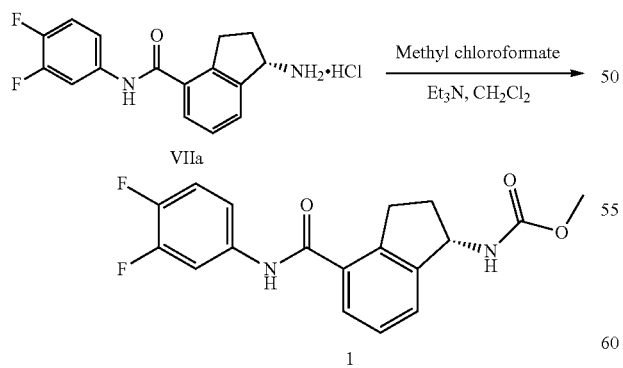

To a solution of 100 mg (0.30 mmol, 1.0 eq.) of (S)-1-amino-N-(3,4-difluorophenyl)-2,3-dihydro-1H-indene-4-carboxamide hydrochloride (VIIa) in 5 mL of methylene chloride at 0° C. was added 0.18 mL (0.13 mmol, 3.0 eq.) of triethylamine followed by 35 μL (0.45 mmol, 1.5 eq.) of methyl chloroformate. The mixture was allowed to warm to room temperature and stirred for 1 h. The mixture was then diluted with 30 mL of ethyl acetate and washed with 30 mL of water, followed by 30 mL of brine. The organic phase was dried (Na$_2$SO$_4$), and the solvent was removed in vacuo. The residue was purified by flash chromatography (SiO$_2$, eluting with a linear gradient of 0-2% methanol/methylene chloride) to provide 60 mg (0.18 mmol, 57%) of O-methyl, N—(S)-(4-((3,4-difluorophenyl)carbamoyl)-2,3-dihydro-1H-inden-1-yl) carbamate (1). LCMS: m/z found 347.2 [M+H]$^+$, RT=1.94 min (Method D); HPLC: RT=7.14 min (Method F); $^1$H NMR (400 MHz, DMSO-d$_6$): δ 10.42 (s, 1H), 7.88-7.94 (m, 1H), 7.64 (d, 1H), 7.57 (d, 1H), 7.33-7.51 (m, 4H), 5.05 (q, 1H), 3.59 (s, 3H), 3.11-3.17 (m, 1H), 2.89-3.10 (m, 1H), 2.37-2.41 (m, 1H), 1.78-1.83 (m, 1H).

Non-Limiting Illustration of Scheme 1

4-Bromo-7-fluoro-2,3-dihydro-1H-inden-1-one (IIb)

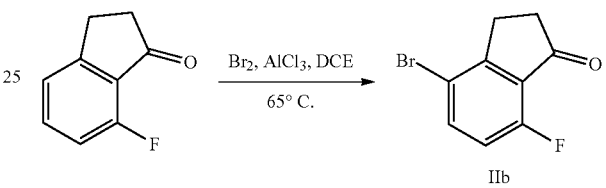

To a solution of 78.8 g (591 mmol, 2.5 eq.) of aluminum trichloride in 600 mL of 1,2-dichloroethane at room temperature were added 35.5 g (236 mmol, 1.0 eq.) of 7-fluoro-2,3-dihydro-1H-inden-1-one and 12.8 mL (248.25 mmol, 1.05 eq) of bromine. The resulting mixture was then heated to 65° C. for 2 h. The mixture was allowed to cool to room temperature, and then poured into a mixture of ice and 700 mL of 1 M HCl. The mixture was extracted with 1.4 L of MTBE, and the organic phase was dried (Na$_2$SO$_4$). The solvent was removed in vacuo and the residue purified by flash chromatography (SiO$_2$, eluting with a linear gradient of 1-20% ethyl acetate/petroleum ether) to provide 46.2 g (193 mmol, 82%) of 4-bromo-7-fluoro-2,3-dihydro-1H-inden-1-one (IIb).

Ethyl 7-fluoro-1-oxo-2,3-dihydro-1H-indene-4-carboxylate (IIIb)

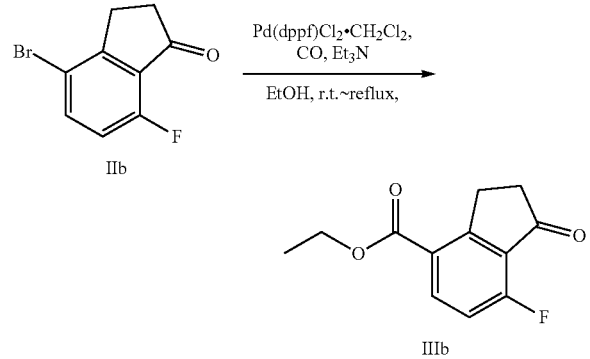

A mixture of 25.5 g (111.33 mmol, 1.0 eq.) of 4-bromo-7-fluoro-2,3-dihydro-1H-inden-1-one (IIb), 8.30 g (10.16 mmol, 0.09 eq.) of Pd(dppf)Cl$_2$.CH$_2$Cl$_2$, and 189 mL (1.36 mol, 12.3 eq.) of trimethylamine in 500 mL of ethanol was degassed and purged with carbon monoxide gas (3 times). The mixture was then stirred at 80° C. for 16 hours under 50 psi of carbon monoxide. On cooling to room temperature, the mixture was filtered, and the solvent was removed in vacuo. The residue was redissolved in 500 mL of methylene chloride and washed with 300 mL of water, followed by 300 mL of brine. The organic phase was dried (Na$_2$SO$_4$), filtered and the solvent was removed in vacuo. The residue was crystallized in 200 mL of 2-isopropoxypropane to provide 24.2 g (108.9 mmol, 98%) of ethyl 7-fluoro-1-oxo-2,3-dihydro-1H-indene-4-carboxylate (IIIb). $^1$H NMR (DMSO-d$_6$, 400 MHz): δ 8.24-8.21 (m, 1H), 7.32-7.28 (m, 1H), 4.34-4.28 (q, 2H), 3.36-3.35 (m, 2H), 2.67 (t, 2H), 1.33 (t, 3H).

N-(3-Chloro-4-fluorophenyl)-7-fluoro-1-oxo-2,3-dihydro-1H-indene-4-carboxamide (251)

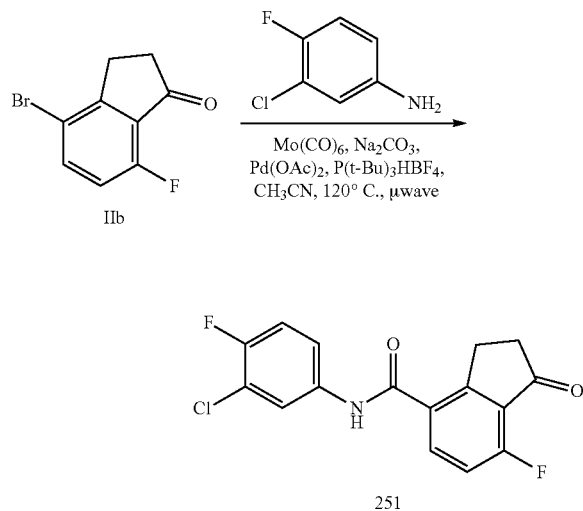

To a solution of 0.50 g (2.20 mmol, 1.0 eq.) of 4-bromo-7-fluoro-2,3-dihydro-1H-inden-1-one (IIb) in 10 mL of acetonitrile in a microwave vial was added 0.63 g (4.40 mmol, 2.0 eq.) of 3-chloro-4-fluoroaniline followed by 0.27 g (4.40 mmol, 2.0 eq.) of sodium carbonate and 0.58 g (2.20 mmol, 1.0 eq.) of molybdenum hexacarbonyl. The reaction mixture was degassed with nitrogen for 10 min and 49 mg (0.22 mmol, 0.1 eq.) of palladium(II) acetate was added followed by 63 mg (0.22 mmol, 0.1 eq.) of P(t-Bu)$_3$HBF$_4$. The mixture was subjected to microwave irradiation maintaining a reaction temperature of 120° C. for 2 h. The mixture was diluted with 50 mL of water and extracted with 3×50 mL of ethyl acetate. The combined organic extracts were washed with 50 mL of brine, dried (Na$_2$SO$_4$), filtered and the solvent was removed in vacuo. The residue was purified by flash chromatography (SiO$_2$, eluting with a linear gradient of 10-40% ethyl acetate/petroleum ether) to provide N-(3-chloro-4-fluorophenyl)-7-fluoro-1-oxo-2,3-dihydro-1H-indene-4-carboxamide (251). LCMS: m/z found 322.2/324.2 [M+H]$^+$, RT=4.05 min (Method A); $^1$H NMR (500 MHz, DMSO-d$_6$): δ 10.58 (s, 1H), 8.09 (dd, 1H), 8.06 (dd, 1H), 7.68-7.65 (m, 1H), 7.44 (dd, 1H), 7.37 (dd, 1H), 3.36-3.34 (m, 2H), 2.70-2.67 (m, 2H).

Ethyl (S)-1-(((S)-tert-butylsulfinyl)amino)-7-fluoro-2,3-dihydro-1H-indene-4-carboxylate (IVb)

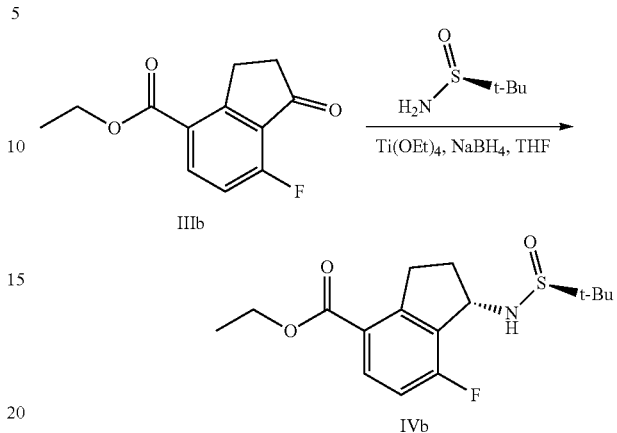

To a solution of 5.45 g (45.0 mmol, 1.0 eq.) of (S)-2-methylpropane-2-sulfinamide in 80 mL of THF under an argon atmosphere was added 14 mL (67.5 mmol, 1.5 eq.) of titanium tetraethoxide. The mixture was stirred at 25° C. for 0.5 h, and 10.0 g (45.00 mmol, 1.0 eq.) of ethyl 7-fluoro-1-oxo-2,3-dihydro-1H-indene-4-carboxylate (IIIb) was added in one portion. The mixture was heated to 65° C. for 16 h and then allowed to cool to room temperature. The mixture was diluted with 80 mL of THF and further cooled to −40° C., and 5.11 g (135.00 mmol, 3.0 eq.) of sodium borohydride was added in one portion. The resulting mixture was stirred at −40° C. for 1 h, allowed to warm to room temperature, and then stirred for a further 3 h. The mixture was cooled to 5° C., and 20 mL of 10% aqueous solution of citric acid were added slowly. The mixture was stirred for 16 hours, and then filtered. The filtrate was concentrated in vacuo, and the residue was purified by flash column chromatography (SiO$_2$, eluting with a linear gradient of 5-50% ethyl acetate/petroleum ether) to provide 2.4 (6.8 mmol, 15%) of ethyl (S)-1-(((S)-tert-butylsulfinyl)amino)-7-fluoro-2,3-dihydro-1H-indene-4-carboxylate (IVb).

(S)-1-(((S)-tert-Butylsulfinyl)amino)-7-fluoro-2,3-dihydro-1H-indene-4-carboxylic Acid (Vb)

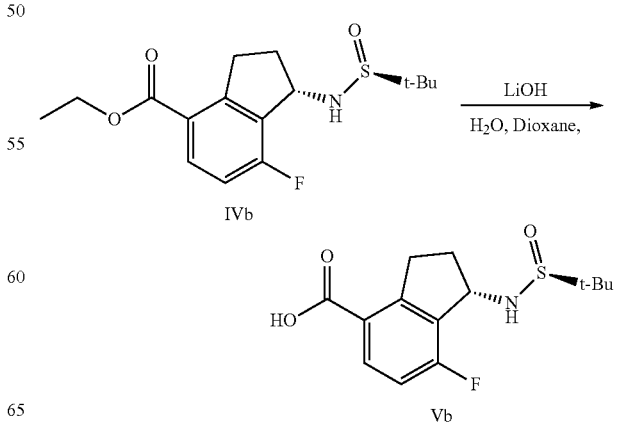

To a solution of 2.4 g (7.3 mmol, 1.0 eq.) of ethyl (S)-1-(((S)-tert-butylsulfinyl)amino)-7-fluoro-2,3-dihydro-1H-indene-4-carboxylate (IVb) in 20 mL of p-dioxane was added a solution of 0.92 g (22.0 mmol, 3.0 eq.) of lithium hydroxide monohydrate in 5 mL of water, and the mixture was stirred at 25° C. for 16 h. The mixture was diluted with 30 mL of water and then the organic solvent was removed in vacuo. The mixture was adjusted to pH 3 with aqueous 3 M HCl and then extracted with 2×80 mL of ethyl acetate. The combined organic extracts were dried ($Na_2SO_4$), filtered, and the solvent removed in vacuo to provide 2.0 g (6.68 mmol, 91%) of (S)-1-(((S)-tert-butylsulfinyl)amino)-7-fluoro-2,3-dihydro-1H-indene-4-carboxylic acid (Vb).

(S)-1-(((S)-tert-Butylsulfinyl)amino)-N-(3-chloro-4-fluorophenyl)-7-fluoro-2,3-dihydro-1H-indene-4-carboxamide (VId) (280)

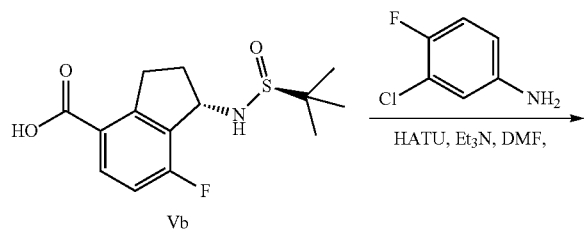

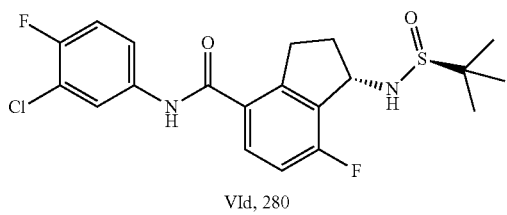

VId, 280

To a solution of 0.60 g (2.0 mmol, 1.0 eq.) of (S)-1-(((S)-tert-butylsulfinyl)amino)-7-fluoro-2,3-dihydro-1H-indene-4-carboxylic acid (Vb) in 6 mL of DMF was added 0.91 g (2.41 mmol, 1.2 eq.) of 1-[bis(dimethylamino)methylene]-1H-1,2,3-triazolo[4,5-b]pyridinium 3-oxide hexafluorophosphate (HATU), followed by 0.83 mL (6.0 mmol, 3.0 eq.) of trimethylamine and 0.35 g (2.4 mmol, 1.2 eq.) of 3-chloro-4-fluoro-aniline. The mixture was stirred at 25° C. for 16 h, and then diluted with 20 mL of water. The mixture was extracted with 2×20 mL of methylene chloride, and the combined organic extracts were washed with 30 mL of water. The organic solution was dried ($Na_2SO_4$), filtered and the solvent was removed in vacuo. The residue was purified by flash chromatography ($SiO_2$, eluting with a linear gradient of 2-10% methanol/methylene chloride) to provide 0.66 g (1.55 mmol, 77%) of (S)-1-(((S)-tert-butylsulfinyl)amino)-N-(3-chloro-4-fluorophenyl)-7-fluoro-2,3-dihydro-1H-indene-4-carboxamide (280). LCMS: m/z found 427.2/429.2 [M+H]$^+$, RT=4.74 min (Method A); $^1$H NMR (400 MHz, DMSO-$d_6$): δ 10.39 (s, 1H), 8.00-8.03 (m, 1H), 7.68-7.72 (m, 1H), 7.62-7.65 (m, 1H), 7.36-7.41 (m, 1H), 7.13-7.17 (m, 1H), 5.67-5.69 (d, 1H), 4.92-4.95 (m, 1H), 3.29-3.34 (m, 1H), 3.02-3.08 (m, 1H), 2.26-2.48 (m, 1H), 2.09-2.15 (m, 1H), 1.06 (s, 9H).

(S)-1-(((R)-tert-Butylsulfinyl)amino)-N-(3-chloro-4-fluorophenyl)-7-fluoro-2,3-dihydro-1H-indene-4-carboxamide (281)

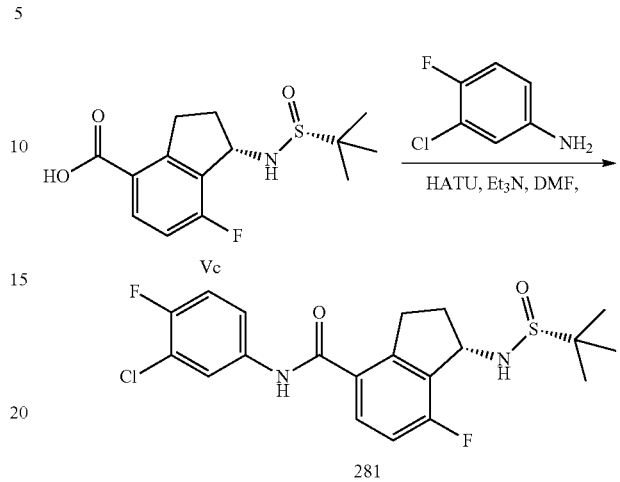

(S)-1-(((R)-tert-Butylsulfinyl)amino)-N-(3-chloro-4-fluorophenyl)-7-fluoro-2,3-dihydro-1H-indene-4-carboxamide (281) was synthesized in similar manner as described above from (S)-1-(((R)-tert-butylsulfinyl)amino)-7-fluoro-2,3-dihydro-1H-indene-4-carboxylic acid (Vc) (derived from (R)-2-methylpropane-2-sulfinamide) and 3-chloro-4-fluoroaniline. LCMS: m/z found 427.2/429.2 [M+H]$^+$, RT=4.58 min (Method A); $^1$H NMR (400 MHz, DMSO-$d_6$): δ 10.37 (s, 1H), 8.01-8.03 (m, 1H), 7.67-7.70 (m, 1H), 7.61-7.64 (m, 1H), 7.36-7.43 (m, 1H), 7.11-7.16 (m, 1H), 5.60-5.63 (d, 1H), 4.89-4.95 (m, 1H), 3.24-3.30 (m, 1H), 3.00-3.05 (m, 1H), 3.35-2.47 (m, 1H), 2.07-2.11 (m, 1H), 1.08 (s, 9H).

(S)-1-Amino-N-(3-chloro-4-fluorophenyl)-7-fluoro-2,3-dihydro-1H-indene-4-carboxamide (VIId, 13)

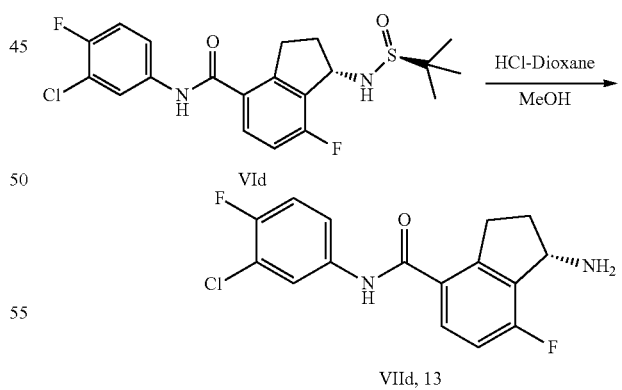

To a solution of 0.55 g (1.29 mmol, 1.0 eq.) of (S)-1-(((S)-tert-butylsulfinyl)amino)-N-(3-chloro-4-fluorophenyl)-7-fluoro-2,3-dihydro-1H-indene-4-carboxamide (VId) in 5 mL of methanol was added 5 mL of a 4 M solution of HCl in p-dioxane. The mixture was stirred at room temperature for 2 h. Volatiles were removed in vacuo, and the residue was redissolved in 30 mL of methylene chloride. The solution was washed with 20 mL of sat. $NaHCO_3$ followed by 20 mL of water, dried ($Na_2SO_4$), filtered and the solvent removed in vacuo. The residue was purified by flash chromatography ($SiO_2$, eluting with a linear gradient of 2-10% methanol/methylene chloride) to provide 0.25 g (0.76 mmol, 59%) of (S)-1-amino-N-(3-chloro-4-fluorophenyl)-7-fluoro-2,3-dihydro-1H-indene-4-carboxamide (VIId, 13). LCMS: m/z found 323.1, [M+H]$^+$; HPLC: RT=1.80 min (Method G).

O-Methyl, N—(S)-(4-((3-chloro-4-fluorophenyl) carbamoyl)-7-fluoro-2,3-dihydro-1H-inden-1-yl) carbamate (19)

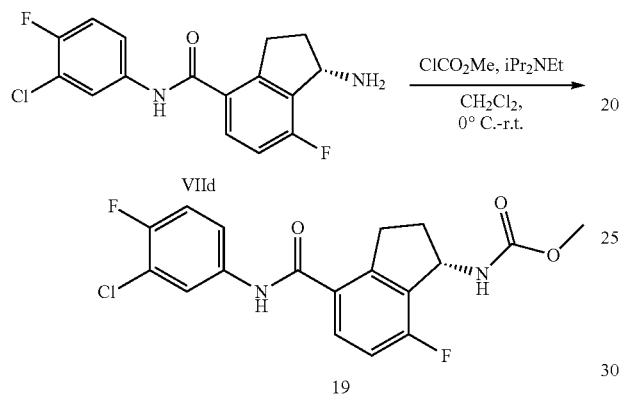

To a solution of 125 mg (0.39 mmol, 1.0 eq.) of (S)-1-amino-N-(3-chloro-4-fluorophenyl)-7-fluoro-2,3-dihydro-1H-indene-4-carboxamide (VIId) in 1 mL of methylene chloride at 0° C. were added 203 μL (1.16 mmol, 3.0 eq.) of N,N-diisopropylethyl amine and 36 μL (0.46 mmol, 1.2 eq.) of methyl chloroformate. The mixture was stirred at room temperature for 16 h. The resulting precipitate was collected by filtration, and the solids were washed with 2×2 mL of methanol. The solids were then stirred in 5 mL of water for 10 min. The suspension was filtered, washed with 2×2 mL of water and dried under high vacuum to provide 87 mg, (0.22 mmol, 57%) of O-methyl, N—(S)-(4-((3-chloro-4-fluorophenyl)carbamoyl)-7-fluoro-2,3-dihydro-1H-inden-1-yl) carbamate (19). LCMS: m/z found 381.1, [M+H]$^+$; HPLC: RT=3.05 min (Method G); $^1$H NMR (DMSO-$d_6$, 400 MHz): δ10.37 (bs, 1H), 8.03 (d, 1H), 7.68-7.63 (m, 3H), 7.41-7.39 (m, 1H), 7.13 (m, 1H), 5.27-5.21 (m, 1H), 3.58 (s, 3H), 3.30-3.19 (m, 1H), 3.01-2.99 (m, 1H), 2.41-2.36 (m, 1H), 1.87-1.86 (m, 1H).

O-Methyl, N—(S)-(7-fluoro-4-((4-fluoro-3-methylphenyl)carbamoyl)-2,3-dihydro-1H-inden-1-yl) carbamate (11)

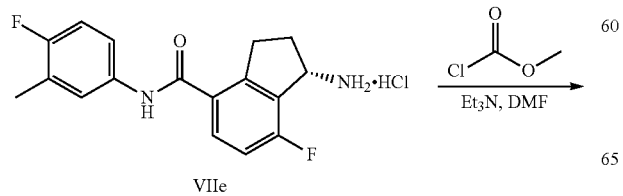

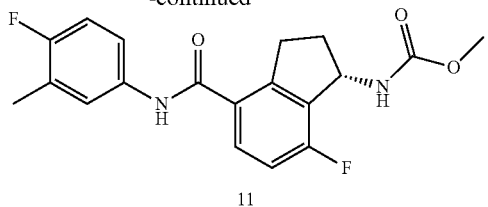

O-Methyl, N—(S)-(7-fluoro-4-((4-fluoro-3-methylphenyl)carbamoyl)-2,3-dihydro-1H-inden-1-yl) carbamate (11) was synthesized in a similar manner as outlined above from (S)-1-amino-7-fluoro-N-(4-fluoro-3-methylphenyl)-2,3-dihydro-1H-indene-4-carboxamide hydrochloride (VIIe) and methyl chloroformate. LCMS: m/z found 361.2 [M+H]$^+$; HPLC: RT=2.85 min (Method G); $^1$H NMR (DMSO-$d_6$, 400 MHz): δ 10.15 (s, 1H), 7.60-7.68 (m, 2H), 7.45-7.55 (m, 1H), 7.05-7.16 (m, 2H), 5.25 (q, 1H) 3.55 (s, 3H), 3.15-3.28 (m, 1H), 2.95-3.06 (m, 1H), 2.28-2.43 (m, 1H), 2.22 (s, 3H), 1.80-1.92 (m, 1H).

Example 2: Non-Limiting Synthesis of Selected 1-(Substituted Amino)-Dihydroindene-4-Carboxamides (Scheme 2)

Scheme 2.

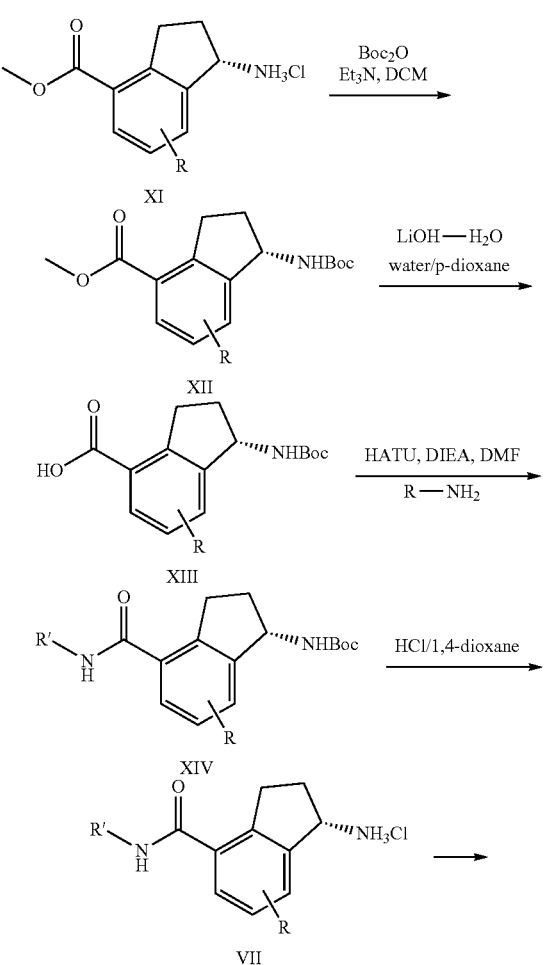

-continued

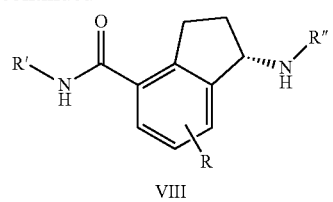

VIII

Non-Limiting Illustration of Scheme 2

Methyl (S)-1-((tert-butoxycarbonyl)amino)-7-fluoro-2,3-dihydro-1H-indene-4-carboxylate (XIIa)

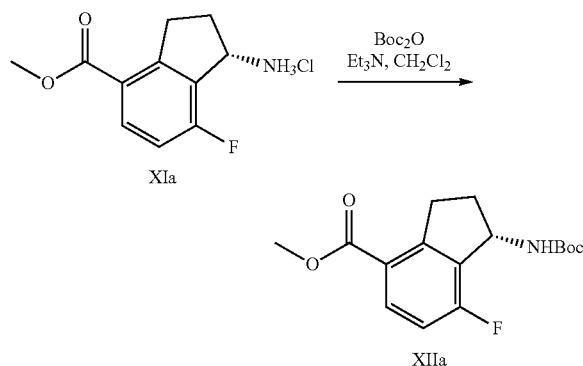

To a solution of 2.53 g (10.3 mmol, 1.0 eq.) of methyl (1S)-1-amino-7-fluoro-2,3-dihydro-1H-indene-4-carboxylate hydrochloride salt (XIa, Netchem 422177-HCl) in 25 mL of THF was added 1.6 mL (11.3 mmol, 1.1 eq.) of trimethylamine. The mixture was cooled to 0° C., and 2.25 g (10.3 mmol, 1.0 eq.) of di-tert-butyl dicarbonate was added. The mixture was allowed to warm to room temperature and stirred for 3 h. The mixture was diluted with 140 mL of ethyl acetate and washed with 70 mL of water, followed by 70 mL of sat. NaHCO$_3$, and then 70 mL of brine. The organic phase was dried (Na$_2$SO$_4$), filtered and the solvent was removed in vacuo to provide 3.19 g (10.3 mmol, 100%) of methyl (S)-1-((tert-butoxycarbonyl)amino)-7-fluoro-2,3-dihydro-1H-indene-4-carboxylate (XIIa). $^1$H NMR (300 MHz, CDCl$_3$) δ 7.95 (m, 1H), 6.95 (t, 1H), 5.37 (m, 1H), 4.77 (m, 1H), 3.89 (s, 3H), 3.43 (m, 1H), 3.19 (m, 1H), 2.55 (m, 1H), 2.00 (m, 1H), 1.48 (s, 9H).

(S)-1-((tert-Butoxycarbonyl)amino)-7-fluoro-2,3-dihydro-1H-indene-4-carboxylic Acid (XIIIa)

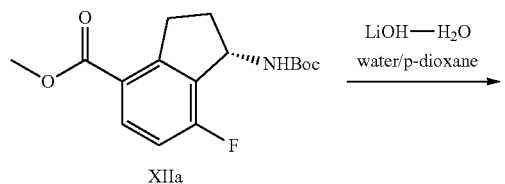

-continued

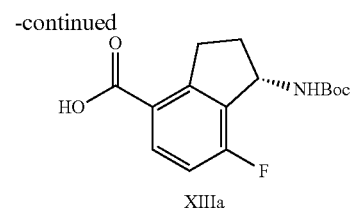

XIIIa

To a solution of 3.19 g (10.3 mmol, 1.0 eq.) of methyl (1S)-1-[(tert-butoxycarbonyl) amino]-7-fluoro-2,3-dihydro-1H-indene-4-carboxylate (XIIa) in 25 mL of 1,4-dioxane was added a solution of 1.30 g (31.0 mmol, 3.0 eq.) of lithium hydroxide monohydrate in 19 mL of water. The mixture was stirred at room temperature for 16 h and Concentrated to Approximately ⅓ volume in vacuo. The mixture was then acidified to pH~4 with 0.5 M citric acid (~37 mL), causing the formation of a white precipitate. The mixture was cooled in an ice bath for 5 min, and the white precipitate was collected by filtration. The solids were washed with 40 mL of water, and dried under high vacuum to provide 3.03 g (10.2 mmol, 96%) of (S)-1-((tert-butoxycarbonyl)amino)-7-fluoro-2,3-dihydro-1H-indene-4-carboxylic acid (XIIIa). $^1$H NMR (300 MHz, DMSO-d$_6$): δ 7.84 (m, 1H), 7.29 (d, 1H), 7.07 (t, 1H), 5.20 (q, 1H), 3.32 (m, 1H), 3.04 (m, 1H), 2.35 (m, 1H), 1.84 (m, 1H), 1.40 (m, 9H).

O-tert-Butyl, N—(S)-(4-((3-chloro-4-fluorophenyl)carbamoyl)-7-fluoro-2,3-dihydro-1H-inden-1-yl)carbamate (XIVa, 10)

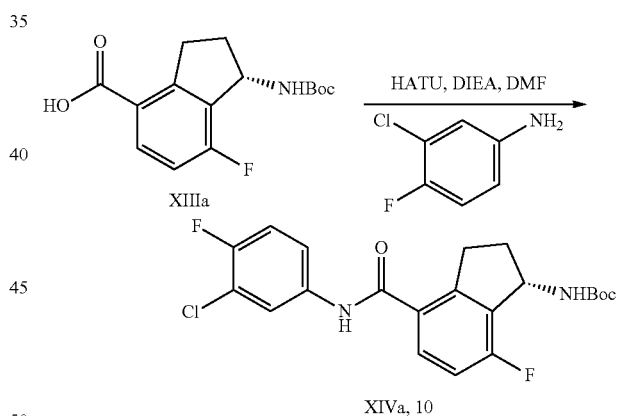

XIVa, 10

To a solution of 3.0 g (10.16 mmol, 1.0 eq.) of ((1S)-1-[(tert-butoxycarbonyl)amino]-7-fluoro-2,3-dihydro-1H-indene-4-carboxylic acid (XIIIa) in 60 mL of anhydrous DMF at 0° C. was added 4.2 g, (11.17 mmol, 1.1 eq.) of 1-[bis(dimethylamino)methylene]-1H-1,2,3-triazolo[4,5-b]pyridinium 3-oxide hexafluorophosphate, followed by 5.3 mL (30.5 mmol, 3.0 eq.) of N,N-diisopropylethylamine. After stirring 10 minutes at 0° C., 1.6 g (11.17 mmol, 1.1 eq.) of 3-chloro-4-fluoroaniline was added, and the mixture was allowed to warm to room temperature. The mixture was stirred at room temperature for 40 h, and then diluted with 200 mL of ethyl acetate. The organic solution was washed with 70 mL of water, followed by 70 mL of sat. NH$_4$Cl, 2×60 mL of sat. NaHCO$_3$, and then 60 mL of brine. The organic phase was dried (Na$_2$SO$_4$) and filtered, and the solvent was removed in vacuo. The resulting solid was crystallized from ethyl acetate/hexanes (~55 mL/35 mL, respectively). First crop: 2.19 g. Second crop: 0.84 g. The mother liquor was evaporated, absorbed on CELITE®, and purified by flash chromatography (SiO₂, eluting with a linear gradient of 30%-60% ethyl acetate/hexanes) to provide an additional 0.36 g of tert-Butyl (S)-(4-((3-chloro-4-fluorophenyl)carbamoyl)-7-fluoro-2,3-dihydro-1H-inden-1-yl) carbamate (XIVa, 10) (combined yield=3.39 g, 79%). ¹H NMR (300 MHz, CDCl₃) δ 7.81 (m, 2H), 7.58 (m, 1H), 7.44 (t, 1H), 7.14 (t, 1H), 6.98 (t, 1H), 5.28 (m, 1H), 4.82 (m, 1H), 3.36 (m, 1H), 3.09 (m, 1H), 2.55 (m, 1H), 2.01 (m, 1H), 1.49 (s, 9H).

(S)-1-Amino-N-(3-chloro-4-fluorophenyl)-7-fluoro-2,3-dihydro-1H-indene-4-carboxamide Hydrochloride (13.HCl)

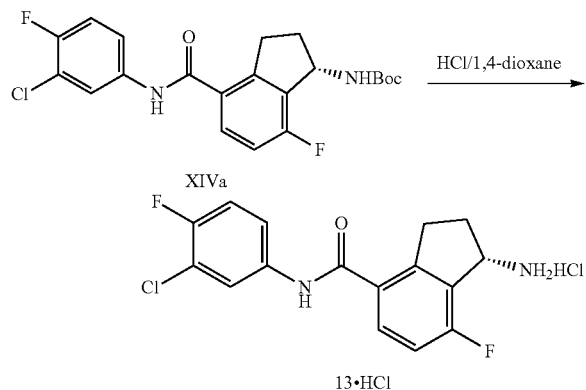

To a solution of 3.38 g (7.99 mmol, 1.0 eq.) of tert-butyl-N-[(1S)-4-[(3-chloro-4-fluorophenyl) carbamoyl]-7-fluoro-2,3-dihydro-1H-inden-1-yl]carbamate (XIVa) in 12 mL of 1,4-dioxane was added 40 mL (160 mmol, 4 M, 20 eq.) of hydrogen chloride in 1,4-dioxane. The mixture was stirred at room temperature for 2 h. The volatiles were removed in vacuo, and 100 mL of diethyl ether was added. The mixture was cooled in an ice bath for 25 min, and the white precipitate was collected by filtration. The solids were washed with 45 mL of diethyl ether and dried under high vacuum to provide 2.87 g (7.99 mmol, 100%) of (S)-1-amino-N-(3-chloro-4-fluorophenyl)-7-fluoro-2,3-dihydro-1H-indene-4-carboxamide hydrochloride (VIId, 13.HCl). ¹H NMR (300 MHz, DMSO-d₆): δ 10.59 (s, 1H), 8.52 (s, 3H), 8.08 (m, 1H), 7.89 (m, 1H), 7.70 (m, 1H), 7.42 (t, 1H), 7.31 (t, 1H), 4.93 (m, 1H), 3.35 (m, 1H), 3.17 (m, 1H), 2.42 (m, 1H), 2.14 (m, 1H).

Example 3: Non-Limiting Synthesis of Selected 1-(n-Linked-Substituted Carbamate)-Dihydroindene-4-Carboxamides O-Pyridin-2-ylmethyl, N—(S)-(4-((3,4-difluorophenyl)carbamoyl)-2,3-dihydro-1H-inden-1-yl) carbamate (3)

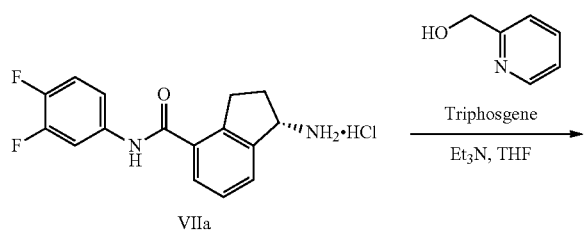

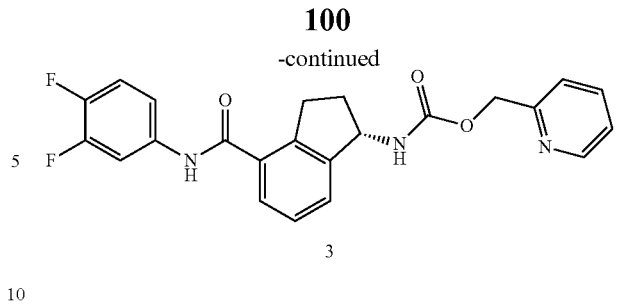

To a solution of 120 mg (0.37 mmol, 1.0 eq.) of (S)-1-amino-N-(3,4-difluorophenyl)-2,3-dihydro-1H-indene-4-carboxamide hydrochloride (VIIa) and 48 mg (0.44 mmol, 1.2 eq.) of pyridin-2-yl methanol in 5 mL of THF at 0° C. was added 0.15 mL (1.1 mmol, 3.0 eq.) of trimethylamine, followed by 54 mg (0.18 mmol, 0.5 eq.) of triphosgene. The mixture was allowed to warm to room temperature and stirred for 3 h. The mixture was then diluted with 30 mL of ethyl acetate and washed with 2×30 mL of water, followed by 30 mL of brine. The organic phase was dried (Na₂SO₄), and the solvent was removed in vacuo. The residue was purified by flash chromatography (SiO₂, eluting with a linear gradient of 0-3% methanol/methylene chloride) to provide 60 mg (0.14 mmol, 38%) of O-pyridin-2-ylmethyl, N—(S)-(4-((3,4-difluorophenyl)carbamoyl)-2,3-dihydro-1H-inden-1-yl) carbamate, which was subsequently treated with 2.0 mL of a 1.25 M solution of HCl in methanol at 0° C. and stirred for 2 h. The solvent was removed in vacuo, and the residue was triturated with n-pentane to provide O-pyridin-2-ylmethyl, N—(S)-(4-((3,4-difluorophenyl)carbamoyl)-2,3-dihydro-1H-inden-1-yl) carbamate hydrochloride salt (3.HCl). LCMS: m/z found=423.2 [M+H]⁺, RT=1.86 min (Method D); HPLC: RT=7.17 min (Method F); ¹H NMR (400 MHz, DMSO-d₆): δ 10.47 (s, 1H), 8.74 (d, 1H), 8.24 (dd, 1H), 8.01 (d, 1H), 7.90-7.95 (m, 1H), 7.67-7.74 (m, 2H), 7.59 (d, 1H), 7.34-7.57 (m, 4H), 5.30 (s, 2H), 5.07 (q, 1H), 3.10-3.25 (m, 1H), 2.93-2.99 (m, 1H), 2.35-3.45 (m, 1H), 1.84-1.89 (m, 1H).

(S)-1-(((S)-tert-Butylsulfinyl)amino)-N-(3-chloro,4-fluorophenyl)-2,3-dihydro-1H-indene-4-carboxamide (VIb)

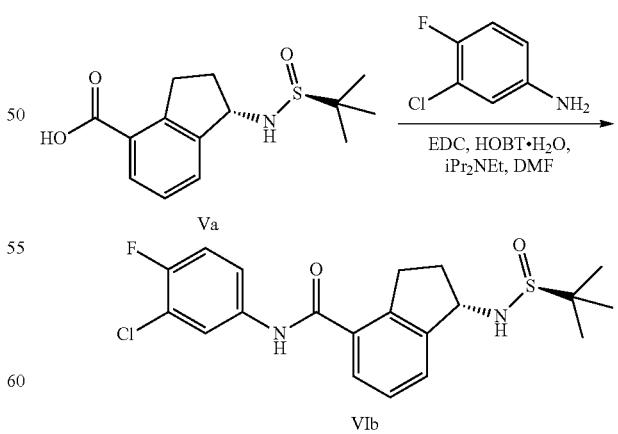

(S)-1-(((S)-tert-Butylsulfinyl)amino)-N-(3-chloro,4-fluorophenyl)-2,3-dihydro-1H-indene-4-carboxamide (VIb) was prepared in a similar manner to VIa using 3-chloro-4-fluoro aniline.

Non-Limiting Illustrative Procedure for Formation of Imidazole Carboxylates

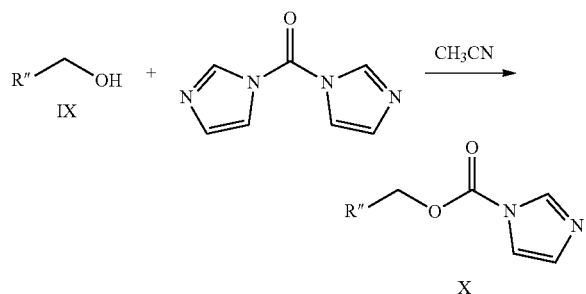

A solution of 1.25 mmol (1.0 eq.) of the alcohol (IX) in 0.5 mL of anhydrous acetonitrile was added to a rapidly stirred mixture of 1.87 mmol (1.5 eq.) of 1,1'-carbonyldiimidazole in 1.5 mL of anhydrous acetonitrile. The reaction mixture was stirred for 40 minutes, and the volatiles were then removed in vacuo. The resulting residue was redissolved in 15 mL of ethyl acetate and washed with 10 mL of water. The layers were separated, and the organic phase was washed with 2×10 mL of sat. NaHCO$_3$, followed by 10 mL of brine. The organic phase was dried (Na$_2$SO$_4$), filtered and evaporated to dryness. The residue was dried under high vacuum to provide the product (X), which was used without further purification.

Non-Limiting Illustrative Procedure for Formation of Carbamates Using Imidazole Carboxylates

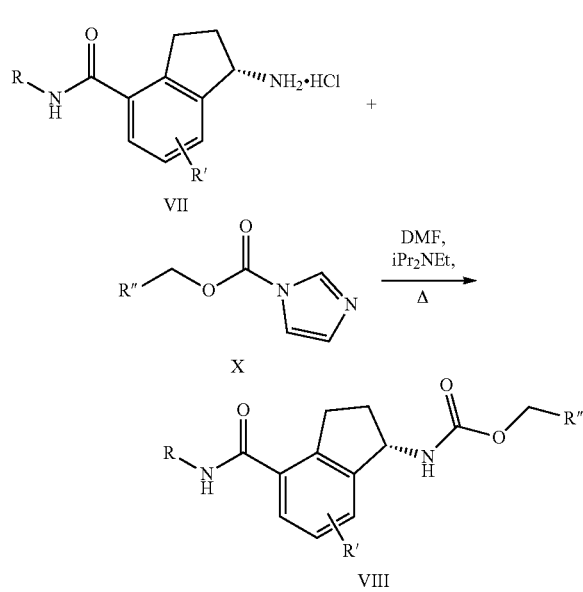

To a solution of 1.0 eq. of VII, 1.3 eq. of X and 0.2 eq. of N,N-dimethylaminopyridine in DMF was added 1.3 eq. of N,N-diisopropylethylamine, and the mixture was stirred until a solution was formed. The mixture was then heated at 65° C. for 16 hours and diluted with ethyl acetate. The mixture was washed with water, followed by two volumes of sat. NaHCO$_3$ and of brine. The organic phase was dried (Na$_2$SO$_4$), filtered and the solvent was removed in vacuo. The residue was purified by flash chromatography to provide VIII.

O-Pyridin-2-ylmethyl, N—(S)-(4-((3,4-difluorophenyl)carbamoyl)-2,3-dihydro-1H-inden-1-yl) carbamate (17)

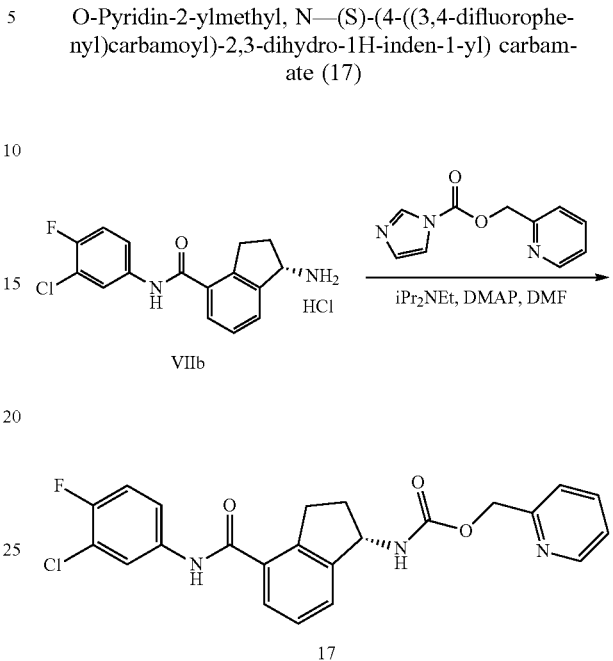

To a solution of 120 mg (0.35 mmol, 1.0 eq.) of (S)-1-amino-N-(3-chloro-4-fluorophenyl)-2,3-dihydro-1H-indene-4-carboxamide hydrochloride, 92 mg (0.45 mmol, 1.3 eq.) of pyridin-2-ylmethyl 1H-imidazole-1-carboxylate and 10 mg (0.07 mmol, 0.2 eq.) of 4-dimethylaminopyridine in 3 mL of DMF was added 80 μL (0.45 mmol, 1.3 eq.) of N,N-diisopropylethylamine, and the reaction mixture was stirred at 70° C. for 16 h. The mixture was then diluted with 25 mL of ethyl acetate and washed with 10 mL of water, followed by 2×10 mL of sat. NaHCO$_3$ and 10 mL of brine. The organic phase was dried (Na$_2$SO$_4$), filtered and the solvent was removed in vacuo. The residue was purified by flash chromatography (SiO$_2$, eluting with a linear gradient of 0-3% methanol/methylene chloride) to provide 70 mg (45%) of O-pyridin-2-ylmethyl, N—(S)-(4-((3,4-difluorophenyl) carbamoyl)-2,3-dihydro-1H-inden-1-yl) carbamate (17). The purified compound was then treated with 1.5 mL of 1.25 M hydrogen chloride in methanol at 0° C., and the mixture stirred for 2 h. The solvent was removed in vacuo and the residue was dried under high vacuum to provide O-pyridin-2-ylmethyl, N—(S)-(4-((3,4-difluorophenyl) carbamoyl)-2,3-dihydro-1H-inden-1-yl) carbamate as the hydrochloride salt (17.HCl). LCMS: m/z found 440.4, 442.4 [M+H]$^+$ (Method D); HPLC: RT=7.52 min (Method F); $^1$H NMR (400 MHz, DMSO-d$_6$): δ 10.43 (s, 1H), 8.71 (d, 1H), 8.15-8.25 (m, 1H), 8.04-8.06 (m, 1H), 7.95-8.00 (m, 1H), 7.55-7.77 (m, 4H), 7.31-7.45 (m, 3H), 5.28 (s, 2H), 5.02-5.08 (m, 1H), 3.12-3.18 (m, 1H), 2.93-2.99 (m, 1H), 2.35-2.45 (m, 1H), 1.81-1.86 (m, 1H).

O—((R)-5-Oxopyrrolidin-2-yl)methyl, N—((S)-4-((3-chloro-4-fluorophenyl)carbamoyl)-2,3-dihydro-1H-inden-1-yl) carbamate (21)

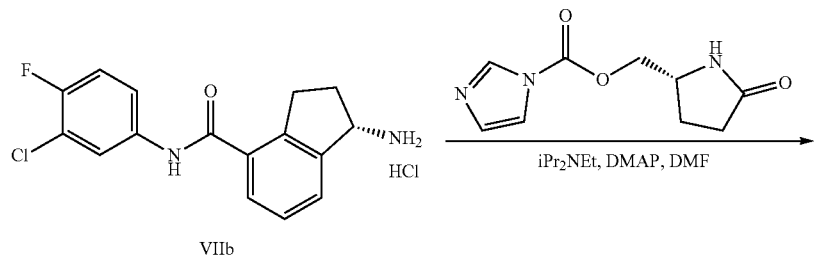

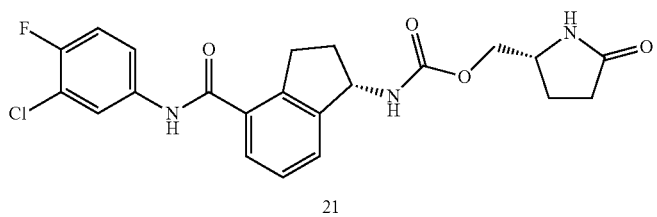

O—((R)-5-Oxopyrrolidin-2-yl)methyl, N—((S)-4-((3-chloro-4-fluorophenyl)carbamoyl)-2,3-dihydro-1H-inden-1-yl) carbamate (21) was synthesized in a similar manner as outlined above from (S)-1-amino-N-(3-chloro-4-fluorophenyl)-2,3-dihydro-1H-indene-4-carboxamide hydrochloride (VIIb) and (R)-(5-oxopyrrolidin-2-yl) methyl 1H-imidazole-1-carboxylate. LCMS: m/z found 446.7, 448.8 [M+H]$^+$ (Method D); HPLC: RT=6.68 min (Method F); $^1$H NMR (400 MHz, DMSO-d$_6$): δ 10.39 (s, 1H) 8.04 (d, 1H), 7.60-7.78 (m, 3H), 7.53 (d, 1H), 7.28-7.42 (m, 3H), 4.99 (q, 1H), 3.87-4.03 (ddd, 2H), 3.73 (bs, 1H), 3.09-3.14 (1, 1H), 2.88-2.97 (m, 1H), 2.47 (m, 1H), 2.13-2.24 (m, 1H), 2.01-2.07 (m, 2H), 1.76-1.83 (m, 2H).

O—((R)-5-Oxopyrrolidin-2-yl)methyl, N—((S)-4-((3-chloro-4-fluorophenyl)carbamoyl)-7-fluoro-2,3-dihydro-1H-inden-1-yl) carbamate (9)

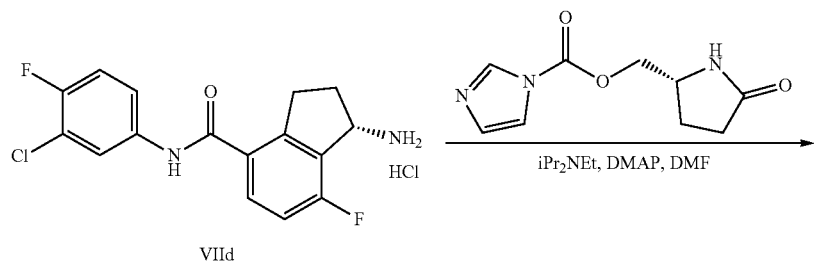

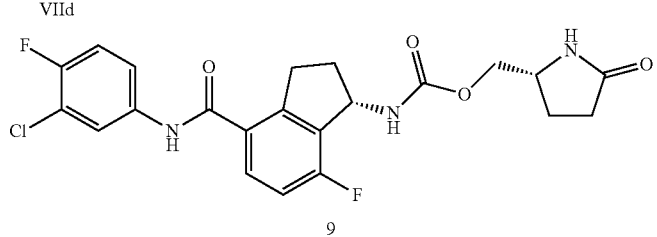

O—((R)-5-Oxopyrrolidin-2-yl)methyl, N—((S)-4-((3-chloro-4-fluorophenyl)carbamoyl)-7-fluoro-2,3-dihydro-1H-inden-1-yl) carbamate (9) was synthesized in a similar manner as outlined above from (S)-1-amino-N-(3-chloro-4-fluorophenyl)-7-fluoro-2,3-dihydro-1H-indene-4-carboxamide hydrochloride (VIId) and (R)-(5-oxopyrrolidin-2-yl) methyl 1H-imidazole-1-carboxylate. LCMS: m/z found 464.1/466.1 [M+H]$^+$ RT=3.87 min (Method A). $^1$H NMR (300 MHz, DMSO-d$_6$): δ 10.38 (s, 1H), 8.02 (m, 1H), 7.74-7.61 (m, 4H), 7.39 (dd, 1H), 7.14 (dd, 1H), 5.26 (m, 1H), 4.03-3.84 (m, 2H), 3.70 (m, 1H), 3.20 (m, 1H), 3.01 (m, 1H), 2.38 (m, 1H), 2.20 (m, 1H), 2.17-1.74 (m, 4H).

O—((S)-5-Oxopyrrolidin-2-yl)methyl, N—((S)-4-((3-chloro-4-fluorophenyl)carbamoyl)-2,3-dihydro-1H-inden-1-yl) carbamate (22)

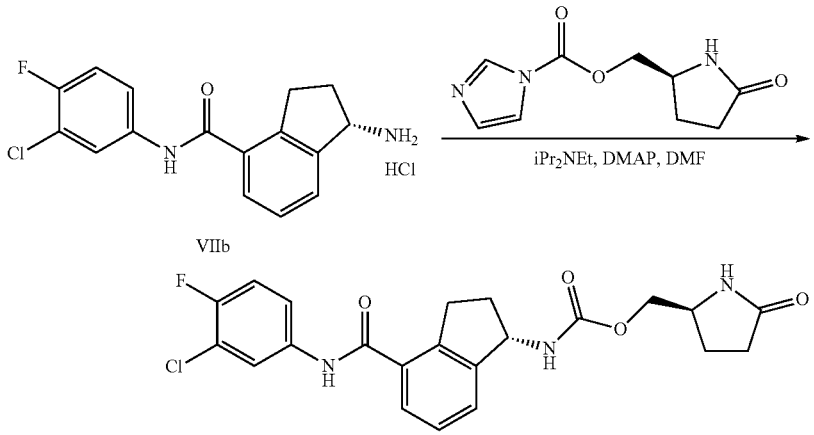

O—((R)-5-Oxopyrrolidin-2-yl)methyl, N—((S)-4-((3-chloro-4-fluorophenyl)carbamoyl)-2,3-dihydro-1H-inden-1-yl) carbamate (22) was synthesized in a similar manner as outlined above from (S)-1-amino-N-(3-chloro-4-fluorophenyl)-2,3-dihydro-1H-indene-4-carboxamide hydrochloride (VIIb) and (S)-(5-oxopyrrolidin-2-yl) methyl 1H-imidazole-1-carboxylate. LCMS: m/z found 446.7, 448.7 [M+H]$^+$ (Method D); HPLC: RT=6.63 min (Method F); $^1$H NMR (400 MHz, DMSO-d$_6$): δ 10.39 (s, 1H), 8.04 (d, 1H), 7.60-7.78 (m, 3H), 7.54 (d, 1H), 7.28-7.40 (m, 3H), 4.03 (q, 1H), 3.85-4.05 (m, 2H), 3.72 (bs, 1H), 3.05-3.18 (m, 1H), 2.83-2.96 (m, 1H), 2.47 (m, 1H), 2.13-2.24 (m, 1H), 2.01-2.07 (m, 2H), 1.71-1.89 (m, 2H).

O-Pyridin-2-ylmethyl, N—(S)-(4-((4-fluoro-3-methylphenyl)carbamoyl)-2,3-dihydro-1H-inden-1-yl) carbamate (23)

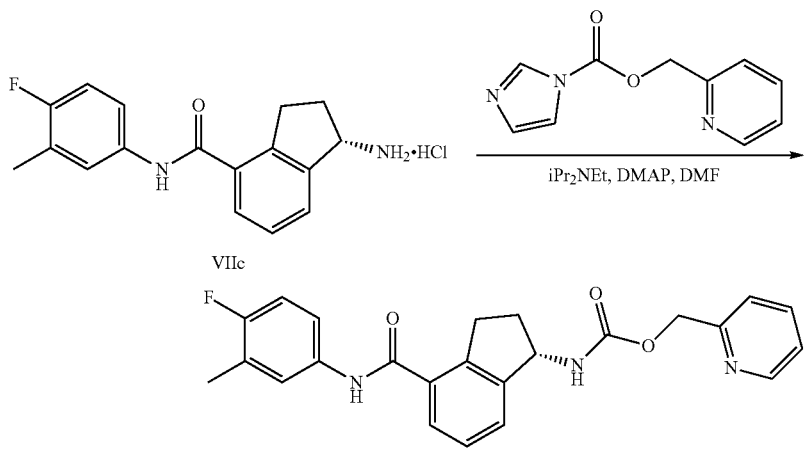

O-Pyridin-2-ylmethyl, N—(S)-(4-((4-fluoro-3-methylphenyl)carbamoyl)-2,3-dihydro-1H-inden-1-yl) carbamate (23) was synthesized in a similar manner as outlined above from (S)-1-amino-N-(4-fluoro-3-methylphenyl)-2,3-dihydro-1H-indene-4-carboxamide hydrochloride (VIIc) and pyridin-2-ylmethyl 1H-imidazole-1-carboxylate. LCMS: m/z found 420.7 [M+H]+ (Method D); HPLC: RT=7.22 min (Method F); $^1$H NMR (400 MHz, DMSO-d$_6$): δ 10.17 (s, 1H), 8.70 (d, 1H), 8.11-8.21 (m, 1H), 7.98 (d, 1H), 7.45-7.70 (m, 5H), 7.28-7.41 (m, 2H), 7.05-7.13 (m, 1H), 5.25 (s, 2H), 5.05 (q, 1H), 3.05-3.19 (m, 1H), 2.87-2.98 (m, 1H), 2.33-2.45 (m, 1H), 2.20 (s, 3H), 1.77-1.90 (m, 1H).

O—((R)-5-Oxopyrrolidin-2-yl)methyl, N—((S)-4-((4-fluoro-3-methylphenyl)carbamoyl)-2,3-dihydro-1H-inden-1-yl) carbamate (24)

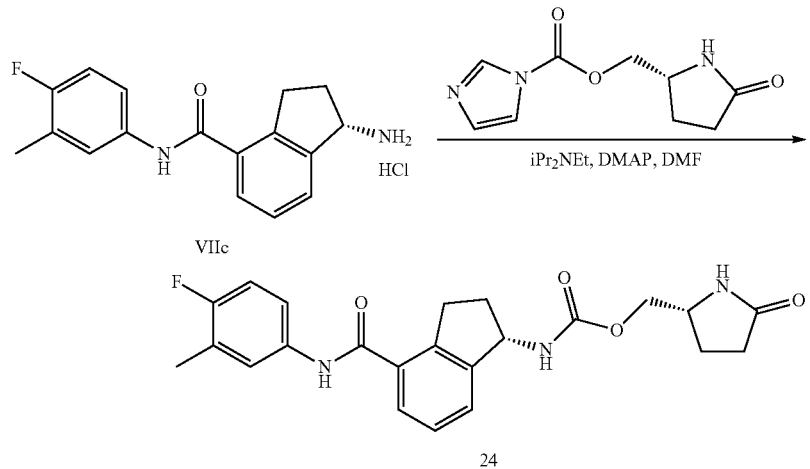

O—((R)-5-Oxopyrrolidin-2-yl)methyl, N—((S)-4-((4-fluoro-3-methylphenyl)carbamoyl)-2,3-dihydro-1H-inden-1-yl) carbamate (24) was synthesized in a similar manner as outlined above from (S)-1-amino-N-(4-fluoro-3-methylphenyl)-2,3-dihydro-1H-indene-4-carboxamide hydrochloride (VIIc) and (R)-(5-oxopyrrolidin-2-yl) methyl-1H-imidazole-1-carboxylate. LCMS: m/z found 426.8 [M+H]+ (Method D); HPLC: RT=6.34 min (Method F); $^1$H NMR (400 MHz, DMSO-d$_6$): δ 10.18 (s, 1H), 7.67-7.80 (m, 3H) 7.51-7.63 (m, 2H), 7.30-7.42 (m, 2H), 7.11 (dd, 1H), 5.06 (m, 1H), 3.90-4.10 (ddd, 2H), 3.70-3.81 (m, 1H), 3.10-3.20 (m, 1H), 2.95-3.05 (m, 1H), 2.31-2.45 (m, 1H), 2.23 (d, 3H), 2.05-2.20 (m, 2H), 1.71-1.90 (m, 2H).

O—((S)-5-Oxopyrrolidin-2-yl)methyl, N—((S)-4-((4-fluoro-3-methylphenyl)carbamoyl)-2,3-dihydro-1H-inden-1-yl) carbamate (25)

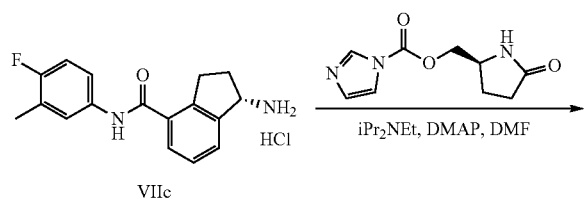

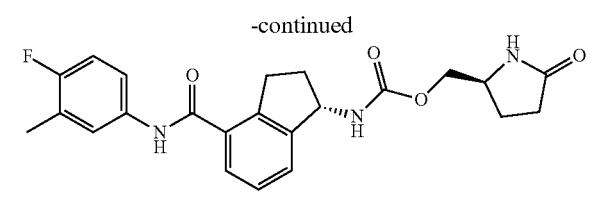

O—((S)-5-Oxopyrrolidin-2-yl)methyl, N—((S)-4-((4-fluoro-3-methylphenyl)carbamoyl)-2,3-dihydro-1H-inden-1-yl) carbamate (25) was synthesized in a similar manner as outlined above from from (S)-1-amino-N-(4-fluoro-3-methylphenyl)-2,3-dihydro-1H-indene-4-carboxamide hydrochloride (VIIc) (S)-(5-oxopyrrolidin-2-yl) methyl-1H-imidazole-1-carboxylate. LCMS: m/z found 426.8 [M+H]+ (Method D); HPLC: RT=6.33 min (Method F); $^1$H NMR (400 MHz, DMSO-d$_6$): δ 10.18 (s, 1H), 7.73-7.84 (m, 3H), 7.48-7.57 (m, 2H), 7.28-7.40 (m, 2H), 7.08 (dd, 1H), 5.03 (m, 1H), 3.98 (m, 2H), 3.70-3.78 (m 1H), 3.07-3.17 (m, 1H), 2.89-2.96 (m, 1H), 2.31-2.42 (m, 1H), 2.18-2.26 (m, 1H), 2.20 (d, 3H), 2.03-2.18 (m, 2H), 1.72-1.86 (m, 2H).

O—((S)-5-Oxopyrrolidin-2-yl)methyl, N—((S)-4-((3-chloro-4-fluorophenyl)carbamoyl)-7-fluoro-2,3-dihydro-1H-inden-1-yl) carbamate (18)

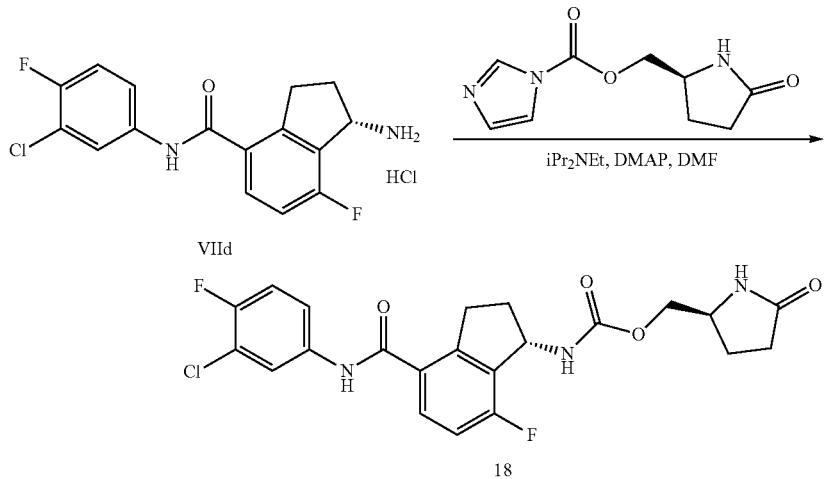

O—((S)-5-Oxopyrrolidin-2-yl)methyl, N—((S)-4-((3-chloro-4-fluorophenyl)carbamoyl)-7-fluoro-2,3-dihydro-1H-inden-1-yl) carbamate (18) was synthesized in a similar manner as outlined above from (S)-1-amino-N-(3-chloro-4-fluorophenyl)-7-fluoro-2,3-dihydro-1H-indene-4-carboxamide hydrochloride (VIId) and (S)-(5-oxopyrrolidin-2-yl)methyl 1H-imidazole-1-carboxylate. LCMS: m/z found 464.3/466.4 [M+H]+ RT=3.90 min (Method A); $^1$H NMR (300 MHz, DMSO-$d_6$): δ 10.42 (s, 1H), 8.05 (dd, 1H), 7.60-7.80 (m, 4H), 7.41 (dd, 1H), 7.16 (dd, 1H), 5.26 (q, 1H), 3.95 (ddd, 2H), 3.66-3.80 (m, 1H), 3.17-3.32 (m, 1H), 2.92-3.10 (m, 1H), 2.31-2.48 (m, 1H), 2.16-2.30 (m, 1H), 2.17-1.70 (m, 4H).

O-2-(2-Oxopyrrolidin-1-yl)ethyl, N—(S)-(4-((3-chloro-4-fluorophenyl)carbamoyl)-7-fluoro-2,3-dihydro-1H-inden-1-yl) carbamate (14)

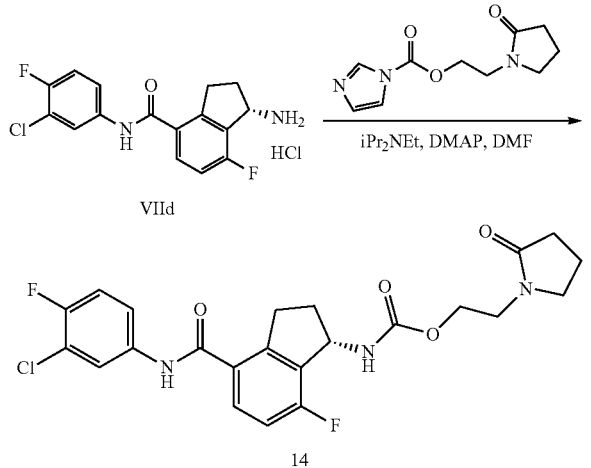

O-2-(2-Oxopyrrolidin-1-yl)ethyl, N—(S)-(4-((3-chloro-4-fluorophenyl)carbamoyl)-7-fluoro-2,3-dihydro-1H-inden-1-yl) carbamate (14) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-(2-oxopyrrolidin-1-yl)ethyl 1H-imidazole-1-carboxylate. LCMS: m/z found 478.4/480.4 [M+H]+, RT=4.10 min (Method A); $^1$H NMR (300 MHz, DMSO-$d_6$): δ 10.41 (s, 1H), 8.04 (dd, 1H), 7.63-7.76 (m, 3H), 7.41 (dd, 1H), 7.16 (dd, 1H), 5.25 (q, 1H), 4.05-4.13 (m, 2H), 3.33-3.48 (m, 4H), 3.18-3.27 (m, 1H), 2.98-3.06 (m, 1H), 2.36-2.46 (m, 1H), 2.20 (t, 2H), 1.85-1.95 (m, 3H).

O-2-Oxo-2-(pyrrolidin-1-yl)ethyl, N—(S)-(4-((3-chloro-4-fluorophenyl)carbamoyl)-7-fluoro-2,3-dihydro-1H-inden-1-yl) carbamate (26)

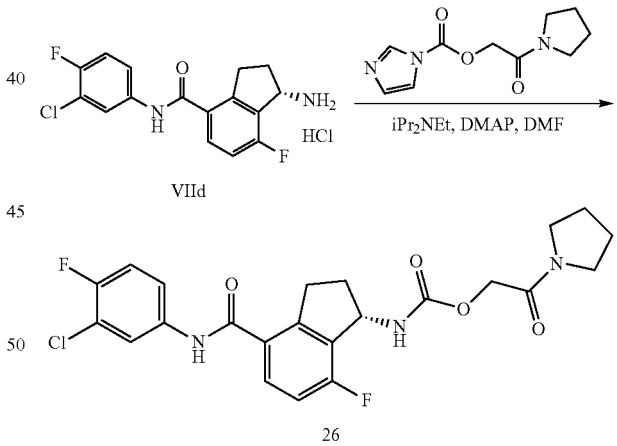

O-2-Oxo-2-(pyrrolidin-1-yl)ethyl, N—(S)-(4-((3-chloro-4-fluorophenyl)carbamoyl)-7-fluoro-2,3-dihydro-1H-inden-1-yl) carbamate (26) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-oxo-2-(pyrrolidin-1-yl)ethyl 1H-imidazole-1-carboxylate. LCMS: m/z found 478.4/480.3 [M+H]+, RT=4.22 min (Method A); $^1$H NMR (300 MHz, DMSO-$d_6$) δ 10.53 (s, 1H), 8.08 (dd, 1H), 7.90 (d, 1H), 7.68-7.76 (m, 2H), 7.41 (dd, 1H), 7.15 (dd, 1H), 5.24 (q, 1H), 4.58 (q, 2H), 3.15-3.45 (m, 5H), 2.96-3.10 (m, 1H), 2.36-2.46 (m, 1H), 1.70-1.97 (m, 5H).

O—((S)-5-Oxopyrrolidin-2-yl)methyl, N—((S)-4-((3-chloro-4-fluorophenyl)carbamoyl)-7-fluoro-2,3-dihydro-1H-inden-1-yl) carbamate (39)

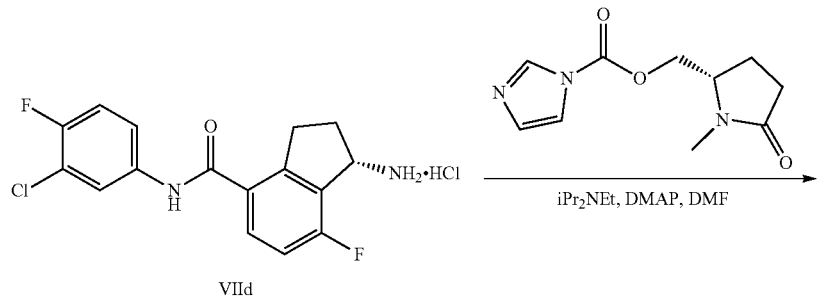

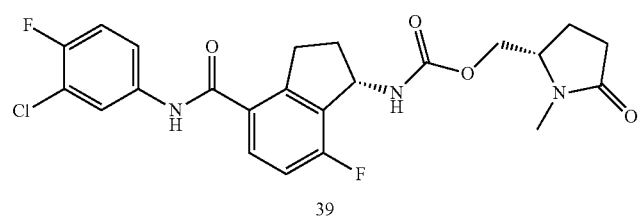

O—((S)-5-Oxopyrrolidin-2-yl)methyl, N—((S)-4-((3-chloro-4-fluorophenyl)carbamoyl)-7-fluoro-2,3-dihydro-1H-inden-1-yl) carbamate (39) was synthesized in a similar manner as outlined above from (S)-1-amino-N-(3-chloro-4-fluorophenyl)-7-fluoro-2,3-dihydro-1H-indene-4-carboxamide hydrochloride (VIId) and (S)-(1-methyl-5-oxopyrrolidin-2-yl)methyl 1H-imidazole-1-carboxylate. LCMS: m/z found 478.2/480.2 [M+H]$^+$ RT=4.05 min (Method A); $^1$H NMR (300 MHz, DMSO-d$_6$) δ 10.39 (s, 1H), 8.04 (dd, 1H), 7.80 (d, 1H), 7.63-7.72 (m, 2H), 7.40 (dd, 1H), 7.16 (dd, 1H), 5.25 (q, 1H), 4.12 (ddd, 2H), 3.66-3.75 (m, 1H), 3.17-3.30 (m, 1H), 2.94-3.07 (m, 1H), 2.71 (s, 3H), 2.22-2.45 (m, 2H) 2.05-2.18 (m, 2H), 1.82-1.95 (m, 1H), 1.66-1.78 (m, 1H).

O—((R)-5-Oxopyrrolidin-2-yl)methyl, N—((S)-4-((3-chloro-4-fluorophenyl)carbamoyl)-7-fluoro-2,3-dihydro-1H-inden-1-yl) carbamate (43)

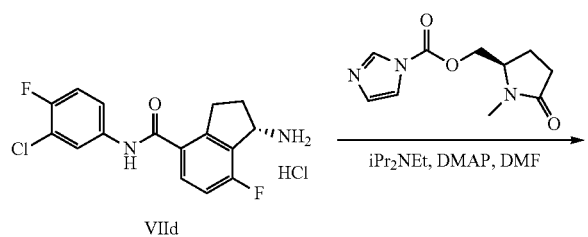

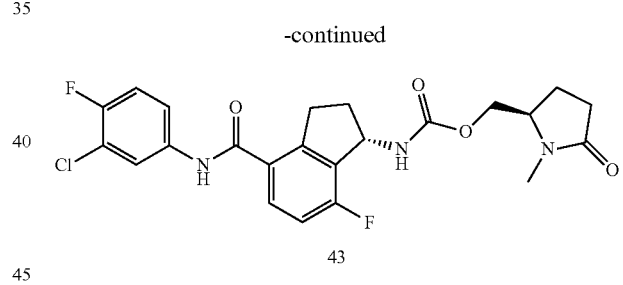

O—((R)-5-Oxopyrrolidin-2-yl)methyl, N—((S)-4-((3-chloro-4-fluorophenyl)carbamoyl)-7-fluoro-2,3-dihydro-1H-inden-1-yl) carbamate (43) was synthesized in a similar manner as outlined above from (S)-1-amino-N-(3-chloro-4-fluorophenyl)-7-fluoro-2,3-dihydro-1H-indene-4-carboxamide hydrochloride (VIId) and (R)-(1-methyl-5-oxopyrrolidin-2-yl)methyl 1H-imidazole-1-carboxylate. LCMS: m/z found 478.2/480.2 [M+H]$^+$ RT=4.02 min (Method A); $^1$H NMR (300 MHz, DMSO-d$_6$) δ 10.39 (s, 1H), 8.04 (dd, 1H), 7.60-7.86 (m, 3H), 7.40 (dd, 1H), 7.15 (dd, 1H), 5.25 (q, 1H), 4.16 (ddd, 2H), 3.66-3.75 (m, 1H), 3.17-3.30 (m, 1H), 2.94-3.07 (m, 1H), 2.72 (s, 3H), 2.22-2.45 (m, 2H) 2.05-2.18 (m, 2H), 1.82-1.95 (m, 1H), 1.66-1.78 (m, 1H).

O—(R)-5-Oxopyrrolidin-3-yl, N—((S)-4-((3-chloro-4-fluorophenyl)carbamoyl)-7-fluoro-2,3-dihydro-1H-inden-1-yl) carbamate (72)

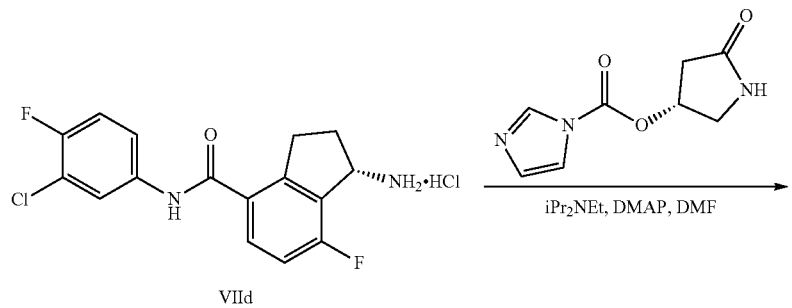

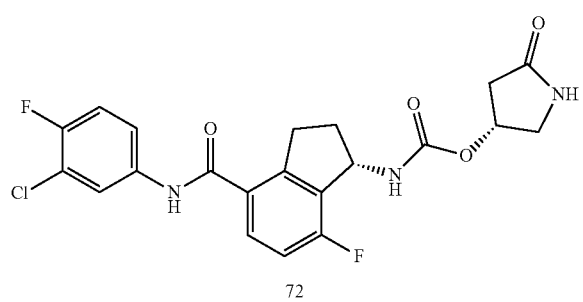

O—(R)-5-Oxopyrrolidin-3-yl, N—((S)-4-((3-chloro-4-fluorophenyl)carbamoyl)-7-fluoro-2,3-dihydro-1H-inden-1-yl) carbamate (72) was synthesized in a similar manner as outlined above from (S)-1-amino-N-(3-chloro-4-fluorophenyl)-7-fluoro-2,3-dihydro-1H-indene-4-carboxamide hydrochloride (VIId) and (R)-5-oxopyrrolidin-3-yl 1H-imidazole-1-carboxylate. LCMS: m/z found 450.1/452.1 [M+H]+ RT=3.76 min (Method A); ¹H NMR (300 MHz, DMSO-d₆) δ 10.39 (s, 1H), 8.04 (dd, 1H), 7.82 (d, 1H), 7.60-7.72 (m, 2H), 7.44 (dd, 1H), 7.15 (dd, 1H), 5.25 (q, 1H), 5.18 (m, 1H), 3.61 (dd, 1H), 3.66-3.75 (m, 1H), 3.12-3.30 (m, 2H), 2.94-3.07 (m, 1H), 2.30-2.65 (m, 3H), 1.82-1.95 (m, 1H).

O-Pyridin-2-ylmethyl, N—(S)-(4-((3-chloro-4-fluorophenyl)carbamoyl)-7-fluoro-2,3-dihydro-1H-inden-1-yl) carbamate (32)

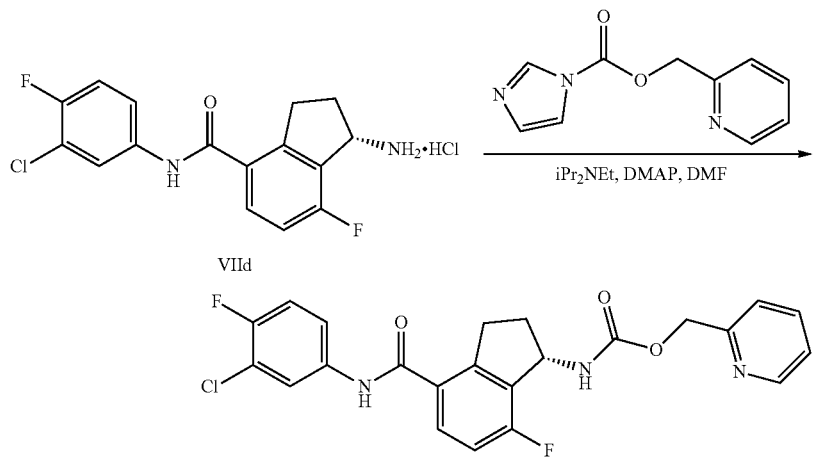

O-Pyridin-2-ylmethyl, N—(S)-(4-((3-chloro-4-fluorophenyl)carbamoyl)-7-fluoro-2,3-dihydro-1H-inden-1-yl) carbamate (32) was synthesized in a similar manner as outlined above from (S)-1-amino-N-(3-chloro-4-fluorophenyl)-7-fluoro-2,3-dihydro-1H-indene-4-carboxamide hydrochloride (VIId) and pyridin-2-ylmethyl 1H-imidazole-1-carboxylate. The purified sample was subsequently converted to the hydrochloride salt using a 1.25 M solution of HCl in methanol. LCMS: m/z found 458.3/460.3 [M+H]$^+$, RT=3.65 min (Method A); $^1$H NMR (300 MHz, d$_4$-methanol) δ 8.84 (dd, 1H), 8.62-8.68 (m, 1H), 8.12 (d, 1H), 8.03-8.07 (m, 1H), 7.92 (d, 1H), 7.68 (dd, 1H), 7.54-7.58 (m, 1H), 7.23 (dd, 1H), 7.05 (dd, 1H), 5.45 (s, 2H), 5.36 (q, 1H), 3.33-3.42 (m, 1H), 3.05-3.18 (m, 1H), 2.46-2.60 (m, 1H), 1.97-2.11 (m, 1H).

O-(6-Methylpyridin-2-yl)methyl, N—(S)-(4-((3-chloro-4-fluorophenyl)carbamoyl)-7-fluoro-2,3-dihydro-1H-inden-1-yl) carbamate (73)

O-(6-Methylpyridin-2-yl)methyl, N—(S)-(4-((3-chloro-4-fluorophenyl)carbamoyl)-7-fluoro-2,3-dihydro-1H-inden-1-yl) carbamate (73) was synthesized in a similar manner as outlined above from (S)-1-amino-N-(3-chloro-4-fluorophenyl)-7-fluoro-2,3-dihydro-1H-indene-4-carboxamide hydrochloride (VIId) and (6-methylpyridin-2-yl)methyl 1H-imidazole-1-carboxylate. The purified sample was subsequently converted to the hydrochloride salt using a 1.25 M solution of HCl in methanol. LCMS: m/z found 472.1/474.1 [M+H]$^+$, RT=3.60 min (Method A); $^1$H NMR (300 MHz, d$_4$-methanol) δ 8.50 (dd, 1H), 7.82-7.96 (m, 3H), 7.69 (dd, 1H), 7.52-7.60 (m, 1H), 7.23 (dd, 1H), 7.08 (dd, 1H), 5.30-5.50 (m, 3H), 5.36 (q, 1H), 3.33-3.42 (m, 1H), 3.05-3.18 (m, 1H), 2.82 (s, 3H), 2.46-2.60 (m, 1H), 1.97-2.10 (m, 1H).

O—(S)-1-(Pyridin-2-yl)ethyl, N—((S)-4-((3-chloro-4-fluorophenyl)carbamoyl)-7-fluoro-2,3-dihydro-1H-inden-1-yl) carbamate (68)

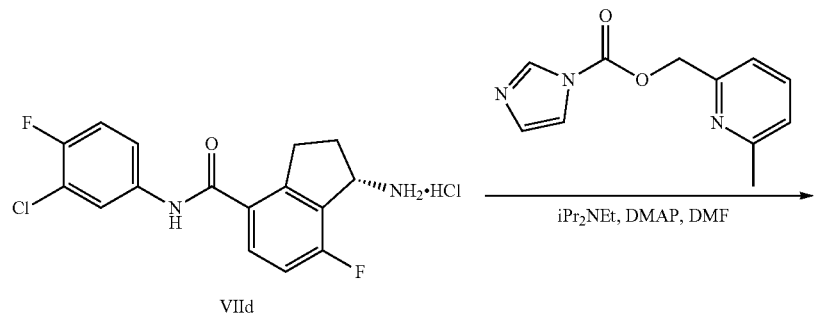

O—(S)-1-(Pyridin-2-yl)ethyl, N—((S)-4-((3-chloro-4-fluorophenyl)carbamoyl)-7-fluoro-2,3-dihydro-1H-inden-1-yl) carbamate (68) was synthesized in a similar manner as outlined above from (S)-1-amino-N-(3-chloro-4-fluorophenyl)-7-fluoro-2,3-dihydro-1H-indene-4-carboxamide hydrochloride (VIId) and (S)-1-(pyridin-2-yl)ethyl 1H-imidazole-1-carboxylate. The purified sample was subsequently converted to the hydrochloride salt using a 1.25 M solution of HCl in methanol. LCMS: m/z found 472.2/474.2 [M+H]+, RT=3.38 min (Method A); ¹H NMR (300 MHz, d₄-methanol): δ 8.81 (dd, 1H), 8.64 (dd, 1H), 8.13 (d, 1H), 8.02 (dd, 1H), 7.91 (d, 1H), 7.68 (dd, 1H), 7.50-7.58 (m, 1H), 7.22 (dd, 1H), 7.09 (dd, 1H), 5.97 (1H, q), 5.30 (m, 1H), 3.51 (m, 1H), 3.02-3.16 (m, 1H), 2.40-2.55 (m, 1H), 1.90-2.05 (m, 1H), 1.97-2.11 (m, 1H), 1.70 (m, 3H).

O-(6-Methoxypyridin-2-yl)methyl, N—(S)-(4-((3-chloro-4-fluorophenyl)carbamoyl)-7-fluoro-2,3-dihydro-1H-inden-1-yl) carbamate (44)

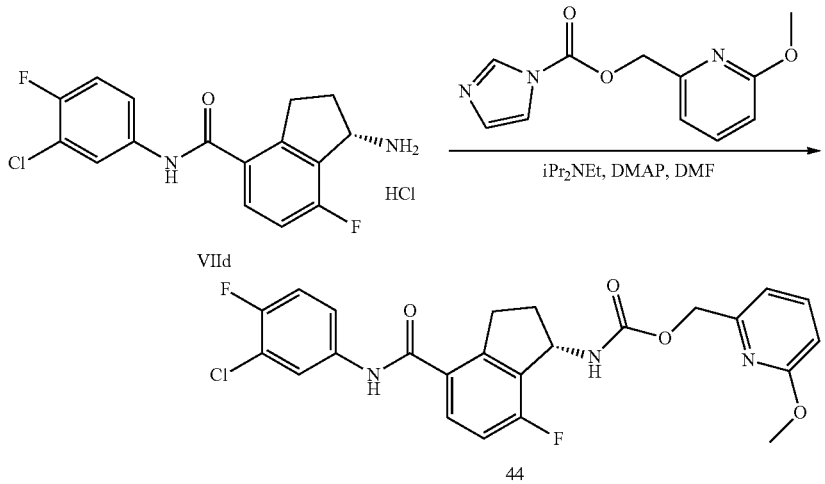

O-(6-Methoxypyridin-2-yl)methyl, N—(S)-(4-((3-chloro-4-fluorophenyl)carbamoyl)-7-fluoro-2,3-dihydro-1H-inden-1-yl) carbamate (44) was synthesized in a similar manner as outlined above from (S)-1-amino-N-(3-chloro-4-fluorophenyl)-7-fluoro-2,3-dihydro-1H-indene-4-carboxamide hydrochloride (VIId) and (6-methoxypyridin-2-yl)methyl 1H-imidazole-1-carboxylate. The purified sample was subsequently converted to the hydrochloride salt using a 1.25 M solution of HCl in methanol. LCMS: m/z found 488.1/490.2 [M+H]+, RT=5.18 min (Method A); ¹H NMR (300 MHz, DMSO-d₆) δ 10.41 (s, 1H), 7.92-8.10 (m, 2H), 7.60-7.78 (m, 3H), 7.40 (m, 1H), 7.18 (m, 1H), 6.95 (dd, 1H), 6.78 (dd, 1H), 5.45 (m, 1H), 5.03 (s, 2H), 3.84 (s, 3H) 3.23-3.38 (m, 1H), 2.94-3.10 (m, 1H), 2.46-2.60 (m, 1H), 1.87-2.01 (m, 1H).

O-(6-(Dimethylamino)pyridin-2-yl)methyl, N—(S)-(4-((3-chloro-4-fluorophenyl)carbamoyl)-7-fluoro-2,3-dihydro-1H-inden-1-yl) carbamate (48)

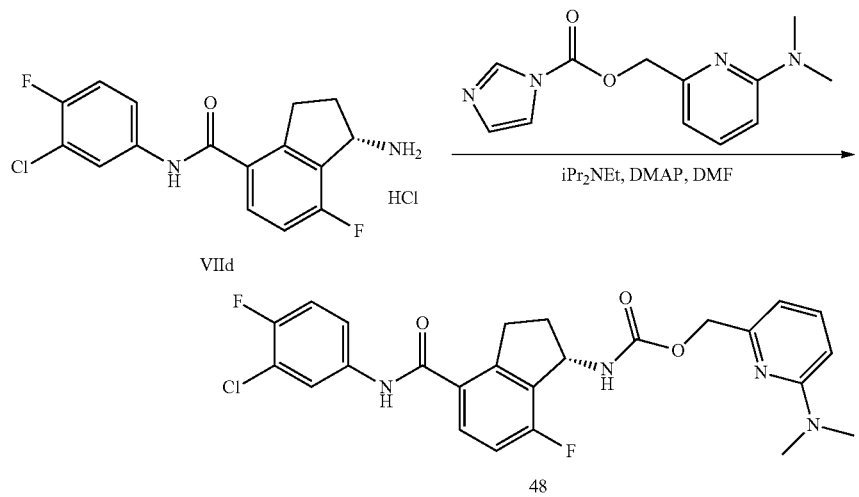

O-(6-(Dimethylamino)pyridin-2-yl)methyl, N—(S)-(4-((3-chloro-4-fluorophenyl)carbamoyl)-7-fluoro-2,3-dihydro-1H-inden-1-yl) carbamate (48) was synthesized in a similar manner as outlined above from (S)-1-amino-N-(3-chloro-4-fluorophenyl)-7-fluoro-2,3-dihydro-1H-indene-4-carboxamide hydrochloride (VIId) and (6-(dimethylamino)pyridin-2-yl)methyl 1H-imidazole-1-carboxylate. The purified sample was subsequently converted to the hydrochloride salt using a 1.25 M solution of HCl in methanol. LCMS: m/z found 501.1/503.1 [M+H]$^+$, RT=3.77 min (Method A); $^1$H NMR (300 MHz, DMSO-d$_6$) δ 10.49 (s, 1H), 7.90-8.10 (m, 2H), 7.60-7.78 (m, 3H), 7.40 (m, 1H), 7.22 (m, 1H), 6.90 (m, 1H), 6.70 (dd, 1H), 5.60 (m, 1H), 5.18 (s, 2H), 2.80-3.40 (m, 8H), 2.46-2.60 (m, 1H), 1.85-2.05 (m, 1H).

O-(6-Morpholinopyridin-2-yl)methyl, N—(S)-(4-((3-chloro-4-fluorophenyl)carbamoyl)-7-fluoro-2,3-dihydro-1H-inden-1-yl) carbamate (42)

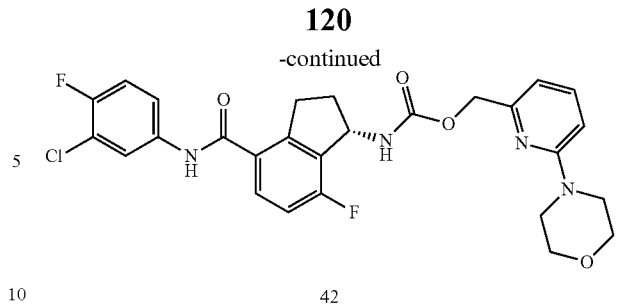

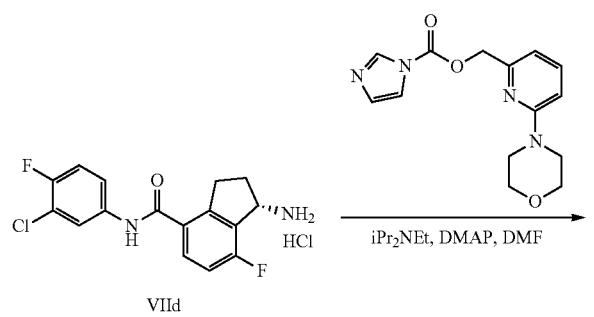

O-(6-Morpholinopyridin-2-yl)methyl, N—(S)-(4-((3-chloro-4-fluorophenyl)carbamoyl)-7-fluoro-2,3-dihydro-1H-inden-1-yl) carbamate (42) was synthesized in a similar manner as outlined above from (S)-1-amino-N-(3-chloro-4-fluorophenyl)-7-fluoro-2,3-dihydro-1H-indene-4-carboxamide hydrochloride (VIId) and (6-morpholinopyridin-2-yl)methyl 1H-imidazole-1-carboxylate. The purified sample was subsequently converted to the hydrochloride salt using a 1.25 M solution of HCl in methanol. LCMS: m/z found 543.3/545.3 [M+H]$^+$, RT=4.08 min (Method A); $^1$H NMR (300 MHz, DMSO-d$_6$) δ 10.43 (s, 1H), 8.02-8.10 (m, 2H), 7.93 (d, 1H), 7.60-7.78 (m, 3H), 7.62 (m, 1H), 7.30 (m, 1H), 6.83 (m, 1H), 6.70 (m, 1H), 5.30 (m, 1H), 4.99 (s, 2H), 3.70 (m, 4H), 3.48 (m, 4H), 3.17-3.32 (m, 1H), 2.90-3.20 (m, 1H), 2.46-2.60 (m, 1H), 1.85-2.03 (m, 1H).

O-(1-(2,2,2-Trifluoroethyl)piperidin-4-yl)methyl, N—(S)-(4-((3-chloro-4-fluorophenyl) carbamoyl)-7-fluoro-2,3-dihydro-1H-inden-1-yl) carbamate (62)

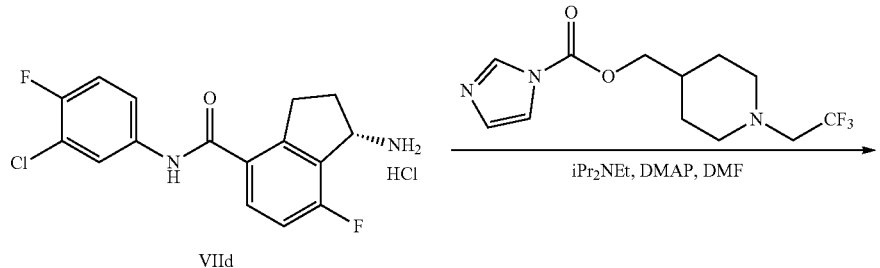

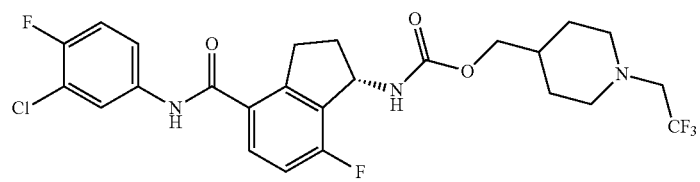

O-(1-(2,2,2-Trifluoroethyl)piperidin-4-yl)methyl, N—(S)-(4-((3-chloro-4-fluorophenyl) carbamoyl)-7-fluoro-2,3-dihydro-1H-inden-1-yl) carbamate (62) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-(2,2,2-trifluoroethyl) piperidin-4-yl)methyl 1H-imidazole-1-carboxylate. The purified sample was subsequently converted to the hydrochloride salt using a 1.25 M solution of HCl in methanol. LCMS: m/z found 546.2/548.2 [M+H]$^+$, RT=3.91 min (Method A); $^1$H NMR (300 MHz, d$_4$-methanol) δ 10.16 (s, 1H), 7.92 (dd, 2H), 7.66 (dd, 1H), 7.50-7.59 (m, 1H), 7.23 (dd, 1H), 7.04 (dd, 1H), 5.35 (m, 1H), 4.20 (q, 2H), 3.93-4.10 (m, 2H), 3.62-3.74 (m, 2H), 3.18-3.40 (m, 3H), 3.03-3.16 (m, 1H), 2.43-2.60 (m, 1H), 1.90-2.11 (m, 4H), 1.58-1.69 (m, 2H).

tert-Butyl 2-(((((S)-4-((3-chloro-4-fluorophenyl) carbamoyl)-7-fluoro-2,3-dihydro-1H-inden-1-yl) carbamoyl)oxy)methyl)-4,4-difluoropyrrolidine-1-carboxylate (54)

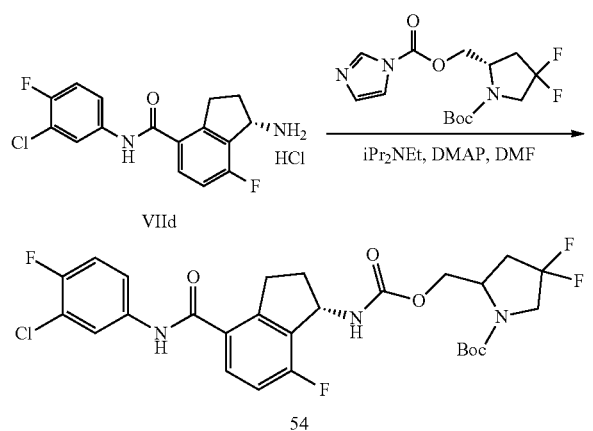

tert-Butyl 2-(((((S)-4-((3-chloro-4-fluorophenyl)carbamoyl)-7-fluoro-2,3-dihydro-1H-inden-1-yl)carbamoyl)oxy) methyl)-4,4-difluoropyrrolidine-1-carboxylate (54) was synthesized in a similar manner as outlined above from (S)-1-amino-N-(3-chloro-4-fluorophenyl)-7-fluoro-2,3-dihydro-1H-indene-4-carboxamide hydrochloride (VIId) and (S)-(1-(tert-butoxycarbonyl)-4,4-difluoropyrrolidin-2-yl) methyl 1H-imidazole-1-carboxylate. LCMS: m/z found 486.1/488.1 [M+H-Boc]$^+$, 608.2/610.2 [M+Na]$^+$, RT=5.84 min (Method A).

O-(4,4-Difluoropyrrolidin-2-yl)methyl, N—((S)-4-((3-chloro-4-fluorophenyl)carbamoyl)-7-fluoro-2,3-dihydro-1H-inden-1-yl) carbamate Hydrochloride (56.HCl)

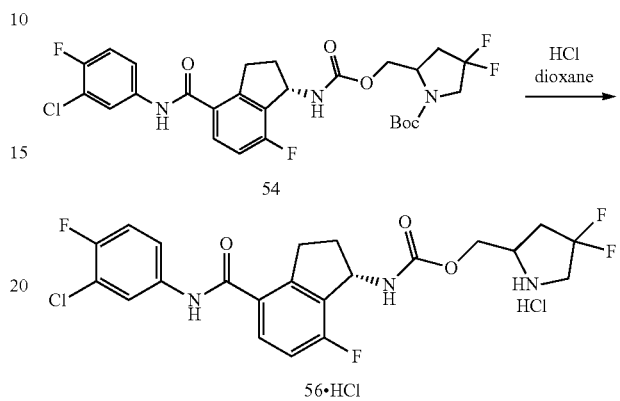

A solution of 96 mg (0.16 mmol) of tert-butyl 2-(((((S)-4-((3-chloro-4-fluorophenyl) carbamoyl)-7-fluoro-2,3-dihydro-1H-inden-1-yl)carbamoyl)oxy)methyl)-4,4-difluoro pyrrolidine-1-carboxylate (54) in 3 mL of 4 M HCl in p-dioxane was stirred at room temperature for 16 h. The volatiles were removed in vacuo, and the residue was resuspended in 15 mL of diethyl ether. The mixture was cooled in an ice bath for 15 min, and the solids were collected by filtration to provide 65 mg (76%) of O-(4,4-difluoropyrrolidin-2-yl)methyl, N—((S)-4-((3-chloro-4-fluorophenyl)carbamoyl)-7-fluoro-2,3-dihydro-1H-inden-1-yl) carbamate hydrochloride (56.HCl)). LCMS: m/z found 486.2/488.2 [M+H]$^+$, RT=3.53 min (Method A); $^1$H NMR (300 MHz, DMSO-d$_6$) δ 10.17 (s, 1H), 7.91-7.95 (m, 1H), 7.65-7.72 (m, 1H), 7.50-7.58 (m, 1H), 7.23 (dd, 1H), 7.06 (dd, 1H), 5.37 (m, 1H), 4.30-4.48 (m, 3H), 3.70-3.90 (m, 2H), 3.28-3.45 (m, 1H), 3.05-3.12 (m, 1H), 2.65-2.85 (m, 1H), 2.38-2.60 (m, 2H), 1.95-2.11 (m, 1H).

O—(S)-Pyrrolidin-2-ylmethyl, N—((S)-4-((3-chloro-4-fluorophenyl)carbamoyl)-7-fluoro-2,3-dihydro-1H-inden-1-yl) carbamate Hydrochloride (69.HCl)

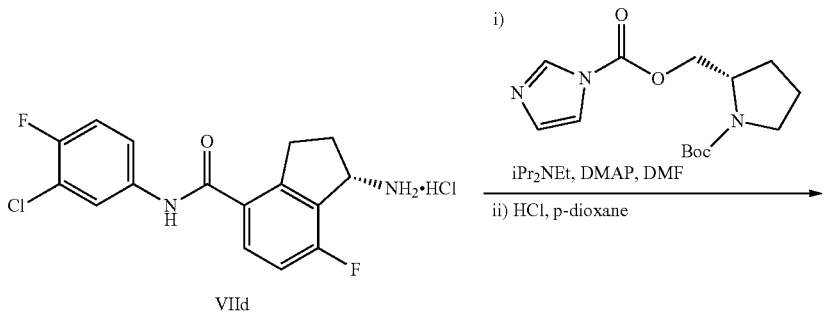

-continued

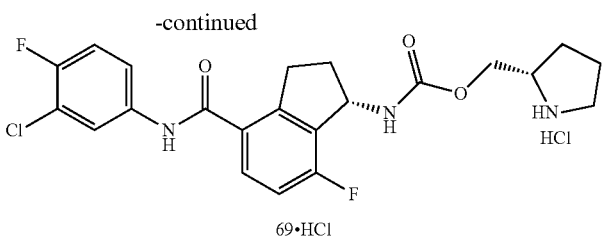
69·HCl

O—(S)-Pyrrolidin-2-ylmethyl, N—((S)-4-((3-chloro-4-fluorophenyl)carbamoyl)-7-fluoro-2,3-dihydro-1H-inden-1-yl)carbamate hydrochloride (69.HCl) was synthesized in a similar manner as outlined above from (S)-1-amino-N-(3-chloro-4-fluorophenyl)-7-fluoro-2,3-dihydro-1H-indene-4-carboxamide hydrochloride (VIId) and ((S)-(1-(tert-butoxycarbonyl)pyrrolidin-2-yl)methyl 1H-imidazole-1-carboxylate followed by acid mediated deprotection. LCMS: m/z found 450.1/452.2 [M+H]$^+$, RT=3.38 min (Method A); $^1$H NMR (300 MHz, d$_4$-methanol) δ 10.09 (s, 1H), 7.93 (dd, 1H), 7.64-7.72 (m, 2H), 7.53-7.59 (m, 1H), 7.23 (dd, 1H), 7.06 (dd, 1H), 5.37 (m, 1H), 4.35 (ddd, 2H), 3.80-3.92 (m, 1H), 3.05-3.40 (m, 3H), 3.41-3.60 (m, 1H), 2.40-2.60 (m, 1H), 1.95-2.30 (m, 4H), 1.77-1.90 (m, 1H).

O-(1-Acetyl-4,4-difluoropyrrolidin-2-yl)methyl, N—((S)-4-((3-chloro-4-fluorophenyl) carbamoyl)-7-fluoro-2,3-dihydro-1H-inden-1-yl) carbamate (61)

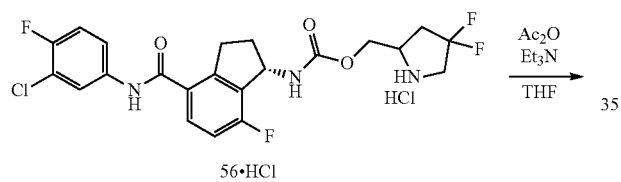
56·HCl

-continued

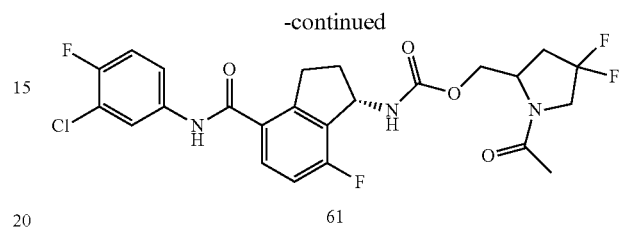
61

A solution of 32 mg (0.06 mmol) of (4,4-difluoropyrrolidin-2-yl)methyl ((S)-4-((3-chloro-4-fluorophenyl)carbamoyl)-7-fluoro-2,3-dihydro-1H-inden-1-yl)carbamate hydrochloride (56.HCl) in 0.5 mL of THF was added 17 μL (0.12 mmol, 2.0 eq.) of trimethylamine, followed by 9 μL (0.09 mmol, 1.5 eq.) of acetic anhydride and the mixture was stirred at room temperature for 2 h. The mixture was diluted with 5 mL of water and the resulting precipitate (61) collected by filtration and dried under high vacuum. LCMS: m/z found 528.2/530.2 [M+H]$^+$, RT=4.56 min (Method A).

O-Pyridin-2-ylmethyl, N—(S)-(7-fluoro-4-((4-fluoro-3-methylphenyl)carbamoyl)-2,3-dihydro-1H-inden-1-yl) carbamate (40)

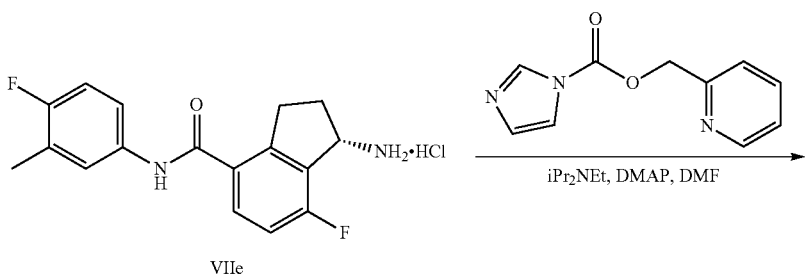
VIIe

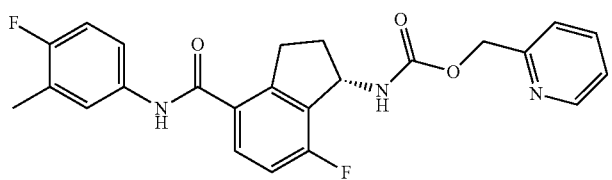
40

O-Pyridin-2-ylmethyl, N—(S)-(7-fluoro-4-((4-fluoro-3-methylphenyl)carbamoyl)-2,3-dihydro-1H-inden-1-yl) carbamate (40) was synthesized in a similar manner as outlined above from (S)-1-amino-N-(3-methyl-4-fluorophenyl)-7-fluoro-2,3-dihydro-1H-indene-4-carboxamide hydrochloride (VIIe) and pyridin-2-ylmethyl 1H-imidazole-1-carboxylate. The purified sample was subsequently converted to the hydrochloride salt using a 1.25 M solution of HCl in methanol. LCMS: m/z found 438.2 [M+H]$^+$; HPLC: RT=2.50 min (Method G); $^1$H NMR (300 MHz, DMSO-d$_6$) δ 10.19 (s, 1H), 8.72 (d, 1H), 8.26 (dd, 1H), 8.04 (d, 1H), 7.60-7.75 (m, 4H), 7.51 (m, 1H), 7.07-7.13 (m, 2H), 5.27 (m, 3H), 3.21-3.36 (m, 1H), 2.96-3.03 (m, 1H), 2.41 (m 1H), 2.20 (s 3H), 1.89-1.93 (m, 1H).

O-Imidazo[1,2-a]pyridin-2-ylmethyl, N—(S)-(4-((3-chloro-4-fluorophenyl)carbamoyl)-7-fluoro-2,3-dihydro-1H-inden-1-yl) carbamate (41)

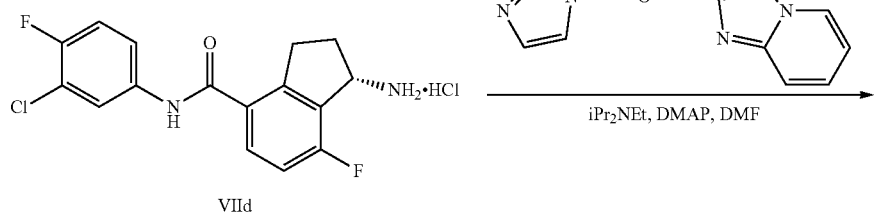

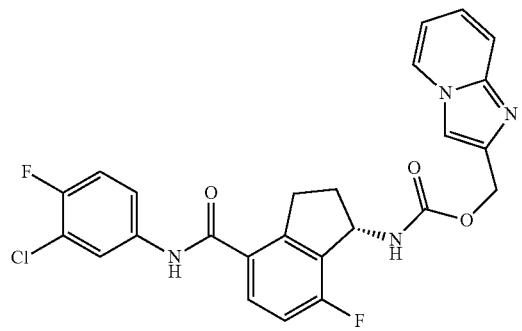

41

O-Imidazo[1,2-a]pyridin-2-ylmethyl, N—(S)-(4-((3-chloro-4-fluorophenyl)carbamoyl)-7-fluoro-2,3-dihydro-1H-inden-1-yl) carbamate (41) was synthesized in a similar manner as outlined above from (S)-1-amino-N-(3-chloro-4-fluorophenyl)-7-fluoro-2,3-dihydro-1H-indene-4-carboxamide hydrochloride (VIId) and imidazo[1,2-a]pyridin-2-ylmethyl 1H-imidazole-1-carboxylate. The purified sample was subsequently converted to the hydrochloride salt using a 1.25 M solution of HCl in methanol. LCMS: m/z found 497.3/499.3 [M+H]$^+$, RT=3.62 min (Method A); $^1$H NMR (300 MHz, DMSO-d$_6$) δ 10.43 (s, 1H), 8.88 (d, 1H), 8.32 (s, 1H), 8.03 (dd, 1H), 7.97 (d, 1H), 7.85-7.92 (m, 2H), 7.60-7.75 (m, 2H), 7.41-7.48 (m, 1H), 7.39 (dd, 1H), 7.12 (dd, 1H), 5.31-5.47 (m, 3H), 3.17-3.31 (m, 1H), 2.95-3.08 (m, 1H), 2.33-2.48 (m, 1H), 1.83-1.97 (m, 1H).

O-(1-Methyl-1H-pyrazol-3-yl)methyl, N—(S)-(4-((3-chloro-4-fluorophenyl)carbamoyl)-7-fluoro-2,3-dihydro-1H-inden-1-yl) carbamate (71)

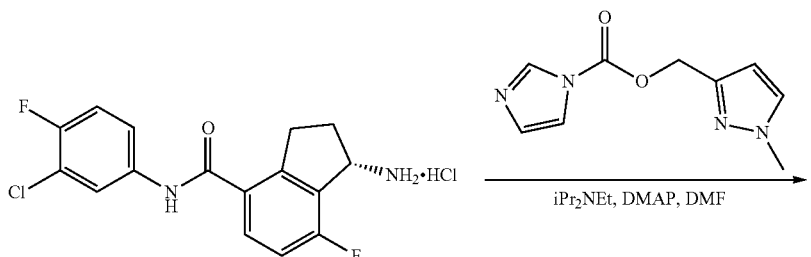

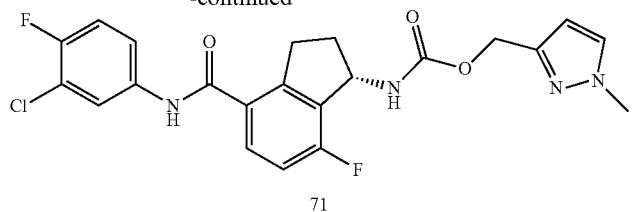

71

O-(1-Methyl-1H-pyrazol-3-yl)methyl, N—(S)-(4-((3-chloro-4-fluorophenyl)carbamoyl)-7-fluoro-2,3-dihydro-1H-inden-1-yl)carbamate (71) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-methyl-1H-pyrazol-3-yl)methyl 1H-imidazole-1-carboxylate. LCMS: m/z found 461.1/463.1 [M+H]$^+$, RT=4.41 min (Method A); $^1$H NMR (300 MHz, DMSO-d$_6$) δ 10.39 (s, 1H), 8.04 (dd, 1H), 7.62-7.72 (m, 4H), 7.40 (dd, 1H), 7.14 (dd, 1H), 6.21 (s, 2H), 5.27 (q, 1H), 3.80 (s, 3H), 3.20-3.32 (m, 1H), 2.85-3.17 (m, 1H), 2.33-2.48 (m, 1H), 1.70-1.97 (m, 1H).

O-3,3,3-Trifluoropropyl, N—(S)-(4-((3-chloro-4-fluorophenyl)carbamoyl)-7-fluoro-2,3-dihydro-1H-inden-1-yl) carbamate (70)

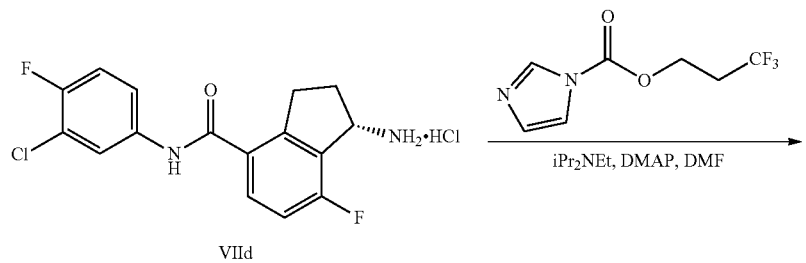

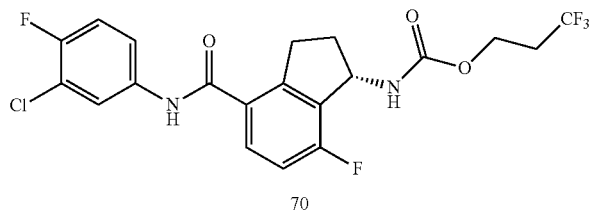

70

O-3,3,3-Trifluoropropyl, N—(S)-(4-((3-chloro-4-fluorophenyl)carbamoyl)-7-fluoro-2,3-dihydro-1H-inden-1-yl) carbamate (70) was synthesized in a similar manner as outlined above from (S)-1-amino-N-(3-chloro-4-fluorophenyl)-7-fluoro-2,3-dihydro-1H-indene-4-carboxamide hydrochloride (VIId) and 3,3,3-trifluoropropyl 1H-imidazole-1-carboxylate. LCMS: m/z found 478.2/480.2 [M+H]$^+$, RT=0.99 min (Method B); $^1$H NMR (300 MHz, CDCl$_3$) δ 7.80 (m, 1H), 7.60-7.64 (m, 2H), 7.36-7.42 (m, 1H), 7.26 (dd, 1H), 7.12 (dd, 1H), 5.38 (m, 1H), 5.03 (m, 1H), 4.30-4.38 (m, 2H), 3.30-3.41 (m, 1H), 3.05-3.20 (m, 1H), 2.40-2.70 (m, 3H), 1.98-2.07 (m, 1H).

O-[(2S)-1-(2,2,2-Trifluoroethyl)pyrrolidin-2-yl]methyl, N-[(1S)-4-[(3-chloro-4-fluorophenyl)carbamoyl]-7-fluoro-2,3-dihydro-1H-inden-1-yl]carbamate Hydrochloride (108.HCl)

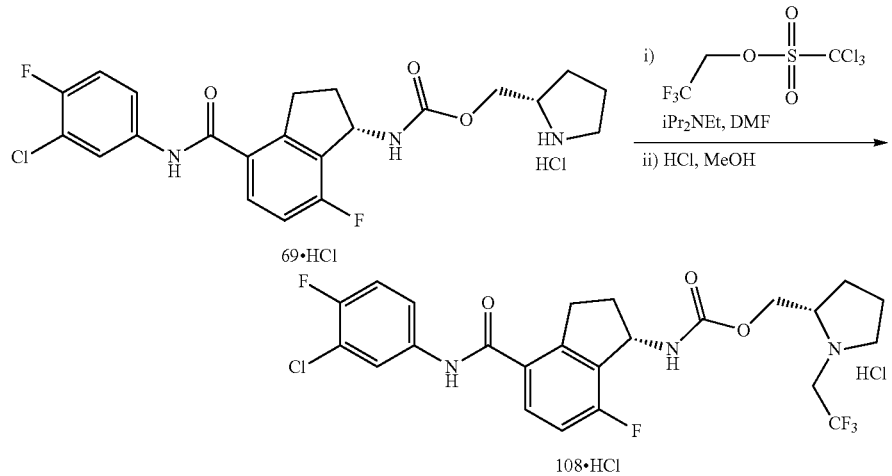

To a solution of 47 mg (0.1 mmol, 1.0 eq.) of ((2S)-pyrrolidin-2-ylmethyl N-[(1S)-4-[(3-chloro-4-fluorophenyl)carbamoyl]-7-fluoro-2,3-dihydro-1H-inden-1-yl]carbamate hydrochloride (69.HCl) and 42 µL (0.24 mmol, 2.4 eq.) of N,N-diisopropylethylamine in 1.4 mL of anhydrous DMF was added 28 µL (0.17 mmol, 1.7 eq.) of 2,2,2-trifluoroethyl trichloromethane sulfonate, and the mixture was allowed to stir at room temperature for 40 h. The mixture was then diluted with 20 mL of ethyl acetate and washed with 2×10 mL of water, followed by 2×10 mL of sat. sodium bicarbonate solution and 10 mL of brine. The organic phase was dried (Na$_2$SO$_4$), filtered, and the solvent was removed in vacuo. The crude material was absorbed onto CELITE® and purified by flash chromatography (SiO$_2$, eluting with a linear gradient of 10-55% ethyl acetate/hexanes). The purified sample was subsequently converted to the hydrochloride salt using a 1.25 M solution of HCl in methanol to provide 44 mg (0.08 mmol, 80%) of O-[(2S)-1-(2,2,2-trifluoroethyl)pyrrolidin-2-yl]methyl N-[(1S)-4-[(3-chloro-4-fluorophenyl)carbamoyl]-7-fluoro-2,3-dihydro-1H-inden-1-yl]carbamate HCl (108.HCl). LCMS: m/z found 532.2/534.2 [M+H]$^+$, RT=4.43 min (Method A); $^1$H NMR (Methanol-d$_4$) 7.93 (m, 1H), 7.69 (m, 1H), 7.56 (m, 1H), 7.23 (t, 1H), 7.06 (t, 1H), 5.38 (m, 1H), 4.54 (m, 1H), 4.43 (m, 1H), 4.30-4.16 (m, 2H), 3.97 (m, 1H), 3.81 (m, 1H), 3.38 (m, 2H), 3.12 (m, 1H), 2.52 (m, 1H), 2.37-1.90 (m, 5H).

(S)-2-((((4-((3-Chloro-4-fluorophenyl)carbamoyl)-7-fluoro-2,3-dihydro-1H-inden-1-yl)carbamoyl)oxy)methyl)pyridine 1-oxide (67)

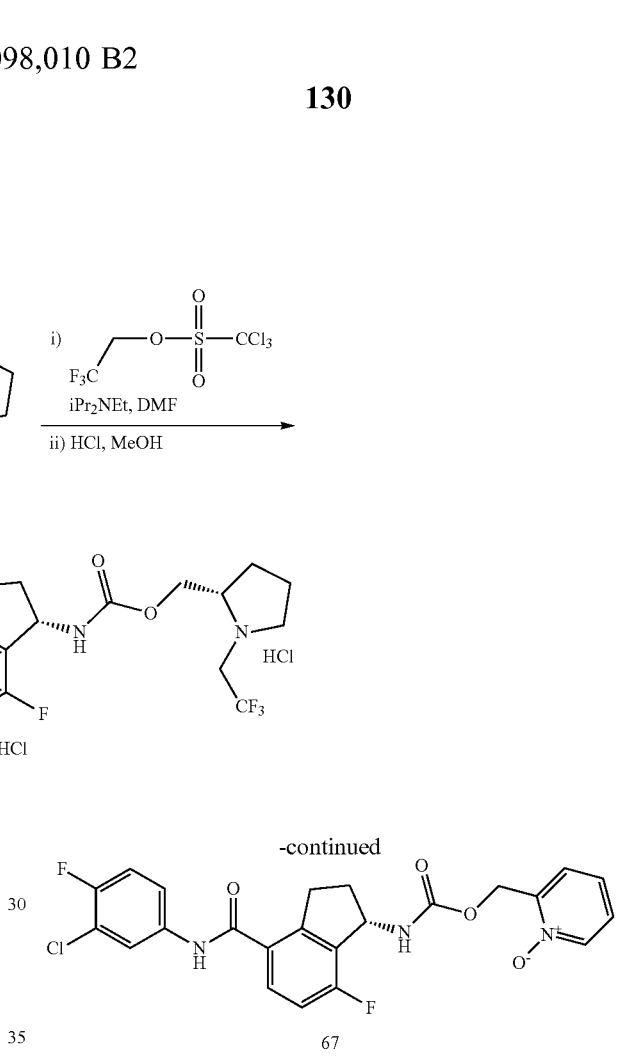

To a solution of 40 mg (0.09 mmol, 1.0 eq.) of pyridin-2-ylmethyl N-[(1S)-4-[(3-chloro-4-fluorophenyl)carbamoyl]-7-fluoro-2,3-dihydro-1H-inden-1-yl]carbamate in 4.5 mL of chloroform was added 23 mg (77%, 0.13 mmol, 1.4 eq.) of meta-chloroperbenzoic acid, and the mixture was stirred at room temperature for 16 h. The mixture was diluted with 70 mL of ethyl acetate and washed with 15 mL of sodium bisulfite solution, followed by 2×15 mL of sodium bicarbonate solution. The layers were separated, and the organic phase was filtered to provide an off-white solid. The filtrate was dried (Na$_2$SO$_4$), filtered and combined with the off white solid, and allowed to warm to room temperature and stirred for 16 h. The volatiles were then removed in vacuo, and the residue was absorbed onto CELITE® and purified by flash chromatography (SiO$_2$, eluting with a linear gradient of 3-10% methanol/methylene chloride) to provide 23 mg (0.05 mmol, 56%) of (S)-2-((((4-((3-chloro-4-fluorophenyl) carbamoyl)-7-fluoro-2,3-dihydro-1H-inden-1-yl) carbamoyl)oxy)methyl)pyridine 1-oxide (67). LCMS: m/z found 474.1/476.2 [M+H]$^+$, RT=3.92 min (Method A); $^1$H NMR (300 MHz, DMSO-d$_6$) δ 10.41 (s, 1H), 8.27-8.36 (m, 1H), 8.00-8.14 (m, 2H), 7.60-7.77 (m, 2H), 7.35-7.48 (m, 4H), 7.18 (t, 1H), 5.31 (m, 1H), 5.17 (s, 2H), 3.12-3.31 (m, 1H), 3.04 (m, 1H), 2.38-2.47 (m, 1H), 1.94 (m, 1H).

O-Thiazol-4-ylmethyl, N—(S)-(4-((3-chloro-4-fluorophenyl)carbamoyl)-7-fluoro-2,3-dihydro-1H-inden-1-yl) carbamate (124)

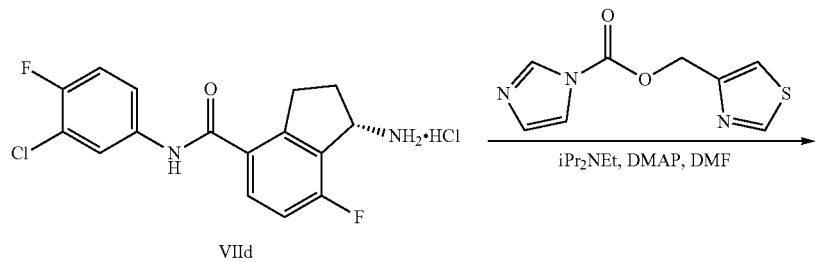

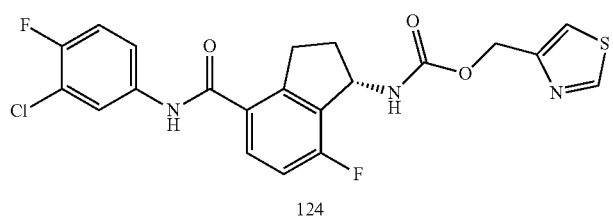

O-Thiazol-4-ylmethyl, N—(S)-(4-((3-chloro-4-fluorophenyl)carbamoyl)-7-fluoro-2,3-dihydro-1H-inden-1-yl) carbamate (124) was synthesized in a similar manner as outlined above from (S)-1-amino-N-(3-chloro-4-fluorophenyl)-7-fluoro-2,3-dihydro-1H-indene-4-carboxamide hydrochloride (VIId) and (thiazol-4-ylmethyl 1H-imidazole-1-carboxylate. LCMS (Method H); m/z found 464.1/466.1 [M+H]$^+$; HPLC (Method K) RT=10.79 min; $^1$H NMR (500 MHz, DMSO-d$_6$) δ 10.39 (s, 1H), 9.10 (d, 1H), 8.04 (dd, 1H), 7.83 (d, 1H), 7.58-7.69 (m, 3H), 7.41 (dd, 1H), 7.15 (dd, 1H), 5.30 (q, 1H), 5.14 (s, 2H), 3.18-3.25 (m, 1H), 2.94-3.06 (m, 1H), 2.29-2.48 (m, 1H), 1.73-1.96 (m, 1H).

O-Thiazol-5-ylmethyl, N—(S)-(4-((3-chloro-4-fluorophenyl)carbamoyl)-7-fluoro-2,3-dihydro-1H-inden-1-yl) carbamate (91)

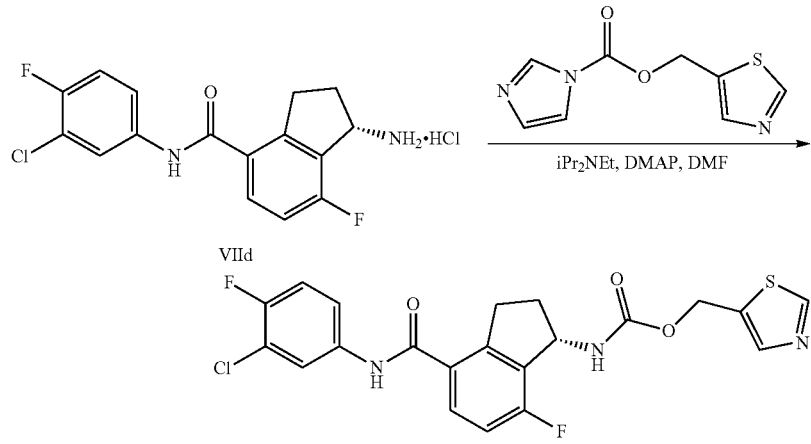

O-Thiazol-5-ylmethyl, N—(S)-(4-((3-chloro-4-fluorophenyl)carbamoyl)-7-fluoro-2,3-dihydro-1H-inden-1-yl) carbamate (91) was synthesized in a similar manner as outlined above from (S)-1-amino-N-(3-chloro-4-fluorophenyl)-7-fluoro-2,3-dihydro-1H-indene-4-carboxamide hydrochloride (VIId) and thiazol-5-ylmethyl 1H-imidazole-1-carboxylate. LCMS (Method H); m/z found 464.1/466.1 [M+H]⁺; HPLC (Method K) RT=10.78 min; ¹H NMR (500 MHz, DMSO-d₆) δ 10.43 (s, 1H), 9.09 (d, 1H), 8.04 (dd, 1H), 7.94 (s, 1H), 7.86 (d, 1H), 7.63-7.72 (m, 2H), 7.41 (dd, 1H), 7.14 (dd, 1H), 5.30 (q, 1H), 5.14 (s, 2H), 3.18-3.25 (m, 1H), 2.94-3.06 (m, 1H), 2.29-2.48 (m, 1H), 1.73-1.96 (m, 1H).

O-Thiazol-2-ylmethyl, N—(S)-(4-((3-chloro-4-fluorophenyl)carbamoyl)-7-fluoro-2,3-dihydro-1H-inden-1-yl) carbamate (92)

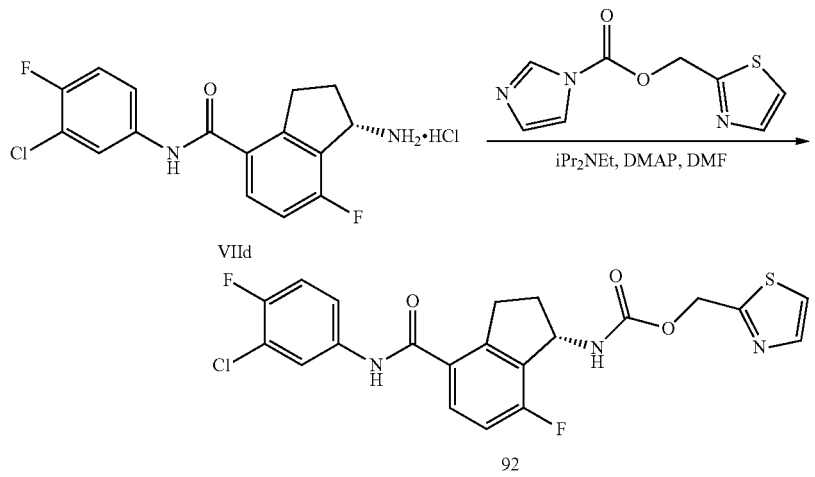

O-Thiazol-2-ylmethyl, N—(S)-(4-((3-chloro-4-fluorophenyl)carbamoyl)-7-fluoro-2,3-dihydro-1H-inden-1-yl) carbamate (92) was synthesized in a similar manner as outlined above from (S)-1-amino-N-(3-chloro-4-fluorophenyl)-7-fluoro-2,3-dihydro-1H-indene-4-carboxamide hydrochloride (VIId) and thiazol-2-ylmethyl 1H-imidazole-1-carboxylate. LCMS (Method H); m/z found 464.0/466.0 [M+H]⁺; HPLC (Method K) RT=10.57 min; ¹H NMR (500 MHz, d₄-methanol) δ 8.54 (bs, 1H), 7.92 (dd, 1H), 7.78 (d, 1H), 7.66 (dd, 1H), 7.62 (d, 1H), 7.55 (d, 1H), 7.23 (dd, 1H), 7.04 (dd, 1H), 5.35-5.45 (m, 3H), 3.25-3.35 (m, 1H), 3.08-3.15 (m, 1H), 2.46-2.58 (m, 1H), 1.98-2.08 (m, 1H).

O-Oxazol-4-ylmethyl, N—(S)-(4-((3-chloro-4-fluorophenyl)carbamoyl)-7-fluoro-2,3-dihydro-1H-inden-1-yl) carbamate (93)

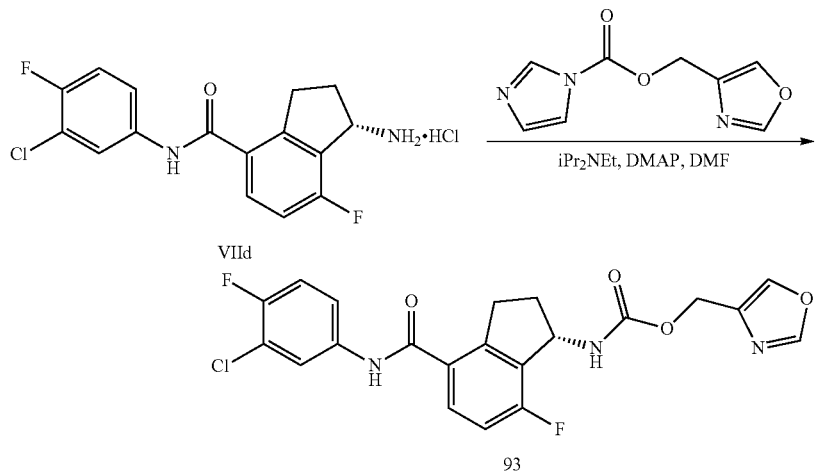

O-Thiazol-4-ylmethyl, N—(S)-(4-((3-chloro-4-fluorophenyl)carbamoyl)-7-fluoro-2,3-dihydro-1H-inden-1-yl) carbamate (93) was synthesized in a similar manner as outlined above from (S)-1-amino-N-(3-chloro-4-fluorophenyl)-7-fluoro-2,3-dihydro-1H-indene-4-carboxamide hydrochloride (VIId) and oxazol-4-ylmethyl 1H-imidazole-1-carboxylate. LCMS (Method H); m/z found 448.1/450.1 [M+H]+; HPLC (Method K) RT=10.65 min; $^1$H NMR (500 MHz, d$_4$-methanol) δ 8.19 (s, 1H), 7.94 (s. 1H), 7.91 (dd, 1H), 7.64 (dd, 1H), 7.55 (m, 1H), 7.22 (dd, 1H), 7.03 (dd, 1H), 5.36 (q, 1H), 5.05 (s, 2H), 3.18-3.25 (m, 1H), 2.94-3.06 (m, 1H), 2.29-2.48 (m, 1H), 1.73-1.96 (m, 1H).

O-Oxazol-2-ylmethyl, N—(S)-(4-((3-chloro-4-fluorophenyl)carbamoyl)-7-fluoro-2,3-dihydro-1H-inden-1-yl) carbamate (94)

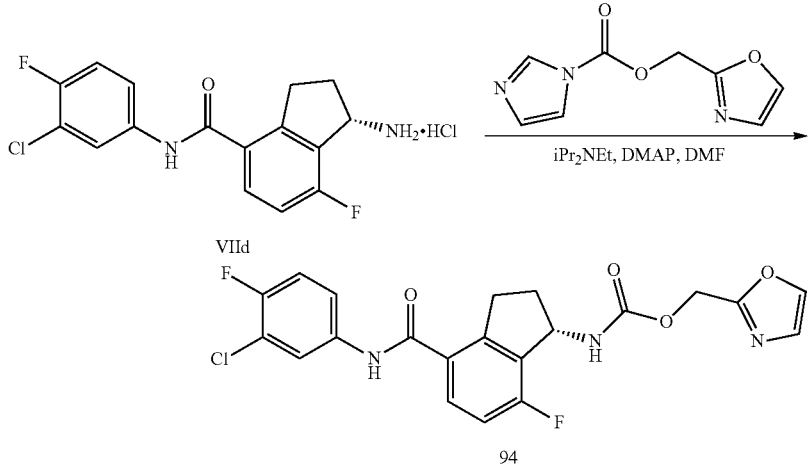

O-Oxazol-2-ylmethyl, N—(S)-(4-((3-chloro-4-fluorophenyl)carbamoyl)-7-fluoro-2,3-dihydro-1H-inden-1-yl) carbamate (94) was synthesized in a similar manner as outlined above from (S)-1-amino-N-(3-chloro-4-fluorophenyl)-7-fluoro-2,3-dihydro-1H-indene-4-carboxamide hydrochloride (VIId) and oxazol-2-ylmethyl 1H-imidazole-1-carboxylate. LCMS (Method H); m/z found 448.1/450.1 [M+H]+; HPLC (Method K) RT=10.36 min; $^1$H NMR (500 MHz, d$_4$-methanol) δ 7.89-7.94 (m, 2H), 7.66 (dd, 1H), 7.55 (d, 1H), 7.22 (dd, 1H), 7.19 (s, 1H), 7.04 (dd, 1H), 5.35 (q, 1H), 5.19 (ABq, 2H), 3.25-3.35 (m, 1H), 3.08-3.15 (m, 1H), 2.46-2.58 (m, 1H), 1.98-2.08 (m, 1H).

O-Oxazol-5-ylmethyl, N—(S)-(4-((3-chloro-4-fluorophenyl)carbamoyl)-7-fluoro-2,3-dihydro-1H-inden-1-yl) carbamate (95)

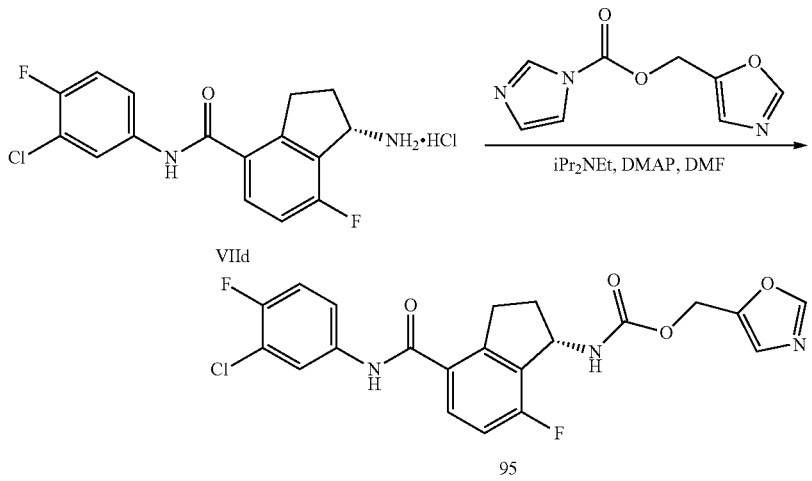

O-Oxazol-5-ylmethyl, N—(S)-(4-((3-chloro-4-fluorophenyl)carbamoyl)-7-fluoro-2,3-dihydro-1H-inden-1-yl) carbamate (95) was synthesized in a similar manner as outlined above from (S)-1-amino-N-(3-chloro-4-fluorophenyl)-7-fluoro-2,3-dihydro-1H-indene-4-carboxamide hydrochloride (VIId) and oxazol-5-ylmethyl 1H-imidazole-1-carboxylate. LCMS (Method H); m/z found 448.1/450.1 [M+H]$^+$; HPLC (Method K) RT=10.29 min; $^1$H NMR (500 MHz, d$_4$-methanol) δ 8.55 (s, 1H), 8.20 (s, 1H), 7.92 (dd, 1H), 7.66 (dd, 1H), 7.55 (d, 1H), 7.22 (dd, 1H), 7.20 (s, 1H), 7.03 (dd, 1H), 5.36 (q, 1H), 5.19 (s, 2H), 3.25-3.35 (m, 1H), 3.08-3.15 (m, 1H), 2.46-2.58 (m, 1H), 1.98-2.08 (m, 1H).

O-(1-Methyl-1H-imidazol-2-yl)methyl, N—(S)-(4-((3-chloro-4-fluorophenyl)carbamoyl)-7-fluoro-2,3-dihydro-1H-inden-1-yl) carbamate (137)

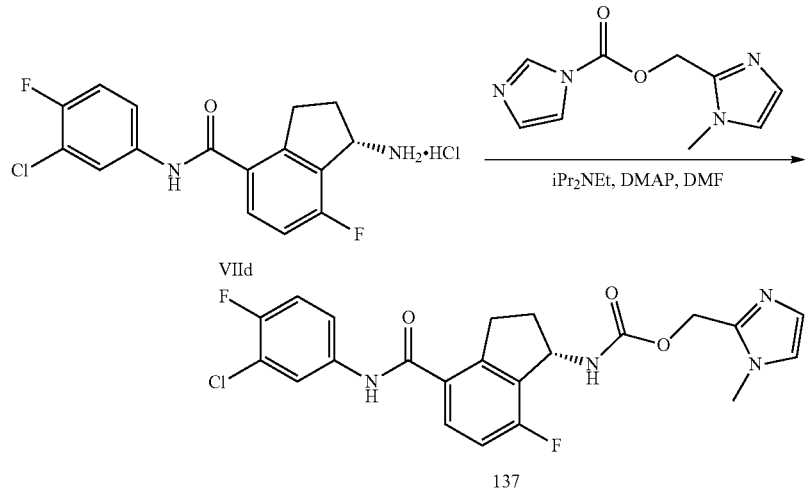

O-(1-Methyl-1H-imidazol-2-yl)methyl, N—(S)-(4-((3-chloro-4-fluorophenyl)carbamoyl)-7-fluoro-2,3-dihydro-1H-inden-1-yl) carbamate (137) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-methyl-1H-imidazol-2-yl)methyl 1H-imidazole-1-carboxylate. LCMS (Method H); m/z found 461.2/463.2 [M+H]$^+$; HPLC (Method K) RT=10.24 min; $^1$H NMR (400 MHz, DMSO-d$_6$) δ 10.40 (s, 1H), 8.04 (dd, 1H), 7.83 (d, 1H), 7.57-7.73 (m, 2H), 7.41 (dd, 1H), 7.14 (m, 2H), 6.84 (d, 1H), 5.23-5.34 (m, 1H), 4.96-5.13 (m, 2H), 3.65 (s, 3H), 3.15-3.25 (m, 1H), 2.92-3.05 (m, 1H), 2.14-2.48 (m, 1H), 1.83-1.95 (m, 1H).

O-(3-Fluoropyridin-2-yl)methyl, N—(S)-(4-((3-chloro-4-fluorophenyl)carbamoyl)-7-fluoro-2,3-dihydro-1H-inden-1-yl) carbamate (138)

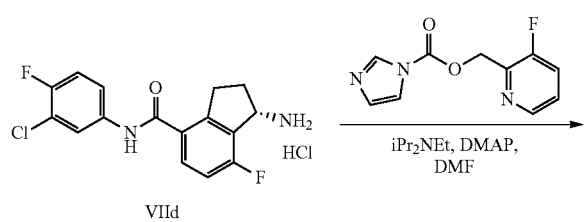

-continued

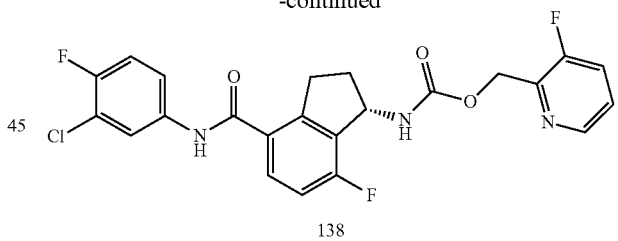

O-(3-Fluoropyridin-2-yl)methyl, N—(S)-(4-((3-chloro-4-fluorophenyl)carbamoyl)-7-fluoro-2,3-dihydro-1H-inden-1-yl) carbamate (138) was synthesized in a similar manner as outlined above from (S)-1-amino-N-(3-chloro-4-fluorophenyl)-7-fluoro-2,3-dihydro-1H-indene-4-carboxamide hydrochloride (VIId) and (3-fluoropyridin-2-yl)methyl 1H-imidazole-1-carboxylate. LCMS (Method H); m/z found 476.1/478.1 [M+H]$^+$; HPLC (Method K) RT=10.95 min; $^1$H NMR (400 MHz, DMSO-d$_6$) δ 10.38 (s, 1H), 8.40-8.42 (m, 1H), 8.02 (dd, 1H), 7.82 (d, 1H), 7.61-7.70 (m, 3H), 7.47 (m, 1H), 7.39 (dd, 1H), 7.13 (dd, 1H), 5.21-5.30 (m, 1H), 5.29 (s, 2H), 3.17-3.22 (m, 1H), 2.95-3.05 (m, 1H), 1.80-1.93 (m, 2H).

O-(5-Fluoropyridin-2-yl)methyl, N—(S)-(4-((3-chloro-4-fluorophenyl)carbamoyl)-7-fluoro-2,3-dihydro-1H-inden-1-yl) carbamate (109)

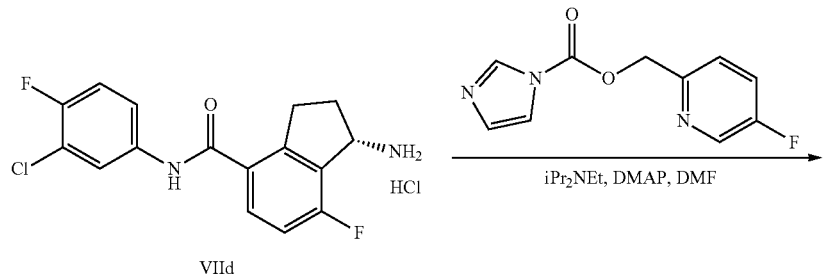

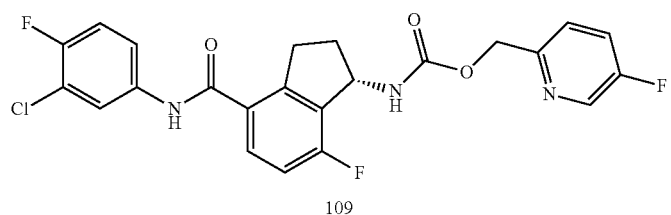

O-(5-Fluoropyridin-2-yl)methyl, N—(S)-(4-((3-chloro-4-fluorophenyl)carbamoyl)-7-fluoro-2,3-dihydro-1H-inden-1-yl) carbamate (109) was synthesized in a similar manner as outlined above from (S)-1-amino-N-(3-chloro-4-fluorophenyl)-7-fluoro-2,3-dihydro-1H-indene-4-carboxamide hydrochloride (VIId) and (5-fluoropyridin-2-yl)methyl 1H-imidazole-1-carboxylate. LCMS (Method H); m/z found 476.1/478.1 [M+H]$^+$; HPLC (Method M) RT=10.79 min; $^1$H NMR (400 MHz, CD$_3$OD) δ=8.42 (d, 1H), 7.92 (dd, 1H), 7.60-7.72 (m, 2H), 7.47-7.59 (m, 2H), 7.22 (dd, 1H), 7.05 (dd, 1H), 5.38 (m, 1H), 5.19 (s, 2H), 3.32-3.38 (m, 1H), 3.03-3.17 (m, 1H), 2.53 (m, 1H), 2.03 (m, 1H).

O-Quinolin-2-ylmethyl, N—(S)-(4-((3-chloro-4-fluorophenyl)carbamoyl)-7-fluoro-2,3-dihydro-1H-inden-1-yl) carbamate (151)

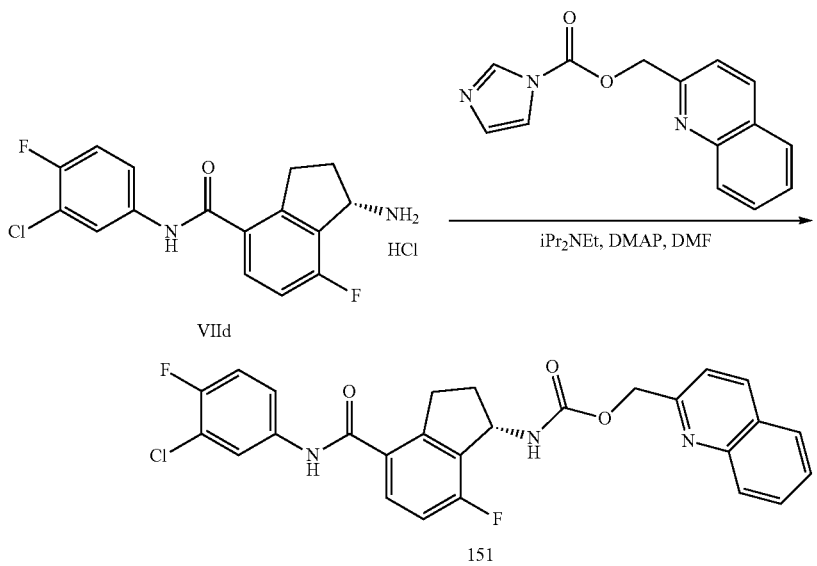

O-Quinolin-2-ylmethyl, N—(S)-(4-((3-chloro-4-fluorophenyl)carbamoyl)-7-fluoro-2,3-dihydro-1H-inden-1-yl) carbamate (151) was synthesized in a similar manner as outlined above from (S)-1-amino-N-(3-chloro-4-fluorophenyl)-7-fluoro-2,3-dihydro-1H-indene-4-carboxamide hydrochloride (VIId) and quinolin-2-ylmethyl 1H-imidazole-1-carboxylate. LCMS (Method H); m/z found 508.1/510.1 [M+H]$^+$; HPLC (Method M) RT=11.83 min; $^1$H NMR (400 MHz, DMSO-d$_6$) δ 10.42 (s, 1H), 8.42 (d, 1H), 7.91-8.11 (m, 4H), 7.75-7.82 (m, 1H), 7.58-7.74 (m, 3H), 7.52 (d, 1H), 7.42 (t, 1H), 7.18 (br t, 1H), 5.31 (m, 3H), 3.17-3.22 (m, 1H), 2.95-3.05 (m, 1H), 1.80-1.93 (m, 2H).

O-(4-Methoxypyridin-2-yl)methyl, N—(S)-(4-((3-chloro-4-fluorophenyl)carbamoyl)-7-fluoro-2,3-dihydro-1H-inden-1-yl) carbamate (140)

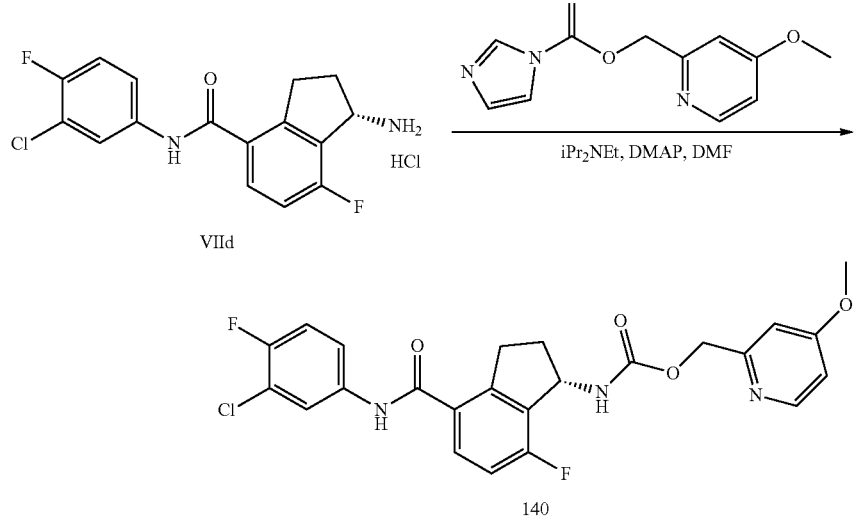

O-(4-Methoxypyridin-2-yl)methyl, N—(S)-(4-((3-chloro-4-fluorophenyl)carbamoyl)-7-fluoro-2,3-dihydro-1H-inden-1-yl) carbamate (140) was synthesized in a similar manner as outlined above from (S)-1-amino-N-(3-chloro-4-fluorophenyl)-7-fluoro-2,3-dihydro-1H-indene-4-carboxamide hydrochloride (VIId) and (4-methoxypyridin-2-yl)methyl 1H-imidazole-1-carboxylate. LCMS (Method H) m/z found 488.1/490.1 [M+H]$^+$; HPLC (Method M) RT=9.64 min; $^1$H NMR (500 MHz, DMSO-d$_6$) δ 10.55 (s, 1H), 8.36 (d, 1H), 8.05 (dd, 1H), 7.96 (d, 1H), 7.65-7.75 (m, 2H), 7.42 (dd, 1H), 7.07-7.20 (m, 1H), 6.86-6.97 (m, 2H), 5.24-5.36 (m, 1H), 5.10-5.03 (m, 2H), 3.84 (s, 3H), 3.23 (m, 1H), 3.04 (m, 1H), 1.90-2.05 (m, 1H), 1.83 (m, 1H).

O-(5-Cyanopyridin-2-yl)methyl, N—(S)-(4-((3-chloro-4-fluorophenyl)carbamoyl)-7-fluoro-2,3-dihydro-1H-inden-1-yl) carbamate (172)

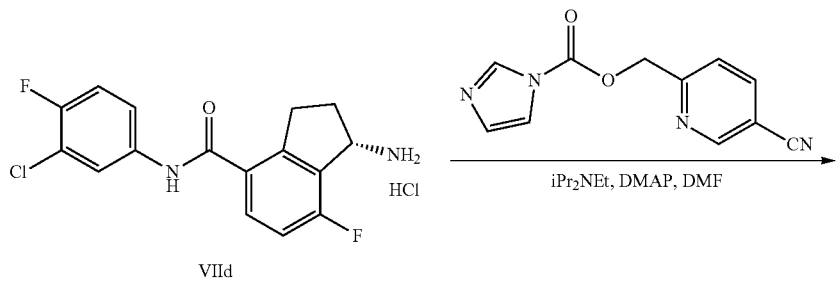

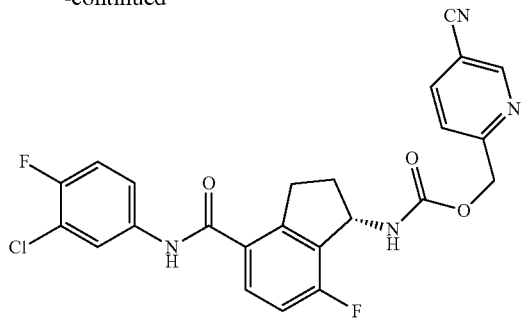

172

O-(5-Cyanopyridin-2-yl)methyl, N—(S)-(4-((3-chloro-4-fluorophenyl)carbamoyl)-7-fluoro-2,3-dihydro-1H-inden-1-yl) carbamate (172) was synthesized in a similar manner as outlined above from (S)-1-amino-N-(3-chloro-4-fluorophenyl)-7-fluoro-2,3-dihydro-1H-indene-4-carboxamide hydrochloride (VIId) and (5-cyanopyridin-2-yl)methyl 1H-imidazole-1-carboxylate. LCMS (Method H) m/z found 483.4/485.4 [M+H]$^+$; HPLC (Method M) RT=11.00 min; $^1$H NMR (400 MHz, DMSO-d$_6$) δ 10.42 (s, 1H), 9.01 (s, 1H), 8.38 (d, 1H), 8.03-8.10 (m, 2H), 7.59-7.80 (m, 2H), 7.54 (d, 1H), 7.42 (dd, 1H), 7.18 (dd, 1H), 5.25-5.35 (m, 1H), 5.21 (s, 2H), 3.20-3.30 (m, 1H), 2.94-3.10 (m, 1H), 2.29-2.46 (m, 1H), 1.79-2.06 (m, 1H).

O-(6-Cyanopyridin-2-yl)methyl, N—(S)-(4-((3-chloro-4-fluorophenyl)carbamoyl)-7-fluoro-2,3-dihydro-1H-inden-1-yl)carbamate (150)

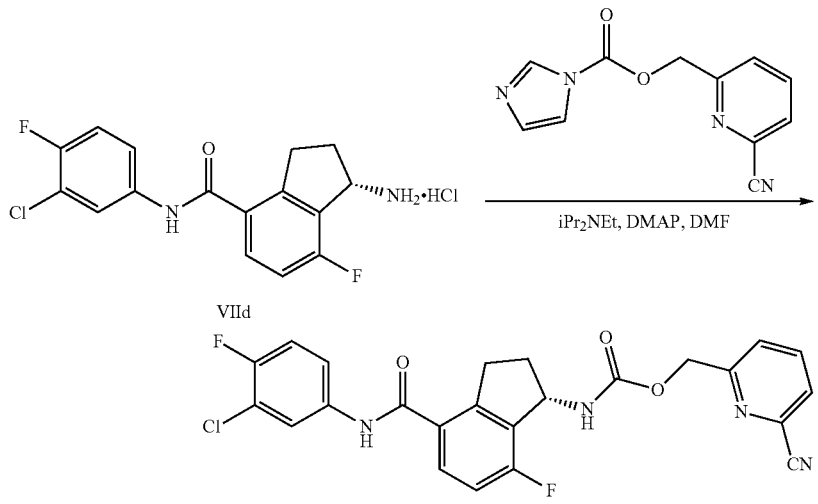

150

O-(6-Cyanopyridin-2-yl)methyl, N—(S)-(4-((3-chloro-4-fluorophenyl)carbamoyl)-7-fluoro-2,3-dihydro-1H-inden-1-yl)carbamate (150) was synthesized in a similar manner as outlined above from (S)-1-amino-N-(3-chloro-4-fluorophenyl)-7-fluoro-2,3-dihydro-1H-indene-4-carboxamide hydrochloride (VIId) and (6-cyanopyridin-2-yl)methyl 1H-imidazole-1-carboxylate. LCMS (Method H) m/z found 483.4/485.4 [M+H]$^+$; HPLC (Method M) RT=11.63 min; $^1$H NMR (500 MHz, DMSO-d$_6$) δ 10.38 (s, 1H), 8.11 (m, 1H), 7.97-8.06 (m, 3H), 7.63-7.74 (m, 3H), 7.41 (dd, 1H), 7.16 (dd, 1H), 5.27-5.31 (m, 1H), 5.18 (s, 2H), 3.20-3.30 (m, 1H), 3.00-3.07 (m, 1H), 2.38-2.50 (m, 1H), 1.92-1.96 (m, 1H).

O-(3-Methylpyrazin-2-yl)methyl, N—(S)-(4-((3-chloro-4-fluorophenyl)carbamoyl)-7-fluoro-2,3-dihydro-1H-inden-1-yl) carbamate (173)

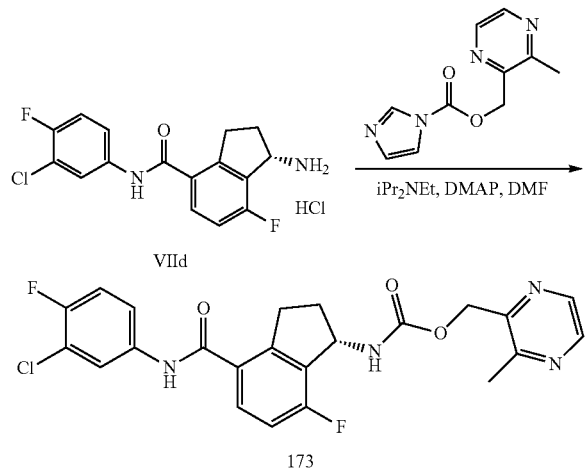

O-(3-Methylpyrazin-2-yl)methyl, N—(S)-(4-((3-chloro-4-fluorophenyl)carbamoyl)-7-fluoro-2,3-dihydro-1H-inden-1-yl)carbamate (173) was synthesized in a similar manner as outlined above from (S)-1-amino-N-(3-chloro-4-fluorophenyl)-7-fluoro-2,3-dihydro-1H-indene-4-carboxamide hydrochloride (VIId) and (3-methylpyrazin-2-yl)methyl 1H-imidazole-1-carboxylate. LCMS (Method H) m/z found 473.4/475.4 [M+H]$^+$; HPLC (Method L) RT=10.58 min; $^1$H NMR (400 MHz, DMSO-d$_6$) δ 10.40 (s, 1H), 8.37-8.67 (m, 2H), 8.03 (dd, 1H), 7.89 (d, 1H), 7.63-7.71 (m, 2H), 7.41 (dd, 1H), 7.16 (dd, 1H), 5.16-5.34 (m, 3H), 3.16-3.27 (m, 1H), 2.94-3.07 (m, 1H), 2.56 (s, 3H), 2.38-2.50 (m, 1H), 1.84-1.96 (m, 1H).

O-(5-Methylpyrazin-2-yl)methyl, N—(S)-(4-((3-chloro-4-fluorophenyl)carbamoyl)-7-fluoro-2,3-dihydro-1H-inden-1-yl)carbamate (152)

O-(5-Methylpyrazin-2-yl)methyl, N—(S)-(4-((3-chloro-4-fluorophenyl)carbamoyl)-7-fluoro-2,3-dihydro-1H-inden-1-yl)carbamate (152) was synthesized in a similar manner as outlined above from (S)-1-amino-N-(3-chloro-4-fluorophenyl)-7-fluoro-2,3-dihydro-1H-indene-4-carboxamide hydrochloride (VIId) and (5-methylpyrazin-2-yl)methyl 1H-imidazole-1-carboxylate. LCMS (Method H) m/z found 472.9/475.0 [M+H]$^+$; HPLC (Method L) RT=11.14 min; $^1$H NMR (400 MHz, CDCl$_3$) δ 8.53 (bs, 1H), 8.44 (s, 1H), 7.80 (dd, 1H), 7.55-7.66 (m, 2H), 7.39-7.71 (m, 1H), 7.14 (dd, 1H), 6.94 (dd, 1H), 5.36-5.48 (m, 1H), 5.25-5.41 (m, 3H), 3.33-3.48 (m, 1H), 3.09-3.20 (m, 1H), 2.55-2.67 (m, 1H), 2.58 (s, 3H), 2.04-2.12 (m, 1H).

O-Pyridin-2-ylmethyl, N—(S)-(4-((3-cyano-4-fluorophenyl)carbamoyl)-7-fluoro-2,3-dihydro-1H-inden-1-yl)carbamate Hydrochloride (126.HCl)

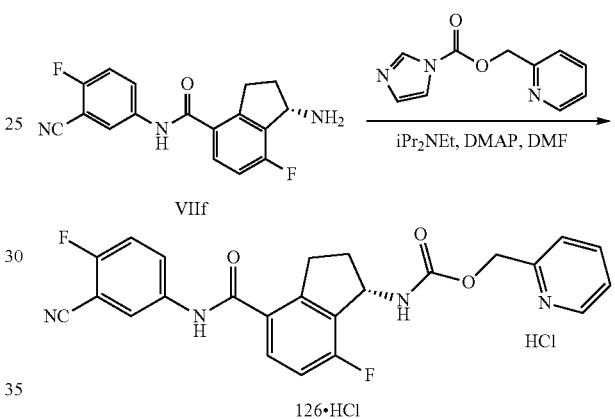

O-Pyridin-2-ylmethyl, N—(S)-(4-((3-cyano-4-fluorophenyl)carbamoyl)-7-fluoro-2,3-dihydro-1H-inden-1-yl)carbamate hydrochloride (126.HCl) was prepared in a similar manner as described above from (S)-1-amino-N-(3-cyano-4-fluorophenyl)-7-fluoro-2,3-dihydro-1H-indene-4-carboxamide hydrochloride (VIIf) and pyridin-2-ylmethyl 1H-imidazole-1-carboxylate. The purified compound was

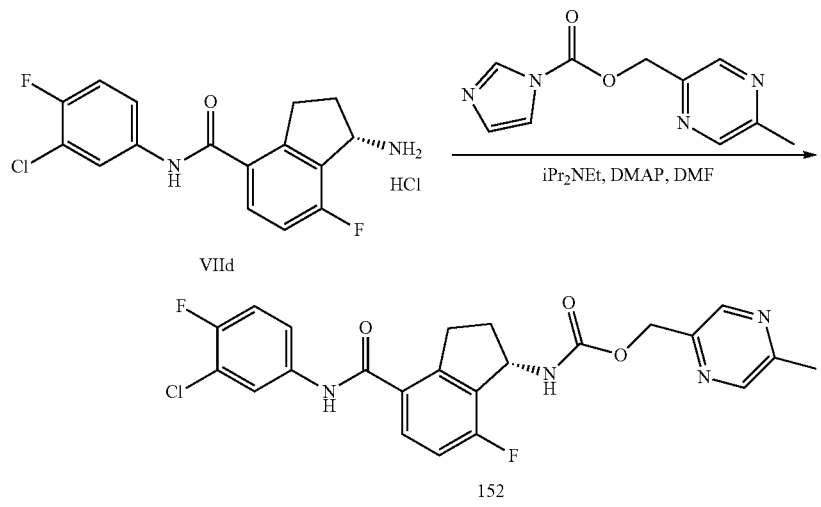

subsequently converted to the hydrochloride salt using a 1.25 M solution of HCl in methanol. LCMS: m/z found 449.1/450.2 [M+H]⁺, RT=3.07 min (Method A); ¹H NMR (300 MHz, Methanol-d₄) δ 8.83 (d, 1H), 8.62 (t, 1H), 8.15 (m, 1H), 8.09 (d, 1H), 8.05-7.89 (m, 2H), 7.77-7.66 (m, 1H), 7.38 (t, 1H), 7.07 (t, 1H), 5.45 (s, 2H), 5.38 (t, 1H), 3.46-3.32 (m, 1H), 3.22-3.07 (m, 1H), 2.64-2.45 (m, 1H), 2.14-1.96 (m, 1H).

O-Pyridin-2-ylmethyl, N—(S)-(4-((3-(difluoromethyl)-4-fluorophenyl)carbamoyl)-7-fluoro-2,3-dihydro-1H-inden-1-yl)carbamate Hydrochloride (148.HCl)

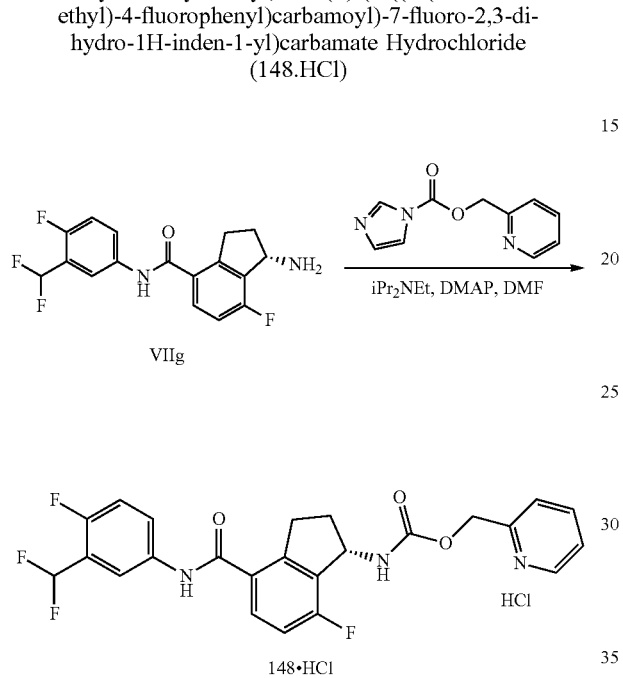

O-Pyridin-2-ylmethyl, N—(S)-(4-((3-(difluoromethyl)-4-fluorophenyl)carbamoyl)-7-fluoro-2,3-dihydro-1H-inden-1-yl)carbamate hydrochloride (148.HCl) was prepared in a similar manner as described above from (S)-1-amino-N-(3-difluoromethyl-4-fluorophenyl)-7-fluoro-2,3-dihydro-1H-indene-4-carboxamide hydrochloride (VIIg) and pyridin-2-ylmethyl 1H-imidazole-1-carboxylate. The purified compound was subsequently converted to the hydrochloride salt using a 1.25 M solution of HCl in methanol. LCMS: m/z found 474.1/475.2 [M+H]⁺, RT=3.37 min (Method A); ¹H NMR (300 MHz, Methanol-d₄) δ 8.90-8.81 (m, 1H), 8.68 (t, 1.6 Hz, 1H), 8.15 (d, 1H), 8.07 (t, 1H), 8.07 (m, 1H), 7.88-7.77 (m, 1H), 7.76-7.65 (m, 1H), 7.31-7.15 (m, 1H), 7.13-6.97 (m, 2H), 5.47 (s, 2H), 5.37 (t, 1H), 3.45-3.27 (m, 1H), 3.22-3.04 (m, 1H), 2.63-2.45 (m, 1H), 2.14-1.96 (m, 1H).

tert-Butyl 4-(2-hydroxyethyl)-1H-pyrazole-1-carboxylate

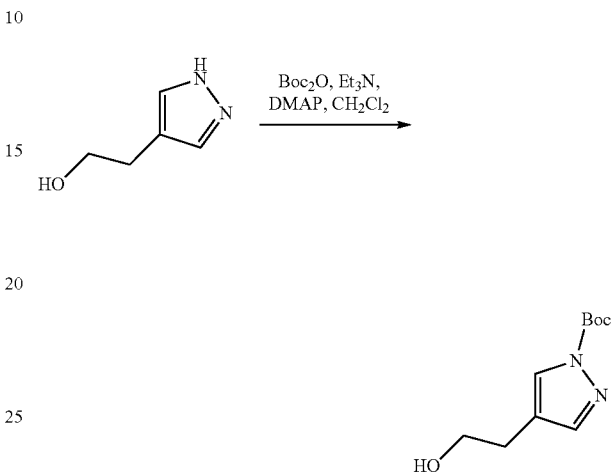

To a solution of 0.5 g (4.45 mmol, 1.0 eq.) of 2-(1H-pyrazol-4-yl)ethan-1-ol in 15 mL of methylene chloride was added 54 mg (0.44 mmol, 0.1 eq.) of 4,4-dimethylaminopyridine (54 mg, 0.44 mmol, 0.1 eq), followed by 0.93 mL (6.68 mmol, 1.5 eq.) of triethylamine and 1.06 g (4.90 mmol, 1.1 eq.) of di-tert-butyl dicarbonate. The resulting mixture was stirred at room temperature for 16 h. The mixture was diluted with 25 mL of methylene chloride and washed with 5 mL of water, followed by 5 mL of brine. The organic phase was dried (Na₂SO₄), filtered and the solvent removed in vacuo. The residue was purified by flash chromatography (SiO₂, eluting with a linear gradient of 0-100% ethyl acetate-hexanes) to provide 0.8 g (3.8 mmol, 84%) of tert-butyl 4-(2-hydroxyethyl)-1H-pyrazole-1-carboxylate.

O-2-(1H-Pyrazol-4-yl)ethyl, N—(S)-(4-((3-chloro-4-fluorophenyl)carbamoyl)-7-fluoro-2,3-dihydro-1H-inden-1-yl) carbamate (110)

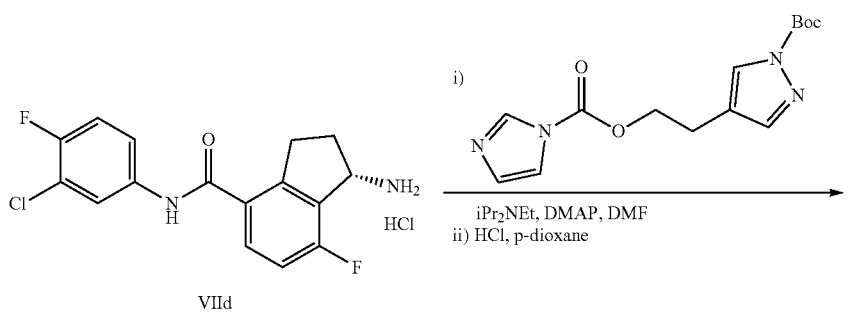

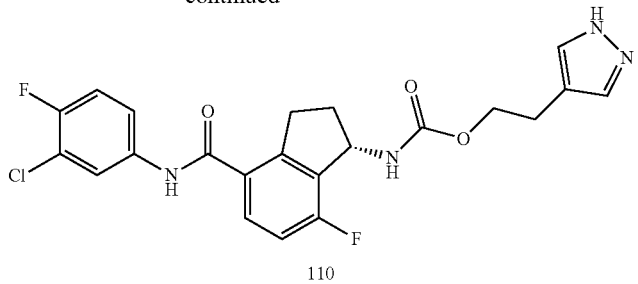

110 tert-Butyl (S)-4-(2-(((4-((3-chloro-4-fluorophenyl)carbamoyl)-7-fluoro-2,3-dihydro-1H-inden-1-yl)carbamoyl)oxy)ethyl)-1H-pyrazole-1-carboxylate was synthesized in a similar manner as outlined above from (S)-1-amino-N-(3-chloro-4-fluorophenyl)-7-fluoro-2,3-dihydro-1H-indene-4-carboxamide hydrochloride (VIId) and tert-butyl 4-(2-((1H-imidazole-1-carbonyl)oxy)ethyl)-1H-pyrazole-1-carboxylate. The resulting N-Boc protected pyrazole was subsequently dissolved in p-dioxane and treated with a 4 M solution of HCl in p-dioxane such that the final HCl concentration was 1 M. The volatiles were removed in vacuo and the residue was triturated with diethyl ether to provide O-2-(1H-pyrazol-4-yl)ethyl, N—(S)-(4-((3-chloro-4-fluorophenyl)carbamoyl)-7-fluoro-2,3-dihydro-1H-inden-1-yl) carbamate (110). LCMS (Method H) m/z found 461.2/463.2 [M+H]$^+$; HPLC (Method K) RT=10.30 min; $^1$H NMR (400 MHz, DMSO-$d_6$) δ=10.42 (s, 1H), 8.05 (dd, 1H), 7.63-7.85 (m, 3H), 7.55 (s, 2H), 7.41 (dd, 1H), 7.16 (dd, 1H), 5.23-5.29 (m, 1H), 4.10 (m, 2H), 3.17-3.29 (m, 1H), 2.95-3.08 (m, 1H), 2.73 (m, 2H), 2.29-2.44 (m, 1H), 1.82-1.94 (m, 1H).

O-2-Hydroxyethyl, N—(S)-(4-((3-chloro-4-fluorophenyl)carbamoyl)-7-fluoro-2,3-dihydro-1H-inden-1-yl) carbamate (141)

O-2-((tert-Butyldimethylsilyl)oxy)ethyl, N—(S)-(4-((3-chloro-4-fluorophenyl)carbamoyl)-7-fluoro-2,3-dihydro-1H-inden-1-yl) carbamate was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-((tert-butyldimethylsilyl)oxy)ethyl 1H-imidazole-1-carboxylate. To a solution of 60 mg (0.11 mmol, 1.0 eq.) of the resulting O-TBS protected alcohol in 2 mL of THF was added 0.23 mL (0.23 mmol, 2.0 eq.) of a 1.0 M solution of tetrabutylammonium fluoride in THF. The mixture was stirred at room temperature for 2 h, and the solvent was removed in vacuo. The residue was purified by flash chromatography (SiO$_2$, eluting with a linear gradient of 10-100% ethyl acetate/hexanes) to provide O-2-hydroxyethyl, N—(S)-(4-((3-chloro-4-fluorophenyl)carbamoyl)-7-fluoro-2,3-dihydro-1H-inden-1-yl) carbamate (141). LCMS (Method H) m/z found 411.2/413.2 [M+H]$^+$; HPLC (Method K) RT=5.86 min; $^1$H NMR (400 MHz, DMSO-$d_6$) δ 10.40 (s, 1H), 8.04 (dd, 1H), 7.63-7.70 (m, 3H), 7.41 (dd, 1H), 7.15 (dd, 1H), 5.26 (q, 1H), 4.73 (t, 1H), 3.98 (t, 2H), 3.54 (q, 2H), 3.19-3.28 (m, 1H), 2.95-3.05 (m, 1H), 2.35-2.45 (m, 1H), 1.83-1.95 (m, 1H).

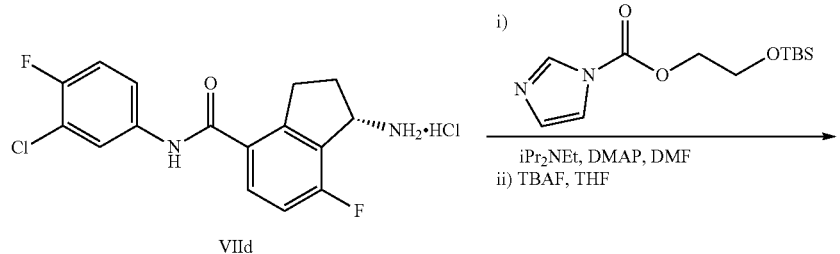

VIId

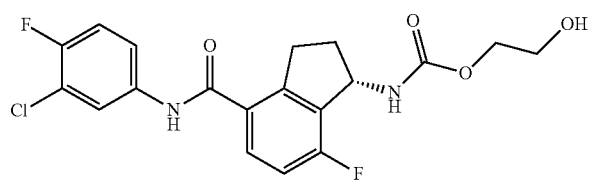

141

O-3-Hydroxypropyl, N—(S)-(4-((3-chloro-4-fluorophenyl)carbamoyl)-7-fluoro-2,3-dihydro-1H-inden-1-yl) carbamate (155)

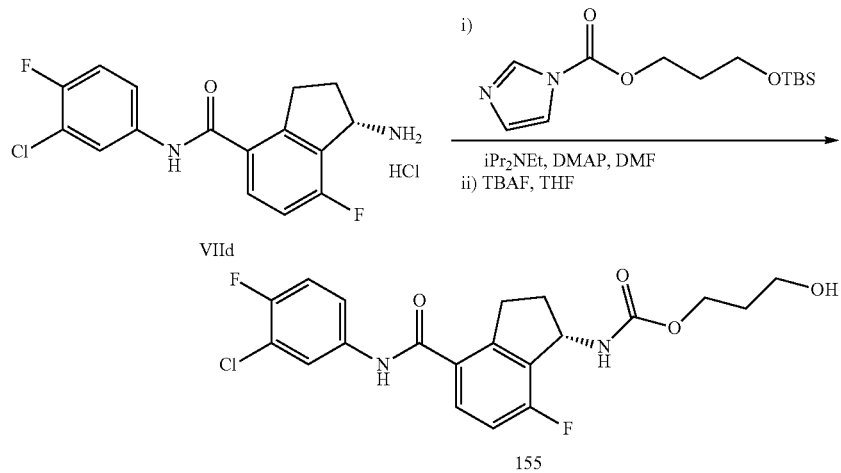

O-3-Hydroxypropyl, N—(S)-(4-((3-chloro-4-fluorophenyl)carbamoyl)-7-fluoro-2,3-dihydro-1H-inden-1-yl) carbamate (155) was synthesized in a similar manner as outlined above from (S)-1-amino-N-(3-chloro-4-fluorophenyl)-7-fluoro-2,3-dihydro-1H-indene-4-carboxamide hydrochloride (VIId) and 3-((tert-butyldimethylsilyl)oxy) propyl 1H-imidazole-1-carboxylate followed by TBAF mediated desilylation. LCMS (Method H) m/z found 425.2/427.2 [M+H]$^+$; HPLC (Method L) RT=10.53 min.

O-cis-4-Hydroxycyclohexyl, N—((S)-4-((3-chloro-4-fluorophenyl)carbamoyl)-7-fluoro-2,3-dihydro-1H-inden-1-yl) carbamate (154)

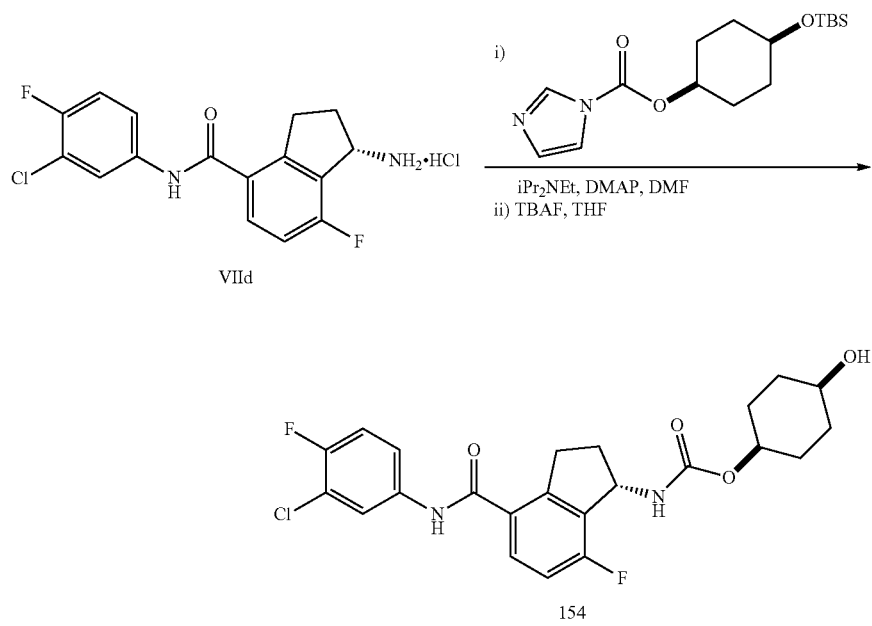

O-cis-4-Hydroxycyclohexyl, N—((S)-4-((3-chloro-4-fluorophenyl)carbamoyl)-7-fluoro-2,3-dihydro-1H-inden-1-yl)carbamate (154) was synthesized in a similar manner as outlined above from (S)-1-amino-N-(3-chloro-4-fluorophenyl)-7-fluoro-2,3-dihydro-1H-indene-4-carboxamide hydrochloride (VIId) and cis-4-((tert-butyldimethylsilyl)oxy)cyclohexyl 1H-imidazole-1-carboxylate followed by TBAF mediated desilylation. LCMS (Method H) m/z found 463.2/465.2 [M−H], RT=2.19 min; HPLC (Method L) RT=10.39 min.

O-trans-4-Hydroxycyclohexyl, N—((S)-4-((3-chloro-4-fluorophenyl)carbamoyl)-7-fluoro-2,3-dihydro-1H-inden-1-yl) carbamate (156)

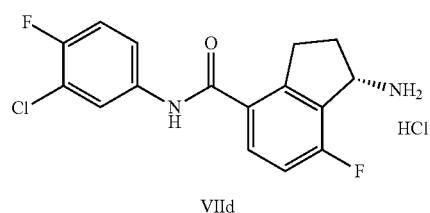
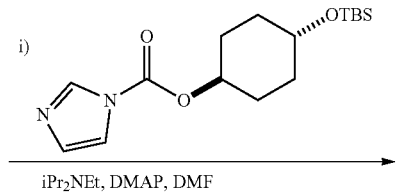
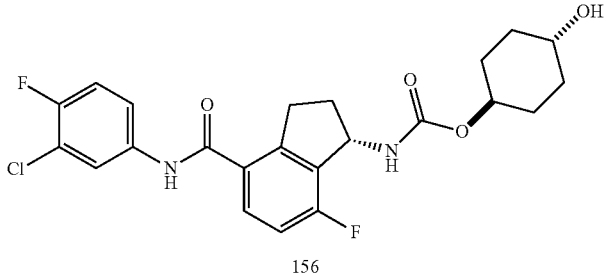

O-trans-4-Hydroxycyclohexyl, N—((S)-4-((3-chloro-4-fluorophenyl)carbamoyl)-7-fluoro-2,3-dihydro-1H-inden-1-yl) carbamate (156) was synthesized in a similar manner as outlined above from (S)-1-amino-N-(3-chloro-4-fluorophenyl)-7-fluoro-2,3-dihydro-1H-indene-4-carboxamide hydrochloride (VIId) and trans-4-((tert-butyldimethylsilyl)oxy) cyclohexyl 1H-imidazole-1-carboxylate followed by TBAF mediated desilylation. LCMS (Method H) m/z found 465.2/467.2 [M+H]⁺, RT=2.19 min; HPLC (Method L) RT=10.86 min.

O-(4-Chloropyridin-2-yl)methyl, N—(S)-(4-((3-chloro-4-fluorophenyl)carbamoyl)-7-fluoro-2,3-dihydro-1H-inden-1-yl) carbamate Hydrochloride (80)

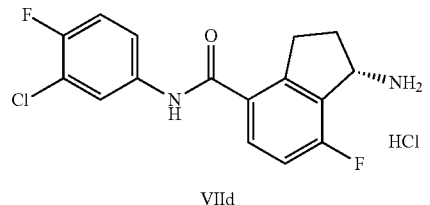
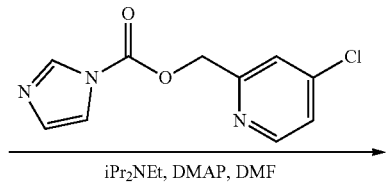
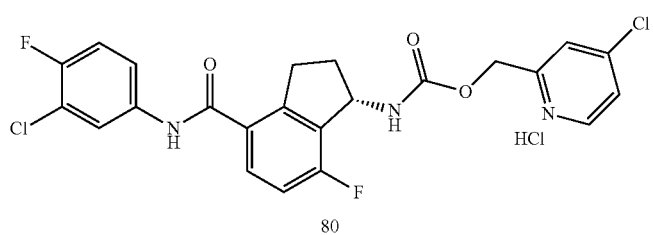

O-(4-Chloropyridin-2-yl)methyl, N—(S)-(4-((3-chloro-4-fluorophenyl)carbamoyl)-7-fluoro-2,3-dihydro-1H-inden-1-yl) carbamate (80) was synthesized in a similar manner as outlined above from (S)-1-amino-N-(3-chloro-4-fluorophenyl)-7-fluoro-2,3-dihydro-1H-indene-4-carboxamide hydrochloride (VIId) and (4-chloropyridin-2-yl)methyl 1H-imidazole-1-carboxylate. The purified compound was subsequently converted to the hydrochloride salt using a 1.25 M solution of HCl in methanol. LCMS: m/z found 492.1/494.0 [M+H]$^+$ (Method A), RT: 4.87 minutes. $^1$H NMR (300 MHz, d$_4$-methanol) δ 8.75 (d, 1H), 8.10 (s, 1H), 8.02 (m, 1H), 7.92 (m, 1H), 7.68 (m, 1H), 7.55 (m, 1H), 7.22 (t, 1H), 7.05 (t, 1H), 5.39 (m, 3H), 3.37 (m, 1H), 3.12 (m, 1H), 2.53 (m, 1H), 2.04 (m, 1H).

O-(6-(Trifluoromethyl)pyridin-2-yl)methyl, N—(S)-(4-((3-chloro-4-fluorophenyl)carbamoyl)-7-fluoro-2,3-dihydro-1H-inden-1-yl) carbamate (168)

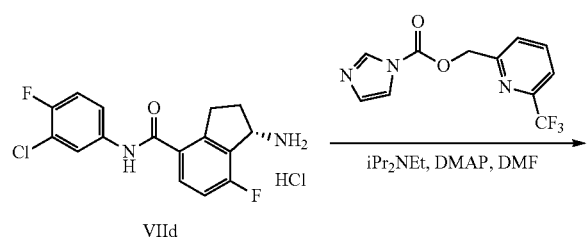

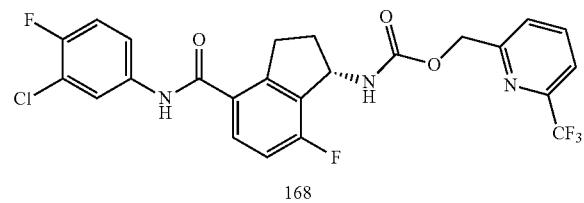

168

O-(6-(Trifluoromethyl)pyridin-2-yl)methyl, N—(S)-(4-((3-chloro-4-fluorophenyl)carbamoyl)-7-fluoro-2,3-dihydro-1H-inden-1-yl)carbamate (168) was prepared in a similar manner as described above from (S)-1-amino-N-(3-chloro-4-fluorophenyl)-7-fluoro-2,3-dihydro-1H-indene-4-carboxamide hydrochloride (VIId) and (6-(trifluoromethyl)pyridin-2-yl)methyl 1H-imidazole-1-carboxylate. LCMS: m/z found 526.1/528.1 [M+H]$^+$, RT=5.48 min (Method A); $^1$H NMR (300 MHz, Chloroform-d) δ 7.89 (t, 1H), 7.80 (dd, 1H), 7.67 (s, 1H), 7.66-7.51 (m, 3H), 7.46-7.34 (m, 1H), 7.13 (t, 1H), 6.99 (t, 1H), 5.50-5.10 (m, 3H), 3.46-3.33 (m, 1H), 3.23-3.06 (m, 1H), 2.71-2.52 (m, 1H), 2.16-1.98 (m, 1H), 1.26 (t, 1H).

O-(5-(Trifluoromethyl)pyridin-2-yl)methyl, N—(S)-(4-((3-chloro-4-fluorophenyl)carbamoyl)-7-fluoro-2,3-dihydro-1H-inden-1-yl) carbamate (169)

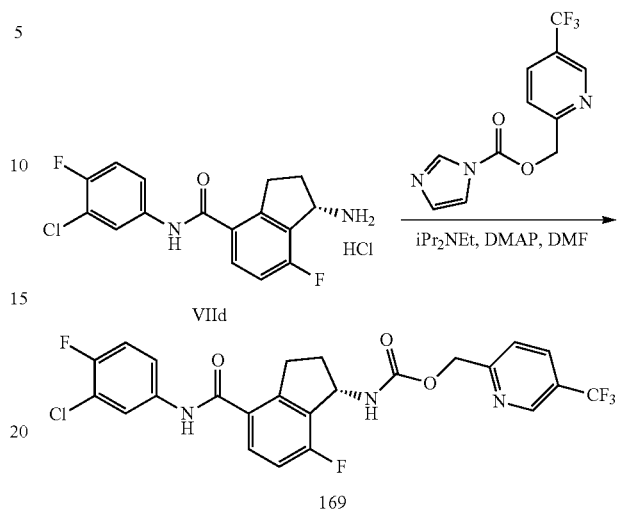

169

O-(5-(Trifluoromethyl)pyridin-2-yl)methyl, N—(S)-(4-((3-chloro-4-fluorophenyl)carbamoyl)-7-fluoro-2,3-dihydro-1H-inden-1-yl) carbamate (169) was prepared in a similar manner as described above from (S)-1-amino-N-(3-chloro-4-fluorophenyl)-7-fluoro-2,3-dihydro-1H-indene-4-carboxamide hydrochloride (VIId) and (5-(trifluoromethyl)pyridin-2-yl)methyl 1H-imidazole-1-carboxylate. LCMS: m/z found 526.1/528.0 [M+H]$^+$, RT=5.39 min (Method A); $^1$H NMR (300 MHz, DMSO-d$_6$) δ 10.40 (s, 1H), 8.94 (s, 1H), 8.27 (d, 1H), 8.04 (d, 2H), 7.76-7.65 (m, 1H), 7.61 (d, 2H), 7.40 (t, 1H), 7.16 (t, 1H), 5.25 (d, 3H), 3.20 (m, 2H), 3.02 (m, 1H), 1.99-1.88 (m, 1H).

O-Pyrazin-2-ylmethyl, N—(S)-(4-((3-chloro-4-fluorophenyl)carbamoyl)-7-fluoro-2,3-dihydro-1H-inden-1-yl) carbamate (78)

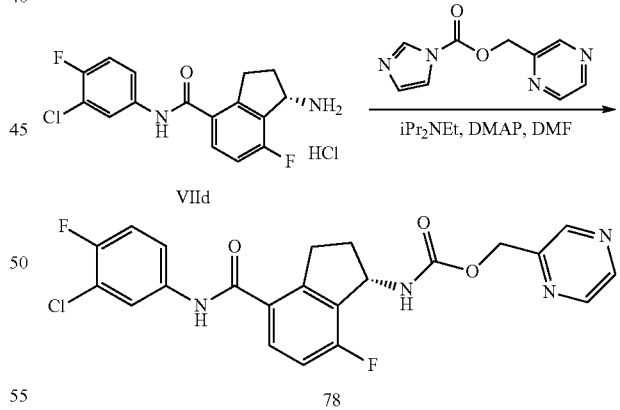

78

O-Pyrazin-2-ylmethyl, N—(S)-(4-((3-chloro-4-fluorophenyl)carbamoyl)-7-fluoro-2,3-dihydro-1H-inden-1-yl) carbamate (78) was synthesized in a similar manner as outlined above from (S)-1-amino-N-(3-chloro-4-fluorophenyl)-7-fluoro-2,3-dihydro-1H-indene-4-carboxamide hydrochloride (VIId) and pyrazin-2-ylmethyl 1H-imidazole-1-carboxylate. LCMS: m/z found 459.1/461.2 [M+H]$^+$ (Method A), RT: 4.24 minutes. $^1$H NMR (300 MHz, d-DMSO) δ 10.87 (s, 1H), 8.64 (m, 3H), 8.03 (m, 2H), 7.67 (m, 2H), 7.41 (t, 1H), 7.17 (t, 1H), 5.28 (m, 1H), 5.20 (s, 2H), 3.22 (m, 1H), 3.03 (m, 1H), 2.42 (m, 1H), 1.93 (m, 1H).

O-2-(Pyridin-2-yl)ethyl, N—(S)-(4-((3-chloro-4-fluorophenyl)carbamoyl)-7-fluoro-2,3-dihydro-1H-inden-1-yl) carbamate Hydrochloride (83.HCl)

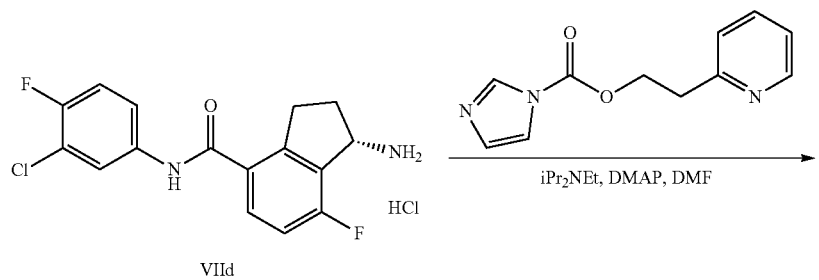

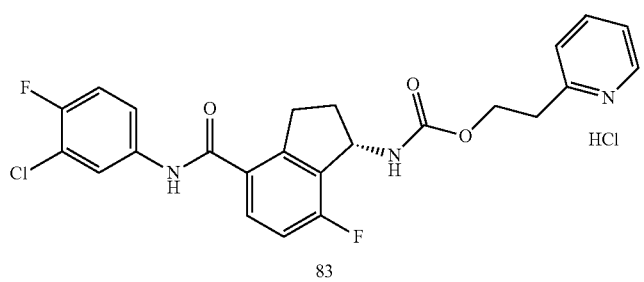

O-2-(Pyridin-2-yl)ethyl, N—(S)-(4-((3-chloro-4-fluorophenyl)carbamoyl)-7-fluoro-2,3-dihydro-1H-inden-1-yl) carbamate (83) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-(pyridin-2-yl)ethyl 1H-imidazole-1-carboxylate. The purified compound was subsequently converted to the hydrochloride salt using a 1.25 M solution of HCl in methanol. LCMS: m/z found 472.1/474.2 [M+H]$^+$ (Method A), RT: 3.47 minutes. $^1$H NMR (300 MHz, d$_4$-methanol) δ 8.76 (d, 1H), 8.57 (m, 1H), 8.05 (d, 1H), 7.98 (t, 1H), 7.92 (m, 1H), 7.65 (m, 1H), 7.55 (m, 1H), 7.22 (t, 1H), 7.03 (t, 1H), 5.25 (m, 1H), 4.52 (m, 2H), 3.41 (m, 2H), 3.24 (m, 1H), 3.07 (m, 1H), 2.45 (m, 1H), 1.92 (m, 1H).

O-2-(4-Methylthiazol-5-yl)ethyl, N—(S)-(4-((3-chloro-4-fluorophenyl)carbamoyl)-7-fluoro-2,3-dihydro-1H-inden-1-yl) carbamate (105)

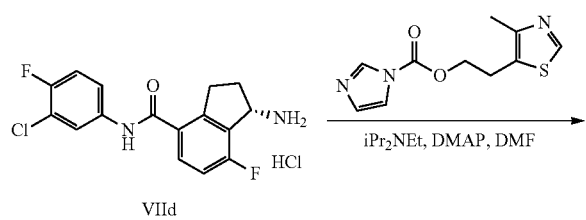

-continued

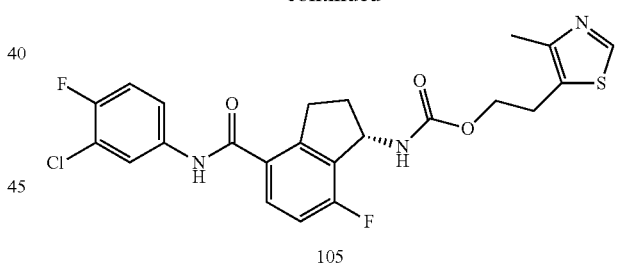

O-2-(4-Methylthiazol-5-yl)ethyl, N—(S)-(4-((3-chloro-4-fluorophenyl)carbamoyl)-7-fluoro-2,3-dihydro-1H-inden-1-yl)carbamate (105) was prepared in a similar manner as described above from (S)-1-amino-N-(3-chloro-4-fluorophenyl)-7-fluoro-2,3-dihydro-1H-indene-4-carboxamide hydrochloride (VIId) and 2-(4-methylthiazol-5-yl)ethyl 1H-imidazole-1-carboxylate. LCMS: m/z found 492.0/494.1 [M+H]$^+$; HPLC: RT=4.06 min (Method A); $^1$H NMR (300 MHz, DMSO-d$_6$) δ 10.40 (s, 1H), 8.87 (s, 1H), 8.09-8.00 (m, 1H), 7.79-7.60 (m, 3H), 7.41 (t, 1H), 7.15 (t, 1H), 5.24 (q, 1H), 4.15 (t, 2H), 3.32-3.15 (m, 1H), 3.12-2.92 (m, 3H), 2.46-2.22 (m, 4H), 1.94-1.80 (m, 1H).

O-Isoxazol-3-ylmethyl, N—(S)-(4-((3-chloro-4-fluorophenyl)carbamoyl)-7-fluoro-2,3-dihydro-1H-inden-1-yl) carbamate (82)

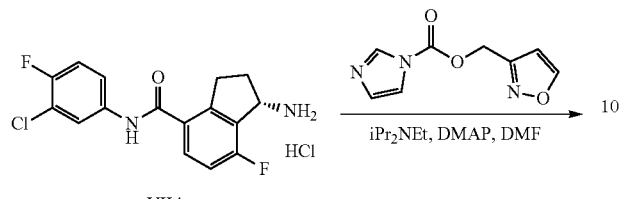

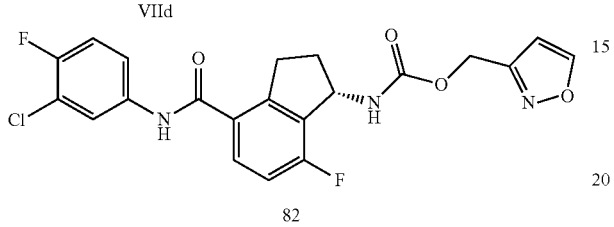

O-Isoxazol-3-ylmethyl, N—(S)-(4-((3-chloro-4-fluorophenyl)carbamoyl)-7-fluoro-2,3-dihydro-1H-inden-1-yl) carbamate (82) was synthesized in a similar manner as outlined above from (S)-1-amino-N-(3-chloro-4-fluorophenyl)-7-fluoro-2,3-dihydro-1H-indene-4-carboxamide hydrochloride (VIId) and isoxazol-3-ylmethyl 1H-imidazole-1-carboxylate. LCMS: m/z found 448.1/450.1 [M+H]+ (Method A), RT: 4.60 minutes. $^1$H NMR (300 MHz, DMSO-$d_6$) δ 10.40 (s, 1H), 8.93 (d, 1H), 8.04 (m, 1H), 7.95 (d, 1H), 7.66 (m, 2H), 7.41 (t, 1H), 7.16 (t, 1H), 6.56 (d, 1H), 5.29 (q, 1H), 5.15 (s, 2H), 3.22 (m, 1H), 3.03 (m, 1H), 2.43 (m, 1H), 1.90 (m, 1H).

O-Pyrimidin-4-ylmethyl, N—(S)-(4-((3-chloro-4-fluorophenyl)carbamoyl)-7-fluoro-2,3-dihydro-1H-inden-1-yl) carbamate (85)

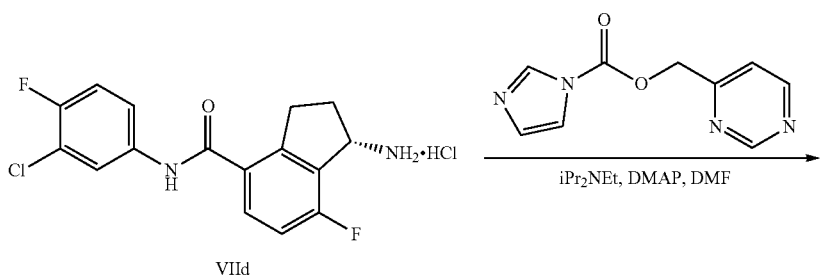

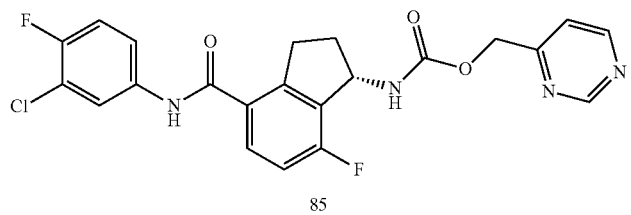

O-Pyrimidin-4-ylmethyl, N—(S)-(4-((3-chloro-4-fluorophenyl)carbamoyl)-7-fluoro-2,3-dihydro-1H-inden-1-yl) carbamate (85) was synthesized in a similar manner as outlined above from (S)-1-amino-N-(3-chloro-4-fluorophenyl)-7-fluoro-2,3-dihydro-1H-indene-4-carboxamide hydrochloride (VIId) and pyrimidin-4-ylmethyl 1H-imidazole-1-carboxylate. LCMS: m/z found 459.1/461.2 [M+H]+ (Method A), RT: 4.14 minutes. $^1$H NMR (300 MHz, DMSO-$d_6$) δ 10.41 (s, 1H), 9.15 (s, 1H), 8.83 (d, 1H), 8.06 (m, 2H), 7.68 (m, 2H), 7.41 (m, 2H), 7.18 (t, 1H), 5.29 (q, 1H), 5.14 (s, 2H), 3.24 (m, 1H), 3.04 (m, 1H), 2.44 (m, 1H), 1.94 (m, 1H).

O-(1-Methyl-1H-1,2,4-triazol-3-yl)methyl, N—(S)-(4-((3-chloro-4-fluorophenyl)carbamoyl)-7-fluoro-2,3-dihydro-1H-inden-1-yl) carbamate (102)

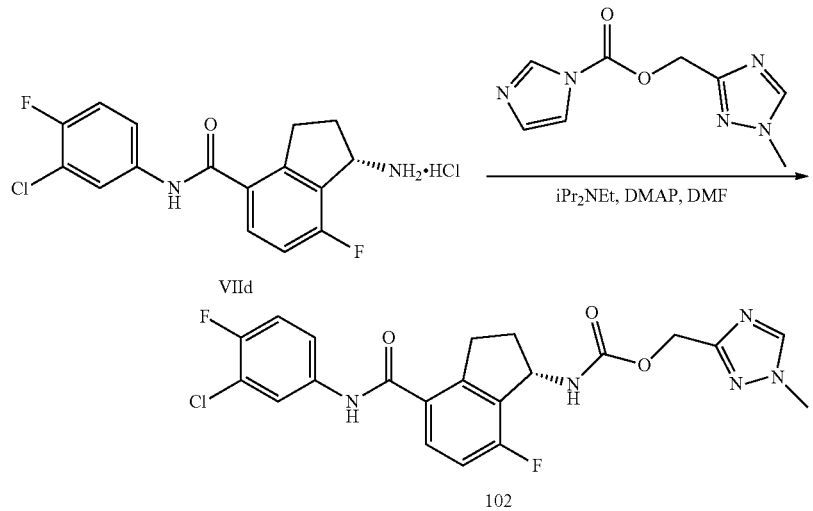

O-(1-Methyl-1H-1,2,4-triazol-3-yl)methyl, N—(S)-(4-((3-chloro-4-fluorophenyl)carbamoyl)-7-fluoro-2,3-dihydro-1H-inden-1-yl) carbamate (102) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-methyl-1H-1,2,4-triazol-3-yl)methyl 1H-imidazole-1-carboxylate. LCMS: m/z found 462.1/464.0 [M+H]+, RT=3.90 min (Method A). $^1$H NMR (300 MHz, DMSO-$d_6$): δ 10.39 (s, 1H), 8.43 (s, 1H), 7.99-8.09 (m, 1H), 7.80 (d, 1H), 7.60-7.75 (m, 2H), 7.40 (m, 1H), 7.15 (t, 1H), 5.28 (q, 1H), 5.92-5.09 (m, 2H), 3.85 (s, 3H), 3.19 (m, 1H), 2.93-3.10 (m, 1H), 2.35-2.46 (m, 1H), 1.80-1.99 (m, 1H).

Methyl 1-((2-(trimethylsilyl)ethoxy)methyl)-1H-1,2,4-triazole-3-carboxylate

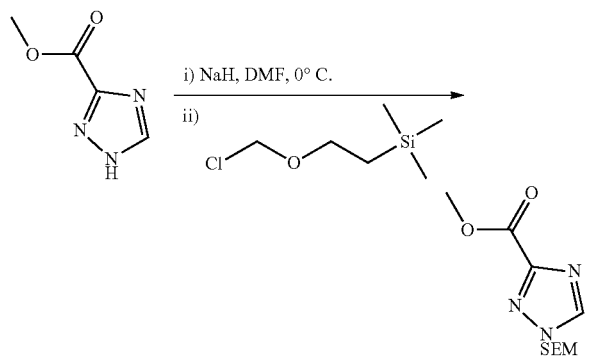

To a suspension of 0.63 g (60% in mineral oil, 15.7 mmol, 1.0 eq.) of sodium hydride in 15 mL of anhydrous DMF at 0° C. under a nitrogen atmosphere was added a solution of 2.0 g (15.7 mmol, 1.0 eq.) of methyl 1H-1,2,4-triazole-3-carboxylate in 50 mL of anhydrous DMF dropwise. The mixture was stirred at 0° C. for 30 min, and 2.78 mL (15.7 mmol, 1.0 eq.) of [2-(chloromethoxy)ethyl]trimethylsilane was added dropwise. The mixture was stirred at 0° C. for a further 30 minutes, then at room temperature for one hour. The mixture was then poured into 150 mL of ice water and extracted with 3×100 mL of diethyl ether. The combined organics were dried (MgSO$_4$), filtered, and the solvent was removed in vacuo. The residue was purified by flash chromatography (SiO$_2$, eluting with a gradient of 5-65% ethyl acetate/hexanes) to provide 1.82 g (7.1 mmol, 45%) of methyl 1-((2-(trimethylsilyl)ethoxy)methyl)-1H-1,2,4-triazole-3-carboxylate. $^1$H NMR (300 MHz, CDCl$_3$) δ 8.02 (s, 1H), 5.91 (s, 2H), 4.02 (s, 3H), 3.71-3.58 (m, 2H), 0.97-0.79 (m, 2H), −0.03 (s, 9H).

(1-((2-(Trimethylsilyl)ethoxy)methyl)-1H-1,2,4-triazol-3-yl)methanol

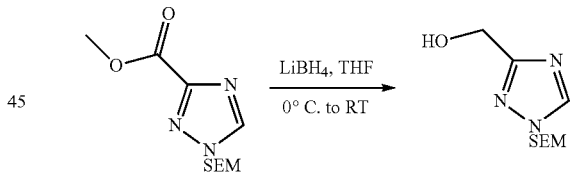

To a solution of 0.8 g (3.1 mmol, 1.0 eq.) of methyl 1-{[2-(trimethylsilyl)ethoxy]methyl}-1,2,4-triazole-3-carboxylate, in 7.5 mL of anhydrous THF at 0° C. under a nitrogen atmosphere was added 0.78 mL (3.1 mmol, 1.0 eq.) of a 4 M solution of lithium borohydride THF dropwise. The mixture was allowed to warm to room temperature and stirred for 30 min. The reaction mixture was then re-cooled in an ice bath and sodium sulfate decahydrate was added. The reaction mixture was subsequently allowed to stir at room temperature overnight. The reaction mixture was cooled in an ice bath, and 5 drops of water were added. After stirring for 10 minutes, the reaction mixture was filtered through sodium sulfate and CELITE® and the filter cake was washed with 40 mL of methylene chloride. The combined filtrate was washed with 10 mL water and 10 mL brine. The organics were dried (Na$_2$SO$_4$), filtered, and the solvent was removed in vacuo to provide 0.72 g of crude (1-((2-(trimethylsilyl)ethoxy)methyl)-1H-1,2,4-triazol-3-yl)methanol.

163

(1-((2-(Trimethylsilyl)ethoxy)methyl)-1H-1,2,4-triazol-3-yl)methyl 1H-imidazole-1-carboxylate

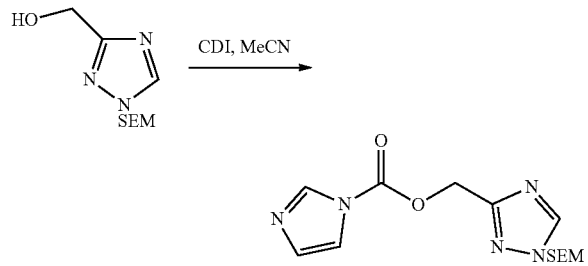

(1-((2-(Trimethylsilyl)ethoxy)methyl)-1H-1,2,4-triazol-3-yl)methyl 1H-imidazole-1-carboxylate was synthesized in a similar manner as outlined above from (1-((2-(trimethylsilyl)ethoxy) methyl)-1H-1,2,4-triazol-3-yl)methanol and 1,1'-carbonyldiimidazole.

O-(1-{[2-(Trimethylsilyl)ethoxy]methyl}-1,2,4-triazol-3-yl)methyl, N—N-[(1S)-4-[(3-chloro-4-fluorophenyl)carbamoyl]-7-fluoro-2,3-dihydro-1H-inden-1-yl]carbamate

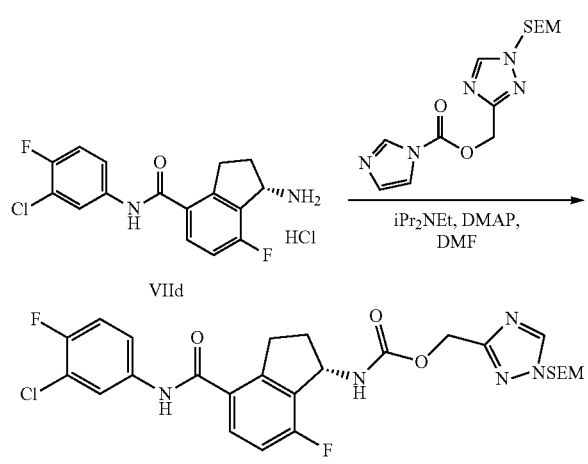

O-(1-{[2-(Trimethylsilyl)ethoxy]methyl}-1,2,4-triazol-3-yl)methyl, N-[(1S)-4-[(3-chloro-4-fluorophenyl)carbamoyl]-7-fluoro-2,3-dihydro-1H-inden-1-yl]carbamate was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-((2-(trimethylsilyl)ethoxy) methyl)-1H-1,2,4-triazol-3-yl)methyl 1H-imidazole-1-carboxylate.

O-(1H-1,2,4-Triazol-3-yl)methyl, N—(S)-(4-((3-chloro-4-fluorophenyl)carbamoyl)-7-fluoro-2,3-dihydro-1H-inden-1-yl) carbamate (195)

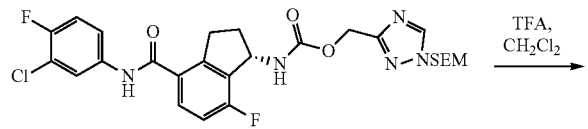

164

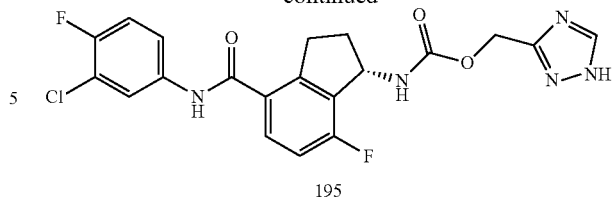

To a solution of 67 mg (0.12 mmol, 1.0 eq.) of (1-{[2-(trimethylsilyl)ethoxy]methyl}-1,2,4-triazol-3-yl)methyl N-[(1S)-4-[(3-chloro-4-fluorophenyl)carbamoyl]-7-fluoro-2,3-dihydro-1H-inden-1-yl]carbamate in 4 mL of methylene chloride was added 0.8 mL of trifluoroacetic acid. After stirring for 2 hours at room temperature, 5 mL of toluene was added, and the volatiles were removed in vacuo. The residue was taken up in 35 mL of ethyl acetate and washed with saturated aqueous 2×20 mL of NaHCO$_3$, followed by 15 mL of brine. The organic phase was dried over (Na$_2$SO$_4$), filtered, and the solvent was removed in vacuo. The residue was absorbed on CELITE® and purified by flash chromatography (SiO$_2$, eluting with a gradient of 1.5-10% methanol/methylene chloride) to provide 30 mg (0.07 mmol, 58%) of O-(1H-1,2,4-triazol-3-yl)methyl, N—(S)-(4-((3-chloro-4-fluorophenyl)carbamoyl)-7-fluoro-2,3-dihydro-1H-inden-1-yl)carbamate (195). LCMS: m/z found 448.1/450.1 [M+H]$^+$, RT=3.67 min (Method A). $^1$H NMR (300 MHz, DMSO-d$_6$) δ 14.00 (m, 1H), 10.40 (s, 1H), 8.54 (s, 0.7H, triazole tautomer), 8.04 (m, 1H), 7.92 (m, 0.3H, triazole tautomer), 7.81 (m, 1H), 7.67 (m, 2H), 7.41 (t, 1H), 7.15 (t, 1H), 5.28 (q, 1H), 5.15-4.99 (m, 2H), 3.21 (m, 1H), 3.02 (m, 1H), 2.47-2.35 (m, 1H), 1.91 (s, 1H).

1-((2-(Trimethylsilyl)ethoxy)methyl)-1H-pyrazole-3/5-carbaldehyde

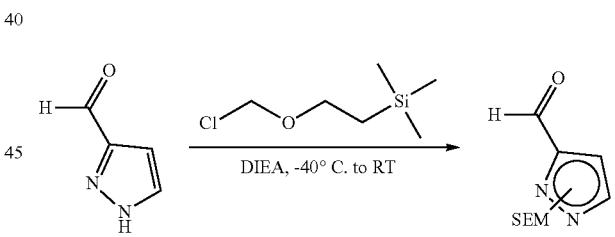

To a suspension of 0.60 g (6.24 mmol, 1.0 eq.) of 1H-pyrazole-3-carbaldehyde in 12 mL of methylene chloride at −40° C. under a nitrogen atmosphere was added 1.63 mL (9.37 mmol, 1.5 eq.) of N,N-diisopropylethyl amine, followed by 1.66 mL (9.37 mmol, 1.5 eq.) of [2-(chloromethoxy)ethyl]trimethylsilane. The mixture was allowed to warm to room temperature and stirred for 16 h. The reaction mixture was then diluted with 20 mL brine, and extracted with 3×30 mL of methylene chloride. The combined organic extracts were dried (Na$_2$SO$_4$), filtered, and the solvent was removed in vacuo. The residue was absorbed on CELITE® and purified by flash chromatography (SiO$_2$, eluting with a gradient of 0-30% ethyl acetate/hexanes) to provide 1 g (66%) of a mixture of 1-((2-(trimethylsilyl)ethoxy)methyl)-1H-pyrazole-5-carbaldehyde and 1-((2-(trimethylsilyl)ethoxy)methyl)-1H-pyrazole-3-carbaldehyde in an approximately 1:1 ratio.

(1-((2-(Trimethylsilyl)ethoxy)methyl)-1H-pyrazol-3/5-yl)methanol

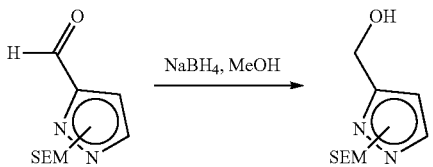

To a solution of 0.73 g (1.61 mmol, approximately 1:1 mixture of regioisomers) of 1-((2-(trimethylsilyl)ethoxy)methyl)-1H-pyrazole-3/5-carbaldehyde in 12 mL of methanol was added 36 mg (0.96 mmol, 0.6 eq.) of sodium borohydride and the mixture was stirred at room temperature for 45 min. The volatiles were removed in vacuo, and the residue was resuspended in 40 mL of water. The mixture was extracted with 2×40 mL of ethyl acetate and the combined organic extracts were dried (MgSO$_4$), filtered, and the solvent was removed in vacuo to provide 0.74 g of crude (1-((2-(trimethylsilyl)ethoxy)methyl)-1H-pyrazol-3/5-yl)methanol.

(1-((2-(Trimethylsilyl)ethoxy)methyl)-1H-pyrazol-3/5-yl)methyl 1H-imidazole-1-carboxylate

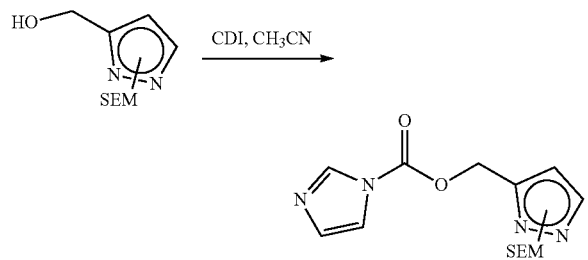

(1-((2-(Trimethylsilyl)ethoxy)methyl)-1H-pyrazol-3/5-yl)methyl 1H-imidazole-1-carboxylate was synthesized in a similar manner as outlined above from (1-((2-(trimethylsilyl)ethoxy) methyl)-1H-pyrazol-3/5-yl)methanol and 1,1'-carbonyldiimidazole.

O-(1-((2-(Trimethylsilyl)ethoxy)methyl)-1H-pyrazol-5-yl)methyl, N—(S)-(4-((3-chloro-4-fluorophenyl)carbamoyl)-7-fluoro-2,3-dihydro-1H-inden-1-yl) carbamate

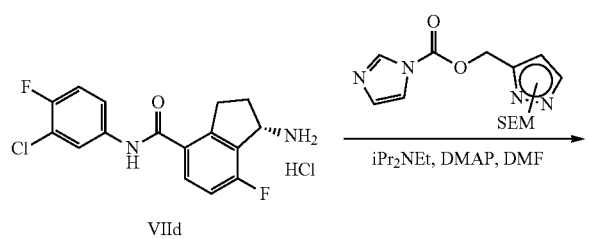

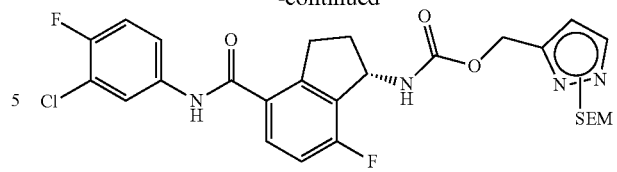

O-(1-((2-(Trimethylsilyl)ethoxy)methyl)-1H-pyrazol-5-yl)methyl, N—(S)-(4-((3-chloro-4-fluorophenyl) carbamoyl)-7-fluoro-2,3-dihydro-1H-inden-1-yl) carbamate was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-((2-(trimethylsilyl)ethoxy)methyl)-1H-pyrazol-3/5-yl) methyl 1H-imidazole-1-carboxylate.

O-(1H-Pyrazol-3-yl)methyl, N—(S)-(4-((3-chloro-4-fluorophenyl)carbamoyl)-7-fluoro-2,3-dihydro-1H-inden-1-yl) carbamate (193)

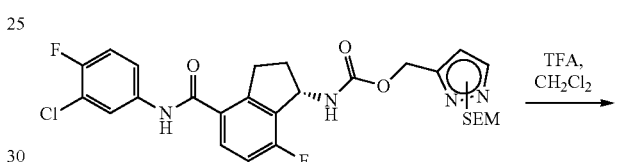

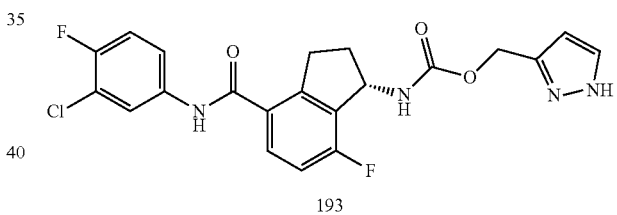

To a solution of 74 mg (0.13 mmol) of (1-((2-(trimethylsilyl)ethoxy)methyl)-1H-pyrazol-5-yl)methyl (S)-(4-((3-chloro-4-fluorophenyl)carbamoyl)-7-fluoro-2,3-dihydro-1H-inden-1-yl)carbamate in 4 mL of methylene chloride was added 1 mL of trifluoroacetic acid. The mixture was stirred at room temperature for 16 h, and 4 mL of toluene was then added. The volatiles were removed in vacuo, and the residue was redissolved in 30 mL of ethyl acetate. The solution was washed with 2×15 mL of sat. sodium bicarbonate solution, followed by 15 mL of brine. The organic phase was dried (Na$_2$SO$_4$), filtered, and the solvent was removed in vacuo. The residue was absorbed on CELITE® and purified by flash chromatography (SiO$_2$, eluting with a gradient of 35-100% ethyl acetate/hexanes) to provide 21 mg (36%) of O-(1H-pyrazol-3-yl)methyl, N—(S)-(4-((3-chloro-4-fluorophenyl)carbamoyl)-7-fluoro-2,3-dihydro-1H-inden-1-yl) carbamate (193). LCMS: m/z found 447.1/449.1 [M+H]$^+$, RT=4.16 min (Method A). $^1$H NMR (300 MHz, DMSO-d$_6$) δ 12.76 (s, 1H), 10.39 (s, 1H), 8.04 (m, 1H), 7.75-7.59 (m, 4H), 7.41 (t, 1H), 7.15 (t, 1H), 6.26 (m, 1H), 5.29 (q, 1H), 5.01 (s, 2H), 3.23 (m, 1H), 3.01 (m, 1H), 2.44 (m, 1H), 1.89 (m, 1H).

167

Methyl 1-(methyl-d₃)-1H-1,2,4-triazole-3-carboxylate

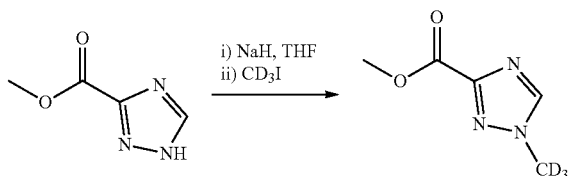

To a suspension of 2.0 g (15.7 mmol, 1.0 eq.) of methyl 1H-1,2,4-triazole-3-carboxylate in 60 mL of anhydrous THF at 0° C. under a nitrogen atmosphere was added 0.69 g (17.3 mmol, 1.1 eq.) of a 60% dispersion of sodium hydride in mineral oil. The mixture was allowed to warm to room temperature and then heated to reflux under a nitrogen atmosphere for 6.5 h. The mixture was allowed to cool to room temperature and 2.51 g (1.08 mL, 17.3 mmol, 1.1 eq.) of iodomethane-d₃ was added. The reaction mixture was then heated at reflux for a further 16 h. On cooling to room temperature, the volatiles were removed in vacuo and the residue was redissolved in 20 mL water and extracted with 3×25 mL of methylene chloride. The combined organic extracts were dried (Na₂SO₄), filtered, and the solvent was removed in vacuo. The residue was purified by flash chromatography (SiO₂, eluting with a linear gradient of 0-7% methanol/methylene chloride) to provide 1.19 g (8.2 mmol 52%) of methyl 1-(methyl-d₃)-1H-1,2,4-triazole-3-carboxylate ¹H NMR (400 MHz, CDCl₃) δ 8.13 (s, 1H), 4.00 (m, 3H).

(1-(Methyl-d₃)-1H-1,2,4-triazol-3-yl)methan-d₂-ol

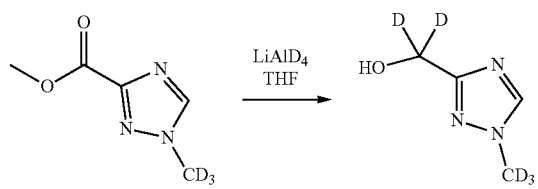

168

To a suspension of 73 mg (1.7 mmol, 1.0 eq.) of lithium aluminum deuteride in 1.3 mL of anhydrous THF at 0° C. under a nitrogen atmosphere was slowly added a suspension of 250 mg (1.7 mmol, 1.0 eq.) of methyl 1-methyl-1,2,4-triazole-3-carboxylate in 8 mL of anhydrous 1,2-dimethoxyethane. The mixture was allowed to warm to room temperature and stirred for 4 h. The mixture was then cooled to 0° C. and quenched by the slow addition of 73 µL water, followed by 73 µL of 15% aqueous sodium hydroxide solution and 220 µL of water. The mixture was further diluted with 10 mL of diethyl ether, stirred for 10 mins and then filtered. The filtrate was evaporated to dryness to provide 82 mg of (1-(methyl-d₃)-1H-1,2,4-triazol-3-yl)methan-d₂-ol. The filtride was stirred in a mixture of 10 mL of diethyl ether, 3 mL of 2-methyl-THF and sodium sulfate for 16 h. Filtration through a cotton plug and evaporation to dryness of the filtrate provided an additional 40 mg (60% combined yield) of (1-(methyl-d₃)-1H-1,2,4-triazol-3-yl)methan-d₂-ol. ¹H NMR (400 MHz, CDCl₃) δ 8.00 (s, 1H).

(1-(Methyl-d₃)-1H-1,2,4-triazol-3-yl)methyl-d₂ 1H-imidazole-1-carboxylate

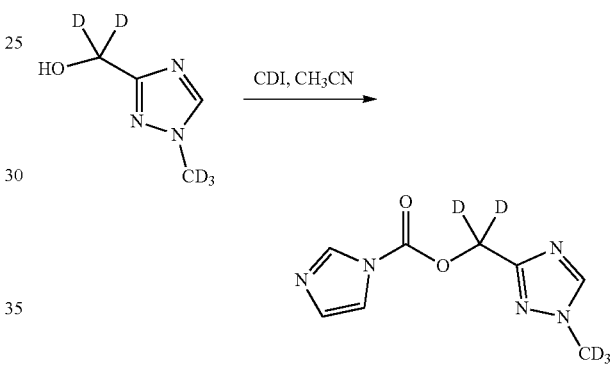

(1-(Methyl-d₃)-1H-1,2,4-triazol-3-yl)methyl-d₂ 1H-imidazole-1-carboxylate was synthesized in a similar manner as outlined above from (1-(methyl-d₃)-1H-1,2,4-triazol-3-yl)methan-d₂-ol and 1,1'-carbonyldiimidazole. ¹H NMR (400 MHz, CDCl₃) δ 8.16 (m, 1H), 8.06 (m, 1H), 7.45 (m, 1H), 7.05 (m, 1H).

O-((1-(Methyl-d₃)-1H-1,2,4-triazol-3-yl)methyl-d₂, N—(S)-(4-((3-chloro-4-fluorophenyl) carbamoyl)-7-fluoro-2,3-dihydro-1H-inden-1-yl) carbamate (252)

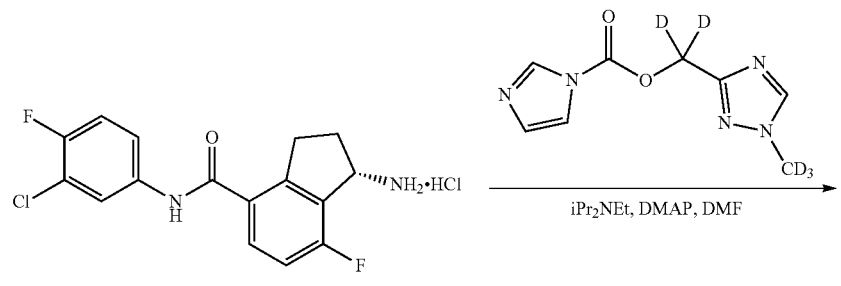

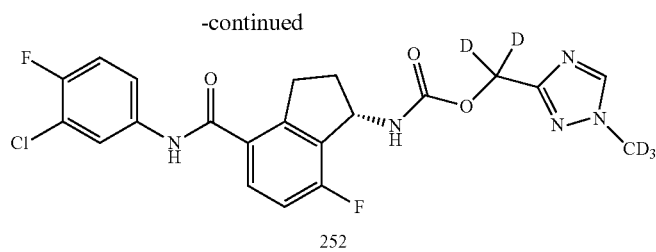

252

O-((1-(Methyl-d₃)-1H-1,2,4-triazol-3-yl)methyl-d₂), N—(S)-(4-((3-chloro-4-fluorophenyl)carbamoyl)-7-fluoro-2,3-dihydro-1H-inden-1-yl) carbamate (252) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-(methyl-d₃)-1H-1,2,4-triazol-3-yl)methyl-d₂ 1H-imidazole-1-carboxylate. LCMS: m/z found 467.3/469.3 [M+H]⁺, RT=3.87 min (Method A). ¹H NMR (300 MHz, DMSO-d₆): δ 10.41 (s, 1H), 8.43 (s, 1H), 8.04 (m, 1H), 7.82 (d, 1H), 7.73-7.61 (m, 2H), 7.41 (dd, 1H), 7.16 (dd, 1H), 5.28 (m, 1H), 3.23 (m, 1H), 3.01 (m, 1H), 2.48-2.34 (m, 1H), 1.88 (m, 1H).

Silver (I) Diallyl Phosphate:

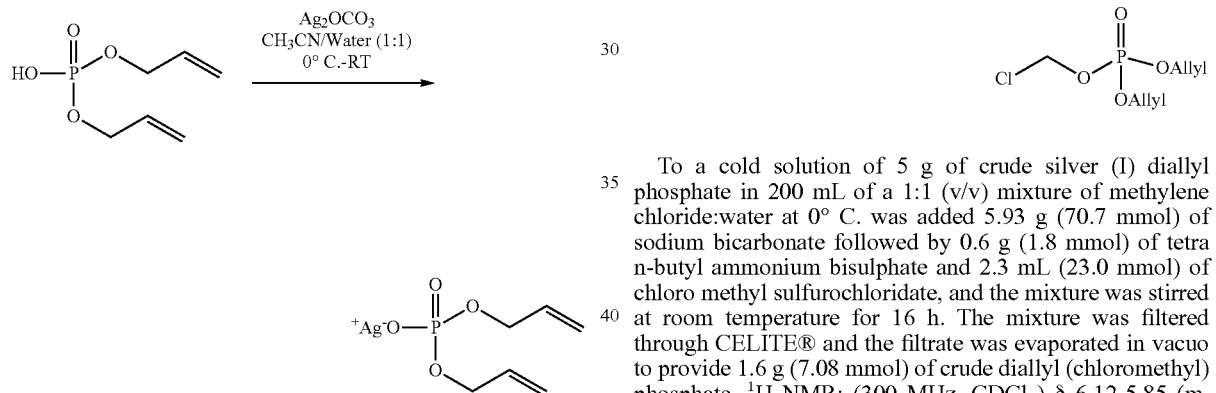

To a solution 11.0 g (61.7 mmol, 1.0 eq) of diallyl hydrogen phosphate (synthesized according to Snitynsky & Lowary, 2014, Org. Lett. 16:212) in 100 mL of 1:1 (v/v) acetonitrile:water at 0° C. was added 20.0 g (72.5 mmol, 1.2 eq) of silver carbonate. The solution was stirred at room temperature for 1 h and then lyophilized to provide 30 g of a crude mixture containing silver (I) diallyl phosphate. ¹H NMR: (400 MHz, DMSO-d₆) δ 6.22-6.15 (m, 2H), 5.49-5.41 (d, 2H), 5.30-5.21 (d, 2H), 4.61-4.42 (m, 4H).

Diallyl (Chloromethyl) Phosphate:

To a cold solution of 5 g of crude silver (I) diallyl phosphate in 200 mL of a 1:1 (v/v) mixture of methylene chloride:water at 0° C. was added 5.93 g (70.7 mmol) of sodium bicarbonate followed by 0.6 g (1.8 mmol) of tetra n-butyl ammonium bisulphate and 2.3 mL (23.0 mmol) of chloro methyl sulfurochloridate, and the mixture was stirred at room temperature for 16 h. The mixture was filtered through CELITE® and the filtrate was evaporated in vacuo to provide 1.6 g (7.08 mmol) of crude diallyl (chloromethyl) phosphate. ¹H NMR: (300 MHz, CDCl₃) δ 6.12-5.85 (m, 2H), 5.75-5.62 (d, 2H), 5.21-5.20 (m, 4H), 4.72-4.52 (m, 4H).

O-(1-(((Bis(allyloxy)phosphoryl)oxy)methyl)-1H-1,2,4-triazol-3-yl)methyl, N—(S)-(4-((3-chloro-4-fluorophenyl)carbamoyl)-7-fluoro-2,3-dihydro-1H-inden-1-yl) carbamate

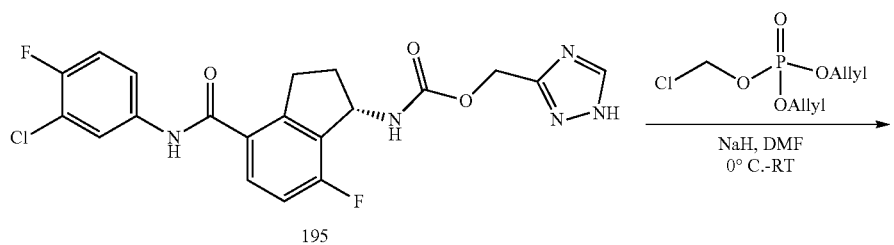

195

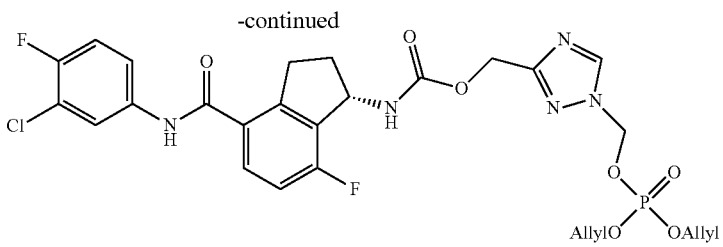

To a solution 21 mg (0.54 mmol, 1.5 eq.) of a 60% dispersion of sodium hydride in mineral oil in 3 mL of DMF under a nitrogen atmosphere at 0° C. was added 160 mg (0.36 mmol, 1.0 eq.) of (1H-1,2,4-triazol-3-yl)methyl (S)-(4-((3-chloro-4-fluorophenyl)carbamoyl)-7-fluoro-2,3-dihydro-1H-inden-1-yl)carbamate (195). The mixture was stirred at 0° C. for 30 min and 161 mg of crude diallyl (chloromethyl) phosphate was added. The mixture was allowed to warm to room temperature and stirred for a further 16 h. The mixture was then quenched with 10 mL of a saturated solution of aqueous citric acid, diluted with 20 mL of water and extracted in with 3×50 mL of ethyl acetate. The combined organic extracts were dried (Na$_2$SO$_4$), filtered and the solvent was removed in vacuo. The residue was purified by semi-preparative HPLC to provide 50 mg (0.08 mmol, 22%) of)-(1-(((bis(allyloxy)phosphoryl)oxy)methyl)-1H-1,2,4-triazol-3-yl)methyl, N—(S)-(4-((3-chloro-4-fluorophenyl)carbamoyl)-7-fluoro-2,3-dihydro-1H-inden-1-yl) carbamate. LCMS: m/z found 638.4/640.4 [M+H]$^+$, RT=2.45 min (Method H).

O-(1-((Phosphonoxy)methyl)-1H-1,2,4-triazol-3-yl) methyl, N—(S)-(4-((3-chloro-4-fluorophenyl)carbamoyl)-7-fluoro-2,3-dihydro-1H-inden-1-yl) carbamate (253)

To a solution of 50 mg (0.08 mmol, 1.0 eq.) of O-(1-(((bis(allyloxy)phosphoryl)oxy)methyl)-1H-1,2,4-triazol-3-yl)methyl, N—(S)-(4-((3-chloro-4-fluorophenyl)carbamoyl)-7-fluoro-2,3-dihydro-1H-inden-1-yl) carbamate in 3 mL of THF was added 37 mg (0.23 mmol, 3.0 eq.) of 1,3 dimethylbarbutic acid. The mixture was degassed with argon for 15 min and 27 mg (0.023 mmol, 0.3 eq.) of tetrakis (triphenylphosphine)palladium (0) was added. The mixture was stirred at room temperature for 5 h, filtered through CELITE® and the pad was washed with 5 mL of THF. The solvent was removed in vacuo and the residue was purified by semi-preparative HPLC to provide 20 mg (0.04 mmol, 46%) of)-(1-((phosphonoxy)methyl)-1H-1,2,4-triazol-3-yl) methyl, N—(S)-(4-((3-chloro-4-fluorophenyl)carbamoyl)-7-fluoro-2,3-dihydro-1H-inden-1-yl)carbamate. The product was subsequently stirred in an aqueous solution of 6 mg (0.072 mmol, 2.0 eq.) of sodium bicarbonate in 0.5 mL of water for 1 h and subsequently lyophilized to provide 21 mg of sodium (S)-(3-((((4-((3-chloro-4-fluorophenyl)carbamoyl)-7-fluoro-2,3-dihydro-1H-inden-1-yl)carbamoyl)oxy) methyl)-1H-1,2,4-triazol-1-yl)methyl phosphate (253). LCMS: m/z found 558.3/560.3 [M+H]$^+$ (free acid), RT=1.66 min (Method H); $^1$H NMR (300 MHz, CD$_3$OD): δ 8.75 (s, 1H), 7.92 (dd, 1H), 7.64 (dd, 1H), 7.57-7.53 (m, 1H), 7.22 (t, 1H), 7.04 (t, 1H), 5.80 (d, 2H), 5.37 (t, 1H), 5.13 (ABq, 2H), 3.31-3.25 (m, 1H), 3.13-3.08 (m, 1H), 2.53-2.47 (m, 1H), 2.06-2.01 (m, 1H); $^{31}$P NMR (121.5 MHz, CD$_3$OD): δ 3.72 ppm; Chiral HPLC: RT=1.49 min.

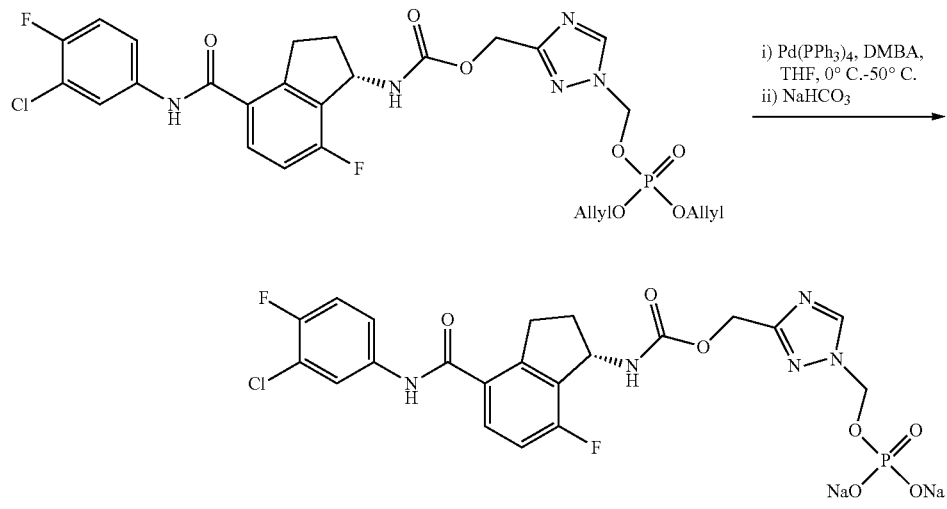

253, disodium salt

O-(1-(((Bis(allyloxy)phosphoryl)oxy)methyl)-1H-pyrazol-3-yl)methyl, N—(S)-(4-((3-chloro-4-fluorophenyl)carbamoyl)-7-fluoro-2,3-dihydro-1H-inden-1-yl) carbamate

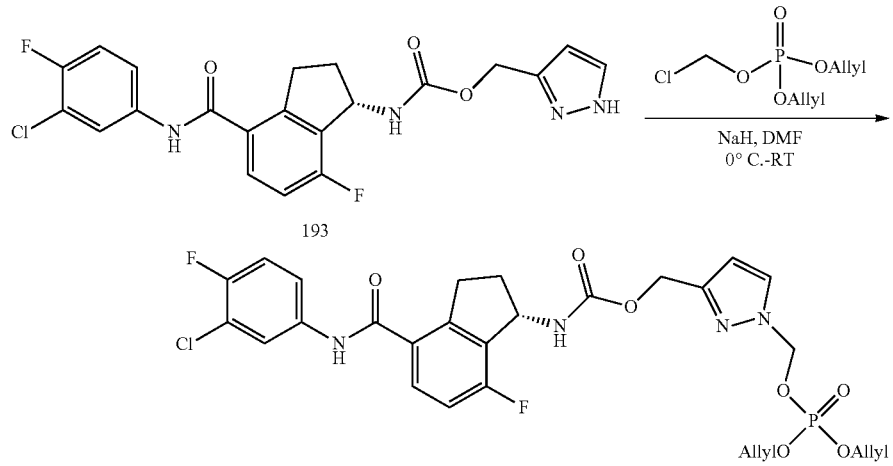

O-(1-(((Bis(allyloxy)phosphoryl)oxy)methyl)-1H-pyrazol-3-yl)methyl, N—(S)-(4-((3-chloro-4-fluorophenyl)carbamoyl)-7-fluoro-2,3-dihydro-1H-inden-1-yl) carbamate was synthesized in a similar manner as described above from O-(1H-pyrazol-5-yl)methyl, N—(S)-(4-((3-chloro-4-fluorophenyl) carbamoyl)-7-fluoro-2,3-dihydro-1H-inden-1-yl) carbamate (193) and diallyl (chloromethyl) phosphate.

Sodium (S)-(3-((((4-((3-chloro-4-fluorophenyl)carbamoyl)-7-fluoro-2,3-dihydro-1H-inden-1-yl)carbamoyl)oxy)methyl)-1H-pyrazol-1-yl)methyl phosphate (254)

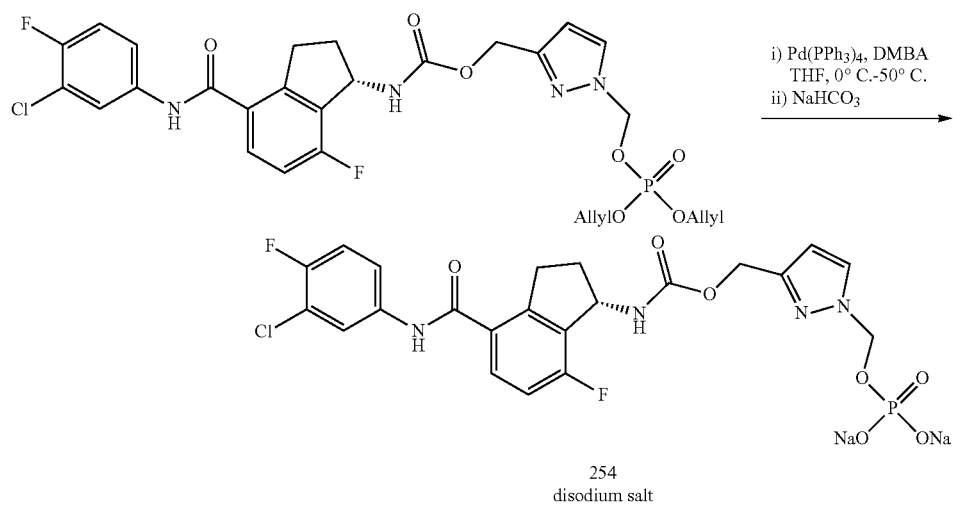

Sodium (S)-(3-((((4-((3-chloro-4-fluorophenyl)carbamoyl)-7-fluoro-2,3-dihydro-1H-inden-1-yl)carbamoyl)oxy) methyl)-1H-pyrazol-1-yl)methyl phosphate (254) was synthesized in a similar manner as described above from O-(1-(((bis(allyloxy)phosphoryl)oxy) methyl)-1H-pyrazol-5-yl)methyl, N—(S)-(4-((3-chloro-4-fluorophenyl)carbamoyl)-7-fluoro-2,3-dihydro-1H-inden-1-yl) carbamate; LCMS; m/z found 557.3/559.3 [M+H]$^+$ (free acid), RT=1.86 min (Method D); $^1$H NMR (300 MHz, CD$_3$OD): δ 7.96-7.93 (m, 2H), 7.67 (dd, 1H), 7.60-7.54 (m, 1H), 7.24 (dd, 1H), 7.06 (dd, 1H), 6.34 (d, 1H), 5.74 (d, 2H), 5.42-5.37 (m, 1H), 5.10 (s, 2H), 3.31-3.28 (m, 1H), 3.15-3.10 (m, 1H), 2.57-2.49 (m, 1H), 2.08-1.90 (m, 1H); $^{31}$P NMR (121.5 MHz, CD$_3$OD): 4.17 ppm.

O-(1-Methyl-1H-pyrazol-5-yl)methyl, N—(S)-(4-((3-chloro-4-fluorophenyl)carbamoyl)-7-fluoro-2,3-dihydro-1H-inden-1-yl) carbamate (103)

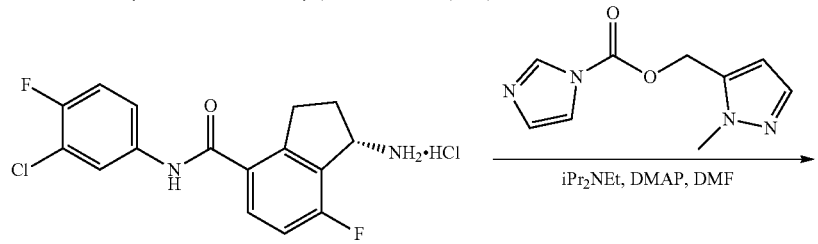

O-(1-Methyl-1H-pyrazol-5-yl)methyl, N—(S)-(4-((3-chloro-4-fluorophenyl)carbamoyl)-7-fluoro-2,3-dihydro-1H-inden-1-yl) carbamate (103) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-methyl-1H-pyrazol-5-yl)methyl 1H-imidazole-1-carboxylate. LCMS: m/z found 461.1/463.2 [M+H]$^+$, RT=4.44 min (Method A). $^1$H NMR (300 MHz, DMSO-d$_6$) δ 10.39 (s, 1H), 8.03 (m, 1H), 7.84 (d, 1H), 7.67 (m, 2H), 7.38 (m, 2H), 7.15 (t, 1H), 6.29 (m, 1H), 5.28 (m, 1H), 5.13 (m, 2H), 3.81 (s, 3H), 3.20 (m, 1H), 3.02 (m, 1H), 2.43 (m, 1H), 1.88 (m, 1H).

O-(1-Isopropyl-1H-pyrazol-5-yl)methyl, N—(S)-(4-((3-chloro-4-fluorophenyl)carbamoyl)-7-fluoro-2,3-dihydro-1H-inden-1-yl) carbamate (106)

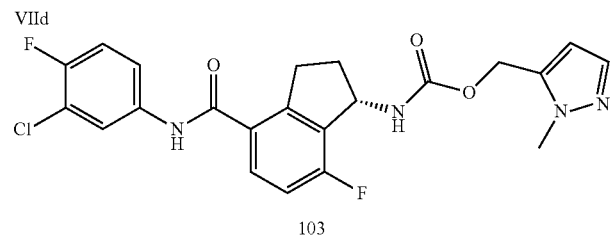

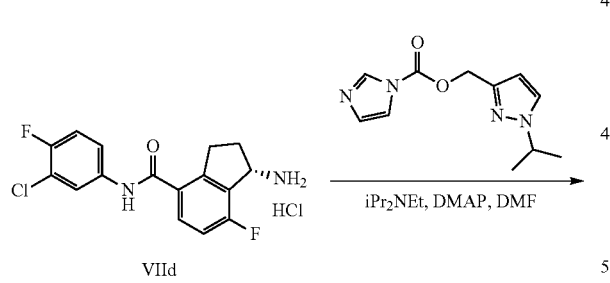

O-(1-Isopropyl-1H-pyrazol-5-yl)methyl, N—(S)-(4-((3-chloro-4-fluorophenyl)carbamoyl)-7-fluoro-2,3-dihydro-1H-inden-1-yl) carbamate (106) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-isopropyl-1H-pyrazol-3-yl)methyl 1H-imidazole-1-carboxylate. LCMS: m/z found 489.2/491.2 [M+H]$^+$, RT=4.94 min (Method A). $^1$H NMR (300 MHz, DMSO-d$_6$) δ 10.41 (s, 1H), 8.04 (m, 1H), 7.76-7.64 (m, 4H), 7.41 (t, 1H), 7.15 (t, 1H), 6.22 (m, 1H), 5.28 (q, 1H), 4.96 (s, 2H), 4.46 (m, 1H), 3.19 (m, 1H), 3.04 (m, 1H), 2.40 (m, 1H), 1.89 (m, 1H), 1.39 (d, 6H).

O-2-(1H-Pyrazol-1-yl)ethyl, N—(S)-(4-((3-chloro-4-fluorophenyl)carbamoyl)-7-fluoro-2,3-dihydro-1H-inden-1-yl) carbamate (133)

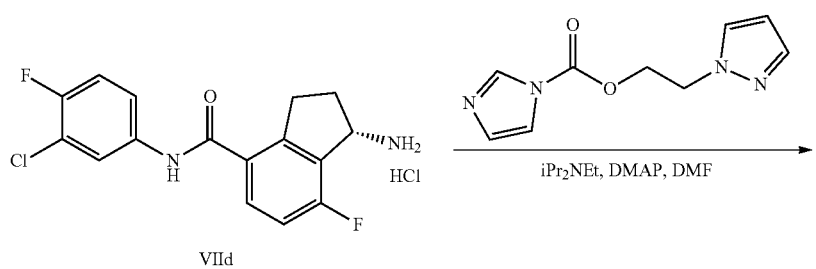

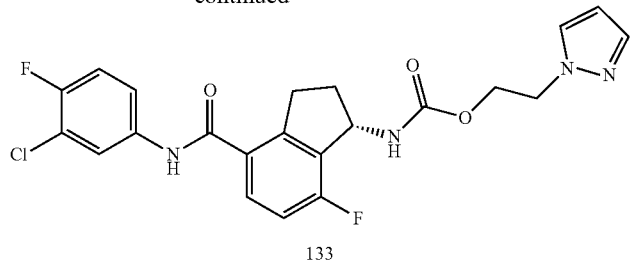

133

O-2-(1H-Pyrazol-1-yl)ethyl, N—(S)-(4-((3-chloro-4-fluorophenyl)carbamoyl)-7-fluoro-2,3-dihydro-1H-inden-1-yl) carbamate (133) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-(1H-pyrazol-1-yl)ethyl 1H-imidazole-1-carboxylate. LCMS: m/z found 461.1/463.2 [M+H]$^+$, RT=4.40 min (Method A). $^1$H NMR (300 MHz, DMSO-d$_6$) δ 10.39 (s, 1H), 8.04 (m, 1H), 7.78-7.63 (m, 4H), 7.44 (m, 2H), 7.15 (t, 1H), 6.24 (m, 1H), 5.24 (q, 1H), 4.33 (m, 4H), 3.22 (m, 1H), 3.02 (m, 1H), 2.37 (m, 1H), 1.87 (m, 1H).

O-(5-Methoxypyridin-2-yl)methyl, N—(S)-(4-((3-chloro-4-fluorophenyl)carbamoyl)-7-fluoro-2,3-dihydro-1H-inden-1-yl) carbamate Hydrochloride (107.HCl)

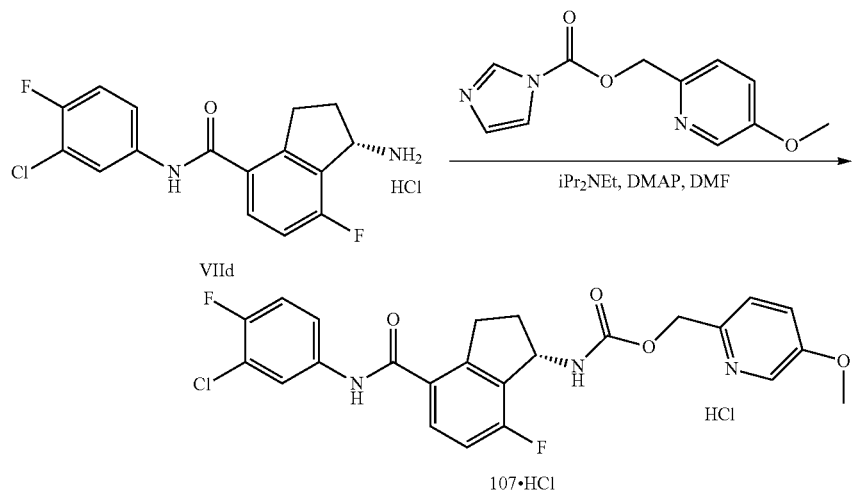

O-(5-Methoxypyridin-2-yl)methyl, N—(S)-(4-((3-chloro-4-fluorophenyl)carbamoyl)-7-fluoro-2,3-dihydro-1H-inden-1-yl) carbamate (107.HCl) was synthesized in a similar manner as outlined above from (S)-1-amino-N-(3-chloro-4-fluorophenyl)-7-fluoro-2,3-dihydro-1H-indene-4-carboxamide hydrochloride (VIId) and (5-methoxypyridin-2-yl)methyl 1H-imidazole-1-carboxylate. The purified compound was subsequently converted to the hydrochloride salt using a 1.25 M solution of HCl in methanol. LCMS m/z found 488.1/490.1 [M+H]$^+$, RT=3.98 min (Method A). $^1$H NMR (300 MHz, Methanol-d$_4$) δ 8.54 (m, 1H), 8.20 (m, 1H), 8.00 (d, 1H), 7.92 (m, 1H), 7.67 (m, 1H), 7.54 (m, 1H), 7.23 (t, 1H), 7.04 (t, 1H), 5.30 (m, 3H), 4.06 (s, 3H), 3.36 (m, 1H), 3.11 (m, 1H), 2.51 (m, 1H), 2.01 (m, 1H).

O—((R)-Morpholin-3-yl)methyl, N—((S)-4-((3-chloro-4-fluorophenyl)carbamoyl)-7-fluoro-2,3-dihydro-1H-inden-1-yl) carbamate Hydrochloride (139.HCl)

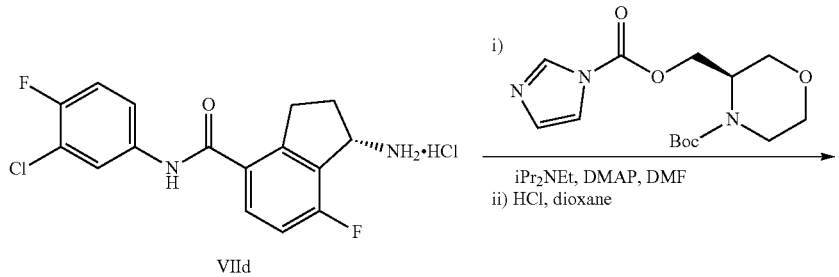

O—((R)-Morpholin-3-yl)methyl, N—((S)-4-((3-chloro-4-fluorophenyl)carbamoyl)-7-fluoro-2,3-dihydro-1H-inden-1-yl) carbamate hydrochloride (139.HCl) was synthesized in a similar manner as outlined above from (S)-1-amino-N-(3-chloro-4-fluorophenyl)-7-fluoro-2,3-dihydro-1H-indene-4-carboxamide hydrochloride (VIId) and tert-butyl (R)-3-(((1H-imidazole-1-carbonyl)oxy) methyl)morpholine-4-carboxylate, followed by deprotection with HCl in 1,4-dioxane. LCMS: m/z found 466.1/468.2 [M+H]$^+$, RT=3.34 min (Method A). $^1$H NMR (300 MHz, Methanol-d$_4$) δ 7.93 (m, 1H), 7.68 (m, 1H), 7.55 (m, 1H), 7.23 (t, 1H), 7.06 (t, 1H), 5.37 (m, 1H), 4.29 (m, 2H), 4.03 (m, 2H), 3.78-3.57 (m, 5H), 3.34 (m, 1H), 3.12 (m, 1H), 2.53 (m, 1H), 2.04 (m, 1H).

O—((S)-Morpholin-3-yl)methyl, N—((S)-4-((3-chloro-4-fluorophenyl)carbamoyl)-7-fluoro-2,3-dihydro-1H-inden-1-yl) carbamate Hydrochloride (180.HCl)

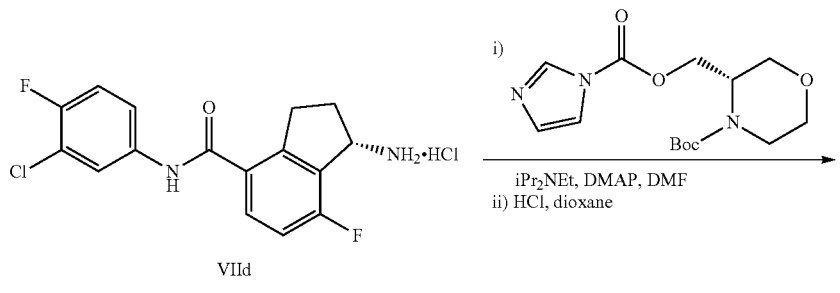

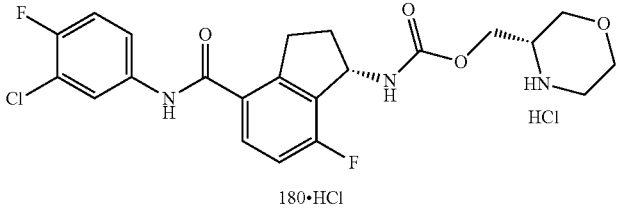

181

O—((S)-Morpholin-3-yl)methyl, N—((S)-4-((3-chloro-4-fluorophenyl)carbamoyl)-7-fluoro-2,3-dihydro-1H-inden-1-yl) carbamate hydrochloride (180.HCl) was synthesized in a similar manner as outlined above from (S)-1-amino-N-(3-chloro-4-fluorophenyl)-7-fluoro-2,3-dihydro-1H-indene-4-carboxamide hydrochloride (VIId) and tert-butyl (S)-3-(((1H-imidazole-1-carbonyl)oxy) methyl)morpholine-4-carboxylate, followed by deprotection with HCl in 1,4-dioxane. LCMS: m/z found 466.1/468.2 [M+H]$^+$, RT=3.32 min (Method A). $^1$H NMR (300 MHz, Methanol-d$_4$) δ 7.98-7.88 (m, 1H), 7.69 (dd, 1H), 7.62-7.50 (m, 1H), 7.23 (m, 1H), 7.07 (t, 1H), 5.38 (m, 1H), 4.29 (d, 2H), 4.15-3.96 (m, 2H), 3.83-3.55 (m, 5H), 3.44-3.20 (m, 1H), 3.21-3.03 (m, 1H), 2.53 (m, 1H), 2.07 (m, 1H).

O-(2-Oxooxazolidin-5-yl)methyl, N—((S)-4-((3-chloro-4-fluorophenyl)carbamoyl)-7-fluoro-2,3-dihydro-1H-inden-1-yl) carbamate (132)

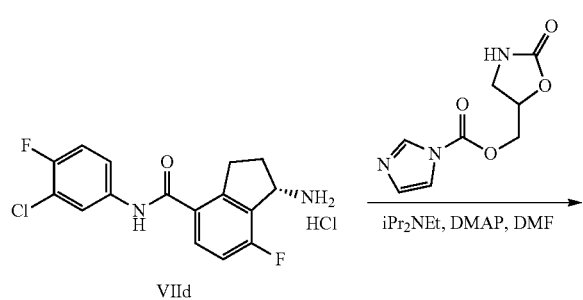

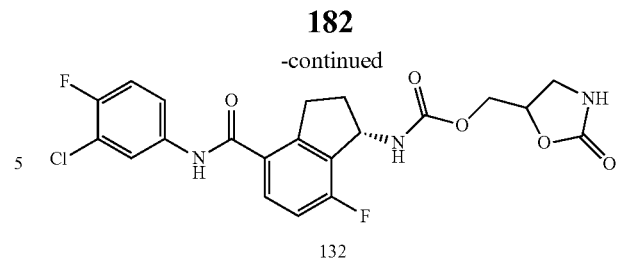

O-(2-Oxooxazolidin-5-yl)methyl, N—((S)-4-((3-chloro-4-fluorophenyl)carbamoyl)-7-fluoro-2,3-dihydro-1H-inden-1-yl) carbamate (132) was prepared in a similar manner as described above from (S)-1-amino-N-(3-chloro-4-fluorophenyl)-7-fluoro-2,3-dihydro-1H-indene-4-carboxamide hydrochloride (VIId) and (2-oxooxazolidin-5-yl)methyl 1H-imidazole-1-carboxylate. LCMS: m/z found 466.1/468.1 [M+H]$^+$; HPLC: RT=3.86 min (Method A); $^1$H NMR (300 MHz, Methanol-d$_4$) δ 8.00-7.90 (m, 1H), 7.68 (q, 1H), 7.64-7.52 (m, 1H), 7.25 (t, 1H), 7.07 (t, 1H), 5.38 (t, 1H), 4.80 (m, 2H), 4.39-4.25 (m, 2H), 3.72 (t, 1H), 3.52-3.31 (m, 1H), 3.21-3.03 (m, 1H), 2.64-2.45 (m, 1H), 2.14-1.96 (m, 1H).

O—(S)-5-Oxopyrrolidin-3-yl, N—((S)-4-((3-chloro-4-fluorophenyl)carbamoyl)-7-fluoro-2,3-dihydro-1H-inden-1-yl) carbamate (166)

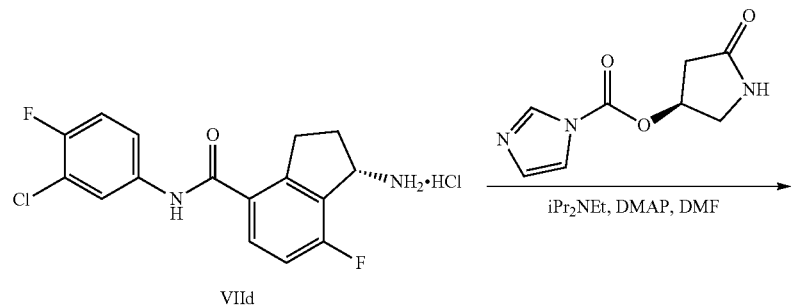

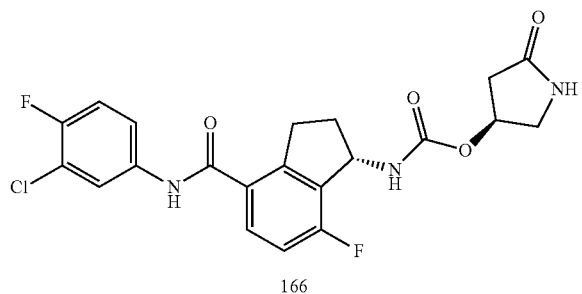

O—(S)-5-Oxopyrrolidin-3-yl, N—((S)-4-((3-chloro-4-fluorophenyl)carbamoyl)-7-fluoro-2,3-dihydro-1H-inden-1-yl) carbamate (166) was synthesized in a similar manner as outlined above from (S)-1-amino-N-(3-chloro-4-fluorophenyl)-7-fluoro-2,3-dihydro-1H-indene-4-carboxamide hydrochloride (VIId) and (S)-5-oxopyrrolidin-3-yl 1H-imidazole-1-carboxylate. LCMS: m/z found 450.1/452.1 [M+H]$^+$, RT=3.77 min (Method A). $^1$H NMR (300 MHz, DMSO-d$_6$) δ 10.39 (s, 1H), 8.04 (m, 1H), 7.82 (d, 1H), 7.75-7.59 (m, 3H), 7.41 (t, 1H), 7.15 (t, 1H), 5.34-5.15 (m, 2H), 3.59 (m, 1H), 3.16 (m, 2H), 3.00 (m, 1H), 2.63 (m, 1H), 2.41 (m, 1H), 2.03 (d, 1H), 1.90 (m, 1H).

O-2-Fluoroethyl, N—(S)-(4-((3-chloro-4-fluorophenyl)carbamoyl)-7-fluoro-2,3-dihydro-1H-inden-1-yl) carbamate (76)

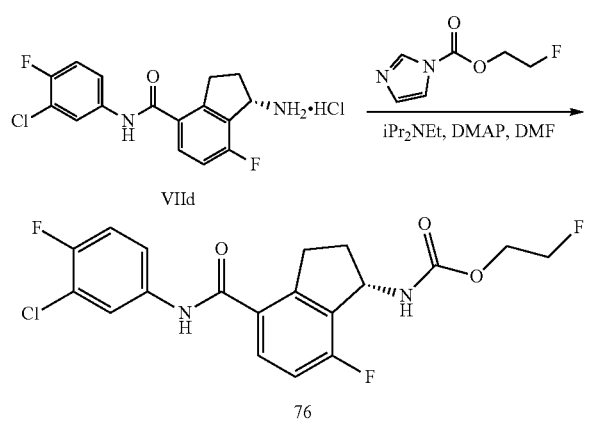

O-2-Fluoroethyl, N—(S)-(4-((3-chloro-4-fluorophenyl)carbamoyl)-7-fluoro-2,3-dihydro-1H-inden-1-yl) carbamate (76) was prepared in a similar manner as described above from (S)-1-amino-N-(3-chloro-4-fluorophenyl)-7-fluoro-2,3-dihydro-1H-indene-4-carboxamide hydrochloride (VIId) and 2-fluoroethyl 1H-imidazole-1-carboxylate. LCMS: m/z found 413.2/415.1 [M+H]$^+$; HPLC: RT=0.95 min (Method B); $^1$H NMR (300 MHz, DMSO-d$_6$) δ 10.39 (s, 1H), 8.04 (dd, 1H), 7.83 (d, 1H), 7.75-7.59 (m, 2H), 7.40 (t, 1H), 7.15 (t, 1H), 5.34-5.20 (m, 1H), 4.71-4.62 (m, 1H), 4.55-4.46 (m, 1H), 4.32-4.23 (m, 1H), 4.22-4.14 (m, 1H), 3.29-3.15 (m, 1H), 3.10-2.92 (m, 1H), 2.47-2.32 (m, 1H), 1.99-1.83 (m, 1H).

O-Pyrimidin-2-ylmethyl, N—(S)-(4-((3-chloro-4-fluorophenyl)carbamoyl)-7-fluoro-2,3-dihydro-1H-inden-1-yl) carbamate (79)

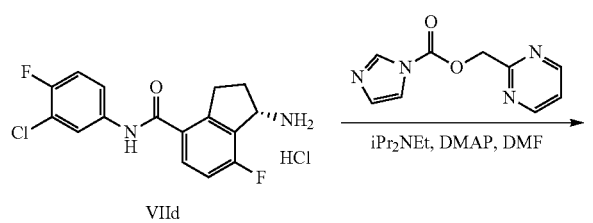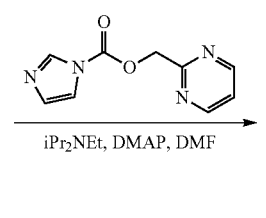

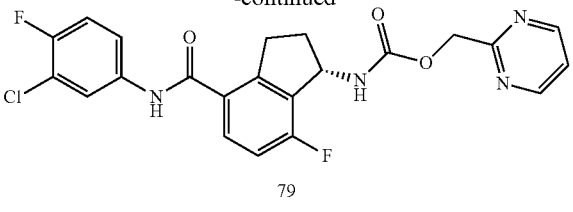

O-Pyrimidin-2-ylmethyl, N—(S)-(4-((3-chloro-4-fluorophenyl)carbamoyl)-7-fluoro-2,3-dihydro-1H-inden-1-yl) carbamate (79) was prepared in a similar manner as described above from (S)-1-amino-N-(3-chloro-4-fluorophenyl)-7-fluoro-2,3-dihydro-1H-indene-4-carboxamide hydrochloride (VIId) and pyrimidin-2-ylmethyl 1H-imidazole-1-carboxylate. LCMS: m/z found 459.2/461.2 [M+H]$^+$; HPLC: RT=0.89 min (Method B); $^1$H NMR (300 MHz, Chloroform-d) δ 8.76 (d, 2H), 7.81 (dd, 2.6 Hz, 1H), 7.66-7.55 (m, 2H), 7.44-7.35 (m, 1H), 7.13 (t, 1H), 7.00 (t, 1H), 5.49-5.30 (m, 4H), 3.49-3.31 (m, 1H), 3.25-3.07 (m, 1H), 2.71-2.52 (m, 1H), 2.17-1.90 (m, 1H).

O-3-(2-Oxopyrrolidin-1-yl)propyl, N—(S)-(4-((3-chloro-4-fluorophenyl)carbamoyl)-7-fluoro-2,3-dihydro-1H-inden-1-yl) carbamate (86)

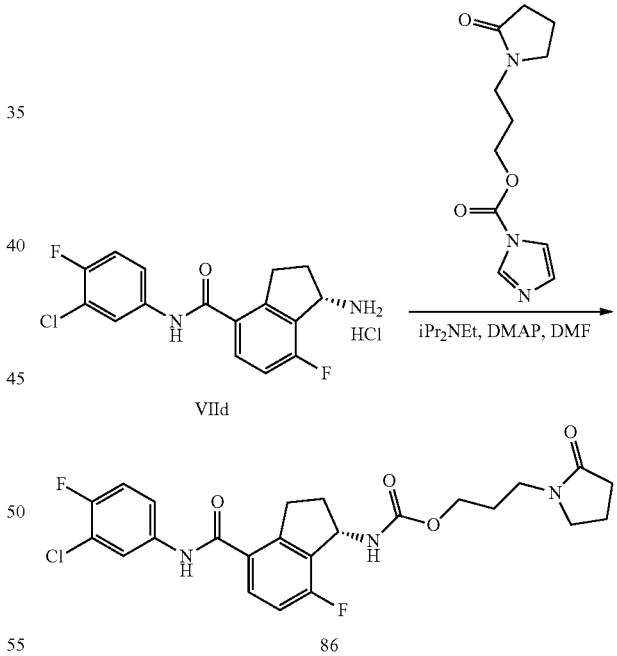

O-3-(2-Oxopyrrolidin-1-yl)propyl, N—(S)-(4-((3-chloro-4-fluorophenyl)carbamoyl)-7-fluoro-2,3-dihydro-1H-inden-1-yl) carbamate (86) was prepared in a similar manner as described above from (S)-1-amino-N-(3-chloro-4-fluorophenyl)-7-fluoro-2,3-dihydro-1H-indene-4-carboxamide hydrochloride (VIId) and 3-(2-oxopyrrolidin-1-yl)propyl 1H-imidazole-1-carboxylate. LCMS: m/z found 492.2/494.2 [M+H]$^+$; HPLC: RT=0.89 min (Method B). $^1$H NMR (300 MHz, DMSO-d$_6$) δ 10.39 (s, 1H), 8.09-7.99 (m, 1H), 7.75-7.60 (m, 3H), 7.40 (t, 1H), 7.15 (t, 1H), 5.26 (q, 1H), 3.99-3.92 (m, 2H), 3.26-3.17 (m, 2H), 3.09-2.92 (m, 1H), 2.42-2.35 (m, 1H), 2.20 (t, 2H), 2.02-1.85 (m, 3H), 1.74 (t, 3H), 1.23 (s, 2H).

O-2,2-Difluoroethyl, N—(S)-(4-((3-chloro-4-fluoro-phenyl)carbamoyl)-7-fluoro-2,3-dihydro-1H-inden-1-yl) carbamate (84)

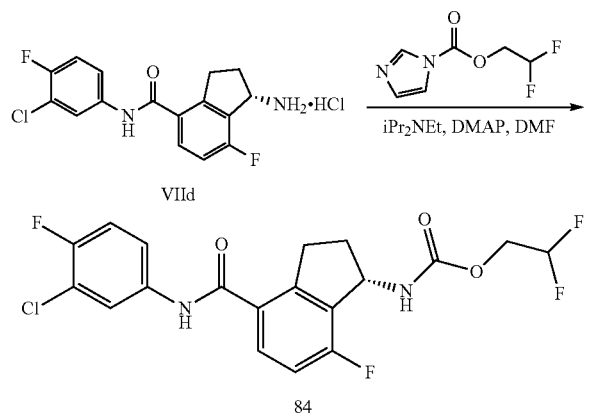

O-2,2-Difluoroethyl, N—(S)-(4-((3-chloro-4-fluorophenyl)carbamoyl)-7-fluoro-2,3-dihydro-1H-inden-1-yl)carbamate (84) was prepared in a similar manner as described above from (S)-1-amino-N-(3-chloro-4-fluorophenyl)-7-fluoro-2,3-dihydro-1H-indene-4-carboxamide hydrochloride (VIId) and 2,2-difluoroethyl 1H-imidazole-1-carboxylate. LCMS: m/z found 431.1/433.1 [M+H]$^+$; HPLC: RT=0.98 min (Method B); $^1$H NMR (300 MHz, DMSO-d$_6$) δ 10.39 (s, 1H), 8.08-7.97 (m, 2H), 7.75-7.58 (m, 1H), 7.39 (t, 1H), 7.14 (t, 1H), 6.21 (d, 1H), 5.26 (q, 1H), 4.24 (t, 2H), 3.26-3.15 (m, 1H), 3.10-2.92 (m, 1H), 2.50-2.35 (m, 2H), 1.99-1.83 (m, 1H).

O-2,2,2-Trifluoroethyl, N—(S)-(4-((3-chloro-4-fluorophenyl)carbamoyl)-7-fluoro-2,3-dihydro-1H-inden-1-yl) carbamate (88)

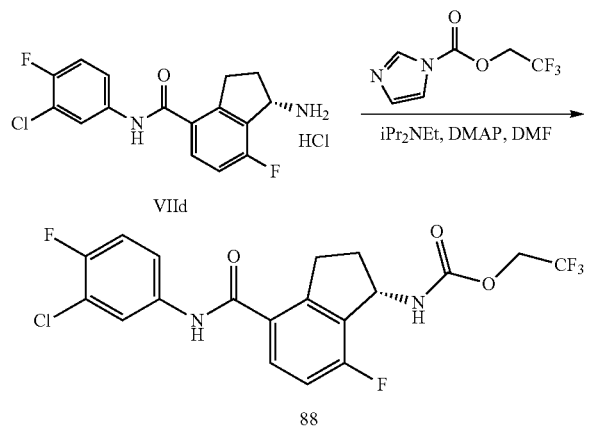

O-2,2,2-Trifluoroethyl, N—(S)-(4-((3-chloro-4-fluorophenyl)carbamoyl)-7-fluoro-2,3-dihydro-1H-inden-1-yl) carbamate (88) was prepared in a similar manner as described above from (S)-1-amino-N-(3-chloro-4-fluorophenyl)-7-fluoro-2,3-dihydro-1H-indene-4-carboxamide hydrochloride (VIId) and 2,2,2-trifluoroethyl 1H-imidazole-1-carboxylate. LCMS: m/z found 449.1/451.1 [M+H]$^+$; HPLC: RT=5.21 min (Method A); $^1$H NMR (300 MHz, DMSO-d$_6$) δ 10.41 (s, 1H), 8.21 (d, 1H), 8.05 (dd, 1H), 7.77-7.60 (m, 2H), 7.41 (t, 1H), 7.17 (t, 1H), 5.29 (q, 1H), 4.79-4.56 (m, 2H), 3.34-3.17 (m, 1H), 3.12-2.95 (m, 1H), 2.51-2.35 (m, 1H), 1.96-1.83 (m, 1H).

O-(8-Methylimidazo[1,2-a]pyridin-2-yl)methyl, N—(S)-(4-((3-chloro-4-fluorophenyl) carbamoyl)-7-fluoro-2,3-dihydro-1H-inden-1-yl) carbamate Hydrochloride (87.HCl)

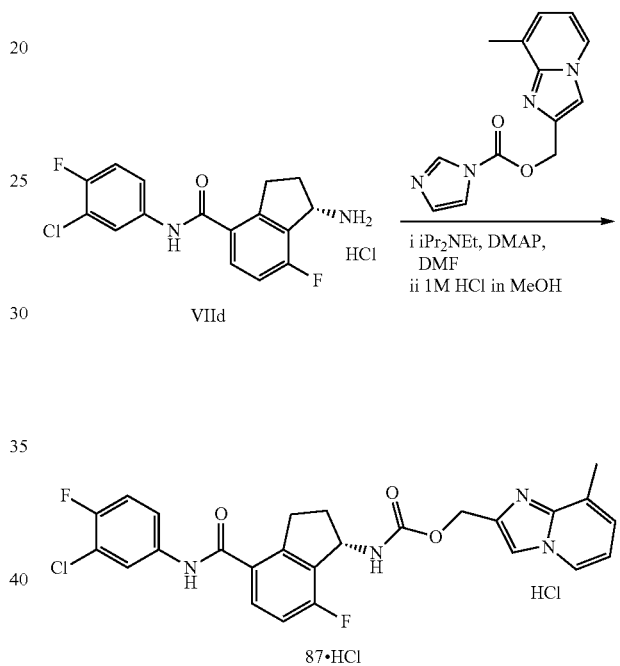

O-(8-Methylimidazo[1,2-a]pyridin-2-yl)methyl, N—(S)-(4-((3-chloro-4-fluorophenyl)carbamoyl)-7-fluoro-2,3-dihydro-1H-inden-1-yl) carbamate hydrochloride (87.HCl) was prepared in a similar manner as described above from (S)-1-amino-N-(3-chloro-4-fluorophenyl)-7-fluoro-2,3-dihydro-1H-indene-4-carboxamide hydrochloride (VIId) and (8-methylimidazo[1,2-a]pyridin-2-yl)methyl 1H-imidazole-1-carboxylate. The purified compound was subsequently converted to the hydrochloride salt using a 1.25 M solution of HCl in methanol. LCMS: m/z found 511.1/513.1 [M+H]$^+$; HPLC: RT=3.71 min (Method A); $^1$H NMR (300 MHz, DMSO-d$_6$) δ 10.43 (s, 1H), 8.74 (d, 1H), 8.32 (s, 1H), 8.02 (dd, 2H), 7.73-7.66 (m, 3H), 7.41 (m, 2H), 7.16 (t, 1H), 5.38-5.21 (m, 3H), 3.20 (m, 1H), 3.06 (m, 1H), 2.58 (s, 3H), 1.93 (s, 1H).

O-3-(1H-Imidazol-1-yl)propyl, N—(S)-(4-((3-chloro-4-fluorophenyl)carbamoyl)-7-fluoro-2,3-dihydro-1H-inden-1-yl) carbamate Hydrochloride (125.HCl)

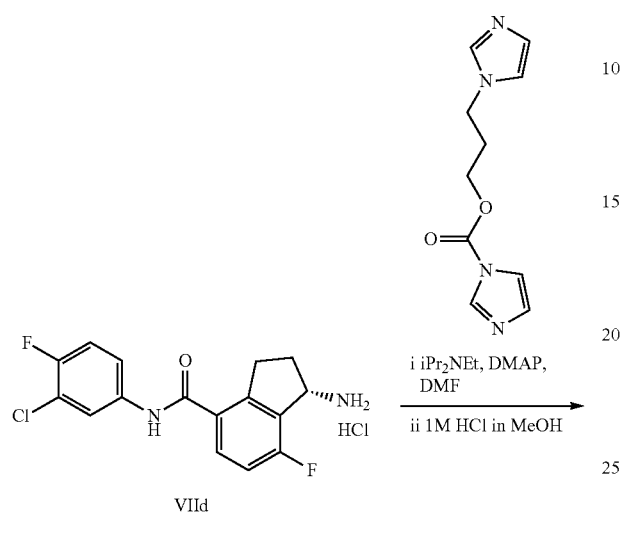

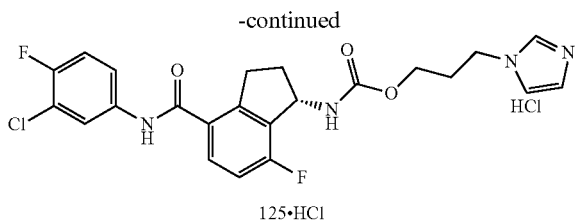

O-3-(1H-Imidazol-1-yl)propyl, N—(S)-(4-((3-chloro-4-fluorophenyl)carbamoyl)-7-fluoro-2,3-dihydro-1H-inden-1-yl)carbamate hydrochloride (125.HCl) was prepared in a similar manner as described above from (S)-1-amino-N-(3-chloro-4-fluorophenyl)-7-fluoro-2,3-dihydro-1H-indene-4-carboxamide hydrochloride (VIId) and 3-(1H-imidazol-1-yl)propyl 1H-imidazole-1-carboxylate. The purified compound was subsequently converted to the hydrochloride salt using a 1.25 M solution of HCl in methanol. LCMS: m/z found 475.1/477.1 [M+H]⁺; HPLC: RT=3.43 min (Method A); ¹H NMR (300 MHz, Methanol-d₄) δ 9.50 (dd, 1H), 9.29-9.18 (m, 2H), 9.19-9.07 (m, 1H), 8.80 (t, 1H), 8.71 (s, 1H), 8.63 (t, 1H), 8.54 (s, 1H), 6.93 (t, 1H), 5.76-5.50 (m, 5H), 4.76-4.58 (m, 1H), 4.18-4.00 (m, 1H), 3.76-3.49 (m, 3H).

O-2-(1H-Imidazol-1-yl)ethyl, N—(S)-(4-((3-chloro-4-fluorophenyl)carbamoyl)-7-fluoro-2,3-dihydro-1H-inden-1-yl) carbamate Hydrochloride (96.HCl)

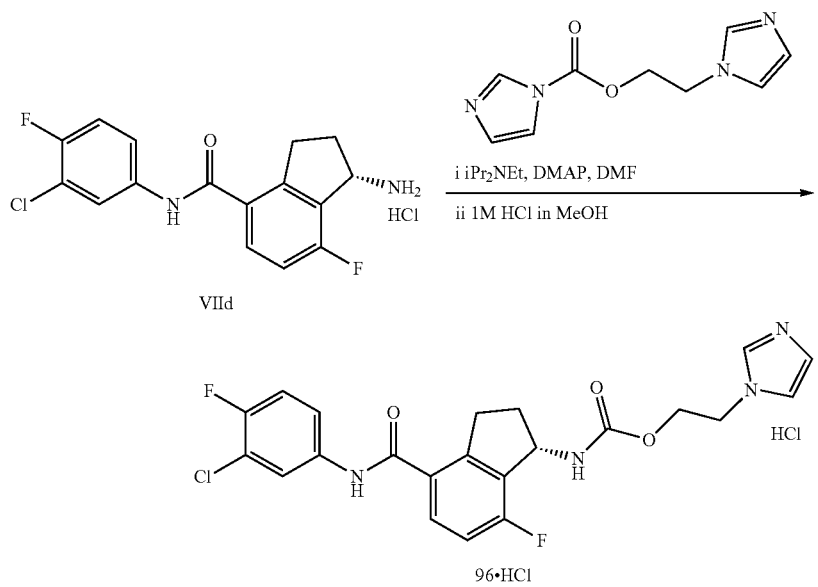

O-2-(1H-Imidazol-1-yl)ethyl, N—(S)-(4-((3-chloro-4-fluorophenyl)carbamoyl)-7-fluoro-2,3-dihydro-1H-inden-1-yl) carbamate hydrochloride (961.HCl) was prepared in a similar manner as described above from (S)-1-amino-N-(3-chloro-4-fluorophenyl)-7-fluoro-2,3-dihydro-1H-indene-4-carboxamide hydrochloride (VIId) and 2-(1H-imidazol-1-yl)ethyl 1H-imidazole-1-carboxylate. The purified compound was subsequently converted to the hydrochloride salt using a 1.25 M solution of HCl in methanol. LCMS: m/z found 461.1/463.1 [M+H]⁺, RT=3.36 min (Method A); ¹H NMR (300 MHz, Methanol-d₄) δ 8.97 (s, 1H), 7.95 (dd, 1H), 7.75-7.51 (m, 4H), 7.25 (t, 1H), 7.07 (t, 1H), 5.32 (t, 1H), 4.59-4.42 (m, 4H), 3.30 (m, 1H), 3.20-3.02 (m, 1H), 2.60-2.42 (m, 1H), 2.09-1.93 (m, 1H).

O-2-Phenoxyethyl, N—(S)-(4-((3-chloro-4-fluorophenyl)carbamoyl)-7-fluoro-2,3-dihydro-1H-inden-1-yl) carbamate (99)

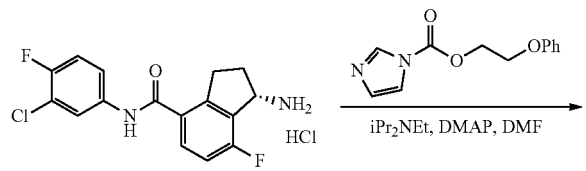

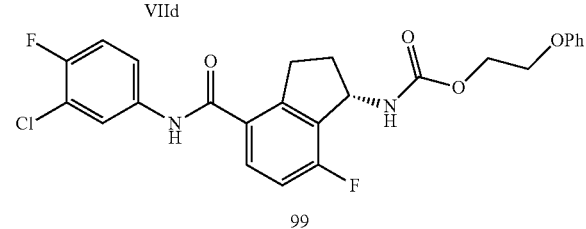

O-2-Phenoxyethyl, N—(S)-(4-((3-chloro-4-fluorophenyl)carbamoyl)-7-fluoro-2,3-dihydro-1H-inden-1-yl) carbamate (99) was prepared in a similar manner as described above from (S)-1-amino-N-(3-chloro-4-fluorophenyl)-7-fluoro-2,3-dihydro-1H-indene-4-carboxamide hydrochloride (VIId) and 2-phenoxyethyl 1H-imidazole-1-carboxylate. LCMS: m/z found 487.0/487.9 [M+H]$^+$; HPLC: RT=5.53 min (Method A); $^1$H NMR (300 MHz, Chloroform-d) δ 7.80 (dd, 1H), 7.64-7.53 (m, 2H), 7.46-7.28 (m, 1H), 7.36-7.20 (m, 3H), 7.13 (t, 1H), 7.05-6.87 (m, 4H), 5.42-5.36 (m, 1H), 5.11-5.05 (m, 1H), 4.46 (t, 2H), 4.18 (t, 1H), 3.47-3.30 (m, 1H), 3.23-3.06 (m, 1H), 2.64-2.55 (m, 1H), 2.17-1.88 (m, 1H).

O-Cyclopentyl, N—(S)-(4-((3-chloro-4-fluorophenyl)carbamoyl)-7-fluoro-2,3-dihydro-1H-inden-1-yl) carbamate (131)

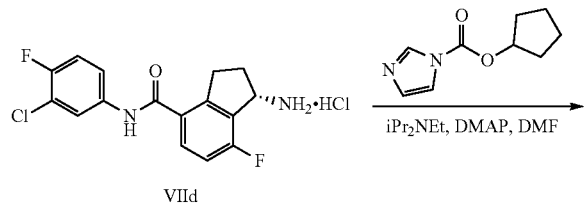

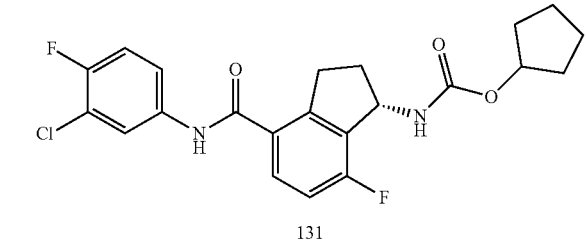

O-Cyclopentyl, N—(S)-(4-((3-chloro-4-fluorophenyl)carbamoyl)-7-fluoro-2,3-dihydro-1H-inden-1-yl) carbamate (131) was prepared in a similar manner as described above from (S)-1-amino-N-(3-chloro-4-fluorophenyl)-7-fluoro-2,3-dihydro-1H-indene-4-carboxamide hydrochloride (VIId) and cyclopentyl 1H-imidazole-1-carboxylate. LCMS: m/z found 435.1/437.1 [M+H]$^+$; HPLC: RT=5.46 min (Method A); $^1$H NMR (300 MHz, Chloroform-d) δ 7.83 (dd, 1H), 7.70-7.55 (m, 2H), 7.46-7.37 (m, 1H), 7.15 (t, 1H), 7.00 (t, 1H), 5.42-5.30 (m, 1H), 5.20-5.10 (m, 1H), 4.95-4.80 (m, 1H), 3.47-3.30 (m, 1H), 3.23-3.06 (m, 1H), 2.64-2.50 (m, 1H), 2.15-1.95 (m, 1H), 1.95-1.65 (m, 8H).

O—(R)-Tetrahydrofuran-3-yl, N—((S)-4-((3-chloro-4-fluorophenyl)carbamoyl)-7-fluoro-2,3-dihydro-1H-inden-1-yl) carbamate (170)

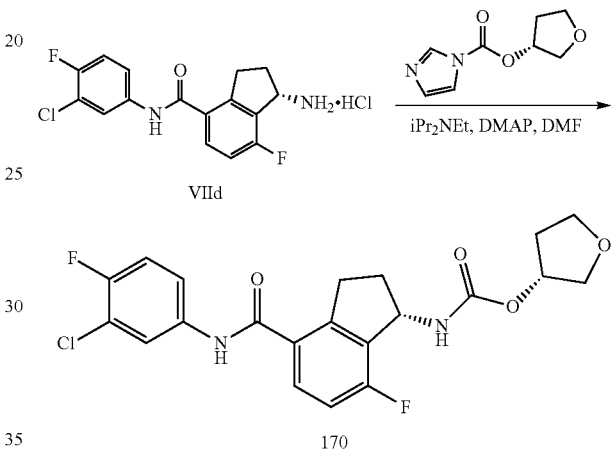

O—(R)-Tetrahydrofuran-3-yl, N—((S)-4-((3-chloro-4-fluorophenyl)carbamoyl)-7-fluoro-2,3-dihydro-1H-inden-1-yl) carbamate (170) was prepared in a similar manner as described above from (S)-1-amino-N-(3-chloro-4-fluorophenyl)-7-fluoro-2,3-dihydro-1H-indene-4-carboxamide hydrochloride (VIId) and (R)-tetrahydrofuran-3-yl 1H-imidazole-1-carboxylate. LCMS: m/z found 437.1/439.0 [M+H]$^+$; HPLC: RT=4.38 min (Method A); $^1$H NMR (300 MHz, Chloroform-d) δ 8.10 (m, 1H), 7.80 (d, 1H), 7.67-7.53 (m, 2H), 7.40 (s, 1H), 7.25 (m, 1H), 7.13 (t, 1H), 6.99 (t, 1H), 5.47-5.24 (m, 2H), 5.03-4.96 (m, 1H), 3.86 (s, 5H), 3.47-3.30 (m, 1H), 3.22-3.04 (m, 1H), 2.66-2.50 (m, 1H), 2.25-1.91 (m, 4H).

O—(S)-Tetrahydrofuran-3-yl, N—((S)-4-((3-chloro-4-fluorophenyl)carbamoyl)-7-fluoro-2,3-dihydro-1H-inden-1-yl) carbamate (181)

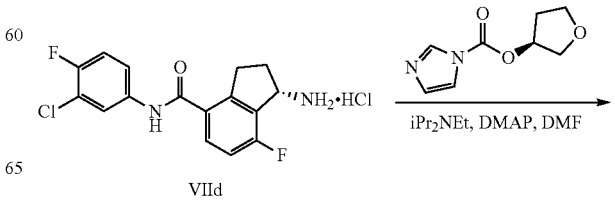

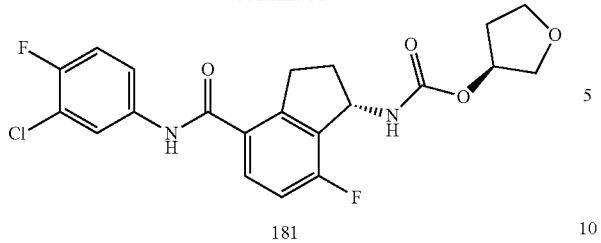

181

O—(S)-Tetrahydrofuran-3-yl, N—((S)-4-((3-chloro-4-fluorophenyl)carbamoyl)-7-fluoro-2,3-dihydro-1H-inden-1-yl)carbamate (181) was prepared in a similar manner as described above from (S)-1-amino-N-(3-chloro-4-fluorophenyl)-7-fluoro-2,3-dihydro-1H-indene-4-carboxamide hydrochloride (VIId) and (S)-tetrahydrofuran-3-yl 1H-imidazole-1-carboxylate. LCMS: m/z found 437.1/439.0 [M+H]$^+$; HPLC: RT=4.38 min (Method A); $^1$H NMR (300 MHz, Chloroform-d) δ 8.10 (m, 1H), 7.80 (d, 1H), 7.67-7.53 (m, 2H), 7.40 (s, 1H), 7.25 (m, 1H), 7.13 (t, 1H), 6.99 (t, 1H), 5.47-5.24 (m, 2H), 5.03-4.96 (m, 1H), 3.86 (s, 5H), 3.47-3.30 (m, 1H), 3.22-3.04 (m, 1H), 2.66-2.50 (m, 1H), 2.25-1.91 (m, 4H).

O-2-Methoxyethyl, N—(S)-(4-((3-chloro-4-fluorophenyl)carbamoyl)-7-fluoro-2,3-dihydro-1H-inden-1-yl) carbamate (111)

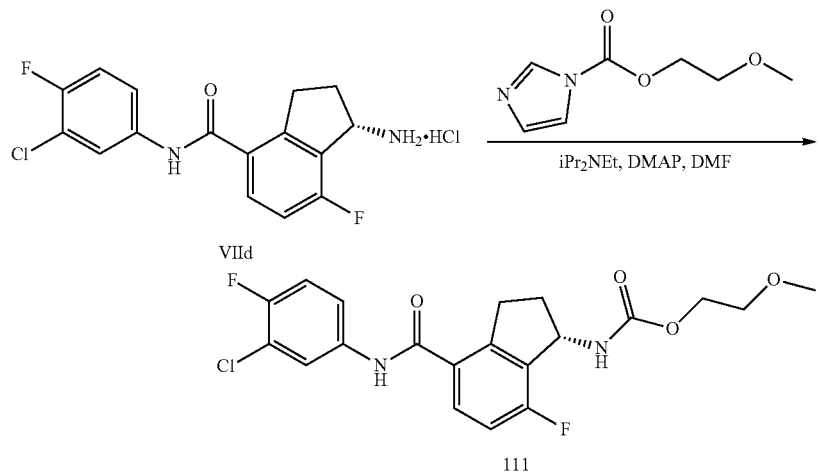

O-2-Methoxyethyl, N—(S)-(4-((3-chloro-4-fluorophenyl)carbamoyl)-7-fluoro-2,3-dihydro-1H-inden-1-yl)carbamate (111) was synthesized in a similar manner as outlined above from (S)-1-amino-N-(3-chloro-4-fluorophenyl)-7-fluoro-2,3-dihydro-1H-indene-4-carboxamide hydrochloride (VIId) and (2-methoxyethyl 1H-imidazole-1-carboxylate. LCMS: m/z found 425.3/427.3 [M+H]$^+$, RT=2.22 min (Method H); HPLC: RT=10.47 min (Method L); $^1$H NMR (400 MHz, DMSO-d$_6$): δ 10.40 (s, 1H), 8.03-8.07 (m, 1H), 7.63.7.77 (m, 3H), 7.41 (d, 1H), 7.15 (d, 1H), 5.26 (m, 1H), 4.09 (t, 2H), 3.51 (t, 2H), 3.21 (s, 3H), 3.01 (m, 1H), 2.48 (m, 1H), 2.36-2.45 (m, 1H), 1.90 (m, 1H).

O-3-Methoxypropyl, N—(S)-(4-((3-chloro-4-fluoro-phenyl)carbamoyl)-7-fluoro-2,3-dihydro-1H-inden-1-yl) carbamate (114)

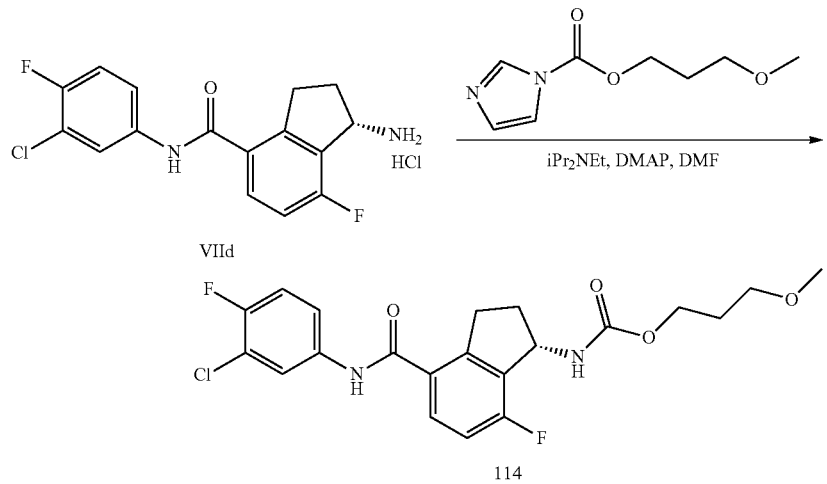

O-3-Methoxypropyl, N—(S)-(4-((3-chloro-4-fluorophenyl)carbamoyl)-7-fluoro-2,3-dihydro-1H-inden-1-yl) carbamate (114) was synthesized in a similar manner as outlined above from (S)-1-amino-N-(3-chloro-4-fluorophenyl)-7-fluoro-2,3-dihydro-1H-indene-4-carboxamide hydrochloride (VIId) and (3-methoxypropyl 1H-imidazole-1-carboxylate. LCMS: m/z found 439.1/441.1 [M+H]$^+$, RT=2.09 min (Method H); HPLC: RT=10.72 min (Method L); $^1$H NMR (400 MHz, DMSO-d$_6$): δ 10.37 (s, 1H), 8.02 (dd, 1H), 7.59-7.70 (m, 3H), 7.39 (dd, 1H), 7.13 (dd, 1H), 5.19-5.30 (m, 1H), 3.94-4.07 (m, 2H), 3.36 (t, 2H), 3.18-3.23 (m, 4H), 2.93-3.04 (m, 1H), 2.32-2.42 (m, 1H), 1.87 (m, 1H), 1.77 (t, 2H).

O-2-Acetamidoethyl, N—(S)-(4-((3-chloro-4-fluoro-phenyl)carbamoyl)-7-fluoro-2,3-dihydro-1H-inden-1-yl) carbamate (157)

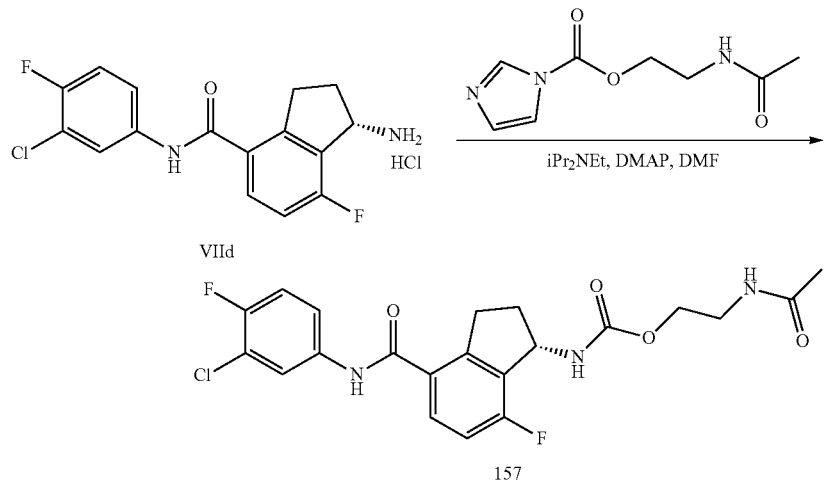

O-2-Acetamidoethyl, N—(S)-(4-((3-chloro-4-fluorophenyl)carbamoyl)-7-fluoro-2,3-dihydro-1H-inden-1-yl)carbamate (157) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-acetamidoethyl 1H-imidazole-1-carboxylate. LCMS: m/z found 452.1/454.1 [M+H]⁺, RT=1.80 min (Method H); HPLC: RT=10.19 min (Method L); ¹H NMR (400 MHz, DMSO-d₆): δ 10.39 (s, 1H), 8.03 (dd, 1H), 7.94 (m, 1H), 7.57-7.74 (m, 3H), 7.39 (dd, 1H), 7.13 (dd, 1H), 5.21-5.29 (m, 1H), 3.93-3.99 (m, 2H), 3.17-3.26 (m, 3H), 2.94-3.05 (m, 1H), 2.34-2.43 (m, 1H), 1.83-1.94 (m, 1H), 1.80 (s, 3H).

O—((S)-Tetrahydrofuran-2-yl)methyl, N—((S)-4-((3-chloro-4-fluorophenyl)carbamoyl)-7-fluoro-2,3-dihydro-1H-inden-1-yl) carbamate (142)

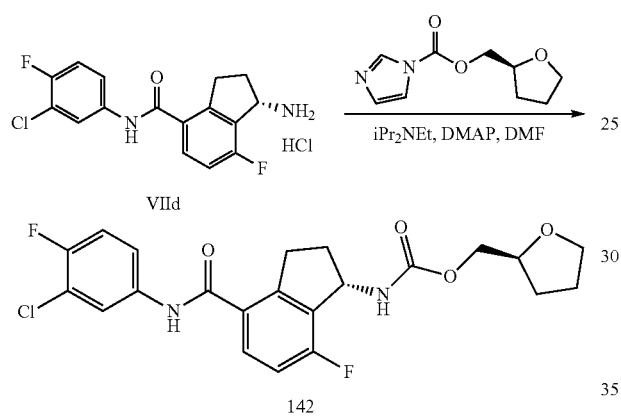

O—((S)-Tetrahydrofuran-2-yl)methyl, N—((S)-4-((3-chloro-4-fluorophenyl)carbamoyl)-7-fluoro-2,3-dihydro-1H-inden-1-yl)carbamate (142) was synthesized in a similar manner as outlined above from (S)-1-amino-N-(3-chloro-4-fluorophenyl)-7-fluoro-2,3-dihydro-1H-indene-4-carboxamide hydrochloride (VIId) and (S)-(tetrahydrofuran-2-yl)methyl 1H-imidazole-1-carboxylate. LCMS: 98.41%, m/z: 450.9/452.9 [M+H]⁺ RT=2.07 min (Method H); HPLC: RT=7.39 min (Method M); ¹H NMR (400 MHz, DMSO-d₆): δ 10.40 (s, 1H), 8.05 (d, 1H), 7.60-7.76 (m, 3H), 7.41 (dd, 1H), 7.15 (dd, 1H), 5.25 (m, 1H), 3.84-4.02 (m, 2H), 3.69-3.79 (m, 1H), 3.70-3.76 (m, 1H), 3.63 (m, 1H), 3.28 (m, 1H), 2.95-3.06 (m, 1H), 2.50 (m, 1H), 1.73-1.96 (m, 3H), 1.54 (m, 1H).

O—((R)-Tetrahydrofuran-2-yl)methyl, N—((S)-4-((3-chloro-4-fluorophenyl)carbamoyl)-7-fluoro-2,3-dihydro-1H-inden-1-yl) carbamate (112)

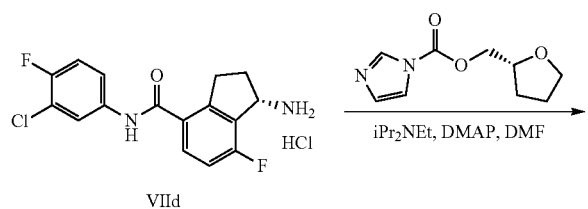

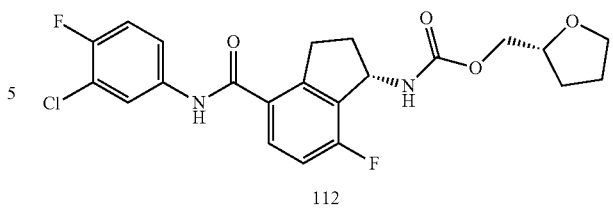

O—((R)-Tetrahydrofuran-2-yl)methyl, N—((S)-4-((3-chloro-4-fluorophenyl)carbamoyl)-7-fluoro-2,3-dihydro-1H-inden-1-yl) carbamate (112) was synthesized in a similar manner as outlined above from (S)-1-amino-N-(3-chloro-4-fluorophenyl)-7-fluoro-2,3-dihydro-1H-indene-4-carboxamide hydrochloride (VIId) and (R)-(tetrahydrofuran-2-yl)methyl 1H-imidazole-1-carboxylate. LCMS: m/z found 451.3/453.3 [M+H]⁺, RT=2.27 min (Method H); HPLC: RT=10.3 min (Method M); ¹H NMR (400 MHz, DMSO-d₆): δ 10.40 (s, 1H), 8.04 (dd, 1H), 7.61-7.77 (m, 3H), 7.41 (dd, 1H), 7.15 (dd, 1H), 5.26 (m, 1H), 3.89-4.03 (m, 3H), 3.70-3.78 (m, 1H), 3.59-3.67 (m, 1H), 3.19-3.28 (m, 1H), 3.00 (m, 1H), 2.40 (m, 1H), 1.74-1.97 (m, 4H), 1.57 (m, 1H).

O-Tetrahydro-2H-pyran-4-yl, N—(S)-(4-((3-chloro-4-fluorophenyl)carbamoyl)-7-fluoro-2,3-dihydro-1H-inden-1-yl) carbamate (113)

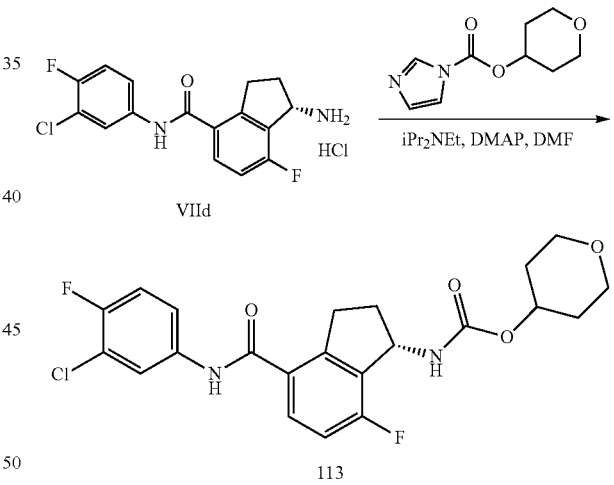

O-Tetrahydro-2H-pyran-4-yl, N—(S)-(4-((3-chloro-4-fluorophenyl)carbamoyl)-7-fluoro-2,3-dihydro-1H-inden-1-yl) carbamate (113) was synthesized in a similar manner as outlined above from (S)-1-amino-N-(3-chloro-4-fluorophenyl)-7-fluoro-2,3-dihydro-1H-indene-4-carboxamide hydrochloride (VIId) and tetrahydro-2H-pyran-4-yl 1H-imidazole-1-carboxylate. LCMS: m/z found 451.3/453.3 [M+H]⁺, RT=2.26 min (Method H); HPLC: RT=10.6 min (Method M); ¹H NMR (400 MHz, DMSO-d₆): δ 10.40 (s, 1H), 8.04 (dd, 1H), 7.61-7.77 (m, 3H), 7.41 (dd, 1H), 7.15 (dd, 1H), 5.22-5.33 (m, 1H), 4.70-4.77 (m, 1H), 3.76-3.89 (m, 2H), 3.53 (dd, 1H), 3.38-3.47 (m, 1H), 3.17-3.26-3.17 (m, 1H), 2.94-3.06 (m, 1H), 2.34-2.44 (m, 1H), 1.82-1.92 (m, 2H), 1.73 (m, 1H), 1.46-1.55 (m, 2H).

O-2-Morpholinoethyl, N—(S)-(4-((3-chloro-4-fluorophenyl)carbamoyl)-7-fluoro-2,3-dihydro-1H-inden-1-yl) carbamate (153)

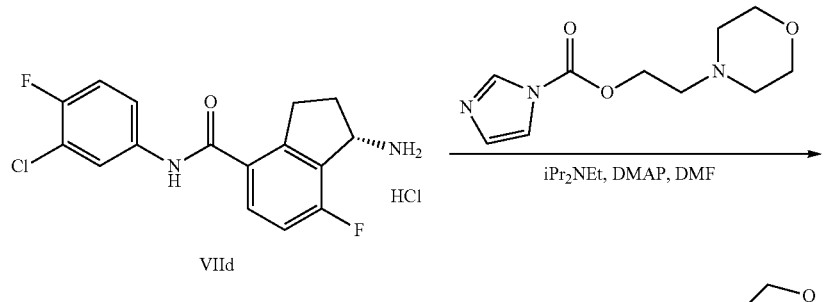

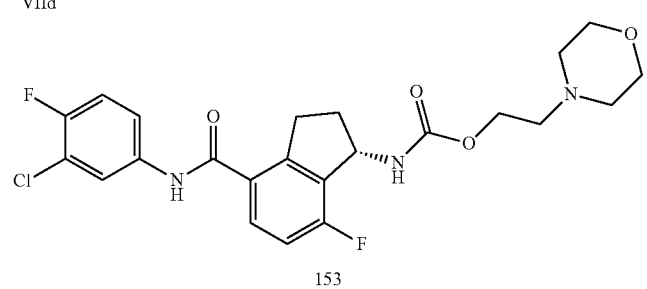

O-2-Morpholinoethyl, N—(S)-(4-((3-chloro-4-fluorophenyl)carbamoyl)-7-fluoro-2,3-dihydro-1H-inden-1-yl) carbamate (153) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-morpholinoethyl 1H-imidazole-1-carboxylate. LCMS: m/z found 480.2/482.2 [M+H]$^+$, RT=1.75 min (Method H); HPLC: RT=7.97 min (Method M); $^1$H NMR (400 MHz, DMSO-d$_6$): δ 10.43 (s, 1H), 8.05 (d, 1H), 7.62-7.77 (m, 3H), 7.41 (dd, 1H), 7.15 (dd, 1H), 5.26 (m, 1H), 4.02-4.18 (m, 2H), 3.49-3.62 (m, 4H), 3.17-3.28 (m, 2H), 2.94-3.06 (m, 1H), 2.41 (s, 4H), 1.81-1.95 (m, 1H), 1.77 (m, 2H).

O-2-(Piperidin-1-yl)ethyl, N—(S)-(4-((3-chloro-4-fluorophenyl)carbamoyl)-7-fluoro-2,3-dihydro-1H-inden-1-yl) carbamate (147)

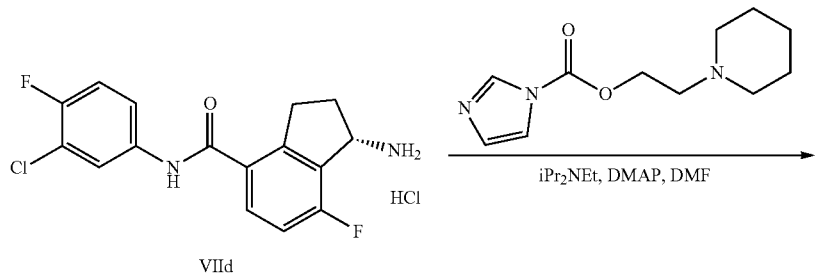

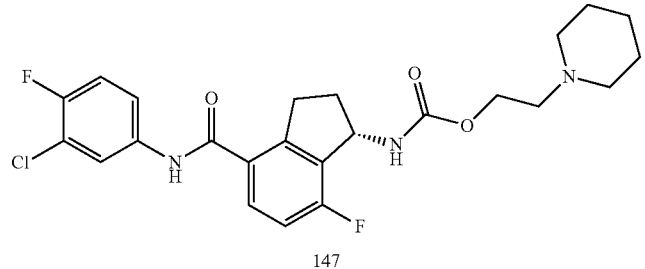

O-2-(Piperidin-1-yl)ethyl, N—(S)-(4-((3-chloro-4-fluorophenyl)carbamoyl)-7-fluoro-2,3-dihydro-1H-inden-1-yl) carbamate (147) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-(piperidin-1-yl)ethyl 1H-imidazole-1-carboxylate. LCMS: m/z found 478.2/480.2 [M+H]$^+$, RT=1.91 min (Method H); HPLC: RT=10.35 min (Method L); $^1$H NMR (400 MHz, DMSO-d$_6$) δ ppm 10.42 (s, 1H), 8.04 (dd, 1H), 7.62-7.75 (m, 3H), 7.40 (dd, 1H), 7.14 (dd, 1H), 5.24 (q, 1H), 3.91-4.18 (m, 2H), 3.15-3.22 (m, 1H), 2.99-3.16 (m, 1H), 2.41-2.49 (m, 3H), 2.32-2.40 (m, 4H), 1.80-1.91 (m, 1H), 1.45-1.49 (m, 4H), 1.35-1.37 (m, 2H).

O-(4-Oxoazetidin-2-yl)methyl, N—((S)-4-((3-chloro-4-fluorophenyl)carbamoyl)-7-fluoro-2,3-dihydro-1H-inden-1-yl) carbamate (213)

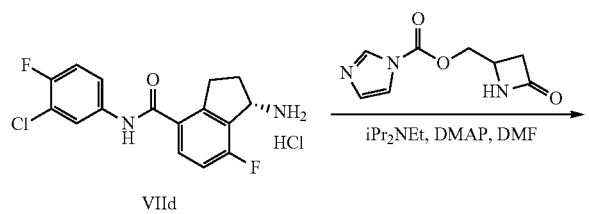

O-(4-Oxoazetidin-2-yl)methyl, N—((S)-4-((3-chloro-4-fluorophenyl)carbamoyl)-7-fluoro-2,3-dihydro-1H-inden-1-yl)carbamate (213) was synthesized in a similar manner as outlined above from (S)-1-amino-N-(3-chloro-4-fluorophenyl)-7-fluoro-2,3-dihydro-1H-indene-4-carboxamide hydrochloride (VIId) and (4-oxoazetidin-2-yl)methyl 1H-imidazole-1-carboxylate. LCMS: m/z found 478.3/480.2 [M+H]$^+$, RT=1.87 min (Method H); HPLC: RT=10.43 min (Method N).

O—((R)-6-Oxopiperidin-2-yl)methyl, N—((S)-4-((3-chloro-4-fluorophenyl)carbamoyl)-7-fluoro-2,3-dihydro-1H-inden-1-yl) carbamate (198)

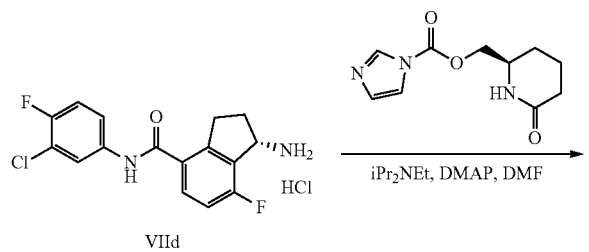

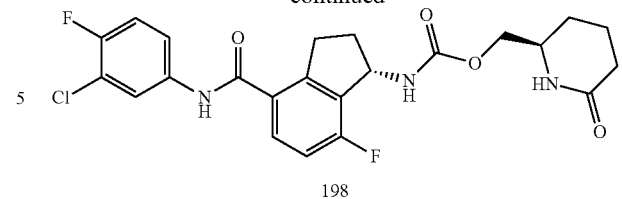

O—((R)-6-Oxopiperidin-2-yl)methyl, N—((S)-4-((3-chloro-4-fluorophenyl)carbamoyl)-7-fluoro-2,3-dihydro-1H-inden-1-yl) carbamate (198) was synthesized in a similar manner as outlined above from (S)-1-amino-N-(3-chloro-4-fluorophenyl)-7-fluoro-2,3-dihydro-1H-indene-4-carboxamide hydrochloride (VIId) and (R)-(6-oxopiperidin-2-yl)methyl 1H-imidazole-1-carboxylate. LCMS: m/z found 450.2/452.2 [M+H]$^+$, RT=2.05 min (Method H); HPLC: RT=5.88 min (Method M).

O—((S)-6-Oxopiperidin-2-yl)methyl, N—((S)-4-((3-chloro-4-fluorophenyl)carbamoyl)-7-fluoro-2,3-dihydro-1H-inden-1-yl) carbamate (212)

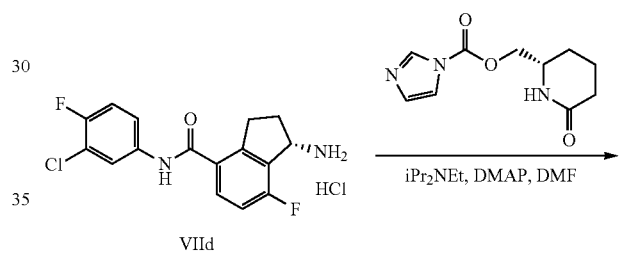

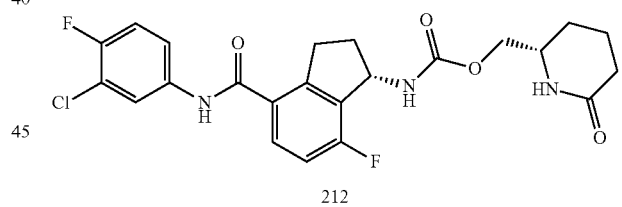

O((S)-6-Oxopiperidin-2-yl)methyl, N—((S)-4-((3-chloro-4-fluorophenyl)carbamoyl)-7-fluoro-2,3-dihydro-1H-inden-1-yl) carbamate (212) was synthesized in a similar manner as outlined above from (S)-1-amino-N-(3-chloro-4-fluorophenyl)-7-fluoro-2,3-dihydro-1H-indene-4-carboxamide hydrochloride (VIId) and (S)-(6-oxopiperidin-2-yl)methyl 1H-imidazole-1-carboxylate. LCMS: m/z found 478.3/480.2 [M+H]$^+$, RT=2.09 min (Method H); HPLC: RT=10.82 min (Method N); $^1$H NMR (500 MHz, DMSO-d$_6$): 10.40 (s, 1H), 8.04 (dd, 1H), 7.61-7.74 (m, 3H), 7.41 (dd, 1H), 7.32 (s, 1H), 7.16 (dd, 1H), 5.23-5.32 (q, 1H), 3.95 (ABq, 2H), 3.45-3.53 (m, 1H), 3.18-3.28 (m, 1H), 2.93-3.05 (m, 1H), 2.35-2.42 (m, 1H), 2.00-2.16 (m, 2H), 1.90 (m, 1H), 1.71-1.82 (m, 2H), 1.52-1.63 (m, 1H), 1.49 (m, 1H).

O—(R)-6-Oxopiperidin-3-yl, N—((S)-4-((3-chloro-4-fluorophenyl)carbamoyl)-7-fluoro-2,3-dihydro-1H-inden-1-yl)carbamate (199)

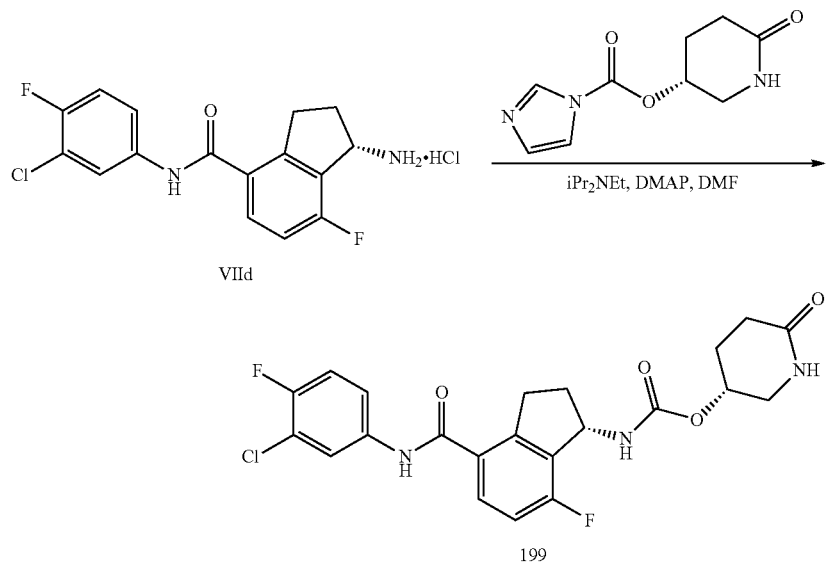

O—(R)-6-Oxopiperidin-3-yl, N—((S)-4-((3-chloro-4-fluorophenyl)carbamoyl)-7-fluoro-2,3-dihydro-1H-inden-1-yl) carbamate (199) was synthesized in a similar manner as outlined above from (S)-1-amino-N-(3-chloro-4-fluorophenyl)-7-fluoro-2,3-dihydro-1H-indene-4-carboxamide hydrochloride (VIId) and (R)-6-oxopiperidin-3-yl 1H-imidazole-1-carboxylate. LCMS: m/z found 464.2/466.2 [M+H]$^+$, RT=1.80 min (Method H); HPLC: RT=9.71 min (Method K); $^1$H NMR (400 MHz, DMSO-d$_6$): 10.40 (s, 1H), 8.05 (dd, 1H), 7.78 (d, 1H), 7.63 (m, 2H), 7.37-7.47 (m, 2H), 7.15 (dd, 1H), 5.18-5.34 (m, 1H), 4.92 (m, 1H), 3.41 (m, 1H), 3.13-3.27 (m, 2H), 2.89-3.08 (m, 1H), 2.15-2.50 (m, 2H), 2.11-2.27 (m, 1H), 1.92 (m, 3H).

O—(S)-6-Oxopiperidin-3-yl, N—((S)-4-((3-chloro-4-fluorophenyl)carbamoyl)-7-fluoro-2,3-dihydro-1H-inden-1-yl) carbamate (200)

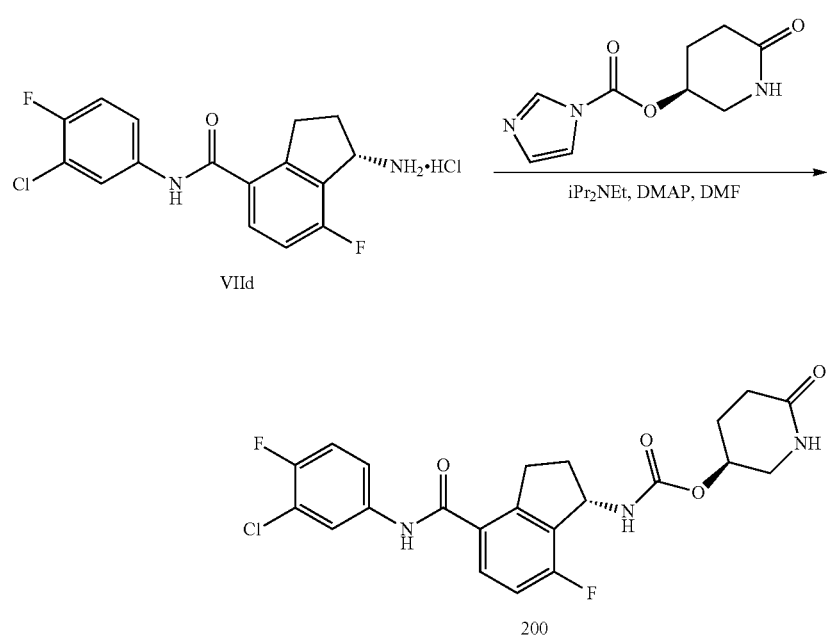

O—(S)-6-Oxopiperidin-3-yl, N—((S)-4-((3-chloro-4-fluorophenyl)carbamoyl)-7-fluoro-2,3-dihydro-1H-inden-1-yl) carbamate (200) was synthesized in a similar manner as outlined above from (S)-1-amino-N-(3-chloro-4-fluorophenyl)-7-fluoro-2,3-dihydro-1H-indene-4-carboxamide hydrochloride (VIId) and (S)-6-oxopiperidin-3-yl 1H-imidazole-1-carboxylate. LCMS: m/z found 464.2/466.2 [M+H]$^+$, RT=1.80 min (Method H); HPLC: RT=9.74 min (Method K); $^1$H NMR (400 MHz, DMSO-d$_6$): 10.37 (s, 1H), 8.01 (dd, 1H), 7.75 (d, 1H), 7.60-7.69 (m, 2H), 7.37 (m, 2H), 7.12 (dd, 1H), 5.20-5.32 (m, 1H), 4.87 (s, 1H), 3.36 (m, 1H), 3.11-3.22 (m, 2H), 2.98 (m, 1H), 2.34-2.43 (m, 1H), 2.12-2.21 (m, 2H), 1.80-1.96 (m, 3H).

O—(S)-2-Cyanoethyl, N-4-(3-chloro-4-fluorophenylcarbamoyl)-7-fluoro-2,3-dihydro-1H-inden-1-yl carbamate (255)

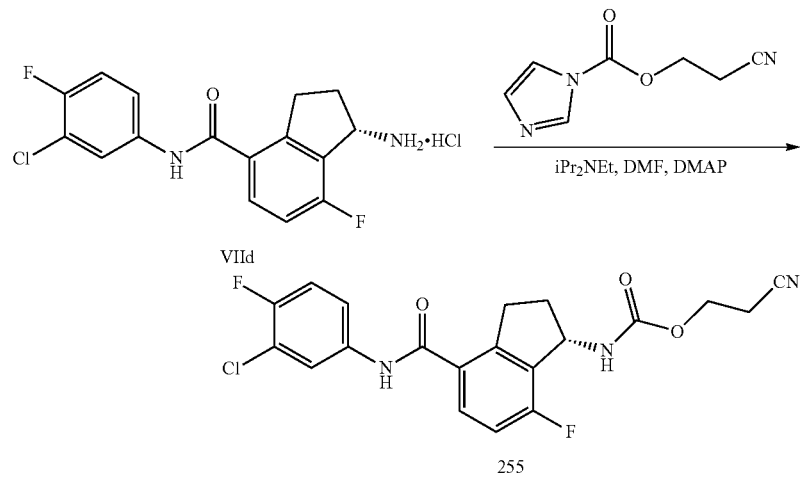

O—(S)-2-Cyanoethyl, N-4-(3-chloro-4-fluorophenylcarbamoyl)-7-fluoro-2,3-dihydro-1H-inden-1-yl carbamate (255) was synthesized in a similar manner as described above from (S)-1-amino-N-(3-chloro-4-fluorophenyl)-7-fluoro-2,3-dihydro-1H-indene-4-carboxamide hydrochloride (VIId) and 2-cyanoethyl 1H-imidazole-1-carboxylate. LCMS: m/z found 420.2/422.2 [M+H]$^+$, RT=4.32 min (Method A); $^1$H NMR (400 MHz, DMSO-d$_6$): δ 10.40 (bs, 1H), 8.04 (dd, 1H), 7.92 (d, 1H), 7.72-7.63 (m, 2H), 7.41 (dd, 1H), 7.16 (dd, 1H), 5.27 (q, 1H), 4.16 (t, 2H), 3.33-3.20 (m, 1H), 3.06-2.98 (m, 1H), 2.85 (t, 2H), 2.43-2.39 (m, 1H), 1.93-1.88 (m, 1H).

O—(S)-3-Cyanopropyl, N-4-(3-chloro-4-fluorophenylcarbamoyl)-7-fluoro-2,3-dihydro-1H-inden-1-yl carbamate (256)

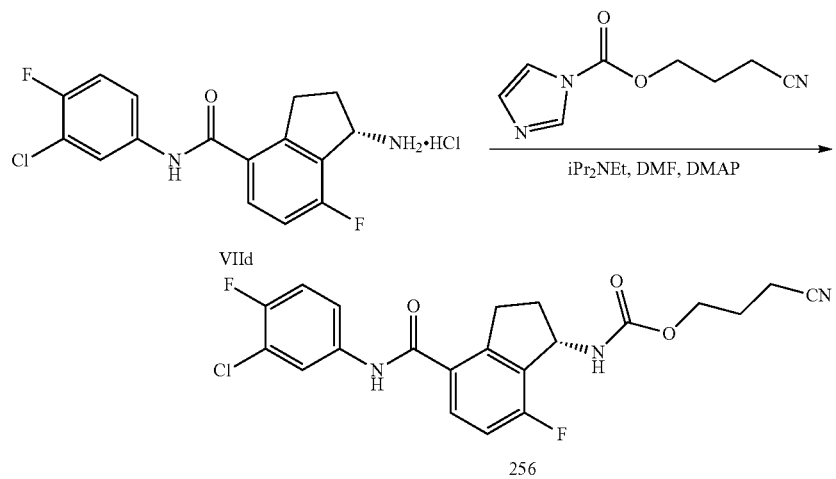

205

O—(S)-3-Cyanopropyl, N-4-(3-chloro-4-fluorophenyl-carbamoyl)-7-fluoro-2,3-dihydro-1H-inden-1-yl carbamate (256) was synthesized in a similar manner as described above from (S)-1-amino-N-(3-chloro-4-fluorophenyl)-7-fluoro-2,3-dihydro-1H-indene-4-carboxamide hydrochloride (VIId) and 3-cyanopropyl 1H-imidazole-1-carboxylate. LCMS: m/z found 434.3/436.3 [M+H]$^+$, RT=4.47 min (Method A); $^1$H NMR (400 MHz, DMSO-d$_6$): δ 10.40 (bs, 1H), 8.04 (dd, 1H), 7.73-7.64 (m, 3H), 7.41 (m, 1H), 7.16 (dd, 1H), 5.27 (q, 1H), 4.04 (t, 2H), 3.35-3.30 (m, 1H), 3.03-2.99 (m, 1H), 2.54-2.51 (t, 2H), 2.45-2.40 (m, 1H), 1.90-1.85 (m, 3H).

O-(1,1-Dioxidothiomorpholin-3-yl)methyl, N—((S)-4-((3-chloro-4-fluorophenyl)carbamoyl)-7-fluoro-2,3-dihydro-1H-inden-1-yl) carbamate Hydrochloride (177)

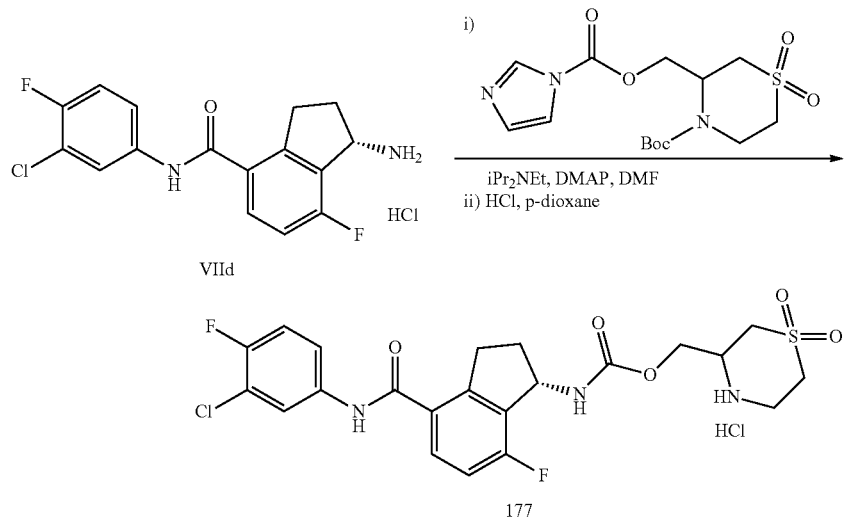

2-((tert-Butyldimethylsilyl)oxy)ethyl (S)-(4-((3-chloro-4-fluorophenyl)carbamoyl)-7-fluoro-2,3-dihydro-1H-inden-1-yl)carbamate (177) was synthesized in a similar manner as outlined above from (S)-1-amino-N-(3-chloro-4-fluorophenyl)-7-fluoro-2,3-dihydro-1H-indene-4-carboxamide hydrochloride (VIId) and tert-butyl 3-(((1H-imidazole-1-carbonyl)oxy)methyl)thiomorpholine-4-carboxylate 1,1-dioxide, followed by acid mediated Boc deprotection. LCMS: (Method H) m/z found 514.3/515.3 [M+H]$^+$, RT=1.88 min; HPLC: (Method K) RT=9.91 min; $^1$H NMR (400 MHz, CD$_3$OD) δ 7.92 (dd, 1H), 7.68 (dd, 1H), 7.51-7.59 (m, 1H), 7.23 (dd, 1H), 7.06 (dd, 1H), 5.38 (q, 1H), 4.23-4.43 (m, 2H), 4.01 (m, 1H), 3.81 (m, 1H), 3.48-3.58 (m, 2H), 3.36-3.44 (m, 3H), 3.07-3.17 (m, 1H), 2.53 (m, 1H), 2.05 (m, 1H), 1.37 (m, 1H).

tert-Butyl 4-((benzyloxy)methyl)piperidine-1-carboxylate

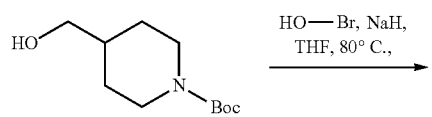

206

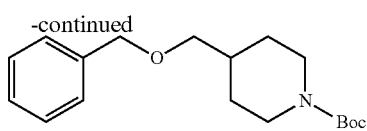

To a solution of 2.5 g (11.6 mmol, 1.0 eq.) of (tert-butyl 4-(hydroxymethyl)piperidine-1-carboxylate in 125 mL of anhydrous THF at 0° C. under a nitrogen atmosphere was added 1.02 g (25.5 mmol, 2.2 eq., 60% dispersion in mineral oil) of sodium hydride. The mixture was stirred at 15 min and 4.36 g (25.5 mmol, 2.2 eq.) of benzyl bromide was added. The mixture was then heated to 80° C. for 3 h. The mixture was allowed to cool to room temperature and quenched with 10 mL of ice water. The mixture was extracted with 2×125 mL of ethyl acetate and the combined organic extracts washed with 2×150 mL of brine. The organic solution was dried (Na$_2$SO$_4$), filtered and the solvent removed in vacuo. The residue was purified by flash chromatography (SiO$_2$, eluting with 10% ethyl acetate-petroleum ether) to provide 2.7 g (8.8 mmol, 76%) of tert-butyl 4-((benzyloxy)methyl)piperidine-1-carboxylate. LCMS: (Method H) m/z found 306.3 [M+H]$^+$, RT=2.64 min; $^1$H NMR (400 MHz, CDCl$_3$) δ 7.26-7.36 (m, 5H), 4.99 (s, 2H), 4.09 (bs, 2H), 3.06 (d, 2H), 2.69 (t, 2H), 1.71-1.79 (m, 3H), 1.45 (s, 9H), 1.13-1.19 (m, 2H).

4-((Benzyloxy)methyl)piperidine hydrochloride

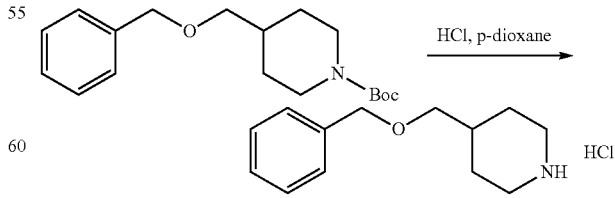

To a solution of 2.7 g (8.8 mmol, 1.0 eq.) of tert-butyl 4-((benzyloxy)methyl)piperidine-1-carboxylate in 50 mL of anhydrous p-dioxane at 0° C. was added 50 mL of a 4 M solution of HCl in p-dioxane. The mixture was allowed to warm to room temperature and stirred for 3 h. The solvent was then removed in vacuo and the residue was triturated with n-pentane to provide 2.1 g 4-((benzyloxy)methyl)piperidine hydrochloride. LCMS: (Method H) m/z found 206.1 [M+H]+, RT=1.51 min; 1H NMR (400 MHz, DMSO-d6) δ ppm 9.00 (bs, 1H), 8.66 (bs, 1H), 7.26-7.37 (m, 5H), 4.46 (s, 2H), 3.02-3.30 (m, 5H), 2.82 (m, 2H), 1.78-1.85 (m, 2H), 1.37-1.47 (m, 2H).

1-(4-((Benzyloxy)methyl)piperidin-1-yl)ethan-1-one

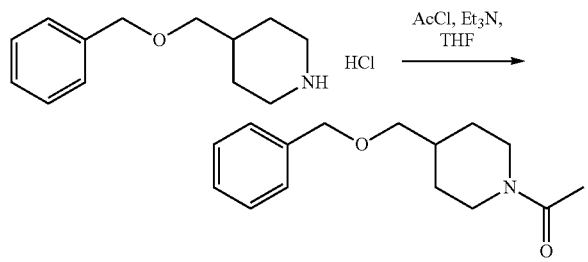

To a solution of 0.5 g (2.1 mmol, 1.0 eq.) of 4-((benzyloxy)methyl)piperidine hydrochloride in 10 mL of anhydrous THF at 0° C. was added 1.4 mL (10.3 mmol, 5.0 eq.) of triethylamine followed by 0.30 mL (4.1 mmol, 2.0 eq.) of acetyl chloride. The mixture was allowed to warm to room temperature and stirred for 3 h. The reaction was quenched with 10 mL of ice water and extracted with 2×25 mL of ethyl acetate. The combined organic extracts were washed with 2×50 mL of brine, dried (Na2SO4), filtered and the solvent was removed in vacuo to provide 0.45 g of 1-(4-((benzyloxy)methyl)piperidin-1-yl)ethan-1-one. LCMS (Method H) m/z found 248.4 [M+H]+, RT=1.74 min.

2-(4-((Benzyloxy)methyl)piperidin-1-yl)-2-oxoethyl Acetate

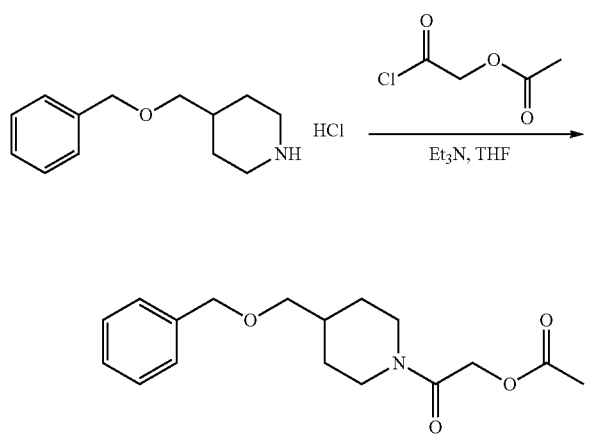

2-(4-((Benzyloxy)methyl)piperidin-1-yl)-2-oxoethyl acetate was synthesized in a similar manner as outlined above from 4-((benzyloxy)methyl)piperidine hydrochloride and 2-chloro-2-oxoethyl acetate.

1-(4-((Benzyloxy)methyl)piperidin-1-yl)-2-methoxy-ethan-1-one

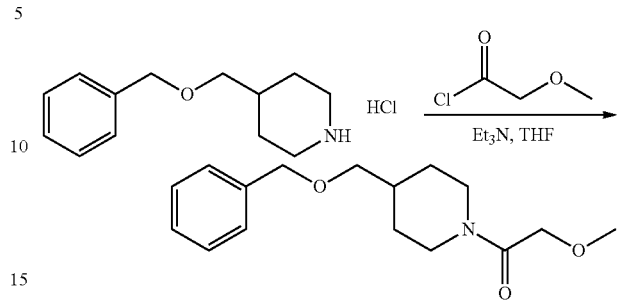

1-(4-((Benzyloxy)methyl)piperidin-1-yl)-2-methoxy-ethan-1-one was synthesized in a similar manner as outlined above from 4-((benzyloxy)methyl)piperidine hydrochloride and methoxyacetyl chloride.

4-((Benzyloxy)methyl)-N-methylpiperidine-1-carboxamide

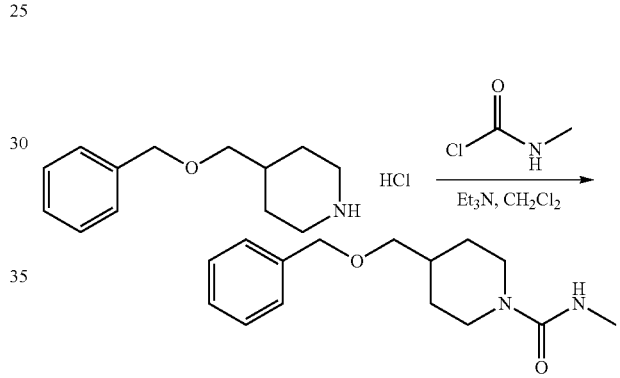

4-((Benzyloxy)methyl)-N-methylpiperidine-1-carboxamide was synthesized in a similar manner as outlined above from 4-((benzyloxy)methyl)piperidine hydrochloride and N-methylcarbamoyl chloride.

N-Substituted Piperidine Methanol—Debenzylation

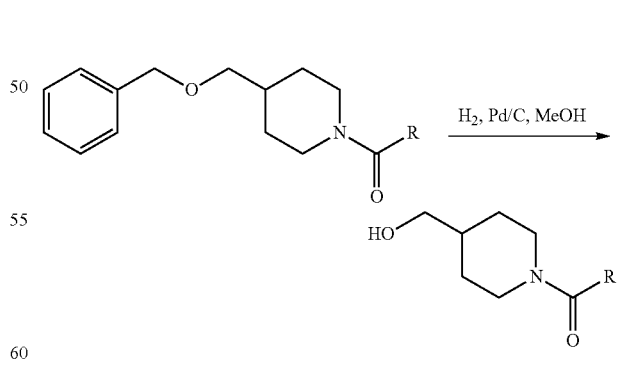

A solution of 2 mmol of the 4-((benzyloxy)methyl)-piperidine in 15 mL of methanol containing 0.3 g of 10% palladium on carbon was stirred under a hydrogen atmosphere for 16 h. The mixture was filtered through CELITE®, and the pad washed with 2×10 mL of methanol. The solvent removed in vacuo to provide the corresponding alcohol.

O-(1-Acetylpiperidin-4-yl)methyl, N—(S)-(4-((3-chloro-4-fluorophenyl)carbamoyl)-7-fluoro-2,3-dihydro-1H-inden-1-yl) carbamate (174)

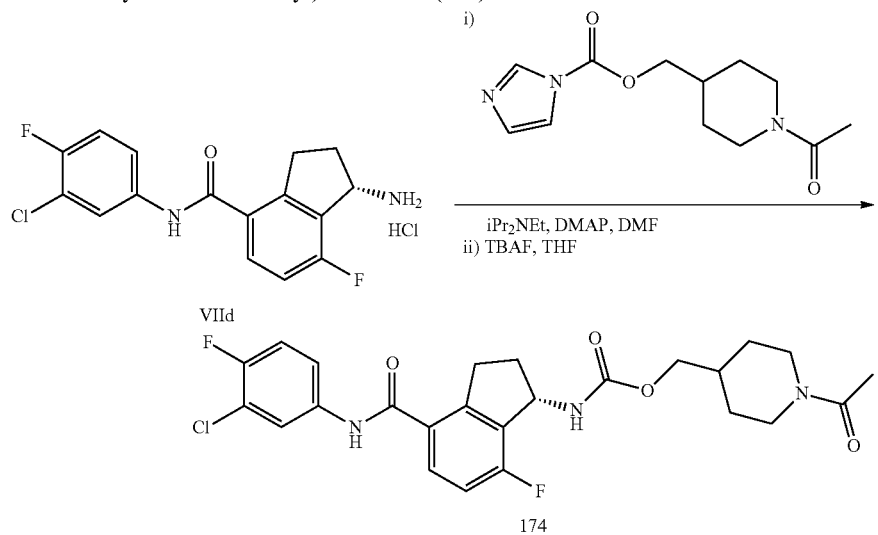

O-(1-Acetylpiperidin-4-yl)methyl, N—(S)-(4-((3-chloro-4-fluorophenyl)carbamoyl)-7-fluoro-2,3-dihydro-1H-inden-1-yl) carbamate (174) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-acetylpiperidin-4-yl)methyl 1H-imidazole-1-carboxylate. LCMS (Method H) m/z found 506.4/508.4 [M+H]$^+$, RT=2.16 min; HPLC (Method M) RT=10.84 min; $^1$H NMR (500 MHz, DMSO-d$_6$) δ ppm 10.39 (s, 1H), 8.04 (dd, 1H), 7.61-7.71 (m, 3H), 7.41 (dd, 1H), 7.15 (dd, 1H), 5.20-5.31 (m, 1H), 4.36 (d, 1H), 3.75-3.93 (m, 3H), 3.16-3.28 (m, 2H), 2.94-3.07 (m, 2H), 2.36-2.44 (m, 1H), 1.98 (s, 3H), 1.77-1.90 (m, 2H), 1.58-1.69 (m, 2H), 1.09-1.19 (m, 1H), 0.95-1.04 (m, 1H).

O-(1-(2-Methoxyacetyl)piperidin-4-yl)methyl, N—(S)-(4-((3-chloro-4-fluorophenyl)carbamoyl)-7-fluoro-2,3-dihydro-1H-inden-1-yl) carbamate (185)

O-(1-(2-Methoxyacetyl)piperidin-4-yl)methyl, N—(S)-(4-((3-chloro-4-fluorophenyl)carbamoyl)-7-fluoro-2,3-dihydro-1H-inden-1-yl) carbamate (185) was synthesized in a similar manner as outlined above from (S)-1-amino-N-(3-chloro-4-fluorophenyl)-7-fluoro-2,3-dihydro-1H-indene-4-carboxamide hydrochloride (VIId) and ((1-(2-methoxyacetyl)piperidin-4-yl)methyl 1H-imidazole-1-carboxylate. LCMS (Method H) m/z found 536.3/538.3 [M+H]$^+$, RT=2.18 min; HPLC: (Method M) RT=10.84 min; $^1$H NMR (400 MHz, DMSO-d$_6$) δ 10.39 (s, 1H), 8.04 (dd, 1H), 7.59-7.69 (m, 3H), 7.39 (dd, 1H), 7.15 (dd, 1H), 5.21 (q, 1H), 4.31 (m, 1H), 3.96-4.08 (m, 2H), 3.81-3.93 (m, 2H), 3.74 (m, 1H), 3.25 (s, 3H), 3.16-3.21 (m, 2H), 2.89-3.02 (m, 2H), 2.34-2.44 (m, 1H), 1.76-1.93 (m, 2H), 1.64 (m, 2H), 0.9-1.17 (m, 2H).

O-(1-(Methylcarbamoyl)piperidin-4-yl)methyl, N—(S)-(4-((3-chloro-4-fluorophenyl)carbamoyl)-7-fluoro-2,3-dihydro-1H-inden-1-yl) carbamate (176)

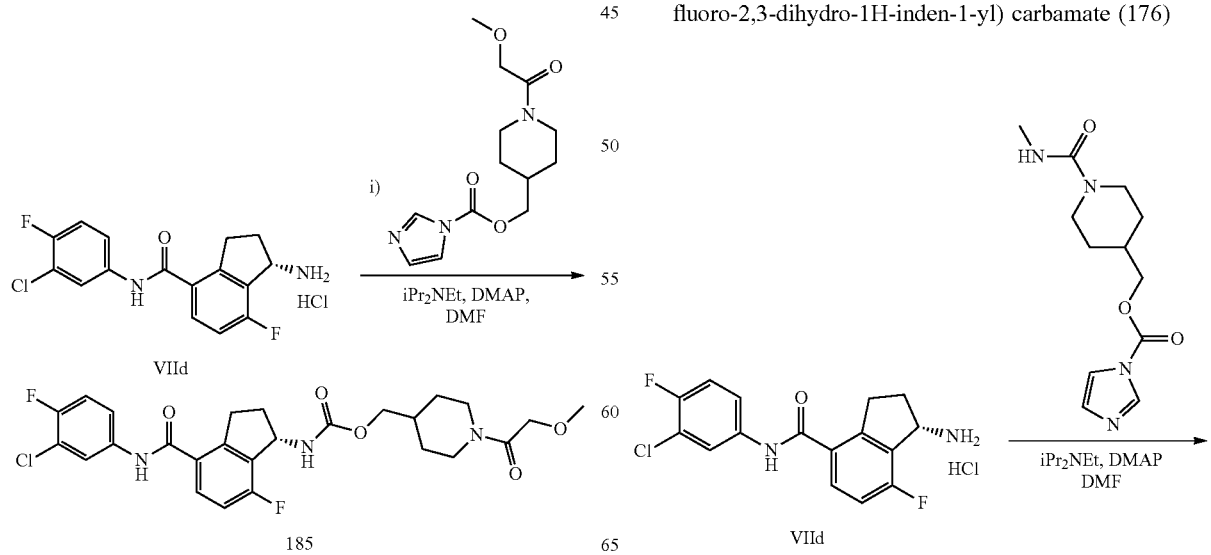

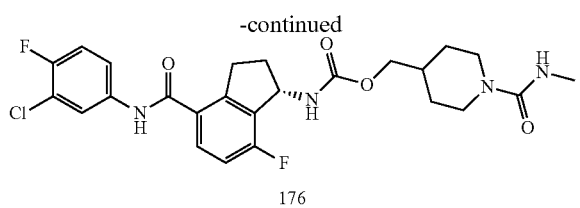

176

O-(1-(Methylcarbamoyl)piperidin-4-yl)methyl, N—(S)-(4-((3-chloro-4-fluorophenyl)carbamoyl)-7-fluoro-2,3-dihydro-1H-inden-1-yl) carbamate (176) was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-(methylcarbamoyl)piperidin-4-yl)methyl 1H-imidazole-1-carboxylate. LCMS (Method H) m/z found 521.4/523.4 [M+H]+, RT=2.14 min; HPLC: (Method M) RT=10.84 min; $^1$H NMR (400 MHz, DMSO-d$_6$) δ 10.40 (s, 1H), 8.05 (d, 1H), 7.60-7.71 (m, 3H), 7.41 (dd, 1H), 7.15 (dd, 1H), 6.35 (d, 1H), 5.26 (d, 1H), 3.76-3.98 (m, 4H), 3.15-3.27 (m, 2H), 2.88-3.08 (m, 2H), 2.59-2.73 (m, 2H), 2.32-2.40 (m, 2H), 1.88 (m, 1H), 1.73 (m, 1H), 1.58 (m, 2H), 1.05 (m, 2H).

O-(1-(2-Hydroxyacetyl)piperidin-4-yl)methyl, N—(S)-(4-((3-chloro-4-fluorophenyl)carbamoyl)-7-fluoro-2,3-dihydro-1H-inden-1-yl) carbamate (175)

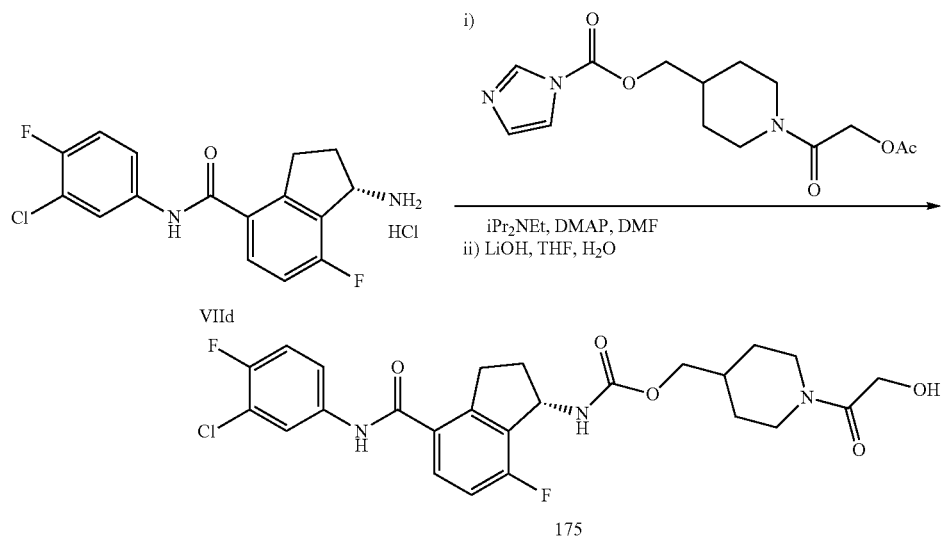

175

(S)-2-(4-(((((4-((3-Chloro-4-fluorophenyl)carbamoyl)-7-fluoro-2,3-dihydro-1H-inden-1-yl)carbamoyl)oxy)methyl)piperidin-1-yl)-2-oxoethyl acetate was synthesized in a similar manner as outlined above from (S)-1-amino-N-(3-chloro-4-fluorophenyl)-7-fluoro-2,3-dihydro-1H-indene-4-carboxamide hydrochloride (VIId) and (1-(2-acetoxyacetyl)piperidin-4-yl)methyl 1H-imidazole-1-carboxylate. The resulting ester was subsequently hydrolysed by stirring with 2 eq. of lithium hydroxide in 1:1 (v/v) THF/H$_2$O for 1 h to provide O-(1-(2-hydroxyacetyl)piperidin-4-yl)methyl, N—(S)-(4-((3-chloro-4-fluorophenyl)carbamoyl)-7-fluoro-2,3-dihydro-1H-inden-1-yl)carbamate (175). LCMS (Method H) m/z found 522.4/524.4 [M+H]+, RT=2.12 min; HPLC (Method M) RT=10.19 min; $^1$H NMR (400 MHz, DMSO-d$_6$) δ 10.40 (s, 1H), 8.05 (d, 1H), 7.61-7.74 (m, 3H), 7.40 (dd, 1H), 7.15 (dd, 1H), 5.26 (d, 1H), 4.45 (t, 1H), 4.35 (d, 1H), 4.00-4.12 (m, 2H), 3.87 (m, 2H), 3.67 (d, 1H), 2.86-3.08 (m, 3H), 2.56-2.70 (m, 1H), 2.40.

Cyclopropyl (4-nitrophenyl) carbonate

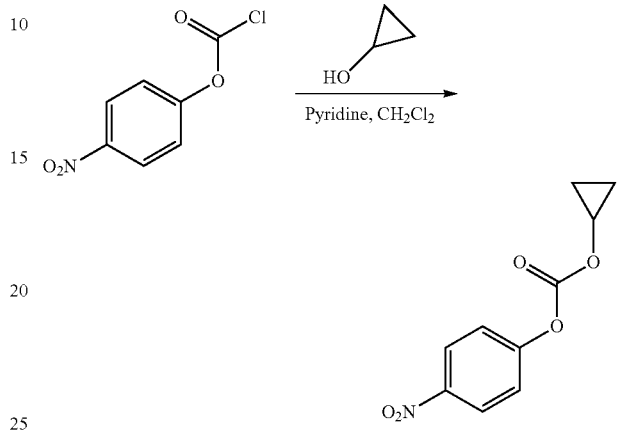

To a solution of 1.5 g (7.44 mmol, 1.0 eq.) of 4-nitrophenyl chloroformate in 25 mL of methylene chloride at 0° C. was added 0.5 g (8.61 mmol, 1.16 eq.) of cyclopropanol followed by 0.63 g (8.05 mmol, 1.08 eq) of pyridine. The resulting solution was stirred at 0° C. for 1.5 h. The mixture was diluted with 5 mL of methylene chloride and 10 mL of 0.1 M aqueous sulfuric acid. The organic phase was then washed with 10 mL of sat. NaHCO$_3$, 10 mL of water and 10 mL of brine. The organic phase was dried (Na$_2$SO$_4$), filtered and concentrated to a volume of approximately 5 mL, and 10 mL of cyclohexane was added. The resulting yellow solid was removed, and the filtrate was evaporated to provide 0.8 g (3.58 mmol, 48%) of cyclopropyl (4-nitrophenyl) carbonate. $^1$H NMR (400 MHz, CDCl3): δ 8.26-8.19 (m, 2H), 7.34-7.25 (m, 2H), 4.25-4.19 (m, 1H), 0.85-0.69 (m, 4H).

O-Cyclopropyl, N—(S)-(4-((3-chloro-4-fluorophenyl)carbamoyl)-7-fluoro-2,3-dihydro-1H-inden-1-yl)carbamate (226)

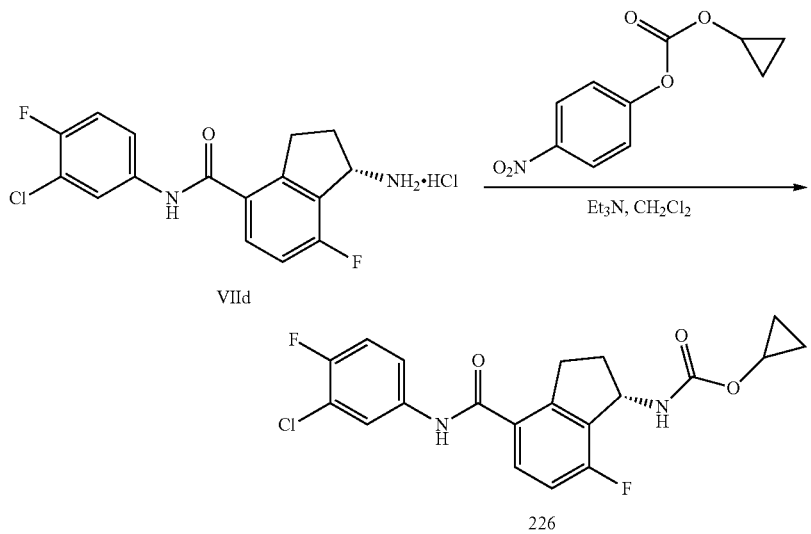

To a mixture of 0.5 g (1.55 mmol, 1.0 eq.) of (S)-1-amino-N-(3-chloro-4-fluorophenyl)-7-fluoro-2,3-dihydro-1H-indene-4-carboxamide hydrochloride (VIId) and 0.69 g (3.10 mmol, 2.0 eq.) of cyclopropyl (4-nitrophenyl) carbonate in 10 mL of methylene chloride was added 0.78 g (7.75 mmol, 5.0 eq.) of trimethylamine, and the mixture was stirred at 15° C. for 12 h. The solvent was removed in vacuo, and the residue was purified by semi-prep HPLC to provide 0.23 g (0.56 mmol, 36%) of O-cyclopropyl, N—(S)-(4-((3-chloro-4-fluorophenyl)carbamoyl)-7-fluoro-2,3-dihydro-1H-inden-1-yl)carbamate (226) LCMS: m/z found 407.1/409.1 [M+H]$^+$; $^1$H NMR (400 MHz, DMSO-d$_6$): δ 10.39 (s, 1H), 8.04-8.01 (m, 1H), 7.69-7.62 (m, 3H), 7.42-7.37 (m, 1H), 7.15-7.11 (m, 1H), 5.27-5.22 (m, 1H), 3.97-3.94 (m, 1H), 3.23-3.16 (m, 1H), 3.03-2.97 (m, 1H), 2.41-2.31 (m, 1H), 1.90-1.81 (m, 1H), 0.63-0.59 (m, 2H), 0.56-0.54 (m, 2H).

Example 4: Non-Limiting Synthesis of Selected 1-(O-Linked-Substituted Carbamate/Carbonate)-Dihydroindene-4-Carboxamides (Scheme 3)

Scheme 3.

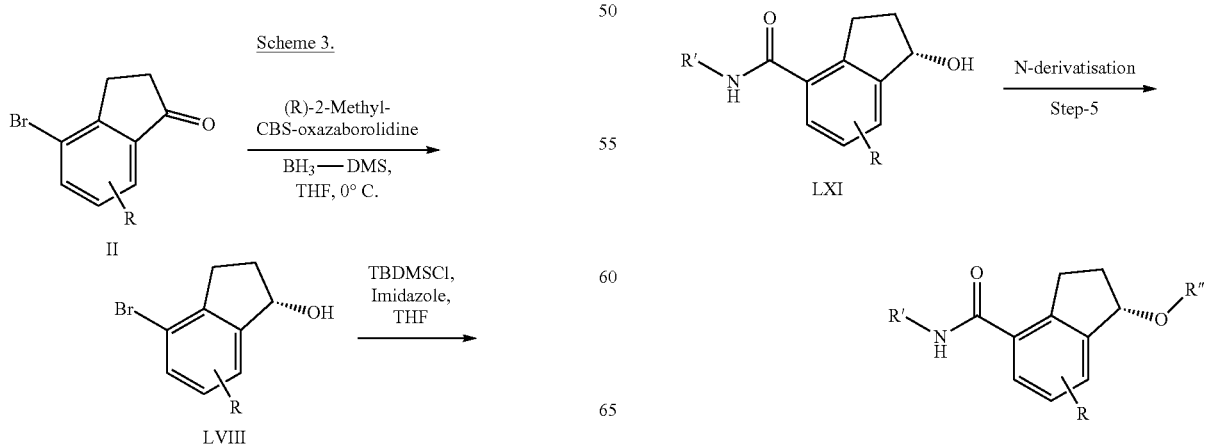

Non-Limiting Illustration of Scheme 3

(S)-4-Bromo-7-fluoro-2,3-dihydro-1H-inden-1-ol (LVIIIa)

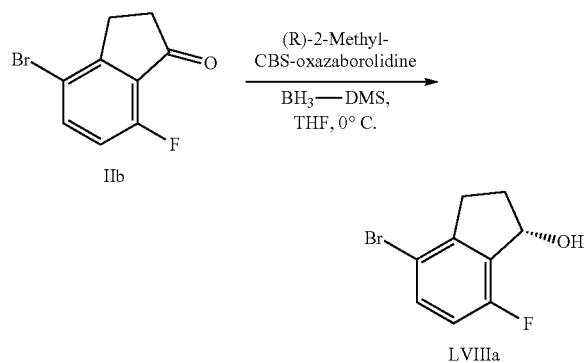

To a solution of 0.96 g (3.49 mmol, 1.0 eq.) of (R)-2-methyl-CBS-oxazaborolidine in 30 mL of anhydrous THF at 0° C. under a nitrogen atmosphere was added 10.47 mL (20.96 mmol, 6.0 eq.) of a 2.0 M solution of borane-DMS solution THF. After stirring for 15 minutes, a solution of 4.0 g (17.46 mmol, 5.0 eq.) of 4-bromo-7-fluoro-2,3-dihydro-1H-inden-1-one (IIb) in 10 mL of anhydrous THF was added. The resulting mixture was stirred for 30 min. The reaction mixture was quenched by the addition of methanol, followed by concentration under reduced pressure to provide 3.6 g of crude (S)-4-bromo-7-fluoro-2,3-dihydro-1H-inden-1-ol (LVIIIa). $^1$H NMR (500 MHz, DMSO-$d_6$) δ 7.45-7.50 (m, 1H), 6.98-7.01 (m, 1H), 5.34-5.41 (m, 1H), 5.32-5.33 (m, 1H), 2.77-3.01 (m, 1H), 2.74-2.76 (m, 1H), 2.29-2.34 (m, 1H), 1.90-1.92 (m, 1H).

(S)-(4-Bromo-7-fluoro-2,3-dihydro-1H-inden-1-yloxy)(tert-butyl)dimethylsilane (LIXa)

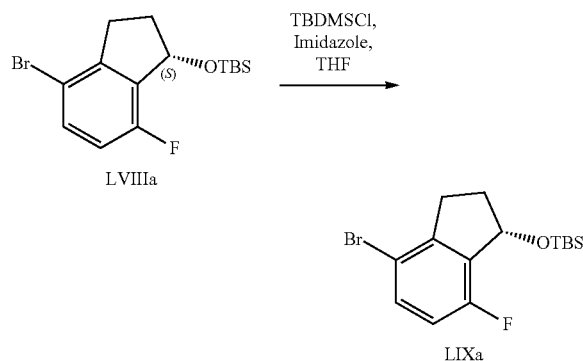

To a solution of 3.6 g of crude (S)-4-bromo-7-fluoro-2,3-dihydro-1H-inden-1-ol (LVIIIa) in 40 mL of anhydrous THF under a nitrogen atmosphere were added 1.87 g (31.17 mmol) of imidazole. The mixture was cooled to 0° C., and 2.71 g (18.7 mmol) of tert-butyldimethylsilyl chloride was added. After stirring for 6 h, the mixture was quenched by addition of water and extracted with 2×90 mL of ethyl acetate. The combined organic extracts were washed with 2×100 mL of brine, dried (Na$_2$SO$_4$), filtered and the solvent removed in vacuo to provide 4.0 g of crude (S)-(4-bromo-7-fluoro-2,3-dihydro-1H-inden-1-yloxy)(tert-butyl)dimethylsilane (LIXa). $^1$H NMR (400 MHz, DMSO-$d_6$) δ 7.49-7.52 (m, 1H), 6.99-7.03 (m, 1H), 5.53-5.55 (m, 1H), 2.95-3.02 (m, 1H), 2.72-2.80 (m, 1H), 2.36-2.44 (m, 1H), 1.90-1.94 (m, 1H), 0.89 (s, 9H), 0.20 (s, 6H).

(S)-1-(tert-Butyldimethylsilyloxy)-N-(3-chloro-4-fluorophenyl)-7-fluoro-2,3-dihydro-1H-indene-4-carboxamide (LXa)

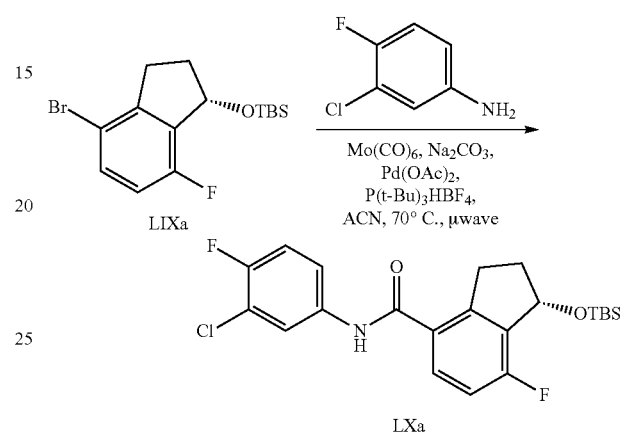

A solution of 4.6 g (13.3 mmol) of (S)-(4-bromo-7-fluoro-2,3-dihydro-1H-inden-1-yloxy)(tert-butyl)dimethylsilane (LIXa), 3.85 g (26.6 mmol) of 3-chloro-4-fluoroaniline, 2.82 g (26.6 mmol) of sodium carbonate, and 3.51 g (13.3 mmol) of Mo(CO)$_6$ (3.51 g, 13.32 mmol) in 90 mL of acetonitrile was degassed with nitrogen for 10 min, and 0.30 g (1.3 mmol) of Pd(OAc)$_2$ and 0.39 g (1.3 mmol) of P(t-Bu)$_3$HBF$_4$ were added. The reaction mixture was subjected to microwave irradiation maintaining a reaction temperature of 70° C. for 1 h. The reaction was quenched by the addition of water and extracted with 2×125 mL of ethyl acetate. The combined organic extracts were washed with 2×150 mL of brine, dried (Na$_2$SO$_4$), filtered and the solvent was removed in vacuo. The residue was purified by flash chromatography (SiO$_2$, eluting with a linear gradient of 10-50% ethyl acetate/petroleum ether) to provide 1.35 g (3.1 mmol) of (S)-1-(tert-butyldimethylsilyloxy)-N-(3-chloro-4-fluorophenyl)-7-fluoro-2,3-dihydro-1H-indene-4-carboxamide (LXa). LCMS: m/z found 438.56 [M+H]$^+$; $^1$H NMR (500 MHz, DMSO-$d_6$) δ 10.39 (s, 1H), 8.02-8.04 (m, 1H), 7.63-7.71 (m, 2H), 7.39-7.42 (m, 1H), 7.15-7.19 (m, 1H), 5.48-5.50 (m, 1H), 3.25-3.31 (m, 1H), 3.01 (m, 1H), 2.35-2.36 (m, 1H), 1.92 (m, 1H), 0.87 (s, 9H), 0.13 (s, 6H).

(S)—N-(3-Chloro-4-fluorophenyl)-7-fluoro-1-hydroxy-2,3-dihydro-1H-indene-4-carboxamide (81)

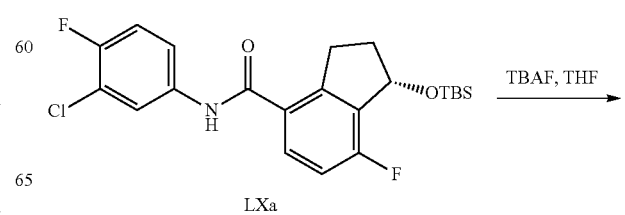

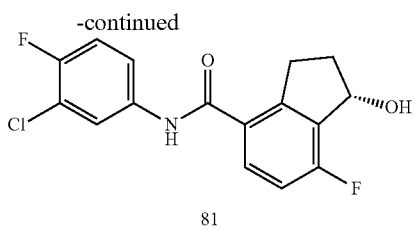

81

To a solution of 1.0 g (2.28 mmol, 1.0 eq.) of (S)-1-(tert-butyldimethylsilyloxy)-N-(3-chloro-4-fluorophenyl)-7-fluoro-2,3-dihydro-1H-indene-4-carboxamide (LXa) in 20 mL of THF was added 2.74 mL (2.74 mmol, 1.2 eq.) of a 1.0 M solution of tetra-n-butylammonium fluoride (TBAF) in THF. The mixture was stirred at room temperature for 15 h and quenched by addition of saturated aqueous solution of ammonium chloride. The mixture was extracted with 2×50 mL of ethyl acetate, and the combined organic extracts were washed with 2×100 mL of brine, dried (Na₂SO₄), filtered and the solvent was removed in vacuo. The residue was purified by flash chromatography (SiO₂, eluting with a linear gradient of 0-50% ethyl acetate/petroleum ether) to provide 0.6 g (1.85 mmol, 81%) of (S)—N-(3-chloro-4-fluorophenyl)-7-fluoro-1-hydroxy-2,3-dihydro-1H-indene-4-carboxamide (81). LCMS: m/z found 324.1/326.1 [M+H]⁺, RT=1.88 min (Method H). ¹H NMR (500 MHz, DMSO-d₆) δ 10.37 (s, 1H), 8.03-8.05 (m, 1H), 7.6-7.70 (m, 2H), 7.39-7.42 (m, 1H), 7.13-7.17 (m, 1H), 5.33-5.34 (m, 1H), 5.27-5.29 (m, 1H), 3.25-3.28 (m, 1H), 3.16-3.17 (m, 1H) 2.25-2.29 (m, 1H), 1.92-1.94 (m, 1H).

(S)-4-(3-Chloro-4-fluorophenylcarbamoyl)-7-fluoro-2,3-dihydro-1H-inden-1-yl Methyl Carbonate (123)

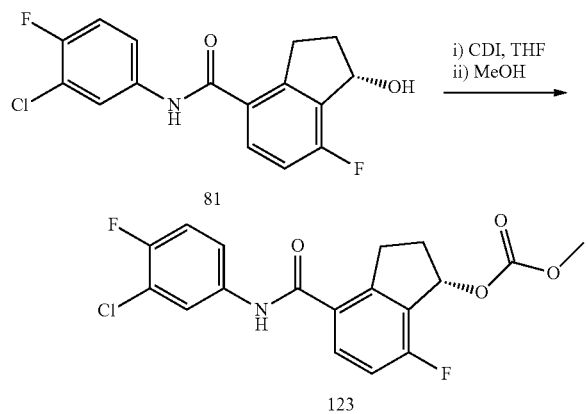

To a solution of 0.20 g (0.62 mmol, 1.0 eq.) of (S)—N-(3-chloro-4-fluorophenyl)-7-fluoro-1-hydroxy-2,3-dihydro-1H-indene-4-carboxamide (0.2 g, 0.62 mmol) in 2 mL of THF was added 0.20 g (1.24 mmol, 2.0 eq.) of 1,1'-carbonyldiimidazole. After stirring at room temperature for 30 min, 40 mg (1.24 mmol, 2.0 eq.) of methanol was added and the mixture was stirred for a further 15 h. The solvent was removed in vacuo, and the residue was purified by semi-preparative to provide 0.08 g of (S)-4-(3-chloro-4-fluorophenylcarbamoyl)-7-fluoro-2,3-dihydro-1H-inden-1-yl methyl carbonate (123) (80 mg). LCMS: m/z found 380.2/382.2 [M+H]⁺, RT=2.38 minutes (Method H); ¹H NMR (500 MHz, DMSO-d₆) δ 10.44 (s, 1H), 8.03-8.05 (m, 1H), 7.81-7.84 (m, 1H), 7.63-7.66 (m, 1H), 7.39-7.43 (m, 1H), 7.25-7.28 (m, 1H), 6.25-6.27 (m, 1H), 3.74 (s, 3H), 3.28-3.31 (m, 1H), 3.14-3.16 (m, 1H), 2.49-2.52 (m, 1H), 2.15 (m, 1H, m).

(S)-4-((3-Chloro-4-fluorophenyl)carbamoyl)-7-fluoro-2,3-dihydro-1H-inden-1-yl (pyridin-2-ylmethyl) carbonate (90)

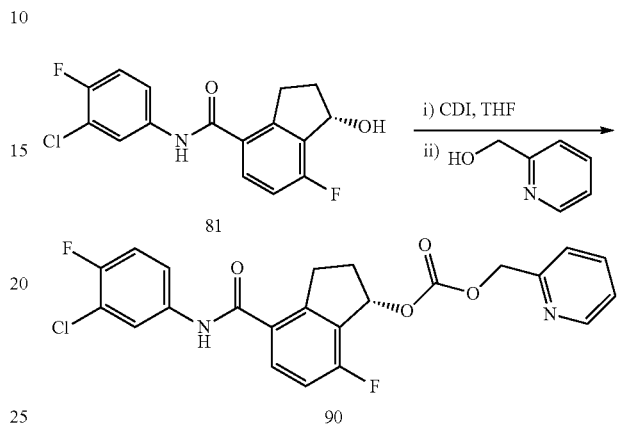

(S)-4-((3-chloro-4-fluorophenyl)carbamoyl)-7-fluoro-2,3-dihydro-1H-inden-1-yl (pyridin-2-ylmethyl) carbonate (90) was synthesized in a similar manner as outlined above from (S)—N-(3-chloro-4-fluorophenyl)-7-fluoro-1-hydroxy-2,3-dihydro-1H-indene-4-carboxamide (81) and pyridin-2-ylmethanol. LCMS: m/z found 459.1/461.1 [M+H]⁺, RT=2.34 min (Method H); ¹H NMR (400 MHz, DMSO-d₆) δ 10.45 (s, 1H), 8.57 (m, 1H), 8.04 (m, 1H), 7.84 (m, 2H), 7.66 (m, 1H), 7.46-7.32 (m, 3H), 7.28 (t, 1H), 6.31 (m, 1H), 5.25 (s, 2H), 3.35 (m, 1H), 3.15 (m, 1H), 2.61-2.50 (m, 1H), 2.19 (m, 1H).

N—(S)-4-((3-Chloro-4-fluorophenyl)carbamoyl)-7-fluoro-2,3-dihydro-1H-inden-1-yl, O-(pyridin-2-ylmethyl) carbamate (74)

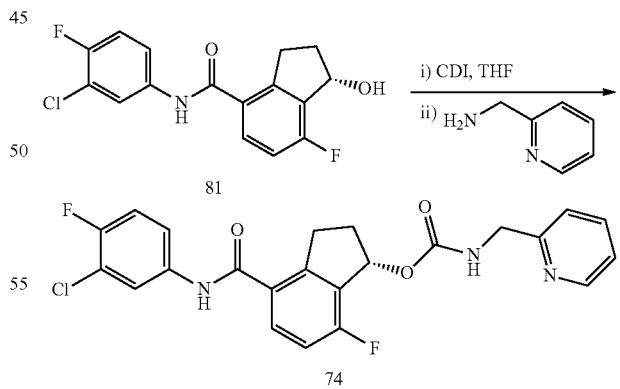

N—(S)-4-((3-Chloro-4-fluorophenyl)carbamoyl)-7-fluoro-2,3-dihydro-1H-inden-1-yl, O-(pyridin-2-ylmethyl) carbamate (74) was synthesized in a similar manner as outlined above from (S)—N-(3-chloro-4-fluorophenyl)-7-fluoro-1-hydroxy-2,3-dihydro-1H-indene-4-carboxamide (81) and pyridin-2-ylmethanamine. LCMS: m/z found 458.1/460.1 [M+H]⁺, RT=2.01 min (Method H); ¹H NMR (500 MHz, DMSO-d$_6$) δ 10.44 (s, 1H), 8.50 (m, 1H), 8.05 (m, 1H), 7.84-7.74 (m, 3H), 7.66 (m, 1H), 7.42 (t, 1H), 7.32-7.22 (m, 3H), 6.29 (m, 1H), 4.31 (m, 2H), 3.29 (m, 1H), 3.13 (m, 1H), 2.44 (m, 1H), 2.09 (m, 1H).

O—(S)-4-((3-Chloro-4-fluorophenyl)carbamoyl)-7-fluoro-2,3-dihydro-1H-inden-1-yl, N-methyl Carbamate (89)

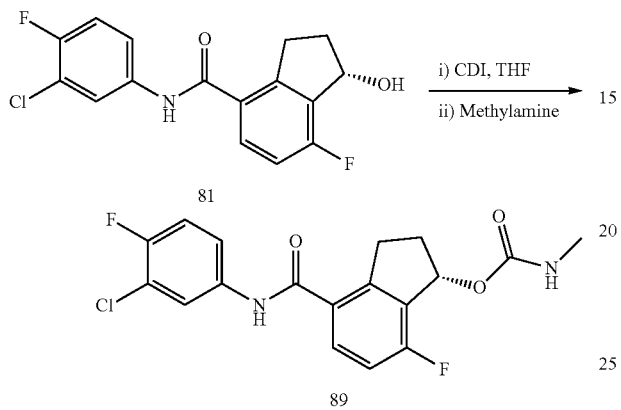

O—(S)-4-((3-Chloro-4-fluorophenyl)carbamoyl)-7-fluoro-2,3-dihydro-1H-inden-1-yl, N-methyl carbamate (89) was synthesized in a similar manner as outlined above from (S)—N-(3-chloro-4-fluorophenyl)-7-fluoro-1-hydroxy-2,3-dihydro-1H-indene-4-carboxamide (81) and methylamine. LCMS: m/z found 379.1/381.1 [M−H]$^+$, RT=2.23 min (Method H); $^1$H NMR (400 MHz, DMSO-d$_6$) δ 10.42 (s, 1H), 8.04 (m, 1H), 7.79 (m, 1H), 7.70-7.60 (m, 1H), 7.41 (t, 1H), 7.23 (t, 1H), 7.04-6.97 (m, 1H), 6.23 (m, 1H), 3.27-3.05 (m, 2H), 2.59 (d, 3H), 2.42 (m, 1H), 2.08-1.98 (m, 1H).

Example 5: Non-Limiting Synthesis of Selected 1-(Substituted Urea)-Dihydroindene-4-Carboxamides (S)—N-(3,4-Difluorophenyl)-1-(3-methylureido)-2,3-dihydro-1H-indene-4-carboxamide (2)

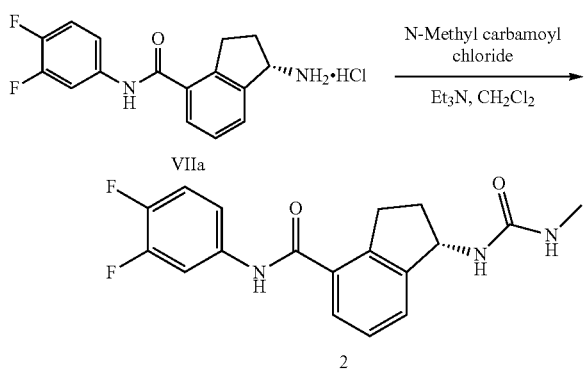

To a solution of 100 mg (0.30 mmol, 1.0 eq.) of (S)-1-amino-N-(3,4-difluorophenyl)-2,3-dihydro-1H-indene-4-carboxamide hydrochloride (VIIa) in 5 mL of methylene chloride at 0° C. was added 0.18 mL (0.13 mmol, 3.0 eq.) of triethylamine followed by 42 mg (0.45 mmol, 1.5 eq.) of N-methyl carbamoyl chloride. The mixture was allowed to warm to room temperature and stirred for 1 h. The mixture was then diluted with 30 mL of ethyl acetate and washed with 30 mL of water, followed by 30 mL of brine. The organic phase was dried (Na$_2$SO$_4$), and the solvent was removed in vacuo. The residue was purified by flash chromatography (SiO$_2$, eluting with a linear gradient of 0-3% methanol/methylene chloride) to provide 64 mg (0.18 mmol, 62%) of (S)—N-(3,4-difluorophenyl)-1-(3-methylureido)-2,3-dihydro-1H-indene-4-carboxamide (2). LCMS: m/z found 347.2 [M+H]$^+$, RT=1.72 min (Method D); HPLC: RT=6.26 min (Method F); $^1$H NMR (400 MHz, DMSO-d$_6$): δ 10.47 (s, 1H), 7.88-7.94 (m, 1H), 7.55 (d, 1H), 7.32-7.43 (m, 4H), 6.29 (d, 1H), 5.72 (m, 1H), 5.13 (q, 1H), 3.0-3.16 (m, 1H), 2.91-2.98 (m, 1H), 2.60 (d, 3H), 2.35-2.41 (m, 1H), 1.65-1.74 (m, 1H).

(S)—N-(3-Chloro-4-fluorophenyl)-7-fluoro-1-(3-methylureido)-2,3-dihydro-1H-indene-4-carboxamide (20)

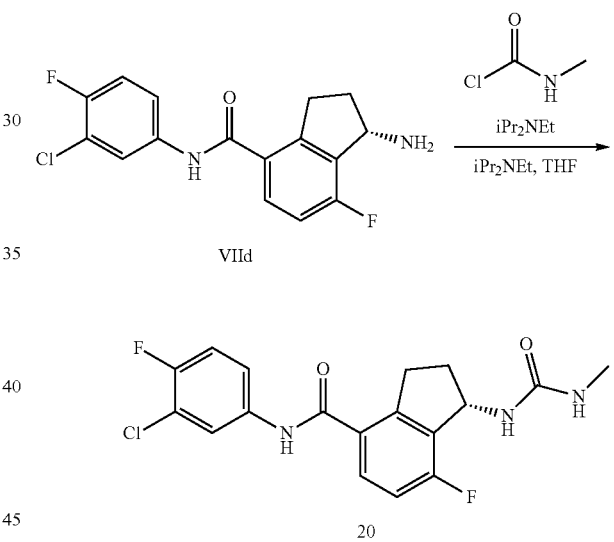

To a solution of 125 mg (0.39 mmol, 1.0 eq.) of (S)-1-amino-N-(3-chloro-4-fluorophenyl)-7-fluoro-2,3-dihydro-1H-indene-4-carboxamide (VIId) in 1 mL of THF were added 203 μL (1.16 mmol, 3.0 eq.) of N,N-diisopropylethyl amine and 72 mg (0.77 mmol, 2.0 eq.) of N-methylcarbamoyl chloride. The mixture was stirred at room temperature for 16 h. The resulting precipitate was collected by filtration, and the solids washed with 2×2 mL of methanol. The solids were then stirred in 5 mL of water for 10 min. The suspension was filtered, washed with 2×2 mL of water and dried under high vacuum to provide 62 mg (0.16 mmol, 41%) of (S)—N-(3-chloro-4-fluorophenyl)-7-fluoro-1-(3-methylureido)-2,3-dihydro-1H-indene-4-carboxamide (20). LCMS: m/z found 380.0, [M+H]$^+$; HPLC: RT=2.60 min (Method G); $^1$H NMR (DMSO, 400 MHz): δ 10.37 (brs, 1H), 8.04-8.01 (m, 1H), 7.68-7.66 (m, 2H), 7.39 (t, 1H), 7.13 (m, 1H), 6.34 (d, 1H), 5.57-5.55 (m, 1H), 5.34-5.29 (m, 1H), 3.19-3.15 (m, 1H), 3.00-2.99 (m, 1H), 2.55 (s, 3H), 2.33-2.30 (m, 1H), 1.84-1.74 (m, 1H).

(S)-7-Fluoro-N-(4-fluoro-3-methylphenyl)-1-(3-methylureido)-2,3-dihydro-1H-indene-4-carboxamide (12)

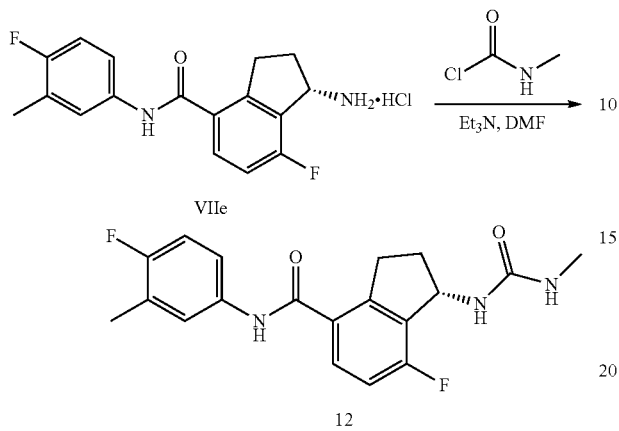

(S)-7-Fluoro-N-(4-fluoro-3-methylphenyl)-1-(3-methylureido)-2,3-dihydro-1H-indene-4-carboxamide (12) was synthesized in a similar manner as outlined above from (S)-1-amino-7-fluoro-N-(4-fluoro-3-methylphenyl)-2,3-dihydro-1H-indene-4-carboxamide hydrochloride (VIIe) and N-methyl carbamoyl chloride. LCMS: m/z found 360.3 [M+H]$^+$; HPLC: RT=2.44 min (Method G); $^1$H NMR (DMSO-d$_6$, 400 MHz): δ 10.15 (s, 1H), 7.61-7.68 (m, 2H), 7.50-7.57 (m, 1H), 7.07-7.14 (m, 2H), 6.36 (d, 1H), 5.55-5.63 (m, 1H), 5.31 (q, 1H), 3.17-3.26 (m, 1H), 2.92-3.03 (m, 1H), 2.55 (d, 3H), 2.23-2.38 (m, 1H), 2.22 (s, 3H), 1.77-1.90 (m, 1H).

(S)—N-(3-Chloro-4-fluorophenyl)-1-(3-cyclopropylureido)-7-fluoro-2,3-dihydro-1H-indene-4-carboxamide (209)

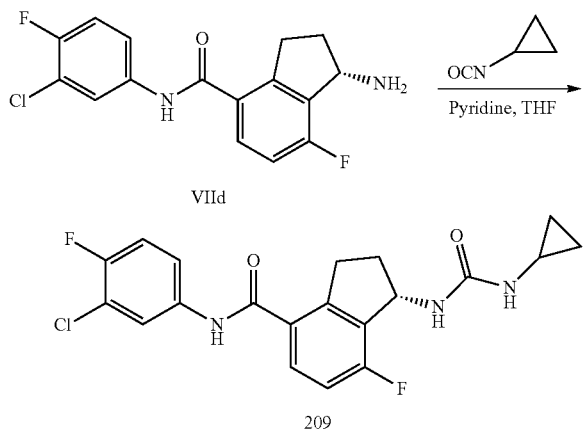

To a solution of 0.20 g (0.62 mmol, 1.0 eq) of (1S)-1-amino-N-(3-chloro-4-fluoro-phenyl)-7-fluoro-indane-4-carboxamide free base (VIId) in 5 mL of anhydrous THF was added 0.15 g (1.86 mmol, 3.0 eq.) of pyridine followed by 0.15 g (1.86 mmol, 3.0 eq.) of isocyanatocyclopropane, and the mixture was stirred at 15° C. for 12 hr. The solvent was removed in vacuo, and the residue was purified by semi-prep-HPLC to provide 100 mg (0.25 mmol, 40%) of (1S)—N-(3-chloro-4-fluoro-phenyl)-1-(cyclopropylcarbamoylamino)-7-fluoro-indane-4-carboxamide (209). LCMS: m/z found 406.1/408.1 [M+H]$^+$; $^1$H NMR (400 MHz, DMSO-d$_6$): δ 10.37 (s, 1H), 8.02-8.05 (m, 1H), 7.63-7.69 (m, 2H), 7.37-7.42 (m, 1H), 7.12-7.16 (m, 1H), 6.25-6.28 (d, 1H), 6.00 (s, 1H), 5.33-5.39 (m, 1H), 3.18-3.24 (m, 1H), 2.97-3.01 (m, 1H), 2.33-2.49 (m, 2H), 1.82-1.90 (m, 1H), 0.51-0.59 (m, 2H), 0.29-0.35 (m, 2H).

(S)—N-(3-chloro-4-fluorophenyl)-7-fluoro-1-(3-(pyridin-2-ylmethyl)ureido)-2,3-dihydro-1H-indene-4-carboxamide Hydrochloride (149.HCl)

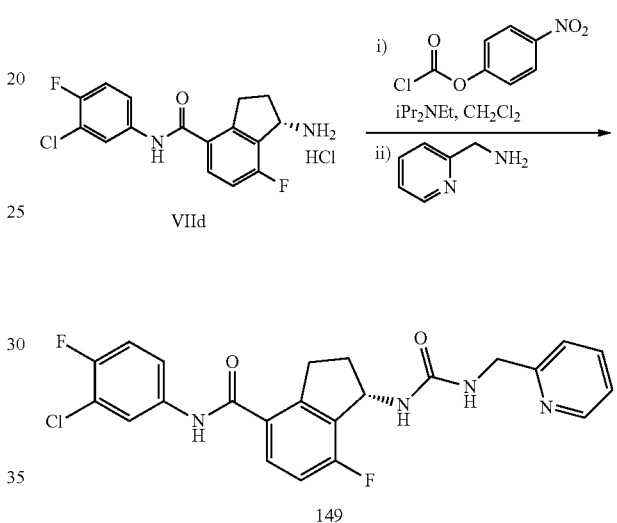

A solution of 70 mg (0.19 mmol, 1.0 eq.) of (1S)-1-amino-N-(3-chloro-4-fluorophenyl)-7-fluoro-2,3-dihydro-1H-indene-4-carboxamide hydrochloride (VIId) in 1.5 mL of methylene chloride containing 68 μL (0.39 mmol, 2.0 eq.) of N,N-diisopropylethylamine was added dropwise to a solution of 51 mg (0.25 mmol, 1.3 eq.) of 4-nitrophenyl chloroformate in 1.5 mL of methylene chloride at 0° C. over a period of approximately 5 minutes. The mixture was stirred at 0° C. for 30 min, and 70 μL (0.68 mmol, 3.6 eq.) of 2-pyridinemethylamine was added. The mixture was allowed to warm to room temperature and stirred for 16 h. The volatiles were then removed in vacuo, and the residue was absorbed onto CELITE® and purified by flash chromatography (SiO$_2$, eluting with a linear gradient of 1.5-10% methanol/methylene chloride) to provide 58 mg (0.13 mmol, 66%) of (S)—N-(3-chloro-4-fluorophenyl)-7-fluoro-1-(3-(pyridin-2-ylmethyl)ureido)-2,3-dihydro-1H-indene-4-carboxamide (149). The purified sample was subsequently converted to the hydrochloride salt using a 1.25 M solution of HCl in methanol. LCMS: m/z found 457.1/459.1 [M+H]$^+$, RT=3.22 min (Method A); $^1$H NMR (300 MHz, Methanol-d$_4$) δ 8.74 (m, 1H), 8.61 (dd, 1H), 8.06-7.91 (m, 3H), 7.66 (m, 1H), 7.55 (m, 1H), 7.22 (t, 1H), 7.05 (dd, 1H), 5.45 (m, 1H), 4.69 (s, 2H), 3.36 (m, 1H), 3.10 (m, 1H), 2.49 (m, 1H), 2.02 (m, 1H).

(S)—N-(3-Chloro-4-fluorophenyl)-7-fluoro-1-(3-(pyridin-2-ylmethyl)ureido)-2,3-dihydro-1H-indene-4-carboxamide (194)

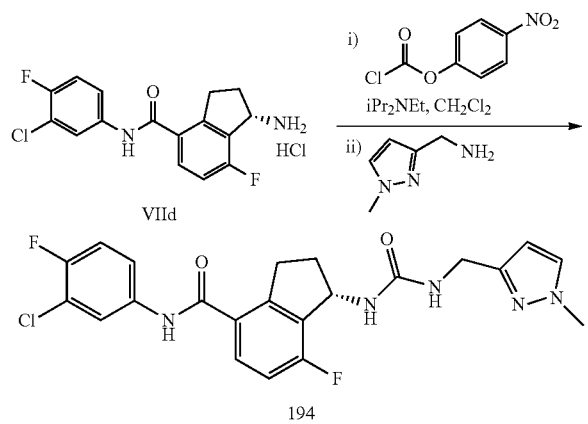

(S)—N-(3-Chloro-4-fluorophenyl)-7-fluoro-1-(3-(pyridin-2-ylmethyl)ureido)-2,3-dihydro-1H-indene-4-carboxamide (194) was synthesized in a similar manner as outlined above from (S)-1-amino-N-(3-chloro-4-fluorophenyl)-7-fluoro-2,3-dihydro-1H-indene-4-carboxamide hydrochloride (VIId), 4-nitrophenyl chloroformate and (1-methyl-1H-pyrazol-3-yl)methylamine. LCMS: m/z found 460.2/462.2 [M+H]$^+$, RT=3.81 min (Method A). $^1$H NMR (300 MHz, DMSO-d$_6$): δ 10.40 (s, 1H), 8.04 (m, 1H), 7.63-7.71 (m, 2H), 7.57 (m, 1H), 7.41 (dd, 1H), 7.16 (dd, 1H), 6.40 (m, 1H), 6.07 (m, 1H), 6.00 (m, 1H), 5.35 (m, 1H), 4.15 (d, 2H), 3.77 (s, 3H), 3.19 (m, 1H), 3.02 (m, 1H), 2.36 (m, 1H), 1.84 (m, 1H).

(S)—N-(3-Chloro-4-fluorophenyl)-7-fluoro-1-(3-(pyridin-3-yl)ureido)-2,3-dihydro-1H-indene-4-carboxamide (144)

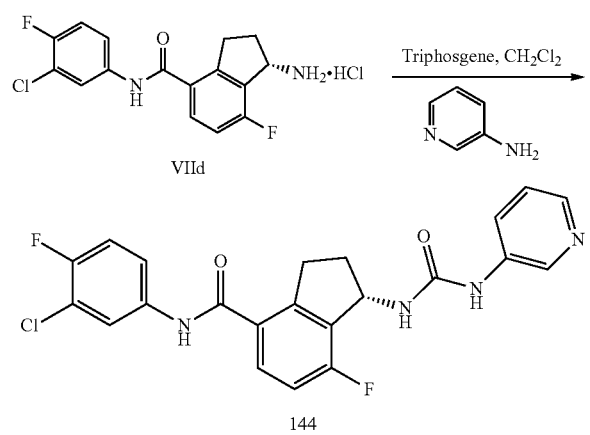

To a solution of 18 mg (0.20 mmol, 1.2 eq.) of pyridin-3-amine in 5 mL of anhydrous methylene chloride (5 mL) was added 21 mg (0.10 mmol, 0.6 eq.) of triphosgene followed 68 L (0.16 mmol, 3.0 eq) of triethylamine. The resulting mixture was stirred at room temperature for 3 h, and the solvent was removed in vacuo. The residue was redissolved in 1 mL of DMF and 60 mg (0.16 mmol, 1.0 eq.) of (S)-1-amino-N-(3-chloro-4-fluorophenyl)-7-fluoro-2,3-dihydro-1H-indene-4-carboxamide hydrochloride (VIId) was added, and the solution stirred at room temperature for 16 h. The mixture was diluted with 20 mL of water and extracted with 2×75 mL of ethyl acetate. The combined organic extracts were washed with 15 mL of water and 15 mL of brine, dried (Na$_2$SO$_4$), filtered and the solvent was removed in vacuo. The residue was purified by flash chromatography (SiO$_2$, eluting with a linear gradient of 0-5% methanol/methylene chloride) to provide 30 mg (41%) of (S)—N-(3-chloro-4-fluorophenyl)-7-fluoro-1-(3-pyridin-3-ylureido)-2,3-dihydro-1H-indene-4-carboxamide (144). LCMS: m/z found 443.2/445.2 [M+H]$^+$, RT=1.92 min (Method H); HPLC: RT=10.18 min (Method K); $^1$H NMR (400 MHz, DMSO-d$_6$) δ 10.42 (s, 1H), 8.54 (d, 1H), 8.49 (s, 1H), 8.12 (dd, 1H), 8.06 (dd, 1H), 7.91 (m, 1H), 7.72 (m, 1H), 7.64-7.74 (m, 1H), 7.42 (dd, 1H), 7.27 (dd, 1H), 7.19 (dd, 1H), 6.82 (d, 1H), 5.43 (q, 1H), 3.23-3.27 (m, 1H), 3.02-3.10 (m, 1H), 2.40-2.43 (m, 1H), 1.0-1.97, (m, 1H).

(S)—N-(3-Chloro-4-fluorophenyl)-7-fluoro-1-(3-(pyridin-4-yl)ureido)-2,3-dihydro-1H-indene-4-carboxamide (145)

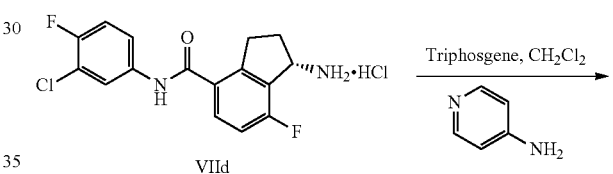

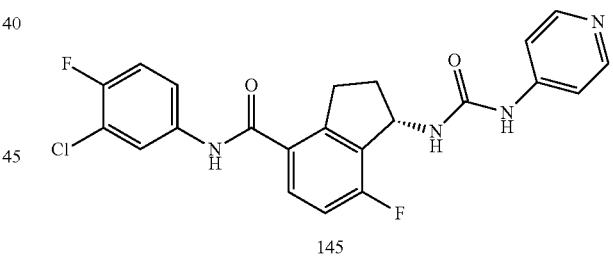

(S)—N-(3-Chloro-4-fluorophenyl)-7-fluoro-1-(3-(pyridin-4-yl)ureido)-2,3-dihydro-1H-indene 4-carboxamide (145) was synthesized in a similar manner as outlined above from (S)-1-amino-N-(3-chloro-4-fluorophenyl)-7-fluoro-2,3-dihydro-1H-indene-4-carboxamide hydrochloride (VIId), triphosgene and pyridin-4-amine. LCMS: m/z found 443.2/445.2 [M+H]$^+$, RT=1.91 min (Method H); HPLC: RT=9.20 min (Method K); $^1$H NMR (400 MHz, DMSO-d$_6$) δ 10.41 (s, 1H) 8.81 (s, 1H), 8.29 (d, 2H), 8.05 (dd, 1H), 7.73 (dd, 1H), 7.64-7.70 (m, 1H), 7.37-7.43 (m, 3H), 7.19 (dd, 1H), 6.96 (d, 1H), 5.44 (q, 1H), 3.23-3.27 (m, 1H), 3.02-3.10 (m, 1H), 2.40-2.43 (m, 1H), 1.90-1.97, (m, 1H).

Example 6: Non-Limiting Synthesis of Selected 1-(Substituted Sulfonamido)-Dihydroindene-4-Carboxamides Sulfonamide Formation

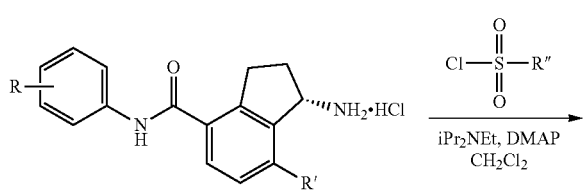

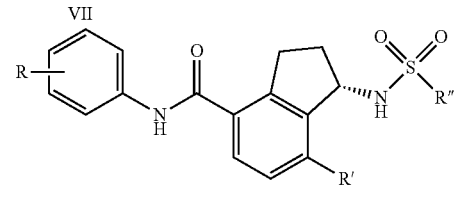

To a solution of VII (1.0 eq.) and N,N-diisopropylethyl amine (2.5 eq.) in methylene chloride at 0° C. was added catalytic 4-dimethyl aminopyridine followed by the sulfonyl chloride (1.5 eq.), and the mixture was stirred at room temperature for 16 h. The reaction was quenched with water and extracted with ethyl acetate. The combined organic extracts were washed with brine, dried (Na$_2$SO$_4$), filtered and concentrated in vacuo. The residue was purified by flash chromatography (SiO$_2$)

(S)—N-(3-chloro-4-fluorophenyl)-7-fluoro-1-(methylsulfonamido)-2,3-dihydro-1H-indene-4-carboxamide (117)

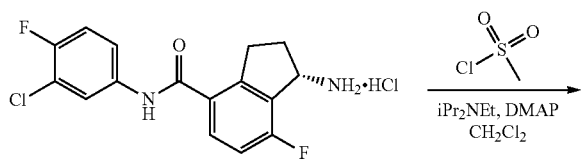

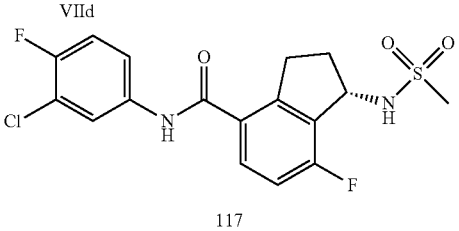

To a solution of 50 mg (0.13 mmol, 1.0 eq.) of (S)-1-amino-N-(3-chloro-4-fluorophenyl)-7-fluoro-2,3-dihydro-1H-indene-4-carboxamide hydrochloride (VIId) and 60 μL (0.35 mmol, 2.5 eq.) of N,N-diisopropylethyl amine in 2 mL of methylene chloride at 0° C. was added 4 mg of 4-dimethyl aminopyridine followed by 16 μL (0.21 mmol, 1.5 eq.) of methanesulfonyl chloride (1.5 eq.), and the mixture was stirred at room temperature for 16 h. The reaction was quenched with 2 mL of water and extracted with 2×10 mL of ethyl acetate. The combined organic extracts were washed with brine, dried (Na$_2$SO$_4$), filtered and concentrated in vacuo. The residue was purified by by flash chromatography (SiO$_2$, eluting with 2% methanol/methylene chloride) to provide 25 mg (45%) of (S)—N-(3-chloro-4-fluorophenyl)-7-fluoro-1-(methylsulfonamido)-2,3-dihydro-1H-indene-4-carboxamide (117). LCMS: m/z found 401.1/403.1 [M+H]$^+$; HPLC (Method M) RT=10.26 min; $^1$H NMR (500 MHz, DMSO-d$_6$) δ ppm 10.40 (s, 1H), 8.04 (dd, 1H), 7.75 (dd, 1H), 7.63-7.68 (m, 2H), 7.41 (dd, 1H), 7.20 (dd, 1H), 5.07 (m, 1H), 3.21-3.29 (m, 1H), 3.01-3.09 (m, 1H), 2.99 (s, 3H), 2.39-2.49 (m, 1H), 1.86-2.01 (m, 1H).

(S)—N-(3-Chloro-4-fluorophenyl)-1-(ethylsulfonamido)-7-fluoro-2,3-dihydro-1H-indene-4-carboxamide (232)

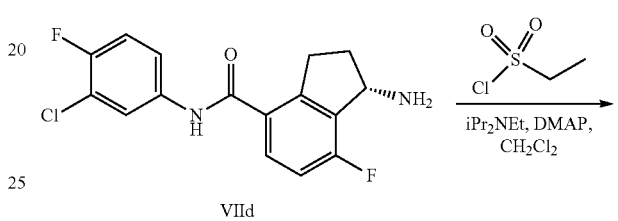

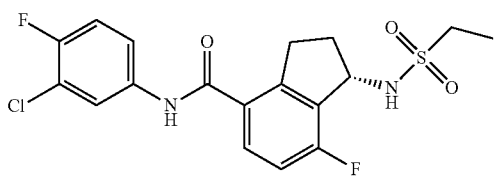

(S)—N-(3-Chloro-4-fluorophenyl)-1-(ethyl sulfonamido)-7-fluoro-2,3-dihydro-1H-indene-4-carboxamide (232) was prepared in a similar manner as described above from (S)-1-amino-N-(3-chloro-4-fluorophenyl)-7-fluoro-2,3-dihydro-1H-indene-4-carboxamide hydrochloride (VIId) and ethanesulfonyl chloride. LCMS: m/z found 415.2/417.1 [M+H]$^+$; HPLC: RT=4.27 min (Method A); $^1$H NMR (400 MHz, DMSO-d$_6$) δ 10.43 (s, 1H), 8.05 (d, 1H), 7.74 (d, 1H), 7.66 (d, 2H), 7.42 (t, 1H), 7.21 (t, 1H), 5.07-4.99 (m, 1H), 3.32-3.21 (m, 1H), 3.16-2.97 (m, 3H), 2.46-2.37 (m, 1H), 2.06-1.97 (m, 1H), 1.29-1.18 (m, 3H).

(S)—N-(3-Chloro-4-fluorophenyl)-7-fluoro-1-(propylsulfonamido)-2,3-dihydro-1H-indene-4-carboxamide (233)

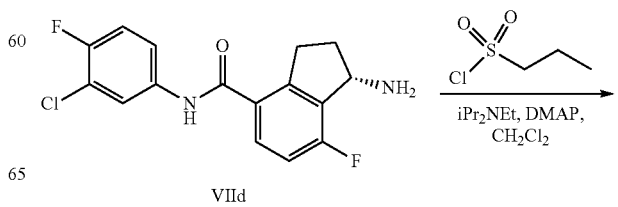

227

-continued

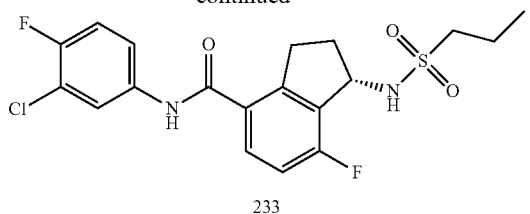

233

(S)—N-(3-Chloro-4-fluorophenyl)-7-fluoro-1-(propylsulfonamido)-2,3-dihydro-1H-indene-4-carboxamide (233) was prepared in a similar manner as described above from (S)-1-amino-N-(3-chloro-4-fluorophenyl)-7-fluoro-2,3-dihydro-1H-indene-4-carboxamide hydrochloride (VIId) and propane-1-sulfonyl chloride. LCMS: m/z found 429.1/431.2 [M+H]+; HPLC: RT=4.64 min (Method A); $^1$H NMR (400 MHz, DMSO-$d_6$) δ 10.42 (s, 1H), 8.04 (dd, 1H), 7.77-7.68 (m, 1H), 7.69-7.60 (m, 2H), 7.40 (t, 1H), 7.19 (t, 1H), 5.08-4.97 (m, 1H), 3.33-3.20 (m, 2H), 3.13-2.95 (m, 2H), 2.54-2.34 (m, 1H), 2.06-1.98 (m, 1H), 1.70 (h, 2H), 0.99 (t, 3H).

(S)—N-(3-Chloro-4-fluorophenyl)-1-(cyclopropane-sulfonamido)-7-fluoro-2,3-dihydro-1H-indene-4-carboxamide (128)

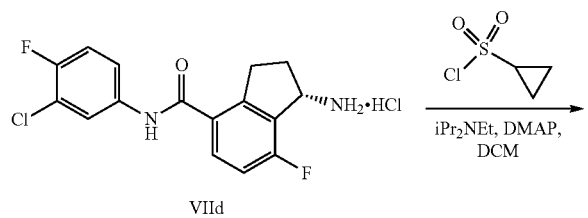

(S)—N-(3-Chloro-4-fluorophenyl)-1-(cyclopropane-sulfonamido)-7-fluoro-2,3-dihydro-1H-indene-4-carboxamide (128) was prepared in a similar manner as described above from (S)-1-amino-N-(3-chloro-4-fluorophenyl)-7-fluoro-2,3-dihydro-1H-indene-4-carboxamide hydrochloride (VIId) and cyclopropanesulfonyl chloride. LCMS: m/z found 427.1/429.1 [M+H]+; HPLC: RT=4.48 min (Method A); $^1$H NMR (300 MHz, DMSO-$d_6$) δ 10.42 (s, 1H), 8.05 (dd, 1H), 7.80-7.68 (m, 1H), 7.70-7.60 (m, 2H), 7.41 (dd, 1H), 7.20 (dd, 1H), 5.10-5.02 (m, 1H), 3.26 (t, 1H), 3.10-3.00 (m, 1H), 2.65-2.52 (m, 1H), 2.48-2.39 (m, 1H), 2.11 (m, 1H), 0.98 (m, 4H).

228

(S)—N-(3-chloro-4-fluorophenyl)-1-(cyclopropane-sulfonamido)-2,3-dihydro-1H-indene-4-carboxamide (216)

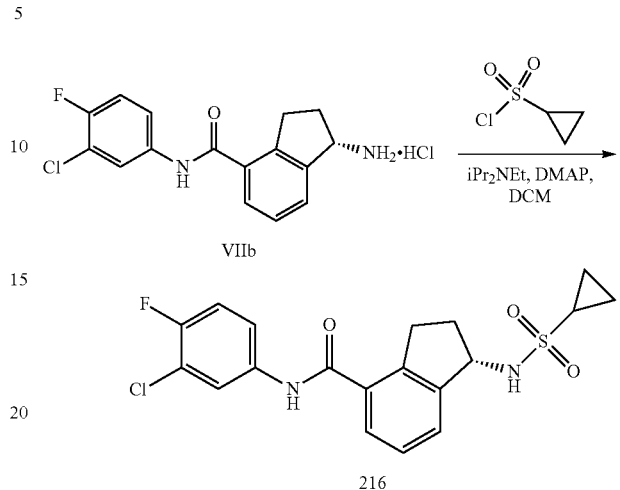

(S)—N-(3-chloro-4-fluorophenyl)-1-(cyclopropanesulfonamido)-2,3-dihydro-1H-indene-4-carboxamide (216) was prepared in a similar manner as described above from (S)-1-amino-N-(3-chloro-4-fluorophenyl)-2,3-dihydro-1H-indene-4-carboxamide hydrochloride (VIIb) and cyclopropanesulfonyl chloride. LCMS: m/z found 409.0/411.0 [M+H]+, 431.0/433.0 [M+Na]+; HPLC: RT=3.13 min (Method G); $^1$H NMR (300 MHz, DMSO-$d_6$) δ 10.40 (s, 1H), 8.04 (dd, 1H), 7.60-7.75 (m, 3H), 7.52 (d, 1H), 7.35-7.42 (m, 2H), 4.82 (q, 1H), 3.08-3.35 (m, 1H), 2.85-3.00 (m, 1H), 2.60-2.70 (m, 1H), 2.55 (m, 1H), 1.85-1.97 (m, 1H), 0.85-1.05 (m, 4H).

(S)—N-(3-Chloro-4-fluorophenyl)-1-((cyclopropyl-methyl)sulfonamido)-7-fluoro-2,3-dihydro-1H-indene-4-carboxamide (221)

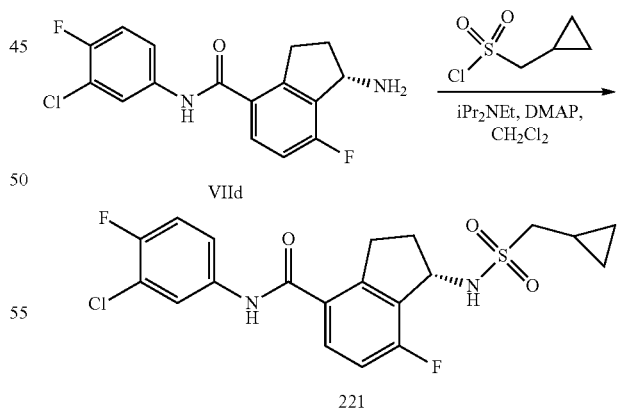

(S)—N-(3-Chloro-4-fluorophenyl)-1-((cyclopropylm-ethyl)sulfonamido)-7-fluoro-2,3-dihydro-1H-indene-4-carboxamide (221) was prepared in a similar manner as described above from (S)-1-amino-N-(3-chloro-4-fluorophenyl)-7-fluoro-2,3-dihydro-1H-indene-4-carboxamide hydrochloride (VIId) and cyclopropylmethanesulfonyl chloride. LCMS: m/z found 441.1/443.2 [M+H]+; HPLC:

RT=4.67 min (Method A); 1H NMR (400 MHz, DMSO-d$_6$) δ 10.43 (s, 1H), 8.05 (dd, 1H), 7.77-7.61 (m, 3H), 7.41 (t, 1H), 7.19 (t, 1H), 5.11-5.01 (m, 1H), 3.33-3.20 (m, 1H), 3.08-2.96 (m, 3H), 2.44-2.36 (m, 1H), 2.07-1.96 (m, 1H), 1.09-1.02 (m, 1H), 0.56 (d, 2H), 0.35 (d, 2H).

(S)—N-(3-Chloro-4-fluorophenyl)-7-fluoro-1-((2-methylpropyl)sulfonamido)-2,3-dihydro-1H-indene-4-carboxamide (234)

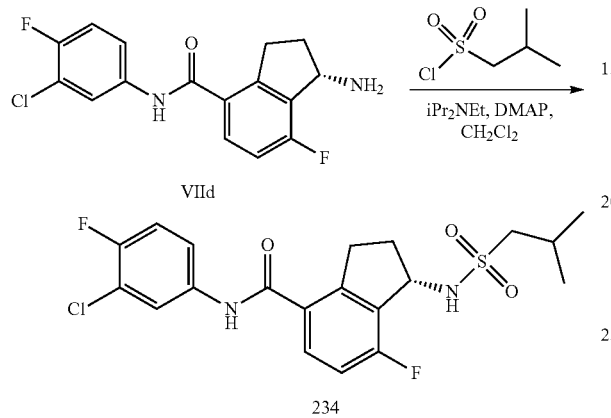

(S)—N-(3-Chloro-4-fluorophenyl)-7-fluoro-1-((2-methylpropyl)sulfonamido)-2,3-dihydro-1H-indene-4-carboxamide (234) was prepared in a similar manner as described above from (S)-1-amino-N-(3-chloro-4-fluorophenyl)-7-fluoro-2,3-dihydro-1H-indene-4-carboxamide hydrochloride (VIId) and 2-methylpropane-1-sulfonyl chloride. LCMS: m/z found 443.2/445.2 [M+H]$^+$; HPLC: RT=4.97 min (Method A); $^1$H NMR (400 MHz, DMSO-d$_6$) δ 10.42 (s, 1H), 8.08-8.00 (m, 1H), 7.77-7.68 (m, 1H), 7.69-7.60 (m, 2H), 7.40 (t, 1H), 7.19 (t, 1H), 5.07-5.00 (m, 1H), 3.31-3.20 (m, 1H), 3.10-2.84 (m, 3H), 2.40 (m, 1H), 2.17-2.07 (m, 1H), 2.04-1.95 (m, 1H), 1.07-0.99 (m, 6H).

(S)—N-(3-Chloro-4-fluorophenyl)-7-fluoro-1-((2-methoxyethyl)sulfonamido)-2,3-dihydro-1H-indene-4-carboxamide (182)

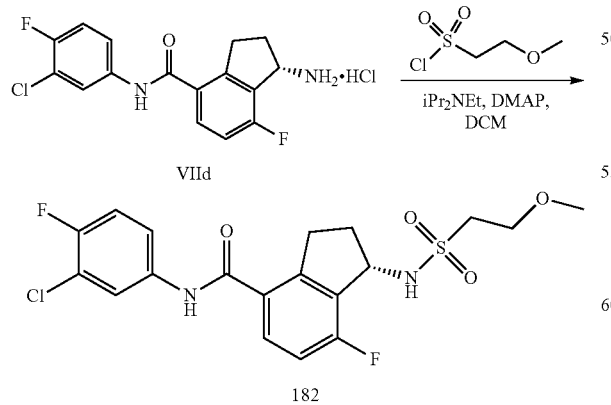

(S)—N-(3-Chloro-4-fluorophenyl)-7-fluoro-1-((2-methoxyethyl)sulfonamido)-2,3-dihydro-1H-indene-4-carboxamide (182) was prepared in a similar manner as described above from (S)-1-amino-N-(3-chloro-4-fluorophenyl)-7-fluoro-2,3-dihydro-1H-indene-4-carboxamide hydrochloride (VIId) and 2-methoxyethane-1-sulfonyl chloride. LCMS: m/z found 445.2/447.1 [M+H]$^+$; HPLC: RT=4.30 min (Method A); $^1$H NMR (300 MHz, Chloroform-d) δ 7.81 (dd, 1H), 7.72-7.57 (m, 2H), 7.48-7.36 (m, 1H), 7.13 (dd, 1H), 7.02 (dd, 1H), 5.23-5.10 (m, 1H), 4.78 (d, 1H), 3.82 (t, 2H), 3.50-3.27 (m, 6H), 3.32-3.09 (m, 1H), 2.63-2.44 (m, 1H), 2.42-2.22 (m, 1H).

(S)—N-(3-Chloro-4-fluorophenyl)-7-fluoro-1-(phenylsulfonamido)-2,3-dihydro-1H-indene-4-carboxamide (183)

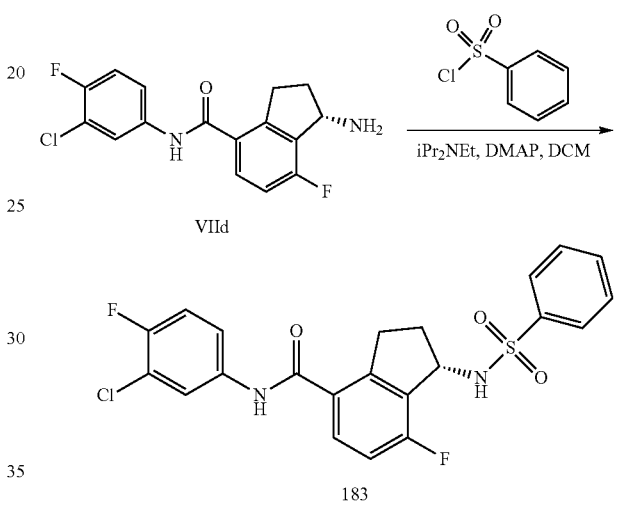

(S)—N-(3-Chloro-4-fluorophenyl)-7-fluoro-1-(phenylsulfonamido)-2,3-dihydro-1H-indene-4-carboxamide (183) was prepared in a similar manner as described above from (S)-1-amino-N-(3-chloro-4-fluorophenyl)-7-fluoro-2,3-dihydro-1H-indene-4-carboxamide hydrochloride (VIId) and benzenesulfonyl chloride. LCMS: m/z found 463.1/465.1 [M+H]$^+$; HPLC: RT=5.11 min (Method A); $^1$H NMR (300 MHz, Methanol-d$_4$) δ 7.99-7.87 (m, 3H), 7.72-7.50 (m, 5H), 7.23 (dd, 1H), 6.99 (dd, 1H), 5.07-4.91 (m, 1H), 3.27 (t, 1H), 3.14-2.97 (m, 1H), 2.32-2.13 (m, 1H), 2.00-1.86 (m, 1H).

(S)—N-(3-Chloro-4-fluorophenyl)-7-fluoro-1-((2-(pyridin-2-yl)ethyl)sulfonamido)-2,3-dihydro-1H-indene-4-carboxamide Hydrochloride (167.HCl)

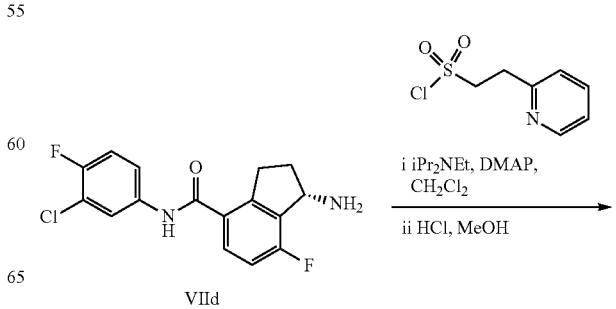

231
-continued

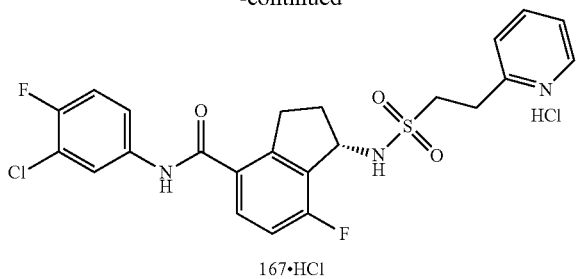

167·HCl (S)—N-(3-Chloro-4-fluorophenyl)-7-fluoro-1-((2-(pyridin-2-yl)ethyl)sulfonamido)-2,3-dihydro-1H-indene-4-carboxamide hydrochloride (167.HCl) was prepared in a similar manner as described above from (S)-1-amino-N-(3-chloro-4-fluorophenyl)-7-fluoro-2,3-dihydro-1H-indene-4-carboxamide hydrochloride (VIId) and 2-(pyridin-2-yl)ethane-1-sulfonyl chloride. The purified compound was subsequently converted to the hydrochloride salt using a 1.25 M solution of HCl in methanol. LCMS: m/z found 492.1/494.1 [M+H]$^+$; RT=5.11 min (Method A); $^1$H NMR (300 MHz, Methanol-d$_4$) δ 8.78 (d, 1H), 8.60 (t, 1H), 8.13 (d, 1H), 8.06-7.89 (m, 2H), 7.79-7.67 (m, 1H), 7.63-7.51 (m, 1H), 7.24 (dd, 1H), 7.12 (dd, 1H), 5.19 (t, 1H), 3.78-3.65 (m, 2H), 3.65-3.56 (m, 2H), 3.47-3.35 (m, 2H), 3.21-3.08 (m, 1H), 2.63-2.47 (m, 1H).

(S)—N-(3-Chloro-4-fluorophenyl)-7-fluoro-1-(pyridine-2-sulfonamido)-2,3-dihydro-1H-indene-4-carboxamide Hydrochloride (184.HCl)

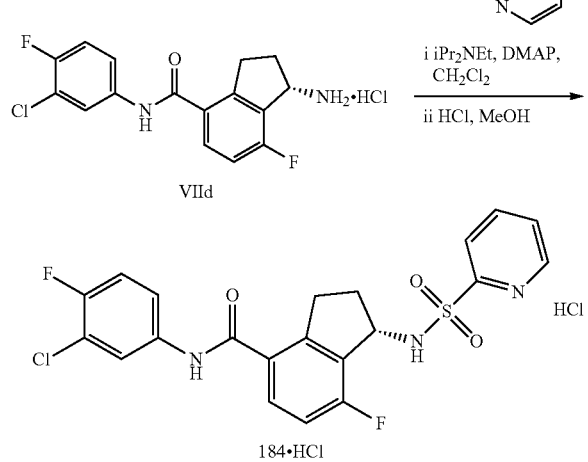

184·HCl (S)—N-(3-Chloro-4-fluorophenyl)-7-fluoro-1-(pyridine-2-sulfonamido)-2,3-dihydro-1H-indene-4-carboxamide hydrochloride (184.HCl) was prepared in a similar manner as described above from (S)-1-amino-N-(3-chloro-4-fluorophenyl)-7-fluoro-2,3-dihydro-1H-indene-4-carboxamide hydrochloride (VIId) and pyridine-2-sulfonyl chloride. The purified compound was subsequently converted to the hydrochloride salt using a 1.25 M solution of HCl in methanol. LCMS: m/z found 464.0/466.1 [M+H]$^+$; HPLC:

232

RT=4.49 min (Method A); $^1$H NMR (300 MHz, DMSO-d$_6$) δ 10.39 (d, 1H), 8.79-8.67 (m, 1H), 8.39 (t, 1H), 8.16-7.90 (m, 2H), 7.75-7.55 (m, 2H), 7.48-7.30 (m, 1H), 7.16-7.01 (m, 1H), 5.10 (dd, 1H), 3.34-3.09 (m, 1H), 3.06-2.78 (m, 1H), 2.26-1.98 (m, 1H), 1.88-1.64 (m, 1H).

(S)—N-(3-Chloro-4-fluorophenyl)-7-fluoro-1-((1-methyl-1H-pyrazole)-3-sulfonamido)-2,3-dihydro-1H-indene-4-carboxamide (101)

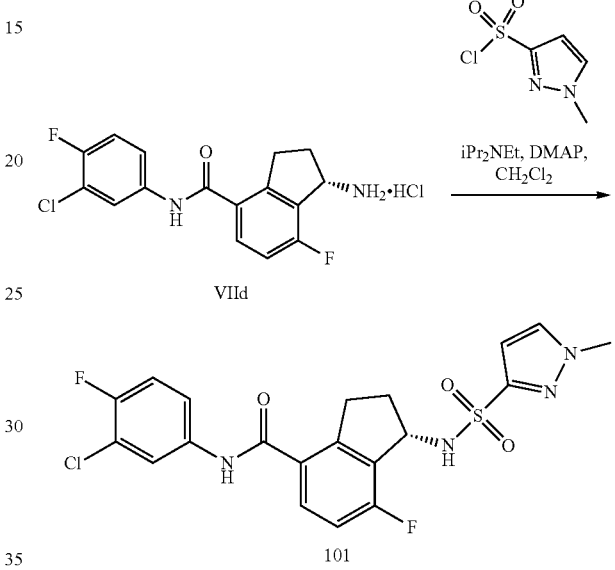

101

(S)—N-(3-Chloro-4-fluorophenyl)-7-fluoro-1-((1-methyl-1H-pyrazole)-3-sulfonamido)-2,3-dihydro-1H-indene-4-carboxamide (101) was synthesized in a similar manner as outlined above from (S)-1-amino-N-(3-chloro-4-fluorophenyl)-7-fluoro-2,3-dihydro-1H-indene-4-carboxamide hydrochloride (VIId) and 1-methyl-1H-pyrazole-3-sulfonyl chloride. LCMS: m/z found 467.5/469.5 [M+H]$^+$, RT=4.29 min (Method A). $^1$H NMR (300 MHz, DMSO-d$_6$): δ 10.39 (s, 1H), 8.15 (d, 1H), 8.03 (m, 1H), 7.89 (d, 1H), 7.74-7.62 (m, 2H), 7.40 (t, 1H), 7.15 (t, 1H), 6.64 (d, 1H), 5.03 (m, 1H), 3.94 (s, 3H), 3.17 (m, 1H), 2.97 (m, 1H), 2.14 (m, 1H), 1.80 (m, 1H).

(S)—N-(3-Chloro-4-fluorophenyl)-7-fluoro-1-((phenylmethyl)sulfonamido)-2,3-dihydro-1H-indene-4-carboxamide (222)

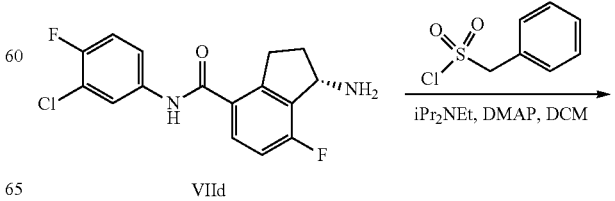

VIId

233

-continued

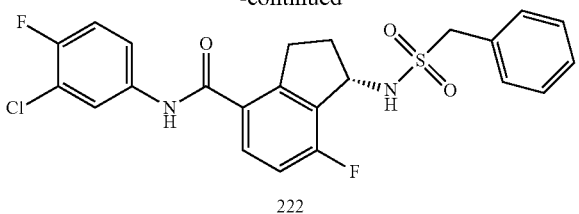

222

(S)—N-(3-Chloro-4-fluorophenyl)-7-fluoro-1-((phenylmethyl)sulfonamido)-2,3-dihydro-1H-indene-4-carboxamide (222) was prepared in a similar manner as described above from (S)-1-amino-N-(3-chloro-4-fluorophenyl)-7-fluoro-2,3-dihydro-1H-indene-4-carboxamide hydrochloride (VIId) and phenylmethanesulfonyl chloride. LCMS: m/z found 477.2/479.2 [M+H]$^+$; HPLC: RT=5.08 min (Method A); $^1$H NMR (400 MHz, DMSO-d$_6$) δ 10.47-10.40 (m, 1H), 8.10-8.01 (m, 1H), 7.83-7.71 (m, 2H), 7.69-7.64 (m, 1H), 7.48-7.35 (m, 6H), 7.23 (q, 1H), 5.13-5.08 (m, 1H), 4.52-4.26 (m, 2H), 3.33-3.20 (m, 1H), 3.07-2.98 (m, 1H), 2.47-2.30 (m, 1H), 2.09-1.86 (m, 1H).

(S)—N-(3-Chloro-4-fluorophenyl)-7-fluoro-1-(morpholine-4-sulfonamido)-2,3-dihydro-1H-indene-4-carboxamide (228)

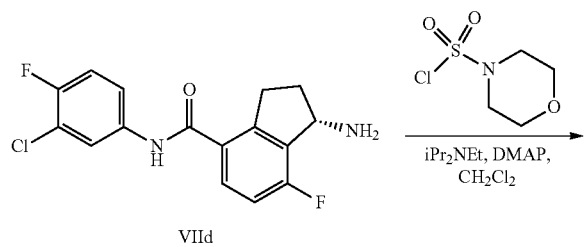

(S)—N-(3-Chloro-4-fluorophenyl)-7-fluoro-1-(morpholine-4-sulfonamido)-2,3-dihydro-1H-indene-4-carboxamide (228) was prepared in a similar manner as described above from (S)-1-amino-N-(3-chloro-4-fluorophenyl)-7-fluoro-2,3-dihydro-1H-indene-4-carboxamide hydrochloride (VIId) and morpholine-4-sulfonyl chloride. LCMS: m/z found 472.2/473.3 [M+H]$^+$; HPLC: RT=4.43 min (Method A); 1H NMR (400 MHz, DMSO-d$_6$) δ 10.43 (s, 1H), 8.04 (dd, 1H), 7.84 (d, 1H), 7.74 (dd, 1H), 7.69-7.60 (m, 1H), 7.40 (t, 1H), 7.20 (t, 1H), 5.01-4.91 (m, 1H), 3.74-3.56 (m, 4H), 3.33-3.20 (m, 1H), 3.11-2.96 (m, 5H), 2.43-2.33 (m, 5H), 2.12-2.00 (m, 1H).

234

(S)—N-(3-Chloro-4-fluorophenyl)-1-(cyclopentanesulfonamido)-7-fluoro-2,3-dihydro-1H-indene-4-carboxamide (239)

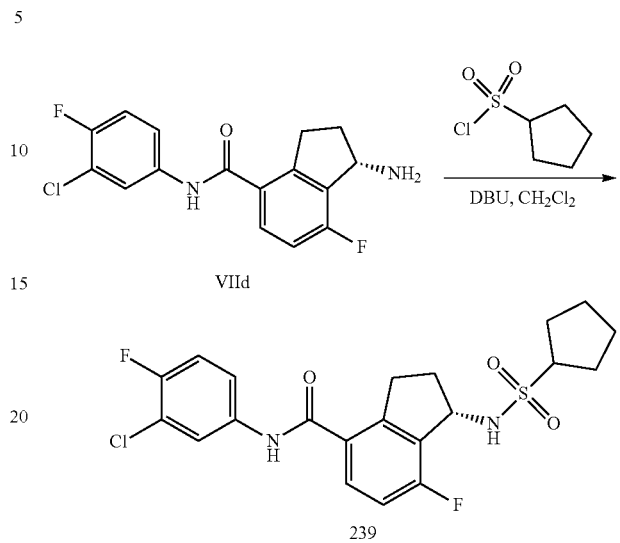

To a solution of 0.1 g (0.28 mmol, 1.0 eq.) of (S)-1-amino-N-(3-chloro-4-fluorophenyl)-7-fluoro-2,3-dihydro-1H-indene-4-carboxamide free base (VIId) in 5 mL of anhydrous methylene chloride under a nitrogen atmosphere was added 0.2 g (0.15 mmol, 0.6 eq.) of 1,8-diazabicyclo[5.4.0]undec-7-ene, and the mixture was cooled to 0° C. To this cooled solution was added dropwise 0.09 g (0.51 mmol, 2.0 eq.) of cyclopentanesulfonyl chloride, and the mixture was allowed to warm to room temperature and stirred for 16 h. The reaction was diluted with 100 mL of ethyl acetate and washed with 10 mL of saturated sodium bicarbonate, 10 mL of water and 10 mL of brine. The organic phase was dried (Na$_2$SO$_4$), filtered and the solvent removed in vacuo. The residue was purified by flash chromatography (SiO$_2$, eluting with a linear gradient of 0-50% ethyl acetate/hexanes) to provide 24.9 mg (0.05 mmol, 22%) of (S)—N-(3-chloro-4-fluorophenyl)-1-(cyclopentanesulfonamido)-7-fluoro-2,3-dihydro-1H-indene-4-carboxamide (239). LCMS: m/z found 455.3/457.2 [M+H]$^+$; HPLC: RT=4.97 min (Method A); $^1$H NMR (400 MHz, DMSO-d$_6$) δ 10.41 (s, 1H), 8.04 (dd, 1H), 7.70-7.75 (dd, 1H), 7.67-7.61 (m, 1H), 7.60 (d, 1H), 7.41 (t, 1H), 7.19 (t, 1H), 5.10-5.00 (m, 1H), 3.65-3.53 (m, 1H), 3.32-3.19 (m, 1H), 3.08-2.95 (m, 1H), 2.41 (m, 1H), 2.03-1.87 (m, 5H), 1.60 (d, 4H).

(S)—N-(3-Chloro-4-fluorophenyl)-7-fluoro-1-((1-methylethyl)sulfonamido)-2,3-dihydro-1H-indene-4-carboxamide (238)

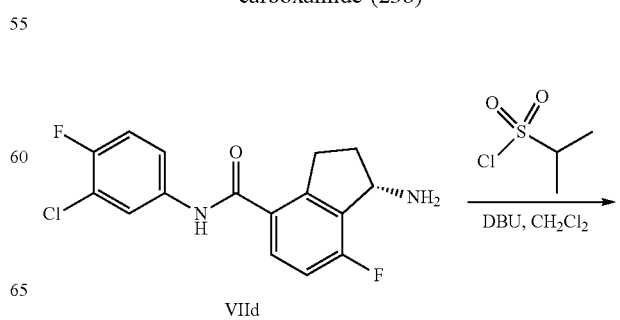

235
-continued

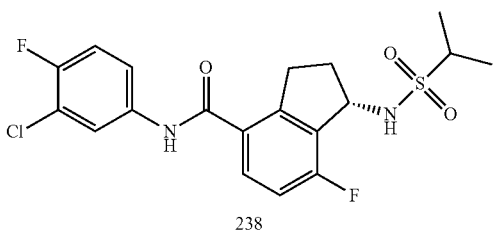

238

(S)—N-(3-Chloro-4-fluorophenyl)-7-fluoro-1-((1-methylethyl)sulfonamido)-2,3-dihydro-1H-indene-4-carboxamide (238) was prepared in a similar manner as described above from (S)-1-amino-N-(3-chloro-4-fluorophenyl)-7-fluoro-2,3-dihydro-1H-indene-4-carboxamide (VIId) and propane-2-sulfonyl chloride. LCMS: m/z found 429.3/431.2 [M+H]$^+$; HPLC: RT=4.58 min (Method A); $^1$H NMR (400 MHz, DMSO-d$_6$) δ 10.43 (s, 1H), 8.06 (dd, 1H), 7.78-7.70 (m, 1H), 7.71-7.62 (m, 1H), 7.60 (d, 1H), 7.42 (t, 1H), 7.21 (t, 1H), 5.09-4.99 (m, 1H), 3.36-3.17 (m, 2H), 3.09-2.97 (m, 1H), 2.47-2.37 (m, 1H), 2.08-1.96 (m, 1H), 1.31-1.24 (m, 6H).

(S)—N-(3-Chloro-4-fluorophenyl)-1-(cyclohexanesulfonamido)-7-fluoro-2,3-dihydro-1H-indene-4-carboxamide (240)

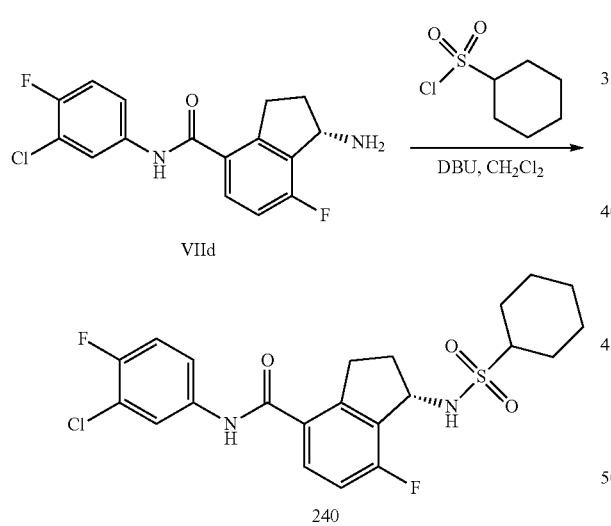

240

(S)—N-(3-Chloro-4-fluorophenyl)-1-(cyclohexanesulfonamido)-7-fluoro-2,3-dihydro-1H-indene-4-carboxamid (240) was prepared in a similar manner as described above from (S)-1-amino-N-(3-chloro-4-fluorophenyl)-7-fluoro-2,3-dihydro-1H-indene-4-carboxamide (VIId) and cyclohexanesulfonyl chloride. LCMS: m/z found 569.3/571.2 [M+H]$^+$; HPLC: RT=5.31 min (Method A); $^1$H NMR (400 MHz, DMSO-d$_6$) δ 10.42 (s, 1H), 8.09-8.01 (m, 1H), 7.74 (dd, 1H), 7.73-7.62 (m, 1H), 7.60 (d, 1H), 7.41 (t, 1H), 7.20 (t, 1H), 5.07-4.97 (m, 1H), 3.34-3.21 (m, 1H), 3.12-2.86 (m, 2H), 2.52-2.36 (m, 1H), 2.09 (bs, 2H), 2.07-1.94 (m, 1H), 1.82 (d, 2H), 1.65 (d, 1H), 1.43-1.24 (m, 4H), 1.21-1.10 (m, 1H).

236

O-tert-Butyl (S)—(N-(4-((3-chloro-4-fluorophenyl)carbamoyl)-7-fluoro-2,3-dihydro-1H-inden-1-yl)sulfamoyl)carbamate

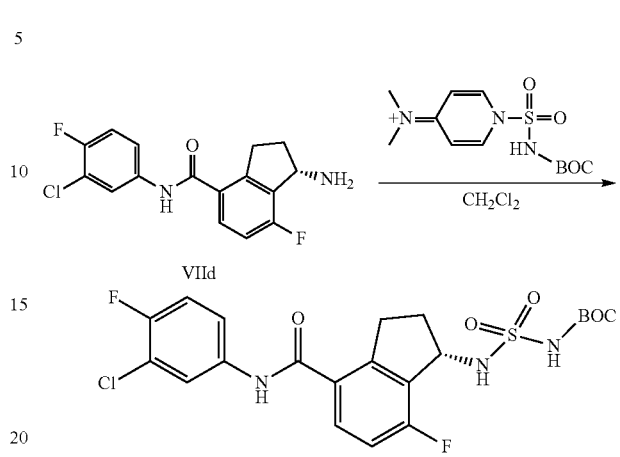

To a solution of 1.5 g (4.65 mmol, 1.0 eq.) of (1S)-1-amino-N-(3-chloro-4-fluoro-phenyl)-7-fluoro-indane-4-carboxamide (VIId) in 20 mL of methylene chloride was added 2.10 g (6.97 mmol, 1.5 eq) of tert-butoxycarbonyl-[(4-dimethyliminio-1-pyridyl)sulfonyl]azanide (Org. Lett., 2001, 3, 2241) and the mixture was stirred at 15° C. for 12 h. The solvent was removed in vacuo, and the residue was purified by flash chromatography (SiO$_2$, eluting with a linear gradient of 10-50% ethyl acetate/petroleum ether) to provide 1.5 g (3.0 mmol, 64%) of O-tert-butyl (S)—(N-(4-((3-chloro-4-fluorophenyl)carbamoyl)-7-fluoro-2,3-dihydro-1H-inden-1-yl)sulfamoyl)carbamate.

O-tert-Butyl (S)—(N-(4-((3-chloro-4-fluorophenyl)carbamoyl)-7-fluoro-2,3-dihydro-1H-inden-1-yl)sulfamoyl)(methyl)carbamate

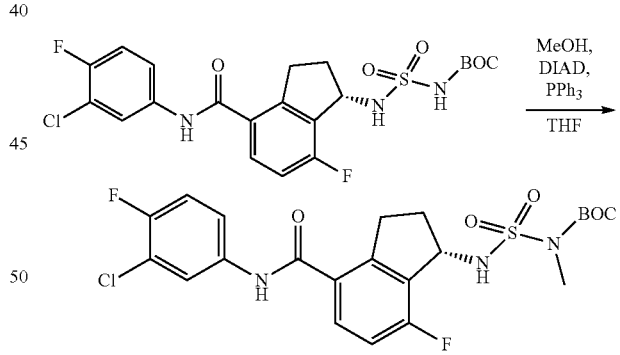

To a solution of 0.50 g (1.0 mmol, 1.0 eq.) of tert-butyl N-[[(1S)-4-[(3-chloro-4-fluoro-phenyl) carbamoyl]-7-fluoro-indan-1-yl]sulfamoyl]carbamate and 41 mg (1.30 mmol, 1.3 eq.) of methanol in 10 mL of anhydrous THF 0° C. were added 0.4 g (1.30 mmol, 1.3 eq.) of triphenylphosphine and 0.26 g (1.30 mmol, 1.3 eq.) of diisopropylazodicarboxylate, and the mixture was stirred at 15° C. for 12 h. The solvent was removed in vacuo, and the residue was purified by flash chromatography (SiO$_2$, eluting with a linear gradient of 10-30% ethyl acetate/petroleum ether) to provide 0.4 g (0.78 mmol, 78%) of O-tert-butyl N-[[(1S)-4-[(3-chloro-4-fluoro-phenyl)carbamoyl]-7-fluoro-indan-1-yl]sulfamoyl]-N-methyl-carbamate.

(S)—N-(3-Chloro-4-fluorophenyl)-7-fluoro-1-((N-methylsulfamoyl)amino)-2,3-dihydro-1H-indene-4-carboxamide (227)

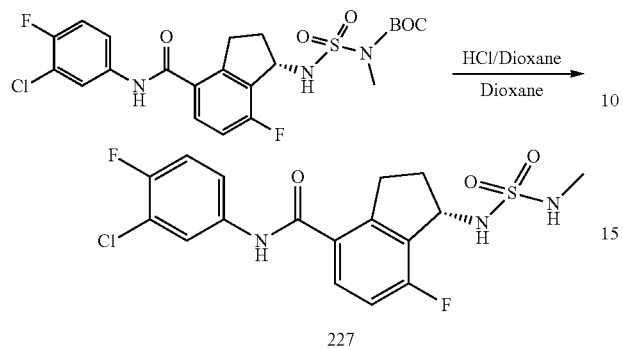

To a solution of 0.35 g (0.68 mmol, 1.0 eq.) of O-tert-butyl N-[[(1S)-4-[(3-chloro-4-fluoro-phenyl)carbamoyl]-7-fluoro-indan-1-yl]sulfamoyl]-N-methyl-carbamate in 10 mL of p-dioxane was added 3 mL of a 4 M solution of HCl in p-dioxane and the mixture was stirred at room temperature for 1 h. The solvent was removed in vacuo and the residue was purified by semi-prep HPLC to provide 0.12 g (0.29 mmol, 43%) of (S)—N-(3-chloro-4-fluorophenyl)-7-fluoro-1-((N-methylsulfamoyl)amino)-2,3-dihydro-1H-indene-4-carboxamide (227) LCMS: m/z found 438.0/440.0 [M+Na]$^+$; $^1$H NMR (400 MHz, DMSO-d$_6$): δ 10.39 (s, 1H), 8.02-8.05 (m, 1H), 7.69-7.73 (m, 1H), 7.62-7.66 (m, 1H), 7.37-7.42 (m, 1H), 7.31-7.34 (d, 1H), 7.15-7.19 (m, 1H), 6.80-6.85 (m, 1H), 4.83-4.88 (m, 1H), 3.22-3.33 (m, 1H), 2.98-3.06 (m, 1H), 2.51-2.53 (d, 3H), 2.32-2.39 (m, 1H), 2.07-2.14 (m, 1H).

Example 7: Non-Limiting Synthesis of Selected 1-(Substituted Amido)-Dihydroindene-4-Carboxamides Carboxamide Formation:

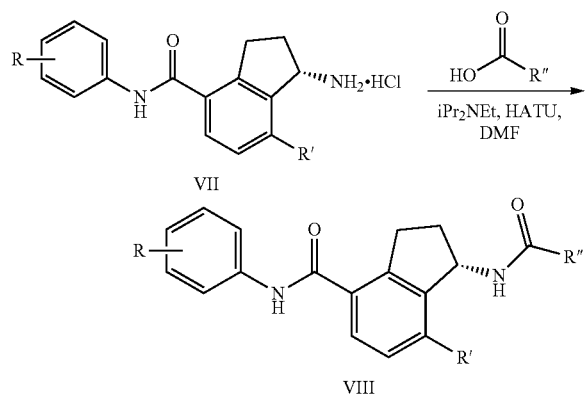

General procedure: To a solution of 1.1 eq. of a carboxylic acid in anhydrous DMF at 0° C. was added 1.1 eq. of 1-[bis(dimethylamino)methylene]-1H-1,2,3-triazolo[4,5-b]pyridinium 3-oxide hexafluorophosphate (HATU) followed by 3.0 eq. of N,N-diisopropylethyl amine. The mixture was stirred at 0° C. for approximately 10 min, and 1.0 eq of VII was added. The mixture was allowed to warm to room temperature and stirred to completion (2-16 h). The mixture was then diluted with ethyl acetate and washed with water, followed by sat. sodium bicarbonate solution and brine. The organic phase was dried (Na$_2$SO$_4$), filtered and the solvent was removed in vacuo. The residue was purified by flash chromatography to provide the corresponding carboxamide.

(S)—N-(3-Chloro-4-fluorophenyl)-7-fluoro-1-(3-(1-methyl-1H-pyrazol-3-yl)propanamido)-2,3-dihydro-1H-indene-4-carboxamide (171)

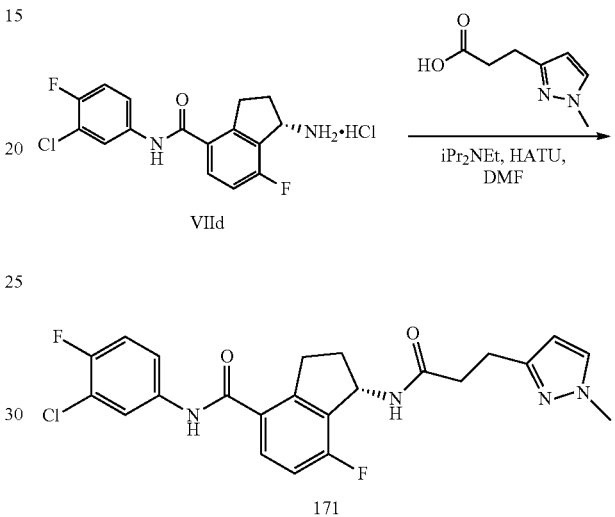

To a solution of 35 mg (0.21 mmol, 1.1 eq.) of 3-(1-methyl-1H-pyrazol-3-yl)propanoic acid in 1 mL of anhydrous DMF at 0° C. was added 82 mg (0.21 mmol, 1.1 eq.) of HATU, followed by 102 μL (0.58 mmol, 3.0 eq.) of N,N-diisopropylethyl amine. The mixture was stirred at 0° C. for 10 min, and 70 mg (0.19 mmol, 1.0 eq.) of (S)-1-amino-N-(3-chloro-4-fluorophenyl)-7-fluoro-2,3-dihydro-1H-indene-4-carboxamide hydrochloride (VIId) was added. The mixture was allowed to warm to room temperature and stirred for 3 h. The mixture was then diluted with 25 mL of ethyl acetate and washed with 15 mL of water followed by 15 mL of sat. sodium bicarbonate solution and 15 mL of brine. The organic phase was dried (Na$_2$SO$_4$), filtered and the solvent was removed in vacuo. The residue was purified by flash chromatography (SiO$_2$, eluting with a linear gradient of 0.5-8.5% methanol/methylene chloride) to provide 71 mg (0.15 mmol, 79%) of (S)—N-(3-chloro-4-fluorophenyl)-7-fluoro-1-(3-(1-methyl-1H-pyrazol-3-yl) propanamido)-2,3-dihydro-1H-indene-4-carboxamide (171). LCMS: m/z found 459.1/461.2 [M+H]$^+$, RT=3.85 min (Method A); $^1$H NMR (300 MHz, DMSO-d$_6$) δ 10.40 (s, 1H), 8.31 (d, 1H), 8.05 (m, 1H), 7.77-7.60 (m, 2H), 7.51 (d, 1H), 7.41 (t, 1H), 7.17 (t, 1H), 6.00 (d, 1H), 5.50 (q, 1H), 3.73 (s, 3H), 3.27-3.14 (m, 1H), 3.13-2.95 (m, 1H), 2.81-2.69 (m, 2H), 2.47-2.28 (m, 3H), 1.84 (m, 1H).

(S)—N-(3-Chloro-4-fluorophenyl)-1-(cyclopropanecarboxamido)-7-fluoro-2,3-dihydro-1H-indene-4-carboxamide (179)

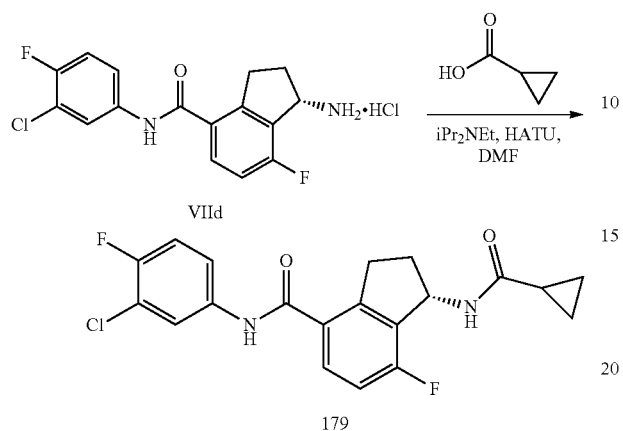

(S)—N-(3-Chloro-4-fluorophenyl)-1-(cyclopropanecarboxamido)-7-fluoro-2,3-dihydro-1H-indene-4-carboxamide (179) was synthesized in a similar manner as outlined above from (S)-1-amino-N-(3-chloro-4-fluorophenyl)-7-fluoro-2,3-dihydro-1H-indene-4-carboxamide hydrochloride (VIId) and cyclopropanecarboxylic acid. LCMS: m/z found 391.2/393.2 [M+H]$^+$, RT=4.24 min (Method A); $^1$H NMR (300 MHz, DMSO-d$_6$): δ 10.40 (s, 1H), 8.51 (d, 1H), 8.04 (m, 1H), 7.74-7.65 (m, 2H), 7.41 (t, 1H), 7.17 (t, 1H), 5.50 (m, 1H), 3.25 (m, 1H), 3.05 (m, 1H), 2.39 (m, 1H), 1.84 (m, 1H), 1.54 (m, 1H), 0.71-0.64 (m, 4H).

(S)—N-(4-((3-Chloro-4-fluorophenyl)carbamoyl)-7-fluoro-2,3-dihydro-1H-inden-1-yl)-1-methyl-1H-pyrazole-3-carboxamide (98)

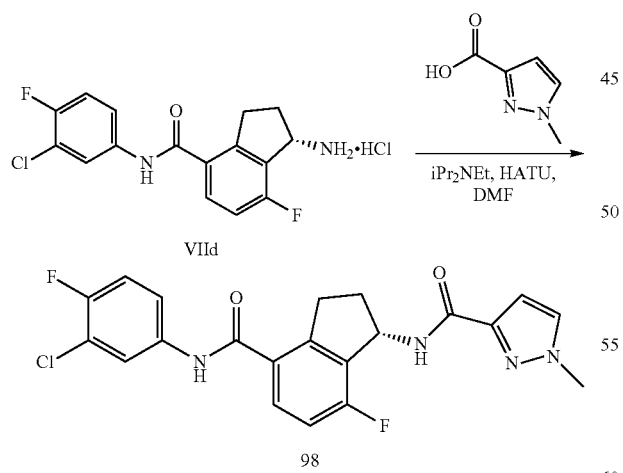

(S)—N-(4-((3-Chloro-4-fluorophenyl)carbamoyl)-7-fluoro-2,3-dihydro-1H-inden-1-yl)-1-methyl-1H-pyrazole-3-carboxamide (98) was synthesized in a similar manner as outlined above from (S)-1-amino-N-(3-chloro-4-fluorophenyl)-7-fluoro-2,3-dihydro-1H-indene-4-carboxamide hydrochloride (VIId) and 1-methyl-1H-pyrazole-3-carboxylic acid. LCMS m/z found 431.1/433.1 [M+H]$^+$, RT=4.24 min (Method A); $^1$H NMR (300 MHz, DMSO-d$_6$) δ 10.39 (s, 1H), 8.43 (d, 1H), 8.05 (m, 1H), 7.76 (d, 1H), 7.69 (m, 2H), 7.42 (t, 1H), 7.13 (t, 1H), 6.64 (d, 1H), 5.72 (q, 1H), 3.88 (s, 3H), 3.35 (m, 1H), 3.06 (m, 1H), 2.43 (m, 1H), 2.04 (m, 1H).

(S)—N-(4-((3-Chloro-4-fluorophenyl)carbamoyl)-7-fluoro-2,3-dihydro-1H-inden-1-yl)-1-methyl-1H-pyrazole-5-carboxamide (100)

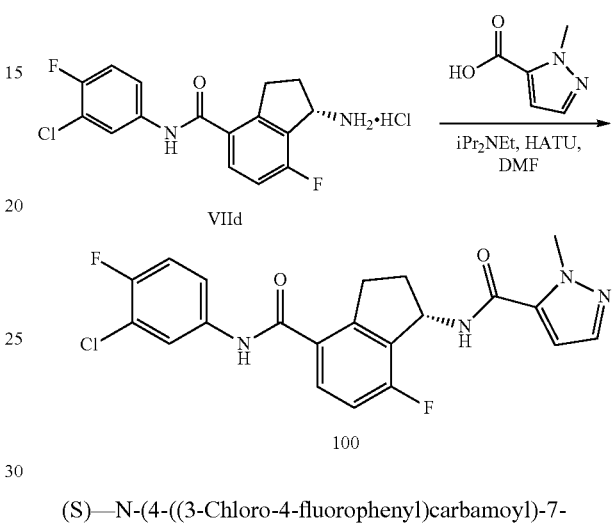

(S)—N-(4-((3-Chloro-4-fluorophenyl)carbamoyl)-7-fluoro-2,3-dihydro-1H-inden-1-yl)-1-methyl-1H-pyrazole-5-carboxamide (100) was synthesized in a similar manner as outlined above from (S)-1-amino-N-(3-chloro-4-fluorophenyl)-7-fluoro-2,3-dihydro-1H-indene-4-carboxamide hydrochloride (VIId) and 1-methyl-1H-pyrazole-5-carboxylic acid. LCMS: m/z found 431.1/433.1 [M+H]$^+$, RT=4.36 min (Method A); $^1$H NMR (300 MHz, DMSO-d$_6$) δ 10.42 (s, 1H), 8.88 (d, 1H), 8.06 (m, 1H), 7.69 (m, 2H), 7.43 (m, 2H), 7.18 (t, 1H), 6.84 (d, 1H), 5.72 (q, 1H), 4.08 (s, 3H), 3.34 (m, 1H), 3.10 (m, 1H), 2.50 (m, 1H), 2.01 (m, 1H).

(S)—N-(4-((3-Chloro-4-fluorophenyl)carbamoyl)-7-fluoro-2,3-dihydro-1H-inden-1-yl)picolinamide (115)

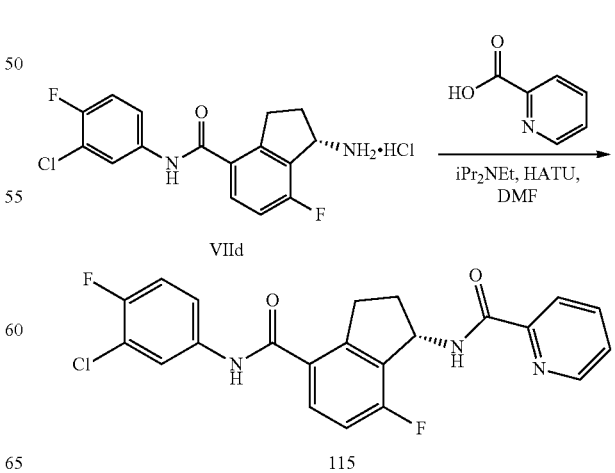

(S)—N-(4-((3-Chloro-4-fluorophenyl)carbamoyl)-7-fluoro-2,3-dihydro-1H-inden-1-yl)picolinamide (115) was synthesized in a similar manner as outlined above from (S)-1-amino-N-(3-chloro-4-fluorophenyl)-7-fluoro-2,3-dihydro-1H-indene-4-carboxamide hydrochloride (VIId) and picolinic acid. LCMS: m/z found 428.1/430.1 [M+H]+; HPLC (Method K) RT=10.91 min; ¹H NMR (500 MHz, DMSO-d₆) δ 10.40 (s, 1H), 9.09 (d, 1H), 8.62 (d, 1H), 7.99-7.80 (m, 3H), 7.59-7.73 (m, 3H), 7.42 (dd, 1H), 7.16 (dd, 1H), 5.74-5.80 (m, 1H), 3.15-3.16 (m, 1H), 3.05-3.13 (m, 1H), 2.49-5.50 (m, 1H), 2.08-2.17 (m, 1H), (S)—N-(4-((3-Chloro-4-fluorophenyl)carbamoyl)-7-fluoro-2,3-dihydro-1H-inden-1-yl)nicotinamide (119)

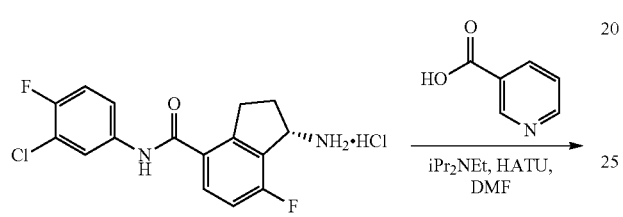

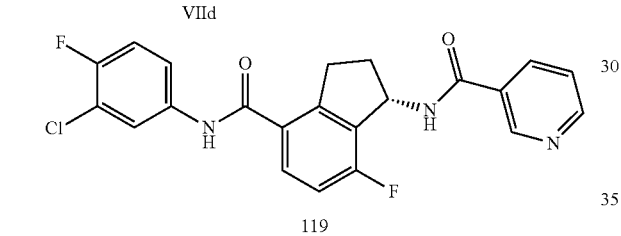

(S)—N-(4-((3-Chloro-4-fluorophenyl)carbamoyl)-7-fluoro-2,3-dihydro-1H-inden-1-yl)nicotinamide (119) was synthesized in a similar manner as outlined above from (S)-1-amino-N-(3-chloro-4-fluorophenyl)-7-fluoro-2,3-dihydro-1H-indene-4-carboxamide hydrochloride (VIId) and nicotinic acid. LCMS: m/z found 428.1/430.1 [M+H]+; HPLC: (Method K) RT=9.88 min; ¹H NMR (400 MHz, DMSO-d₆) δ 10.40 (s, 1H), 9.09 (d, 1H), 9.01 (d, 1H), 8.70 (dd, 1H), 8.18-8.21 (m, 1H), 8.06 (dd, 1H), 7.66-7.75 (m, 2H), 7.50 (dd, 1H), 7.42 (dd, 1H), 7.18 (dd, 1H), 5.75-5.81 (m, 1H), 3.34-3.40 (m, 1H), 3.09-3.15 (m, 1H), 2.53-2.56 (m, 1H), 2.00-2.06 (m, 1H).

(S)—N-(4-((3-Chloro-4-fluorophenyl)carbamoyl)-7-fluoro-2,3-dihydro-1H-inden-1-yl)isonicotinamide (120)

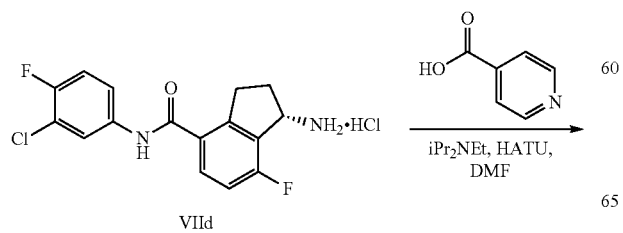

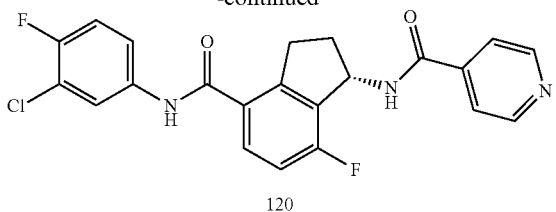

(S)—N-(4-((3-Chloro-4-fluorophenyl)carbamoyl)-7-fluoro-2,3-dihydro-1H-inden-1-yl)isonicotinamide (120) was synthesized in a similar manner as outlined above from (S)-1-amino-N-(3-chloro-4-fluorophenyl)-7-fluoro-2,3-dihydro-1H-indene-4-carboxamide hydrochloride (VIId) and isonicotinic acid. LCMS: m/z found 428.1/430.1 [M+H]+; HPLC: (Method K) RT=9.84 min; ¹H NMR (400 MHz, DMSO-d₆) δ 10.42 (s, 1H), 9.19 (d, 1H), 8.72 (dd, 2H), 8.06 (dd, 1H), 7.66-7.77 (m, 4H), 7.42 (dd, 1H), 7.18 (dd, 1H), 5.76-5.80 (m, 1H), 3.34-3.40 (m, 1H), 3.09-3.15 (m, 1H), 2.53-2.56 (m, 1H), 2.00-2.06 (m, 1H).

(S)—N-(3-Chloro-4-fluorophenyl)-7-fluoro-1-(2-hydroxyacetamido)-2,3-dihydro-1H-indene-4-carboxamide (143)

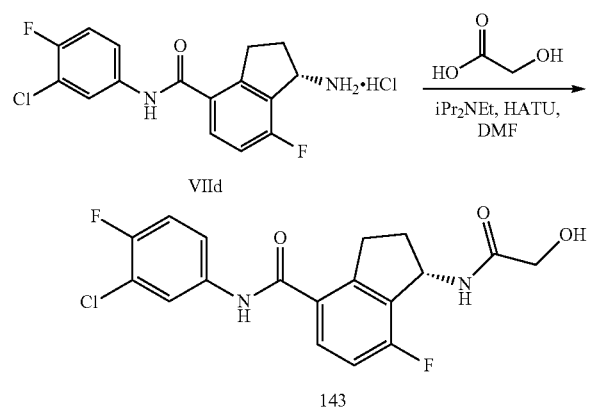

(S)—N-(3-Chloro-4-fluorophenyl)-7-fluoro-1-(2-hydroxyacetamido)-2,3-dihydro-1H-indene-4-carboxamide (143) was synthesized in a similar manner as outlined above from (S)-1-amino-N-(3-chloro-4-fluorophenyl)-7-fluoro-2,3-dihydro-1H-indene-4-carboxamide hydrochloride (VIId) and hydroxyacetic acid. LCMS: m/z found 381.1/383.1 [M+H]+; HPLC: (Method K) RT=9.58 min; ¹H NMR (400 MHz, DMSO-d₆) δ 10.41 (s, 1H), 8.11 (d, 1H), 8.04 (dd, 1H), 7.65-7.71 (m, 2H), 7.41 (dd, 1H), 7.15 (dd, 1H), 5.70 (q, 1H), 5.43 (bs, 1H), 3.82 (s, 2H), 3.25-3.31 (m, 1H), 3.01-3.06 (m, 1H), 2.37-2.41 (m, 1H), 1.94-1.97 (m, 1H).

General Procedure:

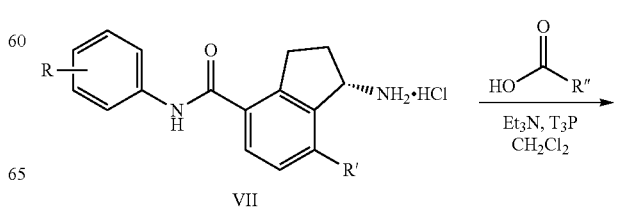

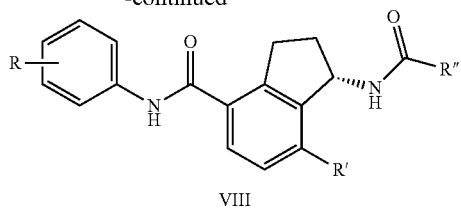

To a solution of 1.0 eq. of a carboxylic acid, 1.0 eq of VII and 2.5 eq. of triethylamine in anhydrous methylene chloride at 0° C. was added 2.5 eq. of propylphosphonic anhydride (T₃P). The mixture was allowed to warm to room temperature and stirred for 16 h. The mixture was then diluted with water and extracted with ethyl acetate. The combined organic extracts were washed with water and brine and then dried (Na₂SO₄), filtered and the solvent was removed in vacuo. The residue was purified by flash chromatography to provide the corresponding carboxamide.

(S)—N-(4-((3-Chloro-4-fluorophenyl)carbamoyl)-7-fluoro-2,3-dihydro-1H-inden-1-yl)thiazole-2-carboxamide (127)

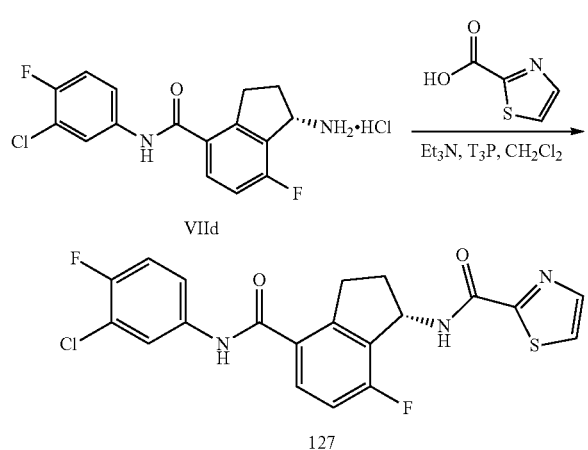

To a solution of 25 mg (0.19 mmol, 1.0 eq.) of a thiazole-2-carboxylic acid, 70 mg (0.19 mmol, 1.0 eq.) of (S)-1-amino-N-(3-chloro-4-fluorophenyl)-7-fluoro-2,3-dihydro-1H-indene-4-carboxamide hydrochloride (VIId) and 67 µL (0.49 mmol, 2.5 eq.) of triethylamine in anhydrous methylene chloride at 0° C. was added 0.16 g (0.49 mmol, 2.5 eq.) of propylphosphonic anhydride (T₃P). The mixture was allowed to warm to room temperature and stirred for 16 h. The mixture was then diluted with 10 mL of water and extracted with 2×20 mL of ethyl acetate. The combined organic extracts were washed with 10 mL of water and 10 mL of brine and then dried (Na₂SO₄), filtered and the solvent was removed in vacuo. The residue was purified by flash chromatography (SiO₂, eluting with a linear gradient of 0-50% ethyl acetate/hexanes) to provide the 49 mg (11.3 mmol, 60%) of (S)—N-(4-((3-chloro-4-fluorophenyl)carbamoyl)-7-fluoro-2,3-dihydro-1H-inden-1-yl)thiazole-2-carboxamide (127). LCMS: m/z found 434.1/436.1 [M+H]⁺; HPLC: (Method K) RT=11.38 min; ¹H NMR (400 MHz, DMSO-d₆) δ 10.40 (s, 1H), 9.32 (d, 1H), 7.73-8.07 (m, 3H), 7.66-7.72 (m, 2H), 7.44 (dd, 1H), 7.14 (dd, 1H), 5.73 (q, 1H), 3.36-3.39 (m, 1H), 3.08-3.12 (m, 1H), 2.44-2.46 (m, 1H), 2.10-2.17 (m, 1H).

(S)—N-(4-((3-Chloro-4-fluorophenyl)carbamoyl)-7-fluoro-2,3-dihydro-1H-inden-1-yl)thiazole-5-carboxamide (116)

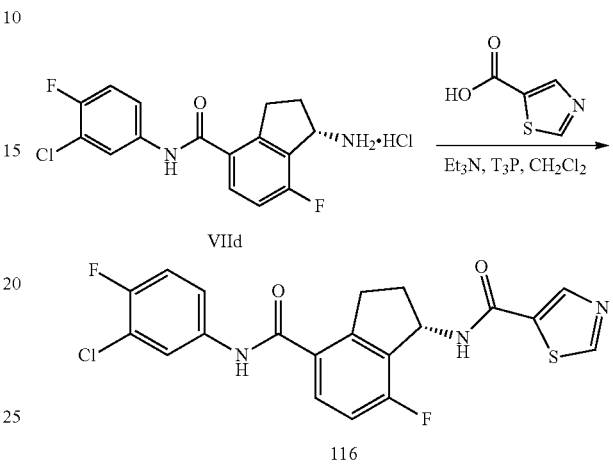

(S)—N-(4-((3-Chloro-4-fluorophenyl)carbamoyl)-7-fluoro-2,3-dihydro-1H-inden-1-yl)thiazole-5-carboxamide (116) was synthesized in a similar manner as outlined above from (S)-1-amino-N-(3-chloro-4-fluorophenyl)-7-fluoro-2,3-dihydro-1H-indene-4-carboxamide hydrochloride (VIId) and thiazole-5-carboxylic acid. LCMS: m/z found 434.1/436.1 [M+H]⁺; HPLC: (Method K) RT=10.19 min; ¹H NMR (400 MHz, DMSO-d₆) δ 10.41 (m, 1H), 9.22 (s, 1H), 9.12 (d, 1H), 8.46 (s, 1H), 8.06 (dd, 1H), 7.75 (dd, 1H), 7.66-7.72 (m, 1H), 7.42 (dd, 1H), 7.20 (dd, 1H), 5.71 (q, 1H), 3.34-3.39 (m, 1H), 3.06-3.12 (m, 1H), 2.50-2.50 (m, 1H), 1.99-2.04 (m, 1H).

(S)—N-(4-((3-Chloro-4-fluorophenyl)carbamoyl)-7-fluoro-2,3-dihydro-1H-inden-1-yl)oxazole-5-carboxamide (129)

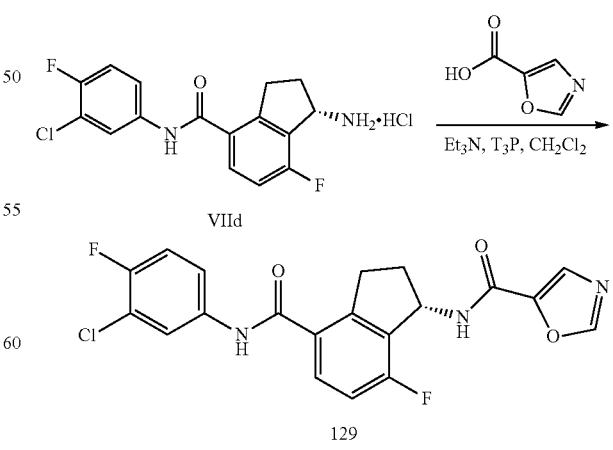

(S)—N-(4-((3-Chloro-4-fluorophenyl)carbamoyl)-7-fluoro-2,3-dihydro-1H-inden-1-yl)oxazole-5-carboxamide (129) was synthesized in a similar manner as outlined above from (S)-1-amino-N-(3-chloro-4-fluorophenyl)-7-fluoro-2,3-dihydro-1H-indene-4-carboxamide hydrochloride (VIId) and oxazole-5-carboxylic acid. LCMS: m/z found 418.2/420.2 [M+H]$^+$; HPLC: (Method K) RT=10.16 min; $^1$H NMR (400 MHz, DMSO-d$_6$) δ 10.42 (s, 1H), 9.09 (d, 1H), 8.55 (s, 1H), 8.06 (dd, 1H), 7.79 (s, 1H), 7.78 (dd, 1H), 7.66-7.72 (m, 1H), 7.42 (dd, 1H), 7.18 (dd, 1H), 5.71 (q, 1H), 3.11-3.13 (m, 1H), 3.05-3.09 (m, 1H), 2.47-2.53 (m, 1H), 1.98-2.01 (m, 1H).

(S)—N-(3-Chloro-4-fluorophenyl)-7-fluoro-1-(2-morpholinoacetamido)-2,3-dihydro-1H-indene-4-carboxamide (118)

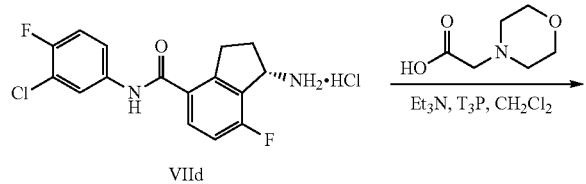

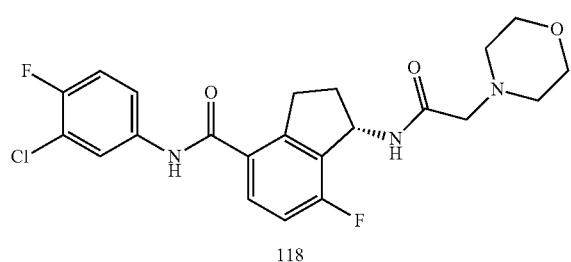

(S)—N-(3-Chloro-4-fluorophenyl)-7-fluoro-1-(2-morpholinoacetamido)-2,3-dihydro-1H-indene-4-carboxamide (118) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-morpholinoacetic acid. LCMS: m/z found 450.3/452.3 [M+H]$^+$; HPLC: (Method K) RT=10.18 min; $^1$H NMR (400 MHz, DMSO-d$_6$) δ 10.39 (s, 1H), 8.20 (d, 1H), 8.05 (dd, 1H), 7.64-7.75 (m, 2H), 7.39 (dd. 1H), 7.16 (dd, 1H). 5.54 (q. 1H), 3.57-3.58 (m, 4H), 3.25-3.29 (m, 1H), 2.93-3.06 (m, 3H), 2.39-2.45 (m, 5H), 1.94-1.97 (m, 1H).

(S)—N-(3-Chloro-4-fluorophenyl)-7-fluoro-1-(2-methoxyacetamido)-2,3-dihydro-1H-indene-4-carboxamide (75)

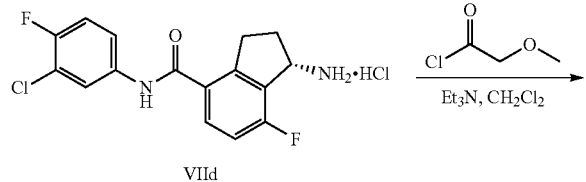

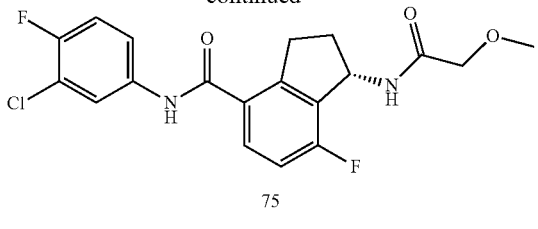

To a solution of 70 mg (0.19 mmol, 1.0 eq.) of (S)-1-amino-N-(3-chloro-4-fluorophenyl)-7-fluoro-2,3-dihydro-1H-indene-4-carboxamide hydrochloride (VIId) and 70 μL (0.5 mmol, 2.5 eq.) of trimethylamine in 2 mL of methylene chloride was added 20 μL (0.21 mmol, 1.1 eq.) of methoxyacetyl chloride, and the mixture was stirred at room temperature for 15 min. The mixture was then diluted with 40 mL of ethyl acetate and washed with 15 mL of water followed by 15 mL of 0.2 M HCl and 15 mL of sat. NaHCO$_3$. The organic phase was dried (Na$_2$SO$_4$), filtered and the solvent removed in vacuo. The residue was purified by flash chromatography (SiO$_2$, eluting with a linear gradient of 35-90% ethyl acetate/hexanes) to provide 60 mg (0.15 mmol, 78%) of (S)—N-(3-chloro-4-fluorophenyl)-7-fluoro-1-(2-methoxyacetamido)-2,3-dihydro-1H-indene-4-carboxamide (75). LCMS: m/z found 395.1/397.0 [M+H]$^+$ (Method A), RT=4.02 minutes. $^1$H NMR (300 MHz, CDCl$_3$) δ 7.83 (m, 2H), 7.61 (m, 1H), 7.44 (m, 1H), 7.15 (t, 1H), 7.02 (t, 1H), 6.79 (d, 1H), 5.62 (q, 1H), 3.94 (s, 2H), 3.46 (m, 1H), 3.41 (s, 3H), 3.14 (m, 1H), 2.61 (m, 1H), 2.03 (m, 1H).

(S)-1-Acetamido-N-(3-chloro-4-fluorophenyl)-7-fluoro-2,3-dihydro-1H-indene-4-carboxamide (77)

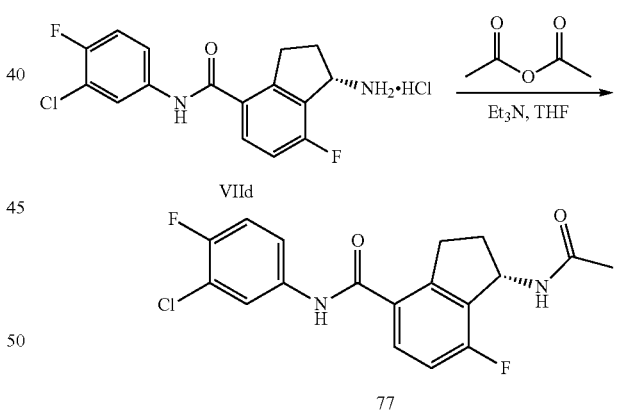

To a solution of 70 mg (0.19 mmol, 1.0 eq.) of (S)-1-amino-N-(3-chloro-4-fluorophenyl)-7-fluoro-2,3-dihydro-1H-indene-4-carboxamide hydrochloride (VIId) and 33 μL (0.24 mmol, 1.2 eq.) of trimethylamine in 2 mL of THF was added 20 μL (0.22 mmol, 1.1 eq.) of acetic anhydride. The resulting suspension was diluted with 2 mL of methylene chloride and stirred at room temperature for 1 h. The mixture was then diluted with 35 mL of methylene chloride and washed with 15 mL of 0.2 M HCl and 15 mL of sat. NaHCO$_3$. The organic phase was dried (Na$_2$SO$_4$), filtered and the solvent was removed in vacuo. The resulting white solid was crystallised from ethanol to provide 29 mg (0.08 mmol, 40%) of (S)-1-acetamido-N-(3-chloro-4-fluorophenyl)-7-fluoro-2,3-dihydro-1H-indene-4-carboxamide (77). LCMS: m/z found 365.1/367.1 [M+H]+ (Method A), RT=3.76 minutes. ¹H NMR (300 MHz, DMSO-d₆): δ 10.40 (s, 1H), 8.30 (d, 1H), 8.05 (m, 1H), 7.74-7.64 (m, 2H), 7.41 (t, 1H), 7.17 (t, 1H), 5.48 (q, 1H), 3.23 (m, 1H), 3.06 (m, 1H), 2.37 (m, 1H), 1.88 (m, 1H), 1.81 (s, 3H).

Example 8: Non-Limiting Synthesis of Selected 1-(Aryl/Heteroaryl-Substituted Amino)-Dihydroindene-4-Carboxamides Non-Limiting Illustration for N-Arylation with a 2-Halo Pyrimidine:

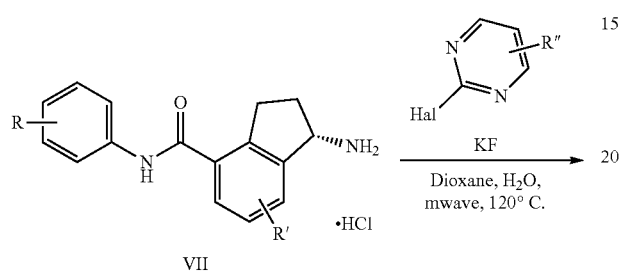

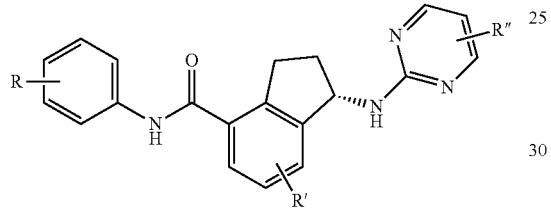

To a solution of 1.0 eq. of VII and 1.20 eq. of a 2-halopyrimidine in H₂O and dioxane was added 2.0 eq. of potassium fluoride. The mixture was subjected to microwave irradiation maintaining a reaction temperature of 120° C. for 1 h. The solvent was removed in vacuo, and the residue was purified by chromatography.

(S)—N-(3-chloro-4-fluorophenyl)-7-fluoro-1-(pyrimidin-2-ylamino)-2,3-dihydro-1H-indene-4-carboxamide (45)

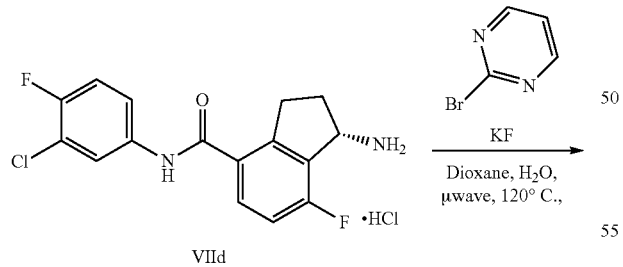

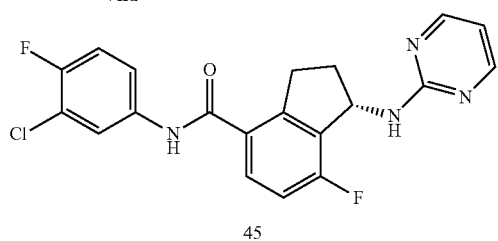

To a solution of 0.14 g (0.34 mmol, 1.0 eq.) of (S)-1-amino-N-(3-chloro-4-fluorophenyl)-7-fluoro-2,3-dihydro-1H-indene-4-carboxamide hydrochloride (VIId) and 75 mg (0.47 mmol, 1.20 eq.) of 2-bromopyrimidine in 2 mL of water and 2 mL of p-dioxane was added 45 mg (0.78 mmol, 2.0 eq.) of potassium fluoride, and the mixture was subjected to microwave irradiation, maintaining a reaction temperature of 120° C. for 1 h. The solvent was removed in vacuo, and the residue was purified by semi-preparative HPLC to provide 77 mg (0.17 mmol, 44%) of (S)—N-(3-chloro-4-fluorophenyl)-7-fluoro-1-(pyrimidin-2-ylamino)-2,3-dihydro-1H-indene-4-carboxamide (45). LCMS: m/z found 401.1/403.1 [M+H]+. HPLC: RT=2.87 min (Method G); ¹H NMR (300 MHz, d₄-methanol) δ 8.54 (d, 2H), 7.94 (dd, 1H), 7.73 (dd, 1H), 7.54-7.58 (m, 1H), 7.23 (dd, 1H), 7.08 (dd, 1H), 6.93 (dd, 1H), 5.86 (q, 1H), 3.38-3.46 (m, 1H), 3.16-3.24 (m, 1H), 2.63-2.70 (m 1H), 2.14-2.21 (m 1H).

(S)—N-(3-Chloro-4-fluorophenyl)-7-fluoro-1-((5-methoxypyrimidin-2-yl)amino)-2,3-dihydro-1H-indene-4-carboxamide (49)

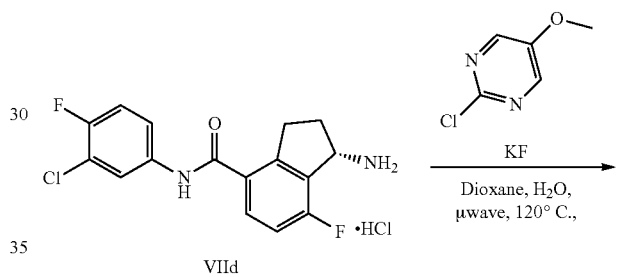

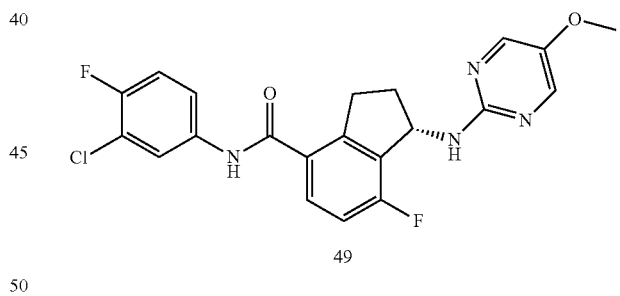

(S)—N-(3-Chloro-4-fluorophenyl)-7-fluoro-1-((5-methoxypyrimidin-2-yl)amino)-2,3-dihydro 1H-indene-4-carboxamide (49) was synthesized in a similar manner as outlined above from (S)-1-amino-N-(3-chloro-4-fluorophenyl)-7-fluoro-2,3-dihydro-1H-indene-4-carboxamide hydrochloride (VIId) and 2-chloro-5-methoxypyrimidine. LCMS: m/z found 431.0/433.0 [M+H]+. HPLC: RT=3.10 min (Method G); ¹H NMR (400 MHz, d₄-methanol) δ 8.32 (s, 2H), 7.94 (dd, 1H), 7.72 (dd, 1H), 7.56 (m, 1H), 7.23 (dd, 1H), 7.08 (dd, 1H), 7.86 (m, 1H), 3.88 (s, 3H), 3.34-3.43 (m, 1H), 3.17-3.21 (m, 1H), 2.63-2.65 (m 1H), 2.14-2.16 (m 1H).

2-Chloro-4-(pyridin-2-yl)pyrimidine a. (E)-3-(Dimethylamino)-1-(pyridin-2-yl)prop-2-en-1-one

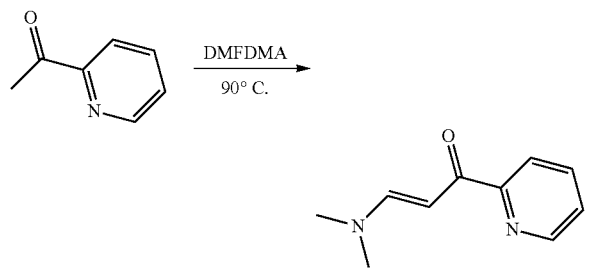

A solution of 4.0 g (33.0 mmol, 1.0 eq.) of 1-(pyridin-2-yl)ethan-1-one in 13.1 mL (99.1 mmol, 3.0 eq) of DMF dimethylacetal was stirred at 90° C. for 12 h. The mixture was allowed to cool to room temperature, and the resulting precipitate was collected by filtration. The solids were washed with 2×5 mL of ethyl acetate and dried under high vacuum to provide, 3.0 g (17.0 mmol, 51%) of (E)-3-(dimethylamino)-1-(pyridin-2-yl)prop-2-en-1-one.

b. 4-(Pyridin-2-yl)-2-aminopyrimidine

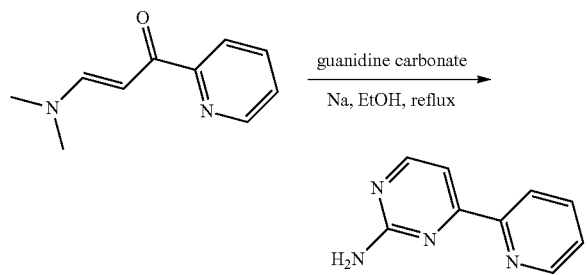

To a solution of 3.31 g (18.4 mmol, 1.1 eq.) of guanidine carbonate in 30 mL of anhydrous ethanol under a nitrogen atmosphere was added 1.0 g (43.6 mmol, 2.5 eq.) of sodium. On complete dissolution of the sodium, 3.0 g (17.0 mmol, 1.0 eq.) of (E)-3-(dimethylamino)-1-(pyridin-2-yl)prop-2-en-1-one were added, and the solution was heated at 80° C. for 12 h. The mixture was allowed to cool to room temperature, and the solvent was removed in vacuo. The resulting residue was washed with 2×20 mL of ice-cooled water, the solids collected by filtration and dried under high vacuum to provide 2.0 g (11.6 mmol, 68%) of 6-(pyridin-2-yl)-2-aminopyrimidine.

c. 6-(Pyridin-2-yl)pyrimidin-2(1H)-one

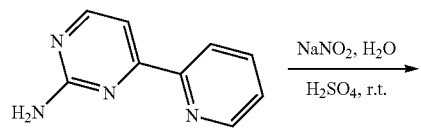

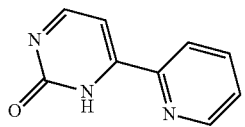

To a solution of 2.0 g (11.6 mmol, 1.0 eq.) of 6-(pyridin-2-yl)-2-aminopyrimidine in 20 mL of concentrated sulfuric acid containing 5% water at 8° C. was added 4.0 g (58.1 mmol, 5.0 eq.) of sodium nitrite, and the mixture was stirred at 8° C. for 2 hours. The reaction mixture was adjusted to pH 10 by the addition of 6 M aq. sodium hydroxide solution, and the mixture was extracted with 3×20 mL of 30% isopropanol in chloroform. The combined organic extracts were dried (Na$_2$SO$_4$), filtered and the solvent removed in vacuo to provide 2.0 g (11.6 mmol, 99%) of 6-(pyridin-2-yl)pyrimidin-2(1H)-one.

d. 2-Chloro-4-(pyridin-2-yl)pyrimidine

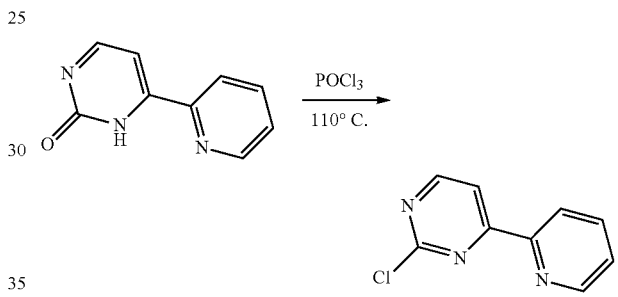

A solution of 1.7 g (9.8 mmol, 1.0 eq.) of 6-(pyridin-2-yl)pyrimidin-2(1H)-one in 27 mL (290 mmol, 30.0 eq.) of phosphorus oxychloride was stirred at 110° C. for 2 hours. The mixture was allowed to cool to room temperature and poured over a mixture of ice and water. The mixture was then adjusted to pH 14 with 6 M sodium hydroxide solution and extracted with 2×50 mL of methylene chloride. The combined organic extracts were dried (Na$_2$SO$_4$) filtered and the solvent was removed in vacuo to provide 0.7 g (3.36 mmol, 34%) of 2-chloro-4-(pyridin-2-yl) pyrimidine.

(S)—N-(3-Chloro-4-fluorophenyl)-7-fluoro-1-((4-(pyridin-2-yl)pyrimidin-2-yl)amino)-2,3-dihydro-1H-indene-4-carboxamide (50)

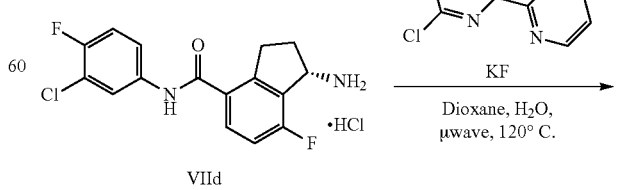

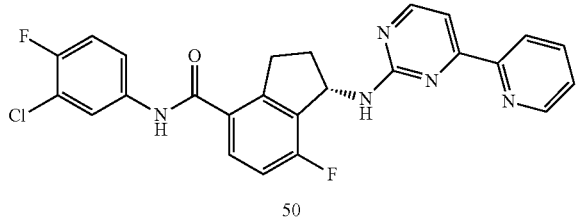

50

To a solution of 0.15 g (0.42 mmol, 1.0 eq.) of (S)-1-amino-N-(3-chloro-4-fluorophenyl)-7-fluoro-2,3-dihydro-1H-indene-4-carboxamide hydrochloride (VIId) in 2 mL of water and 2 mL of p-dioxane were added 0.12 g (0.63 mmol, 1.5 eq.) of 2-chloro-4-(pyridin-2-yl)pyrimidine and 73 mg (1.25 mmol, 3.0 eq.) of potassium fluoride. The mixture was subjected to microwave irradiation, maintaining a reaction temperature of 120° C. for 1 h. The solvent was removed in vacuo and the residue was purified by semi-preparative HPLC to provide 27 mg (0.06 mmol, 14%) of (S)—N-(3-chloro-4-fluorophenyl)-7-fluoro-1-((4-(pyridin-2-yl)pyrimidin-2-yl)amino)-2,3-dihydro-1H-indene-4-carboxamide (50). LCMS: m/z found 478.2/480.2 [M+H]$^+$. HPLC: RT=3.23 min (Method G); $^1$H NMR (400 MHz, d$_4$-methanol) δ 8.86 (d, 1H), 8.60 (d, 1H), 8.53-8.58 (m, 1H), 8.26-8.31 (m, 1H), 7.96 (dd, 1H), 7.80-7.92 (m, 1H), 7.75 (dd, 1H), 7.55-7.70 (m, 1H), 7.46 (dd, 1H), 7.10 (dd, 1H), 6.251-6.21 (m, 1H), 3.46-3.55 (m, 1H), 3.21-3.28 (m, 1H), 2.68-2.80 (m, 1H), 2.22-2.29 (m, 1H).

(S)—N-(3-Chloro-4-fluorophenyl)-7-fluoro-1-(pyridin-2-ylamino)-2,3-dihydro-1H-indene-4-carboxamide Hydrochloride (97)

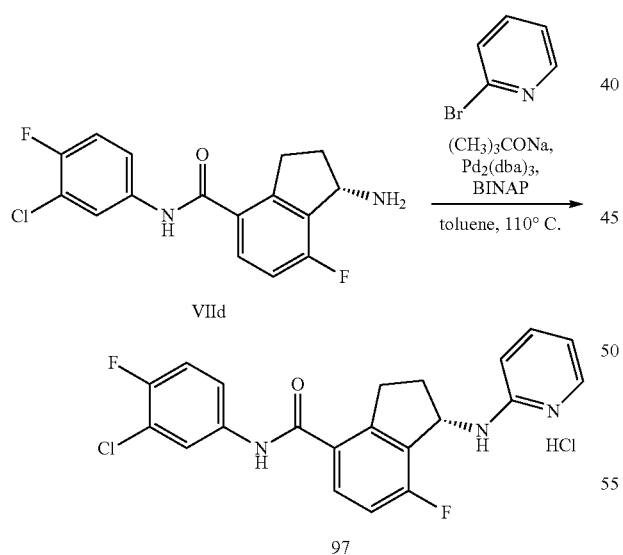

97

To a mixture of 0.15 g (0.46 mmol, 1.0 eq.) of (S)-1-amino-N-(3-chloro-4-fluorophenyl)-7-fluoro-2,3-dihydro-1H-indene-4-carboxamide free base (VIId) and 44 µL (0.46 mmol, 1.0 eq) of 2-bromopyridine in 10 mL of toluene was added 28 mg (0.046 mmol, 0.1 eq.) of BINAP followed by 133 mg (1.39 mmol, 3.0 eq) of sodium-tert-butoxide and 21 mg (0.023 mmol, 0.05 eq) of Pd$_2$(dba)$_3$, and the mixture was stirred at 110° C. for 15 h. The mixture was allowed to cool to room temperature, and the solvent was removed in vacuo. The residue was purified by prep-HPLC under neutral pH to provide 20 mg of (S)—N-(3-chloro-4-fluorophenyl)-7-fluoro-1-(pyridin-2-ylamino)-2,3-dihydro-1H-indene-4-carboxamide (97), which was converted to the hydrochloride salt using HCl in methanol. LCMS: m/z found 400.1/402.1 [M+H]$^+$, RT=2.36 min (Method G); $^1$H NMR (DMSO-d$_6$, 400 MHz): δ 10.52 (s, 1H), 9.18 (s, 1H), 8.06-8.05 (m, 1H), 7.99-7.97 (m, 1H), 7.90 (m, 1H) 7.82-7.80 (m, 1H), 7.65 (m, 1H), 7.43-7.38 (m, 1H), 7.26-7.24 (m, 1H), 7.06 (m, 1H), 6.89 (m, 1H) 5.69 (m, 1H), 3.31-3.29 (m, 1H), 3.15-3.08 (m, 1H), 2.59-2.57 (m, 1H), 2.06 (m, 1H).

(S)-2-((4-((3-Chloro-4-fluorophenyl)carbamoyl)-7-fluoro-2,3-dihydro-1H-inden-1-yl)amino)pyrimidine-4-carboxamide (104)

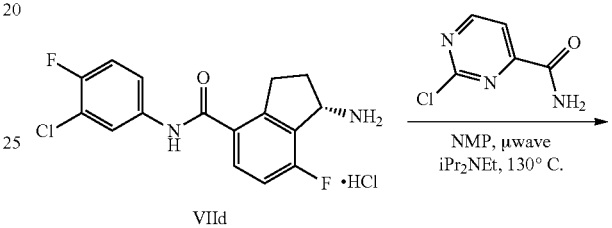

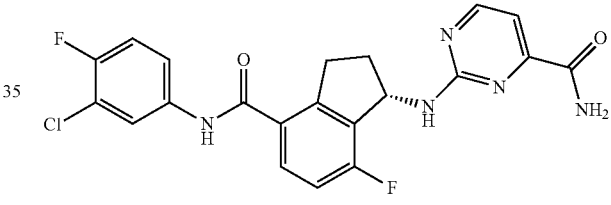

104

To a solution of 0.07 g (0.19 mmol, 1.0 eq.) of (S)-1-amino-N-(3-chloro-4-fluorophenyl)-7-fluoro-2,3-dihydro-1H-indene-4-carboxamide hydrochloride (VIId) and 30 mg (0.21 mmol, 1.10 eq.) of 2-chloropyrimidine-4-carboxamide in 2 mL of NMP was added 0.07 ml (0.39 mmol, 2.0 eq.) of N,N-diisopropylethylamine, and the mixture was subjected to microwave irradiation maintaining a reaction temperature of 130° C. for 1 h. The mixture was diluted with 50 mL of ethyl acetate and washed 2×20 ml of water followed by 10 mL of brine. The organic phase was dried (Na$_2$SO$_4$), filtered and the solvent was removed in vacuo. The residue was purified by flash chromatography (SiO$_2$, eluting with a linear gradient of 0-30% ethyl acetate/hexanes) to provide 24 mg (0.05 mmol, 29%) of (S)-2-((4-((3-chloro-4-fluorophenyl)carbamoyl)-7-fluoro-2,3-dihydro-1H-inden-1-yl)amino)pyrimidine-4-carboxamide (104). LCMS: m/z found 444.1/446.1 [M+H]$^+$. HPLC: RT=4.13 min (Method A); $^1$H NMR (300 MHz, Methanol-d$_4$) δ 8.50 (d, 1H), 7.93 (dd, 1H), 7.61-7.72 (m, 1H), 7.50-7.60 (m, 1H), 7.16-7.28 (m, 2H), 7.03 (t, 1H), 5.88-5.95 (m, 1H), 3.07-3.48 (m, 2H), 2.55-2.66 (m, 1H), 2.10 (m, 1H).

(S)—N-(3-Chloro-4-fluorophenyl)-7-fluoro-1-(pyrimidin-4-ylamino)-2,3-dihydro-1H-indene-4-carboxamide (196)

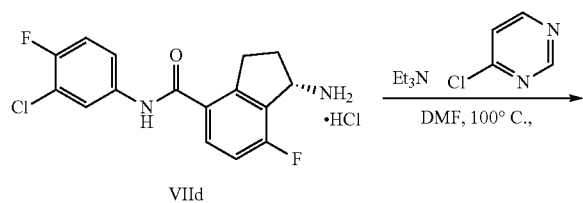

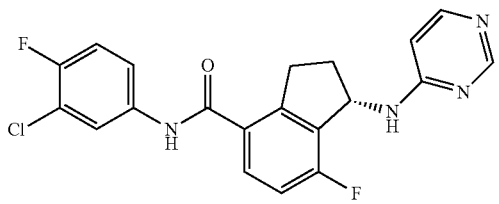

196

To a stirred solution of 40 mg (0.11 mmol, 1.0 eq.) of (S)-1-amino-N-(3-chloro-4-fluorophenyl)-7-fluoro-2,3-dihydro-1H-indene-4-carboxamide hydrochloride (VIId) and 20 mg (0.13 mmol, 1.2 eq.) of 4-chloropyrimidine in 5 ml of DMF at 0° C. was added 24 mg (0.22 mmol, 2.0 eq.) of triethylamine. The reaction mixture was allowed to warm to room temperature and then stirred at 100° C. for 1 h. The reaction was diluted with 5 ml of water and extracted with 3×10 mL of ethyl acetate. The combined organic extracts were washed with 5 mL of brine, dried (Na$_2$SO$_4$), filtered and the solvent removed in vacuo. LCMS: m/z found 401.2/403.2 [M+H]$^+$ (Method H) RT=1.87 min.

(S)—N-(3-Chloro-4-fluorophenyl)-7-fluoro-1-((4-methoxypyrimidin-2-yl)amino)-2,3-dihydro-1H-indene-4-carboxamide (159)

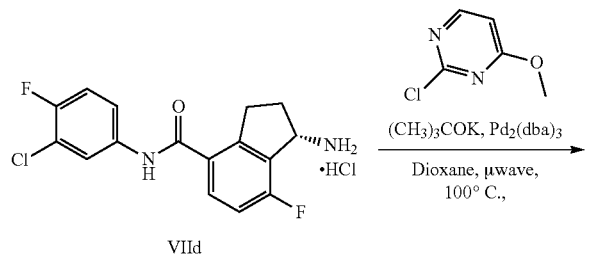

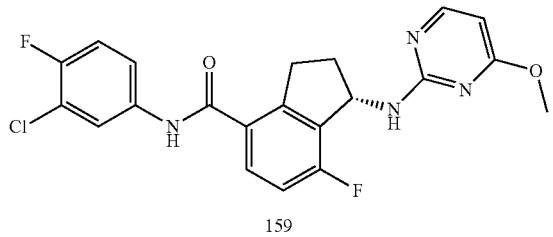

159

To a solution of 60 mg (0.167 mmol, 1 eq.) of (S)-1-amino-N-(3-chloro-4-fluorophenyl)-7-fluoro-2,3-dihydro-1H-indene-4-carboxamide hydrochloride (VIId) and 29 mg (0.20 mmol, 1.2 eq.) of 2-chloro-4-methoxypyrimidine in 10 ml of p-dioxane was added 48 mg (0.501 mmol, 3.0 eq.) of potassium tert-butoxide. The solution was degassed with argon for 10 min and 16 mg (0.016 mmol, 0.1 eq.) of Pd$_2$(dba)$_3$ and 7 mg (0.016 mmol, 0.1 eq) of 1,3-bis[2,6-bis(1-methylethyl)phenyl]-1H-imidazolium chloride were added. The mixture was subject to microwave irradiation maintaining a reaction temperature of 100° C. for 1 h. The mixture was diluted with 5 ml of water and extracted with 3×10 mL of ethyl acetate. The combined organic extracts were washed with 5 mL of brine, dried (Na$_2$SO$_4$), filtered and the solvent removed in vacuo. The residue was purified by semi-preparative HPLC to provide 24 mg (33%) of (S)—N-(3-chloro-4-fluorophenyl)-7-fluoro-1-((4-methoxypyrimidin-2-yl)amino)-2,3-dihydro-1H-indene-4-carboxamide (159). LCMS: m/z found 431.2/433.2 [M+H]$^+$ (Method H); HPLC: 9.61 min (Method M); $^1$H NMR (400 MHz, DMSO-d$_6$) δ ppm 10.40 (s, 1H), 8.03-8.08 (m, 2H), 7.65-7.71 (m, 3H), 7.42 (t, 1H), 7.12 (t, 1H), 6.05 (d, 1H), 5.77 (m, 1H), 3.78 (s, 3H), 3.05-3.27 (m, 1H), 3.01-3.09 (m, 1H), 2.39-2.49 (m, 1H), 1.95-2.15 (m, 1H).

(S)—N-(3-Chloro-4-fluorophenyl)-7-fluoro-1-((4-methoxypyrimidin-2-yl)amino)-2,3-dihydro-1H-indene-4-carboxamide (160)

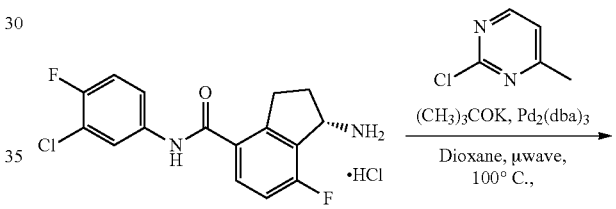

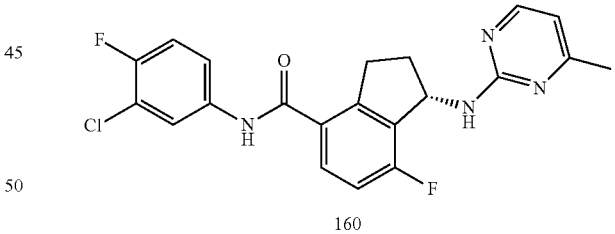

160

(S)—N-(3-Chloro-4-fluorophenyl)-7-fluoro-1-((4-methoxypyrimidin-2-yl)amino)-2,3-dihydro-1H-indene-4-carboxamide (160) was prepared in a similar manner as described above from (S)-1-amino-N-(3-chloro-4-fluorophenyl)-7-fluoro-2,3-dihydro-1H-indene-4-carboxamide hydrochloride (VIId) and 2-chloro-4-methylpyrimidine. LCMS: m/z found 415.2/417.2 [M+H]$^+$, RT=2.21 min (Method H); HPLC: RT=11.33 min (Method M); $^1$H NMR (400 MHz, DMSO-d$_6$) δ ppm 10.40 (s, 1H), 8.16 (d, 1H), 8.06 (dd, 1H), 7.66-7.69 (m, 2H), 7.39-7.48 (m, 2H), 7.11 (t, 1H), 6.49 (d, 1H), 5.79 (m, 1H), 3.21-3.27 (m, 1H), 3.01-3.09 (m, 1H), 2.39-2.49 (m, 1H), 2.25 (s, 3H), 1.86-2.01 (m, 1H).

(S)—N-(3-Chloro-4-fluorophenyl)-7-fluoro-1-((2-methoxypyrimidin-4-yl)amino)-2,3-dihydro-1H-indene-4-carboxamide (161)

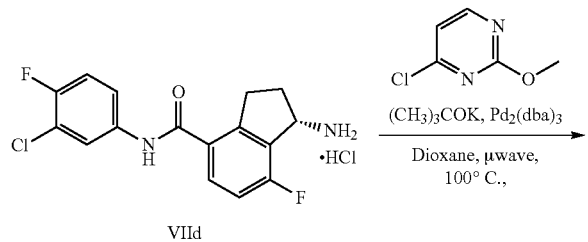

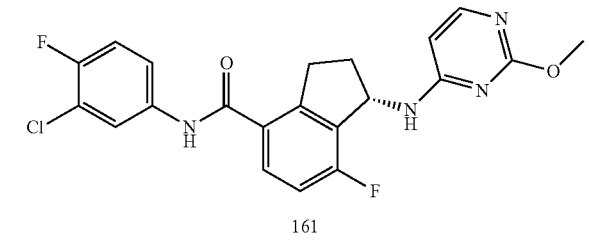

(S)—N-(3-Chloro-4-fluorophenyl)-7-fluoro-1-((2-methoxypyrimidin-4-yl)amino)-2,3-dihydro-1H-indene-4-carboxamide (161) was prepared in a similar manner as described above from (S)-1-amino-N-(3-chloro-4-fluorophenyl)-7-fluoro-2,3-dihydro-1H-indene-4-carboxamide hydrochloride (VIId) and 4-chloro-2-methoxypyrimidine. LCMS: m/z found 431.1/433.1 [M+H]$^+$, RT=1.66 min (Method H); HPLC: RT=8.90 min (Method M); $^1$H NMR (400 MHz, DMSO-d$_6$) δ ppm 10.42 (s, 1H), 8.04-8.08 (m, 1H), 7.89-7.85 (m, 2H), 7.65-7.75 (m, 2H), 7.42 (t, 1H), 7.18 (t, 1H), 6.11 (m, 1H), 5.77 (m, 1H), 3.77 (s, 3H), 3.21-3.27 (m, 1H), 3.01-3.09 (m, 1H), 2.42-2.45 (m, 1H), 1.95-1.99 (m, 1H).

(S)—N-(3-Chloro-4-fluorophenyl)-7-fluoro-1-(thiazol-2-ylamino)-2,3-dihydro-1H-indene-4-carboxamide (146)

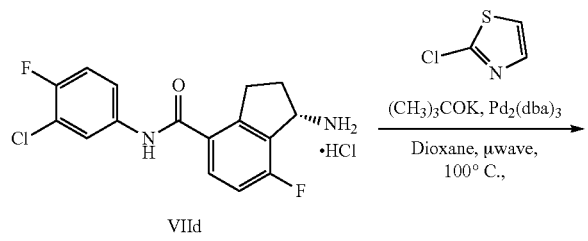

(S)—N-(3-Chloro-4-fluorophenyl)-7-fluoro-1-(thiazol-2-ylamino)-2,3-dihydro-1H-indene-4-carboxamide (146) was prepared in a similar manner as described above from (S)-1-amino-N-(3-chloro-4-fluorophenyl)-7-fluoro-2,3-dihydro-1H-indene-4-carboxamide hydrochloride (VIId) and 2-chlorothiazole. LCMS: m/z found 406.2/408.2 [M+H]$^+$, RT=1.98 min (Method H); HPLC: RT=11.20 min (Method M); $^1$H NMR (400 MHz, DMSO-d$_6$) δ ppm 10.42 (s, 1H), 8.04-8.06 (dd, 1H), 7.95-7.97 (d, 1H), 7.72-7.75 (m, 1H), 7.65-7.69 (m, 1H), 7.3-7.43 (t, 1H), 7.16-7.20 (t, 1H), 7.04-7.05 (d, 1H), 6.62-6.63 (d, 1H), 5.44-5.47 (m, 1H), 3.22-3.33 (m, 1H), 2.99-3.14 (m, 1H), 2.33-2.49 (m, 1H), 1.95-2.06 (m, 1H).

(S)—N-(3-Chloro-4-fluorophenyl)-7-fluoro-1-((5-methylpyrimidin-2-yl)amino)-2,3-dihydro-1H-indene-4-carboxamide (162)

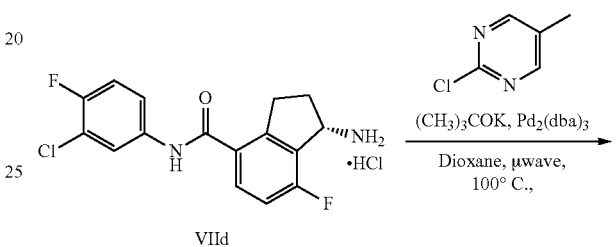

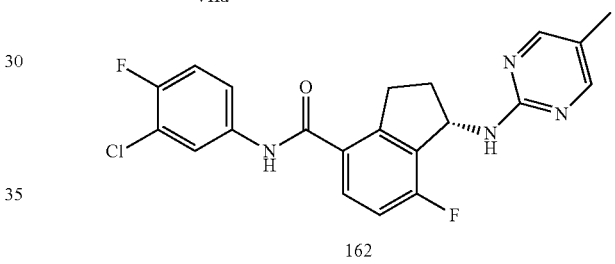

(S)—N-(3-Chloro-4-fluorophenyl)-7-fluoro-1-((5-methylpyrimidin-2-yl)amino)-2,3-dihydro-1H-indene-4-carboxamide (162) was prepared in a similar manner as described above from (S)-1-amino-N-(3-chloro-4-fluorophenyl)-7-fluoro-2,3-dihydro-1H-indene-4-carboxamide hydrochloride (VIId) and 2-chloro-5-methylpyrimidine. LCMS: m/z found 415.2/417.2[M+H]$^+$, RT=2.30 min (Method H); HPLC: RT=11.66 min (Method M); $^1$H NMR (400 MHz, DMSO-d$_6$) δ ppm 10.40 (s. 1H). 8.16 (s. 2H). 8.05-8.06 (dd, 1H), 7.66-7.70 (m, 2H), 7.35-7.44 (m, 2H), 7.09-7.14 (t, 1H), 5.76-5.74 (m, 1H), 3.22-3.33 (m, 1H), 2.99-3.14 (m, 1H), 2.33-2.49 (m, 1H), 2.06 (s, 3H), 1.95-2.04 (m, 1H).

(S)—N-(3-Chloro-4-fluorophenyl)-7-fluoro-1-((6-methoxypyrimidin-4-yl)amino)-2,3-dihydro-1H-indene-4-carboxamide (163)

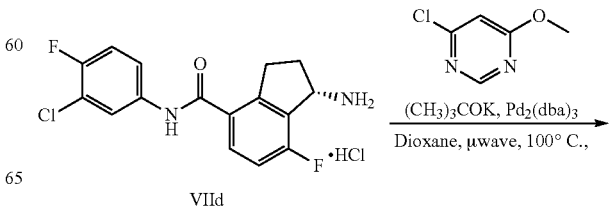

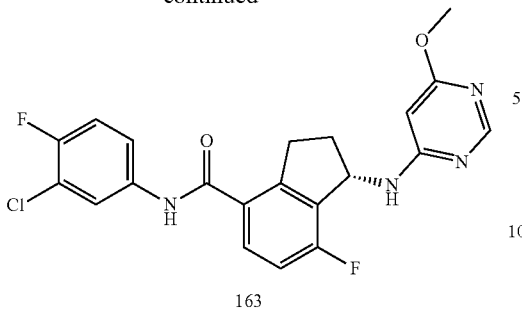

163

(S)—N-(3-Chloro-4-fluorophenyl)-7-fluoro-1-((6-methoxypyrimidin-4-yl)amino)-2,3-dihydro-1H-indene-4-carboxamide (163) was prepared in a similar manner as described above from (S)-1-amino-N-(3-chloro-4-fluorophenyl)-7-fluoro-2,3-dihydro-1H-indene-4-carboxamide hydrochloride (VIId) and 4-chloro-6-methoxypyrimidine. LCMS: m/z found 431.2/433.2 [M+H]$^+$, RT=2.18 min (Method H); HPLC: RT=11.01 min (Method M); $^1$H NMR (400 MHz, DMSO-d$_6$) δ ppm 10.42 (s, 1H), 8.21 (s, 1H), 8.04-8.06 (dd, 1H), 7.71-7.74 (m, 1H), 7.68-7.66 (m, 1H), 7.59 (d, 1H), 7.39-7.43 (t, 1H), 7.15-7.18 (t, 1H), 5.79 (m, 2H), 3.79 (s, 3H), 3.22-3.31 (m, 1H), 3.05-3.14 (m, 1H), 2.47-2.49 (m, 1H), 1.94-1.99 (m, 1H).

(S)—N-(3-Chloro-4-fluorophenyl)-1-((4,6-dimethylpyrimidin-2-yl)amino)-7-fluoro-2,3-dihydro-1H-indene-4-carboxamide (164)

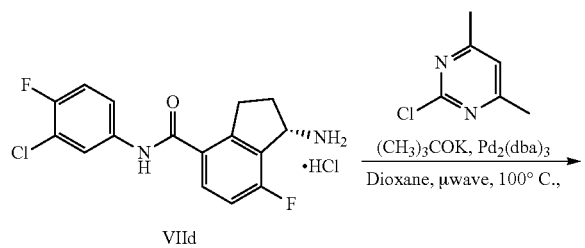

VIId

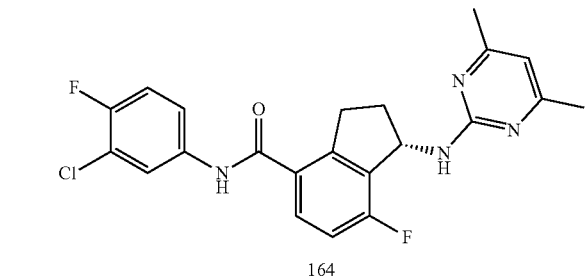

164

(S)—N-(3-Chloro-4-fluorophenyl)-1-((4,6-dimethylpyrimidin-2-yl)amino)-7-fluoro-2,3-dihydro-1H-indene-4-carboxamide (164) was prepared in a similar manner as described above from (S)-1-amino-N-(3-chloro-4-fluorophenyl)-7-fluoro-2,3-dihydro-1H-indene-4-carboxamide hydrochloride (VIId) and 2-chloro-4,6-dimethylpyrimidine. LCMS: m/z found 429.2/431.2 [M+H]$^+$, RT=2.17 min (Method H); HPLC: RT=10.68 min (Method M); $^1$H NMR (400 MHz, DMSO-d$_6$) δ ppm 10.40 (s, 1H), 8.05 (d, 1H), 7.65-7.66 (m, 2H), 7.35-7.44 (m, 2H), 7.08-7.11 (t, 1H), 6.38 (s, 1H), 5.80-5.82 (m, 1H), 3.29-3.20 (m, 1H), 3.01-3.05 (m, 1H), 2.49-2.41 (m, 1H), 2.21 (s, 6H) 1.95-1.89 (m, 1H).

2-Chloro-7-(4-methoxybenzyl)-7H-pyrrolo[2,3-d]pyrimidine

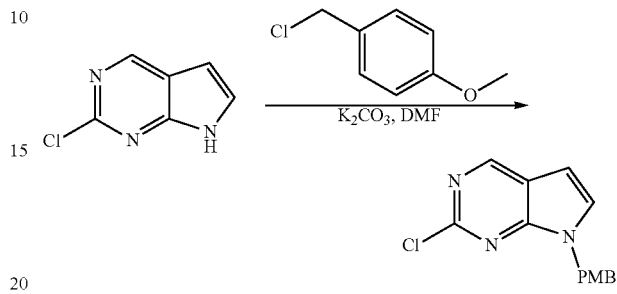

To a mixture of 0.3 g (1.95 mmol, 1.0 eq.) of 2-chloro-7H-pyrrolo[2,3-d]pyrimidine and 0.41 g (2.93 mmol, 1.5 eq.) of potassium carbonate in 5 mL of DMF at 0° C. was added 0.46 g (2.93 mmol, 1.5 eq.) of 4-methoxybenzyl chloride dropwise. The mixture was then stirred at room temp for 16 h. The reaction was diluted with 5 mL of water and extracted with 3×10 mL of ethyl acetate. The combined organic extracts were washed with 5 mL of brine, dried (Na$_2$SO$_4$), filtered, and the solvent was removed in vacuo to provide 0.48 g (1.76 mmol, 90%) of 2-chloro-7-(4-methoxybenzyl)-7H-pyrrolo[2,3-d]pyrimidine. LCMS: m/z found 274.1 [M+H]$^+$ (Method H); $^1$H NMR (400 MHz, CDCl3) δ 8.79 (s, 1H), 7.26 (s, 1H), 7.18-7.21 (m, 1H), 7.12 (d, 1H), 6.85-6.87 (m, 2H), 6.54 (d, 1H), 5.34 (s, 2H), 3.79 (s, 3H).

(S)—N-(3-Chloro-4-fluorophenyl)-7-fluoro-1-((7-(4-methoxybenzyl)-7H-pyrrolo[2,3-d]pyrimidin-2-yl)amino)-2,3-dihydro-1H-indene-4-carboxamide (197)

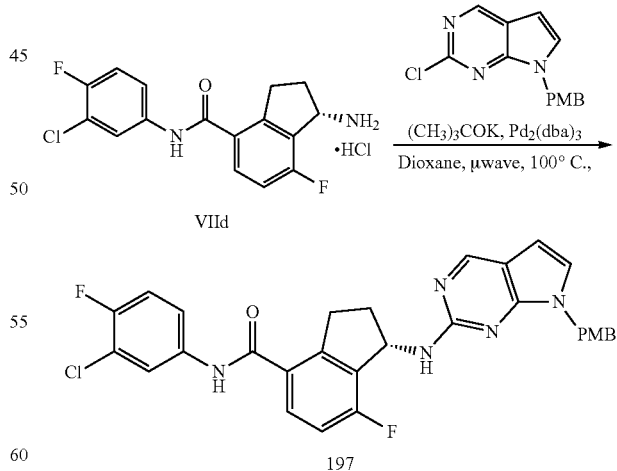

197

(S)—N-(3-Chloro-4-fluorophenyl)-7-fluoro-1-((7-(4-methoxybenzyl)-7H-pyrrolo[2,3-d]pyrimidin-2-yl)amino)-2,3-dihydro-1H-indene-4-carboxamide (197) was prepared in a similar manner as described above from (S)-1-amino-N-(3-chloro-4-fluorophenyl)-7-fluoro-2,3-dihydro-1H-indene-4-carboxamide hydrochloride (VIId) and 2-chloro-7-(4-methoxybenzyl)-7H-pyrrolo[2,3-d]pyrimidine. LCMS: m/z found 560.2/562.2 [M+H]+, RT=1.97 min (Method H); HPLC: RT=10.81 min (Method M); $^1$H NMR (400 MHz, DMSO-$d_6$) δ 10.39 (s, 1H), 8.52 (s, 1H), 8.04-8.06 (m, 1H), 7.65-7.71 (m, 2H), 7.39-7.43 (t, 1H), 7.13-7.24 (m, 3H), 7.11-7.12 (m, 2H), 6.83-6.85 (d, 2H), 6.33 (d, 1H), 5.85 (d, 1H), 5.13 (s, 2H), 3.69 (s, 3H), 3.28-3.31 (m, 1H), 3.05-3.13 (m, 1H), 2.49-2.50 (m, 1H), 2.01-2.08 (m, 1H).
Example 9: Non-Limiting Synthesis of Selected 1-(Substituted Amino-Dihydrobenzofuran-4-Carboxamides (Scheme 4)
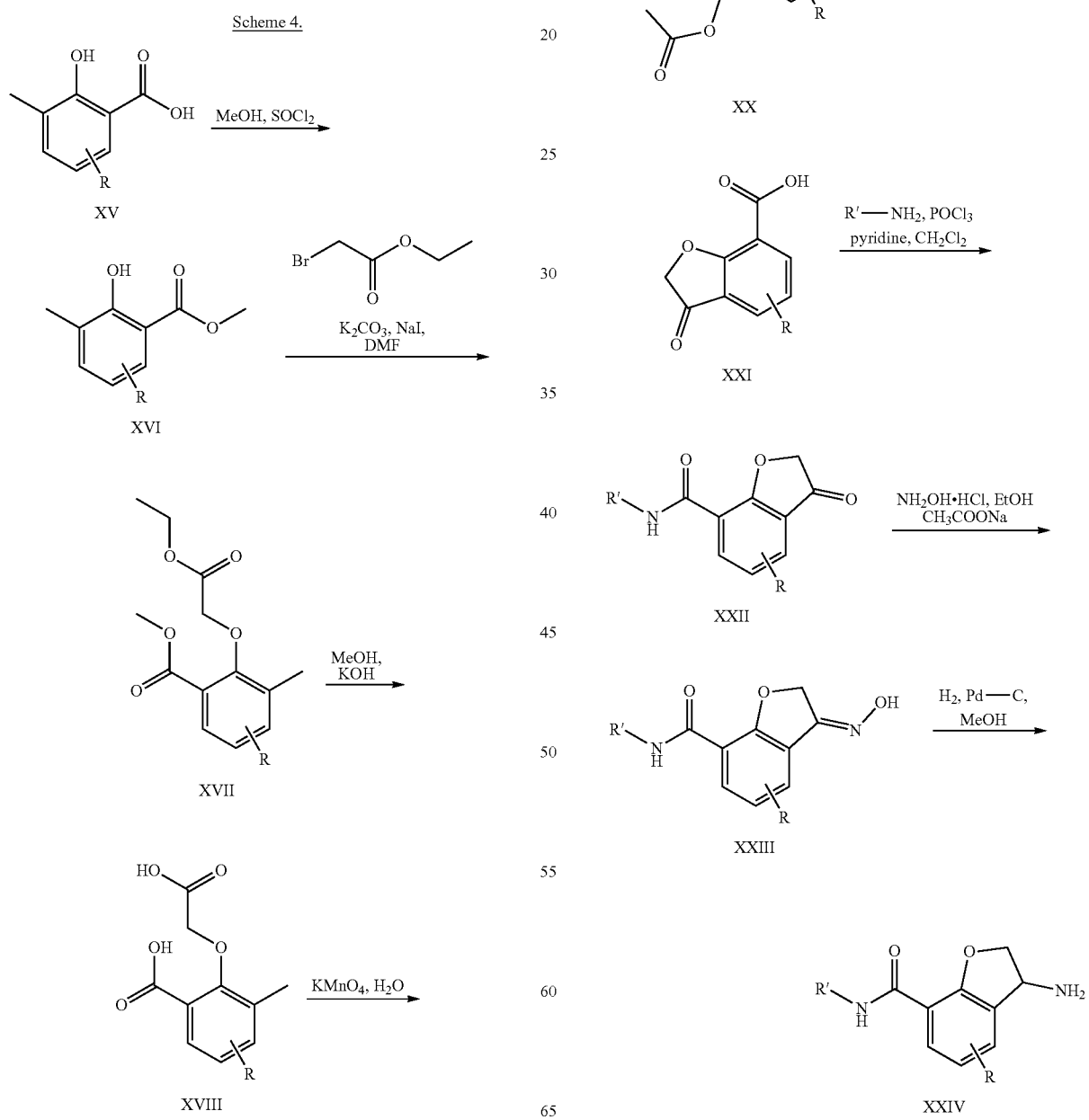

Non-Limiting Illustration of Scheme 4

Methyl 2-hydroxy-3-methylbenzoate (XVIa)

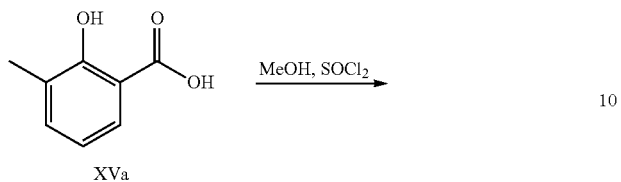

To a solution of 20.0 g (131.4 mmol, 1.0 eq.) of 5-methylsalicylic acid (XVa) in 300 mL of methanol was slowly added 45.89 g (394.3 mmol, 3.0 eq.) of thionyl chloride, and the mixture was heated at reflux for 12 h. The mixture was then allowed to cool to room temperature, and the volatiles were removed in vacuo. The resulting oil was partitioned between 100 mL of water and 100 mL of ethyl acetate. The layers were separated and the aqueous phase was extracted with 2×100 mL of ethyl acetate. The combined organic extracts were washed with 200 mL of sat. NaHCO$_3$ solution, dried (Na$_2$SO$_4$) and the solvent was removed in vacuo to provide 15 g (90.3 mmol, 69%) of methyl 2-hydroxy-3-methylbenzoate (XVIa).

Methyl 2-(2-ethoxy-2-oxoethoxy)-3-methylbenzoate (XVIIa)

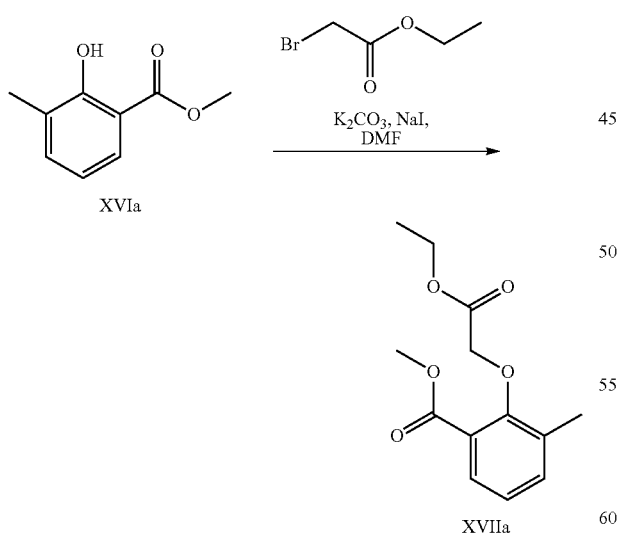

To a solution of 28.0 g (169 mmol, 1.0 eq.) of methyl 2-hydroxy-3-methylbenzoate (XVIa) in 280 mL of DMF at 0° C. was added 42.23 g (253 mmol, 1.5 eq.) of ethyl 2-bromoacetate followed by 38.0 g (253 mmol, 1.5 eq.) of sodium iodide and 34.9 g (253 mmol, 1.5 eq.) of potassium carbonate. The reaction mixture was allowed to warm to room temperature and stirred for 12 h. The mixture was then poured into 500 mL of water and extracted with 3×500 mL of ethyl acetate. The combined organic extracts were dried (Na$_2$SO$_4$) and the solvent was removed in vacuo to provide 26 g (103 mmol, 61%) of methyl 2-(2-ethoxy-2-oxoethoxy)-3-methylbenzoate (XVIIa).

2-(Carboxymethoxy)-3-methylbenzoic Acid (XVIIIa)

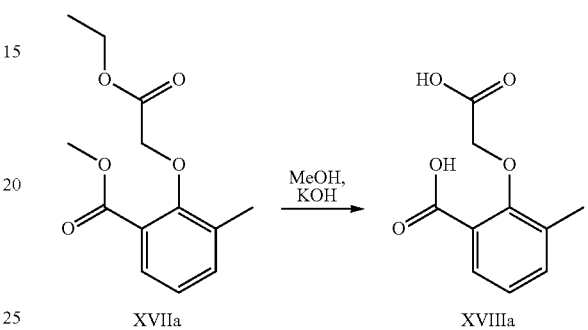

To a solution of 21 g (83.3 mmol, 1.0 eq.) of methyl 2-(2-ethoxy-2-oxoethoxy)-3-methylbenzoate (XVIIa) in 150 mL of methanol was added 10 g (250 mmol, 3.0 eq.) of sodium hydroxide, and the mixture was heated to reflux for 2 h. The mixture was allowed to cool to room temperature and the solvent was removed in vacuo. The resulting white solid was dissolved in water and cooled to 0° C. To this solution was added concentrated hydrochloric acid dropwise to pH 1. The resulting white precipitate was collected by filtration and dried under high vacuum to provide 15 g (71.4 mmol, 84%) of 2-(carboxymethoxy)-3-methylbenzoic acid (XVIIIa).

2-(Carboxymethoxy)isophthalic Acid (XIXa)

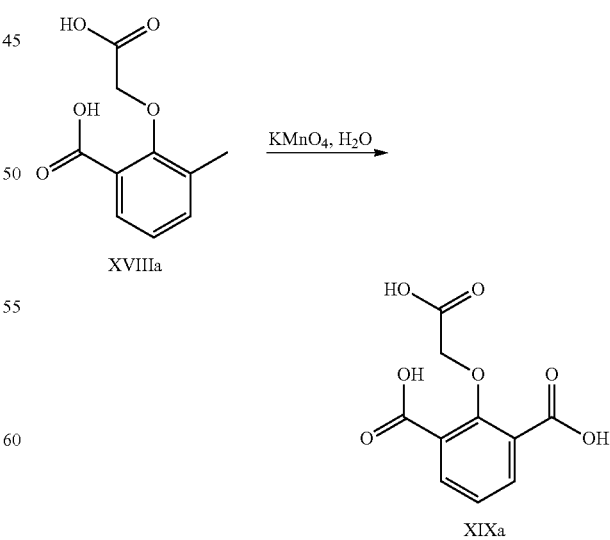

To a suspension of 10.0 g (47.6 mmol, 1.0 eq.) of 2-(carboxymethoxy)-3-methylbenzoic acid (XVIIIa) in 100 mL of water was slowly added 37.7 g (238.0 mmol, 5.0 eq.) of potassium permanganate. The resulting mixture was then heated to reflux for 2 h. A further 37.7 g (238.0 mmol, 5.0 eq.) of potassium permanganate was added and the resulting mixture was heated at reflux for 2 h. The reaction mixture was then filtered, and filtrate was concentrated in vacuo. The resulting white solid was dissolved in water and cooled to 0° C. To this solution was added concentrated hydrochloric acid dropwise to pH 1. The resulting white precipitate was collected by filtration and dried under high vacuum to provide 2.8 g (11.7 mmol, 25%) of 2-(carboxymethoxy) isophthalic acid (XIXa).

A solution of 1.4 g (6.4 mmol, 1.0 eq.) of 3-acetoxybenzofuran-7-carboxylic acid (XXa) in 30 mL of conc. HCl/H₂O/MeOH (1:10:40 v/v/v) was heated at reflux for 1 h. The mixture was allowed to cool to room temperature and the methanol removed in vacuo. The resulting solid was collected by filtration, washed with water and dried under high vacuum to provide 0.9 g (5.0 mmol, 79%) of 3-oxo-2,3-dihydrobenzofuran-7-carboxylic acid (XXIa).

N-(3,4-difluorophenyl)-3-oxo-2,3-dihydrobenzofuran-7-carboxamide (XXIIa)

3-Acetoxybenzofuran-7-carboxylic Acid (XXa)

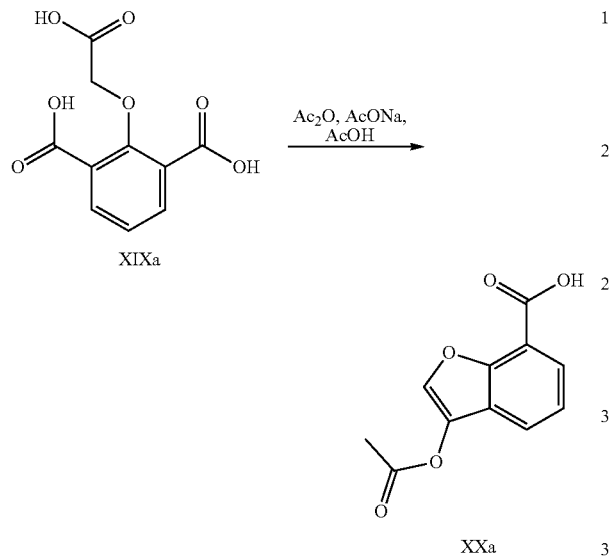

XIXa

XXa

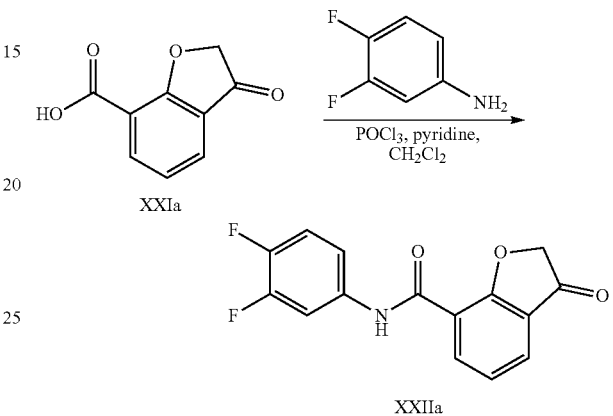

XXIa

XXIIa

To a mixture of 3.5 g (14.5 mmol, 1.0 eq.) of 2-(carboxymethoxy)isophthalic acid (XIXa) and 1.48 g (17.4 mmol, 1.2 eq.) of sodium acetate in 12 mL of acetic acid was added 20 mL of acetic anhydride and the resulting mixture was heated at reflux for 5 h. The mixture was allowed to cool to room temperature and poured into 150 mL of ice water. The mixture was then extracted with 3×50 mL of ethyl acetate, and the combined organic extracts were dried (Na₂SO₄). The solvent was removed in vacuo, and the residue was purified by flash chromatography on (SiO₂, eluting with 10% ethyl acetate/hexanes) to provide 1.6 g (7.3 mmol, 50%) of 3-acetoxybenzofuran-7-carboxylic acid (XXa).

To a solution of 0.5 g (2.80 mmol, 1.0 eq.) of 3-oxo-2,3-dihydrobenzofuran-7-carboxylic acid (XXIa) in 10 mL of methylene chloride were added 0.54 g (4.21 mmol, 1.5 eq.) of 3,4-difluoroaniline and 0.34 mL (4.21 mmol, 1.5 eq.) of pyridine. The reaction mixture was cooled to 0° C., and 0.65 g (4.21 mmol, 1.5 eq.) of phosphorus oxychloride was added. The mixture was stirred at 0° C. for 1 h and then poured into ice. The mixture was extracted with 2×50 mL of ethyl acetate, and the combined organic extracts were washed with 50 mL of sat. NaHCO₃ solution. The organic phase was dried (Na₂SO₄), and the solvent was removed in vacuo. The residue was purified by flash chromatography (SiO₂, eluting with 25% ethyl acetate/hexanes) to provide 0.37 g (1.3 mmol, 45%) of N-(3,4-difluorophenyl)-3-oxo-2,3-dihydrobenzofuran-7-carboxamide (XXIIa).

N-(3,4-Difluorophenyl)-3-(hydroxyimino)-2,3-dihydrobenzofuran-7-carboxamide (XXIIIa)

3-Oxo-2,3-dihydrobenzofuran-7-carboxylic Acid (XXIa)

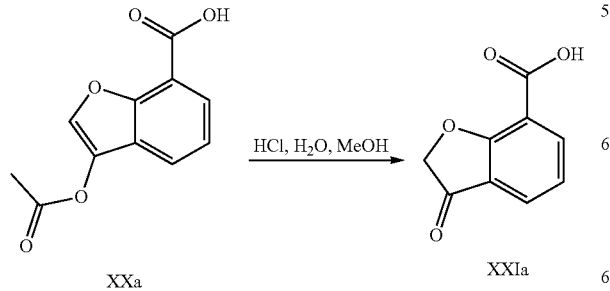

XXa

XXIa

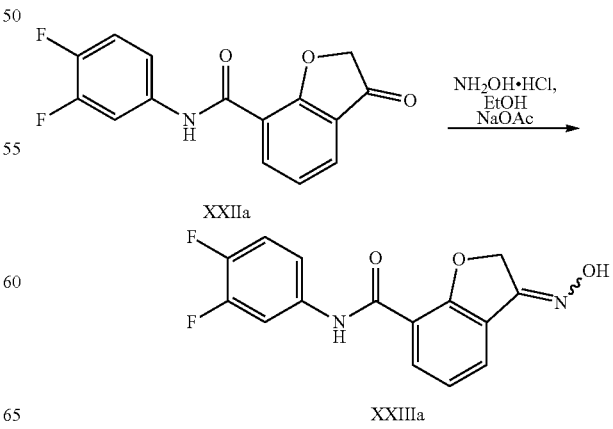

XXIIa

XXIIIa

To a solution of 1.0 g (3.44 mmol, 1.0 eq.) of N-(3,4-difluorophenyl)-3-oxo-2,3-dihydrobenzofuran-7-carboxamide (XXIIa) in 10 mL of ethanol was added 0.85 g (10.34 mmol, 3.0 eq.) of sodium acetate, followed by 0.71 g (10.3 mmol, 3.0 eq.) of hydroxylamine hydrochloride. The mixture was stirred at room temperature for 12 h. The mixture was poured in 50 mL of water and extracted with 2×50 mL of ethyl acetate. The combined organic extracts were dried (Na$_2$SO$_4$) and the solvent was removed in vacuo to provide 0.9 g (3.0 mmol, 85%) of N-(3,4-difluorophenyl)-3-(hydroxyimino)-2,3-dihydrobenzofuran-7-carboxamide (XXIIIa).

(+) 3-Amino-N-(3,4-difluorophenyl)-2,3-dihydrobenzofuran-7-carboxamide (XXIVa)

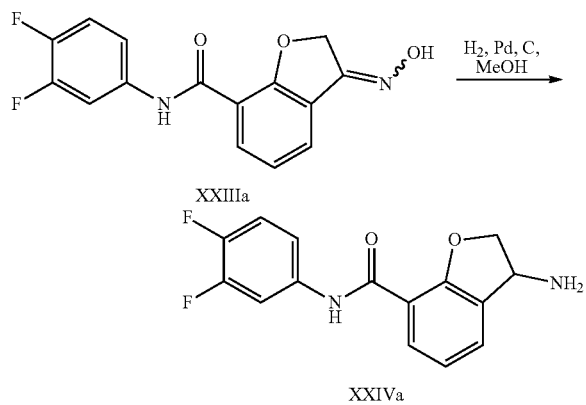

A solution of 0.5 g (1.64 mmol, 1.0 eq.) of N-(3,4-difluorophenyl)-3-(hydroxyimino)-2,3-dihydrobenzofuran-7-carboxamide (XXIIIa) in 20 mL of methanol containing 0.2 g of 10% palladium on carbon was stirred under a hydrogen atmosphere at room temperature for 24 h. The mixture was then filtered through CELITE® and the solvent was removed in vacuo. The residue was purified by flash chromatography (SiO$_2$, eluting with 5% methanol/methylene chloride) to provide 0.28 g (0.96 mmol, 59%) of (±) 3-amino-N-(3,4-difluorophenyl)-2,3-dihydrobenzofuran-7-carboxamide (XXIVa).

O-Methyl, N-(7-((3,4-difluorophenyl)carbamoyl)-2,3-dihydrobenzofuran-3-yl) carbamate (4, 5, 6)

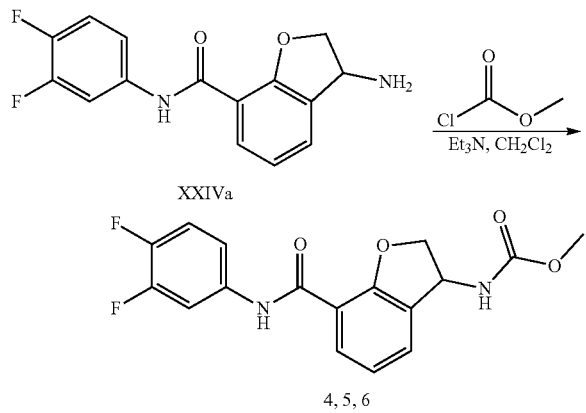

To a solution of 140 mg (0.48 mmol, 1.0 eq.) of 3-amino-N-(3,4-difluorophenyl)-2,3-dihydrobenzofuran-7-carboxamide (XXIVa) in 2 mL of methylene chloride at 0° C. was added 0.33 mL (1.92 mmol, 4.0 eq.) of N,N-diisopropylethylamine, followed by 69 mg (0.72 mmol, 1.5 eq.) of methyl chloroformate. The mixture was allowed to warm to room temperature and stirred for 2 h. The mixture was diluted with 10 mL of water and extracted with 2×25 mL of ethyl acetate. The combined organic extracts were dried (Na$_2$SO$_4$) and filtered, and the solvent was removed in vacuo. The residue was purified by flash chromatography (SiO$_2$, eluting with 30% ethyl acetate/hexanes) to provide 90 mg (0.25 mmol, 52%) of (+)-O-methyl, N-(7-((3,4-difluoro phenyl)carbamoyl)-2,3-dihydrobenzofuran-3-yl) carbamate (4). The enantiomers were subsequently separated by SFC (Waters SFC investigator. Isocratic mobile phase LIQUID.CO$_2$: 0.3% DEA IPA (80:20), Column: CHIRALCEL OJ-H 21×250 mm 5 μm column, flow rate: 60 ml/min).

O-Methyl, N-(7-((3,4-difluorophenyl)carbamoyl)-2,3-dihydrobenzofuran-3-yl) carbamate, enantiomer 1 (5). LCMS: m/z found, 349.6 [M+H]$^+$; HPLC: RT=7.38 min (Method F); $^1$H NMR (400 MHz, DMSO-d$_6$) δ 9.99 (s, 1H), 7.90-7.95 (m, 2H), 7.69 (d, 1H), 7.40-7.54 (m, 3H), 7.06 (dd, 1H), 5.39 (m, 1H), 4.86 (t, 1H), 4.38-4.45 (q, 1H), 3.58 (s, 3H).

O-Methyl, N-(7-((3,4-difluorophenyl)carbamoyl)-2,3-dihydrobenzofuran-3-yl) carbamate, enantiomer 2 (6). LCMS: m/z found 349.5 [M+H]$^+$; HPLC: RT=7.36 min (Method F); $^1$H NMR (400 MHz, DMSO-d$_6$) δ 9.99 (s, 1H), 7.91-7.95 (m, 2H), 7.69 (d, 1H), 7.40-7.54 (m, 3H), 7.06 (dd, 1H), 5.39 (m, 1H), 4.86 (t, 1H), 4.39-4.45 (q, 1H), 3.58 (s, 3H).

N-(3,4-difluorophenyl)-3-(3-methylureido)-2,3-dihydrobenzofuran-7-carboxamide (7, 8)

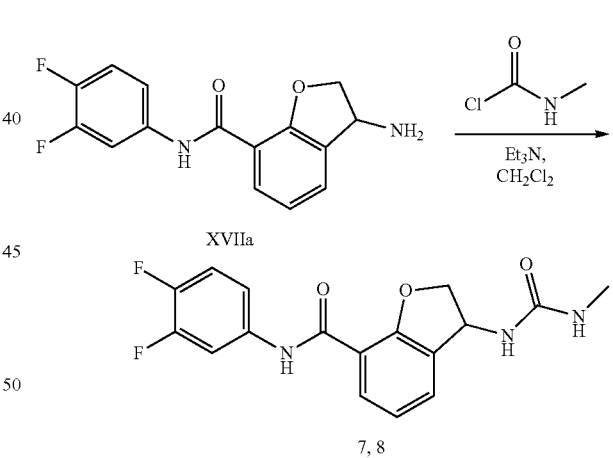

To a solution of 90 mg (0.31 mmol, 1.0 eq.) of (3-amino-N-(3,4-difluorophenyl)-2,3-dihydrobenzofuran-7-carboxamide (XVIIa) in 2 mL of methylene chloride at 0° C. was added 0.17 mL (0.92 mmol, 3.0 eq.) of N,N-diisopropylethylamine, followed by 70 mg (0.72 mmol, 2.3 eq.) of N-methyl carbamoyl chloride. The mixture was allowed to warm to room temperature and stirred for 2 h. The mixture was then diluted with 10 mL of ethyl acetate and washed with 10 mL of water. The organic phase was dried (Na$_2$SO$_4$), and the solvent was removed in vacuo. The residue was purified by flash chromatography (SiO$_2$, eluting with a linear gradient of 30% ethyl acetate/hexanes) to provide 62 mg (0.18 mmol, 58%) of (+)-N-(3,4-difluorophenyl)-3-(3- methylureido)-2,3-dihydrobenzofuran-7-carboxamide. The enantiomers were subsequently separated by SFC (Waters SFC investigator, Isocratic, mobile phase LIQUID.CO$_2$: 0.1% DEA IPA (80:20), Column: CHIRALCEL OJ-H 21×250 mm 5 µm column, flow rate: 84 mL/min.

N-(3,4-difluorophenyl)-3-(3-methylureido)-2,3-dihydrobenzofuran-7-carboxamide, enantiomer 1 (7). LCMS: m/z found 348.6 [M+H]$^+$; HPLC: RT=6.46 min (Method F); $^1$H NMR (400 MHz, DMSO-d$_6$): δ 9.99 (s, 1H), 7.90-7.96 (m, 1H), 7.68 (d, 1H), 7.40-7.54 (m, 3H), 7.06 (dd, 1H), 6.63 (d, 1H), 5.83-5.84 (m, 1H), 5.37-5.42 (m, 1H), 4.82 (t, 1H), 4.36-4.40 (m, 1H), 2.67 (s, 3H).

N-(3,4-difluorophenyl)-3-(3-methylureido)-2,3-dihydrobenzofuran-7-carboxamide, enantiomer 2 (8). LCMS: m/z found 348.6 [M+H]$^+$; HPLC: RT=6.46 min (Method F); $^1$H NMR (400 MHz, DMSO-d$_6$): δ 9.99 (s, 1H), 7.90-7.96 (m, 1H), 7.68 (d, 1H), 7.40-7.54 (m, 3H), 7.06 (dd, 1H), 6.63 (d, 1H), 5.83-5.84 (m, 1H), 5.37-5.42 (m, 1H), 4.82 (t, 1H), 4.36-4.40 (m, 1H), 2.67 (s, 3H).

O-Pyridin-2-ylmethyl, N-(7-((3,4-difluorophenyl) carbamoyl)-2,3-dihydro benzofuran-3-yl) carbamate (15, 16)

O-Pyridin-2-ylmethyl, N-(7-((3,4-difluorophenyl)carbamoyl)-2,3-dihydro benzofuran-3-yl) carbamate hydrochloride, enantiomer 1 (15.HCl). LCMS: m/z found 426.7 [M+H]$^+$ (Method D); HPLC: RT=7.29 min (Method F); Chiral HPLC, RT=3.28 min; $^1$H NMR (400 MHz, DMSO-d$_6$): δ 10.00 (s, 1H), 8.55 (d, 1H), 8.19-8.21 (m, 1H), 7.89-7.99 (m, 1H), 7.85 (dd, 1H), 7.70 (d, 1H), 7.55 (d, 1H), 7.30-7.42 (m, 3H), 7.06 (dd, 1H), 5.43 (d, 1H), 5.14 (s, 2H), 4.85 (t, 1H), 4.42-4.52 (m, 1H).

O-Pyridin-2-ylmethyl, N-(7-((3,4-difluorophenyl)carbamoyl)-2,3-dihydro benzofuran-3-yl) carbamate hydrochloride, enantiomer 2 (16.HCl). LCMS: m/z found 426.8 [M+H]$^+$ (Method D); HPLC: RT=7.31 min (Method F); Chiral HPLC, RT=5.24 min; $^1$H NMR (400 MHz, DMSO-d$_6$): δ 10.00 (s, 1H), 8.55 (d, 1H), 8.19-8.21 (m, 1H), 7.89-7.99 (m, 1H), 7.85 (dd, 1H), 7.70 (d, 1H), 7.55 (d, 1H), 7.30-7.42 (m, 3H), 7.06 (dd, 1H), 5.43 (d, 1H), 5.14 (s, 2H), 4.85 (t, 1H), 4.42-4.52 (m, 1H).

Scheme 5.

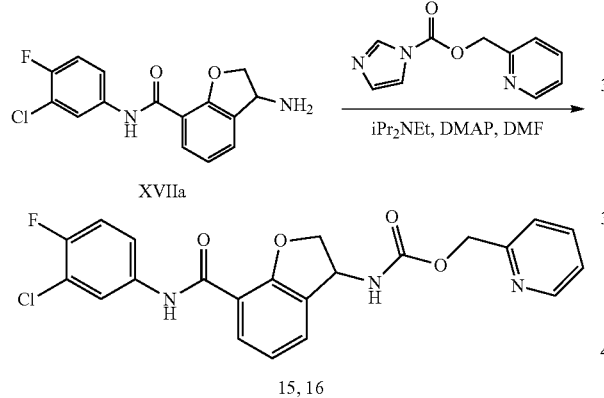

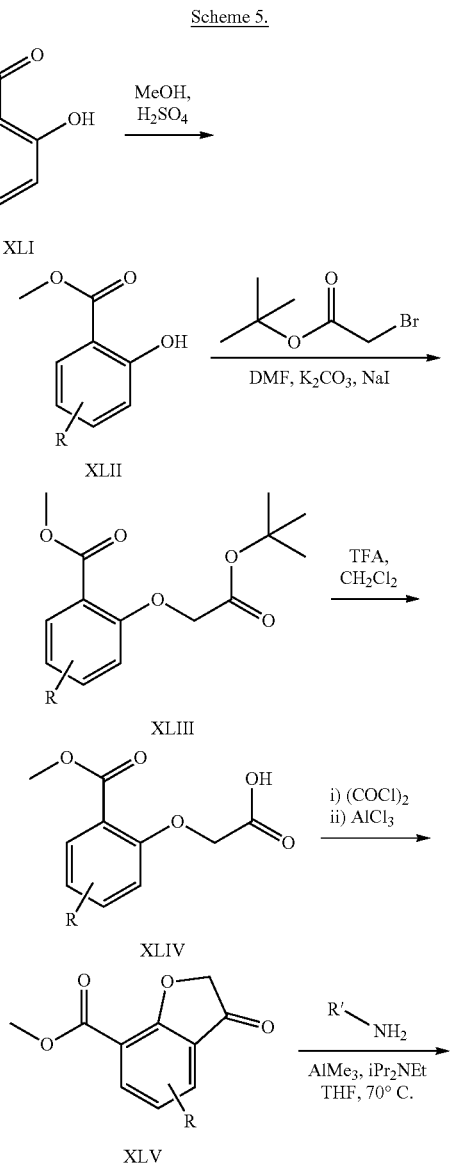

To a solution of 0.20 g (0.6 mmol, 1.0 eq.) of 3-amino-N-(3,4-difluorophenyl)-2,3-dihydrobenzofuran-7-carboxamide (XVIIa) in 6 mL of DMF were added 16 mg (0.12 mmol, 0.2 eq.) of 4-dimethylamino pyridine 0.3 mL (1.78 mmol, 3.0 eq.) of N,N-diisopropylethyl amine and 0.34 g (1.78 mmol, 3.0 eq.) of pyridin-2-ylmethyl 1H-imidazole-1-carboxylate. The mixture was then heated to 70° C. for 6 h. The mixture was allowed to cool to room temperature and poured into 20 mL of water. The mixture was extracted with 2×30 mL of ethyl acetate and washed with 30 mL of cold water. The organic phase was dried (Na$_2$SO$_4$), filtered and the solvent was removed in vacuo. The residue was purified by flash chromatography (SiO$_2$, eluting with 70% ethyl acetate/hexanes) to provide 0.16 g (45%) of racemic O-pyridin-2-ylmethyl, N-(7-((3,4-difluorophenyl) carbamoyl)-2,3-dihydro benzofuran-3-yl) carbamate.

The enantiomers were subsequently separated by SFC (Waters SFC investigator. Isocratic mobile phase LIQUID.CO$_2$: 0.1% DEA IPA (65:35), Column: CHIRALCEL OJ-H 21×250 mm 5 µm, flow rate: 60 ml/min). The resolved enantiomers were treated with 1.5 mL of 1.25 M HCl in methanol for 2 h. The solvent was removed in vacuo, and the residue dried under high vacuum to provide the compounds as the hydrochloride salts.

270

Methyl 2-(2-(tert-butoxy)-2-oxoethoxy)-4-fluorobenzoate (XLIIIa)

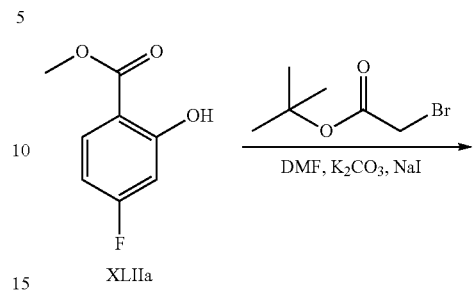

XLIIa

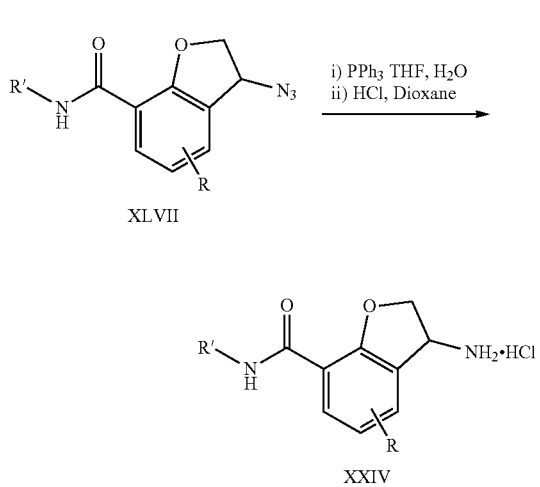

XLIIIa

To a solution of 90 g (0.53 mmol, 1.0 eq.) of methyl 4-fluoro-2-hydroxybenzoate (XLIIa) in 450 mL of DMF at 0° C. were added 119 g (0.79 mol, 1.5 eq.) of sodium iodide and 73 g (1.06 mol, 2.0 eq.) of potassium carbonate (73.05 g, 529 mmol, 2 eq) followed by the slow addition of 66.1 g (0.79 mol, 1.5 eq.) of tert-butyl 2-bromoacetate. The mixture was allowed to warm to room temperature and stirred for 16 h. The mixture was then poured into 1 L of ice water and extracted with 2×1 L of ethyl acetate. The combined organic extracts were washed with 2×500 mL of water, dried (Na$_2$SO$_4$), filtered and the solvent was removed in vacuo. The residue was purified by flash chromatography (SiO$_2$, eluting with 5% ethyl acetate/hexanes) to provide 115 g (0.40 mol, 76%) of methyl 2-(2-(tert-butoxy)-2-oxoethoxy)-4-fluorobenzoate (XLIIIa).

2-(5-Fluoro-2-(methoxycarbonyl)phenoxy)acetic Acid (XLIVa)

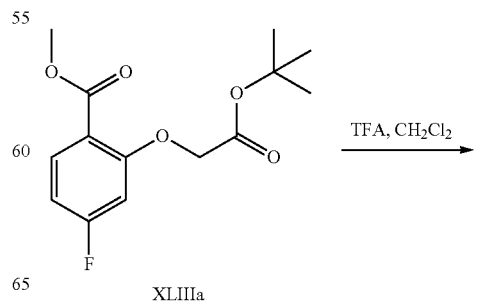

XLIIIa

269

-continued

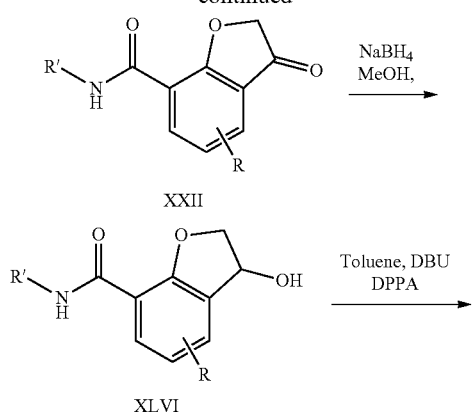

XXII

XLVI

XLVII

XXIV

Methyl 4-fluoro-2-hydroxybenzoate (XLIIa)

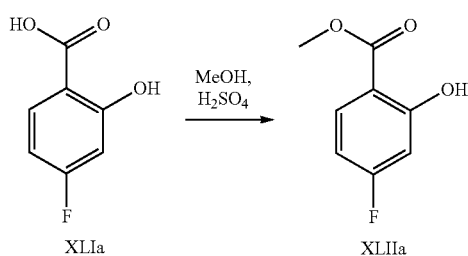

XLIa  XLIIa

To a solution of 100 g (0.64 mol, 1.0 eq.) of 1,4-fluoro-2-hydroxybenzoic acid (XLIa) in 1 L of MeOH at 0° C. was slowly added 100 mL of concentrated sulfuric acid at 0° C. The mixture was allowed to warm to room temperature and then heated at 70° C. for 16 h. The mixture was then allowed to cool to room temperature and concentrated under reduced pressure. The residue was redissolved in 1 L of ethyl acetate and washed with 500 mL of sat. NaHCO$_3$ followed by 500 mL of brine. The organic phase was dried (Na$_2$SO$_4$), filtered and the solvent was removed in vacuo to provide 95 g (0.56 mol, 87%) of methyl 4-fluoro-2-hydroxybenzoate (XLIIa).

-continued

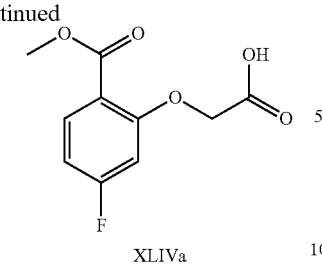

XLIVa

To a solution of 110 g (0.38 mol, 1.0 eq.) of methyl 2-(2-(tert-butoxy)-2-oxoethoxy)-4-fluorobenzoate (XLIIIa) in 500 mL of methylene chloride at 0° C. was added 110 mL of trifluoroacetic acid and the mixture was allowed to warm to room temperature. The mixture was stirred for 4 h, and the volatiles were then removed in vacuo. The residue was redissolved in 1 L of ethyl acetate and washed with 1 L of water. After completion of reaction, reaction mixture was concentrated under reduced pressure and diluted with 1.5 L of ethyl acetate, dried ($Na_2SO_4$), filtered and the solvent was removed in vacuo to provide 75 g (0.33 mol, 85%) of 2-(5-fluoro-2-(methoxycarbonyl)phenoxy)acetic acid (XLIVa).

Methyl 4-fluoro-3-oxo-2,3-dihydrobenzofuran-7-carboxylate (XLVa)

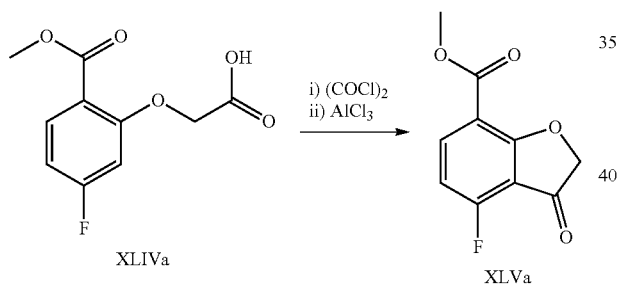

To a solution of 3 g (13.5 mmol, 1.0 eq.) of 2-(5-fluoro-2-(methoxycarbonyl)phenoxy)acetic acid (XLIVa) in 30 mL of methylene chloride at 0° C. was added 3 mL (35 mmol, 2.6 eq.) of oxalyl chloride drop-wise followed by catalytic DMF. The mixture was allowed to warm to room temperature and stirred for 2 h. The solvent was removed in vacuo and the resulting crude acid chloride was redissolved in 30 mL of 1,2-dichloroethane under a nitrogen atmosphere. The mixture was cooled to 0° C. and 4.37 g (32.9 mmol, 2.5 eq.) of aluminum trichloride was added in three portion. The mixture was then heated at 50° C. for 2 h. The mixture was allowed to cool to room temperature and poured onto ice and extracted with 3×50 mL of ethyl acetate. The combined organic extracts were washed with 50 mL of brine, dried ($Na_2SO_4$), filtered and the solvent was removed in vacuo. The above procedure was performed batchwise utilizing 30 g of 2-(5-fluoro-2-(methoxycarbonyl)phenoxy)acetic acid (XLIVa). The residue was purified by flash chromatography ($SiO_2$, eluting with 30% ethyl acetate/hexanes) to provide 3.5 g of methyl 4-fluoro-3-oxo-2,3-dihydrobenzofuran-7-carboxylate (XLVa).

N-(3-Chloro-4-fluorophenyl)-4-fluoro-3-oxo-2,3-dihydrobenzofuran-7-carboxamide (XXIIc)

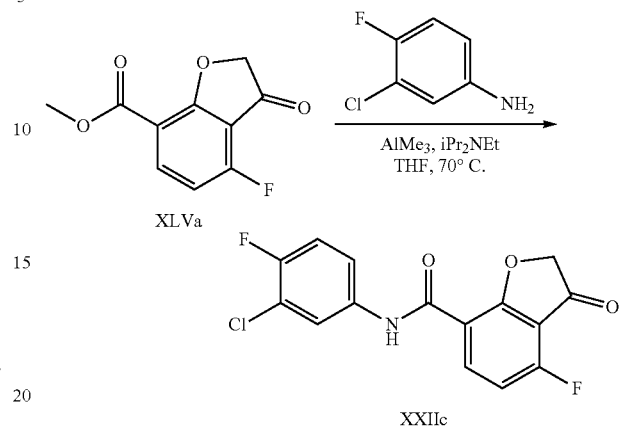

To a solution of 0.4 g (1.9 mmol, 1.0 eq.) of 4-fluoro-3-oxo-2,3-dihydrobenzofuran-7-carboxylate in 4 mL of THF were added 0.83 mL (4.8 mmol, 2.5 eq.) of N,N-diisopropylethylamine and 0.3 g (2.1 mmol, 1.1 eq.) of 3-chloro-4-fluoroaniline. The mixture was cooled to 0° C., and 4.8 mL (9.5 mmol, 5.0 eq.) of a 2 M solution of trimethyl aluminum in toluene was added dropwise over 15 min. The mixture was then heated at 60° C. for 2 h and allowed to cool to room temperature. The mixture was and poured onto ice and extracted with 3×10 mL of ethyl acetate. The combined organic extracts were washed with 20 mL of brine, dried ($Na_2SO_4$), filtered and the solvent was removed in vacuo. The residue was purified by flash chromatography ($SiO_2$, eluting with 30% ethyl acetate/hexanes) to provide 0.33 g (1.0 mmol, 53%) of N-(3-chloro-4-fluorophenyl)-4-fluoro-3-oxo-2,3-dihydrobenzofuran-7-carboxamide (XXIIc).

N-(3-Chloro-4-fluorophenyl)-4-fluoro-3-hydroxy-2,3-dihydrobenzofuran-7-carboxamide (XLVIc)

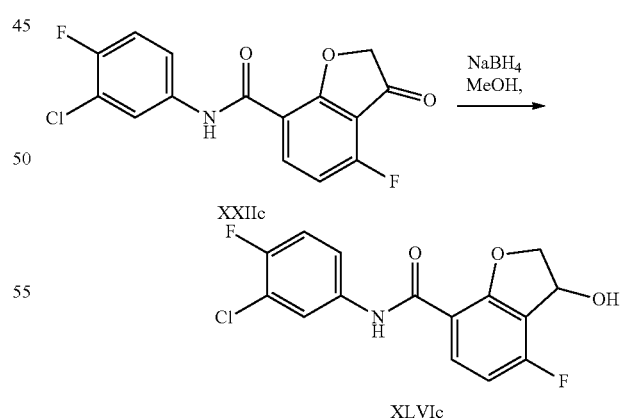

To a solution of 0.4 g (1.2 mmol, 1.0 eq.) of N-(3-chloro-4-fluorophenyl)-4-fluoro-3-oxo-2,3-dihydrobenzofuran-7-carboxamide in 10 mL of methanol at 0° C. was added 0.12 g (3.1 mmol, 2.5 eq.) of sodium borohydride. The reaction mixture was heated to 60° C. for 30 min and then allowed to cool to room temperature. The mixture was diluted with 10 mL of ice water and extracted with 3×20 mL of ethyl acetate. The combined organic extracts were washed with 20 mL of brine, dried (Na$_2$SO$_4$), filtered and the solvent was removed in vacuo. The residue was purified by flash chromatography (SiO$_2$, eluting with 35% ethyl acetate/hexanes) to provide 0.30 g (0.9 mmol, 77%) of N-(3-chloro-4-fluorophenyl)-4-fluoro-3-hydroxy-2,3-dihydrobenzo furan-7-carboxamide (XLVIc).

3-Azido-N-(3-chloro-4-fluorophenyl)-4-fluoro-2,3-dihydrobenzofuran-7-carboxamide (XLVIIc)

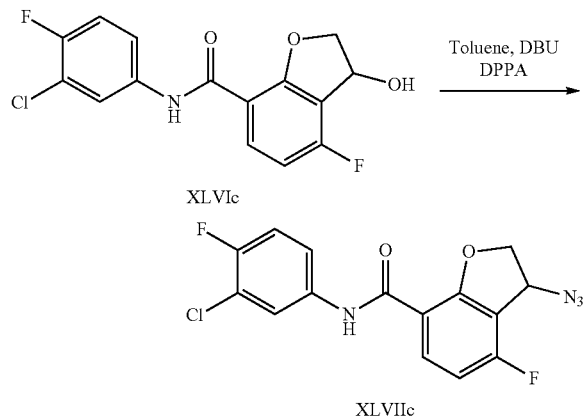

To a solution of 0.5 g (1.4 mmol, 1.0 eq.) of N-(3-chloro-4-fluorophenyl)-4-fluoro-3-hydroxy-2,3-dihydrobenzofuran-7-carboxamide (XLVIc) in 20 mL of toluene at 0° C. were added 0.51 g (1.84 mmol, 1.2 eq.) of diphenylphosphoryl azide and 0.21 g of 1,8-diazabicyclo(5.4.0)undec-7-ene. The mixture was stirred at 0° C. for 3 h and at room temperature for a further 16 h. The mixture was then quenched by the addition of 10 mL of water and diluted with 10 mL of 1 M HCl. The aqueous mixture was extracted with 3×20 mL ethyl acetate and the combined organic extracts were washed with 20 mL of brine. The organic solution was dried (Na$_2$SO$_4$), filtered and the solvent removed in vacuo. The residue was purified by flash chromatography (SiO$_2$, eluting with 10% ethyl acetate/hexanes) to provide 0.40 g (101 mmol, 81%) of 3-azido-N-(3-chloro-4-fluorophenyl)-4-fluoro-2,3-dihydrobenzofuran-7-carboxamide (XLVIIc).

3-Amino-N-(3-chloro-4-fluorophenyl)-4-fluoro-2,3-dihydrobenzofuran-7-carboxamide Hydrochloride (XXIVc)

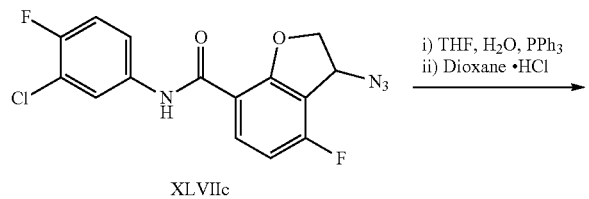

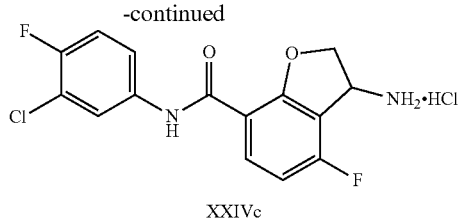

To a solution of 0.7 g (2.0 mmol, 1.0 eq.) of 3-azido-N-(3-chloro-4-fluorophenyl)-4-fluoro-2,3-dihydrobenzofuran-7-carboxamide (XLVIIc) in 7 mL of 98:2 (v/v) THF:water was added 1.57 g (6.0 mmol, 3.0 eq.) of triphenyl phosphine and the mixture was heated to 50° C. for 4 h. The mixture was then diluted with 30 mL of water and extracted with 3×50 mL of ethyl acetate. The combined organic extracts were washed with 50 mL of brine, dried (Na$_2$SO$_4$), filtered and the solvent removed in vacuo. The residue was treated with 5 mL of a 4 M solution of HCl in dioxane for 30 min. The solvent was removed in vacuo. The white cake was triturated with 2×30 mL of diethyl ether followed by 2×30 mL of n-pentane to provide 0.5 g of 3-amino-N-(3-chloro-4-fluorophenyl)-4-fluoro-2,3-dihydrobenzofuran-7-carboxamide hydrochloride (XXIVc).

O-Pyridin-2-ylmethyl, N-(7-((3-chloro-4-fluorophenyl)carbamoyl)-4-fluoro-2,3-dihydrobenzo furan-3-yl) carbamate (191, 192)

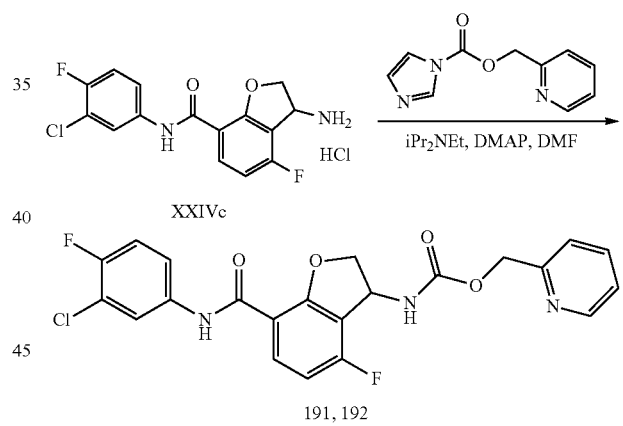

O-Pyridin-2-ylmethyl, N-(7-((3-chloro-4-fluorophenyl)carbamoyl)-4-fluoro-2,3-dihydrobenzo furan-3-yl) carbamate (191, 192) was synthesized in a similar manner as outlined above from 3-amino-N-(3-chloro-4-fluorophenyl)-4-fluoro-2,3-dihydrobenzofuran-7-carboxamide hydrochloride (XXIVc) and pyridin-2-ylmethyl 1H-imidazole-1-carboxylate. The resulting enantiomers were subsequently separated by SFC.

O-Pyridin-2-ylmethyl, N-(7-((3-chloro-4-fluorophenyl)carbamoyl)-4-fluoro-2,3-dihydrobenzo furan-3-yl)carbamate, enantiomer 1 (191). LCMS: m/z found 460.4, 462.4 [M+H]$^+$ (Method D) HPLC: RT=7.68 min (Method F); CHIRAL HPLC: RT=4.48 min; $^1$H NMR (400 MHz, DMSO-d$_6$): δ 9.98 (s, 1H), 8.72-8.73 (d, 1H), 8.40-8.42 (d, 1H), 8.15-8.18 (t, 1H), 8.07-8.09 (m, 1H), 7.81-7.85 (m, 1H), 7.62-7.74 (m, 2H), 7.44-7.49 (t, 1H), 6.93-6.98 (t, 1H), 5.61-5.66 (m, 1H), 5.28 (s, 2H), 4.94-4.99 (t, 1H), 4.58-4.61 (m, 1H).

O-Pyridin-2-ylmethyl, N-(7-((3-chloro-4-fluorophenyl)carbamoyl)-4-fluoro-2,3-dihydrobenzofuran-3-yl)carbamate, enantiomer 2 (192). LCMS: m/z found 460.4, 462.4 [M+H]$^+$ (Method D) HPLC: RT=7.68 min (Method F); CHIRAL HPLC: RT=6.89 min; $^1$H NMR (400 MHz, DMSO-d$_6$): δ 9.98 (s, 1H), 8.72-8.73 (d, 1H), 8.40-8.42 (d, 1H), 8.15-8.18 (t, 1H), 8.07-8.09 (m, 1H), 7.81-7.85 (m, 1H), 7.62-7.74 (m, 2H), 7.44-7.49 (t, 1H), 6.93-6.98 (t, 1H), 5.61-5.66 (m, 1H), 5.28 (s, 2H), 4.94-4.99 (t, 1H), 4.58-4.61 (m, 1H)

O-Methyl, N-(7-((3-chloro-4-fluorophenyl)carbamoyl)-4-fluoro-2,3-dihydrobenzofuran-3-yl) carbamate (187, 188)

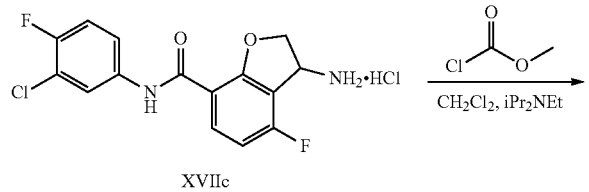

XVIIc

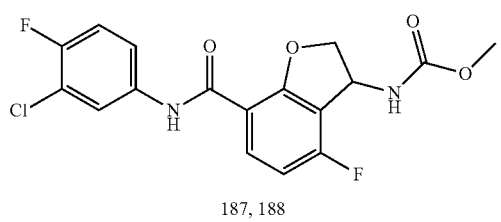

187, 188

O-Methyl N-(7-((3-chloro-4-fluorophenyl)carbamoyl)-4-fluoro-2,3-dihydrobenzofuran-3-yl) carbamate (187, 188) was synthesized in an analogous manner to that described above from 3-amino-N-(3-chloro-4-fluorophenyl)-4-fluoro-2,3-dihydrobenzofuran-7-carboxamide hydrochloride (XVIIc). The resulting enantiomers were subsequently separated by SFC.

O-Methyl, N-(7-((3-chloro-4-fluorophenyl)carbamoyl)-4-fluoro-2,3-dihydrobenzofuran-3-yl) carbamate, enantiomer 1 (187). LCMS: m/z found: 383.2 [M+H]$^+$ (Method D) RT=2.19 min; HPLC: RT=7.76 min (Method F); CHIRAL HPLC: RT=3.97 min; $^1$H NMR (400 MHz, DMSO-d$_6$): 9.93 (s, 1H), 8.03-8.06 (m, 2H), 7.77-7.81 (m, 1H), 7.66-7.70 (m, 1H), 7.41-7.46 (m, 1H), 6.89-6.94 (dd, 1H), 5.55-5.60 (m, 1H), 4.89-4.94 (t, 1H), 4.50-4.53 (m, 1H), 3.59 (s, 3H).

O-Methyl, N-(7-((3-chloro-4-fluorophenyl)carbamoyl)-4-fluoro-2,3-dihydrobenzofuran-3-yl) carbamate, enantiomer 2 (188). LCMS: m/z found: 383.2 [M+H]$^+$ (Method D) RT=2.19 min; HPLC: RT=7.75 min (Method F); CHIRAL HPLC: RT=4.61 min; $^1$H NMR (400 MHz, DMSO-d$_6$): 9.93 (s, 1H), 8.03-8.06 (m, 2H), 7.77-7.81 (m, 1H), 7.66-7.70 (m, 1H), 7.41-7.46 (m, 1H), 6.89-6.94 (dd, 1H), 5.55-5.60 (m, 1H), 4.89-4.94 (t, 1H), 4.50-4.53 (m, 1H), 3.59 (s, 3H).

N-(3-Chloro-4-fluorophenyl)-4-fluoro-3-(3-methylureido)-2,3-dihydrobenzofuran-7-carboxamide (189, 190)

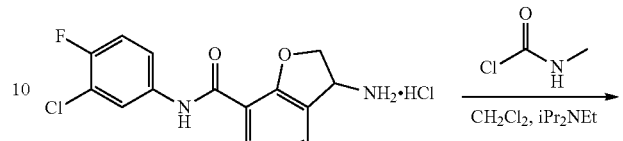

XVIIc

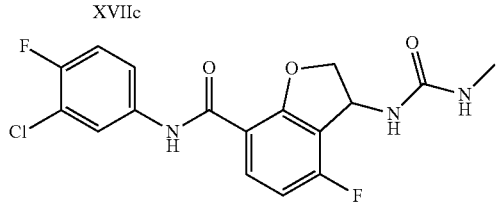

189, 190

N-(3-Chloro-4-fluorophenyl)-4-fluoro-3-(3-methylureido)-2,3-dihydrobenzofuran-7-carboxamide (189, 190) was synthesized in an analogous manner to that described above from 3-amino-N-(3-chloro-4-fluorophenyl)-4-fluoro-2,3-dihydrobenzofuran-7-carboxamide hydrochloride (XVIIc). The resulting enantiomers were subsequently separated by SFC.

N-(3-Chloro-4-fluorophenyl)-4-fluoro-3-(3-methylureido)-2,3-dihydrobenzofuran-7-carboxamide, enantiomer 1 (189). LCMS: m/z found: 382.3 [M+H]$^+$ (Method D); HPLC: RT=6.91 min (Method F); CHIRAL HPLC: RT=3.71 min; $^1$H NMR (400 MHz, DMSO-d$_6$): 9.91 (s, 1H), 8.03-8.05 (m, 1H), 7.75-7.79 (m, 1H), 7.55-7.68 (m, 1H), 7.41-7.46 (m, 1H), 6.88-6.93 (m, 1H), 6.74-6.76 (m, 1H) 5.77-5.78 (m, 1H), 5.54-5.59 (m, 1H), 4.83-4.87 (t, 1H), 4.44-4.48 (m, 1H), 2.58 (s, 3H).

N-(3-Chloro-4-fluorophenyl)-4-fluoro-3-(3-methylureido)-2,3-dihydrobenzofuran-7-carboxamide, enantiomer 2 (190). LCMS: m/z found: 382.3 [M+H]$^+$ (Method D); HPLC: RT=6.86 min (Method F); CHIRAL HPLC: RT=37.89 min; $^1$H NMR (400 MHz, DMSO-d$_6$): 9.91 (s, 1H), 8.03-8.05 (m, 1H), 7.75-7.79 (m, 1H), 7.55-7.68 (m, 1H), 7.41-7.46 (m, 1H), 6.88-6.93 (m, 1H), 6.74-6.76 (m, 1H) 5.77-5.78 (m, 1H), 5.54-5.59 (m, 1H), 4.83-4.87 (t, 1H), 4.44-4.48 (m, 1H), 2.58 (s, 3H).

O-Methyl, N-(4-fluoro-7-((4-fluoro-3-methylphenyl)carbamoyl)-2,3-dihydrobenzofuran-3-yl) carbamate (201, 202)

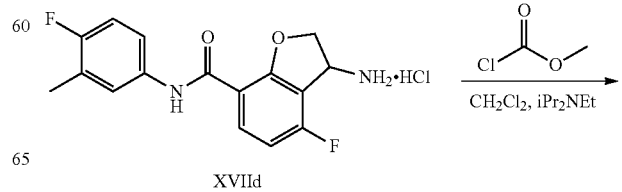

XVIId

277

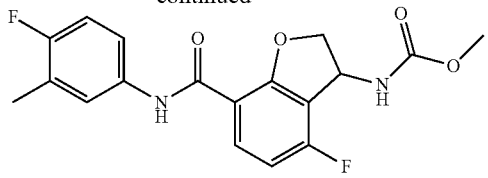

201, 202

O-Methyl N-(4-fluoro-7-((4-fluoro-3-methylphenyl)carbamoyl)-2,3-dihydrobenzofuran-3-yl) carbamate (201, 202) was synthesized in an analogous manner to that described above from 3-amino-4-fluoro-N-(4-fluoro-3-methylphenyl)-2,3-dihydrobenzofuran-7-carboxamide hydrochloride (XVIId) and methyl chloroformate. The resulting enantiomers were subsequently separated by SFC.

O-Methyl, N-(4-fluoro-7-((4-fluoro-3-methylphenyl)carbamoyl)-2,3-dihydrobenzofuran-3-yl) carbamate, enantiomer 1 (201). LCMS: m/z found: 363.2 [M+H]$^+$ (Method D) HPLC: RT=7.46 min (Method F); CHIRAL HPLC: RT=3.97 min; $^1$H NMR (400 MHz, DMSO-d$_6$): δ 9.66 (s, 1H), 8.03 (d, 1H), 7.80 (dd, 1H), 7.52-7.64 (m, 2H), 7.13 (t, 1H), 6.90 (t, 1H), 5.57 (m, 1H), 4.92 (t, 1H), 4.52 (dd, 1H), 3.58 (s, 3H), 2.24 (d, 3H).

O-Methyl, N-(4-fluoro-7-((4-fluoro-3-methylphenyl)carbamoyl)-2,3-dihydrobenzofuran-3-yl) carbamate, enantiomer 2 (202). LCMS: m/z found: 363.2 [M+H]$^+$ (Method D); HPLC: RT=7.46 min (Method F); CHIRAL HPLC: RT=5.78 min; $^1$H NMR (400 MHz, DMSO-d$_6$): δ 9.66 (s, 1H), 8.03 (d, 1H), 7.80 (dd, 1H), 7.52-7.64 (m, 2H), 7.13 (t, 1H), 6.90 (t, 1H), 5.57 (m, 1H), 4.92 (t, 1H), 4.52 (dd, 1H), 3.58 (s, 3H), 2.24 (d, 3H).

4-Fluoro-N-(4-fluoro-3-methylphenyl)-3-(3-methylureido)-2,3-dihydrobenzofuran-7-carboxamide (203, 204)

278

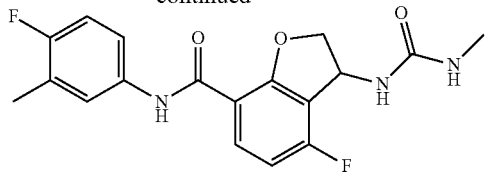

203, 204

4-Fluoro-N-(4-fluoro-3-methylphenyl)-3-(3-methylureido)-2,3-dihydrobenzofuran-7-carboxamide (203, 204) was synthesized in an analogous manner to that described above from 3-amino-4-fluoro-N-(4-fluoro-3-methylphenyl)-2,3-dihydrobenzofuran-7-carboxamide hydrochloride (XVIId) and N-methyl carbamoyl chloride. The resulting enantiomers were subsequently separated by SFC.

4-Fluoro-N-(4-fluoro-3-methylphenyl)-3-(3-methylureido)-2,3-dihydrobenzofuran-7-carboxamide, enantiomer 1 (203). LCMS: m/z found: 362.2 [M+H]$^+$ (Method D); HPLC: RT=6.91 min (Method F); CHIRAL HPLC: RT=3.71 min; $^1$H NMR (400 MHz, DMSO-d$_6$): δ 9.91 (s, 1H), 8.03-8.05 (m, 1H), 7.75-7.79 (m, 1H), 7.55-7.68 (m, 1H), 7.41-7.46 (m, 1H), 6.88-6.93 (m, 1H), 6.74-6.76 (m, 1H), 5.77-5.78 (m, 1H), 5.54-5.59 (m, 1H), 4.83-4.87 (t, 1H), 4.44-4.48 (m, 1H), 2.58 (s, 3H), 2.21 (s, 3H).

4-Fluoro-N-(4-fluoro-3-methylphenyl)-3-(3-methylureido)-2,3-dihydrobenzofuran-7-carboxamide, enantiomer 2 (204). LCMS: m/z found: 362.2 [M+H]$^+$ (Method D); HPLC: RT=6.91 min (Method F); CHIRAL HPLC: RT=7.89 min; $^1$H NMR (400 MHz, DMSO-d$_6$): δ 9.91 (s, 1H), 8.03-8.05 (m, 1H), 7.75-7.79 (m, 1H), 7.55-7.68 (m, 1H), 7.41-7.46 (m, 1H), 6.88-6.93 (m, 1H), 6.74-6.76 (m, 1H), 5.77-5.78 (m, 1H), 5.54-5.59 (m, 1H), 4.83-4.87 (t, 1H), 4.44-4.48 (m, 1H), 2.58 (s, 3H), 2.21 (s, 3H).

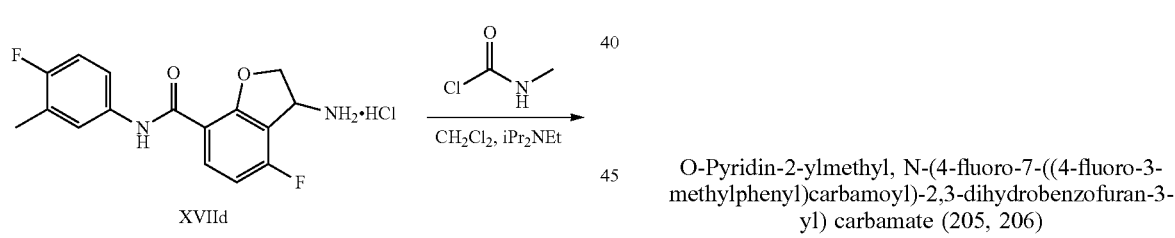

XVIId

O-Pyridin-2-ylmethyl, N-(4-fluoro-7-((4-fluoro-3-methylphenyl)carbamoyl)-2,3-dihydrobenzofuran-3-yl) carbamate (205, 206)

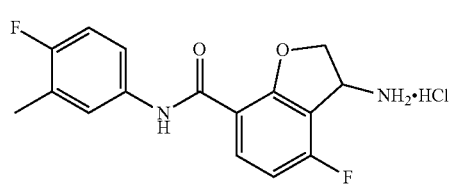 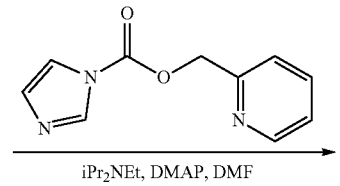

XXIVd

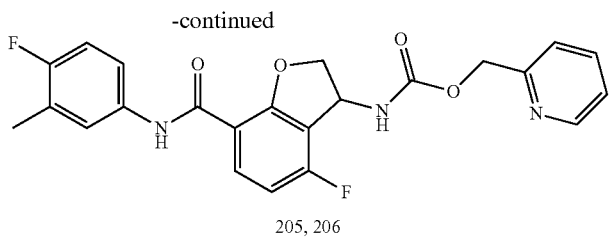

205, 206

O-Pyridin-2-ylmethyl, N-(4-fluoro-7-((4-fluoro-3-methylphenyl)carbamoyl)-2,3-dihydrobenzofuran-3-yl)carbamate (205, 206) was synthesized in a similar manner as outlined above from 3-amino-N-(3-methyl-4-fluorophenyl)-4-fluoro-2,3-dihydrobenzofuran-7-carboxamide hydrochloride (XXIVd) and pyridin-2-ylmethyl 1H-imidazole-1-carboxylate. The resulting enantiomers were subsequently separated by SFC.

O-Pyridin-2-ylmethyl, N-(4-fluoro-7-((4-fluoro-3-methylphenyl)carbamoyl)-2,3-dihydrobenzofuran-3-yl) carbamate, enantiomer 1 (205). LCMS: m/z found 440.3, [M+H]+ (Method D); HPLC: RT=6.60 min (Method F); CHIRAL HPLC: RT=4.23 min; $^1$H NMR (400 MHz, DMSO-d$_6$): δ 9.68 (s, 1H), 8.66 (d, 1H), 8.35 (d, 1H), 8.06 (dd, 1H), 7.80 (dd, 1H), 7.65-7.49 (m, 4H), 7.13 (dd, 1H), 6.92 (dd, 1H), 5.65-5.55 (m, 1H), 5.21 (s, 2H), 4.94 (dd, 1H), 4.56 (dd, 1H), 2.24 (s, 3H).

O-Pyridin-2-ylmethyl, N-(4-fluoro-7-((4-fluoro-3-methylphenyl)carbamoyl)-2,3-dihydrobenzofuran-3-yl)carbamate, enantiomer 2 (206). LCMS: m/z found 440.3, [M+H]+ (Method D); HPLC: RT=6.60 min (Method F); CHIRAL HPLC: RT=7.35 min; $^1$H NMR (400 MHz, DMSO-d$_6$): δ 9.68 (s, 1H), 8.66 (d, 1H), 8.35 (d, 1H), 8.06 (dd, 1H), 7.80 (dd, 1H), 7.65-7.49 (m, 4H), 7.13 (dd, 1H), 6.92 (dd, 1H), 5.65-5.55 (m, 1H), 5.21 (s, 2H), 4.94 (dd, 1H), 4.56 (dd, 1H), 2.24 (s, 3H).

N-(3-chloro-4-fluorophenyl)-3-(cyclopropanesulfonamido)-4-fluoro-2,3-dihydrobenzofuran-7-carboxamide (207, 208)

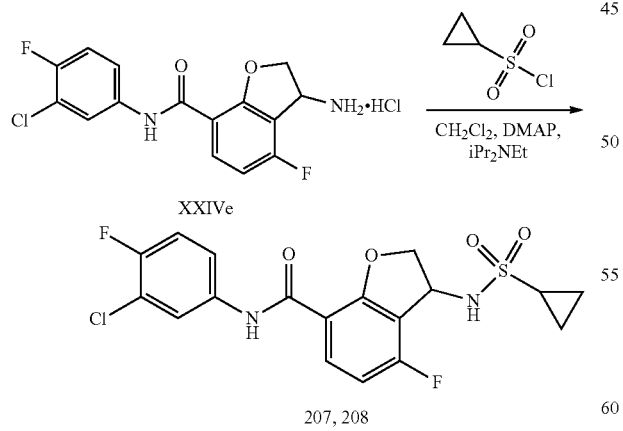

207, 208

N-(3-chloro-4-fluorophenyl)-3-(cyclopropanesulfonamido)-4-fluoro-2,3-dihydrobenzofuran-7-carboxamide (207, 208) was synthesized in an analogous manner to that described above from 3-amino-N-(3-chloro-4-fluorophenyl)-4-fluoro-2,3-dihydrobenzofuran-7-carboxamide hydrochloride (XVIIc) and cyclopropyl sulfonyl chloride. The resulting enantiomers were subsequently separated by SFC.

N-(3-chloro-4-fluorophenyl)-3-(cyclopropanesulfonamido)-4-fluoro-2,3-dihydrobenzofuran-7-carboxamide, enantiomer 1 (207). LCMS: m/z found: 427.3/429.3 [M−H]+ (Method D); HPLC: RT=7.80 min (Method F); CHIRAL HPLC: RT=4.96 min; $^1$H NMR (400 MHz, DMSO-d$_6$): δ 9.98 (s, 1H), 8.02-8.13 (m, 2H), 7.81 (dd, 1H), 7.69 (m, 1H), 7.44 (dd, 1H), 6.95 (dd, 1H), 5.45 (dd, 1H), 4.90 (dd, 1H), 4.68 (dd, 1H), 2.67 (m, 1H), 1.00 (m, 4H).

N-(3-chloro-4-fluorophenyl)-3-(cyclopropanesulfonamido)-4-fluoro-2,3-dihydrobenzofuran-7-carboxamide, enantiomer 2 (208). LCMS: m/z found: 427.3/429.3 [M−H]+ (Method D); HPLC: RT=7.80 min (Method F); CHIRAL HPLC: RT=4.96 min; $^1$H NMR (400 MHz, DMSO-d$_6$): δ 9.98 (s, 1H), 8.02-8.13 (m, 2H), 7.81 (dd, 1H), 7.69 (m, 1H), 7.44 (dd, 1H), 6.95 (dd, 1H), 5.45 (dd, 1H), 4.90 (dd, 1H), 4.68 (dd, 1H), 2.67 (m, 1H), 1.00 (m, 4H).

Example 10: Non-Limiting Synthesis of Selected 1-(Substituted Amino)-Dihydrobenzothiophene-4-Carboxamides (Scheme 6)

Scheme 6.

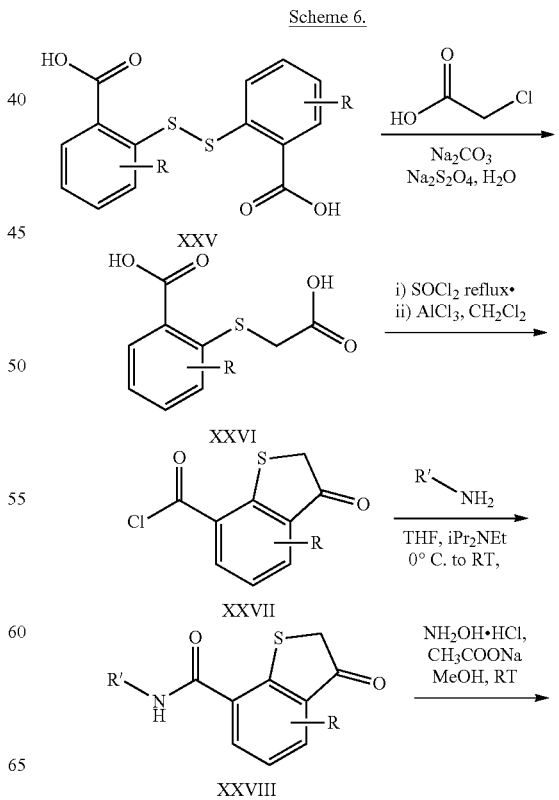

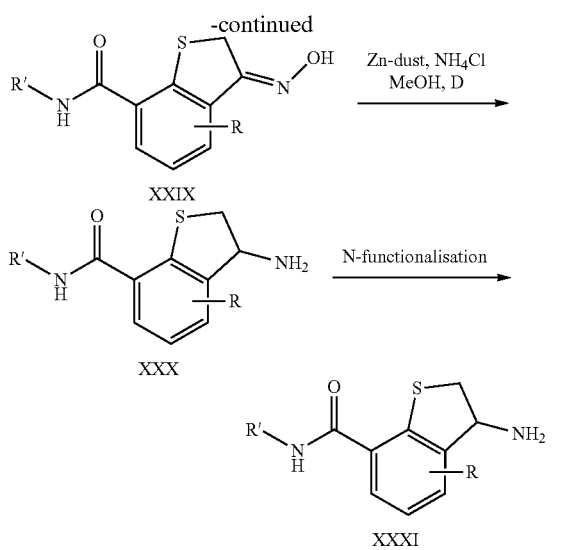

Non-Limiting Illustration of Scheme 6

2-((Carboxymethyl)thio)benzoic Acid (XXVIa)

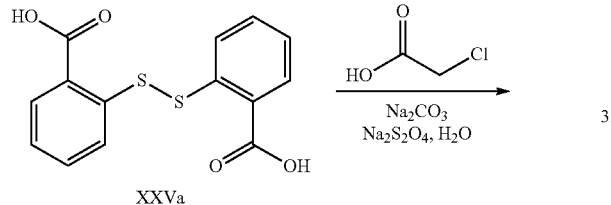

To a solution of 20 g of anhydrous sodium carbonate (189 mmol, 6.0 eq.) in 150 mL of water were added 10 g (32.6 mmol, 1.0 eq.) of 2,2-dithiodisalicylic acid and 14.2 g (82.1 mmol, 2.5 eq.) of sodium dithionite. The mixture was heated at reflux for 30 min. A solution of 15 g (163 mmol, 5.0 eq.) of chloroacetic acid was neutralized with sodium carbonate and then added. The mixture was then heated at reflux for a further 1 h. The mixture was allowed to cool to room temperature and acidified to pH ~3 with concentrated hydrochloric acid. The resulting yellow precipitate was collected by filtration and recrystallized from water, removing insoluble material by hot filtration, to provide 12 g (69%) of 2-((carboxymethyl)thio)benzoic acid (XXVIa). $^1$H NMR (400 MHz, DMSO-$d_6$): δ 13.00 (s, 2H), 7.91-7.89 (q, 1H), 7.54-7.50 (m, 1H), 7.37-7.35 (d, 1H), 7.25-7.21 (m, 1H), 3.8 (s, 2H).

3-Oxo-2,3-dihydrobenzo[b]thiophene-7-carbonyl Chloride (XXVIIa)

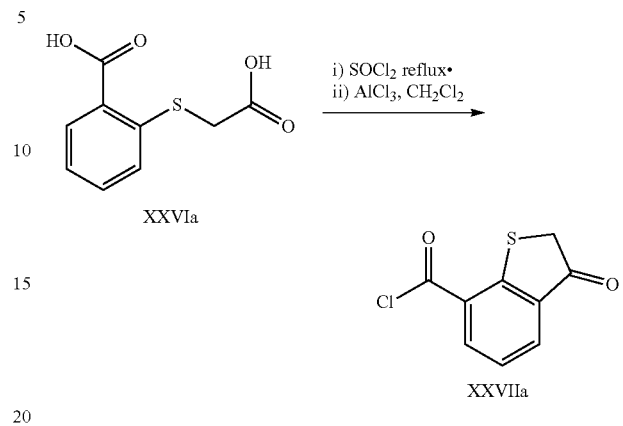

A solution of 6.5 g (30.7 mmol, 1.0 eq.) of 2-((carboxymethyl)thio)benzoic acid (XXVIa) in 40 mL of thionyl chloride was heated at reflux for 2 h. Volatiles were removed in vacuo and the residue was redissolved in 30 mL of 1,2-dichloroethane. The solution was cooled to 0° C. and 10.21 g (76.7 mmol, 2.5 eq.) of aluminium trichloride was added in four approximately equal portions. The mixture was stirred under a nitrogen atmosphere at 0° C. for an additional 20 min, and then allowed to warm to room temperature and stirred for a further 14 h. The reaction was quenched with ice/water, and the mixture was extracted with 3×100 mL of methylene chloride. The combined organic extracts were washed with water, dried (Na$_2$SO$_4$), filtrated and the solvent removed in vacuo to provide 5.1 g (84%) of 3-oxo-2,3-dihydrobenzo[b]thiophene-7-carbonyl chloride (XXVIIa). $^1$H NMR (400 MHz, CDCl$_3$): δ 8.53 (d, 1H), 8.85 (d, 1H), 7.42 (dd, 1H), 3.82 (s, 2H).

N-(3,4-Difluorophenyl)-3-oxo-2,3-dihydrobenzo[b]thiophene-7-carboxamide (XXVIIIa)

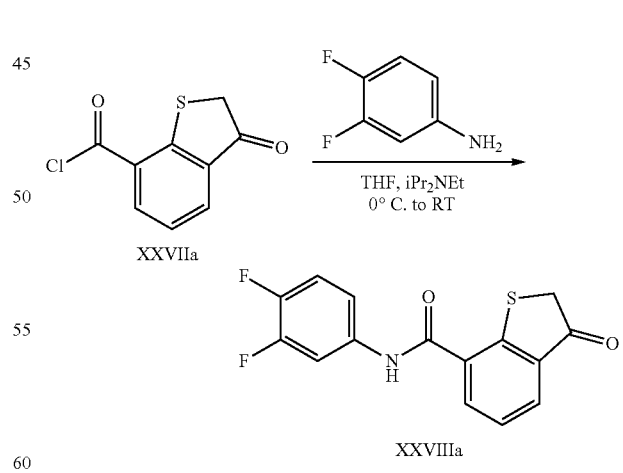

To a solution of 5.8 g (27.48 mmol, 1.0 eq.) of 3-oxo-2,3-dihydrobenzo[b]thiophene-7-carbonyl chloride (XXVIIa) in 60 mL of methylene chloride at 0° C. was added 5.31 g (41.0 mmol, 1.5 eq.) of 3,4-difluoroaniline, followed by 14.3 mL (82.4 mmol, 3.0 eq) of N,N-diisopropylethylamine. The mixture was allowed to warm to room temperature and stirred for 30 min. The reaction was quenched by the addition of 100 mL of water and extracted with 3×100 mL of ethyl acetate. The combined organic extracts were washed with 50 mL of water, dried (Na₂SO₄) and filtered, and the solvent was removed in vacuo. The residue was purified by flash chromatography (SiO₂, eluting with 30% ethyl acetate/hexanes) to provide 3.2 g (38%) of N-(3,4-difluorophenyl)-3-oxo-2,3-dihydrobenzo[b]thiophene-7-carboxamide (XXVIIIa). $^1$H NMR (400 MHz, DMSO-d$_6$): δ 10.6 (s, 1H), 10.17 (s, 1H), 8.15 (d, 1H), 7.97 (dd, 2H), 7.58-7.45 (m, 3H), 6.58 (s, 1H).

N-(3,4-Difluorophenyl)-3-(hydroxyimino)-2,3 dihydrobenzo[b]thiophene-7-carboxamide (XXIXa)

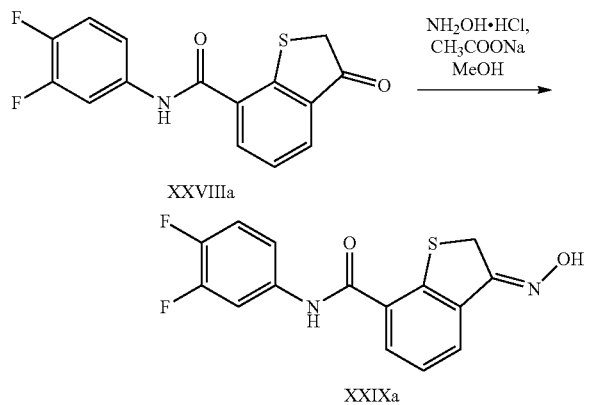

To a solution of 3.1 g (10.2 mmol, 1.0 eq.) of N-(3,4-difluorophenyl)-3-oxo-2,3-dihydrobenzo[b]thiophene-7-carboxamide (XXVIIIa) in 30 mL of methanol were added 2.1 g (30.5 mmol, 3.0 eq.) of hydroxylamine hydrochloride and 2.5 g (30.5 mmol, 3.0 eq.) of sodium acetate, and the mixture was stirred at room temperature for 16 h. The mixture was diluted with 150 mL of water and extracted with 3×75 mL of ethyl acetate. The combined organic extracts were washed with 50 mL of water, dried (Na₂SO₄) and filtered, and the solvent was removed in vacuo to provide 3.0 g (92%) of N-(3,4-difluorophenyl)-3-(hydroxyimino)-2,3 dihydrobenzo[b]thiophene-7-carboxamide (XXIXa). $^1$H NMR (400 MHz, DMSO-d$_6$): δ 11.6 (s, 1H), 10.52 (s, 1H), 8.03 (d, 1H), 7.91 (dd, 2H), 7.80 (d, 1H), 7.54-7.44 (m, 2H) 7.34 (t, 1H).

3-Amino-N-(3,4-difluorophenyl)-2,3-dihydrobenzo[b]thiophene-7-carboxamide (XXXa)

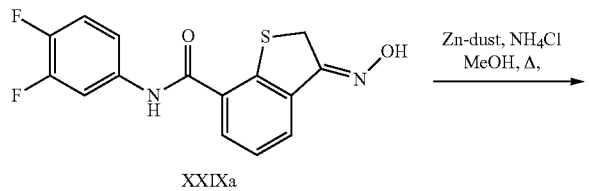

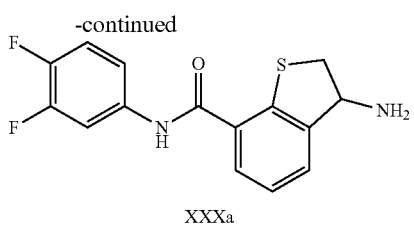

To a solution of 0.5 g (1.56 mmol, 1.0 eq.) of (N-(3,4-difluorophenyl)-3-(hydroxyimino)-2,3-dihydrobenzo[b]thiophene-7-carboxamide (XXIXa) in 5 mL of methanol were added 1.0 g (15.6 mmol, 10.0 eq.) of zinc dust and 0.83 g (15.6 mmol, 10.0 eq.) of ammonium chloride. The reaction mixture was heated at reflux for 30 min. The mixture was then allowed to cool to room temperature and filtered through CELITE®. The pad was washed with 100 mL of ethyl acetate, and the organic solution was washed with 40 mL of water. The organic phase was dried (Na₂SO₄), filtered and the solvent removed in vacuo to provide 0.48 g of crude (+)-3-amino-N-(3,4-difluorophenyl)-2,3-dihydrobenzo[b]thiophene-7-carboxamide (XXIXa), which was used without further purification.

O-Methyl, N-(7-((3,4-difluorophenyl)carbamoyl)-2,3-dihydrobenzo[b]thiophen-3-yl)carbamate (30, 31)

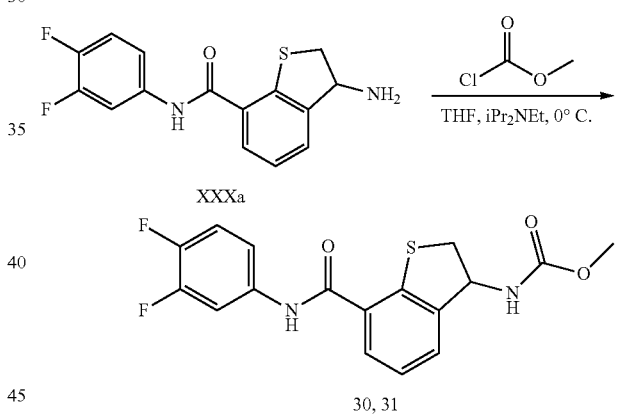

To a solution of 0.45 g (1.47 mmol, 1.0 eq.) of 3-amino-N-(3,4-difluorophenyl)-2,3-dihydrobenzo[b]thiophene-7-carboxamide (XXXa) in 5 mL of methylene chloride at 0° C. was added 0.77 mL (4.41 mmol, 3.0 eq.) of N,N-diisopropylethylamine followed by 0.18 g (2.2 mmol, 1.5 eq.) of methyl chloroformate. The mixture was allowed to warm to room temperature and stirred for 1 hr. The reaction mixture was then diluted with 25 ml of water and extracted with 2×25 mL of methylene chloride. The combined organic extracts were washed with 25 mL of water, dried (Na₂SO₄) and filtered, and the solvent was removed in vacuo. The residue was purified by flash chromatography (SiO₂, eluting with 80% ethyl acetate/hexanes) to provide 0.14 g (26%) of racemic O-methyl, N-(7-((3,4-difluorophenyl)carbamoyl)-2,3-dihydrobenzo[b]thiophen-3-yl)carbamate. The enantiomers were subsequently separated by SFC (Waters SFC investigator). Mobile phase:—Line-A:—Liq. CO₂, Line-B:–0.1% diethylamine in methanol. Isocratic ratio (A-B) (55-45), Column: CHIRALPAK AD-H (21×250) mm, 5 μm, flow rate: 80 g/min).

O-Methyl, N-(7-((3,4-difluorophenyl)carbamoyl)-2,3-dihydrobenzo[b]thiophen-3-yl)carbamate, enantiomer 1 (30). LCMS: m/z found: 363.6 [M−H], (Method C), HPLC: HPLC-04, RT=7.161 min (Method F); Chiral HPLC, RT=2.52 min; $^1$H NMR (400 MHz, DMSO-$d_6$): δ 10.43 (s, 1H), 7.91-7.83 (m, 2H), 7.49-7.42 (m, 1H), 7.34-7.42 (m, 1H), 7.30-7.34 (m, 1H), 7.23-7.28 (m, 1H), 5.27-5.34 (m, 1H), 3.60 (s, 3H), 3.40-3.46 (m, 1H), 3.00-3.05 (m, 1H).

O-Methyl, N-(7-((3,4-difluorophenyl)carbamoyl)-2,3-dihydrobenzo[b]thiophen-3-yl)carbamate, enantiomer 2 (31). LCMS: m/z found: 363.6 [M−H] (Method C), HPLC: HPLC-04, RT=7.17 min (Method F); Chiral HPLC, 6.26 min; $^1$H NMR (400 MHz, DMSO-$d_6$): δ 10.43 (s, 1H), 7.91-7.83 (m, 2H), 7.49-7.42 (m, 1H), 7.34-7.42 (m, 1H), 7.30-7.34 (m, 1H), 7.23-7.28 (m, 1H), 5.27-5.34 (m, 1H), 3.60 (s, 3H), 3.40-3.46 (m, 1H), 3.00-3.05 (m, 1H).

O-Methyl, N-(7-((3-chloro-4-fluorophenyl)carbamoyl)-2,3-dihydrobenzo[b]thiophen-3-yl) carbamate (37, 38)

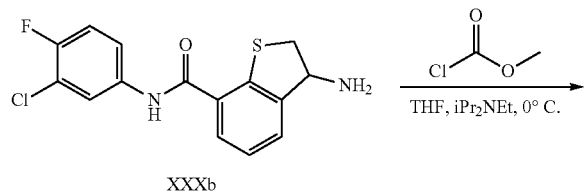

XXXb

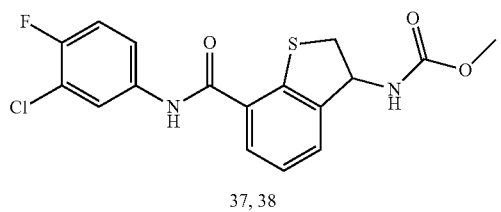

37, 38

O-Methyl, N-(7-((3-chloro-4-fluorophenyl)carbamoyl)-2,3-dihydrobenzo[b]thiophen-3-yl)carbamate (37, 38) was synthesized in an analogous manner to that described above from 3-amino-N-(3-chloro-4-fluorophenyl)-2,3-dihydrobenzo[b]thiophene-7-carboxamide (XXXb).

O-Methyl, N-(7-((3-chloro-4-fluorophenyl)carbamoyl)-2,3-dihydrobenzo[b]thiophen-3-yl) carbamate, enantiomer 1 (37). LCMS: m/z found: 379.7/381.7 [M−H] (Method C), HPLC: RT=7.462 min (Method F); Chiral HPLC, RT=2.23 min; $^1$H NMR (400 MHz, DMSO-$d_6$): δ 10.45 (s, 1H), 8.05 (dd, 1H), 7.81-7.93 (m, 2H), 7.69-7.72 (m, 1H), 7.26-7.45 (m, 3H), 5.33 (q, 1H), 3.61 (s, 3H), 3.47-3.60 (m, 1H), 3.00-3.08 (m, 1H).

O-Methyl, N-(7-((3-chloro-4-fluorophenyl)carbamoyl)-2,3-dihydrobenzo[b]thiophen-3-yl) carbamate, enantiomer 2 (38). LCMS: m/z found: 363.6 [M−H] (Method C); HPLC: RT=7.458 min (Method F); Chiral HPLC, RT 3.37 min; $^1$H NMR (400 MHz, DMSO-$d_6$): δ 10.45 (s, 1H), 8.05 (dd, 1H), 7.81-7.93 (m, 2H), 7.69-7.72 (m, 1H), 7.26-7.45 (m, 3H), 5.33 (q, 1H), 3.61 (s, 3H), 3.47-3.60 (m, 1H), 3.00-3.08 (m, 1H).

O-Pyridin-2-ylmethyl, N-(7-((3,4-difluorophenyl)carbamoyl)-2,3-dihydrobenzo[b]thiophen-3-yl) carbamate Hydrochloride (33.HCl, 34.HCl)

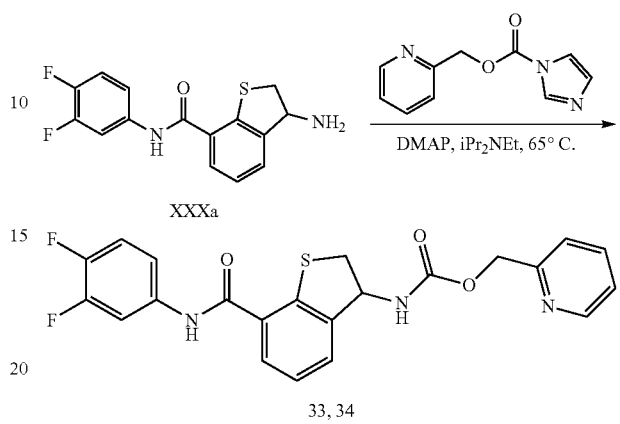

33, 34

To a solution of 0.4 g (1.3 mmol, 1.0 eq.) of 3-amino-N-(3,4-difluorophenyl)-2,3-dihydrobenzo[b]thiophene-7-carboxamide (XXXa) in 4 mL of DMF was added 30 mg (0.26 mmol, 0.2 eq.) of 4-dimethylaminopyridine followed by 0.28 mL (0.36 mmol, 1.2 eq.) of N,N-diisopropylethylamine. A solution of 0.32 g (1.6 mmol, 1.2 eq.) of pyridin-2-ylmethyl 1H-imidazole-1-carboxylate in 1 mL of DMF was then added and the mixture was stirred at 65° C. for 16 h. The mixture was diluted with 20 mL of water and extracted with 2×50 mL of ethyl acetate. The combined organic extracts were washed with 50 mL of brine, dried ($Na_2SO_4$) and filtered, and the solvent removed in vacuo. The residue was purified by flash chromatography ($SiO_2$, eluting with 3% methanol/methylene chloride) to provide 0.12 g (21%) of racemic O-pyridin-2-ylmethyl, N-(7-((3,4-difluorophenyl)carbamoyl)-2,3-dihydrobenzo[b]thiophen-3-yl)carbamate hydrochloride.

The enantiomers were subsequently separated by SFC (Waters SFC investigator. Mobile phase: Line A was 0.1% DEA in Hexane, Line B was 0.1% DEA in IPA:MeOH (30:70). Isoctratic ratio (A-B) (68-32), Column: CHIRALPAK AD-H 21×250 mm, 5 μm, flow rate: 18 g/min). The resolved enantiomers were then treated with 1 mL of 0.25 M HCl in methanol for 30 min. The solvent was removed in vacuo and the residues dried under high vacuum to provide the title compounds as their hydrochloride salts.

O-Pyridin-2-ylmethyl, N-(7-((3,4-difluorophenyl)carbamoyl)-2,3-dihydrobenzo[b]thiophen-3-yl) carbamate hydrochloride, enantiomer 1 (33.HCl). LCMS: m/z found: 440.7 [M−H] (Method C); HPLC: RT=7.16 min (Method F); Chiral HPLC, RT=3.97 min; $^1$H NMR (400 MHz, DMSO-$d_6$): δ 10.51 (s, 1H), 8.68 (d, 1H), 8.24 (d, 1H), 8.10 (dd 1H), 7.94-7.90 (dd, 2H), 7.62 (d, 1H), 7.52-7.60 (m, 2H), 7.36-7.49 (m, 2H), 7.28 (dd, 1H), 5.32-5.36 (m, 1H), 5.26 (s, 2H), 3.48-3.45 (m, 1H), 3.12-3.07 (m, 1H).

O-Pyridin-2-ylmethyl, N-(7-((3,4-difluorophenyl)carbamoyl)-2,3-dihydrobenzo[b]thiophen-3-yl)carbamate hydrochloride, enantiomer 2 (34.HCl). LCMS: m/z found: 440.7 [M−H] (Method C); HPLC: RT=7.18 min (Method F); Chiral HPLC, RT=5.46 min; $^1$H NMR (400 MHz, DMSO-$d_6$): δ 10.51 (s, 1H), 8.68 (d, 1H), 8.24 (d, 1H), 8.10 (dd 1H), 7.94-7.90 (dd, 2H), 7.62 (d, 1H), 7.52-7.60 (m, 2H), 7.36-

7.49 (m, 2H), 7.28 (dd, 1H), 5.32-5.36 (m, 1H), 5.26 (s, 2H), 3.48-3.45 (m, 1H), 3.12-3.07 (m, 1H).

O-Pyridin-2-ylmethyl, N-(7-((3-chloro-4-fluorophenyl)carbamoyl)-2,3-dihydrobenzo[b]thiophen-3-yl) carbamate (35, 36)

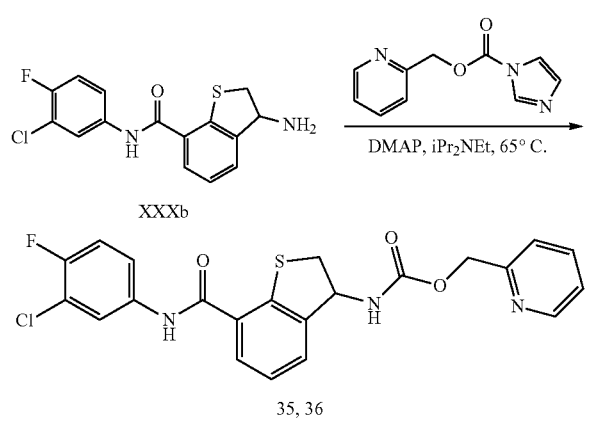

Pyridin-2-ylmethyl (7-((3-chloro-4-fluorophenyl)carbamoyl)-2,3-dihydrobenzo[b]thiophen-3-yl)carbamate (35, 36) was synthesized in an analogous manner to that described above from 3-amino-N-(3-chloro-4-fluorophenyl)-2,3-dihydrobenzo[b]thiophene-7-carboxamide (XXXb).

O-Pyridin-2-ylmethyl, N-(7-((3-chloro-4-fluorophenyl)carbamoyl)-2,3-dihydrobenzo[b]thiophen-3-yl) carbamate, enantiomer 1 (35). LCMS: m/z found: 458.7/460.7 [M−H] (Method C); HPLC RT=7.73 min (Method E); Chiral HPLC, RT=5.26 min; $^1$H NMR (400 MHz, DMSO-d$_6$): δ 10.47 (s, 1H), 8.63 (d, 1H), 8.21 (d, 1H), 7.85-8.12 (m, 3H), 7.63-7.73 (m, 1H), 7.35-7.55 (m, 3H), 7.25-7.32 (dd, 1H), 5.36 (q, 1H), 5.21 (s, 3H), 3.45-3.50 (m, 1H) 3.10-3.14 (m, 1H).

O-Pyridin-2-ylmethyl, N-(7-((3-chloro-4-fluorophenyl)carbamoyl)-2,3-dihydrobenzo[b]thiophen-3-yl) carbamate, enantiomer 2 (36). LCMS: m/z found: 458.7/460.7 [M−H] (Method C); HPLC: RT=7.18 min (Method F); Chiral HPLC, RT=5.46 min; $^1$H NMR (400 MHz, DMSO-d$_6$): δ 10.47 (s, 1H), 8.63 (d, 1H), 8.21 (d, 1H), 7.85-8.12 (m, 3H), 7.63-7.73 (m, 1H), 7.35-7.55 (m, 3H), 7.25-7.32 (dd, 1H), 5.36 (q, 1H), 5.21 (s, 2H), 3.45-3.50 (m, 1H) 3.10-3.14 (m, 1H).

O-Methyl, N-(7-((3,4-difluorophenyl)carbamoyl)-4-fluoro-2,3-dihydrobenzo[b]thiophen-3-yl) carbamate (55, 57)

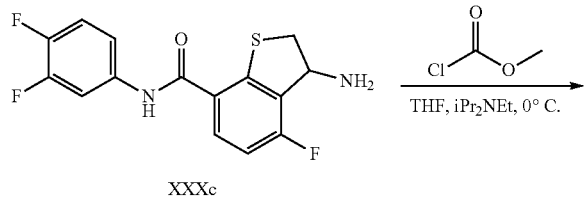

-continued

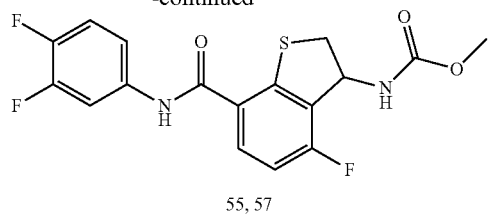

O-Methyl, N-(7-((3,4-difluorophenyl)carbamoyl)-4-fluoro-2,3-dihydrobenzo[b]thiophen-3-yl) carbamate (55, 57) was synthesized in an analogous manner to that described above from 3-amino-N-(3,4-difluorophenyl)-4-fluoro-2,3-dihydrobenzo[b]thiophene-7-carboxamide (XXXc) and methyl chloroformate.

O-Methyl, N-(7-((3,4-difluorophenyl)carbamoyl)-4-fluoro-2,3-dihydrobenzo[b]thiophen-3-yl) carbamate, enantiomer 1 (55). LCMS: m/z found: 381.2 [M−H] (Method C); HPLC: RT=7.94 min (Method E); Chiral HPLC, RT=4.34 min; $^1$H NMR (400 MHz, DMSO-d$_6$): δ 10.46 (s, 1H), 7.95-8.07 (m, 2H), 7.83-7.91 (m, 1H), 7.38-7.55 (m, 2H), 7.12 (dd, 1H), 5.52 (m, 1H), 3.48 (m, 4H), 3.10-3.14 (m, 1H).

O-Methyl, N-(7-((3,4-difluorophenyl)carbamoyl)-4-fluoro-2,3-dihydrobenzo[b]thiophen-3-yl) carbamate, enantiomer 2 (57). LCMS: m/z found: 381.3 [M−H] (Method C); HPLC: RT=7.93 min (Method E); Chiral HPLC, RT 8.18 min; 1H NMR (400 MHz, DMSO-d$_6$): δ 10.46 (s, 1H), 7.95-8.07 (m, 2H), 7.83-7.91 (m, 1H), 7.38-7.55 (m, 2H), 7.12 (dd, 1H), 5.52 (m, 1H), 3.48 (m, 4H), 3.10-3.14 (m, 1H).

O-Methyl, N-(7-((3-chloro-4-fluorophenyl)carbamoyl)-4-fluoro-2,3-dihydrobenzo[b]thiophen-3-yl) carbamate (58, 59)

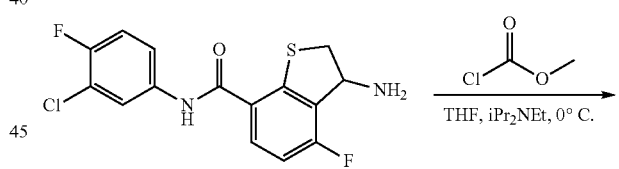

O-Methyl, N-(7-((3-chloro-4-fluorophenyl)carbamoyl)-4-fluoro-2,3-dihydrobenzo[b]thiophen-3-yl) carbamate (58, 59) was synthesized in an analogous manner to that described above from 3-amino-N-(3-chloro-4-fluorophenyl)-4-fluoro-2,3-dihydrobenzo[b]thiophene-7-carboxamide (XXXd) and methyl chloroformate.

O-Methyl, N-(7-((3-chloro-4-fluorophenyl)carbamoyl)-4-fluoro-2,3-dihydrobenzo[b]thiophen-3-yl) carbamate, enantiomer 1 (58). LCMS: m/z found: 399.1/401.1 [M−H] (Method D); HPLC: RT=7.60 min (Method F); Chiral HPLC, RT=6.61 min; $^1$H NMR (400 MHz, DMSO-$d_6$): δ 10.46 (s, 1H), 7.99-8.05 (m, 2H), 7.94-7.96 (m, 1H), 7.67-7.69 (m, 1H), 7.43 (dd, 1H), 7.12 (dd, 1H), 5.52 (m, 1H), 3.57 (m, 4H), 3.10-3.18 (m, 1H).

O-Methyl, N-(7-((3-chloro-4-fluorophenyl)carbamoyl)-4-fluoro-2,3-dihydrobenzo[b]thiophen-3-yl) carbamate, enantiomer 2 (59). LCMS: m/z found: 399.1/401.1 [M−H] (Method D); HPLC: RT=8.32 min (Method F); Chiral HPLC, RT=6.61 min; $^1$H NMR (400 MHz, DMSO-$d_6$): δ 10.46 (s, 1H), 7.99-8.05 (m, 2H), 7.94-7.96 (m, 1H), 7.67-7.69 (m, 1H), 7.43 (dd, 1H), 7.12 (dd, 1H), 5.52 (m, 1H), 3.57 (m, 4H), 3.10-3.18 (m, 1H).

O-Pyridin-2-ylmethyl, N-(7-((3,4-difluorophenyl)carbamoyl)-4-fluoro-2,3-dihydrobenzo[b]thiophen-3-yl) carbamate (63, 64)

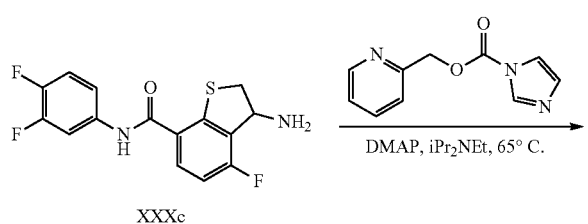

XXXc

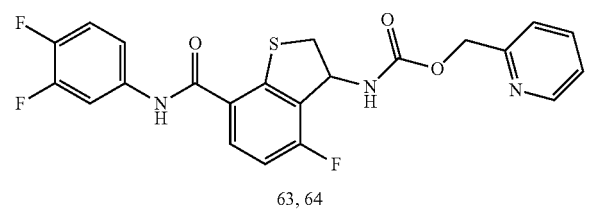

63, 64

O-Pyridin-2-ylmethyl, N-(7-((3,4-difluorophenyl)carbamoyl)-4-fluoro-2,3-dihydrobenzo[b]thiophen-3-yl)carbamate (63, 64) was synthesized in an analogous manner to that described above from 3-amino-N-(3,4-difluorophenyl)-4-fluoro-2,3-dihydrobenzo[b]thiophene-7-carboxamide (XXXc) and pyridin-2-ylmethyl 1H-imidazole-1-carboxylate.

O-Pyridin-2-ylmethyl, N-(7-((3,4-difluorophenyl)carbamoyl)-4-fluoro-2,3-dihydrobenzo[b]thiophen-3-yl) carbamate, enantiomer 1 (63). LCMS: m/z found: 460.2/462.2 [M+H] (Method C); HPLC: RT=7.28 min (Method E); Chiral HPLC, RT=5.20 min; $^1$H NMR (400 MHz, DMSO-$d_6$): δ 10.50 (s, 1H), 8.64 (d, 1H), 8.27 (d, 1H), 8.01-8.06 (m, 2H), 7.85-7.93 (m, 1H), 7.40-7.58 (m, 3H), 7.14 (dd, 1H), 5.55 (m, 1H), 5.20 (s, 2H), 4.03 (m, 1H) 3.17 (m, 1H).

O-Pyridin-2-ylmethyl, N-(7-((3,4-difluorophenyl)carbamoyl)-4-fluoro-2,3-dihydrobenzo[b]thiophen-3-yl) carbamate, enantiomer 2 (64). LCMS: m/z found: 460.3/462.3 [M+H] (Method C); HPLC: RT=7.28 min (Method E); Chiral HPLC, RT=6.89 min; $^1$H NMR (400 MHz, DMSO-$d_6$): δ 10.50 (s, 1H), 8.64 (d, 1H), 8.27 (d, 1H), 8.01-8.06 (m, 2H), 7.85-7.93 (m, 1H), 7.40-7.58 (m, 3H), 7.14 (dd, 1H), 5.55 (m, 1H), 5.20 (s, 2H), 4.03 (m, 1H) 3.17 (m, 1H).

O-Pyridin-2-ylmethyl, N-(7-((3-chloro-4-fluorophenyl)carbamoyl)-4-fluoro-2,3-dihydrobenzo[b]thiophen-3-yl) carbamate (65, 66)

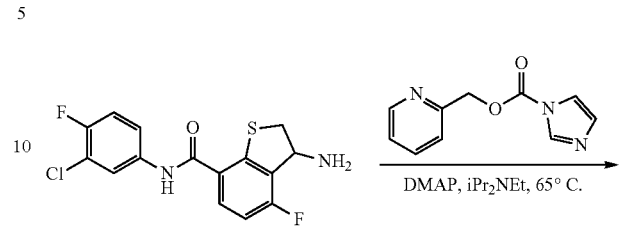

XXXd

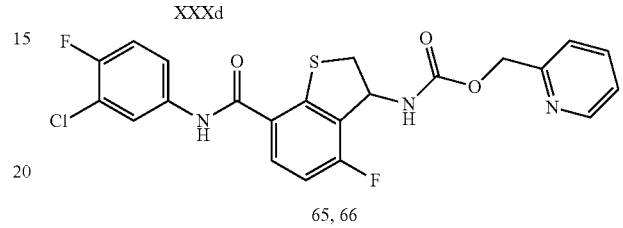

65, 66

O-Pyridin-2-ylmethyl, N-(7-((3-chloro-4-fluorophenyl)carbamoyl)-4-fluoro-2,3-dihydrobenzo[b]thiophen-3-yl) carbamate (65, 66) was synthesized in an analogous manner to that described above from 3-amino-N-(3-chloro-4-fluorophenyl)-4-fluoro-2,3-dihydrobenzo[b]thiophene-7-carboxamide (XXXd) and pyridin-2-ylmethyl 1H-imidazole-1-carboxylate.

O-Pyridin-2-ylmethyl, N-(7-((3-chloro-4-fluorophenyl)carbamoyl)-4-fluoro-2,3-dihydrobenzo[b]thiophen-3-yl) carbamate, enantiomer 1 (65). LCMS: m/z found: 476.2/478.2 [M+H] (Method C); HPLC: RT=7.59 min (Method F); Chiral HPLC, RT=7.08 min; $^1$H NMR (400 MHz, DMSO-$d_6$): δ 10.51 (s, 1H), 8.66 (d, 1H), 8.27 (d, 1H), 8.02-8.13 (m, 3H), 7.69-7.71 (m, 1H), 7.51-7.60 (m, 2H), 7.43 (dd, 1H), 7.13 (dd, 1H), 5.57 (m, 1H), 5.22 (s, 2H), 3.61 (m, 1H) 3.15 (m, 1H).

O-Pyridin-2-ylmethyl, N-(7-((3-chloro-4-fluorophenyl)carbamoyl)-4-fluoro-2,3-dihydrobenzo[b]thiophen-3-yl) carbamate, enantiomer 2 (66). LCMS: m/z found: 460.3/462.3 [M+H] (Method C); HPLC: RT=7.59 min (Method F); Chiral HPLC, RT=8.47 min; $^1$H NMR (400 MHz, DMSO-$d_6$): δ 10.51 (s, 1H), 8.66 (d, 1H), 8.27 (d, 1H), 8.02-8.13 (m, 3H), 7.69-7.71 (m, 1H), 7.51-7.60 (m, 2H), 7.43 (dd, 1H), 7.13 (dd, 1H), 5.57 (m, 1H), 5.22 (s, 2H), 3.61 (m, 1H) 3.15 (m, 1H).

Example 11: Non-Limiting Synthesis of Selected 1-(Substituted Amino)-2-Hydroxy-Dihydroindene-4-Carboxamides (Scheme 7)

Scheme 7.

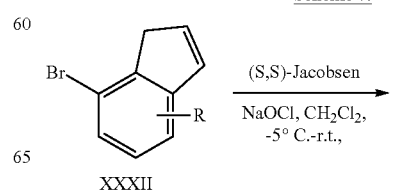

XXXII

Non-Limiting Illustration of Scheme 7

(1aS,6aR)-5-Bromo-1a,6a-dihydro-6H-indeno[1,2-b]oxirene

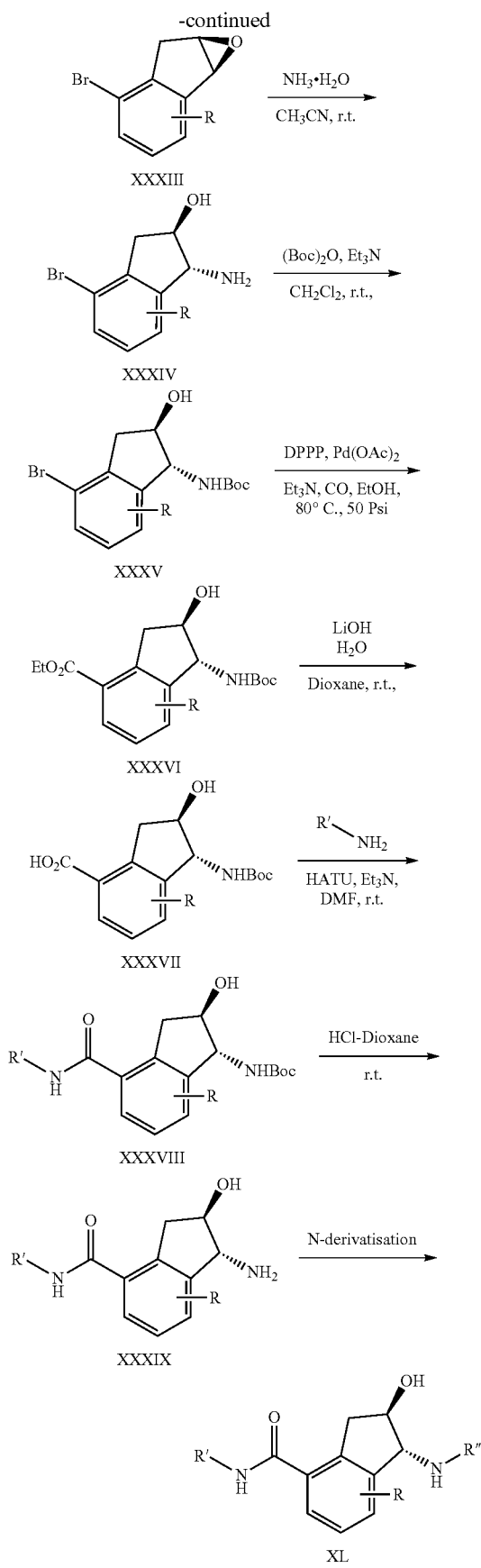

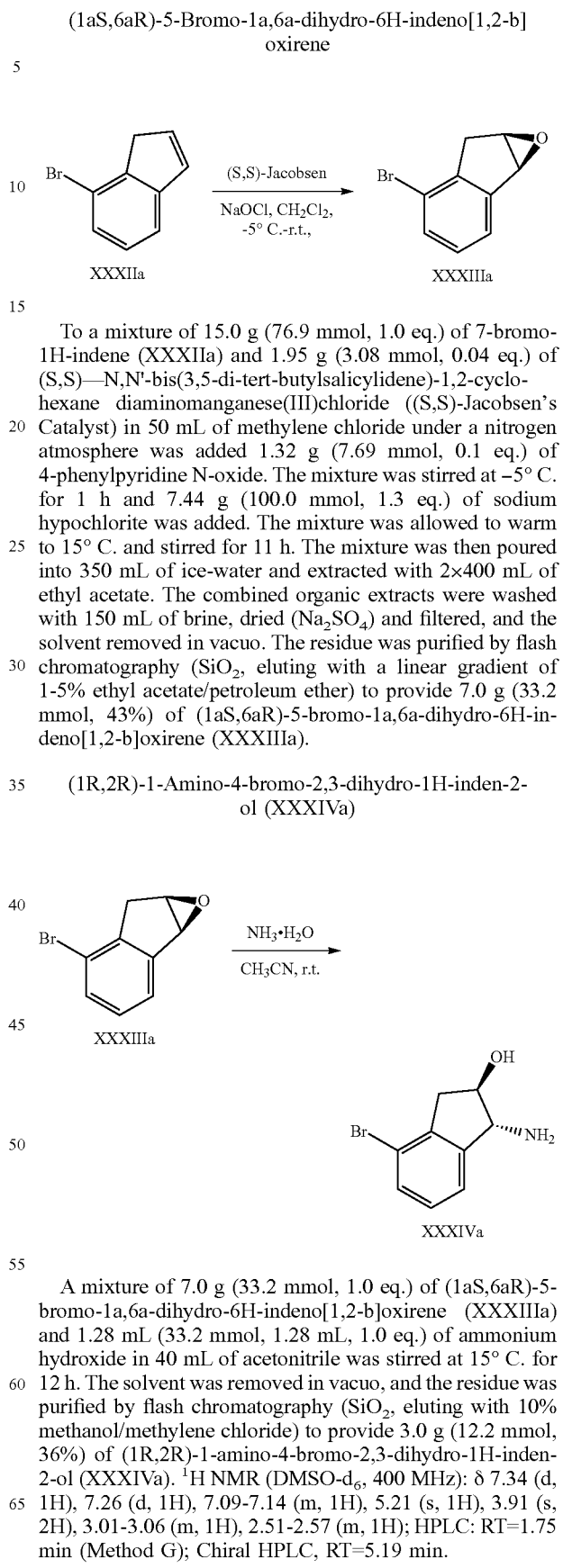

To a mixture of 15.0 g (76.9 mmol, 1.0 eq.) of 7-bromo-1H-indene (XXXIIa) and 1.95 g (3.08 mmol, 0.04 eq.) of (S,S)—N,N'-bis(3,5-di-tert-butylsalicylidene)-1,2-cyclohexane diaminomanganese(III)chloride ((S,S)-Jacobsen's Catalyst) in 50 mL of methylene chloride under a nitrogen atmosphere was added 1.32 g (7.69 mmol, 0.1 eq.) of 4-phenylpyridine N-oxide. The mixture was stirred at −5° C. for 1 h and 7.44 g (100.0 mmol, 1.3 eq.) of sodium hypochlorite was added. The mixture was allowed to warm to 15° C. and stirred for 11 h. The mixture was then poured into 350 mL of ice-water and extracted with 2×400 mL of ethyl acetate. The combined organic extracts were washed with 150 mL of brine, dried ($Na_2SO_4$) and filtered, and the solvent removed in vacuo. The residue was purified by flash chromatography ($SiO_2$, eluting with a linear gradient of 1-5% ethyl acetate/petroleum ether) to provide 7.0 g (33.2 mmol, 43%) of (1aS,6aR)-5-bromo-1a,6a-dihydro-6H-indeno[1,2-b]oxirene (XXXIIIa).

(1R,2R)-1-Amino-4-bromo-2,3-dihydro-1H-inden-2-ol (XXXIVa)

A mixture of 7.0 g (33.2 mmol, 1.0 eq.) of (1aS,6aR)-5-bromo-1a,6a-dihydro-6H-indeno[1,2-b]oxirene (XXXIIIa) and 1.28 mL (33.2 mmol, 1.28 mL, 1.0 eq.) of ammonium hydroxide in 40 mL of acetonitrile was stirred at 15° C. for 12 h. The solvent was removed in vacuo, and the residue was purified by flash chromatography ($SiO_2$, eluting with 10% methanol/methylene chloride) to provide 3.0 g (12.2 mmol, 36%) of (1R,2R)-1-amino-4-bromo-2,3-dihydro-1H-inden-2-ol (XXXIVa). $^1$H NMR (DMSO-$d_6$, 400 MHz): δ 7.34 (d, 1H), 7.26 (d, 1H), 7.09-7.14 (m, 1H), 5.21 (s, 1H), 3.91 (s, 2H), 3.01-3.06 (m, 1H), 2.51-2.57 (m, 1H); HPLC: RT=1.75 min (Method G); Chiral HPLC, RT=5.19 min.

O-tert-Butyl ((1R,2R)-4-bromo-2-hydroxy-2,3-dihydro-1H-inden-1-yl) carbamate (XXXVa)

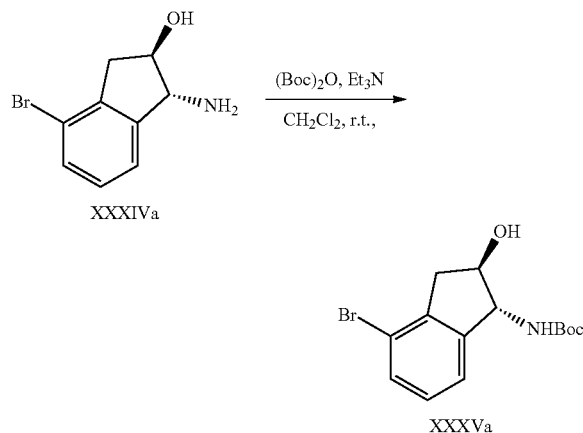

To a mixture of 3.0 g (13.2 mmol, 1.0 eq.) of (1R,2R)-1-amino-4-bromo-2,3-dihydro-1H-inden-2-ol (XXXIVa) and 2.92 g (21.0 mmol, 1.6 eq.) of trimethylamine in 200 mL of methylene chloride was added 2.93 g (13.4 mmol, 1.02 eq.) of di-tert-butyl dicarbonate, and the mixture was stirred at room temperature for 12 h. The solvent was removed in vacuo and the residue was purified by flash chromatography (SiO$_2$, eluting with 10% methanol/methylene chloride) to provide 3.0 g (8.2 mmol, 62%) of O-tert-butyl ((1R,2R)-4-bromo-2-hydroxy-2,3-dihydro-1H-inden-1-yl)carbamate (XXXVa).

Ethyl (1R,2R)-1-((tert-butoxycarbonyl)amino)-2-hydroxy-2,3-dihydro-1H-indene-4-carboxylate (XXXVIa)

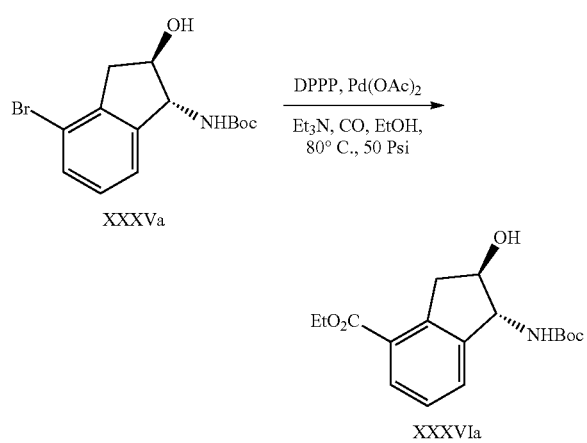

To a solution of 2.9 g (8.84 mmol, 1.0 eq.) of tert-butyl ((1R,2R)-4-bromo-2-hydroxy-2,3-dihydro-1H-inden-1-yl) carbamate (XXXVa) in 10 mL of ethanol were added 1.09 g (2.65 mmol, 0.3 eq.) of 1,3-bis(diphenylphosphino)propane, 0.2 g (0.88 mmol, 0.1 eq.) of palladium acetate and 4.9 mL (35.3 mmol, 4.0 eq.) of trimethylamine. The suspension was degassed under vacuum and purged with carbon monoxide. The mixture was then stirred under 50 psi of carbon monoxide at 80° C. for 16 hours. The mixture was allowed to cool to room temperature and poured into 20 mL of ice-water. The mixture was then extracted with 2×100 mL of ethyl acetate and the combined organic extracts were washed with 2×50 mL of brine, dried (Na$_2$SO$_4$) and filtered, and the solvent was removed in vacuo. The residue was purified by flash chromatography (SiO$_2$, eluting with a linear gradient of 20-50% ethyl acetate/petroleum ether) to provide 1.0 g (3.1 mmol, 35%) of ethyl (1R,2R)-1-((tert-butoxycarbonyl)amino)-2-hydroxy-2,3-dihydro-1H-indene-4-carboxylate (XXXVIa) and 1.2 g (3.5 mmol, 41%) of recovered tert-butyl ((1R,2R)-4-bromo-2-hydroxy-2,3-dihydro-1H-inden-1-yl)carbamate (XXXVa).

(1R,2R)-1-((tert-Butoxycarbonyl)amino)-2-hydroxy-2,3-dihydro-1H-indene-4-carboxylic Acid (XXXVIIa)

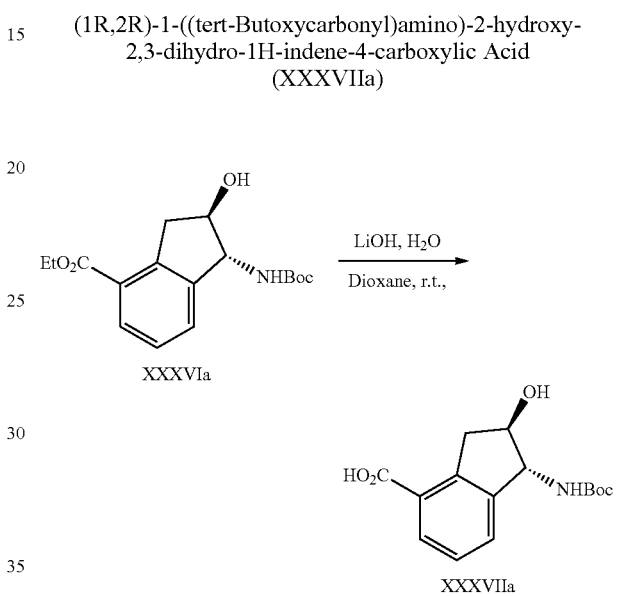

To a solution of 1.0 g (3.11 mmol, 1.0 eq.) of ethyl (1R,2R)-1-((tert-butoxycarbonyl) amino)-2-hydroxy-2,3-dihydro-1H-indene-4-carboxylate (XXXVIa) in 30 mL of p-dioxane was added a solution of 0.39 g (9.33 mmol, 3.0 eq.) of lithium hydroxide monohydrate in 10 mL of water, and the mixture was stirred at room temperature for 6 h. The p-dioxane was removed in vacuo and the resulting mixture was extracted with 10 mL of ethyl acetate. The aqueous phase was acidified to pH 4 with 1 M HCl solution, and then the mixture was freeze-dried to provide 1.3 g of crude (1R,2R)-1-((tert-butoxycarbonyl)amino)-2-hydroxy-2,3-dihydro-1H-indene-4-carboxylic acid (XXXVIIa).

O-tert-Butyl ((1R,2R)-4-((3-chloro-4-fluorophenyl) carbamoyl)-2-hydroxy-2,3-dihydro-1H-inden-1-yl) carbamate (XXXVIIIa)

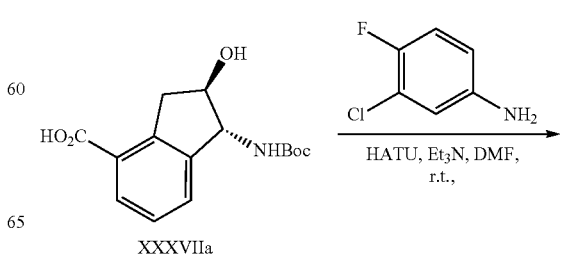

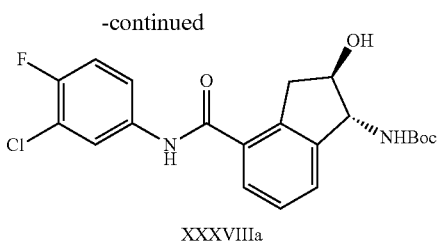

XXXVIIIa

To a mixture of 1.3 g (4.43 mmol, 1.0 eq.) of (1R,2R)-1-((tert-butoxycarbonyl)amino)-2-hydroxy-2,3-dihydro-1H-indene-4-carboxylic acid (XXXVIIa) and 2.53 g (6.65 mmol, 1.5 eq.) of 1-[bis(dimethylamino)methylene]-1H-1,2,3-triazolo[4,5-b]pyridinium 3-oxide hexafluorophosphate in 20 mL of DMF was added 3.1 mL (22.2 mmol, 5.0 eq.) of triethylamine. The mixture was stirred to room temperature for 10 min, and 0.48 g (3.28 mmol, 0.74 eq.) of 3-chloro-4-fluoroaniline were added. The reaction was stirred at room temperature for a further 12 h. The mixture was then diluted with 50 mL of water and extracted with 3×50 mL of ethyl acetate. The combined organic extracts were washed with 100 mL of brine, dried (Na$_2$SO$_4$) and filtered, and the solvent was removed in vacuo. The residue was purified by flash chromatography (SiO$_2$, eluting with a linear gradient of 20-50% ethyl acetate/petroleum ether) to provide 0.65 g (1.54 mmol, 35%) of O-tert-butyl ((1R,2R)-4-((3-chloro-4-fluorophenyl)carbamoyl)-2-hydroxy-2,3-dihydro-1H-inden-1-yl)carbamate (XXXVIIIa). $^1$H NMR (DMSO-d$_6$, 400 MHz): δ 10.34 (s, 1H), 8.01-8.04 (m, 1H) 7.93 (s, 1H), 7.24-7.52 (m, 5H), 5.26 (d, 1H), 4.68-4.72 (m, 1H), 4.17-4.22 (m, 1H), 3.27 (m, 1H), 2.78-2.84 (m, 1H), 1.42 (s, 9H).

(1R,2R)-1-Amino-N-(3-chloro-4-fluorophenyl)-2-hydroxy-2,3-dihydro-1H-indene-4-carboxamide (XXXIXa)

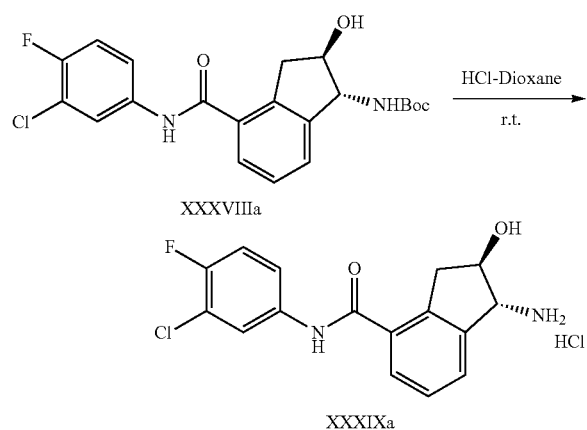

A solution of 0.65 g (1.54 mmol 1.0 eq.) of tert-butyl ((1R,2R)-4-((3-chloro-4-fluorophenyl)carbamoyl)-2-hydroxy-2,3-dihydro-1H-inden-1-yl)carbamate (XXXVIIIa) in 10 mL of 4 M HCl in p-dioxane was stirred at room temperature for 2 hr. The volatiles were removed in vacuo, and the residue was dried under high vacuum to provide 0.55 g of ((1R,2R)-1-amino-N-(3-chloro-4-fluorophenyl)-2-hydroxy-2,3-dihydro-1H-indene-4-carboxamide hydrochloride salt (XXXIXa).

O-Methyl, N-((1R,2R)-4-((3-chloro-4-fluorophenyl)carbamoyl)-2-hydroxy-2,3-dihydro-1H-inden-1-yl) carbamate (46)

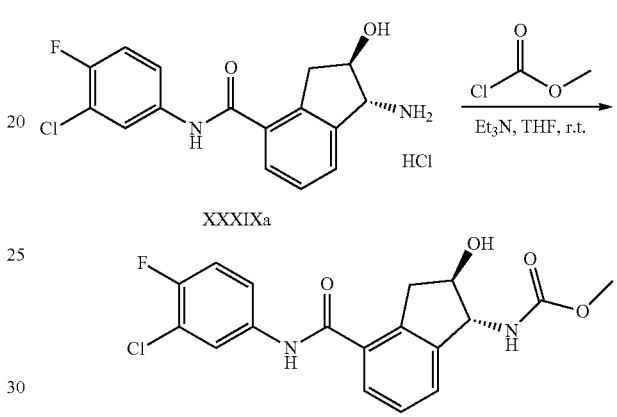

O-Methyl, N-((1R,2R)-4-((3-chloro-4-fluorophenyl)carbamoyl)-2-hydroxy-2,3-dihydro-1H-inden-1-yl)carbamate (46) was prepared in a similar manner as described above from ((1R,2R)-1-amino-N-(3-chloro-4-fluorophenyl)-2-hydroxy-2,3-dihydro-1H-indene-4-carboxamide hydrochloride salt (XXXIXa) and methyl chloroformate. LCMS: m/z found 379.2/381.2 [M+H]$^+$; $^1$H NMR (300 MHz, DMSO-d$_6$) δ 10.39 (s, 1H), 8.06 (dd, 1H), 7.58-7.67 (m, 3H), 7.29-7.44 (m, 3H), 5.35 (d, 1H), 4.78 (t, 1H), 4.23 (q, 1H), 3.62 (s, 3H), 2.83-2.89 (m, 1H).

O-Pyridin-2-ylmethyl, N-((1R,2R)-4-((3-chloro-4-fluorophenyl)carbamoyl)-2-hydroxy-2,3-dihydro-1H-inden-1-yl) carbamate (51)

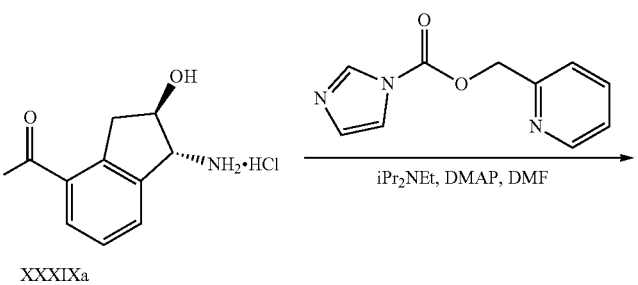

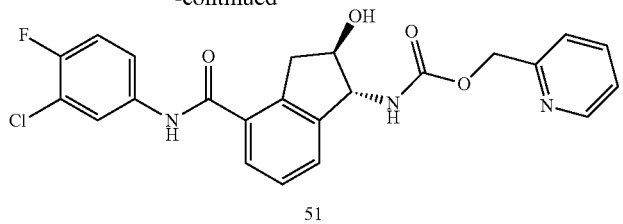

51

O-Pyridin-2-ylmethyl, N-((1R,2R)-4-((3-chloro-4-fluorophenyl)carbamoyl)-2-hydroxy-2,3-dihydro-1H-inden-1-yl)carbamate (51) was prepared in a similar manner as described above from ((1R,2R)-1-amino-N-(3-chloro-4-fluorophenyl)-2-hydroxy-2,3-dihydro-1H-indene-4-carboxamide hydrochloride salt (XXXIXa) and pyridin-2-ylmethyl 1H-imidazole-1-carboxylate. LCMS: m/z found 456.3/458.2 [M+H]$^+$; HPLC: RT=2.11 min (Method G); $^1$H NMR (300 MHz, DMSO-d$_6$) δ 10.38 (s, 1H), 8.54 (d, 1H), 8.04 (dd, 1H), 7.81-7.90 (m, 2H), 7.62-7.69 (m, 2H), 7.56 (d, 1H), 7.31-7.42 (m, 6H), 5.37 (d, 1H), 5.15 (s, 2H), 4.78 (t, 1H), 4.22 (m, 1H), 2.81-2.87 (dd, 1H).

(1R,2R)—N-(3-Chloro-4-fluorophenyl)-2-hydroxy-1-(3-methylureido)-2,3-dihydro-1H-indene-4-carboxamide (47)

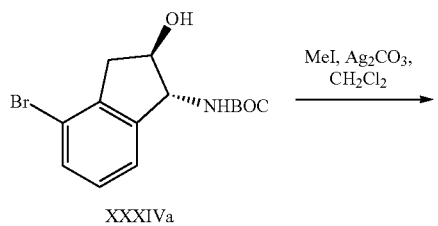

XXXIXa

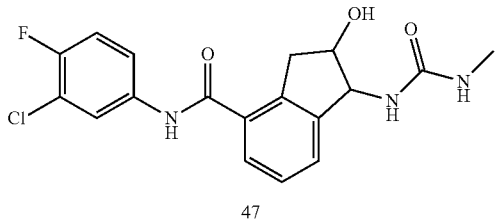

47

(1R,2R)—N-(3-Chloro-4-fluorophenyl)-2-hydroxy-1-(3-methylureido)-2,3-dihydro-1H-indene-4-carboxamide (47) was prepared in a similar manner as described above from ((1R,2R)-1-amino-N-(3-chloro-4-fluorophenyl)-2-hydroxy-2,3-dihydro-1H-indene-4-carboxamide hydrochloride salt (XXXIXa) and N-methyl carbamoyl chloride. LCMS: m/z found 378.1/380.2 [M+H]$^+$, 400.2/402.2 [M+Na]$^+$; HPLC: RT=2.23 min (Method G); $^1$H NMR (300 MHz, DMSO-d$_6$) δ 10.37 (s, 1H), 8.06 (dd, 1H), 7.62-7.69, (m, 1H), 8.57 (d, 1H), 7.42 (dd, 1H), 7.32-7.39 (m, 2H), 6.34 (d, 1H) 5.78 (q, 1H), 5.31 (d, 1H), 4.85 (t, 1H), 4.13 (m, 1H), 2.86 (m, 1H), 2.62 (s, 3H).

O-tert-Butyl ((1R,2R)-4-bromo-2-methoxy-2,3-dihydro-1H-inden-1-yl)carbamate

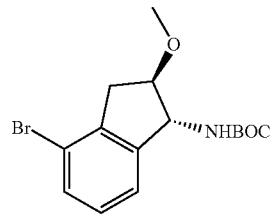

XXXIVa

To a mixture of 10 g (30.47 mmol, 1.0 eq.) of tert-butyl ((1R,2R)-4-bromo-2-hydroxy-2,3-dihydro-1H-inden-1-yl)carbamate (XXXIVa) in 30 mL of methylene chloride were added 25.2 g (91.4 mmol, 3.0 eq.) of silver carbonate and 5.69 mL (91.41 mmol, 3.0 eq.) of iodomethane. The mixture was stirred at 60° C. for 72 h. The reaction mixture was filtered, and the solvent removed in vacuo. The residue was re-suspended in 100 mL of methylene chloride and washed with 2×100 mL of brine, dried (Na$_2$SO$_4$), filtered and the solvent removed in vacuo. The residue was purified by column chromatography (SiO$_2$, eluting with a linear gradient of 5-100% ethyl acetate/petroleum ether) to provide 1.5 g (4.38 mmol, 14%) of tert-butyl ((1R,2R)-4-bromo-2-methoxy-2,3-dihydro-1H-inden-1-yl)carbamate and 6 g (18.3 mmol, 60%) of recovered O-tert-butyl ((1R,2R)-4-bromo-2-methoxy-2,3-dihydro-1H-inden-1-yl)carbamate (XXXIVa). $^1$H NMR (CDCl$_3$, 400 MHz): δ 7.42-7.40 (m, 1H), 7.27-7.22 (m, 1H), 7.13-7.09 (m, 1H), 5.13-5.12 (m, 1H), 4.77-4.75 (m, 1H), 4.00-3.96 (m, 1H), 3.50 (s, 3H), 3.34-3.28 (m, 1H), 2.88-2.83 (m, 1H), 1.49 (s, 9H).

O-Methyl, N-((1R,2R)-4-((3-chloro-4-fluorophenyl)carbamoyl)-2-methoxy-2,3-dihydro-1H-inden-1-yl)carbamate (130)

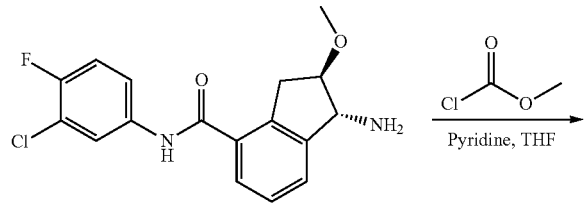

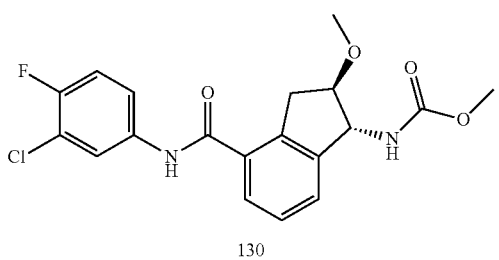

130

To a solution of 0.1 g (0.27 mmol, 1.0 eq.) of (1R,2R)-1-amino-N-(3-chloro-4-fluorophenyl)-2-methoxy-2,3-dihydro-1H-indene-4-carboxamide in hydrochloride (synthesized in a similar manner as described above from O-tert-butyl ((1R,2R)-4-bromo-2-methoxy-2,3-dihydro-1H-inden-1-yl)carbamate in 5 mL of anhydrous THF were added 0.11 mL (1.35 mmol, 5.0 eq.) of pyridine and 42 µL (0.54 mmol, 2.0 eq.) of methyl chloroformate. The mixture was stirred at room temperature for 15 h and then at 40° C. for a further 15 h. The solvent was removed in vacuo and the residue was re-suspended in 100 mL of methylene chloride. The organic solution was washed with 2×100 mL of brine, dried (Na$_2$SO$_4$), filtered and the solvent removed in vacuo. The residue was purified by semi-prep HPLC to provide 16 mg (15%) of O-methyl, N-((1R,2R)-4-((3-chloro-4-fluorophenyl)carbamoyl)-2-methoxy-2,3-dihydro-1H-inden-1-yl)carbamate (130). LCMS: m/z found [M+H]$^+$393.1/395.1; $^1$H NMR: (DMSO, 400 MHz): δ 8.07-8.05 (m, 1H), 7.78-7.76 (m, 1H), 7.68-7.61 (m, 2H), 7.44-7.32 (m, 3H), 4.92-4.88 (m, 1H), 4.02-3.97 (m, 1H), 3.61 (s, 3H) 3.52-3.42 (m, 1H), 3.45-3.34 (m, 3H), 2.82-2.86 (m, 1H).

(1R,2R)—N-(3-Chloro-4-fluorophenyl)-2-methoxy-1-(3-methylureido)-2,3-dihydro-1H-indene-4-carboxamide (165)

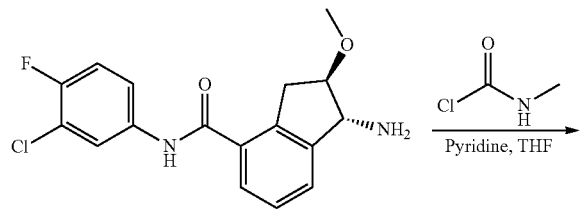

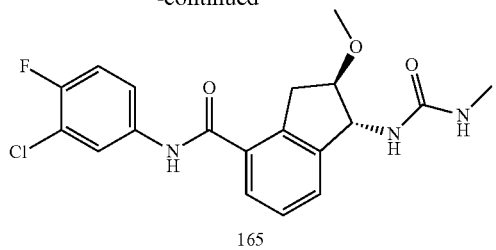

165

(1R,2R)—N-(3-Chloro-4-fluorophenyl)-2-methoxy-1-(3-methylureido)-2,3-dihydro-1H-indene-4-carboxamide (165) was prepared in a similar manner as described above from (1R,2R)-1-amino-N-(3-chloro-4-fluorophenyl)-2-methoxy-2,3-dihydro-1H-indene-4-carboxamide and methylcarbamoyl chloride. LCMS: m/z found [M+H]$^+$392.1/394.1; $^1$H NMR: (DMSO, 400 MHz): δ 10.40 (s, 1H), 8.08-8.06 (m, 1H), 7.69-7.60 (m, 2H), 7.44-7.34 (m, 3H), 6.43-6.41 (m, 1H) 5.76-5.5 (m, 1H), 5.03-5.00 (m, 1H), 3.95-3.90 (m, 1H), 3.50-3.46 (m, 1H), 3.35 (s, 1H), 2.93-2.87 (m, 1H), 2.62-2.61 (m, 3H).

O-Pyridin-2-ylmethyl, N-((1R,2R)-4-((3-chloro-4-fluorophenyl)carbamoyl)-7-fluoro-2-methoxy-2,3-dihydro-1H-inden-1-yl) carbamate (178)

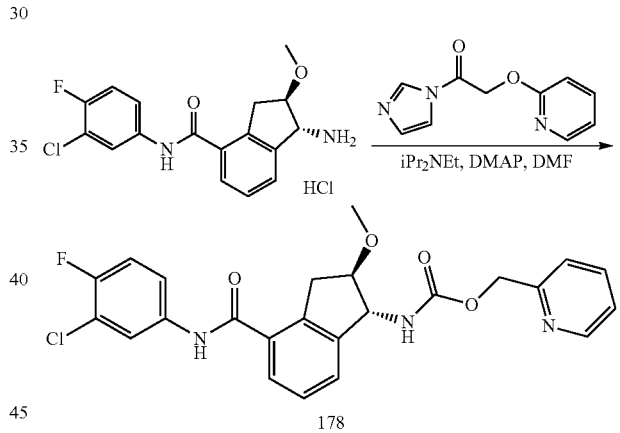

178

To a mixture of 0.20 g (0.54 mmol, 1.0 eq.) of (1R,2R)-1-amino-N-(3-chloro-4-fluoro-phenyl)-2-methoxy-indane-4-carboxamide, 0.13 g (0.65 mmol, 1.21 eq.) of 2-pyridylmethyl imidazole-1-carboxylate, and 0.013 g (0.11 mmol, 0.21 eq.) of DMAP in 10 mL of anhydrous DMF was added 0.09 g (0.71 mmol, 1.32 eq.) of N,N-diisopropylethylamine. The mixture was then heated to 65° C. for 12 h. The mixture was quenched by the addition of 30 mL of water and extracted with 2×30 mL of ethyl acetate. The combined organic extracts were washed with 2×50 mL of brine, dried (Na$_2$SO$_4$), filtered and the solvent was removed in vacuo. The residue was re-suspended in 15 mL of methylene chloride and stirred for 1 h. The solids were collected by filtration and washed with 10 mL of methylene chloride to provide 69 mg (0.14 mmol, 27%) of O-pyridin-2-ylmethyl, N-((1R,2R)-4-((3-chloro-4-fluorophenyl)carbamoyl)-7-fluoro-2-methoxy-2,3-dihydro-1H-inden-1-yl)carbamate (178). LCMS: m/z found 470.1/472.1 [M+H]$^+$, 492.1/494.1 [M+Na]$^+$; $^1$H NMR (400 MHz, DMSO-d$_6$): δ 10.41 (s, 1H), 8.56 (d, 1H), 8.07-8.01 (m, 2H), 7.84 (m, 1H), 7.67-7.61 (m, 2H), 7.43-7.34 (m, 5H), 5.16 (s, 2H), 4.95-4.91 (m, 1H), 4.07-4.01 (m, 1H), 3.54-3.47 (m, 1H), 3.35 (s, 3H), 2.93-2.88 (dd, 1H).

Example 12: Non-Limiting Synthesis of Selected 1-(Substituted Amino)-2,2-Dimethyl-Dihydroindene-4-Carboxamides (Scheme 8)

Scheme 8.

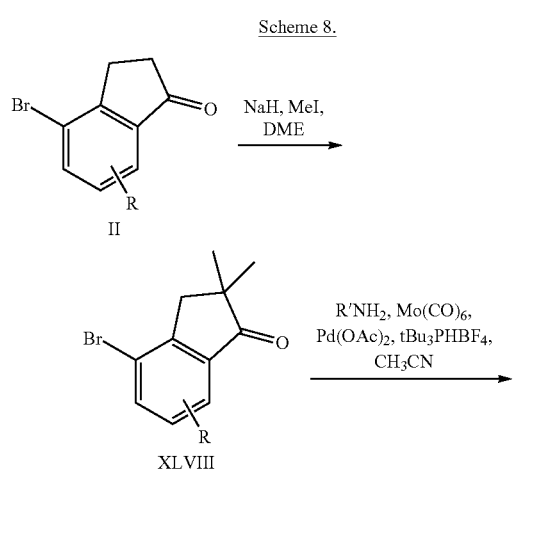

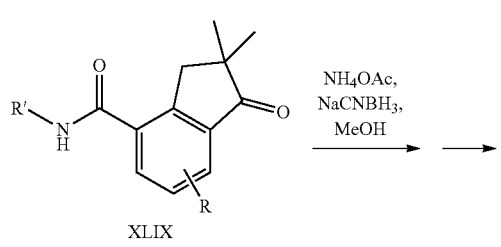

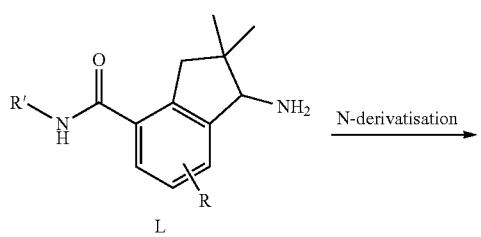

Non-Limiting Illustration of Scheme 8

4-Bromo-7-fluoro-2,2-dimethyl-2,3-dihydro-1H-inden-1-one (XLVIIIa)

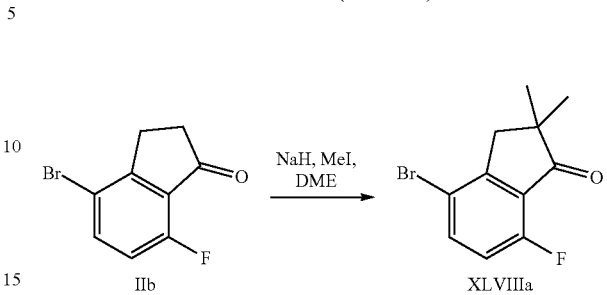

To a solution of 3.0 g (13.1 mmol, 1.0 eq.) of 4-bromo-7-fluoro-2,3-dihydro-1H-inden-1-one (IIb) in dry 30 mL of anhydrous DME at 0° C. under a nitrogen atmosphere was added 1.57 g (60% dispersion in mineral oil, 39.3 mmol, 3.0 eq.) of sodium hydride portionwise. The mixture was stirred at 0° C. for 30 minutes, and 5.5 g (39.3 mmol, 3.0 eq.) of methyl iodide was added dropwise. The mixture was stirred 0° C. for a further 1 h and quenched by the slow addition of saturated ammonium chloride solution. The mixture was then extracted with 2×200 mL of ethyl acetate and the combined organic extracts were washed with 30 mL of water followed by 30 mL of brine. The organic solution was dried (Na$_2$SO$_4$), filtered and the solvent was removed in vacuo. The residue purified by flash chromatography (SiO$_2$, eluting with a linear gradient of 0-20% ethyl acetate/petroleum ether) to provide 3.0 g (11.6 mmol, 89%) of (4-bromo-7-fluoro-2,2-dimethyl-2,3-dihydro-1H-inden-1-one (XLVIIIa). LCMS: (Method H); m/z found 257/259 [M+H]$^+$; $^1$H NMR (400 MHz, CDCl$_3$) δ=7.69-7.72 (m, 1H), 6.92-6.96 (m, 1H), 2.93 (s, 2H), 1.25 (s, 6H).

N-(3-Chloro-4-fluorophenyl)-7-fluoro-2,2-dimethyl-1-oxo-2,3-dihydro-1H-indene-4-carboxamide (XLIXa)

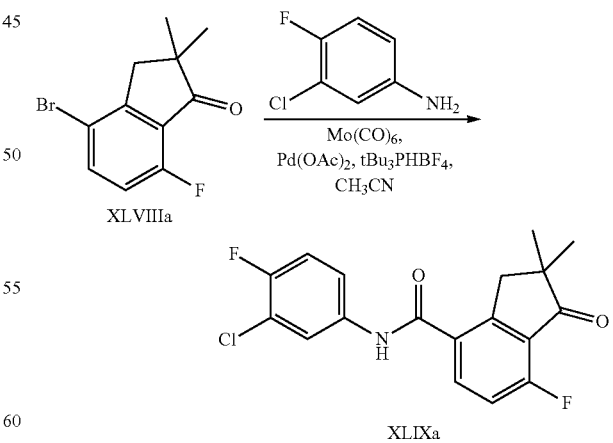

A solution of 1.0 g (3.9 mmol, 1.0 eq.) of 4-bromo-7-fluoro-2,2-dimethyl-2,3-dihydro-1H-inden-1-one (XVLIIIa) in 15 mL of acetonitrile was degassed with nitrogen for approximately 5 minutes. To the degassed solution was added 1.12 g (7.75 mmol, 2.0 eq.) of 3-chloro-4-fluoroaniline followed by 0.82 g (7.8 mmol, 2.0 eq.) of sodium, 1.02 g (3.9 mmol, 1.0 eq.) of molybdenumhexacarbonyl and 0.11 g (0.39 mmol, 0.1 eq.) of tri-tert-butylphosphonium tetrafluoroborate. The mixture was then degassed with nitrogen for approximately 20 minutes and 17 mg (0.39 mmol, 0.1 eq.) of palladium acetate was added. The mixture was heated at 70° C. for 16 h. On cooling to room temperature, the mixture was filtered through CELITE® and the pad was washed with 100 mL of ethyl acetate. The solvent was removed in vacuo, and the residue purified by flash chromatography (SiO$_2$, eluting with a linear gradient of 0-30% ethyl acetate/petroleum ether) to provide 0.37 g (1.1 mmol, 28%) of N-(3-chloro-4-fluorophenyl)-7-fluoro-2,2-dimethyl-1-oxo-2,3-dihydro-1H-indene-4-carboxamide (XLIXa). LCMS: (Method H) m/z found 350/352 [M+H]$^+$; $^1$H NMR (400 MHz, CDCl$_3$) δ 7.87-7.90 (m, 1H), 7.85 (bs, 1H), 7.83-7.84 (m, 1H), 7.41-7.44 (m, 1H), 7.09-7.18 (m, 2H), 3.34 (s, 2H), 1.23 (s, 6H).

1-Amino-N-(3-chloro-4-fluorophenyl)-7-fluoro-2,2-dimethyl-2,3-dihydro-1H-indene-4-carboxamide (La)

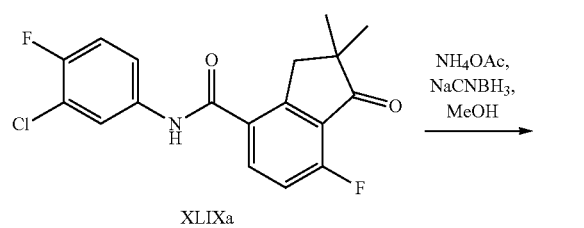

To a stirred solution of 1.0 g (2.8 mmol, 1.0 eq.) of N-(3-chloro-4-fluorophenyl)-7-fluoro-2,2-dimethyl-1-oxo-2,3-dihydro-1H-indene-4-carboxamide (XLIXa) in 10 mL of anhydrous methanol was added 3.3 g (42.9 mmol, 15 eq.) of ammonium acetate followed by 0.26 g (4.29 mmol) of sodium cyanoborohydride. The mixture was then heated to 60° C. for 16 h. The solvent was removed in vacuo and the residue was partitioned between 50 mL of sat. sodium bicarbonate solution and 100 mL of ethyl acetate. The aqueous phase was extracted with 100 mL of ethyl acetate and the combined organic extracts were dried (Na$_2$SO$_4$), filtered and the solvent was removed in vacuo to provide 0.8 g (2.3 mmol, 80%) of 1-amino-N-(3-chloro-4-fluorophenyl)-7-fluoro-2,2-dimethyl-2,3-dihydro-1H-indene-4-carboxamide (La). LCMS: (Method H) m/z found 334/336 [M-NH$_2$]+; $^1$H NMR (400 MHz, DMSO-d$_6$) δ 10.33 (s, 1H), 8.02-8.05 (m, 1H), 7.61-7.67 (m, 2H), 7.40-7.59 (m, 1H), 7.10-7.14 (m, 1H), 3.94 (s, 1H), 3.02-3.06 (m, 1H), 2.77-2.81 (m, 1H), 1.94 (m, 2H) 1.06 (s, 3H), 1.03 (s, 3H).

O-Methyl, N-(4-((3-chloro-4-fluorophenyl)carbamoyl)-7-fluoro-2,2-dimethyl-2,3-dihydro-1H-inden-1-yl) carbamate (121, 122)

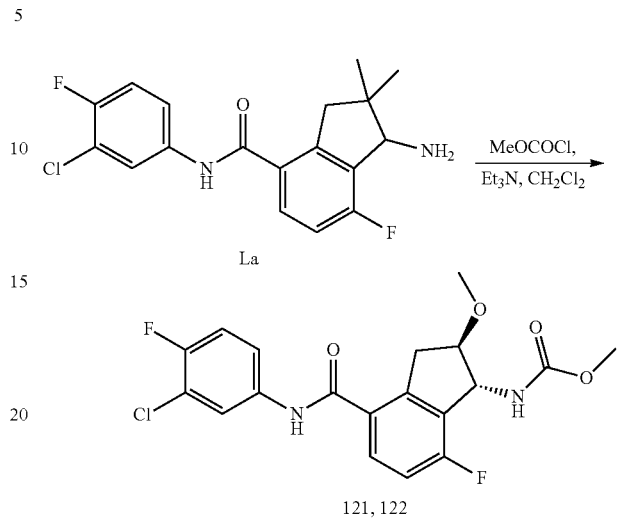

O-Methyl, N-(4-((3-chloro-4-fluorophenyl)carbamoyl)-7-fluoro-2,2-dimethyl-2,3-dihydro-1H-inden-1-yl)carbamate (141, 142) was synthesized in a similar manner as outlined above from 1-amino-N-(3-chloro-4-fluorophenyl)-7-fluoro-2,2-dimethyl-2,3-dihydro-1H-indene-4-carboxamide (La) and methyl chloroformate. The resulting enantiomers were subsequently separated by SFC (Waters SFC investigator. Isocratic mobile phase LIQUID.CO$_2$: 0.3% DEA methanol (80:20), Column: Lux-Amylose-2, 30×250 mm 5 μm column, flow rate: 60 ml/min).

O-Methyl, N-(4-((3-chloro-4-fluorophenyl)carbamoyl)-7-fluoro-2,2-dimethyl-2,3-dihydro-1H-inden-1-yl) carbamate, enantiomer 1 (121). LCMS: m/z found 409.3/411.3 [M+H]$^+$; HPLC: RT=11.10 min (Method K); Chiral HPLC: RT=2.64 min; $^1$H NMR (DMSO, 400 MHz): δ 10.37 (s, 1H), 8.03 (dd, 1H), 7.70 (dd, 1H), 7.62-7.65 (m, 1H), 7.56 (d, 1H), 7.43 (dd, 1H), 7.16 (dd, 1H), 4.85 (d, 1H), 3.57 (s, 3H), 2.95 (ABq, 2H), 1.06 (s, 3H), 0.98 (s, 3H).

O-Methyl, N-(4-((3-chloro-4-fluorophenyl)carbamoyl)-7-fluoro-2,2-dimethyl-2,3-dihydro-1H-inden-1-yl) carbamate, enantiomer 2 (122). LCMS: m/z found 409.3/411.3 [M+H]$^+$; HPLC: RT=11.15 min (Method K); Chiral HPLC: RT=4.25 min; $^1$H NMR (DMSO, 400 MHz): δ 10.37 (s, 1H), 8.03 (dd, 1H), 7.70 (dd, 1H), 7.62-7.65 (m, 1H), 7.56 (d, 1H), 7.43 (dd, 1H), 7.16 (dd, 1H), 4.85 (d, 1H), 3.57 (s, 3H), 2.95 (ABq, 2H), 1.06 (s, 3H), 0.98 (s, 3H).

N-(3-Chloro-4-fluorophenyl)-7-fluoro-2,2-dimethyl-1-(3-methylureido)-2,3-dihydro-1H-indene-4-carboxamide (249, 134)

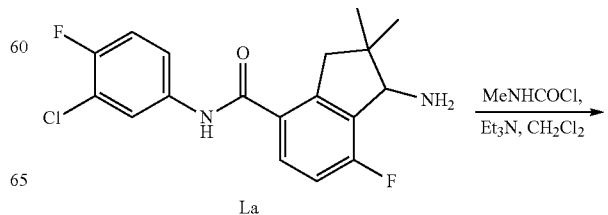

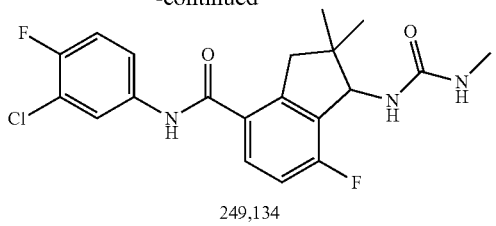
249, 134

N-(3-Chloro-4-fluorophenyl)-7-fluoro-2,2-dimethyl-1-(3-methylureido)-2,3-dihydro-1H-indene-4-carboxamide (249, 134) was synthesized in a similar manner as outlined above from 1-amino-N-(3-chloro-4-fluorophenyl)-7-fluoro-2,2-dimethyl-2,3-dihydro-1H-indene-4-carboxamide (La) and N-methyl carbamoyl chloride. The resulting enantiomers were subsequently separated by SFC (Waters SFC investigator. Isocratic mobile phase LIQUID.CO$_2$: 0.3% DEA methanol (75:25), Column: Chiralpak IA 30×250 mm 5 m column, flow rate: 60 ml/min).

N-(3-Chloro-4-fluorophenyl)-7-fluoro-2,2-dimethyl-1-(3-methylureido)-2,3-dihydro-1H-indene-4-carboxamide, enantiomer 1 (249). LCMS: m/z found 408.3/410.3 [M+H]$^+$; HPLC: RT=10.52 min (Method K); Chiral HPLC: RT=1.26 min; $^1$H NMR (DMSO, 400 MHz): δ 10.37 (s, 1H), 8.03 (dd, 1H), 7.60-7.70 (m, 2H), 7.41 (dd, 1H), 7.15 (dd, 1H), 6.27 (d, 1H), 5.59 (q, 1H), 4.99 (d, 1H), 2.91 (ABq, 2H), 2.55 (d, 3H), 1.04 (s, 3H), 0.95 (s, 3H).

N-(3-Chloro-4-fluorophenyl)-7-fluoro-2,2-dimethyl-1-(3-methylureido)-2,3-dihydro-1H-indene-4-carboxamide, enantiomer 2 (134). LCMS: m/z found 408.3/410.3 [M+H]$^+$; HPLC: RT=10.49 min (Method K); Chiral HPLC: RT=1.67 min; $^1$H NMR (DMSO, 400 MHz): δ 10.37 (s, 1H), 8.03 (dd, 1H), 7.60-7.70 (m, 2H), 7.41 (dd, 1H), 7.15 (dd, 1H), 6.27 (d, 1H), 5.59 (q, 1H), 4.99 (d, 1H), 2.91 (ABq, 2H), 2.55 (d, 3H), 1.04 (s, 3H), 0.95 (s, 3H).

O-Pyridin-2-ylmethyl, N-(4-((3-chloro-4-fluorophenyl)carbamoyl)-7-fluoro-2,2-dimethyl-2,3-dihydro-1H-inden-1-yl) carbamate (135, 136)

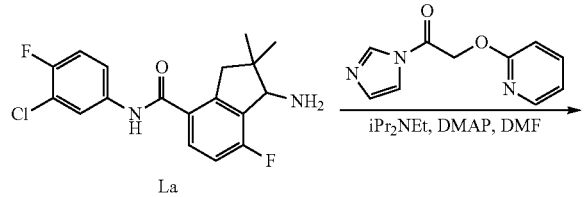
135, 136

O-Pyridin-2-ylmethyl, N-(4-((3-chloro-4-fluorophenyl)carbamoyl)-7-fluoro-2,2-dimethyl-2,3-dihydro-1H-inden-1-yl) carbamate (135, 136) was synthesized in a similar manner as outlined above from 1-amino-N-(3-chloro-4-fluorophenyl)-7-fluoro-2,2-dimethyl-2,3-dihydro-1H-indene-4-carboxamide (La) pyridin-2-ylmethyl 1H-imidazole-1-carboxylate. The resulting enantiomers were subsequently separated by SFC (Waters SFC investigator. Isocratic mobile phase LIQUID.CO$_2$: 0.3% DEA methanol (70:30), Column: Lux-Amylose-2, 30×250 mm 5 μm column, flow rate: 60 ml/min).

O-Pyridin-2-ylmethyl, N-(4-((3-chloro-4-fluorophenyl)carbamoyl)-7-fluoro-2,2-dimethyl-2,3-dihydro-1H-inden-1-yl) carbamate, enantiomer 1 (135). LCMS: m/z found 486.3/488.3 [M+H]$^+$; HPLC: RT=11.32 min (Method K); Chiral HPLC: RT=3.17 min; $^1$H NMR (DMSO, 400 MHz): δ 10.38 (s, 1H), 8.53 (d, 1H), 8.05 (dd, 1H), 7.82-7.87 (m, 1H), 7.72 (dd, 1H), 7.65-7.72 (m, 1H), 7.37-7.43 (m, 2H), 7.34 (dd, 1H), 7.18 (dd, 1H), 5.15 (s, 2H), 4.89 (d, 1H), 3.02 (ABq, 2H), 1.08 (s, 3H), 1.02 (s, 3H).

O-Pyridin-2-ylmethyl, N-(4-((3-chloro-4-fluorophenyl)carbamoyl)-7-fluoro-2,2-dimethyl-2,3-dihydro-1H-inden-1-yl) carbamate, enantiomer 2 (136). LCMS: m/z found 486.3/488.3 [M+H]$^+$; HPLC: RT=11.30 min (Method K); Chiral HPLC: RT=5.48 min; $^1$H NMR (DMSO, 400 MHz): δ 10.38 (s, 1H), 8.53 (d, 1H), 8.05 (dd, 1H), 7.82-7.87 (m, 1H), 7.72 (dd, 1H), 7.65-7.72 (m, 1H), 7.37-7.43 (m, 2H), 7.34 (dd, 1H), 7.18 (dd, 1H), 5.15 (s, 2H), 4.89 (d, 1H), 3.02 (ABq, 2H), 1.08 (s, 3H), 1.02 (s, 3H).

Example 13: Non-Limiting Synthesis of Selected 1-Methyl-1-(Substituted Amino)-Dihydroindene-4-Carboxamides (Scheme 9)

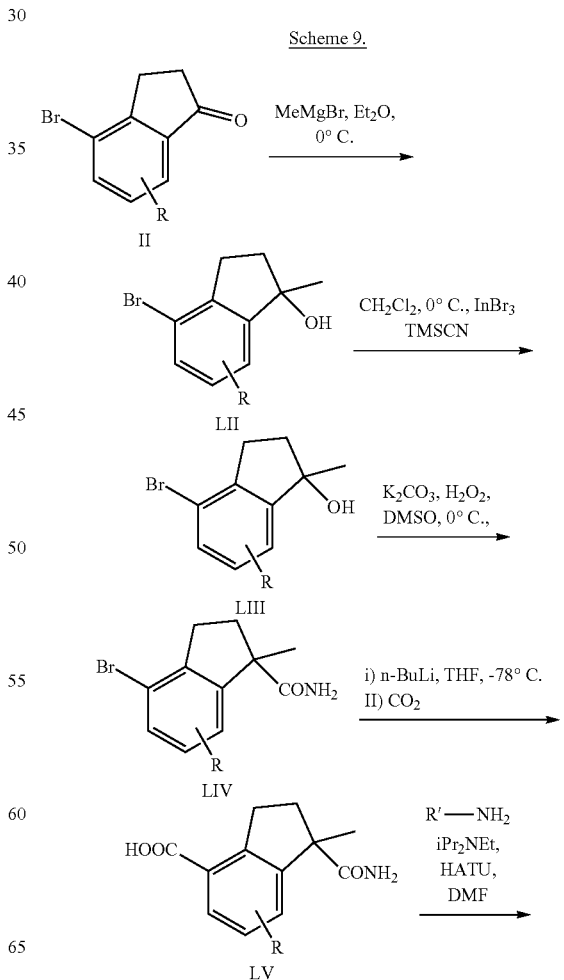

-continued

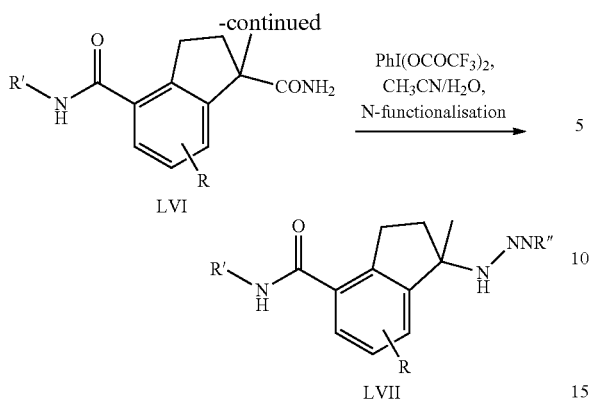

Non-Limiting Illustration of Scheme 9

4-Bromo-7-fluoro-1-methyl-2,3-dihydro-1H-inden-1-ol (LIIa)

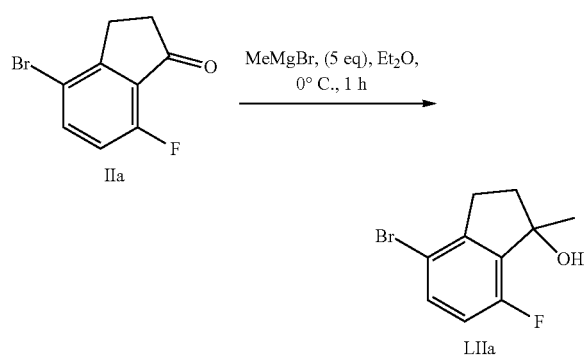

To a solution of 10.0 g (43.7 mmol, 1.0 eq.) of 4-bromo-7-fluoro-2,3-dihydro-1H-inden-1-one (IIa) in 300 mL of anhydrous diethyl ether at 0° C. was added 73 mL (219 mmol, 5.0 eq) of a 3 M solution of methyl magnesium bromide in diethyl ether over approximately 30 min, and mixture was stirred at 0° C. for a further 1 h. The reaction was quenched by the slow addition of 100 mL of a sat. aqueous ammonium chloride solution and extracted with 3×200 mL ethyl acetate. The combined organic extracts were washed with 100 mL brine, dried ($Na_2SO_4$), filtered, and the solvent was removed in vacuo to provide 9.0 g 4-bromo-7-fluoro-1-methyl-2,3-dihydro-1H-inden-1-ol (LIIa). $^1$H NMR (500 MHz, DMSO-$d_6$): δ 7.50-7.45 (m, 1H), 6.89-6.98 (m, 1H), 2.99-3.08 (m, 1H), 2.78-2.89 (m, 1H), 2.25 (t, 2H), 1.70 (s, 3H).

4-Bromo-7-fluoro-1-methyl-2,3-dihydro-1H-indene-1-carbonitrile (LIIIa)

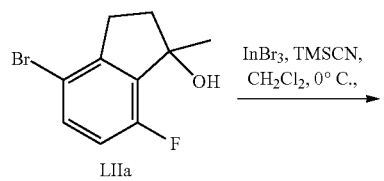

-continued

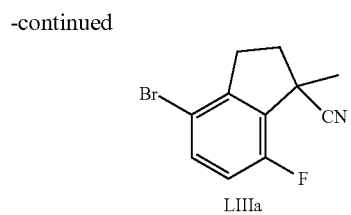

To a solution of 0.77 mL (6.12 mmol, 3.0 eq.) of TMSCN in 20 mL of methylene chloride at 0° C. was added 43 mg, (0.12 mmol, 0.06 eq.) of $InBr_3$. The reaction mixture was stirred for 5 min and a solution of 0.5 g (2.04 mmol, 1 eq.) of 4-bromo-7-fluoro-1-methyl-2,3-dihydro-1H-inden-1-ol (LIIa) in 50 mL of methylene chloride was added. The mixture was stirred further for 3 h at room temperature and then quenched by addition of 15 mL of water. The mixture was extracted with 3×20 mL of methylene chloride, and the combined organic extracts were washed with 10 mL brine, dried ($Na_2SO_4$), filtered, and the solvent was removed in vacuo to provide 0.40 g of crude 4-bromo-7-fluoro-1-methyl-2,3-dihydro-1H-indene-1-carbonitrile (LIIIa). LCMS: m/z found 254.2, [M+H]$^+$.

4-Bromo-7-fluoro-1-methyl-2,3-dihydro-1H-indene-1-carboxamide (LIVa)

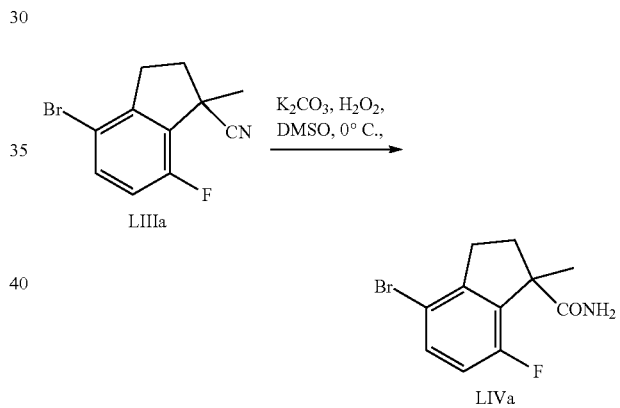

To a solution of 5.0 g (19.7 mmol, 1.0 eq.) of 4-bromo-7-fluoro-1-methyl-2,3-dihydro-1H-indene-1-carbonitrile (LIIIa) in 50 mL of DMSO at 25° C. was added 5.4 g (39.4 mmol, 2.0 eq.) of potassium carbonate, and the resulting mixture was stirred 20 min. The mixture was then cooled to 0° C. and a solution of 5.3 mL (78.72 mmol, 4.0 eq.) of 50% $H_2O_2$ added dropwise. The reaction mixture was stirred for 3 h at 0° C. and then allowed to warm to room temperature. To the reaction mixture was then added to 70 mL of water, and extracted with 3×100 mL of ethyl acetate. The combined organic extracts were washed with 30 mL of brine, dried ($Na_2SO_4$), filtered, and the solvent removed in vacuo. The residue was purified by silica gel chromatography ($SiO_2$, eluting with a linear gradient of 0-30% ethyl acetate/petroleum ether) to provide 1.5 g (5.53 mmol, 28%) of 4-bromo-7-fluoro-1-methyl-2,3-dihydro-1H-indene-1-carboxamide (LIVa). LCMS m/z found 271.9, [M+H]$^+$ (Method H); $^1$H NMR (CDCl$_3$, 400 MHz) δ 7.38-7.35 (m, 1H), 6.82 (t, 1H), 5.20-5.60 (s, 2H) 2.98-3.07 (m, 2H), 2.69-2.76 (m, 1H), 2.02-2.09 (m, 1H), 1.65 (s, 3H).

1-Carbamoyl-7-fluoro-1-methyl-2,3-dihydro-1H-indene-4-carboxylic Acid (LVa)

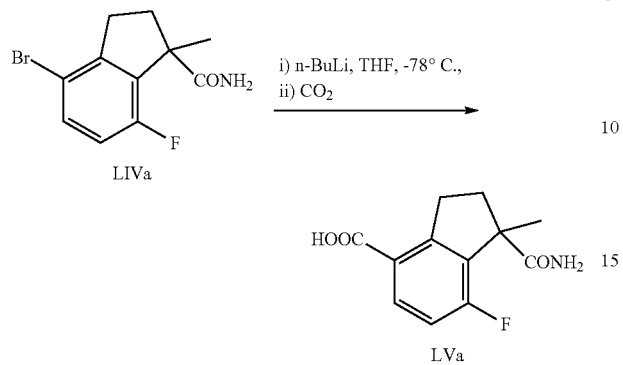

To a solution of 2.0 g (7.4 mmol, 1.0 eq.) of 4-bromo-7-fluoro-1-methyl-2,3-dihydro-1H-indene-1-carboxamide (LIVa) in dry 20 mL of THF at −78° C. under a nitrogen atmosphere was added 5.8 mL (14.7 mmol, 2.0 eq) of 2.5 M solution of n-butyl lithium in hexane. The reaction mixture was stirred for 10 min at −78° C. and then $CO_2$ gas was purged through the system for 10 min. The resulting mixture was stirred for 20 min at −78° C., and then allowed to warm to room temperature. The reaction mixture was quenched with 50 mL of saturated ammonium chloride solution. The mixture was diluted with 100 mL of ethyl acetate and 50 mL of 1 M HCl and the layers were separated. The solvent was removed in vacuo to provide 0.6 g (2.5 mmol, 34%) of 1-carbamoyl-7-fluoro-1-methyl-2,3-dihydro-1H-indene-4-carboxylic acid (LVa). LCMS: m/z found 238.0 [M+H]$^+$ (Method H); $^1$H NMR: (DMSO-d$_6$, 300 MHz) δ 12.95 (s, 1H), 7.83 (dd, 1H), 6.90-7.10 (m, 3H), 3.23-3.32, (m, 2H), 3.32-3.43 (m, 1H), 1.93-1.99 (m, 1H), 1.43 (s, 3H).

N4-(3-Chloro-4-fluorophenyl)-7-fluoro-1-methyl-2,3-dihydro-1H-indene-1,4-dicarboxamide (LVIa)

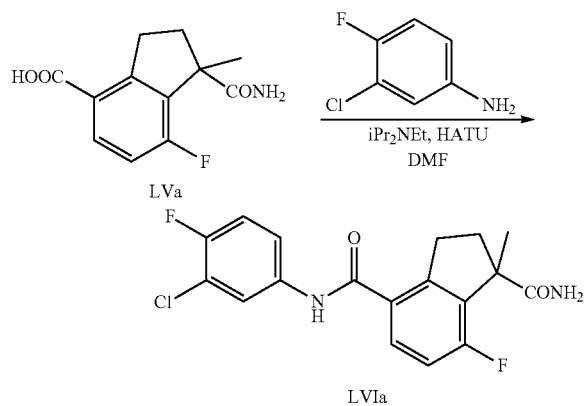

To a stirred solution of 0.3 g (1.3 mmol, 1.0 eq) of 1-carbamoyl-7-fluoro-1-methyl-2,3-dihydro-1H-indene-4-carboxylic acid (LVa) in 15 mL of anhydrous DMF was added 0.22 g (1.5 mmol, 1.2 eq.) of 3-chloro-4-fluoroaniline followed by 0.72 g (1.9 mmol, 1.5 eq.) of HATU and 0.7 mL (3.8 mmol, 3.0 eq.) of N,N-diisopropylethylamine. The solution was stirred at room temperature for 16 h. The mixture was then diluted with 15 mL of ethyl acetate, washed with 2×10 mL of water and 10 mL of brine. The organic solution was dried (MgSO$_4$), filtered and the solvent removed in vacuo. The residue was purified by flash chromatography (SiO$_2$, eluting with a linear gradient of 0-60% ethyl acetate/petroleum ether) to provide 0.25 g (0.64 mmol, 49%) of N-4-(3-chloro-4-fluorophenyl)-7-fluoro-1-methyl-2,3-dihydro-1H-indene-1,4-dicarboxamide (LVIa). LCMS: m/z found 363.3, [M−H]$^-$ (Method H).

O-Methyl, N-(4-((3-chloro-4-fluorophenyl)carbamoyl)-7-fluoro-1-methyl-2,3-dihydro-1H-inden-1-yl) carbamate (217, 218)

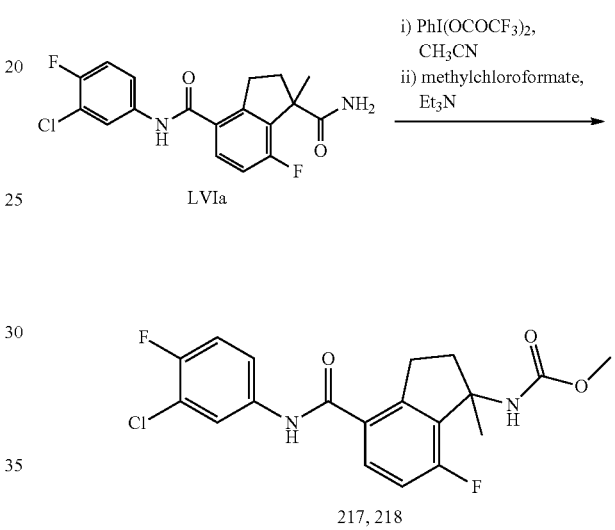

To a solution of 0.35 g (0.96 mmol, 1.0 eq.) of N$^4$-(3-chloro-4-fluorophenyl)-7-fluoro-1-methyl-2,3-dihydro-1H-indene-1,4-dicarboxamide (LVIa) in 20 mL of acetonitrile was added 0.82 g (1.92 mmol, 2.0 eq.) of PhI(OCOCF$_3$). The mixture was stirred at room temperature for 2 h, and 0.3 mL (3.85 mmol, 4.0 eq) of methyl chloroformate and 0.27 mL (1.92 mmol, 2.0 eq.) of triethylamine was added. The resulting mixture was stirred at room temperature for 2 h, and then 10 mL of water was added. The mixture was extracted with 3×20 mL of ethyl acetate, and the combined organic extracts were washed with 10 mL of brine, dried (Na$_2$SO$_4$), filtered and the solvent removed in vacuo. The residue was purified by semi-prep HPLC and the enantiomers were subsequently separated by SFC.

O-Methyl, N-(4-((3-chloro-4-fluorophenyl)carbamoyl)-7-fluoro-1-methyl-2,3-dihydro-1H-inden-1-yl) carbamate, enantiomer 1 (217). LCMS: m/z found 395.30, [M+H]$^+$, RT=2.34 min (Method H); Chiral HPLC: RT=2.50 min; $^1$H NMR (DMSO-d$_6$, 400 MHz) δ 10.36 (s, 1H), 8.03 (dd, 1H), 7.59-7.67 (m, 3H), 7.40 (dd, 1H), 7.69 (dd, 1H), 3.44 (s, 3H), 3.02-3.26 (m, 3H), 1.95-2.07 (m, 1H), 1.49 (s, 3H).

O-Methyl, N-(4-((3-chloro-4-fluorophenyl)carbamoyl)-7-fluoro-1-methyl-2,3-dihydro-1H-inden-1-yl) carbamate, enantiomer 2 (218). LCMS: m/z found 395.30, [M+H]$^+$, RT=2.34 min (Method H); Chiral HPLC: RT=2.87 min; $^1$H NMR (DMSO-d$_6$, 400 MHz) δ 10.36 (s, 1H), 8.03 (dd, 1H), 7.59-7.67 (m, 3H), 7.40 (dd, 1H), 7.69 (dd, 1H), 3.44 (s, 3H), 3.02-3.26 (m, 3H), 1.95-2.07 (m, 1H), 1.49 (s, 3H).

N-(3-Chloro-4-fluorophenyl)-7-fluoro-1-methyl-1-(3-methylureido)-2,3-dihydro-1H-indene-4-carboxamide (215, 250)

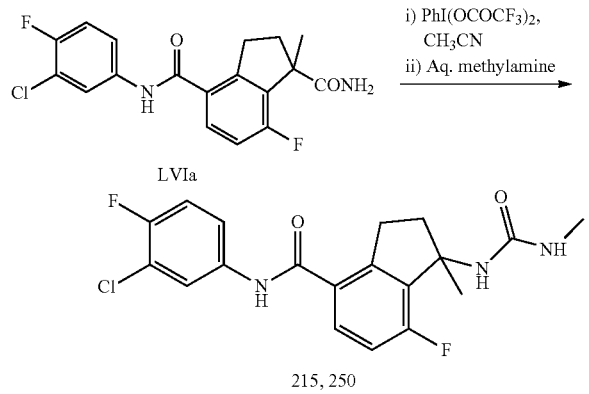

To solution of 0.40 g (1.1 mmol, 1.0 eq.) of $N^4$-(3-chloro-4-fluorophenyl)-7-fluoro-1-methyl-2,3-dihydro-1H-indene-1,4-dicarboxamide (LVIa) in 10 mL in acetonitrile was added 0.95 g (2.2 mmol, 2.0 eq.) of PhI(OCOCF$_3$)$_2$. The mixture was stirred at room temperature for 2 h, and 5 mL of methylamine (40% solution in water) were added. The mixture was stirred for an additional 2 h and then diluted with 10 mL of water. The mixture was extracted with 3×20 mL of ethyl acetate, and the combined organic extracts were washed with 10 mL of brine, dried (Na$_2$SO$_4$), filtered and the solvent was removed in vacuo. The residue was purified by flash chromatography (SiO$_2$, eluting with a linear gradient of 0-30% ethyl acetate/petroleum ether), and the enantiomers were subsequently separated by SFC.

N-(3-Chloro-4-fluorophenyl)-7-fluoro-1-methyl-1-(3-methylureido)-2,3-dihydro-1H-indene-4-carboxamide, enantiomer 1 (215). LCMS: m/z found 394.3, [M+H]$^+$, RT=1.95 min (Method H); Chiral HPLC: RT=3.51 min; $^1$H NMR (DMSO-d$_6$, 400 MHz) δ (DMSO-d$_6$, 400 MHz) δ 10.33 (s, 1H), 8.03 (dd, 1H), 7.57-7.67 (m, 2H), 7.40 (dd, 1H), 7.06 (dd, 1H), 6.30 (s, 1H), 5.61-5.65 (m, 1H), 3.13-3.21 (m, 1H, m), 3.00-3.08 (m, 1H), 2.61-2.66 (m, 1H), 2.47 (s, 3H), 1.93-2.00 (m, 1H), 1.48 (s, 3H).

N-(3-Chloro-4-fluorophenyl)-7-fluoro-1-methyl-1-(3-methylureido)-2,3-dihydro-1H-indene-4-carboxamide, enantiomer 2 (250). LCMS: m/z found 394.3, [M+H]$^+$, RT=1.95 min (Method H); Chiral HPLC: RT=4.55 min; $^1$H NMR (DMSO-d$_6$, 400 MHz) δ 0.33 (s, 1H), 8.03 (dd, 1H), 7.57-7.67 (m, 2H), 7.40 (dd, 1H), 7.06 (dd, 1H), 6.30 (s, 1H), 5.61-5.65 (m, 1H), 3.13-3.21 (m, 1H, m), 3.00-3.08 (m, 1H), 2.61-2.66 (m, 1H), 2.47 (s, 3H), 1.93-2.00 (m, 1H), 1.48 (s, 3H).

O-Pyridin-2-ylmethyl, N-(4-((3-chloro-4-fluorophenyl)carbamoyl)-7-fluoro-1-methyl-2,3-dihydro-1H-inden-1-yl) carbamate (224, 225)

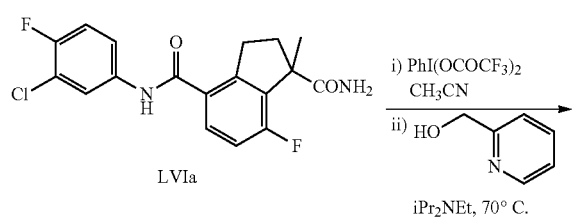

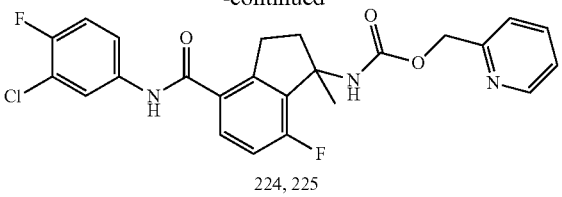

To solution of 0.40 g (1.1 mmol, 1.0 eq.) of $N^4$-(3-chloro-4-fluorophenyl)-7-fluoro-1-methyl 2,3-dihydro-1H-indene-1,4-dicarboxamide (LVIa) in 10 mL in acetonitrile was added 0.95 g (2.2 mmol, 2.0 eq.) of PhI(OCOCF$_3$)$_2$. The mixture was stirred at room temperature for 2 h and 0.17 mL (2.2 mmol, 2.0 eq) of 2-pyridinemethanol followed by 0.37 mL (2.2 mmol, 2.0 eq.) of N,N-diisopropylethylamine was added. The resulting mixture was heated at 70° C. for 16 h. The mixture was allowed to cool to room temperature, and the solvent was removed in vacuo. The residue was redissolved in 10 mL of water and extracted with 3×20 mL of ethyl acetate. The combined organic extracts were washed with 10 mL of brine, dried (Na$_2$SO$_4$), filtered and the solvent removed in vacuo. The residue was purified by reverse phase chromatography and the enantiomers subsequently separated by SFC.

O-Pyridin-2-ylmethyl, N-(4-((3-chloro-4-fluorophenyl)carbamoyl)-7-fluoro-1-methyl-2,3-dihydro-1H-inden-1-yl) carbamate, enantiomer 1 (224). LCMS: m/z found 395.30, [M+H]$^+$ (Method H); Chiral HPLC: RT=3.51 min; $^1$H NMR (DMSO-d$_6$, 400 MHz) δ 10.39 (s, 1H), 8.50 (d, 1H), 8.02 (dd, 1H), 7.91 (s, 1H), 7.80 (t, 1H), 7.67-7.59 (m, 2H), 7.42-7.28 (m, 3H), 7.07 (t, 1H), 4.99 (s, 2H), 3.29-3.15 (m, 1H), 3.11-3.05 (m, 1H), 2.59-2.56 (m, 1H), 2.02-1.99 (m, 1H) 1.52 (s, 3H).

O-Pyridin-2-ylmethyl, N-(4-((3-chloro-4-fluorophenyl)carbamoyl)-7-fluoro-1-methyl-2,3-dihydro-1H-inden-1-yl) carbamate, enantiomer 2 (225). LCMS: m/z found 472.29, [M+H]$^+$ (Method H); Chiral HPLC: RT=5.21 min; $^1$H NMR (DMSO-d$_6$, 400 MHz) δ 10.39 (s, 1H), 8.50 (d, 1H), 8.02 (dd, 1H), 7.91 (bs, 1H), 7.80 (t, 1H), 7.67-7.59 (m, 2H), 7.42-7.28 (m, 3H), 7.07 (t, 1H), 4.99 (s, 2H), 3.29-3.15 (m, 1H), 3.11-3.05 (m, 1H), 2.59-2.56 (m, 1H), 2.02-1.99 (m, 1H) 1.52 (s, 3H).

Example 14: Non-Limiting Synthesis of Selected Substituted 2,5-Dioxo-2',3'-Dihydrospiro[Imidazolidine-4,1'-Indene]-4'-Carboxamides (Scheme 10)

Scheme 10.

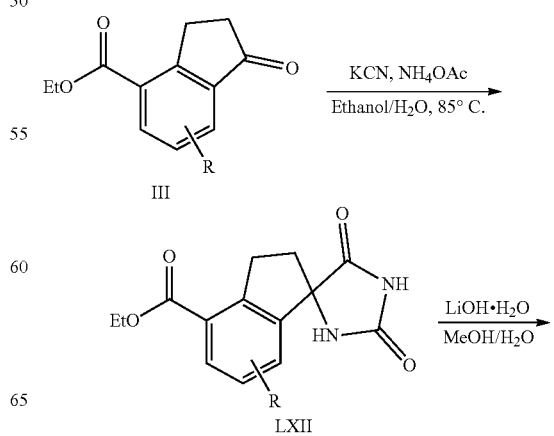

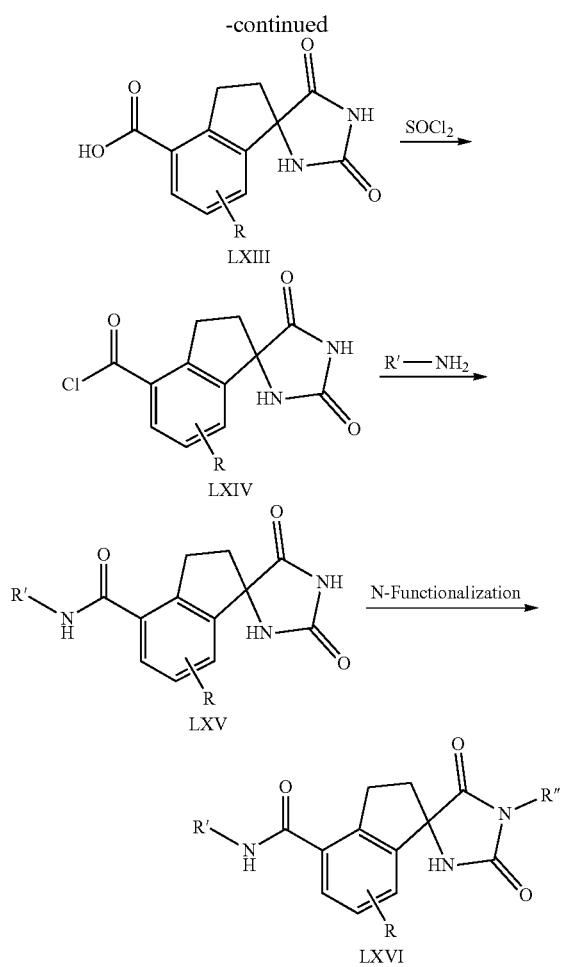

Ethyl 7'-fluoro-2,5-dioxo-2',3'-dihydrospiro[imidazolidine-4,1'-indene]-4'-carboxylate (LXIIa)

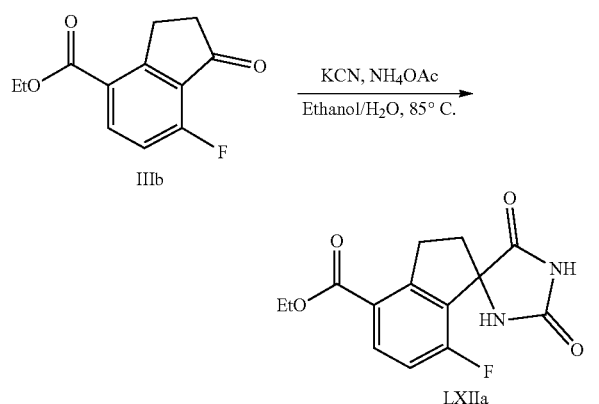

To 6.0 g (27.0 mmol, 1.0 eq.) of ethyl 7-fluoro-1-oxo-indane-4-carboxylate (IIIb) in 50 mL of 1:1 (v/v) ethanol:water in a sealed tube was added 3.52 g (54.0 mmol, 2.0 eq.) of potassium cyanide followed by 26.0 g (270 mmol, 10.0 eq.) of ammonium carbonate. The sealed tube was then heated at 85° C. for 15 hr. The mixture was allowed to cool to room temperature and diluted with 60 mL of water. The mixture was then extracted with 3×90 mL of ethyl acetate and the combined organic extracts were washed with 3×90 mL of brine, dried (Na$_2$SO$_4$), filtered and the solvent was removed in vacuo. The residue was purified by trituration with 10 mL of ethyl acetate followed by 5 mL of petroleum ether to provide 3.0 g (10.3 mmol, 38%) of ethyl 7'-fluoro-2,5-dioxo-2',3'-dihydrospiro[imidazolidine-4,1'-indene]-4'-carboxylate (LXIIa). $^1$H NMR (400 MHz, DMSO-d$_6$): δ 10.98 (s, 1H), 8.54 (s, 1H), 8.03-7.91 (m, 1H), 7.26-7.22 (m, 1H), 4.36-4.28 (m, 2H), 3.38-3.32 (m, 2H), 2.59-2.50 (m, 1H), 2.27-2.24 (m, 1H), 1.34-1.27 (m, 3H).

7'-Fluoro-2,5-dioxo-2',3'-dihydrospiro[imidazolidine-4,1'-indene]-4'-carboxylic Acid (LXIIIa)

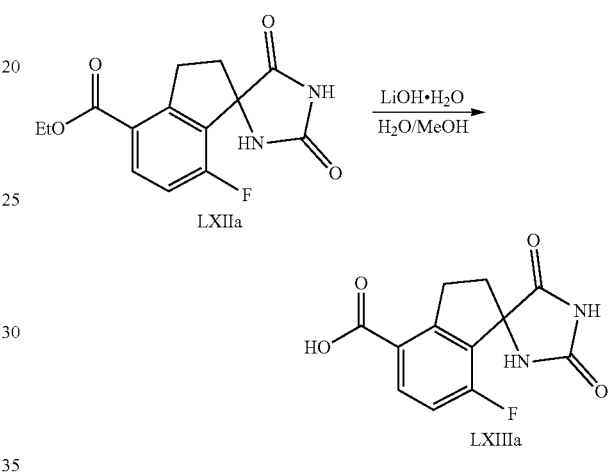

To a solution of 3.0 g (10.3 mmol, 1.0 eq.) of ethyl 7'-fluoro-2,5-dioxo-spiro [imidazolidine-4,1'-indane]-4'-carboxylate (LXIIa) in 20 mL of 1:1 (v/v) methanol:water was added 1.23 g (29.3 mmol, 3.0 eq.) of lithium hydroxide monohydrate and the mixture was stirred at room temperature for 15 h. The methanol was removed in vacuo and the aqueous solution was acidified with 10 mL of 1 M HCl. The mixture was extracted with 3×30 mL of ethyl acetate and the combined organic extracts were washed with 3×20 mL of brine, dried (Na$_2$SO$_4$), filtered and the solvent was removed in vacuo to provide 2.4 g (8.0 mmol, 78%) of 7'-fluoro-2,5-dioxo-2',3'-dihydrospiro[imidazolidine-4,1'-indene]-4'-carboxylic acid (LXIIIa). $^1$H NMR (400 MHz, DMSO-d$_6$): δ 12.92 (s, 1H), 10.99-10.87 (m, 1H), 8.55 (s, 1H), 8.02-7.97 (m, 1H), 7.24-7.19 (m, 1H), 3.40-3.36 (m, 2H), 2.57-2.55 (m, 1H), 2.27-2.24 (m, 1H).

7'-Fluoro-2,5-dioxo-2',3'-dihydrospiro[imidazolidine-4,1'-indene]-4'-carbonyl Chloride (LXIVa)

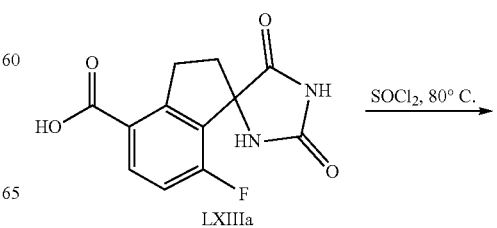

-continued

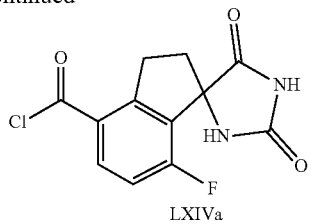
LXIVa

A solution of 2.95 g (9.81 mmol, 1.0 eq.) of 7'-fluoro-2,5-dioxo-2',3'-dihydrospiro [imidazolidine-4,1'-indene]-4'-carboxylic acid (LXIIIa) in 10 mL of thionyl chloride was stirred at 80° C. for 1 h. The mixture was allowed to cool to room temperature and concentrated in vacuo to provide 2.77 g of 7'-fluoro-2,5-dioxo-2',3'-dihydrospiro[imidazolidine-4,1'-indene]-4'-carbonyl chloride (LXIVa).

N-(3-Chloro-4-fluorophenyl)-7'-fluoro-2,5-dioxo-2',3'-dihydrospiro[imidazolidine-4,1'-indene]-4'-carboxamide (257, 258)

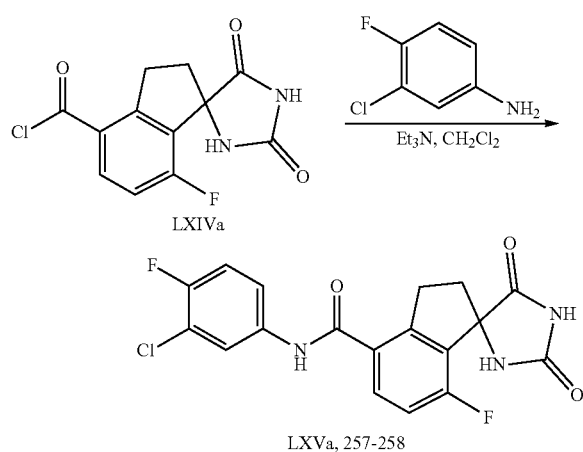
LXIVa

LXVa, 257-258

To a solution of 2.77 g (9.73 mmol, 1.0 eq.) of 7'-fluoro-2,5-dioxo-2',3'-dihydrospiro[imidazolidine-4,1'-indene]-4'-carbonyl chloride (LXIVa) in 20 mL of methylene chloride was added 6.8 mL (48.6 mmol, 5.0 eq.) of triethylamine and 1.42 g (9.73 mmol, 1.0 eq.) of 3-chloro-4-fluoro-aniline and the mixture was stirred at room temperature for 15 h. The solvent was removed in vacuo and the residue was purified by preparative HPLC to provide 1.5 g (3.83 mmol, 39%) of N-(3-chloro-4-fluoro-phenyl)-7'-fluoro-2,5-dioxo-spiro [imidazolidine-4,1'-indane]-4'-carboxamide (LXVa).

A 0.5 g sample of the racemate was separated by SFC (Thar SFC80 preparative SFC; Column: Chiralpak AD-H 250×30 mm i.d. 5μ; Mobile phase: 58% CO₂/ethanol (0.1% NH₄OH); Flow rate: 70 g/min), to provide:

N-(3-chloro-4-fluoro-phenyl)-7'-fluoro-2,5-dioxo-spiro [imidazolidine-4,1'-indane]-4'-carboxamide, enantiomer 1, (257). 130 mg. LCMS: m/z found 392.0/394.0 [M+H]⁺ (Method A), RT 3.67 min; SFC: RT 3.19 min; ¹H NMR (400 MHz, DMSO-d₆): δ 10.96 (s, 1H), 10.50 (s, 1H), 8.58 (s, 1H), 8.06-8.03 (m, 1H), 7.83-7.80 (m, 1H), 7.68-7.65 (m, 1H), 7.44-7.42 (m, 1H), 7.40-7.24 (m, 1H), 3.29-3.16 (m, 2H), 2.61-2.55 (m, 1H), 2.28-2.21 (m, 1H) and N-(3-chloro-4-fluoro-phenyl)-7'-fluoro-2,5-dioxo-spiro [imidazolidine-4,1'-indane]-4'-carboxamide, enantiomer 2, (258). 170 mg. LCMS: m/z found 392.0/394.0 [M+H]⁺ (Method A), RT 3.69 min; SFC: RT 3.78 min; 1H NMR (400 MHz, DMSO-d₆): δ 10.98 (s, 1H), 10.50 (s, 1H), 8.58 (s, 1H), 8.06-8.03 (m, 1H), 7.83-7.80 (m, 1H), 7.68-7.65 (m, 1H), 7.44-7.42 (m, 1H), 7.40-7.24 (m, 1H), 3.29-3.16 (m, 2H), 2.61-2.55 (m, 1H), 2.28-2.21 (m, 1H).

N-(3-Chloro-4-fluorophenyl)-7'-fluoro-2,5-dioxo-1-(pyridin-2-ylmethyl)-2',3'-dihydrospiro[imidazolidine-4,1'-indene]-4'-carboxamide (259, 260)

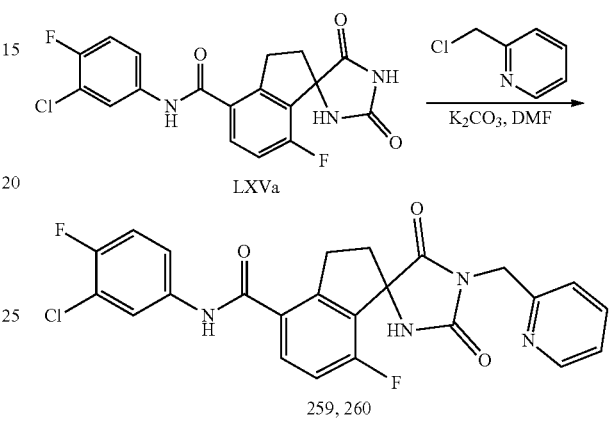
LXVa 259, 260

To a solution of 0.5 g (1.28 mmol, 1.0 eq.) of N-(3-chloro-4-fluorophenyl)-7'-fluoro-2,5-dioxo-2',3'-dihydrospiro[imidazolidine-4,1'-indene]-4'-carboxamide (LXVa) in 5 mL of DMF was added 0.53 g (3.83 mmol, 3.0 eq) of potassium carbonate and 0.20 g (1.53 mmol, 1.2 eq.) of 2-(chloromethyl)pyridine and the mixture was stirred at room temperature for 15 h. Additional quantities of 0.09 g (0.638 mmol, 0.5 eq.) of potassium carbonate and 0.08 g of 2-(chloromethyl)pyridine were added and the mixture was stirred at room temperature for a further 5 h. The solvent was then removed in vacuo and the residue was purified by preparative HPLC to provide 0.36 g (0.75 mmol, 58%) of racemic N-(3-chloro-4-fluorophenyl)-7'-fluoro-2,5-dioxo-1-(pyridin-2-ylmethyl)-2',3'-dihydrospiro[imidazolidine-4,1'-indene]-4'-carboxamide which was subsequently resolved into the individual enantiomers by SFC. (Thar SFC80 preparative SFC; Column: Chiralpak AD-H 250×30 mm i.d. 5μ; Mobile phase: 55% CO₂/ethanol (0.1% NH₄OH); Flow rate: 70 g/min) to provide:

N-(3-chloro-4-fluoro-phenyl)-7'-fluoro-2,5-dioxo-1-(2-pyridylmethyl) spiro[imidazolidine-4,1'-indane]-4'-carboxamide, enantiomer 1 (259). 125 mg. LCMS: m/z found 483.3/485.3 [M+H]⁺, RT=3.41 min (Method A); SFC: RT 1.88 min; ¹H NMR (400 MHz, DMSO-d₆): δ 10.52 (s, 1H), 9.02 (s, 1H), 8.52 (m, 1H), 8.06-8.04 (m, 1H), 7.82-7.80 (m, 2H), 7.80-7.65 (m, 1H), 7.45-7.40 (m, 1H), 7.32-7.28 (m, 3H), 4.75 (m, 2H), 3.41-3.32 (m, 1H), 3.30-3.25 (m, 1H), 2.69-2.61 (m, 1H), 2.38-2.31 (m, 1H) and N-(3-chloro-4-fluoro-phenyl)-7-fluoro-2,5-dioxo-1-(2-pyridylmethyl)spiro [imidazolidine-4,1'-indane]-4'-carboxamide, enantiomer 2 (260). 149 mg as a white solid. LCMS: m/z found 483.3/485.3 [M+H]⁺, RT=3.41 min (Method A); SFC: RT 2.96 min; ¹H NMR (400 MHz, DMSO-d₆): δ 10.52 (s, 1H), 9.02 (s, 1H), 8.52 (m, 1H), 8.06-8.04 (m, 1H), 7.82-7.80 (m, 2H), 7.80-7.65 (m, 1H), 7.45-7.40 (m, 1H), 7.32-7.28 (m, 3H), 4.75 (m, 2H), 3.41-3.32 (m, 1H), 3.30-3.25 (m, 1H), 2.69-2.61 (m, 1H), 2.38-2.31 (m, 1H).

N-(3-Chloro-4-fluoro-phenyl)-7'-fluoro-1-methyl-2,5-dioxo-spiro[imidazolidine-4,1'-indane]-4'-carboxamide (261, 262):

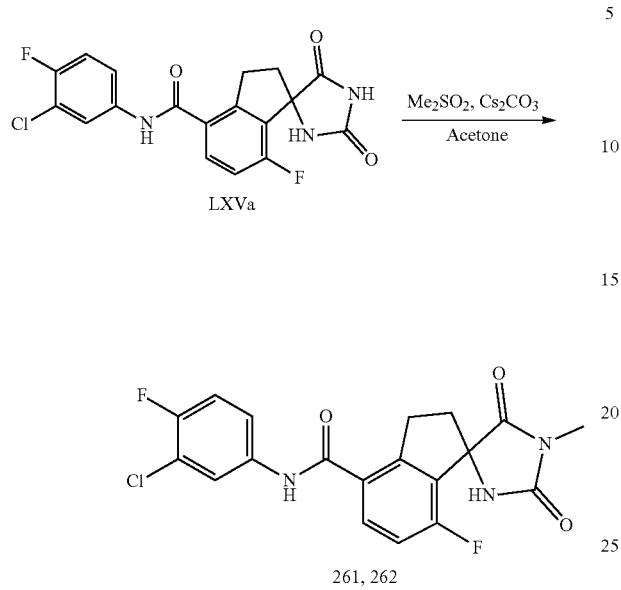

To a solution of 0.3 g (0.76 mmol, 1.0 eq.) of N-(3-chloro-4-fluoro-phenyl)-7'-fluoro-2,5-dioxo-spiro[imidazolidine-4,1'-indane]-4'-carboxamide (LXVa) in 3 mL of acetone was added 0.37 g (1.15 mmol, 1.5 eq.) of cesium carbonate and 0.11 g (0.84 mmol, 80 µL, 1.1 eq.) of dimethyl sulfate and the mixture was stirred at room temperature for 15 h. The solvent was removed in vacuo and the residue was purified by semi-preparative HPLC to provide 120 mg (0.30 mmol, 39%) of racemic N-(3-chloro-4-fluoro-phenyl)-7'-fluoro-1-methyl-2,5-dioxo-spiro [imidazolidine-4,1'-indane]-4'-carboxamide.

The enantiomers were subsequently separated by SFC (Thar SFC80 preparative SFC; Column: Chiralpak AD-H 250×30 mm i.d. 5µ; Mobile phase: 58% CO$_2$/methanol (0.1% NH$_4$OH); Flow rate: 70 g/min) to provide:

N-(3-chloro-4-fluoro-phenyl)-7'-fluoro-1-methyl-2,5-dioxo-spiro [imidazolidine-4,1'-indane]-4'-carboxamide, enantiomer 1 (261). 50 mg. LCMS: m/z found 406.2/408.2 [M+H]$^+$, RT: 3.82 min (Method A); SFC: RT 3.05 min; $^1$H NMR (400 MHz, DMSO-d$_6$): δ 10.52 (s, 1H), 8.90 (s, 1H), 8.05-8.04 (m, 1H), 7.84-7.81 (m, 1H), 7.65 (m, 1H), 7.45-7.40 (m, 1H), 7.28-7.24 (m, 1H), 3.29 (m, 2H), 2.94 (m, 3H), 2.63-2.58 (m, 1H), 2.27-2.26 (m, 1H) and N-(3-chloro-4-fluoro-phenyl)-7'-fluoro-1-methyl-2,5-dioxo-spiro [imidazolidine-4,1'-indane]-4'-carboxamide, enantiomer 2 (262). 55 mg. LCMS: m/z found 406.2/408.2 [M+H]$^+$, RT: 3.82 min (Method A); SFC: RT 3.38 min; $^1$H NMR (400 MHz, DMSO-d$_6$): δ 10.52 (s, 1H), 8.90 (s, 1H), 8.05-8.04 (m, 1H), 7.84-7.81 (m, 1H), 7.65 (m, 1H), 7.45-7.40 (m, 1H), 7.28-7.24 (m, 1H), 3.29 (m, 2H), 2.94 (m, 3H), 2.63-2.58 (m, 1H), 2.27-2.26 (m, 1H).

Example 15: Non-Limiting Synthesis of Selected Substituted 7-(Substituted Amino)-6,7-Dihydro-5H-Cyclopenta[b]Pyridine-4-Carboxamides (Scheme 11)

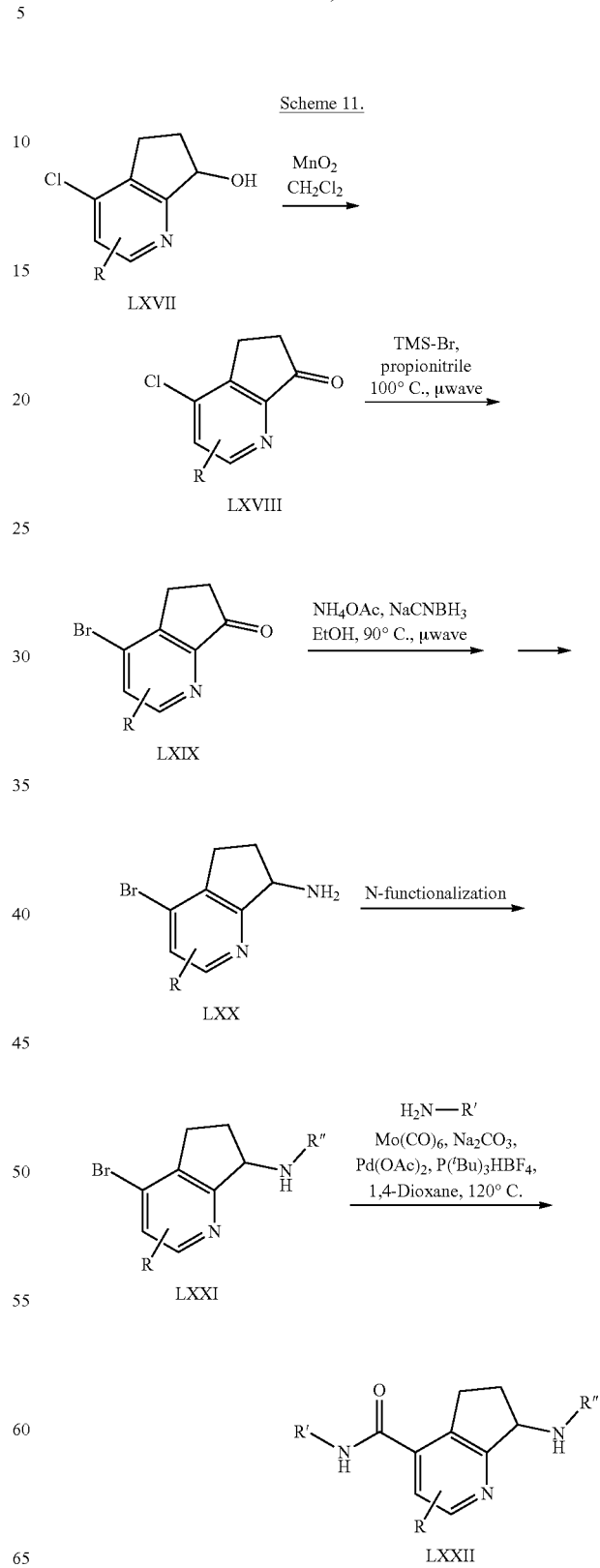

4-Chloro-5H-cyclopenta[b]pyridin-7(6H)-one (LXVIIIa)

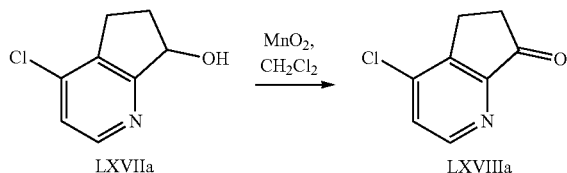 [SMILES: OC1CCc2c(Cl)ccnc21 ; O=C1CCc2c(Cl)ccnc21]

To a solution of 12.5 g (73.7 mmol, 1.0 eq.) of 4-chloro-6,7-dihydro-5H-cyclopenta[b]pyridin-7-ol (LXVIIa) in 250 mL of methylene chloride was added 96.1 g (1.1 mol, 15.0 eq.) of manganese dioxide and the mixture was stirred at room temperature for 20 h. The mixture was filtered through CELITE® and the pad was washed with 250 mL of methylene chloride. The solvent was removed in vacuo and the residue was purified by flash chromatography (SiO$_2$, eluting with a linear gradient of 0-30% ethyl acetate/petroleum ether) to provide 4.9 g (29.2 mmol, 40%) of 4-chloro-5H-cyclopenta[b]pyridin-7(6H)-one (LXVIIIa). $^1$H NMR (500 MHz, CDCl$_3$): δ 2.80-2.82 (t, 2H), 3.16-3.19 (t, 2H), 7.48-7.49 (d, 1H), 8.67-8.68 (d, 1H).

4-Bromo-5H-cyclopenta[b]pyridin-7(6H)-one (LXIXa)

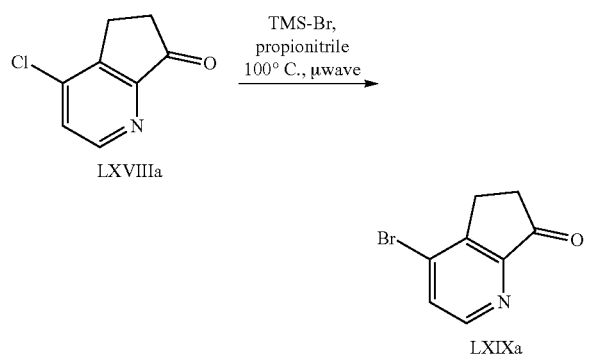

To a solution of 5.0 g (29.9 mmol, 1.0 eq.) of 4-chloro-5H-cyclopenta[b]pyridin-7(6H)-one (LXVIIIa) in 50 mL of propionitrile was added 9.1 g (59.7 mmol, 2.0 eq.) of bromotrimethylsilane. The mixture was subjected to microwave irradiation maintaining a reaction temperature of 100° C. for 2 h. Then mixture was then diluted with 100 mL of water and extracted with 3×250 mL of ethyl acetate. The combined organic extracts were dried (Na$_2$SO$_4$), filtered and the solvent was removed in vacuo. The residue was purified by flash chromatography (SiO$_2$, eluting with a linear gradient of 10-40% ethyl acetate/petroleum ether) to provide 3.1 g (14.6 mmol, 50%) of 4-bromo-5H-cyclopenta[b]pyridin-7(6H)-one (LXIXa). LCMS: m/z found 214.0/216.0 [M+H]$^+$, RT=1.29 min (Method-H); $^1$H NMR (400 MHz, CDCl$_3$): δ 2.80-2.83 (t, 2H), 3.12-3.19 (t, 2H), 7.67-7.68 (d, 1H), 8.57-8.58 (d, 1H).

4-Bromo-6,7-dihydro-5H-cyclopenta[b]pyridin-7-amine (LXXa)

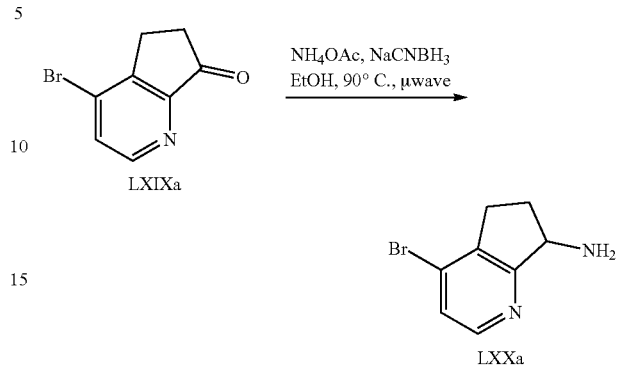

To a solution of 0.5 g (2.36 mmol, 1.0 eq.) of 4-bromo-5H-cyclopenta[b]pyridin-7(6H)-one (LXIXa) in 10 mL of ethanol was added 2.7 g (35.4 mmol, 15.0 eq.) of ammonium acetate followed by 0.3 g (4.72 mmol, 1.5 eq.) of sodium cyanoborohydride. The mixture was subjected to microwave irradiation maintaining a reaction temperature of 90° C. for 1 h. The mixture was then diluted with 10 mL of water and extracted with 3×25 mL of ethyl acetate. The aqueous layer was basified with 10% sodium hydroxide solution and then further extracted with 3×50 mL of ethyl acetate. The combined organic extracts were dried (Na$_2$SO$_4$), filtered and the solvent was removed in vacuo to provide 0.42 g of crude 4-bromo-6,7-dihydro-5H-cyclopenta[b]pyridin-7-amine (LXXa). LCMS: m/z found 213.1/215.1 [M+H]$^+$, RT=1.22 min (Method H).

1-(4-Bromo-6,7-dihydro-5H-cyclopenta[b]pyridin-7-yl)-3-methylurea (LXXIa)

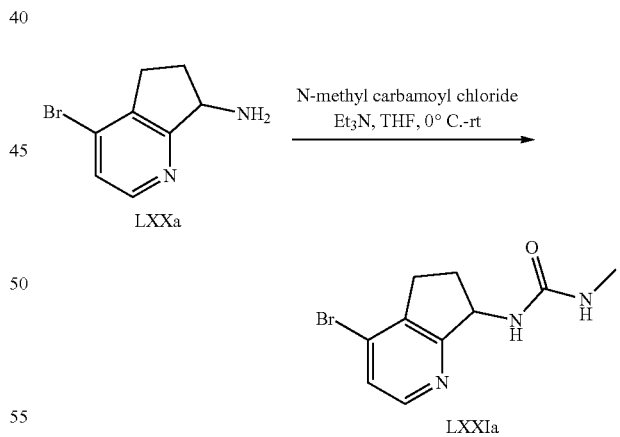

To a solution of 0.42 g (1.97 mmol, 1.0 eq.) of 4-bromo-6,7-dihydro-5H-cyclopenta[b]pyridin-7-amine (LXXa) in 8 mL of THF at 0° C. was added 0.6 g (0.82 mL, 5.9 mmol, 3.0 eq.) of triethylamine followed by 0.22 g (2.37 mmol, 1.2 eq.) of N-methyl carbamoyl chloride. The mixture was stirred at RT for 15 h and then quenched by addition of 10 mL of water. The mixture was extracted with 3×25 mL of ethyl acetate and the combined organic extracts were dried (Na$_2$SO$_4$), filtered and the solvent was removed in vacuo to provide 0.32 g of 1-(4-bromo-6,7-dihydro-5H-cyclopenta[b]

pyridin-7-yl)-3-methylurea (LXXIa). LCMS: m/z found 272.0/274.0 [M+H]+, RT=1.17 min (Method H).

N-(3-Chloro-4-fluorophenyl)-7-(3-methylureido)-6,7-dihydro-5H-cyclopenta[b]pyridine-4-carboxamide (263)

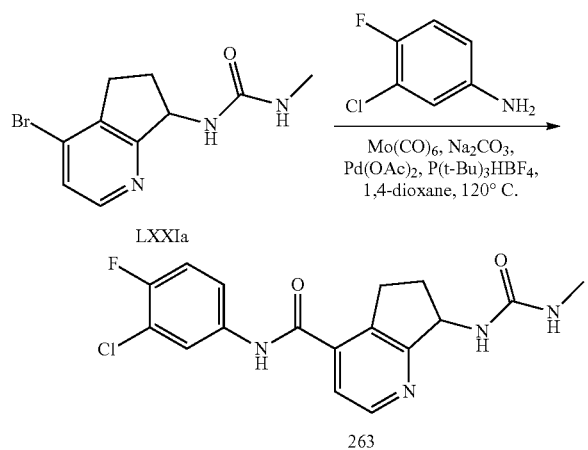

To a solution of 0.32 g (1.18 mmol, 1.0 eq.) of 1-(4-bromo-6,7-dihydro-5H-cyclopenta[b]pyridin-7-yl)-3-methylurea (LXXIa) in 6 mL of 1,4-dioxane was added 0.34 g (2.37 mmol, 2.0 eq.) of 3-chloro-4-fluoroaniline followed by 0.25 g (2.37 mmol, 2.0 eq.) of sodium carbonate and 0.31 g (1.18 mmol, 1.0 eq.) of molybdenum hexacarbonyl. The mixture was degassed with nitrogen for 10 min and 34 mg (0.12 mmol, 0.1 eq.) of (t-Bu)₃HBF₄ and 26 mg (0.12 mmol, 0.1 eq.) of palladium (II) acetate were added, maintaining the mixture under a nitrogen atmosphere. The mixture was subjected to microwave irradiation maintaining a reaction temperature of 120° C. for 3 h. The mixture was then diluted with 10 mL of water and extracted with 3×20 mL of ethyl acetate. The combined organic extracts were washed with 2×30 mL of brine, dried (Na₂SO₄), filtered and the solvent was removed in vacuo. The residue was purified by semi-prep HPLC to provide 0.03 g, (0.083 mmol, 7%) of N-(3-chloro-4-fluorophenyl)-7-(3-methylureido)-6,7-dihydro-5H-cyclopenta[b]pyridine-4-carboxamide (263). LCMS: m/z found 363.3/365.3 [M+1]+, RT=1.85 min (Method A); HPLC: RT=8.81 min; ¹H NMR (500 MHz, DMSO-d₆): δ 10.50 (s, 1H), 8.56 (d, 1H), 8.03 (d, 1H), 7.66 (dd, 1H), 7.49 (d, 1H), 7.42 (dd, 1H), 6.28 (d, 1H), 5.84 (bq, 1H), 5.03-5.07 (m, 1H), 3.08-3.14 (m, 1H), 2.91-2.98 (m, 1H), 2.58 (d, 3H), 1.73-1.79 (m, 1H), 1.27-1.29 (m, 1H).

O-Methyl, N-(4-bromo-6,7-dihydro-5H-cyclopenta[b]pyridin-7-yl)carbamate (LXXIb)

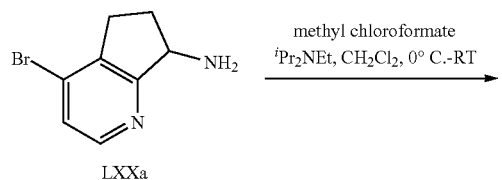

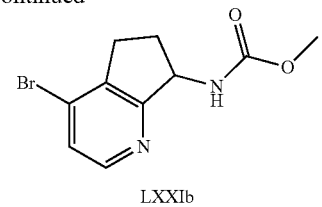

To a solution of 200 mg (0.94 mmol, 1.0 eq.) of 4-bromo-6,7-dihydro-5H-cyclopenta[b]pyridin-7-amine (LXXa) in 10 mL of methylene chloride at 0° C. was added 0.37 g (2.83 mmol, 3.0 eq.) of N,N-diisopropylethylamine followed by 0.13 g (1.42 mmol, 1.5 eq.) of methyl chloroformate. The mixture was allowed to warm to room temperature and stirred at for 2 h. The mixture was then diluted with 20 mL of water and extracted with 3×30 mL of ethyl acetate. The combined organic extracts were washed with 30 mL of brine, dried (Na₂SO₄), filtered and the solvent was removed in vacuo. The residue was purified by flash chromatography (SiO₂, eluting with a linear gradient of 0-15% ethyl acetate/petroleum ether) to provide 150 mg (0.55 mmol, 59%) of O-methyl, N-(4-bromo-6,7-dihydro-5H-cyclopenta[b]pyridin-7-yl) carbamate (LXXIb). LCMS: m/z found 271.05 [M+H]+, RT=1.72 min (Method H).

O-Methyl, N-(4-((3-chloro-4-fluorophenyl)carbamoyl)-6,7-dihydro-5H-cyclopenta[b]pyridin-7-yl) carbamate (264)

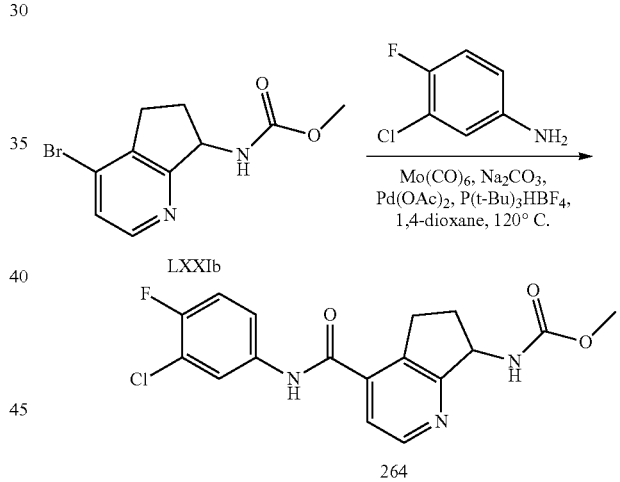

To a solution of 100 mg (0.37 mmol, 1.0 eq.) of methyl (4-bromo-6,7-dihydro-5H-cyclopenta[b]pyridin-7-yl)carbamate (LXXIb) in 10 mL of 1,4-dioxane was added 0.07 g (0.48 mmol, 1.3 eq.) of 3-chloro-4-fluoroaniline followed by 0.08 g (0.75 mmol, 2.0 eq.) of sodium carbonate and 0.10 g (0.75 mmol, 1.0 eq.) of molybdenum hexacarbonyl. The mixture was degassed with nitrogen for 10 min and 11 mg (0.037 mmol, 0.1 eq.) of (t-Bu)₃HBF₄ and 8 mg (0.037 mmol, 0.1 eq.) of palladium (II) acetate were added, maintaining the mixture under a nitrogen atmosphere. The mixture was subjected to microwave irradiation maintaining a reaction temperature of 120° C. for 3 h. The mixture was then diluted with 10 mL of water and extracted with 3×20 mL of ethyl acetate. The combined organic extracts were washed with 2×30 mL of brine, dried (Na₂SO₄), filtered and the solvent was removed in vacuo. The residue was purified by semi-prep HPLC to provide 12 mg (0.033 mmol, 9%) of O-methyl, N-(4-((3-chloro-4-fluorophenyl)carbamoyl)-6,7- dihydro-5H-cyclopenta[b]pyridin-7-yl) carbamate (264). LCMS: m/z found 364.1/366.1 [M+H]+, RT=3.43 min (Method A); $^1$H NMR (300 MHz, DMSO-d$_6$): δ 10.64 (s, 1H), 8.56 (d, 1H), 8.04 (dd, 1H), 7.69-7.64 (m, 1H), 7.56 (d, 1H), 7.51 (d, 1H), 7.44 (t, 1H), 5.03 (q, 1H), 3.58 (s, 3H), 3.18-3.10 (m, 1H), 3.01-2.93 (m, 1H), 2.45-2.41 (m, 1H), 1.88-1.82 (m, 1H).

O-Pyridin-2-ylmethyl, N-(4-bromo-6,7-dihydro-5H-cyclopenta[b]pyridin-7-yl) carbamate (LXXIc)

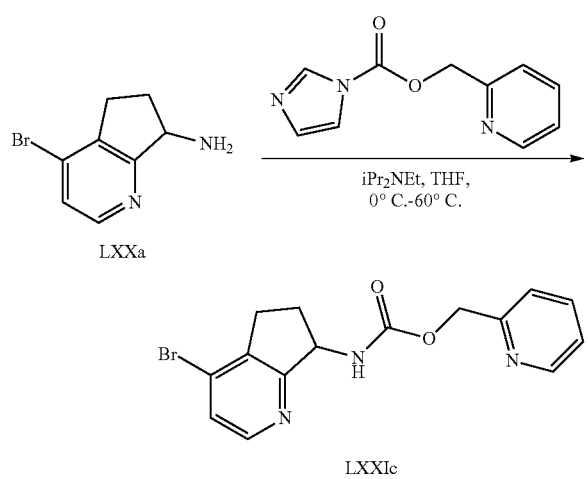

To a solution of 0.70 g (3.3 mmol, 1.0 eq.) of 4-bromo-6,7-dihydro-5H-cyclopenta[b]pyridin-7-amine (LXXIc) in 10 mL of methylene chloride at 0° C. was added 1.3 g (9.9 mmol, 3.0 eq.) of N,N-diisopropylethylamine followed by 1.0 g (5.0 mmol, 1.5 eq) of pyridin-2-ylmethyl 1H-imidazole-1-carboxylate and the reaction mixture was heated to 60° C. for 15 h. The mixture was allowed to cool to room temperature, diluted with 100 mL of water and extracted with 3×70 mL of ethyl acetate. The combined organic extracts were washed with 50 mL of brine, dried (Na$_2$SO$_4$), filtered and the solvent was removed in vacuo to provide 0.50 g (1.4 mmol, 44%) of O-pyridin-2-ylmethyl, N-(4-bromo-6,7-dihydro-5H-cyclopenta[b]pyridin-7-yl) carbamate (LXXIc). LCMS: m/z found 348.3/350.3 [M+H]+, RT=1.68 min (Method H).

O-Pyridin-2-ylmethyl, N-(4-((3-chloro-4-fluorophenyl)carbamoyl)-6,7-dihydro-5H-cyclopenta[b]pyridin-7-yl) carbamate (265, 266, 267)

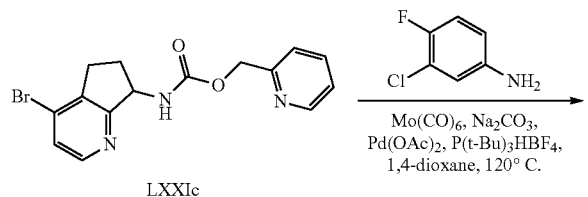

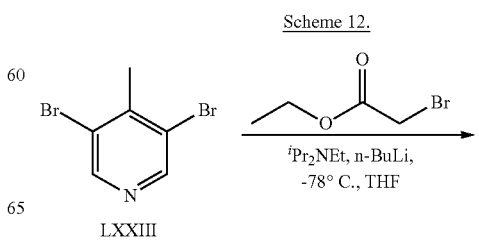

265, 266, 267

To a solution of 0.50 g (1.4 mmol, 1.0 eq.) of O-pyridin-2-ylmethyl, N-(4-bromo-6,7-dihydro-5H-cyclopenta[b]pyridin-7-yl)carbamate (LXXIc) in 20 mL of 1,4-dioxane was added 0.25 g (1.73 mmol, 1.3 eq.) of 3-chloro-4-fluoroaniline followed by 0.30 g (2.88 mmol, 2.0 eq.) of sodium carbonate and 0.38 g (1.44 mmol, 1.0 eq.) of molybdenum hexacarbonyl. The mixture was degassed with nitrogen for 10 min and 42 mg (0.14 mmol, 0.1 eq.) of (t-Bu)$_3$HBF$_4$ and 32 mg (0.14 mmol, 0.1 eq.) of palladium (II) acetate were added, maintaining the mixture under a nitrogen atmosphere. The mixture was subjected to microwave irradiation maintaining a reaction temperature of 120° C. for 3 h. The mixture was then diluted with 20 mL of water and extracted with 3×50 mL of ethyl acetate. The combined organic extracts were washed with 2×30 mL of brine, dried (Na$_2$SO$_4$), filtered and the solvent was removed in vacuo. The residue was purified by semi-preparative HPLC to provide 41 mg (0.09 mmol, 6%) of racemic O-pyridin-2-ylmethyl, N-(4-((3-chloro-4-fluorophenyl)carbamoyl)-6,7-dihydro-5H-cyclopenta[b]pyridin-7-yl) carbamate (265). The enantiomers were subsequently resolved by SFC (Waters SFC investigator. Isocratic mobile phase CO$_2$:MeOH (55:45), Column: Chiralcel AD-H 30×250 mm 5 μm column, flow rate: 100 mL/min).

O-Pyridin-2-ylmethyl, N-(4-((3-chloro-4-fluorophenyl)carbamoyl)-6,7-dihydro-5H-cyclopenta[b]pyridin-7-yl) carbamate, enantiomer 1 (266). m/z found 441.1/443.1 [M+H]+, RT=3.16 min (Method A); $^1$H NMR (400 MHz, DMSO-d$_6$): δ 10.61 (s, 1H), 8.57 (m, 2H), 8.05 (dd, 1H), 7.87-7.83 (m, 2H), 7.69-7.64 (m, 1H), 7.52 (d, 1H), 7.44 (dd, 2H), 7.34 (dd, 1H), 5.13 (s, 2H), 5.07 (q, 1H), 3.17-3.12 (m, 1H), 3.02-2.95 (m, 1H), 2.49-2.47 (m, 1H), 1.92-1.87 (m, 1H).

O-Pyridin-2-ylmethyl, N-(4-((3-chloro-4-fluorophenyl)carbamoyl)-6,7-dihydro-5H-cyclopenta[b]pyridin-7-yl) carbamate, enantiomer 2 (267). m/z found 441.1/443.1 [M+H]+, RT=3.16 min (Method A); $^1$H NMR (400 MHz, DMSO-d$_6$): δ 10.61 (s, 1H), 8.57 (m, 2H), 8.05 (dd, 1H), 7.87-7.83 (m, 2H), 7.69-7.64 (m, 1H), 7.52 (d, 1H), 7.44 (dd, 2H), 7.34 (dd, 1H), 5.13 (s, 2H), 5.07 (q, 1H), 3.17-3.12 (m, 1H), 3.02-2.95 (m, 1H), 2.49-2.47 (m, 1H), 1.92-1.87 (m, 1H).

Example 16: Non-Limiting Synthesis of Selected Substituted 7-(Substituted Amino)-6,7-dihydro-5H-Cyclopenta[c]Pyridine-4-Carboxamides (Scheme 12)

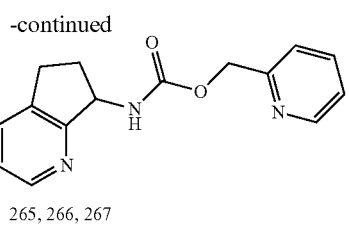

Scheme 12.

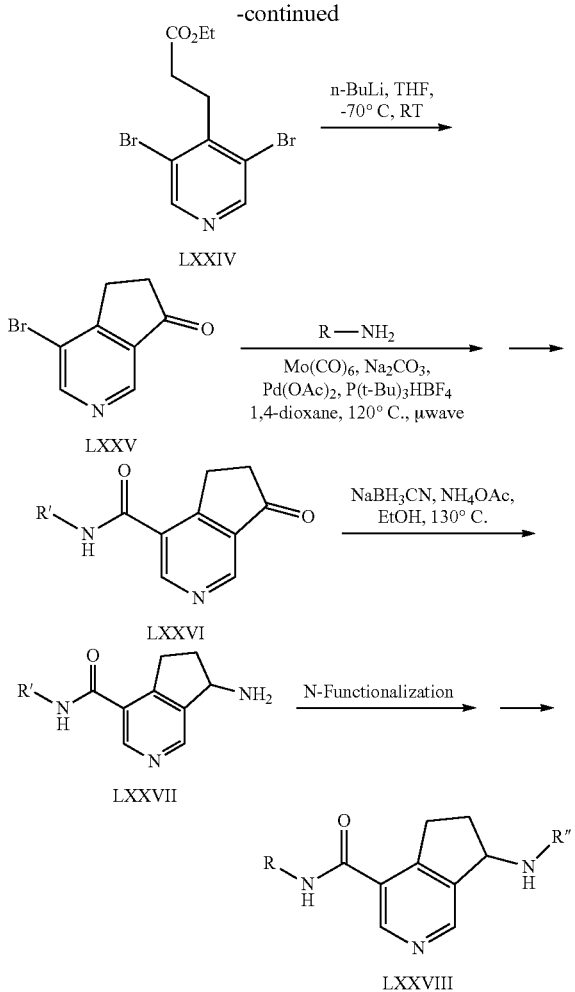

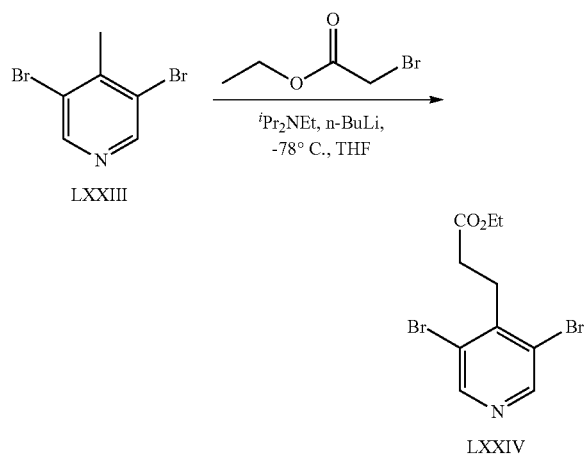

mmol, 1.1 eq.) of a 2 M solution of LDA in THF. The resulting mixture was stirred at −78° C. for 30 min and 16.8 g (100.7 mmol, 2.5 eq.) of ethyl 2-bromoacetate was added. The mixture was stirred at −78° C. for a further 2.5 h and the mixture was then quenched by the slow addition of 10 mL of saturated aqueous ammonium chloride solution. The mixture was diluted with 200 mL of water and extracted with 3×150 mL of ethyl acetate. The combined organic extracts were washed with 200 mL of brine, dried ($Na_2SO_4$), filtered and the solvent was removed in vacuo. The residue was purified by flash chromatography ($SiO_2$, eluting with 0-10% ethyl acetate/petroleum ether) to provide 4.5 g (33%, 13.4 mmol) of ethyl 3-(3,5-dibromopyridin-4-yl) propanoate (LXXIV). LCMS: m/z found 336.03 $[M+H]^+$, RT=2.28 min (Method H); $^1H$ NMR (400 MHz, $CDCl_3$): δ 8.59 (s, 2H), 4.19 (q, 2H), 3.31-3.27 (m, 2H), 2.59-2.55 (m, 2H), 1.28 (t, 3H).

4-Bromo-5H-cyclopenta[c]pyridin-7(6H)-one (LXXV)

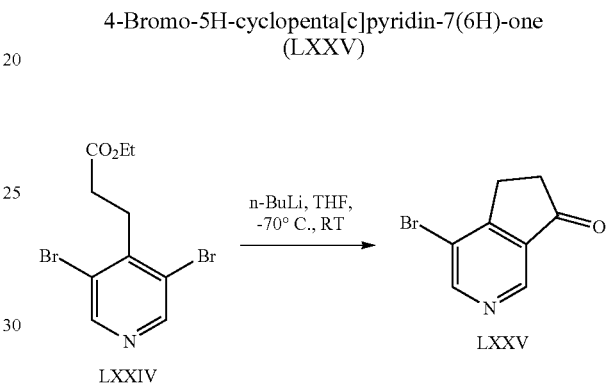

To the solution of 2.4 g (7.2 mmol. 1.0 eq.) of ethyl 3-(3,5-dibromopyridin-4-yl) propanoate (LXXIV) in 30 mL of anhydrous THF at −78° C. under nitrogen atmosphere was added drop-wise 8.9 mL (14.2 mmol, 2.0 eq.) of a 1.6 M solution of n-butyl lithium in hexanes. The mixture was allowed to warm to room temperature and stirred under a nitrogen atmosphere for 2 h. The reaction was quenched by the slow addition of 30 mL of cold water and extracted with 3×50 mL of ethyl acetate. The combined organic extracts were washed with 25 mL of water followed by 25 mL of brine, dried ($Na_2SO_4$), filtered and the solvent was removed in vacuo. The residue was purified flash chromatography ($SiO_2$, eluting with 0-20% ethyl acetate/petroleum ether) to provide 0.61 g (2.8 mmol, 40%) of 4-bromo-5H-cyclopenta[c]pyridin-7(6H)-one (LXXV). LCMS: m/z found 212.1/214.1 $[M+H]^+$, RT=1.69 min (Method H); $^1H$ NMR (500 MHz, $CDCl_3$): δ 9.91 (s, 1H), 8.82 (s, 1H), 3.12-3.14 (m, 2H), 2.75 (m, 2H).

N-(3-Chloro-4-fluorophenyl)-7-oxo-6,7-dihydro-5H-cyclopenta[c]pyridine-4-carboxamide (LXXVIa)

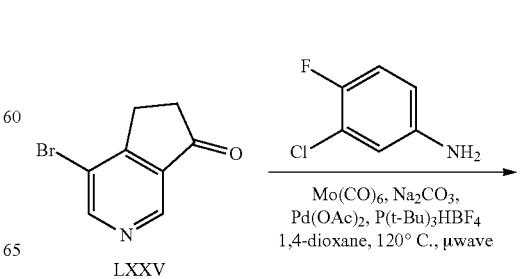

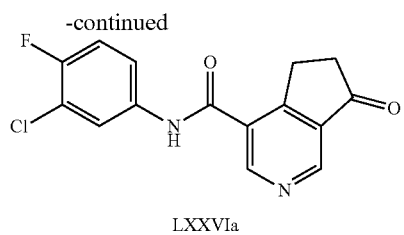

LXXVIa

To a solution of 0.9 g (4.3 mmol, 1.0 eq.) of 4-bromo-5H-cyclopenta[c]pyridin-7(6H)-one (LXXV) in 10 mL of 1,4-dioxane under a nitrogen atmosphere was added 1.2 g (8.5 mmol, 2.0 eq.) of 3-chloro-4-fluoroaniline followed by 0.9 g (8.52 mmol, 2.0 eq.) of sodium carbonate and 1.1 g (4.26 mmol, 1.0 eq.) of molybdenum hexacarbonyl. The reaction mixture was degassed with nitrogen for 10 min and 0.12 g (0.43 mmol, 0.1 eq.) of (t-Bu)$_3$HBF$_4$ and 0.10 g (0.43 mmol, 0.1 eq.) of palladium (II) acetate were added. The mixture was then subjected to microwave irradiation, maintaining a reaction temperature of 120° C. for 3 h. The mixture was then diluted with 20 mL of water and extracted with 3×30 mL of ethyl acetate. The combined organic extracts were washed with 2×50 mL of brine, dried (Na$_2$SO$_4$), filtered and the solvent was removed in vacuo. The residue was purified flash chromatography (SiO$_2$, eluting with 10-50% ethyl acetate/petroleum ether) to provide 0.3 g, (1.0 mmol, 23%) of N-(3-chloro-4-fluorophenyl)-7-oxo-6,7-dihydro-5H-cyclopenta[c]pyridine-4-carboxamide (LXXVIa). LCMS: m/z found 305.2/307.2 [M+1]$^+$, RT 2.01 min (Method H). $^1$H NMR (400 MHz, CDCl$_3$) δ 9.06-9.10 (m, 2H), 7.96 (s, 1H), 7.86-7.88 (m, 1H), 7.44-7.48 (m, 1H), 7.16-7.20 (m, 1H), 3.49-3.56 (m, 2H), 2.78-2.81 (m, 2H).

7-Amino-N-(3-chloro-4-fluorophenyl)-6,7-dihydro-5H-cyclopenta[c]pyridine-4-carboxamide (LXXVIIa)

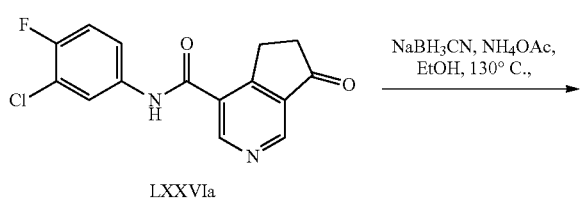

To a solution of 0.20 g (0.65 mmol, 1.0 eq.) of N-(3-chloro-4-fluoro phenyl)-7-oxo-6,7-dihydro-5H-cyclo penta[c]pyridine-4-carboxamide (LXXVIa) in 10 mL of ethanol was added 0.76 g (9.8 mmol, 15.0 eq.) of ammonium acetate and 0.21 g (0.98 mmol, 1.5 eq.) of sodium cyanoborohydride. The mixture was then subjected to microwave irradiation maintaining a reaction temperature of at 100° C. for 3 h. The solvent was removed in vacuo and the residue was resuspended in 30 mL of water and extracted with 3×80 mL of ethyl acetate. The combined organic extracts were washed with 50 mL of brine, dried (Na$_2$SO$_4$), filtered and the solvent was removed in vacuo to provide 0.21 g of 7-amino-N-(3-chloro-4-fluorophenyl)-6,7-dihydro-5H-cyclopenta[c]pyridine-4-carboxamide (LXXVIIa). LCMS: m/z found 303.8/305.8 [M-NH$_2$]+, RT=1.59 min (Method H).

N-(3-Chloro-4-fluorophenyl)-7-(cyclopropanesulfonamido)-6,7-dihydro-5H-cyclopenta[c]pyridine-4-carboxamide (268)

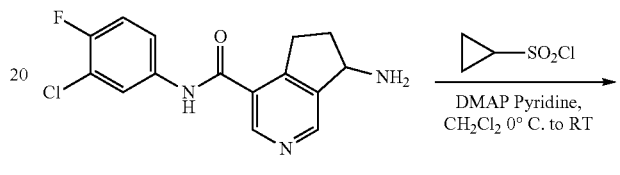

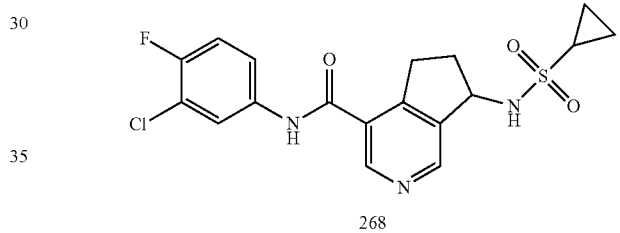

To the solution of 0.1 g (0.32 mmol, 1.0 eq.) of 7-amino-N-(3-chloro-4-fluoro phenyl)-6,7-di hydro-5H-cyclopenta[c]pyridine-4-carboxamide (LXXVIIa) in 2 mL of methylene chloride at 0° C. under a nitrogen atmosphere was added 0.05 g (0.64 mmol, 2.0 eq.) of pyridine and 8 mg (0.06 mmol, 0.2 eq) of DMAP followed by of 0.07 g (0.49 mmol, 1.5 eq.) of cyclopropanesulfonyl chloride and the mixture was stirred at 0° C. for 2 h. The mixture was diluted with 5 mL of water and extracted with 3×10 mL of ethyl acetate. The combined organic extracts were washed with 25 mL of water, 25 mL of brine, dried (Na$_2$SO$_4$), filtered and the solvent was removed in vacuo. The residue was purified by flash chromatography (SiO$_2$, eluting with 0-50% ethyl acetate/petroleum ether) to provide 0.015 g (0.02 mmol, 8%) of racemic N-(3-chloro-4-fluorophenyl)-7-(cyclopropanesulfonamido)-6,7-dihydro-5H-cyclopenta[c]pyridine-4-carboxamide (268). LCMS: m/z found 410.2/412.2 [M+H]$^+$, RT=3.01 min (Method A); $^1$H NMR (500 MHz, DMSO-d$_6$): δ 10.65 (bs, 1H), 8.80 (s, 1H), 8.65 (s, 1H), 8.05-8.07 (m, 1H), 7.77 (bs, 1H), 7.65-7.68 (m, 1H), 7.43 (dd, 1H), 4.98 (dd, 1H), 3.21-3.25 (m, 1H), 3.00-3.20 (m, 1H), 2.72-2.75 (m, 1H), 2.53-2.56 (m, 1H), 1.93-1.98 (m, 1H), 0.96-1.05 (m, 4H).

O-Pyridin-2-ylmethyl-(4-((3-chloro-4-fluorophenyl) carbamoyl)-6,7-dihydro-5H-cyclopenta[c]pyridin-7-yl) carbamate (269, 270, 271)

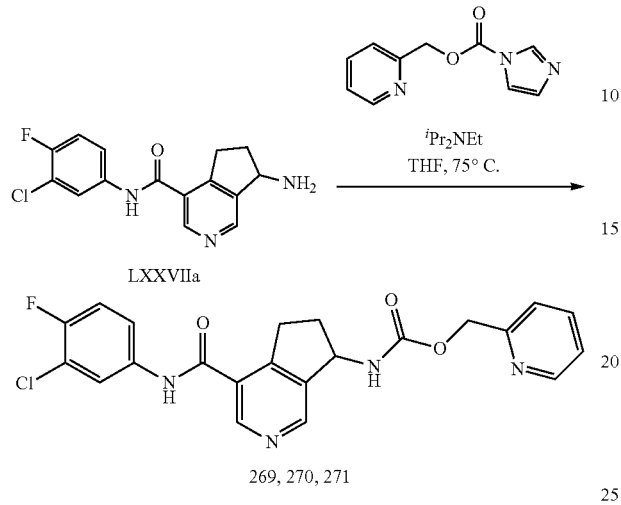

To a solution 0.24 g (0.79 mmol, 1.0 eq.) of 7-amino-N-(3-chloro-4-fluorophenyl)-6,7-dihydro-5H-cyclopenta[c]pyridine-4-carboxamide (LXXVIIa) in 20 mL of THF under a nitrogen atmosphere was added 0.30 g (2.36 mmol, 3.0 eq.) of N,N-diisopropylethylamine followed by 0.24 g (1.18 mmol, 1.5 eq.) of pyridin-2-ylmethyl 1H-imidazole-1-carboxylate and the mixture was stirred at 75° C. for 16 h. The mixture was allowed to cool to room temperature and the solvent was removed in vacuo. The residue was resuspended in 50 mL of water and extracted with 2×20 mL of ethyl acetate. The combined organic extracts were washed with 25 mL of water, 25 mL of brine, dried (Na$_2$SO$_4$), filtered and the solvent was removed in vacuo. The resulting residue was purified by semi-preparative HPLC to provide 66 mg (0.15 mmol, 19%) of racemic O-pyridin-2-ylmethyl, N-(4-((3-chloro-4-fluorophenyl)carbamoyl)-6,7-dihydro-5H-cyclopenta[c]pyridin-7-yl) carbamate (269). The racemic compound was subsequently resolved into the individual enantiomers by SFC. (Waters SFC investigator. Isocratic mobile phase CO$_2$:methanol (80:20), Column: Chiralcel OJ-H 4.6×250 mm 5 μm column, flow rate: 70 mL/min).

O-Pyridin-2-ylmethyl, N-(4-((3-chloro-4-fluorophenyl) carbamoyl)-6,7-dihydro-5H-cyclopenta[c]pyridin-7-yl) carbamate, enantiomer 1 (270): LCMS: m/z found 441.3/443.3 [M+H]$^+$, RT=2.61 min (Method A); $^1$H NMR (500 MHz, DMSO-d$_6$): δ 10.61 (s, 1H), 8.78 (s, 1H), 8.58 (s, 1H), 8.56 (d, 1H), 8.06 (dd, 1H), 8.01 (d, 1H), 7.84 (dd, 1H), 7.68-7.65 (m, 1H), 7.45-7.41 (m, 2H), 7.34 (dd, 1H), 5.21-5.16 (m, 3H), 3.25-3.20 (m, 1H), 3.06-2.99 (m, 1H), 2.47-2.44 (m, 1H), 1.93-1.89 (m, 1H).

O-Pyridin-2-ylmethyl, N-(4-((3-chloro-4-fluorophenyl) carbamoyl)-6,7-dihydro-5H-cyclopenta[c]pyridin-7-yl)carbamate, enantiomer 2 (271): LCMS: m/z found 441.3/443.3 [M+H]$^+$, RT=2.61 min (Method A); $^1$H NMR (500 MHz, DMSO-d$_6$): δ 10.61 (s, 1H), 8.78 (s, 1H), 8.58 (s, 1H), 8.56 (d, 1H), 8.06 (dd, 1H), 8.00 (d, 1H), 7.84 (dt, 1H), 7.68-7.64 (m, 1H), 7.45-7.40 (m, 2H), 7.34 (dd, 1H), 5.21-5.16 (m, 3H), 3.27-3.19 (m, 1H), 3.06-2.99 (m, 1H), 2.46-2.43 (m, 1H), 1.94-1.88 (m, 1H).

Example 17: Non-Limiting Synthesis of Selected Substituted 7-(Substituted Amino)-6,7-Dihydro-5H-Cyclopenta[c]Pyridine-4-Carboxamides (Schemes 13-14)

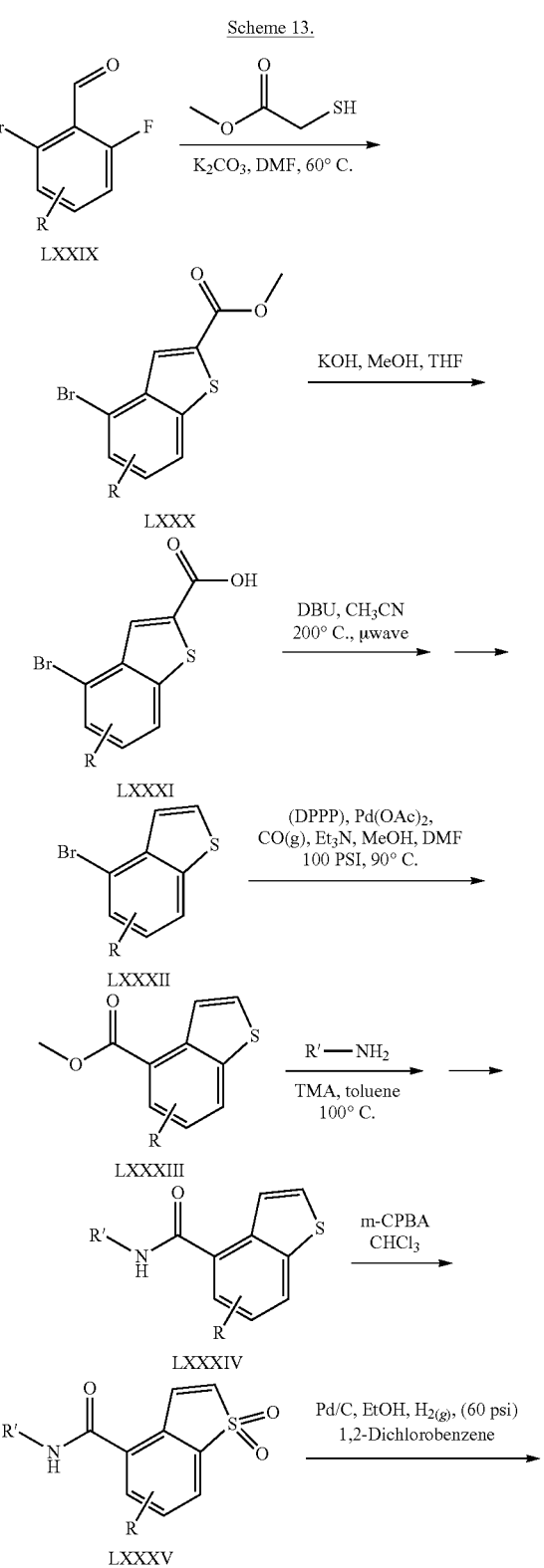

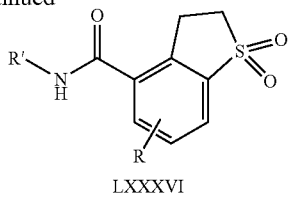

LXXXVI

Methyl 4-bromo-7-fluorobenzo[b]thiophene-2-carboxylate (LXXXa)

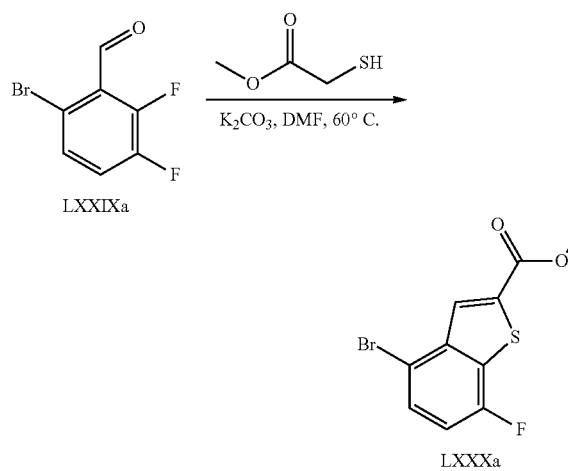

To a solution of 2.4 g (10.9 mmol, 1.0 eq.) of 6-bromo-2,3-difluorobenzaldehyde (LXXIXa) in 25 mL of DMF under a nitrogen atmosphere was added 2.9 g (21.7 mmol, 2.0 eq.) of potassium carbonate followed by 1.15 g (10.9 mmol, 1.0 eq.) of methyl 2-mercaptoacetate and the mixture was heated at 60° C. for 3 h. The mixture was allowed to cool to room temperature, diluted with 50 mL of water and extracted with 3×120 mL of ethyl acetate. The combined organic extracts were washed with 150 mL of brine, dried (Na$_2$SO$_4$), filtered and the solvent was removed in vacuo. The residue was purified by flash chromatography (SiO$_2$, eluting with 0-50% ethyl acetate/petroleum ether) to provide 1.7 g, (5.9 mmol, 54%) of methyl 4-bromo-7-fluorobenzo[b]thiophene-2-carboxylate (LXXXa). $^1$H NMR (400 MHz, CDCl$_3$) δ 8.16 (s, 1H), 7.53 (d, 1H), 7.05 (d, 1H), 3.98 (s, 3H).

4-Bromo-7-fluorobenzo[b]thiophene-2-carboxylic Acid (LXXXIa)

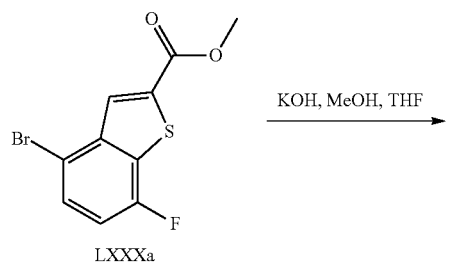

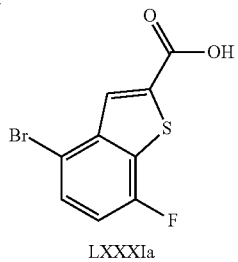

LXXXIa

To a solution of 1.7 g (5.9 mmol, 1.0 eq.) of methyl 4-bromo-7-fluorobenzo[b]thiophene-2-carboxylate (LXXXa) in 30 mL of 2:1 (v/v) THF:methanol was added a solution of 0.66 g (11.8 mmol, 2.0 eq.) of sodium hydroxide in 10 mL of water and the mixture was stirred at room temperature for 15 h. The solvent was removed in vacuo and the residue was resuspended in 20 mL of water and acidified to pH ~2 with 2 M aqueous HCl. The mixture was extracted with 3×100 mL of ethyl acetate and the combined organic extracts were washed with 100 mL of brine, dried (Na$_2$SO$_4$), filtered and the solvent was removed in vacuo to provide 1.24 g (4.5 mmol, 77%) of 4-bromo-7-fluorobenzo[b]thiophene-2-carboxylic acid (LXXXIa). $^1$H NMR (500 MHz, DMSO-d$_6$) δ 14.03 (s, 1H), 7.98 (s, 1H), 7.77 (d, 1H), 7.42 (d, 1H).

4-Bromo-7-fluorobenzo[b]thiophene (LXXXIIa)

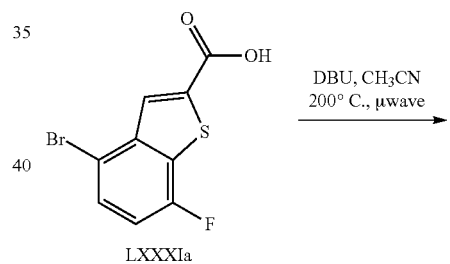

To a solution of 1.0 g (3.6 mmol, 1.0 eq.) of 4-bromo-7-fluorobenzo[b]thiophene-2-carboxylic acid (LXXXIa) in 10 mL of N,N-dimethyacetamide under a nitrogen atmosphere was added 0.55 g (3.6 mmol, 0.1 eq.) of 1,8-diazabicyclo[5.4.0]undec-7-ene and the mixture was subjected to microwave irradiation, maintaining a reaction temperature of 200° C. for 1 h. The mixture was diluted with 20 mL of water and extracted with 3×50 mL of ethyl acetate. The combined organic extracts were washed with 50 mL of brine, dried (Na$_2$SO$_4$), filtered and the solvent was removed in vacuo. The residue was purified by flash chromatography (SiO$_2$, eluting with 0-50% ethyl acetate/petroleum ether) to provide 0.68 g (2.9 mmol, 81%) of 4-bromo-7-fluorobenzo[b]thiophene (LXXXIIa). $^1$H NMR (400 MHz, CDCl$_3$) δ 7.56 (s, 1H), 7.48 (d, 2H), 6.94 (d, 1H).

Methyl 7-fluorobenzo[b]thiophene-4-carboxylate (LXXXIIIa)

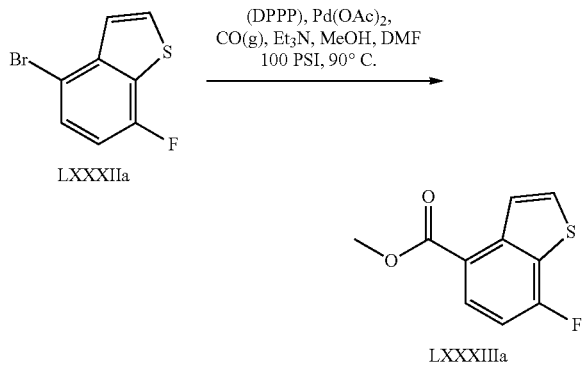

To a solution of 0.4 g (1.7 mmol, 1.0 eq.) of 4-bromo-7-fluorobenzo[b]thiophene (LXXXIIa) in 10 mL of 1:1 (v/v) DMF:methanol under an argon atmosphere was added 0.87 g (8.7 mmol, 5.0 eq.) of triethylamine. The mixture was degassed for with argon for 15 min and 106 mg (0.26 mmol, 0.15 eq.) of 1,3-bis(diphenylphosphino)propane was added followed by 38 mg (0.17 mmol, 0.1 eq.) of palladium (II) acetate. The mixture was further degassed with argon for 5 min and the mixture was stirred in an autoclave at 90° C. for 15 h under 100 psi of carbon monoxide. The solvent was removed in vacuo and the residue was purified using flash chromatography (SiO$_2$, eluting with 0-25% ethyl acetate/petroleum ether) to provide 0.21 g (1.0 mmol, 58%) of methyl 7-fluorobenzo[b]thiophene-4-carboxylate (LXXXIIIa). LCMS: m/z found 211.1 [M+H]$^+$, RT=2.39 min (Method H); $^1$H NMR (400 MHz, CDCl$_3$) δ 8.26 (d, 1H), 8.16 (d, 1H), 7.65 (d, 1H), 7.09 (d, 1H), 3.98 (s, 3H).

N-(3-Chloro-4-fluorophenyl)-7-fluorobenzo[b]thiophene-4-carboxamide (LXXXIVa)

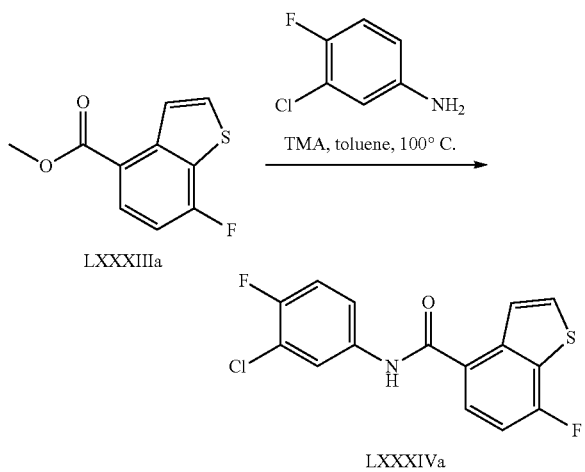

To a solution of 0.21 g (1.0 mmol, 1.0 eq.) of methyl 7-fluorobenzo[b]thiophene-4-carboxylate (LXXXIIIa) in 4 mL of toluene under a nitrogen atmosphere was added 0.22 g (1.5 mmol, 1.5 eq.) of 3-chloro-4-fluoroaniline followed by 1.0 mL (2.0 mmol, 2.0 eq.) of a 2 M solution of trimethyl aluminium in toluene and the mixture was stirred at 100° C. for 15 h. The mixture was allowed to cool to room temperature and quenched by the addition of 10 mL of water. The mixture was extracted with 3×20 mL of ethyl acetate and the combined organic extracts were washed with 50 mL of brine, dried (Na$_2$SO$_4$), filtered and the solvent was removed in vacuo. The residue was purified by flash chromatography (SiO$_2$, eluting with 0-50% ethyl acetate/petroleum ether) to provide 0.25 g, (0.77 mmol, 77%) of N-(3-chloro-4-fluorophenyl)-7-fluorobenzo[b]thiophene-4-carboxamide (LXXXIVa). LCMS: m/z found 326.0/328.0 [M+H]$^+$, RT=2.34 min (Method H); $^1$H NMR (400 MHz, DMSO-d$_6$) δ 10.6 (s, 1H), 8.10 (d, 1H), 8.03 (d, 1H), 7.91 (dd, 2H), 7.71 (d, 1H), 7.43 (dd, 2H).

N-(3-Chloro-4-fluorophenyl)-7-fluorobenzo[b]thiophene-4-carboxamide 1,1-dioxide (LXXXVa)

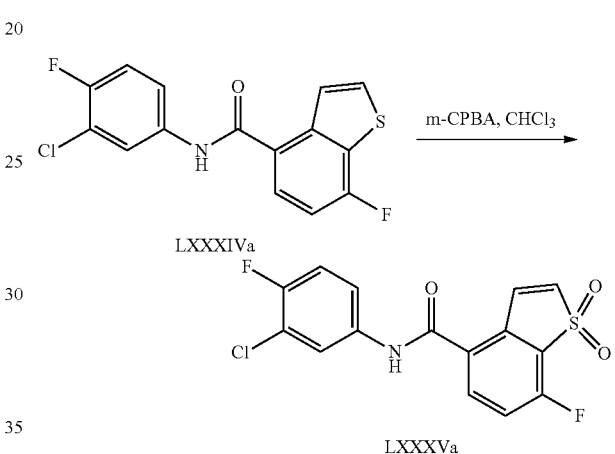

To a stirred solution of 0.25 g (0.77 mmol, 1.0 eq) of N-(3-chloro-4-fluorophenyl)-7-fluorobenzo[b]thiophene-4-carboxamide (LXXXIVa) in 5 mL of chloroform was added 0.41 g (1.54 mmol, 2.0 eq.) of 65% meta-chloroperbenzoic acid and the mixture was stirred at room temperature for 24 h. Then mixture was diluted with 50 mL of chloroform and washed with 20 mL of saturated aqueous sodium bicarbonate, dried (Na$_2$SO$_4$), filtered and the solvent was removed in vacuo. The residue was purified by flash chromatography (SiO$_2$, eluting with 10-30% ethyl acetate/petroleum ether) to provide 0.18 g (0.49 mmol, 64%) of N-(3-chloro-4-fluorophenyl)-7-fluorobenzo[b]thiophene-4-carboxamide 1,1-dioxide (LXXXVa). LCMS: m/z found 356.1/358.1 [M+H]$^+$, RT=2.22 min (Method H).

N-(3-Chloro-4-fluorophenyl)-7-fluoro-2,3-dihydrobenzo[b]thiophene-4-carboxamide 1,1-dioxide (272)

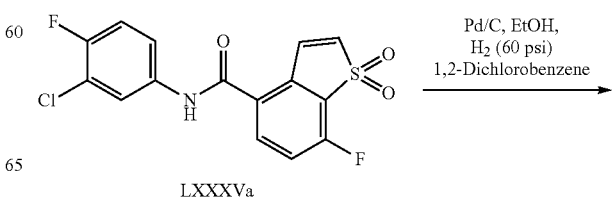

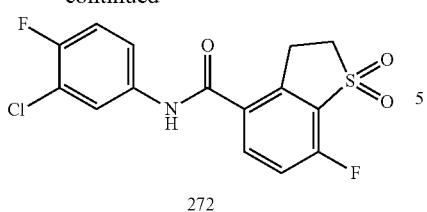

272

To a solution of 0.17 g (0.48 mmol, 1.0 eq) of N-(3-chloro-4-fluorophenyl)-7-fluorobenzo[b]thiophene-4-carboxamide 1,1-dioxide (LXXXVa) in 20 mL (v/v) of 1:1 ethanol: 1,2-dichlorobenzene was added 0.17 g of 10% palladium on carbon (with 50 weight % water added) and the mixture was shaken in a Parr apparatus under 60 psi of hydrogen for 15 h. The mixture was filtered through Celite® and the pad was washed with 10 mL of ethanol. The solvent was removed in vacuo and residue was purified by flash chromatography (SiO$_2$, eluting with 0-15% methanol/methylene chloride) to provide 0.094 g (0.26 mmol, 55%) of N-(3-chloro-4-fluorophenyl)-7-fluoro-2,3-dihydrobenzo[b]thiophene-4-carboxamide 1,1-dioxide (272). LCMS: m/z found 356.1/358.1 [M−H], RT=4.23 min (Method A); $^1$H NMR (400 MHz, DMSO-d$_6$): δ 10.7 (s, 1H), 8.08 (dd, 1H), 8.02 (dd, 1H), 7.64 (dd, 1H), 7.579 (dd, 1H), 7.44 (t, 1H), 3.72 (t, 2H), 3.59 (t, 2H).

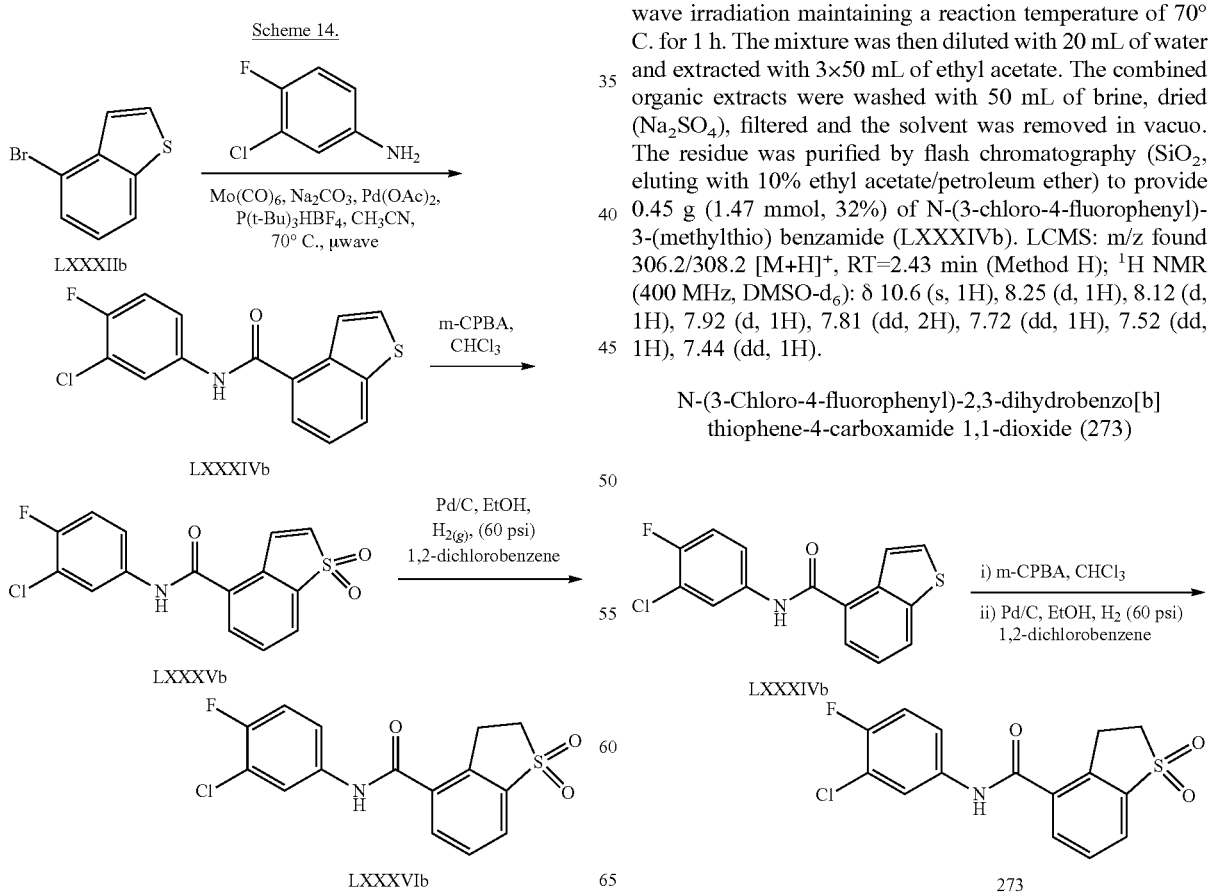

N-(3-Chloro-4-fluorophenyl)-3-(methylthio)benzamide (LXXXIVb)

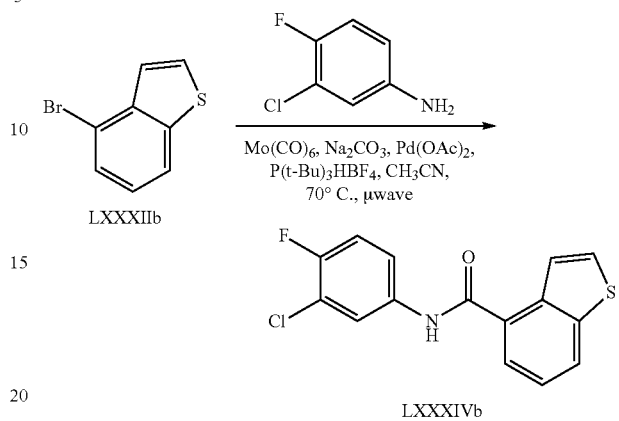

To a solution of 1.0 g (4.69 mmol, 1.0 eq.) of 4-bromobenzo[b]thiophene (LXXXIIb) in 10 mL of acetonitrile was added 1.36 g (9.39 mmol, 2.0 eq.) of 3-chloro-4-fluoroaniline followed by 1.0 g (9.43 mmol, 2.0 eq.) of sodium carbonate and 1.2 g (4.69 mmol, 1.0 eq.) of molybdenum hexacarbonyl. The mixture was degassed with nitrogen for 10 min and 0.14 g (0.47 mmol, 0.1 eq.) of (t-Bu)$_3$HBF$_4$ and 0.105 g (0.4692 mmol, 0.1 eq.) of palladium (II) acetate were added. The mixture was subjected to microwave irradiation maintaining a reaction temperature of 70° C. for 1 h. The mixture was then diluted with 20 mL of water and extracted with 3×50 mL of ethyl acetate. The combined organic extracts were washed with 50 mL of brine, dried (Na$_2$SO$_4$), filtered and the solvent was removed in vacuo. The residue was purified by flash chromatography (SiO$_2$, eluting with 10% ethyl acetate/petroleum ether) to provide 0.45 g (1.47 mmol, 32%) of N-(3-chloro-4-fluorophenyl)-3-(methylthio) benzamide (LXXXIVb). LCMS: m/z found 306.2/308.2 [M+H]$^+$, RT=2.43 min (Method H); $^1$H NMR (400 MHz, DMSO-d$_6$): δ 10.6 (s, 1H), 8.25 (d, 1H), 8.12 (d, 1H), 7.92 (d, 1H), 7.81 (dd, 2H), 7.72 (dd, 1H), 7.52 (dd, 1H), 7.44 (dd, 1H).

N-(3-Chloro-4-fluorophenyl)-2,3-dihydrobenzo[b]thiophene-4-carboxamide 1,1-dioxide (273)

N-(3-Chloro-4-fluorophenyl)-2,3-dihydrobenzo[b]thiophene-4-carboxamide 1,1-dioxide (273) was synthesised in a similar manner to that described above from N-(3-chloro-4-fluorophenyl)benzo[b]thiophene-4-carboxamide (LXXXIVb). LCMS: m/z found 340.1/342.1 [M+H]+, RT=2.13 min (Method H); $^1$H NMR (400 MHz, DMSO-$d_6$): δ 10.7 (s, 1H), 8.06 (dd, 1H), 8.01 (d, 1H), 7.95 (d, 1H), 7.69-7.71 (dd, 1H), 7.63-7.67 (m, 1H), 7.45 (dd, 1H), 3.53-3.58 (m, 2H), 3.59-3.66 (m, 2H).

Example 18: Non-Limiting Synthesis of Selected Substituted 2,3-Dihydrobenzo[d]Isothiazole-4-Carboxamides 1,1-Dioxide (Schemes 15-17)

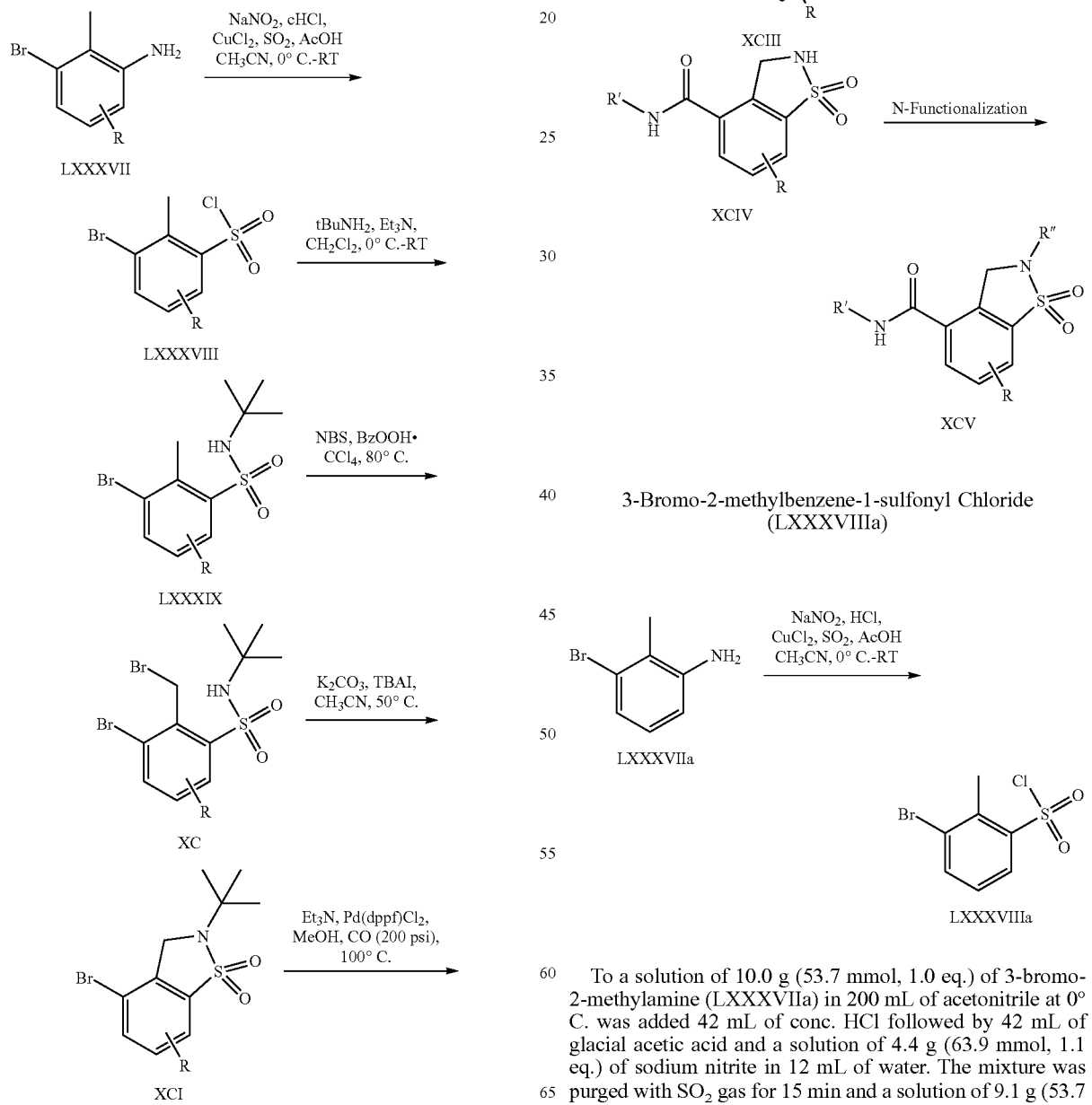

3-Bromo-2-methylbenzene-1-sulfonyl Chloride (LXXXVIIIa)

To a solution of 10.0 g (53.7 mmol, 1.0 eq.) of 3-bromo-2-methylamine (LXXXVIIa) in 200 mL of acetonitrile at 0° C. was added 42 mL of conc. HCl followed by 42 mL of glacial acetic acid and a solution of 4.4 g (63.9 mmol, 1.1 eq.) of sodium nitrite in 12 mL of water. The mixture was purged with SO$_2$ gas for 15 min and a solution of 9.1 g (53.7 mmol, 1.0 eq.) of copper (II) chloride in 12 mL of water was added dropwise at 0° C. The mixture was allowed to warm to room temperature and stirred for 16 h. The mixture was concentrated in vacuo, diluted with 500 mL of water and extracted with 3×500 mL of ethyl acetate. The combined organic extracts were washed with 200 mL of sat. aqueous sodium bicarbonate solution, 200 mL of brine, dried (Na$_2$SO$_4$), filtered and the solvent was removed in vacuo. The residue was purified by trituration with pentane to provide 8.0 g (29.7 mmol, 55%) of 3-bromo-2-methylbenzene-1-sulfonyl chloride (LXXXVIIIa). $^1$H NMR (400 MHz, CDCl$_3$): δ 8.07 (d, 1H), 7.92 (d, 1H), 7.28 (t, 1H), 2.88 (s, 3H).

3-Bromo-N-(tert-butyl)-2-methylbenzenesulfonamide (LXXXIXa)

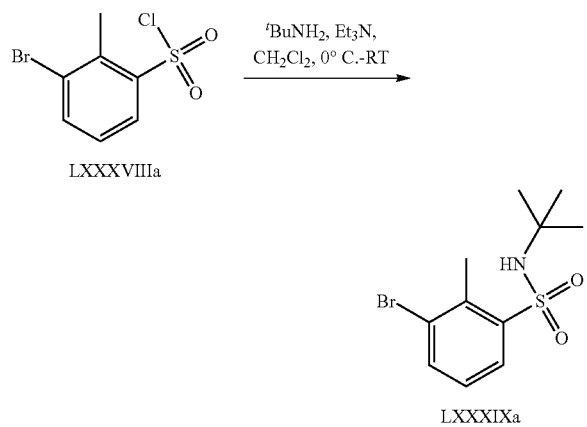

To a solution of 8.0 g (29.7 mmol, 1.0 eq.) of 3-bromo-2-methylbenzene-1-sulfonyl chloride (LXXXVIIIa) in 80 mL of methylene chloride at 0° C. was added 4.5 g (44.5 mmol, 1.5 eq.) of triethylamine, followed by 3.3 g (44.5 mmol, 1.5 eq.) of tert-butylamine. The mixture was allowed to warm to room temperature and stirred for 16 h. The mixture was diluted with 100 mL of water and extracted with 3×200 mL of methylene chloride. The combined organic extracts were washed with 100 mL of water, 100 mL of brine, dried (Na$_2$SO$_4$), filtered and the solvent was removed in vacuo. The residue was purified by trituration with pentane to provide 6.8 g (22.2 mmol, 74%) of 3-bromo-N-(tert-butyl)-2-methylbenzenesulfonamide (LXXXIXa). LCMS: m/z found 304.1/306.1 [M−H], RT=2.35 min (Method H); $^1$H NMR (400 MHz, DMSO-d$_6$): δ 7.94 (dd, 1H), 7.86 (dd, 1H), 7.68 (s, 1H), 7.32 (dd, 1H), 2.66 (s, 3H), 1.11 (s, 9H).

3-Bromo-2-(bromomethyl)-N-(tert-butyl)benzenesulfonamide (XCa)

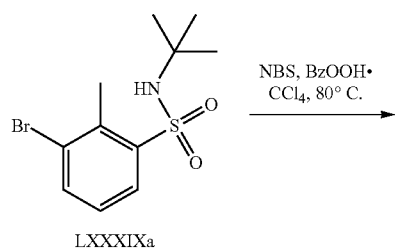

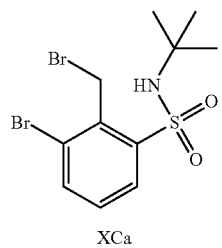

To a solution of 5.0 g (16.3 mmol, 1.0 eq.) of 3-bromo-N-(tert-butyl)-2-methylbenzene sulfonamide (LXXXIXa) in 50 mL of carbon tetrachloride was added 5.8 g (32.6 mmol, 2.0 eq.) of N-bromosuccinimide followed by 0.79 g (3.26 mmol, 0.2 eq.) of benzoyl peroxide. The mixture was then heated at 80° C. for 16 h. The mixture was allowed to cool to room temperature, diluted with 75 mL of water and extracted with 3×100 mL of methylene chloride. The combined organic extracts were washed with 75 mL of water, 75 mL of brine, dried (Na$_2$SO$_4$), filtered and the solvent was removed in vacuo. The residue was purified by flash chromatography (SiO$_2$, eluting with a linear gradient of 5-10% ethyl acetate/petroleum ether) to provide 4.2 g (10.9 mmol, 67%) of 3-bromo-2-(bromomethyl)-N-(tert-butyl)benzenesulfonamide (XCa). $^1$H NMR (400 MHz, DMSO-d$_6$) δ 7.99 (dd, 1H), 7.95 (s, 1H), 7.94 (d, 1H), 7.46 (dd, 1H), 5.07 (s, 2H), 1.16 (s, 9H).

4-Bromo-2-(tert-butyl)-2,3-dihydrobenzo[d]isothiazole 1,1-dioxide (XCIa)

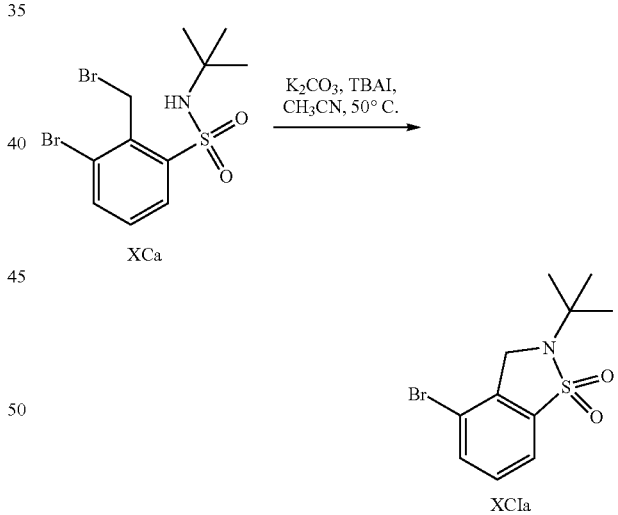

To a solution of 4.2 g (10.9 mmol, 1.0 eq.) of 3-bromo-2-(bromomethyl)-N-(tert-butyl) benzenesulfonamide (XCa) in 42 mL of acetonitrile was added 3.0 g (21.8 mmol, 2.0 eq.) of potassium carbonate followed by 0.8 g (2.18 mmol, 0.2 eq.) of tetrabutylammonium iodide. The mixture was then heated to 50° C. for 16 h. The mixture was allowed to cool to room temperature and the solvent was removed in vacuo. The residue was resuspended in 75 mL of water and extracted with 3×100 mL of ethyl acetate. The combined organic extracts were washed with 75 mL of water, 75 mL of brine, dried (Na$_2$SO$_4$), filtered and the solvent was removed in vacuo. The residue was purified by flash chromatography (SiO$_2$, eluting with a linear gradient of 0-15% ethyl acetate/petroleum ether) to provide 2.8 g (9.24 mmol, 84%) of 4-bromo-2-(tert-butyl)-2,3-dihydrobenzo[d]isothiazole 1,1-dioxide (XCIa). LCMS: m/z found 248.1/250.1 [M+H-tBu]$^+$, RT=2.01 min (Method H); $^1$H NMR (400 MHz, DMSO-d$_6$) δ 7.96 (dd, 1H), 7.84 (dd, 1H), 7.57 (dd, 1H), 4.44 (s, 2H), 1.49 (s, 9H).

Methyl-2-(tert-butyl)-2,3-dihydrobenzo[d]isothiazole-4-carboxylate 1,1-dioxide (XCIIa)

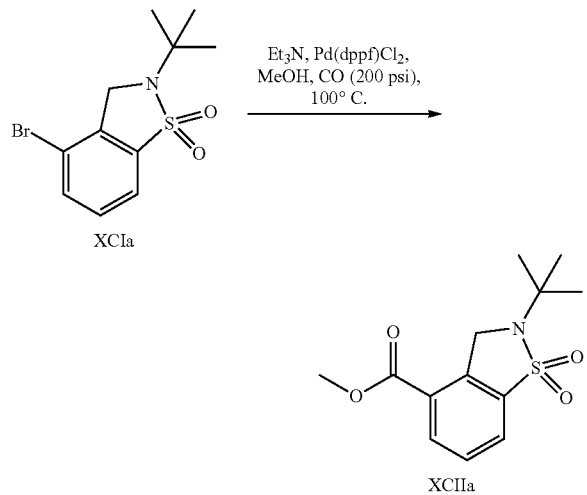

To a solution of 0.6 g (1.98 mmol, 1.0 eq.) of 4-bromo-2-(tert-butyl)-2,3-dihydrobenzo[d]isothiazole 1,1-dioxide (XCIa) in 12 mL of methanol was added 0.6 g (5.94 mmol, 3.0 eq.) of triethylamine followed by 0.32 g (0.40 mmol, 0.2 eq.) of [1,1'-bis(diphenylphosphino) ferrocene]dichloropalladium(II). The mixture was stirred at 100° C. for 16 h under 200 psi of carbon monoxide in sealed steel vessel. The mixture was then filtered through Celite® and the pad washed with 20 mL of methanol. The solvent was removed in vacuo and residue was purified by flash chromatography (SiO$_2$, eluting with a linear gradient of 20-30% ethyl acetate/petroleum ether) to provide 0.4 g (1.41 mmol, 71%) of methyl-2-(tert-butyl)-2,3-dihydrobenzo[d]isothiazole-4-carboxylate 1,1-dioxide (XCIIa). $^1$H NMR (400 MHz, DMSO-d$_6$) δ 8.24 (dd, 1H), 8.07 (dd, 1H), 7.76 (dd, 1H), 4.78 (s, 2H), 3.91 (s, 3H), 1.49 (s, 9H).

2-(tert-Butyl)-N-(3-chloro-4-fluorophenyl)-2,3-dihydrobenzo[d]isothiazole-4-carboxamide 1,1-dioxide (274)

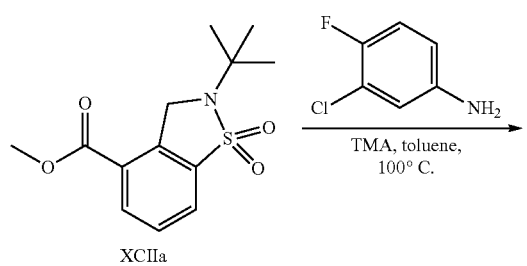

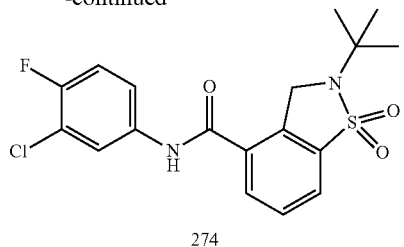

To a solution of 0.4 g (1.41 mmol, 1.0 eq.) of methyl-2-(tert-butyl)-2,3-dihydrobenzo[d]isothiazole-4-carboxylate 1,1-dioxide (XCIIa) in 4 mL of toluene under a nitrogen atmosphere was added 0.31 g (2.12 mmol, 1.5 eq.) of 3-chloro-4-fluoroaniline and 1.4 mL (2.82 mmol, 2.0 eq.) of a 2 M solution of trimethyl aluminum in toluene and the mixture was heated at 100° C. for 16 h. The mixture was allowed to cool to room temperature, quenched with 10 mL of cold water and extracted with 3×30 mL of ethyl acetate. The combined organic extracts were washed with 20 mL of water, 20 mL of brine, dried (Na$_2$SO$_4$), filtered and the solvent was removed in vacuo. The residue was purified by flash chromatography (SiO$_2$, eluting with a linear gradient of 25-30% ethyl acetate/petroleum ether) to provide 0.35 g (0.88 mmol, 62%) of 2-(tert-butyl)-N-(3-chloro-4-fluorophenyl)-2,3-dihydrobenzo[d]isothiazole-4-carboxamide 1,1-dioxide (274). LCMS: m/z found 340.8/342.8 [M+H-$^t$Bu]$^+$, RT=5.14 min (Method A); $^1$H NMR (400 MHz, DMSO-d$_6$) δ 10.72 (s, 1H), 8.15 (d, 1H) 8.08 (dd, 1H), 8.00 (d, 1H), 7.79 (dd, 1H), 7.64-7.68 (m, 1H), 7.45 (t, 1H), 4.78 (s, 2H), 1.48 (s, 9H).

N-(3-Chloro-4-fluorophenyl)-2,3-dihydrobenzo[d]isothiazole-4-carboxamide-1,1-dioxide (275)

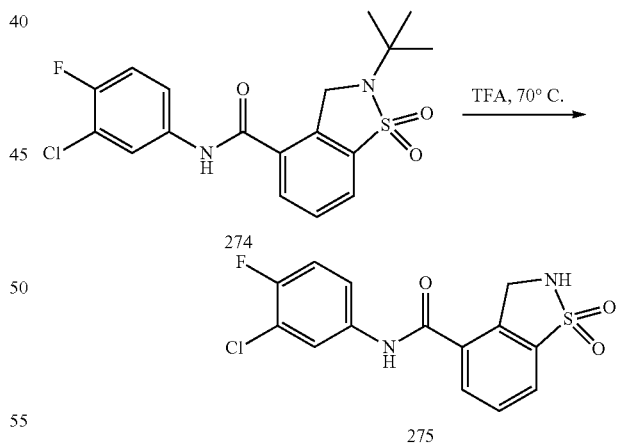

A solution of 0.35 g (0.88 mmol, 1.0 eq.) of 2-(tert-butyl)-N-(3-chloro-4-fluorophenyl)-2,3-dihydrobenzo[d]isothiazole-4-carboxamide 1,1-dioxideb (274) in 3.5 mL of trifluoroacetic acid was stirred at 70° C. for 16 h. The solvent was removed in vacuo and the residue was triturated with pentane to provide 0.28 g (0.82 mmol, 93%) of N-(3-chloro-4-fluorophenyl)-2,3-dihydrobenzo[d]isothiazole-4-carboxamide-1,1-dioxide (275). $^1$H NMR (400 MHz, DMSO-d$_6$): δ 10.68 (s, 1H), 8.14 (d, 1H) 8.06 (dd, 2H), 7.92 (t, 1H), 7.78 (dd, 1H), 7.65-7.69 (m, 1H), 7.44 (dd, 1H), 4.64 (s, 2H).

(2-Bromoethoxy)(tert-butyl)dimethylsilane

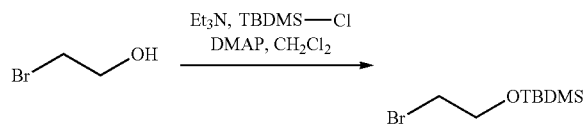

To a solution of 2.0 g (16.0 mmol, 1.0 eq.) of 2-bromoethanol in 10 mL of methylene chloride at 0° C. was added 3.2 g (32.0 mmol, 2.0 eq.) of triethylamine followed by 2.89 g (19.2 mmol, 1.2 eq.) of tert-butyldimethylsilyl chloride and 0.78 g (6.40 mmol, 0.4 eq.) of 4-dimethylamino pyridine and the mixture was stirred at room temperature for 16 h. The mixture was diluted with 50 mL of 1 M HCl and extracted with 2×50 mL of methylene chloride. The combined organic extracts were washed with 30 mL of water, 30 mL of brine, dried ($Na_2SO_4$), filtered and the solvent removed in vacuo to provide 2.9 g (12.2 mmol, 76%) of (2)-bromoethoxy)(tert-butyl)dimethylsilane. $^1$H NMR (400 MHz, $CDCl_3$): δ 3.79 (t, 2H), 3.29 (t, 2H), 0.81 (s, 9H), −0.01 (s, 6H).

2-(2-((tert-Butyldimethylsilyl)oxy)ethyl)-N-(3-chloro-4-fluorophenyl)-2,3-dihydrobenzo-[d]-isothiazole-4-carboxamide 1,1-dioxide (XCVa)

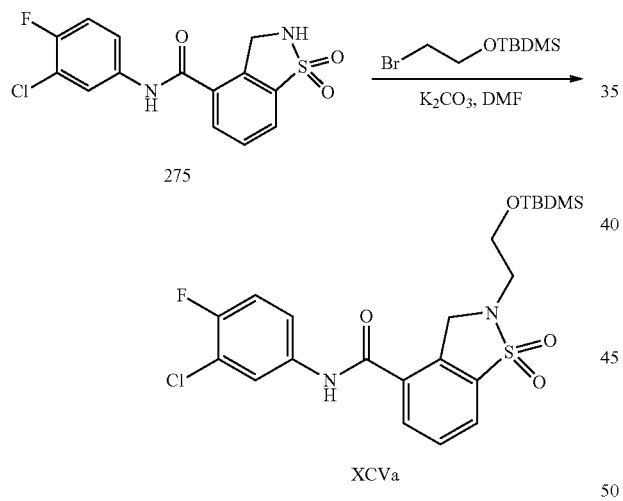

To a solution of 0.28 g (0.82 mmol, 1.0 eq.) of N-(3-chloro-4-fluorophenyl)-2,3-dihydrobenzo[d]isothiazole-4-carboxamide-1,1-dioxide (275) in 3 mL of DMF at was added 0.68 g (2.06 mmol, 2.5 eq.) of (2-bromoethoxy)(tert-butyl)dimethylsilane and 0.34 g (2.47 mmol, 3.0 eq.) of potassium carbonate and the mixture was stirred at room temperature for 16 h. The mixture was diluted with 30 mL of water and extracted with 3×30 mL of ethyl acetate. The combined organic extracts were washed with 30 mL of water, 30 mL of brine, dried ($Na_2SO_4$), filtered and the solvent was in vacuo. The residue was purified by flash chromatography ($SiO_2$, eluting with a linear gradient of 15-25% ethyl acetate/petroleum ether) to provide 0.21 g (0.42 mmol, 51%) of 2-(2-((tert-butyldimethylsilyl)oxy)ethyl)-N-(3-chloro-4-fluorophenyl)-2,3-dihydrobenzo[d]isothiazole-4-carboxamide 1,1-dioxide (XCVa). LCMS: m/z found 499.0/501.0 [M+H]$^+$, RT=2.67 min (Method H); $^1$H NMR (400 MHz, DMSO-$d_6$): δ 10.68 (s, 1H), 8.11 (d, 1H) 8.06 (d, 1H), 8.04 (dd, 1H), 7.77 (dd, 1H), 7.59-7.63 (m, 1H), 7.41 (dd, 1H), 4.77 (s, 2H), 3.82 (t, 2H), 3.31 (t, 2H), 0.8 (s, 9H), −0.04 (s, 6H).

N-(3-Chloro-4-fluorophenyl)-2-(2-hydroxyethyl)-2,3-dihydrobenzo[d]isothiazole-4-carboxamide 1,1-dioxide (276)

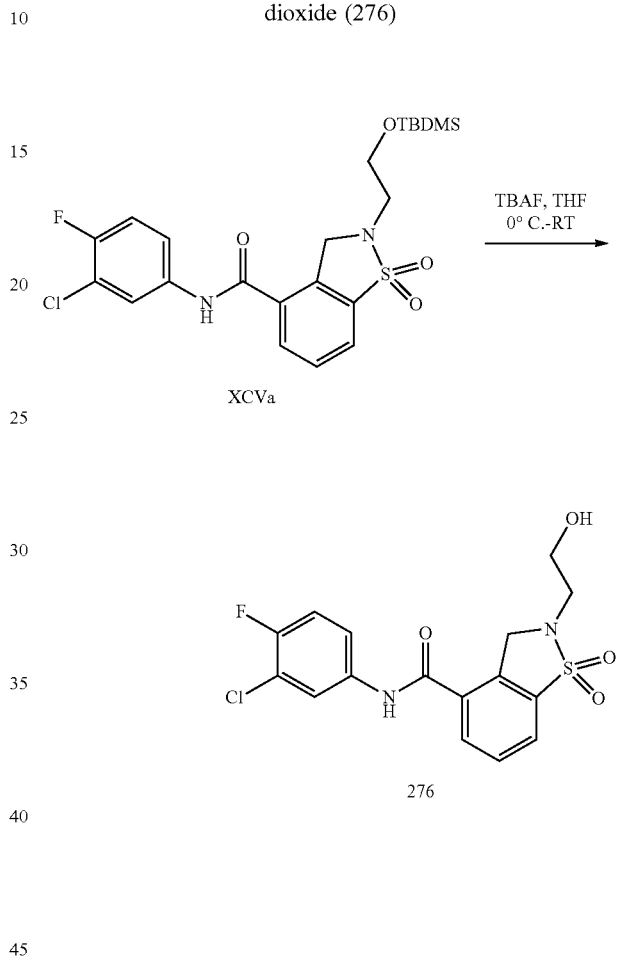

To a solution of 0.17 g (0.34 mmol, 1.0 eq.) of 2-(2-((tert-butyldimethylsilyl)oxy)ethyl)-N-(3-chloro-4-fluorophenyl)-2,3-dihydrobenzo[d]isothiazole-4-carboxamide 1,1-dioxide (XCVa) in 5 mL of THF at 0° C. was added 0.51 mL (0.51 mmol, 1.5 eq.) of a 1 M solution of tetra n-butyl ammonium fluoride in THF and the mixture was stirred at room temperature for 6 h. The mixture was diluted with 20 mL of sat. aqueous ammonium chloride solution and extracted with 3×20 mL of ethyl acetate. The combined organic extracts were washed with 15 mL of water, 15 mL of brine, dried ($Na_2SO_4$), filtered and the solvent was removed in vacuo. The residue was purified by flash chromatography ($SiO_2$, eluting with a linear gradient of 35-45% ethyl acetate/petroleum ether) to provide 0.07 g (0.17 mmol, 49%) of N-(3-chloro-4-fluorophenyl)-2-(2-hydroxyethyl)-2,3-dihydrobenzo[d]isothiazole-4-carboxamide 1,1-dioxide (276). LCMS: m/z found 385.1/387.1 [M+H]$^+$, RT=3.53 min (Method A); $^1$H NMR (500 MHz, DMSO-$d_6$): δ 10.69 (s, 1H), 8.17 (dd, 1H), 8.09 (d, 1H), 8.06 (dd, 1H), 7.81 (dd, 1H), 7.65-7.69 (m, 1H), 7.45 (d, 1H), 4.89 (t, 1H), 4.79 (s, 2H), 3.68 (q, 2H), 3.28 (t, 2H).

Scheme 16.

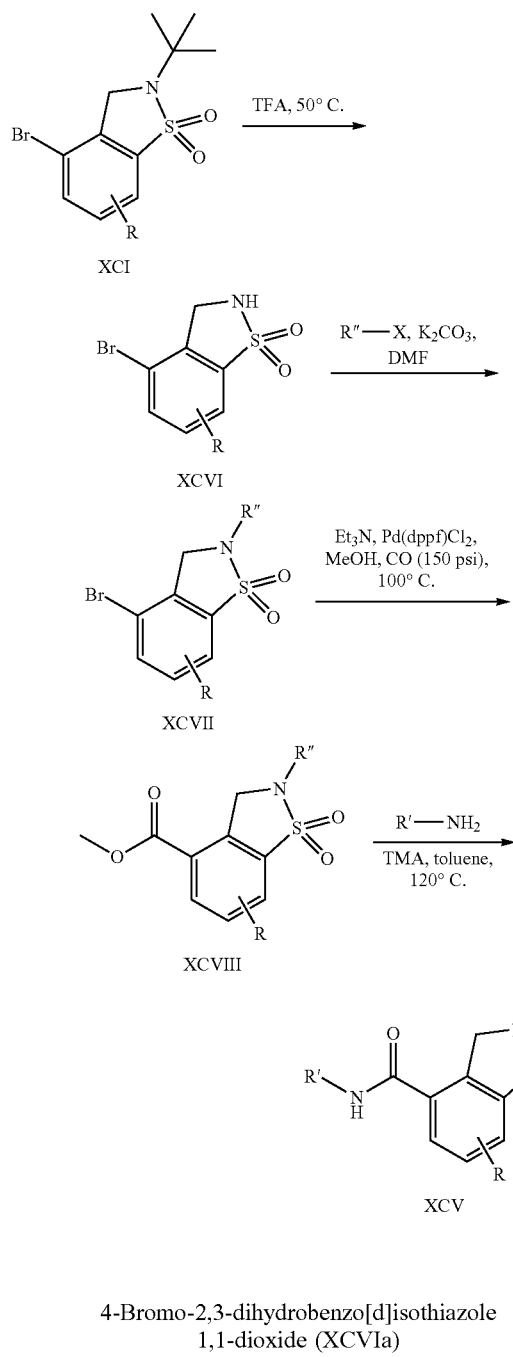

4-Bromo-2,3-dihydrobenzo[d]isothiazole 1,1-dioxide (XCVIa)

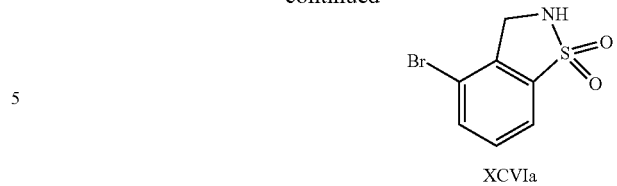

A solution of 0.6 g (1.97 mmol, 1.0 eq.) of 4-bromo-2-(tert-butyl)-2,3-dihydrobenzo-[d]-isothiazole 1,1-dioxide (XCIa) in 5 mL of trifluoroacetic acid was stirred at 50° C. for 16 h. The volatiles were removed in vacuo and the residue was triturated with pentane to provide 0.31 g (1.25 mmol, 63%) of 4-bromo-2,3-dihydrobenzo[d]isothiazole 1,1-dioxide (XCVIa). $^1$H NMR (400 MHz, CDCl$_3$) δ 7.70-7.78 (m, 2H), 7.44 (dd, 1H), 4.78 (bs, 1H), 4.46 (d, 2H).

4-Bromo-2-methyl-2,3-dihydrobenzo[d]isothiazole 1,1-dioxide (XCVIIa)

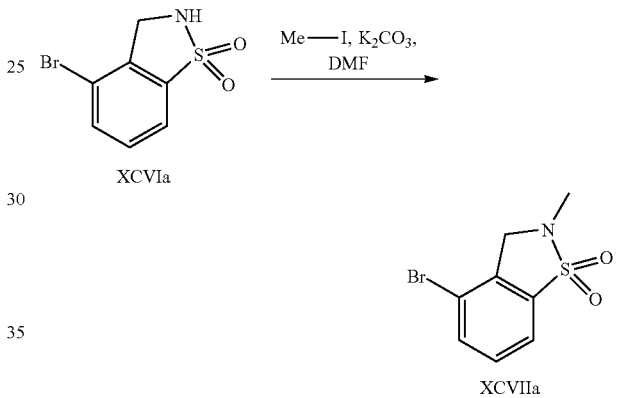

To a solution of 0.30 g (1.2 mmol, 1.0 eq.) of 4-bromo-2,3-dihydrobenzo[d]isothiazole 1,1-dioxide (XCVIa) in 2 mL of DMF was added 0.43 g (3.0 mmol, 2.5 eq.) of methyl iodide followed by 0.42 g (3.0 mmol, 2.5 eq.) of potassium carbonate and the mixture was stirred at room temperature for 16 h. The mixture was diluted with 30 mL of ethyl acetate and washed with 15 mL of water, 15 mL of brine, dried (Na$_2$SO$_4$), filtered and the solvent was removed in vacuo. The residue was purified by flash chromatography (SiO$_2$, eluting with a linear gradient of 25-50% ethyl acetate/petroleum ether) to provide 0.23 g (0.88 mmol, 73%) of 4-bromo-2-methyl-2,3-dihydrobenzo[d]isothiazole 1,1-dioxide (XCVIIa). LCMS: m/z found 261.9/263.9 [M+H]$^+$, RT=1.90 min (Method H); $^1$H NMR (400 MHz, CDCl$_3$) δ 7.75-7.79 (m, 2H), 7.45 (dd, 1H), 4.26 (s, 2H), 3.00 (s, 3H).

Methyl 2-methyl-2,3-dihydrobenzo[d]isothiazole-4-carboxylate 1,1-dioxide (XCVIIIa)

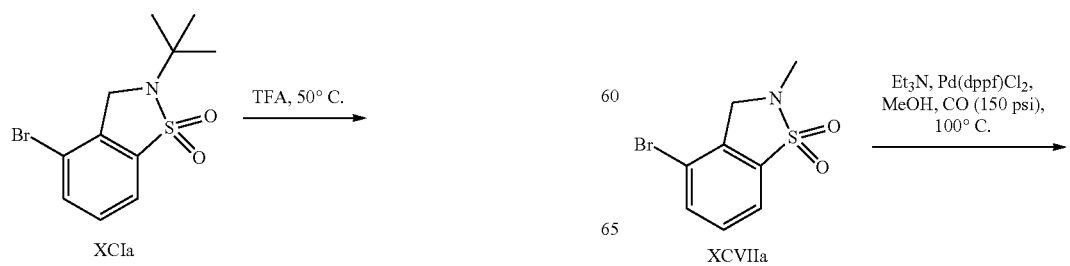

-continued

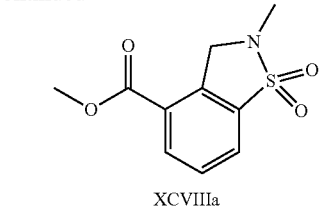

XCVIIIa

To a solution of 0.23 g (0.88 mmol, 1.0 eq.) of 4-bromo-2-methyl-2,3-dihydrobenzo[d]isothiazole 1,1-dioxide (XCVIIa) in 5 mL of methanol was added 0.27 g (2.6 mmol, 3.0 eq.) of triethylamine. The mixture was then degassed with argon for 20 min and 0.07 g (0.088 mmol, 0.1 eq.) of [Pd(dppf)Cl$_2$.CH$_2$Cl$_2$ complex] was added. The mixture was then stirred at 110° C. under 150 psi of CO gas in a steel vessel for 15 h. The mixture was filtered through Celite® and the pad was washed with 10 mL of methanol. The solvent was removed in vacuo and the residue was purified by flash chromatography (SiO$_2$, eluting with a linear gradient of 0-80% ethyl acetate/petroleum ether) to provide 0.14 g (0.56 mmol, 60%) of methyl 2-methyl-2,3-dihydrobenzo[d]isothiazole-4-carboxylate 1,1-dioxide (XCVIIIa). LCMS: m/z found 242.05 [M+H]$^+$, RT=1.77 min (Method H); $^1$H NMR (400 MHz, CDCl$_3$) δ 8.27 (d, 1H), 8.01 (d, 1H), 7.65 (dd, 1H), 4.70 (s, 2H), 3.96 (s, 3H), 3.00 (s, 3H).

N-(3-Chloro-4-fluorophenyl)-2-methyl-2,3-dihydrobenzo[d]isothiazole-4-carboxamide 1,1-dioxide (277)

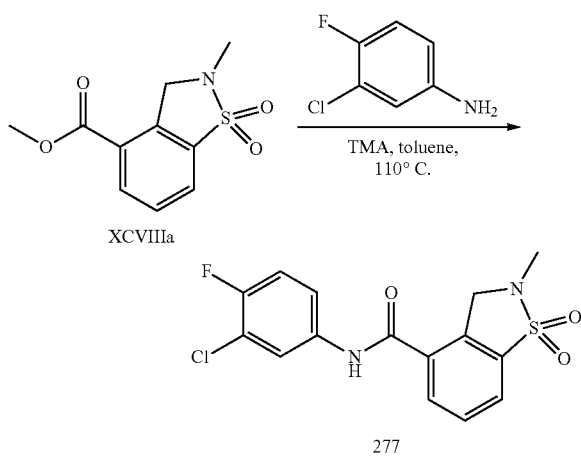

To a solution of 0.11 g (0.46 mmol, 1.0 eq.) of methyl 2-methyl-2,3-dihydrobenzo-[d]-isothiazole-4-carboxylate 1,1-dioxide (XCVIIIa) in 5 mL of toluene under a nitrogen atmosphere was added 0.10 g (0.68 mmol, 1.5 eq.) of 3-chloro-4-fluoroaniline followed by 0.56 mL (1.14 mmol, 2.5 eq.) of a 2 M solution of trimethyl aluminum in toluene and the mixture was stirred at 110° C. for 15 h. The mixture was quenched with 10 mL of cold water and extracted with 3×20 mL of ethyl acetate. The combined organic extracts were washed with 10 mL of water, 10 mL of brine, dried (Na$_2$SO$_4$), filtered and the solvent was removed in vacuo. The residue was purified semi-preparative HPLC to provide 0.07 g (0.20 mmol, 43%) of N-(3-chloro-4-fluorophenyl)-2-methyl-2,3-dihydrobenzo[d]isothiazole-4-carboxamide 1,1-dioxide (277). LCMS: m/z found 355.0/353.0 [M+H]$^+$, RT=4.30 min (Method A); $^1$H NMR (400 MHz, DMSO-d$_6$): δ 10.73 (bs, 1H), 8.17 (d, 1H), 8.10 (d, 1H), 8.06 (dd, 1H), 7.81 (dd, 1H), 7.67 (dd, 1H), 7.44 (dd, 1H), 4.66 (s, 2H), 2.84 (s, 3H).

N-(3-Chloro-4-fluorophenyl)-2-isopropyl-2,3-dihydrobenzo[d]isothiazole-4-carboxamide 1,1-dioxide (278)

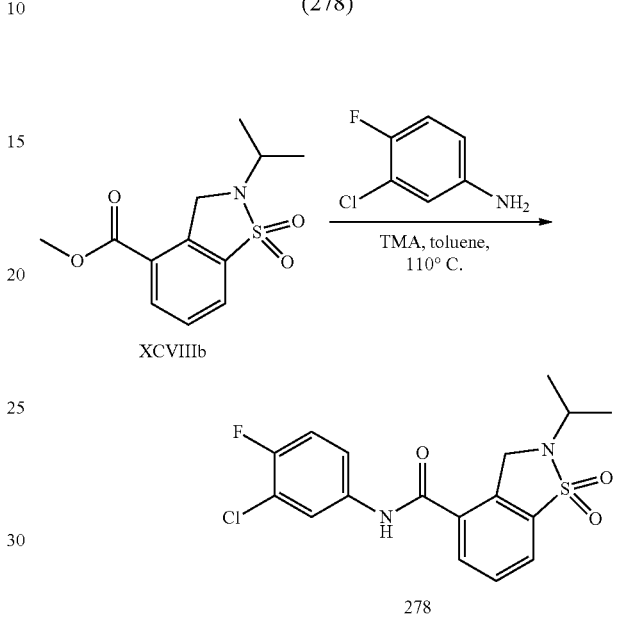

N-(3-Chloro-4-fluorophenyl)-2-isopropyl-2,3-dihydrobenzo[d]isothiazole-4-carboxamide 1,1-dioxide (2787) was synthesised in a similar manner as described above from methyl 2-isopropyl-2,3-dihydrobenzo[d]isothiazole-4-carboxylate 1,1-dioxide (XCVIIIb) and 3-chloro-4-fluoroaniline. LCMS: m/z found 383.1/385.2 [M+H]$^+$, RT=4.72 min (Method A); $^1$H NMR (500 MHz, DMSO-d$_6$): δ 10.72 (s, 1H), 8.16 (d, 1H), 8.06-8.09 (m, 2H), 7.81 (dd, 1H), 7.65-7.68 (m, 1H), 7.45 (dd, 1H), 4.69 (s, 2H), 3.92-3.97 (m, 1H), 1.31 (d, 6H).

Scheme 17.

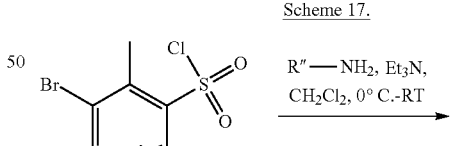

LXXXVIII

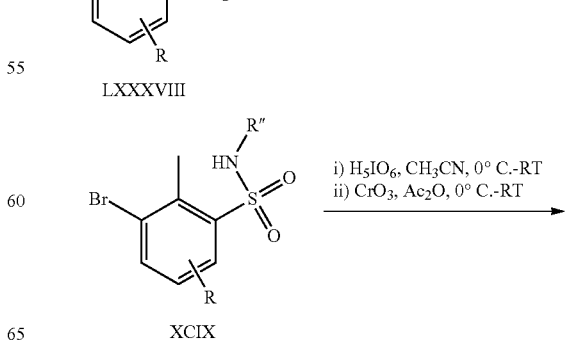

XCIX

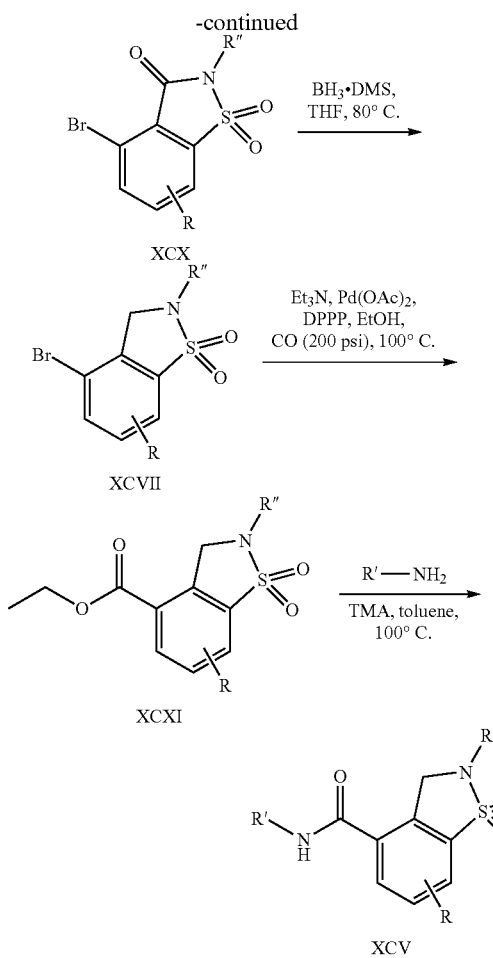

3-Bromo-N-cyclopropyl-2-methylbenzenesulfonamide (XCIXa)

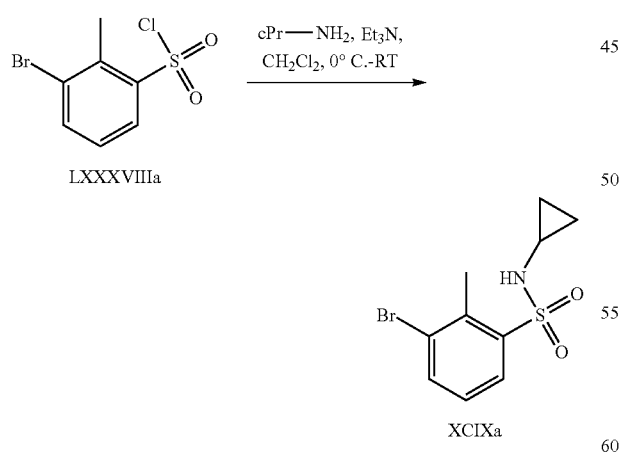

To a solution of 2.4 g (8.92 mmol, 1.0 eq.) of 3-bromo-2-methylbenzenesulfonyl chloride (LXXXVIIIa) in 15 mL of methylene chloride at 0° C. was added 1.35 g (13.4 mmol, 1.5 eq.) of triethyl amine and 0.76 g (13.4 mmol, 1.5 eq.) of cyclopropyl amine. The mixture was allowed to warm to room temperature and stirred for 3 h. The solvent was removed in vacuo and the residue was purified by flash chromatography (SiO$_2$, eluting with a linear gradient of 10-20% ethyl acetate/petroleum ether) to provide 1.7 g (5.9 mmol, 65%) of 3-bromo-N-cyclopropyl-2-methylbenzenesulfonamide (XCIXa). LCMS: m/z found 290.1/292.1 [M+H]$^+$, RT=2.18 min, (Method H); $^1$H NMR (500 MHz, CDCl3): δ 8.05 (dd, 1H), 7.79 (dd, 1H), 7.20 (dd, 1H), 4.93 (s, 1H), 2.72 (s, 3H), 2.31-2.36 (m, 1H), 0.54-0.56 (m, 4H).

4-Bromo-2-cyclopropylbenzo[d]isothiazol-3(2H)-one 1,1-dioxide (XCXa)

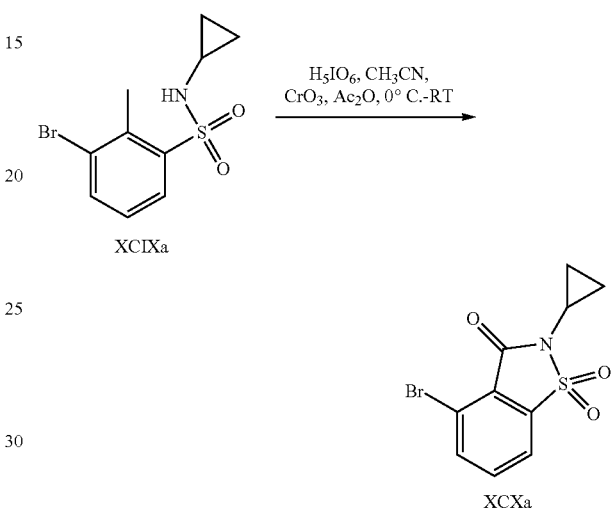

A solution of 3.7 g (16.1 mmol, 7.8 eq.) of periodic acid in 18 mL of acetonitrile was stirred at room temperature for 1 h and 21 mg (0.21 mmol, 0.2 eq.) of chromium trioxide and 1.6 mL (16.1 mmol, 7.8 eq.) of acetic anhydride were added. The mixture was stirred for at room temperature 30 min, cooled to 0° C. and 0.6 g (2.06 mmol, 1.0 eq.) of 3-bromo-N-cyclopropyl-2-methylbenzenesulfonamide (XCIXa) was added. The reaction mixture was allowed to warm to room temperature and stirred further for 16 h. The volatiles were removed in vacuo and the residue was resuspended in 20 mL of water. The mixture was extracted with 3×80 mL of ethyl acetate and the combined organic extracts were washed with 20 mL of water, 20 mL of brine, dried (Na$_2$SO$_4$), filtered and the solvent was removed in vacuo. The residue was purified by trituration with pentane to afford 0.3 g (1.0 mmol, 48%) of 4-bromo-2-cyclopropylbenzo[d]isothiazol-3(2H)-one 1,1-dioxide (XCXa). LCMS: m/z found 302.1/304.1 [M+H]$^+$, RT=2.04 min (Method H).

4-Bromo-2-cyclopropyl-2,3-dihydrobenzo[d]isothiazole 1,1-dioxide (XCVIIc)

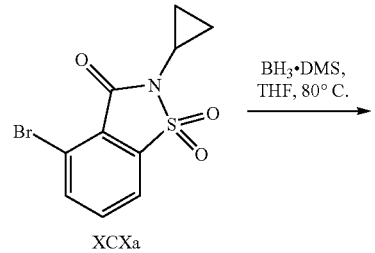

-continued

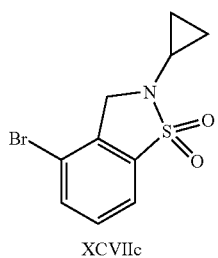

XCVIIc

To a solution of 0.3 g (1.0 mmol, 1.0 eq.) of 4-bromo-2-cyclopropylbenzo[d]isothiazol-3(2H)-one 1,1-dioxide (XCXa) in 3 mL of THF under a nitrogen atmosphere was added 2.5 mL (5.0 mmol, 5.0 eq.) of borane dimethyl sulfide complex at room temperature and the mixture was then heated at 80° C. for 2 h. The mixture was allowed to cool to room temperature and quenched by the addition of 10 mL of ice cold water. The mixture was then extracted with 3×40 mL of ethyl acetate and the combined organic extracts were washed with 10 mL of water, 10 mL of brine, dried (Na$_2$SO$_4$), filtered and the solvent was removed in vacuo. The residue was purified by trituration with pentane to afford 0.20 g (0.70 mmol, 70%) of 4-bromo-2-cyclopropyl-2,3-dihydrobenzo[d]isothiazole 1,1-dioxide (XCVIIc). LCMS: m/z found 287.8/289.8 [M+H]$^+$, RT=2.17 min (Method H).

Ethyl 2-cyclopropyl-2,3-dihydrobenzo[d]isothiazole-4-carboxylate 1,1-dioxide (XCXIa)

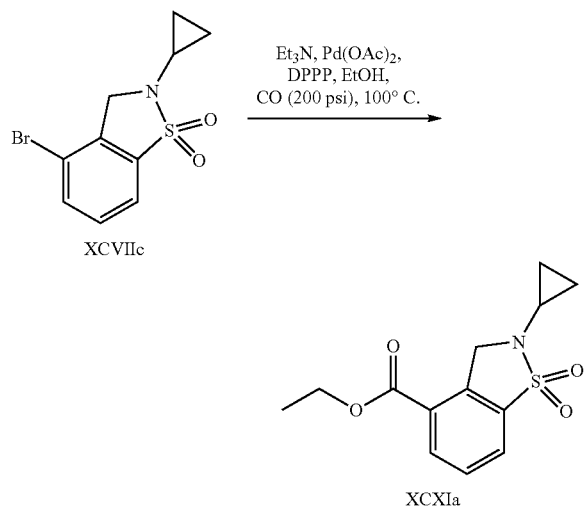

To a solution of 0.50 g (1.73 mmol, 1.0 eq.) of 4-bromo-2-cyclopropyl-2,3-dihydrobenzo[d]isothiazole 1,1-dioxide (XCVIIc) in 10 mL of ethanol in a steel pressure vessel was added 0.72 mL (5.21 mmol, 3.0 eq.) of triethylamine. The mixture was degassed with argon for 30 min and 38 mg (0.17 mmol, 0.1 eq.) of palladium (II) acetate was added, followed by 0.14 g (0.34 mmol, 0.2 eq.) of 1,3-bis(diphenylphosphino)propane. The mixture was then stirred at 100° C. under 200 psi of CO gas for 16 h. The mixture was filtered through Celite® and the pad washed with 10 mL of ethanol. The solvent was removed in vacuo and the residue was purified by flash chromatography (SiO$_2$, eluting with a linear gradient of 10-25% ethyl acetate/petroleum ether) to provide 0.35 g (1.24 mmol, 72%) of ethyl 2-cyclopropyl-2,3-dihydrobenzo[d]isothiazole-4-carboxylate 1,1-dioxide (XCXIa). LCMS: m/z found 282.2 [M+H]$^+$, RT=2.05 min (Method H); $^1$H NMR (400 MHz, CDCl$_3$) δ 8.27 (d, 1H), 7.98 (d, 1H), 7.63 (dd, 1H), 4.78 (s, 2H), 4.42 (q, 2H), 2.61-2.58 (m, 1H), 1.43 (t, 3H), 1.04-1.00 (m, 2H), 0.87-0.82 (m, 2H).

N-(3-Chloro-4-fluorophenyl)-2-cyclopropyl-2,3-dihydrobenzo[d]isothiazole-4-carboxamide 1,1-dioxide (240)

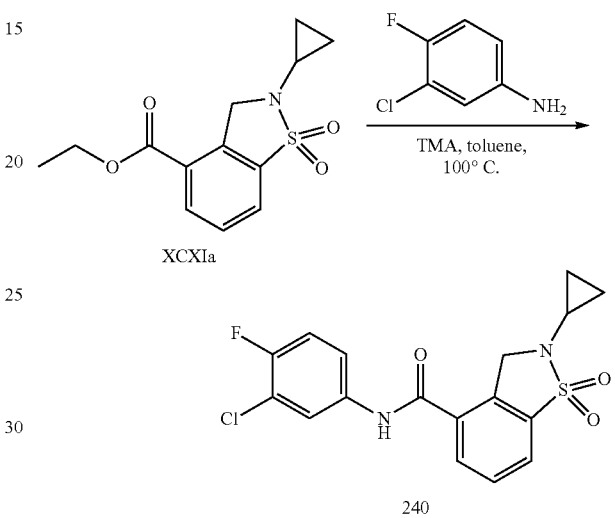

To a solution of 0.3 g (1.06 mmol, 1.0 eq.) of ethyl 2-cyclopropyl-2,3-dihydrobenzo-[d]-isothiazole-4-carboxylate 1,1-dioxide (XCXIa) in 3 mL of toluene at 0° C. under a nitrogen atmosphere was added 0.23 g (1.60 mmol, 1.5 eq.) of 3-chloro-4-fluoroaniline followed by 1.3 mL (2.66 mmol, 2.5 eq.) of a 2 M solution of trimethyl aluminium in toluene and the mixture was heated at 100° C. for 15 h. The mixture was allowed to cool to room temperature and quenched with 10 mL of cold water. The mixture was extracted with 3×50 mL of ethyl acetate and the combined organic extracts were washed with 10 mL of water, 10 mL of brine, dried (Na$_2$SO$_4$), filtered and the solvent was removed in vacuo. The residue was purified by flash chromatography (SiO$_2$, eluting with a linear gradient of 10-30% ethyl acetate/petroleum ether) to provide 70 mg (0.18 mmol, 17%) of N-(3-chloro-4-fluorophenyl)-2-cyclopropyl-2,3-dihydrobenzo[d]isothiazole-4-carboxamide 1,1-dioxide (240). LCMS: m/z found 381.0/383.0 [M+H]$^+$, RT=4.75 min (Method A); $^1$H NMR (400 MHz, DMSO-d$_6$): δ 10.72 (s, 1H), 8.17 (d, 1H), 8.09-8.06 (m, 2H), 7.81 (t, 1H), 7.69-7.65 (m, 1H), 7.45 (dd, 1H), 4.75 (s, 2H), 2.57-2.50 (m, 1H), 0.88-0.74 (m, 4H).

Example 19: Biological Results

Representative compounds of the invention were tested for their abilities to inhibit formation of relaxed circular DNA (rcDNA) in a HepDE19 assay, as described elsewhere herein. Results are illustrated in Table 1.

TABLE 1

| No. | Nomenclature | DE-19 bDNA EC$_{50}$ (µM) |
|---|---|---|
| 1 | O-methyl, N-(S)-(4-((3,4-difluorophenyl)carbamoyl)-2,3-dihydro-1H-inden-1-yl) carbamate | 0.64 |
| 2 | (S)-N-(3,4-difluorophenyl)-1-(3-methylureido)-2,3-dihydro-1H-indene-4-carboxamide | 1.4 |
| 3 | O-pyridin-2-ylmethyl, N-(S)-(4-((3,4-difluorophenyl)carbamoyl)-2,3-dihydro-1H-inden-1-yl) carbamate | 0.50 |
| 4 | O-methyl, N-(7-((3,4-difluorophenyl)carbamoyl)-2,3-dihydrobenzofuran-3-yl) carbamate | 5.3 |
| 5 | O-methyl, N-(7-((3,4-difluorophenyl)carbamoyl)-2,3-dihydrobenzofuran-3-yl) carbamate (enantiomer 1) | 14 |
| 6 | O-methyl, N-(7-((3,4-difluorophenyl)carbamoyl)-2,3-dihydrobenzofuran-3-yl) carbamate (enantiomer 2) | 1.3 |
| 7 | N-(3,4-difluorophenyl)-3-(3-methylureido)-2,3-dihydrobenzofuran-7-carboxamide (enantiomer 1) | 1.9 |
| 8 | N-(3,4-difluorophenyl)-3-(3-methylureido)-2,3-dihydrobenzofuran-7-carboxamide (enantiomer 2) | 23 |
| 9 | O-((R)-5-oxopyrrolidin-2-yl)methyl, N-((S)-4-((3-chloro-4-fluorophenyl)carbamoyl)-7-fluoro-2,3-dihydro-1H-inden-1-yl) carbamate | 0.58 |
| 10 | O-tert-butyl, N-(S)-(4-((3-chloro-4-fluorophenyl)carbamoyl)-7-fluoro-2,3-dihydro-1H-inden-1-yl) carbamate | 0.80 |
| 11 | O-methyl, N-(S)-(7-fluoro-4-((4-fluoro-3-methylphenyl)carbamoyl)-2,3-dihydro-1H-inden-1-yl) carbamate | 0.21 |
| 12 | (S)-7-fluoro-N-(4-fluoro-3-methylphenyl)-1-(3-methylureido)-2,3-dihydro-1H-indene-4-carboxamide | 0.38 |
| 13 | (S)-1-amino-N-(3-chloro-4-fluorophenyl)-7-fluoro-2,3-dihydro-1H-indene-4-carboxamide | 25 |
| 14 | O-2-(2-oxopyrrolidin-1-yl)ethyl, N-(S)-(4-((3-chloro-4-fluorophenyl)carbamoyl)-7-fluoro-2,3-dihydro-1H-inden-1-yl) carbamate | 0.45 |
| 15 | O-pyridin-2-ylmethyl, N-(7-((3,4-difluorophenyl)carbamoyl)-2,3-dihydrobenzofuran-3-yl) carbamate (enantiomer 1) | 1.5 |
| 16 | O-pyridin-2-ylmethyl, N-(7-((3,4-difluorophenyl)carbamoyl)-2,3-dihydrobenzofuran-3-yl)carbamate (enantiomer 2) | 24 |
| 17 | O-pyridin-2-ylmethyl, N-(S)-(4-((3-chloro-4-fluorophenyl)carbamoyl)-2,3-dihydro-1H-inden-1-yl) carbamate | 0.17 |
| 18 | O-((S)-5-oxopyrrolidin-2-yl)methyl, N-((S)-4-((3-chloro-4-fluorophenyl)carbamoyl)-7-fluoro-2,3-dihydro-1H-inden-1-yl) carbamate | 0.34 |
| 19 | O-methyl, N-(S)-(4-((3-chloro-4-fluorophenyl)carbamoyl)-7-fluoro-2,3-dihydro-1H-inden-1-yl) carbamate | 0.17 |
| 20 | (S)-N-(3-chloro-4-fluorophenyl)-7-fluoro-1-(3-methylureido)-2,3-dihydro-1H-indene-4-carboxamide | 0.32 |
| 21 | O-((R)-5-oxopyrrolidin-2-yl)methyl, N-((S)-4-((3-chloro-4-fluorophenyl)carbamoyl)-2,3-dihydro-1H-inden-1-yl) carbamate | 0.58 |
| 22 | O-((S)-5-oxopyrrolidin-2-yl)methyl, N-((S)-4-((3-chloro-4-fluorophenyl)carbamoyl)-2,3-dihydro-1H-inden-1-yl) carbamate | 0.44 |
| 23 | O-pyridin-2-ylmethyl, N-(S)-(4-((4-fluoro-3-methylphenyl)carbamoyl)-2,3-dihydro-1H-inden-1-yl) carbamate | 0.45 |
| 24 | O-((R)-5-oxopyrrolidin-2-yl)methyl, N-((S)-4-((4-fluoro-3-methylphenyl)carbamoyl)-2,3-dihydro-1H-inden-1-yl)carbamate | 1.5 |
| 25 | O-((S)-5-oxopyrrolidin-2-yl)methyl, N-((S)-4-((4-fluoro-3-methylphenyl)carbamoyl)-2,3-dihydro-1H-inden-1-yl) carbamate | 1.1 |
| 26 | O-2-oxo-2-(pyrrolidin-1-yl)ethyl, N-(S)-(4-((3-chloro-4-fluorophenyl)carbamoyl)-7-fluoro-2,3-dihydro-1H-inden-1-yl) carbamate | 0.44 |
| 27 | O-pyridin-2-ylmethyl, N-(7-((3,4-difluorophenyl)carbamoyl)-2,3-dihydrobenzo[b]thiophen-3-yl) carbamate | 1.4 |
| 28 | O-pyridin-2-ylmethyl, N-(7-((3-chloro-4-fluorophenyl)carbamoyl)-2,3-dihydrobenzo[b]thiophen-3-yl) carbamate | 0.76 |
| 29 | O-methyl, N-(7-((3-chloro-4-fluorophenyl)carbamoyl)-2,3-dihydrobenzo[b]thiophen-3-yl) carbamate | 1.6 |
| 30 | O-methyl, N-(7-((3,4-difluorophenyl)carbamoyl)-2,3-dihydrobenzo[b]thiophen-3-yl) carbamate (enantiomer 1) | 1.8 |
| 31 | O-methyl, N-(7-((3,4-difluorophenyl)carbamoyl)-2,3-dihydrobenzo[b]thiophen-3-yl) carbamate (enantiomer 2) | 25 |
| 32 | O-pyridin-2-ylmethyl, N-(S)-(4-((3-chloro-4-fluorophenyl)carbamoyl)-7-fluoro-2,3-dihydro-1H-inden-1-yl) carbamate | 0.11 |
| 33 | O-pyridin-2-ylmethyl, N-(7-((3,4-difluorophenyl)carbamoyl)-2,3-dihydrobenzo[b]thiophen-3-yl) carbamate (enantiomer 1) | 1.1 |
| 34 | O-pyridin-2-ylmethyl, N-(7-((3,4-difluorophenyl)carbamoyl)-2,3-dihydrobenzo[b]thiophen-3-yl) carbamate (enantiomer 2) | 25 |
| 35 | O-pyridin-2-ylmethyl, N-(7-((3-chloro-4-fluorophenyl)carbamoyl)-2,3-dihydrobenzo[b]thiophen-3-yl) carbamate (enantiomer 1) | 0.78 |
| 36 | O-pyridin-2-ylmethyl, N-(7-((3-chloro-4-fluorophenyl)carbamoyl)-2,3-dihydrobenzo[b]thiophen-3-yl) carbamate (enantiomer 2) | 25 |

TABLE 1-continued

| No. | Nomenclature | DE-19 bDNA EC$_{50}$ (μM) |
|---|---|---|
| 37 | O-methyl, N-(7-((3-chloro-4-fluorophenyl)carbamoyl)-2,3-dihydrobenzo[b]thiophen-3-yl) carbamate (enantiomer 1) | 0.95 |
| 38 | O-methyl, N-(7-((3-chloro-4-fluorophenyl)carbamoyl)-2,3-dihydrobenzo[b]thiophen-3-yl) carbamate (enantiomer 2) | 25 |
| 39 | O-((S)-1-methyl-5-oxopyrrolidin-2-yl)methyl, N-((S)-4-((3-chloro-4-fluorophenyl)carbamoyl)-7-fluoro-2,3-dihydro-1H-inden-1-yl) carbamate | 0.60 |
| 40 | O-pyridin-2-ylmethyl, N-(S)-(7-fluoro-4-((4-fluoro-3-methylphenyl)carbamoyl)-2,3-dihydro-1H-inden-1-yl) carbamate | 0.62 |
| 41 | O-imidazo[1,2-a]pyridin-2-ylmethyl, N-(S)-(4-((3-chloro-4-fluorophenyl)carbamoyl)-7-fluoro-2,3-dihydro-1H-inden-1-yl) carbamate | 0.16 |
| 42 | O-(6-morpholinopyridin-2-yl)methyl, N-(S)-(4-((3-chloro-4-fluorophenyl)carbamoyl)-7-fluoro-2,3-dihydro-1H-inden-1-yl) carbamate | 0.27 |
| 43 | O-((R)-1-methyl-5-oxopyrrolidin-2-yl)methyl, N-((S)-4-((3-chloro-4-fluorophenyl)carbamoyl)-7-fluoro-2,3-dihydro-1H-inden-1-yl) carbamate | 0.54 |
| 44 | O-(6-methoxypyridin-2-yl)methyl, N-(S)-(4-((3-chloro-4-fluorophenyl)carbamoyl)-7-fluoro-2,3-dihydro-1H-inden-1-yl) carbamate | 0.38 |
| 45 | (S)-N-(3-chloro-4-fluorophenyl)-7-fluoro-1-(pyrimidin-2-ylamino)-2,3-dihydro-1H-indene-4-carboxamide | 0.25 |
| 46 | O-methyl, N-((1R,2R)-4-((3-chloro-4-fluorophenyl)carbamoyl)-2-hydroxy-2,3-dihydro-1H-inden-1-yl) carbamate | 0.70 |
| 47 | N-(3-chloro-4-fluorophenyl)-2-hydroxy-1-(3-methylureido)-2,3-dihydro-1H-indene-4-carboxamide | 11 |
| 48 | O-(6-(dimethylamino) pyridin-2-yl)methyl, N-(S)-(4-((3-chloro-4-fluorophenyl)carbamoyl)-7-fluoro-2,3-dihydro-1H-inden-1-yl) carbamate | 0.16 |
| 49 | (S)-N-(3-chloro-4-fluorophenyl)-7-fluoro-1-((5-methoxypyrimidin-2-yl)amino)-2,3-dihydro-1H-indene-4-carboxamide | 0.17 |
| 50 | (S)-N-(3-chloro-4-fluorophenyl)-7-fluoro-1-((4-(pyridin-2-yl)pyrimidin-2-yl)amino)-2,3-dihydro-1H-indene-4-carboxamide | 1.0 |
| 51 | O-pyridin-2-ylmethyl, N-((1R,2R)-4-((3-chloro-4-fluorophenyl)carbamoyl)-2-hydroxy-2,3-dihydro-1H-inden-1-yl) carbamate | 0.87 |
| 52 | O-methyl, N-(4-((3,4-difluorophenyl)carbamoyl)-2-hydroxy-2,3-dihydro-1H-inden-1-yl) carbamate | 19 |
| 53 | N-(3,4-difluorophenyl)-2-hydroxy-1-(3-methylureido)-2,3-dihydro-1H-indene-4-carboxamide | 25 |
| 54 | tert-butyl 2-(((((S)-4-((3-chloro-4-fluorophenyl)carbamoyl)-7-fluoro-2,3-dihydro-1H-inden-1-yl)carbamoyl)oxy)methyl)-4,4-difluoropyrrolidine-1-carboxylate | 0.99 |
| 55 | O-methyl, N-(7-((3,4-difluorophenyl)carbamoyl)-4-fluoro-2,3-dihydrobenzo[b]thiophen-3-yl) carbamate (enantiomer 1) | 1.2 |
| 56 | O-(4,4-difluoropyrrolidin-2-yl)methyl, N-(S)-4-((3-chloro-4-fluorophenyl)carbamoyl)-7-fluoro-2,3-dihydro-1H-inden-1-yl) carbamate | 0.50 |
| 57 | O-methyl, N-(7-((3,4-difluorophenyl)carbamoyl)-4-fluoro-2,3-dihydrobenzo[b]thiophen-3-yl) carbamate (enantiomer 2) | 25 |
| 58 | O-methyl, N-(7-((3-chloro-4-fluorophenyl)carbamoyl)-4-fluoro-2,3-dihydrobenzo[b]thiophen-3-yl) carbamate (enantiomer 1) | 0.79 |
| 59 | O-methyl, N-(7-((3-chloro-4-fluorophenyl)carbamoyl)-4-fluoro-2,3-dihydrobenzo[b]thiophen-3-yl) carbamate (enantiomer 2) | 12 |
| 60 | O-pyridin-2-ylmethyl, N-((1R,2R)-4-((3,4-difluorophenyl)carbamoyl)-2-hydroxy-2,3-dihydro-1H-inden-1-yl) carbamate | 25 |
| 61 | O-(1-acetyl-4,4-difluoropyrrolidin-2-yl)methyl, N-((S)-4-((3-chloro-4-fluorophenyl)carbamoyl)-7-fluoro-2,3-dihydro-1H-inden-1-yl) carbamate | 0.40 |
| 62 | O-(1-(2,2,2-trifluoroethyl)piperidin-4-yl)methyl, N-(S)-(4-((3-chloro-4-fluorophenyl)carbamoyl)-7-fluoro-2,3-dihydro-1H-inden-1-yl) carbamate | 1.8 |
| 63 | O-pyridin-2-ylmethyl, N-(7-((3,4-difluorophenyl)carbamoyl)-4-fluoro-2,3-dihydrobenzo[b] thiophen-3-yl) carbamate (enantiomer 1) | 25 |
| 64 | O-pyridin-2-ylmethyl, N-(7-((3,4-difluorophenyl)carbamoyl)-4-fluoro-2,3-dihydrobenzo[b] thiophen-3-yl) carbamate (enantiomer 2) | 0.84 |
| 65 | O-pyridin-2-ylmethyl, N-(7-((3-chloro-4-fluorophenyl)carbamoyl)-4-fluoro-2,3-dihydrobenzo[b]thiophen-3-yl) carbamate (enantiomer 1) | 25 |
| 66 | O-pyridin-2-ylmethyl, N-(7-((3-chloro-4-fluorophenyl)carbamoyl)-4-fluoro-2,3-dihydrobenzo[b]thiophen-3-yl) carbamate (enantiomer 2) | 0.44 |
| 67 | (S)-2-((((4-((3-chloro-4-fluorophenyl)carbamoyl)-7-fluoro-2,3-dihydro-1H-inden-1-yl)carbamoyl)oxy)methyl)pyridine 1-oxide | 0.31 |
| 68 | O-(S)-1-(Pyridin-2-yl)ethyl, N-((S)-4-((3-chloro-4-fluorophenyl)carbamoyl)-7-fluoro-2,3-dihydro-1H-inden-1-yl) carbamate | 0.39 |

TABLE 1-continued

| No. | Nomenclature | DE-19 bDNA EC$_{50}$ (μM) |
|---|---|---|
| 69 | O-(S)-Pyrrolidin-2-ylmethyl, N-((S)-4-((3-chloro-4-fluorophenyl)carbamoyl)-7-fluoro-2,3-dihydro-1H-inden-1-yl) carbamate | 5.1 |
| 70 | O-3,3,3-Trifluoropropyl, N-(S)-(4-((3-chloro-4-fluorophenyl)carbamoyl)-7-fluoro-2,3-dihydro-1H-inden-1-yl) carbamate | 0.29 |
| 71 | O-(1-Methyl-1H-pyrazol-3-yl)methyl, N-(S)-(4-((3-chloro-4-fluorophenyl)carbamoyl)-7-fluoro-2,3-dihydro-1H-inden-1-yl) carbamate | 0.06 |
| 72 | O-(R)-5-Oxopyrrolidin-3-yl, N-((S)-4-((3-chloro-4-fluorophenyl)carbamoyl)-7-fluoro-2,3-dihydro-1H-inden-1-yl) carbamate | 0.24 |
| 73 | O-(6-Methylpyridin-2-yl)methyl, N-(S)-(4-((3-chloro-4-fluorophenyl)carbamoyl)-7-fluoro-2,3-dihydro-1H-inden-1-yl) carbamate | 0.25 |
| 74 | N-(S)-4-((3-chloro-4-fluorophenyl)carbamoyl)-7-fluoro-2,3-dihydro-1H-inden-1-yl, O-(pyridin-2-ylmethyl) carbamate | 1.6 |
| 75 | (S)-N-(3-chloro-4-fluorophenyl)-7-fluoro-1-(2-methoxyacetamido)-2,3-dihydro-1H-indene-4-carboxamide | 1.4 |
| 76 | (S)-N-(3-chloro-4-fluorophenyl)-7-fluoro-1-(3-fluoropropanamido)-2,3-dihydro-1H-indene-4-carboxamide | 0.11 |
| 77 | (S)-1-acetamido-N-(3-chloro-4-fluorophenyl)-7-fluoro-2,3-dihydro-1H-indene-4-carboxamide | 0.20 |
| 78 | O-pyrazin-2-ylmethyl, N-(S)-(4-((3-chloro-4-fluorophenyl)carbamoyl)-7-fluoro-2,3-dihydro-1H-inden-1-yl) carbamate | 0.09 |
| 79 | O-pyrimidin-2-ylmethyl, N-(S)-(4-((3-chloro-4-fluorophenyl)carbamoyl)-7-fluoro-2,3-dihydro-1H-inden-1-yl) carbamate | 0.12 |
| 80 | O-(4-chloropyridin-2-yl)methyl, N-(S)-(4-((3-chloro-4-fluorophenyl)carbamoyl)-7-fluoro-2,3-dihydro-1H-inden-1-yl) carbamate | 0.33 |
| 81 | (S)-N-(3-chloro-4-fluorophenyl)-7-fluoro-1-hydroxy-2,3-dihydro-1H-indene-4-carboxamide | 0.67 |
| 82 | O-isoxazol-3-ylmethyl, N-(S)-(4-((3-chloro-4-fluorophenyl)carbamoyl)-7-fluoro-2,3-dihydro-1H-inden-1-yl) carbamate | 0.13 |
| 83 | O-2-(pyridin-2-yl)ethyl, N-(S)-(4-((3-chloro-4-fluorophenyl)carbamoyl)-7-fluoro-2,3-dihydro-1H-inden-1-yl) carbamate | 0.18 |
| 84 | O-2,2-difluoroethyl, N-(S)-(4-((3-chloro-4-fluorophenyl)carbamoyl)-7-fluoro-2,3-dihydro-1H-inden-1-yl) carbamate | 0.17 |
| 85 | O-pyrimidin-4-ylmethyl, N-(S)-(4-((3-chloro-4-fluorophenyl)carbamoyl)-7-fluoro-2,3-dihydro-1H-inden-1-yl) carbamate | 0.58 |
| 86 | O-3-(2-oxopyrrolidin-1-yl)propyl, N-(S)-(4-((3-chloro-4-fluorophenyl)carbamoyl)-7-fluoro-2,3-dihydro-1H-inden-1-yl) carbamate | 0.43 |
| 87 | O-(8-methylimidazo[1,2-a]pyridin-2-yl)methyl, N-(S)-(4-((3-chloro-4-fluorophenyl)carbamoyl)-7-fluoro-2,3-dihydro-1H-inden-1-yl) carbamate | 0.20 |
| 88 | O-2,2,2-trifluoroethyl, N-(S)-(4-((3-chloro-4-fluorophenyl)carbamoyl)-7-fluoro-2,3-dihydro-1H-inden-1-yl) carbamate | 0.21 |
| 89 | O-(S)-4-((3-chloro-4-fluorophenyl)carbamoyl)-7-fluoro-2,3-dihydro-1H-inden-1-yl, N-methyl carbamate | 0.56 |
| 90 | (S)-4-((3-chloro-4-fluorophenyl)carbamoyl)-7-fluoro-2,3-dihydro-1H-inden-1-yl (pyridin-2-ylmethyl) carbonate | 1.9 |
| 91 | O-thiazol-5-ylmethyl, N-(S)-(4-((3-chloro-4-fluorophenyl)carbamoyl)-7-fluoro-2,3-dihydro-1H-inden-1-yl) carbamate | 0.07 |
| 92 | O-thiazol-2-ylmethyl, N-(S)-(4-((3-chloro-4-fluorophenyl)carbamoyl)-7-fluoro-2,3-dihydro-1H-inden-1-yl) carbamate | 0.18 |
| 93 | O-oxazol-4-ylmethyl, N-(S)-(4-((3-chloro-4-fluorophenyl)carbamoyl)-7-fluoro-2,3-dihydro-1H-inden-1-yl) carbamate | 0.49 |
| 94 | O-oxazol-2-ylmethyl, N-(S)-(4-((3-chloro-4-fluorophenyl)carbamoyl)-7-fluoro-2,3-dihydro-1H-inden-1-yl) carbamate | 0.07 |
| 95 | O-oxazol-5-ylmethyl, N-(S)-(4-((3-chloro-4-fluorophenyl)carbamoyl)-7-fluoro-2,3-dihydro-1H-inden-1-yl) carbamate | 0.06 |
| 96 | O-2-(1H-imidazol-1-yl)ethyl, N-(S)-(4-((3-chloro-4-fluorophenyl)carbamoyl)-7-fluoro-2,3-dihydro-1H-inden-1-yl) carbamate | 0.30 |
| 97 | (S)-N-(3-chloro-4-fluorophenyl)-7-fluoro-1-(pyridin-2-ylamino)-2,3-dihydro-1H-indene-4-carboxamide | 0.22 |
| 98 | (S)-N-(4-((3-chloro-4-fluorophenyl)carbamoyl)-7-fluoro-2,3-dihydro-1H-inden-1-yl)-1-methyl-1H-pyrazole-3-carboxamide | 0.82 |
| 99 | O-2-phenoxyethyl, N-(S)-(4-((3-chloro-4-fluorophenyl)carbamoyl)-7-fluoro-2,3-dihydro-1H-inden-1-yl) carbamate | 1.22 |
| 100 | (S)-N-(4-((3-chloro-4-fluorophenyl)carbamoyl)-7-fluoro-2,3-dihydro-1H-inden-1-yl)-1-methyl-1H-pyrazole-5-carboxamide | 0.74 |

TABLE 1-continued

| No. | Nomenclature | DE-19 bDNA EC$_{50}$ (μM) |
|---|---|---|
| 101 | (S)-N-(3-chloro-4-fluorophenyl)-7-fluoro-1-((1-methyl-1H-pyrazole)-3-sulfonamido)-2,3-dihydro-1H-indene-4-carboxamide | 0.72 |
| 102 | O-(1-methyl-1H-1,2,4-triazol-3-yl)methyl, N-(S)-(4-((3-chloro-4-fluorophenyl)carbamoyl)-7-fluoro-2,3-dihydro-1H-inden-1-yl) carbamate | 0.07 |
| 103 | O-(1-methyl-1H-pyrazol-5-yl)methyl, N-(S)-(4-((3-chloro-4-fluorophenyl)carbamoyl)-7-fluoro-2,3-dihydro-1H-inden-1-yl) carbamate | 0.10 |
| 104 | (S)-2-((4-((3-chloro-4-fluorophenyl)carbamoyl)-7-fluoro-2,3-dihydro-1H-inden-1-yl)amino)pyrimidine-4-carboxamide | 0.16 |
| 105 | O-2-(4-methylthiazol-5-yl)ethyl, N-(S)-(4-((3-chloro-4-fluorophenyl)carbamoyl)-7-fluoro-2,3-dihydro-1H-inden-1-yl) carbamate | 0.19 |
| 106 | O-(1-isopropyl-1H-pyrazol-3-yl)methyl, N-(S)-(4-((3-chloro-4-fluorophenyl)carbamoyl)-7-fluoro-2,3-dihydro-1H-inden-1-yl) carbamate | 0.17 |
| 107 | O-(5-methoxypyridin-2-yl)methyl, N-(S)-(4-((3-chloro-4-fluorophenyl)carbamoyl)-7-fluoro-2,3-dihydro-1H-inden-1-yl) carbamate | 1.2 |
| 108 | O-((S)-1-(2,2,2-trifluoroethyl)pyrrolidin-2-yl)methyl, N-((S)-4-((3-chloro-4-fluorophenyl)carbamoyl)-7-fluoro-2,3-dihydro-1H-inden-1-yl) carbamate | 0.72 |
| 109 | O-(5-fluoropyridin-2-yl)methyl, N-(S)-(4-((3-chloro-4-fluorophenyl)carbamoyl)-7-fluoro-2,3-dihydro-1H-inden-1-yl) carbamate | 0.27 |
| 110 | O-2-(1H-pyrazol-4-yl)ethyl, N-(S)-(4-((3-chloro-4-fluorophenyl)carbamoyl)-7-fluoro-2,3-dihydro-1H-inden-1-yl) carbamate | 0.20 |
| 111 | O-2-methoxyethyl, N-(S)-(4-((3-chloro-4-fluorophenyl)carbamoyl)-7-fluoro-2,3-dihydro-1H-inden-1-yl) carbamate | 0.15 |
| 112 | O-((R)-tetrahydrofuran-2-yl)methyl, N-((S)-4-((3-chloro-4-fluorophenyl)carbamoyl)-7-fluoro-2,3-dihydro-1H-inden-1-yl) carbamate | 0.21 |
| 113 | O-tetrahydro-2H-pyran-4-yl, N-(S)-(4-((3-chloro-4-fluorophenyl)carbamoyl)-7-fluoro-2,3-dihydro-1H-inden-1-yl) carbamate | 0.31 |
| 114 | O-3-methoxypropyl, N-(S)-(4-((3-chloro-4-fluorophenyl)carbamoyl)-7-fluoro-2,3-dihydro-1H-inden-1-yl) carbamate | 0.47 |
| 115 | (S)-N-(4-((3-chloro-4-fluorophenyl)carbamoyl)-7-fluoro-2,3-dihydro-1H-inden-1-yl)picolinamide | 2.2 |
| 116 | (S)-N-(4-((3-chloro-4-fluorophenyl)carbamoyl)-7-fluoro-2,3-dihydro-1H-inden-1-yl)thiazole-5-carboxamide | 1.7 |
| 117 | (S)-N-(3-chloro-4-fluorophenyl)-7-fluoro-1-(methylsulfonamido)-2,3-dihydro-1H-indene-4-carboxamide | 0.52 |
| 118 | (S)-N-(3-chloro-4-fluorophenyl)-7-fluoro-1-(2-morpholinoacetamido)-2,3-dihydro-1H-indene-4-carboxamide | 2.2 |
| 119 | (S)-N-(4-((3-chloro-4-fluorophenyl)carbamoyl)-7-fluoro-2,3-dihydro-1H-inden-1-yl)nicotinamide | 0.28 |
| 120 | (S)-N-(4-((3-chloro-4-fluorophenyl)carbamoyl)-7-fluoro-2,3-dihydro-1H-inden-1-yl)isonicotinamide | 0.24 |
| 121 | O-methyl, N-(4-((3-chloro-4-fluorophenyl)carbamoyl)-7-fluoro-2,2-dimethyl-2,3-dihydro-1H-inden-1-yl) carbamate (enantiomer 1) | 25 |
| 122 | O-methyl, N-(4-((3-chloro-4-fluorophenyl)carbamoyl)-7-fluoro-2,2-dimethyl-2,3-dihydro-1H-inden-1-yl)carbamate (enantiomer 2) | 0.47 |
| 123 | (S)-4-((3-chloro-4-fluorophenyl)carbamoyl)-7-fluoro-2,3-dihydro-1H-inden-1-yl methyl carbonate | 0.76 |
| 124 | O-thiazol-4-ylmethyl, N-(S)-(4-((3-chloro-4-fluorophenyl)carbamoyl)-7-fluoro-2,3-dihydro-1H-inden-1-yl) carbamate | 0.06 |
| 125 | O-3-(1H-imidazol-1-yl)propyl, N-(S)-(4-((3-chloro-4-fluorophenyl)carbamoyl)-7-fluoro-2,3-dihydro-1H-inden-1-yl) carbamate | 0.28 |
| 126 | O-pyridin-2-ylmethyl, N-(S)-(4-((3-cyano-4-fluorophenyl)carbamoyl)-7-fluoro-2,3-dihydro-1H-inden-1-yl) carbamate | 0.24 |
| 127 | (S)-N-(4-((3-chloro-4-fluorophenyl)carbamoyl)-7-fluoro-2,3-dihydro-1H-inden-1-yl)thiazole-2-carboxamide | 0.36 |
| 128 | (S)-N-(3-chloro-4-fluorophenyl)-1-(cyclopropanesulfonamido)-7-fluoro-2,3-dihydro-1H-indene-4-carboxamide | 0.04 |
| 129 | (S)-N-(4-((3-chloro-4-fluorophenyl)carbamoyl)-7-fluoro-2,3-dihydro-1H-inden-1-yl)oxazole-5-carboxamide | 0.41 |
| 130 | O-methyl, N-((1R,2R)-4-((3-chloro-4-fluorophenyl)carbamoyl)-7-fluoro-2-methoxy-2,3-dihydro-1H-inden-1-yl) carbamate | 0.10 |
| 131 | O-cyclopentyl, N-(S)-(4-((3-chloro-4-fluorophenyl)carbamoyl)-7-fluoro-2,3-dihydro-1H-inden-1-yl)carbamate | 0.59 |
| 132 | O-(2-oxo-oxazolidin-5-yl)methyl, N-((S)-4-((3-chloro-4-fluorophenyl)carbamoyl)-7-fluoro-2,3-dihydro-1H-inden-1-yl) carbamate | 0.22 |

TABLE 1-continued

| No. | Nomenclature | DE-19 bDNA EC$_{50}$ (μM) |
|---|---|---|
| 133 | O-2-(1H-pyrazol-1-yl)ethyl, N-(S)-(4-((3-chloro-4-fluorophenyl)carbamoyl)-7-fluoro-2,3-dihydro-1H-inden-1-yl) carbamate | 0.15 |
| 134 | N-(3-chloro-4-fluorophenyl)-7-fluoro-2,2-dimethyl-1-(3-methylureido)-2,3-dihydro-1H-indene-4-carboxamide (enantiomer 2) | 0.36 |
| 135 | O-pyridin-2-ylmethyl, N-(4-((3-chloro-4-fluorophenyl)carbamoyl)-7-fluoro-2,2-dimethyl-2,3-dihydro-1H-inden-1-yl) carbamate (enantiomer 1) | 8.4 |
| 136 | O-pyridin-2-ylmethyl, N-(4-((3-chloro-4-fluorophenyl)carbamoyl)-7-fluoro-2,2-dimethyl-2,3-dihydro-1H-inden-1-yl) carbamate (enantiomer 2) | 0.29 |
| 137 | O-(1-methyl-1H-imidazol-2-yl)methyl, N-(S)-(4-((3-chloro-4-fluorophenyl)carbamoyl)-7-fluoro-2,3-dihydro-1H-inden-1-yl) carbamate | 0.10 |
| 138 | O-(3-fluoropyridin-2-yl)methyl, N-(S)-(4-((3-chloro-4-fluorophenyl)carbamoyl)-7-fluoro-2,3-dihydro-1H-inden-1-yl) carbamate | 0.16 |
| 139 | O-((R)-morpholin-3-yl)methyl, N-((S)-4-((3-chloro-4-fluorophenyl)carbamoyl)-7-fluoro-2,3-dihydro-1H-inden-1-yl) carbamate | 0.62 |
| 140 | O-(4-methoxypyridin-2-yl)methyl, N-(S)-(4-((3-chloro-4-fluorophenyl)carbamoyl)-7-fluoro-2,3-dihydro-1H-inden-1-yl) carbamate | 0.22 |
| 141 | O-2-hydroxyethyl, N-(S)-(4-((3-chloro-4-fluorophenyl)carbamoyl)-7-fluoro-2,3-dihydro-1H-inden-1-yl) carbamate | 0.18 |
| 142 | O-((S)-tetrahydrofuran-2-yl)methyl, N-((S)-4-((3-chloro-4-fluorophenyl)carbamoyl)-7-fluoro-2,3-dihydro-1H-inden-1-yl)carbamate | 0.27 |
| 143 | (S)-N-(3-chloro-4-fluorophenyl)-7-fluoro-1-(2-hydroxyacetamido)-2,3-dihydro-1H-indene-4-carboxamide | 1.5 |
| 144 | (S)-N-(3-chloro-4-fluorophenyl)-7-fluoro-1-(3-(pyridin-3-yl)ureido)-2,3-dihydro-1H-indene-4-carboxamide | 0.85 |
| 145 | (S)-N-(3-chloro-4-fluorophenyl)-7-fluoro-1-(3-(pyridin-4-yl)ureido)-2,3-dihydro-1H-indene-4-carboxamide | 0.93 |
| 146 | (S)-N-(3-chloro-4-fluorophenyl)-7-fluoro-1-(thiazol-2-ylamino)-2,3-dihydro-1H-indene-4-carboxamide | 0.24 |
| 147 | O-2-(piperidin-1-yl)ethyl, N-(S)-(4-((3-chloro-4-fluorophenyl)carbamoyl)-7-fluoro-2,3-dihydro-1H-inden-1-yl) carbamate | 1.1 |
| 148 | O-pyridin-2-ylmethyl, N-(S)-(4-((3-(difluoromethyl)-4-fluorophenyl)carbamoyl)-7-fluoro-2,3-dihydro-1H-inden-1-yl) carbamate | 0.12 |
| 149 | (S)-N-(3-chloro-4-fluorophenyl)-7-fluoro-1-(3-(pyridin-2-ylmethyl)ureido)-2,3-dihydro-1H-indene-4-carboxamide | 0.21 |
| 150 | O-(6-cyanopyridin-2-yl)methyl, N-(S)-(4-((3-chloro-4-fluorophenyl)carbamoyl)-7-fluoro-2,3-dihydro-1H-inden-1-yl) carbamate | 0.15 |
| 151 | O-quinolin-2-ylmethyl, N-(S)-(4-((3-chloro-4-fluorophenyl)carbamoyl)-7-fluoro-2,3-dihydro-1H-inden-1-yl) carbamate | 0.41 |
| 152 | O-(5-methylpyrazin-2-yl)methyl, N-(S)-(4-((3-chloro-4-fluorophenyl)carbamoyl)-7-fluoro-2,3-dihydro-1H-inden-1-yl) carbamate | 0.07 |
| 153 | O-2-morpholinoethyl-N-(S)-(4-((3-chloro-4-fluorophenyl)carbamoyl)-7-fluoro-2,3-dihydro-1H-inden-1-yl) carbamate | 0.47 |
| 154 | O-[cis-4-hydroxycyclohexyl]-N-((S)-4-((3-chloro-4-fluorophenyl)carbamoyl)-7-fluoro-2,3-dihydro-1H-inden-1-yl)carbamate | 0.35 |
| 155 | O-3-hydroxypropyl, N-(S)-(4-((3-chloro-4-fluorophenyl)carbamoyl)-7-fluoro-2,3-dihydro-1H-inden-1-yl) carbamate | 24 |
| 156 | O-[trans-4-hydroxycyclohexyl]-N-((S)-4-((3-chloro-4-fluorophenyl)carbamoyl)-7-fluoro-2,3-dihydro-1H-inden-1-yl) carbamate | 0.22 |
| 157 | O-2-acetamidoethyl, N-(S)-(4-((3-chloro-4-fluorophenyl)carbamoyl)-7-fluoro-2,3-dihydro-1H-inden-1-yl) carbamate | 0.26 |
| 158 | (S)-N-(3-chloro-4-fluorophenyl)-7-fluoro-1-propionamido-2,3-dihydro-1H-indene-4-carboxamide | 0.81 |
| 159 | (S)-N-(3-chloro-4-fluorophenyl)-7-fluoro-1-((4-methoxypyrimidin-2-yl)amino)-2,3-dihydro-1H-indene-4-carboxamide | 0.69 |
| 160 | (S)-N-(3-chloro-4-fluorophenyl)-7-fluoro-1-((4-methylpyrimidin-2-yl)amino)-2,3-dihydro-1H-indene-4-carboxamide | 0.25 |
| 161 | (S)-N-(3-chloro-4-fluorophenyl)-7-fluoro-1-((2-methoxypyrimidin-4-yl)amino)-2,3-dihydro-1H-indene-4-carboxamide | 0.27 |
| 162 | (S)-N-(3-chloro-4-fluorophenyl)-7-fluoro-1-((5-methylpyrimidin-2-yl)amino)-2,3-dihydro-1H-indene-4-carboxamide | 0.15 |
| 163 | (S)-N-(3-chloro-4-fluorophenyl)-7-fluoro-1-((6-methoxypyrimidin-4-yl)amino)-2,3-dihydro-1H-indene-4-carboxamide | 0.07 |

TABLE 1-continued

| No. | Nomenclature | DE-19 bDNA EC$_{50}$ (μM) |
|---|---|---|
| 164 | (S)-N-(3-chloro-4-fluorophenyl)-1-((4,6-dimethylpyrimidin-2-yl)amino)-7-fluoro-2,3-dihydro-1H-indene-4-carboxamide | 1.0 |
| 165 | (1R,2R)-N-(3-chloro-4-fluorophenyl)-2-methoxy-1-(3-methylureido)-2,3-dihydro-1H-indene-4-carboxamide | 0.33 |
| 166 | O-(S)-5-oxopyrrolidin-3-yl, N-((S)-4-((3-chloro-4-fluorophenyl)carbamoyl)-7-fluoro-2,3-dihydro-1H-inden-1-yl) carbamate | 0.14 |
| 167 | (S)-N-(3-chloro-4-fluorophenyl)-7-fluoro-1-((2-(pyridin-2-yl)ethyl)sulfonamido)-2,3-dihydro-1H-indene-4-carboxamide | 0.29 |
| 168 | O-(6-(trifluoromethyl)pyridin-2-yl)methyl, N-(S)-(4-((3-chloro-4-fluorophenyl)carbamoyl)-7-fluoro-2,3-dihydro-1H-inden-1-yl) carbamate | 0.62 |
| 169 | O-(5-(trifluoromethyl) pyridin-2-yl)methyl, N-((S)-(4-((3-chloro-4-fluorophenyl)carbamoyl)-7-fluoro-2,3-dihydro-1H-inden-1-yl) carbamate | 2.2 |
| 170 | O-(R)-tetrahydrofuran-3-yl, N-((S)-4-((3-chloro-4-fluorophenyl)carbamoyl)-7-fluoro-2,3-dihydro-1H-inden-1-yl) carbamate | 0.26 |
| 171 | (S)-N-(3-chloro-4-fluorophenyl)-7-fluoro-1-(3-(1-methyl-1H-pyrazol-3-yl)propanamido)-2,3-dihydro-1H-indene-4-carboxamide | 0.13 |
| 172 | O-(5-cyanopyridin-2-yl)methyl, N-(S)-(4-((3-chloro-4-fluorophenyl)carbamoyl)-7-fluoro-2,3-dihydro-1H-inden-1-yl) carbamate | 0.19 |
| 173 | O-(3-methylpyrazin-2-yl)methyl, N-(S)-(4-((3-chloro-4-fluorophenyl)carbamoyl)-7-fluoro-2,3-dihydro-1H-inden-1-yl) carbamate | 0.12 |
| 174 | O-(1-acetylpiperidin-4-yl)methyl, N-(S)-(4-((3-chloro-4-fluorophenyl)carbamoyl)-7-fluoro-2,3-dihydro-1H-inden-1-yl) carbamate | 0.87 |
| 175 | O-(1-(2-hydroxyacetyl)piperidin-4-yl)methyl, N-(S)-(4-((3-chloro-4-fluorophenyl)carbamoyl)-7-fluoro-2,3-dihydro-1H-inden-1-yl) carbamate | 0.96 |
| 176 | O-(1-(methylcarbamoyl)piperidin-4-yl)methyl, N-(S)-(4-((3-chloro-4-fluorophenyl)carbamoyl)-7-fluoro-2,3-dihydro-1H-inden-1-yl) carbamate | 0.64 |
| 177 | O-(1,1-dioxidothiomorpholin-3-yl)methyl-N-((S)-4-((3-chloro-4-fluorophenyl)carbamoyl)-7-fluoro-2,3-dihydro-1H-inden-1-yl) carbamate | 0.50 |
| 178 | O-pyridin-2-ylmethyl, N-((1R,2R)-4-((3-chloro-4-fluorophenyl)carbamoyl)-2-methoxy-2,3-dihydro-1H-inden-1-yl) carbamate | 0.04 |
| 179 | (S)-N-(3-chloro-4-fluorophenyl)-1-(cyclopropanecarboxamido)-7-fluoro-2,3-dihydro-1H-indene-4-carboxamide | 0.14 |
| 180 | O-((S)-morpholin-3-yl)methyl, N-((S)-4-((3-chloro-4-fluorophenyl)carbamoyl)-7-fluoro-2,3-dihydro-1H-inden-1-yl) carbamate | 0.20 |
| 181 | O-(S)-tetrahydrofuran-3-yl, N-((S)-4-((3-chloro-4-fluorophenyl)carbamoyl)-7-fluoro-2,3-dihydro-1H-inden-1-yl) carbamate | 0.15 |
| 182 | (S)-N-(3-chloro-4-fluorophenyl)-7-fluoro-1-((2-methoxyethyl)sulfonamido)-2,3-dihydro-1H-indene-4-carboxamide | 0.59 |
| 183 | (S)-N-(3-chloro-4-fluorophenyl)-7-fluoro-1-(phenylsulfonamido)-2,3-dihydro-1H-indene-4-carboxamide | 0.65 |
| 184 | (S)-N-(3-chloro-4-fluorophenyl)-7-fluoro-1-(pyridine-2-sulfonamido)-2,3-dihydro-1H-indene-4-carboxamide | 0.66 |
| 185 | O-(1-(2-methoxyacetyl) piperidin-4-yl)methyl, N-(S)-(4-((3-chloro-4-fluorophenyl)carbamoyl)-7-fluoro-2,3-dihydro-1H-inden-1-yl) carbamate | 0.37 |
| 186 | (S)-N-(3-chloro-4-fluorophenyl)-7-fluoro-1-((5-hydroxypyrimidin-2-yl)amino)-2,3-dihydro-1H-indene-4-carboxamide | 1.6 |
| 187 | O-methyl, N-(7-((3-chloro-4-fluorophenyl)carbamoyl)-4-fluoro-2,3-dihydrobenzofuran-3-yl) carbamate (enantiomer 1) | 23 |
| 188 | O-methyl, N-(7-((3-chloro-4-fluorophenyl)carbamoyl)-4-fluoro-2,3-dihydrobenzofuran-3-yl) carbamate (enantiomer 2) | 5.3 |
| 189 | N-(3-chloro-4-fluorophenyl)-4-fluoro-3-(3-methylureido)-2,3-dihydrobenzofuran-7-carboxamide (enantiomer 1) | 0.45 |
| 190 | N-(3-chloro-4-fluorophenyl)-4-fluoro-3-(3-methylureido)-2,3-dihydrobenzofuran-7-carboxamide (enantiomer 2) | 25 |
| 191 | O-pyridin-2-ylmethyl, N-(7-((3-chloro-4-fluorophenyl)carbamoyl)-4-fluoro-2,3-dihydrobenzofuran-3-yl) carbamate (enantiomer 1) | 18 |
| 192 | O-pyridin-2-ylmethyl, N-(7-((3-chloro-4-fluorophenyl)carbamoyl)-4-fluoro-2,3-dihydrobenzofuran-3-yl) carbamate (enantiomer 2) | 0.31 |
| 193 | O-(1H-pyrazol-3-yl)methyl, N-(S)-(4-((3-chloro-4-fluorophenyl)carbamoyl)-7-fluoro-2,3-dihydro-1H-inden-1-yl) carbamate | 0.06 |

TABLE 1-continued

| No. | Nomenclature | DE-19 bDNA EC$_{50}$ (μM) |
|---|---|---|
| 194 | (S)-N-(3-chloro-4-fluorophenyl)-7-fluoro-1-(3-((1-methyl-1H-pyrazol-3-yl)methyl)ureido)-2,3-dihydro-1H-indene-4-carboxamide | 0.16 |
| 195 | O-(1H-1,2,4-triazol-3-yl)methyl, N-(S)-(4-((3-chloro-4-fluorophenyl)carbamoyl)-7-fluoro-2,3-dihydro-1H-inden-1-yl) carbamate | 0.10 |
| 196 | (S)-N-(3-chloro-4-fluorophenyl)-7-fluoro-1-(pyrimidin-4-ylamino)-2,3-dihydro-1H-indene-4-carboxamide | 0.63 |
| 197 | (S)-N-(3-chloro-4-fluorophenyl)-7-fluoro-1-((7-(4-methoxybenzyl)-7H-pyrrolo[2,3-d]pyrimidin-2-yl)amino)-2,3-dihydro-1H-indene-4-carboxamide | 1.2 |
| 198 | O-((R)-6-oxopiperidin-2-yl)methyl, N-((S)-4-((3-chloro-4-fluorophenyl)carbamoyl)-7-fluoro-2,3-dihydro-1H-inden-1-yl) carbamate | 0.22 |
| 199 | O-(R)-6-oxopiperidin-3-yl, N-((S)-4-((3-chloro-4-fluorophenyl)carbamoyl)-7-fluoro-2,3-dihydro-1H-inden-1-yl) carbamate | 0.25 |
| 200 | O-(S)-6-oxopiperidin-3-yl, N-((S)-4-((3-chloro-4-fluorophenyl)carbamoyl)-7-fluoro-2,3-dihydro-1H-inden-1-yl) carbamate | 0.43 |
| 201 | O-methyl, N-(4-fluoro-7-((4-fluoro-3-methylphenyl)carbamoyl)-2,3-dihydrobenzofuran-3-yl)carbamate (enantiomer 1) | 5.5 |
| 202 | O-methyl, N-(4-fluoro-7-((4-fluoro-3-methylphenyl)carbamoyl)-2,3-dihydrobenzofuran-3-yl)carbamate (enantiomer 2) | 0.42 |
| 203 | 4-fluoro-N-(4-fluoro-3-methylphenyl)-3-(3-methylureido)-2,3-dihydrobenzofuran-7-carboxamide (enantiomer 1) | 25 |
| 204 | 4-fluoro-N-(4-fluoro-3-methylphenyl)-3-(3-methylureido)-2,3-dihydrobenzofuran-7-carboxamide (enantiomer 2) | 0.20 |
| 205 | O-pyridin-2-ylmethyl, N-(4-fluoro-7-((4-fluoro-3-methylphenyl)carbamoyl)-2,3-dihydrobenzofuran-3-yl) carbamate (enantiomer 1) | 3.7 |
| 206 | O-pyridin-2-ylmethyl, N-(4-fluoro-7-((4-fluoro-3-methylphenyl)carbamoyl)-2,3-dihydrobenzofuran-3-yl) carbamate (enantiomer 2) | 0.41 |
| 207 | N-(3-chloro-4-fluorophenyl)-3-(cyclopropanesulfonamido)-4-fluoro-2,3-dihydrobenzofuran-7-carboxamide (enantiomer 1) | 14 |
| 208 | N-(3-chloro-4-fluorophenyl)-3-(cyclopropanesulfonamido)-4-fluoro-2,3-dihydrobenzofuran-7-carboxamide (enantiomer 2) | 0.11 |
| 209 | (S)-N-(3-chloro-4-fluorophenyl)-1-(3-cyclopropylureido)-7-fluoro-2,3-dihydro-1H-indene-4-carboxamide | 0.33 |
| 210 | O-methyl, N-((4-((3-chloro-4-fluorophenyl)carbamoyl)-2,2,7-trifluoro-2,3-dihydro-1H-inden-1-yl) carbamate (enantiomer 1) | 15 |
| 211 | N-(3-chloro-4-fluorophenyl)-2,2,7-trifluoro-1-(3-methylureido)-2,3-dihydro-1H-indene-4-carboxamide (enantiomer 1) | 6.9 |
| 212 | O-((S)-6-oxopiperidin-2-yl)methyl, N-((S)-4-((3-chloro-4-fluorophenyl)carbamoyl)-7-fluoro-2,3-dihydro-1H-inden-1-yl) carbamate | 0.27 |
| 213 | O-(4-oxoazetidin-2-yl)methyl, N-((S)-4-((3-chloro-4-fluorophenyl)carbamoyl)-7-fluoro-2,3-dihydro-1H-inden-1-yl) carbamate | 0.33 |
| 214 | O-methyl, N-(4-((3-chloro-4-fluorophenyl)carbamoyl)-7-fluoro-1-methyl-2,3-dihydro-1H-inden-1-yl) carbamate | 2.6 |
| 215 | N-(3-chloro-4-fluorophenyl)-7-fluoro-1-methyl-1-(3-methylureido)-2,3-dihydro-1H-indene-4-carboxamide | 3.8 |
| 216 | (S)-N-(3-chloro-4-fluorophenyl)-1-(cyclopropanesulfonamido)-2,3-dihydro-1H-indene-4-carboxamide | 0.04 |
| 217 | O-methyl, N-(4-((3-chloro-4-fluorophenyl)carbamoyl)-7-fluoro-1-methyl-2,3-dihydro-1H-inden-1-yl)carbamate (enantiomer 1) | 12 |
| 218 | O-methyl, N-(4-((3-chloro-4-fluorophenyl)carbamoyl)-7-fluoro-1-methyl-2,3-dihydro-1H-inden-1-yl)carbamate (enantiomer 2) | 1.9 |
| 219 | O-pyridin-2-ylmethyl, N-(4-((3-chloro-4-fluorophenyl)carbamoyl)-7-fluoro-1-methyl-2,3-dihydro-1H-inden-1-yl) carbamate | 1.5 |
| 220 | O-pyridin-2-ylmethyl, N-(4-((3-chloro-4-fluorophenyl)carbamoyl)-2,2,7-trifluoro-2,3-dihydro-1H-inden-1-yl) carbamate (enantiomer 1) | 10 |
| 221 | (S)-N-(3-chloro-4-fluorophenyl)-1-((cyclopropylmethyl)sulfonamido)-7-fluoro-2,3-dihydro-1H-indene-4-carboxamide | 0.21 |
| 222 | (S)-N-(3-chloro-4-fluorophenyl)-7-fluoro-1-((phenylmethyl)sulfonamido)-2,3-dihydro-1H-indene-4-carboxamide | 0.30 |
| 223 | N-(3-chloro-4-fluorophenyl)-7-fluoro-1-methyl-1-(3-methylureido)-2,3-dihydro-1H-indene-4-carboxamide (enantiomer 1) | 4.52 |
| 224 | O-pyridin-2-ylmethyl, N-(4-((3-chloro-4-fluorophenyl)carbamoyl)-7-fluoro-1-methyl-2,3-dihydro-1H-inden-1-yl) carbamate (enantiomer 1) | 11 |
| 225 | O-pyridin-2-ylmethyl, N-(4-((3-chloro-4-fluorophenyl)carbamoyl)-7-fluoro-1-methyl-2,3-dihydro-1H-inden-1-yl) carbamate (enantiomer 2) | 2.0 |
| 226 | O-cyclopropyl, N-(S)-(4-((3-chloro-4-fluorophenyl)carbamoyl)-7-fluoro-2,3-dihydro-1H-inden-1-yl)carbamate | 0.24 |

TABLE 1-continued

| No. | Nomenclature | DE-19 bDNA EC$_{50}$ (μM) |
|---|---|---|
| 227 | (S)-N-(3-chloro-4-fluorophenyl)-7-fluoro-1-((N-methylsulfamoyl)amino)-2,3-dihydro-1H-indene-4-carboxamide | 0.43 |
| 228 | (S)-N-(3-chloro-4-fluorophenyl)-7-fluoro-1-(morpholine-4-sulfonamido)-2,3-dihydro-1H-indene-4-carboxamide | 0.20 |
| 229 | O-cyclopropyl, N-(S)-(4-((3-chloro-4-fluorophenyl)carbamoyl)-2,3-dihydro-1H-inden-1-yl) carbamate | 0.36 |
| 230 | (S)-N-(3-chloro-4-fluorophenyl)-1-((N-methylsulfamoyl)amino)-2,3-dihydro-1H-indene-4-carboxamide | 0.36 |
| 231 | O-(1,3,4-oxadiazol-2-yl)methyl, N-(S)-(4-((3-chloro-4-fluorophenyl)carbamoyl)-7-fluoro-2,3-dihydro-1H-inden-1-yl) carbamate | 0.13 |
| 232 | (S)-N-(3-chloro-4-fluorophenyl)-1-(ethylsulfonamido)-7-fluoro-2,3-dihydro-1H-indene-4-carboxamide | 0.24 |
| 233 | (S)-N-(3-chloro-4-fluorophenyl)-7-fluoro-1-(propylsulfonamido)-2,3-dihydro-1H-indene-4-carboxamide | 0.33 |
| 234 | (S)-N-(4-chloro-3-fluorophenyl)-7-fluoro-1-((2-methylpropyl)sulfonamido)-2,3-dihydro-1H-indene-4-carboxamide | 0.34 |
| 235 | N-(3-chloro-4-fluorophenyl)-7-fluoro-2-methoxy-1-(3-methylureido)-2,3-dihydro-1H-indene-4-carboxamide | 4.5 |
| 236 | O-methyl, N-(4-((3-chloro-4-fluorophenyl)carbamoyl)-7-fluoro-2-methoxy-2,3-dihydro-1H-inden-1-yl)carbamate | 0.34 |
| 237 | (S)-N-(3-chloro-4-fluorophenyl)-7-fluoro-1-((N-isopropylsulfamoyl)amino)-2,3-dihydro-1H-indene-4-carboxamide | 0.58 |
| 238 | (S)-N-(3-chloro-4-fluorophenyl)-7-fluoro-1-((1-methylethyl)sulfonamido)-2,3-dihydro-1H-indene-4-carboxamide | 0.19 |
| 239 | (S)-N-(3-chloro-4-fluorophenyl)-1-(cyclopentanesulfonamido)-7-fluoro-2,3-dihydro-1H-indene-4-carboxamide | 0.24 |
| 240 | (S)-N-(3-chloro-4-fluorophenyl)-1-(cyclohexanesulfonamido)-7-fluoro-2,3-dihydro-1H-indene-4-carboxamide | 0.51 |
| 241 | N-(3-chloro-4-fluorophenyl)-7-fluoro-3,3-dimethyl-1-(3-methylureido)-2,3-dihydro-1H-indene-4-carboxamide | 24 |
| 242 | (S)-N-(3-chloro-4-fluorophenyl)-1-((N-cyclopropylsulfamoyl)amino)-2,3-dihydro-1H-indene-4-carboxamide | 0.57 |
| 243 | (S)-N-(3-chloro-4-fluorophenyl)-1-((N-cyclopropylsulfamoyl)amino)-7-fluoro-2,3-dihydro-1H-indene-4-carboxamide | 0.16 |
| 244 | O-methyl, N-(4-((3,4-difluorophenyl)carbamoyl)-7-fluoro-2-methoxy-2,3-dihydro-1H-inden-1-yl) carbamate | 2.0 |
| 245 | N-(3,4-difluorophenyl)-7-fluoro-2-methoxy-1-(3-methylureido)-2,3-dihydro-1H-indene-4-carboxamide | 4.9 |
| 246 | O-pyridin-2-ylmethyl, N-(4-((3,4-difluorophenyl)carbamoyl)-7-fluoro-2-methoxy-2,3-dihydro-1H-inden-1-yl)carbamate | 2.7 |
| 247 | O-pyridin-2-ylmethyl, N-(4-((3-chloro-4-fluorophenyl)carbamoyl)-7-fluoro-2-methoxy-2,3-dihydro-1H-inden-1-yl)carbamate | 0.68 |
| 248 | O-(1-(tetrahydro-2H-pyran-2-yl)-1H-1,2,4-triazol-3-yl)methyl, N-((S)-4-((3-chloro-4-fluorophenyl)carbamoyl)-7-fluoro-2,3-dihydro-1H-inden-1-yl) carbamate | 0.15 |
| 249 | N-(3-chloro-4-fluorophenyl)-7-fluoro-2,2-dimethyl-1-(3-methylureido)-2,3-dihydro-1H-indene-4-carboxamide (enantiomer 1) | 13 |
| 251 | N-(3-Chloro-4-fluorophenyl)-7-fluoro-1-oxo-2,3-dihydro-1H-indene-4-carboxamide | 0.55 |
| 252 | ((1-(methyl-d$_3$)-1H-1,2,4-triazol-3-yl)methyl-d$_2$ (S)-(4-((3-chloro-4-fluorophenyl)carbamoyl)-7-fluoro-2,3-dihydro-1H-inden-1-yl)carbamate | 0.13 |
| 253 | (S)-(3-((((4-((3-chloro-4-fluorophenyl)carbamoyl)-7-fluoro-2,3-dihydro-1H-inden-1-yl)carbamoyl)oxy)methyl)-1H-1,2,4-triazol-1-yl)methyl phosphoric acid | 0.12 |
| 254 | (S)-(3-((((4-((3-chloro-4-fluorophenyl)carbamoyl)-7-fluoro-2,3-dihydro-1H-inden-1-yl)carbamoyl)oxy)methyl)-1H-pyrazol-1-yl)methyl phosphoric acid | 0.57 |
| 255 | O-(S)-2-cyanoethyl, N-4-(3-chloro-4-fluorophenylcarbamoyl)-7-fluoro-2,3-dihydro-1H-inden-1-yl carbamate | 0.08 |
| 256 | O-(S)-3-cyanopropyl, N-4-(3-chloro-4-fluorophenylcarbamoyl)-7-fluoro-2,3-dihydro-1H-inden-1-yl carbamate | 0.24 |
| 257 | N-(3-chloro-4-fluorophenyl)-7'-fluoro-2,5-dioxo-2',3'-dihydrospiro[imidazolidine-4,1'-indene]-4'-carboxamide (enantiomer 1) | 25 |
| 258 | N-(3-chloro-4-fluorophenyl)-7'-fluoro-2,5-dioxo-2',3'-dihydrospiro[imidazolidine-4,1'-indene]-4'-carboxamide (enantiomer 2) | 0.57 |
| 259 | N-(3-chloro-4-fluorophenyl)-7'-fluoro-2,5-dioxo-1-(pyridin-2-ylmethyl)-2',3'-dihydrospiro[imidazolidine-4,1'-indene]-4'-carboxamide (enantiomer 1) | 2.9 |
| 260 | N-(3-chloro-4-fluorophenyl)-7'-fluoro-2,5-dioxo-1-(pyridin-2-ylmethyl)-2',3'-dihydrospiro[imidazolidine-4,1'-indene]-4'-carboxamide (enantiomer 2) | 13 |

TABLE 1-continued

| No. | Nomenclature | DE-19 bDNA EC$_{50}$ (μM) |
|---|---|---|
| 261 | N-(3-chloro-4-fluoro-phenyl)-7'-fluoro-1-methyl-2,5-dioxo-spiro[imidazolidine-4,1'-indane]-4'-carboxamide (enantiomer 1) | 2.7 |
| 262 | N-(3-chloro-4-fluoro-phenyl)-7'-fluoro-1-methyl-2,5-dioxo-spiro[imidazolidine-4,1'-indane]-4'-carboxamide (enantiomer 2) | 14 |
| 263 | N-(3-chloro-4-fluorophenyl)-7-(3-methylureido)-6,7-dihydro-5H-cyclopenta[b]pyridine-4-carboxamide | 1.9 |
| 264 | O-methyl, N-(4-((3-chloro-4-fluorophenyl)carbamoyl)-6,7-dihydro-5H-cyclopenta[b]pyridin-7-yl)carbamate | 0.54 |
| 265 | O-pyridin-2-ylmethyl, N-(4-((3-chloro-4-fluorophenyl)carbamoyl)-6,7-dihydro-5H-cyclopenta[b]pyridin-7-yl) carbamate | 0.54 |
| 266 | O-pyridin-2-ylmethyl, N-(4-((3-chloro-4-fluorophenyl)carbamoyl)-6,7-dihydro-5H-cyclopenta[b]pyridin-7-yl)carbamate (enantiomer 1) | 0.43 |
| 267 | O-pyridin-2-ylmethyl, N-(4-((3-chloro-4-fluorophenyl)carbamoyl)-6,7-dihydro-5H-cyclopenta[b]pyridin-7-yl) carbamate (enantiomer 2) | 4.9 |
| 268 | N-(3-chloro-4-fluorophenyl)-7-(cyclopropanesulfonamido)-6,7-dihydro-5H-cyclopenta[c]pyridine-4-carboxamide | 8.2 |
| 269 | O-(pyridin-2-ylmethyl)-N-[(4-((3-chloro-4-fluorophenyl)carbamoyl)-6,7-dihydro-5H-cyclopenta[c]pyridin-7-yl)] carbamate | 2.3 |
| 270 | O-(pyridin-2-ylmethyl)-N-[(4-((3-chloro-4-fluorophenyl)carbamoyl)-6,7-dihydro-5H-cyclopenta[c]pyridin-7-yl)] carbamate (enantiomer 1) | 1.1 |
| 271 | O-(pyridin-2-ylmethyl)-N-[(4-((3-chloro-4-fluorophenyl)carbamoyl)-6,7-dihydro-5H-cyclopenta[c]pyridin-7-yl)]carbamate (enantiomer 2) | 5.7 |
| 272 | N-(3-chloro-4-fluorophenyl)-7-fluoro-2,3-dihydrobenzo[b]thiophene-4-carboxamide 1,1-dioxide | 0.22 |
| 273 | N-(3-chloro-4-fluorophenyl)-2,3-dihydrobenzo[b]thiophene-4-carboxamide 1,1-dioxide | 0.21 |
| 274 | 2-(tert-butyl)-N-(3-chloro-4-fluorophenyl)-2,3-dihydrobenzo[d]isothiazole-4-carboxamide 1,1-dioxide | 4.1 |
| 275 | N-(3-chloro-4-fluorophenyl)-2,3-dihydrobenzo[d]isothiazole-4-carboxamide-1,1-dioxide | 0.25 |
| 276 | N-(3-chloro-4-fluorophenyl)-2-(2-hydroxyethyl)-2,3-dihydrobenzo[d]isothiazole-4-carboxamide 1,1-dioxide | 1.4 |
| 277 | N-(3-chloro-4-fluorophenyl)-2-methyl-2,3-dihydrobenzo[d]isothiazole-4-carboxamide 1,1-dioxide | 2.2 |
| 278 | N-(3-chloro-4-fluorophenyl)-2-isopropyl-2,3-dihydrobenzo[d]isothiazole-4-carboxamide 1,1-dioxide | 1.3 |
| 279 | N-(3-chloro-4-fluorophenyl)-2-cyclopropyl-2,3-dihydrobenzo[d]isothiazole-4-carboxamide 1,1-dioxide | 0.58 |
| 280 | (S)-1-(((S)-tert-butylsulfinyl)amino)-N-(3-chloro-4-fluorophenyl)-7-fluoro-2,3-dihydro-1H-indene-4-carboxamide | 4.6 |
| 281 | (S)-1-(((R)-tert-butylsulfinyl)amino)-N-(3-chloro-4-fluorophenyl)-7-fluoro-2,3-dihydro-1H-indene-4-carboxamide | 4.4 |
| 282 | O-methyl, N-(4-((3-chloro-4-fluorophenyl)carbamoyl)-7-fluoro-3,3-dimethyl-2,3-dihydro-1H-inden-1-yl) carbamate | 15 |

Example 20: Pharmacokinetic Analysis

Determination of Liberation of Active Species Through In Vivo Phosphate Hydrolysis Pharmacokinetic analysis of 254 was conducted via intravenous administration at 2 mpk, and oral administration at 10 mpk, of the test article in female 10-week old CD-1 mice. For intravenously administered test articles, the samples were formulated in 40% polyethyleneglycol 400 (PEG 400), 5% ethanol and 55% Dulbecco's phosphate-buffered saline (DPBS) and dosed at a concentration of 0.2 mg/mL. For orally administered test articles, the samples were formulated in 60% PEG 400, 5% ethanol, 10% propylene glycol, and 25% DPBS and dosed at a concentration of 1.0 mg/mL. Intravenous administration was conducted by a lateral tail vein injection and oral administration was conducted by oral gavage. Each dosing group consisted of 4 mice weighing approximately 35 g each.

Serial non-terminal blood collections were performed at pre-determined time points of 5 min (IV), 15 min (oral), 30 min, 2 h, 4 h, 8 h, and 12 h, and a terminal blood collection was performed 24 h after test article administration. At each serial collection time point, whole blood was collected via a lateral tail nick and via cardiac puncture at the terminal endpoint. For non-terminal blood collections, 40 μL of blood was added to a 1.5 mL microfuge tube containing 2.4 μL of a 50 mM Na-EDTA solution, gently agitated and stored at 4° C. until ready for centrifugation. Centrifugation was conducted for 5 min at 4° C. and 16,000×g to extract plasma and 15 μL of plasma was transferred into a WATERS 1000 μL 96-well deepwell plate, mat sealed, and stored at −80° C. prior to analysis by LC-MS/MS. For terminal blood collections, animals were euthanized at the terminal time point following test article administration via a lethal dose of ketamine/xylazine prior to cardiac puncture. For each animal, 0.5 mL of blood was collected into a lavender EDTA microtainer, and gently agitated prior to cooling to 4° C. Samples were centrifuged for 5 min at 4° C. and 16,000×g and 15 μL of plasma was transferred into a WATERS 1000 μL 96-well deepwell plate, mat sealed, and stored at −80° C. prior to analysis by LC-MS/MS. In preparation for analysis, the frozen plasma samples were thawed at room temperature and plasma proteins were precipitated via the addition of acetonitrile at a ratio of 1:15 (v/v) plasma:acetonitrile. As an internal standard (IS), the acetonitrile was spiked with tolbutamide at 50 ng/mL. Plates were subsequently shaken for 10 min at 250 rpm and proteins pelleted at 3,000 rpm also for 10 min at room temperature. Supernatants were then removed and transferred into a new 96-well deepwell plate. Analytical analysis analysis was conducted against a standard curve of 193 an AB SCIEX QTRAP® 5500 LC-MS/MS system employing a Super C18 column (50×2.1 mm, 3 µM), (5 µL injection volume, flow rate of 0.4 mL/min). The mobile phase consisted of two phases, phase A was a water and 0.05% formic acid mix and phase B was a 50:50 (acetonitrile:methanol) and 0.05% formic acid mixture. The programmed gradient consisted of 20% B for 0.1 min, with a ramp to 98% B to 0.4 min, with B maintained at 98% to 2.45 min, B was then reduced back to 20% by 2.47 min, and the run stopped at 3 min. Observed pharmacokinetic parameters for 193 based on dosing of 254 are detailed in Table 2. *F % for liberation of the parent species was derived from $AUC_{0\text{-}Inf}$ values determined from direct intravenous dosing of 193 in a similar manner as described above.

TABLE 2

| Cmax (mg/mL) | $T_{1/2}$ (h) | $AUC_{0\text{-}24}$ (ng · h/mL) | F (%)* |
|---|---|---|---|
| 4,831 | 4.5 | 6,897 | 56 |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (Is), or a salt, solvate, prodrug, stereoisomer, tautomer, or isotopically labelled derivative thereof, or any mixtures thereof:

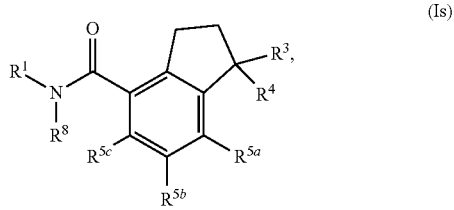

(Is)

wherein:
$R^1$ is selected from the group consisting of optionally substituted phenyl, optionally substituted benzyl, and optionally substituted heteroaryl;
each occurrence of $R^2$ is independently selected from the group consisting of H and $C_1$-$C_6$ alkyl;
$R^3$ is selected from the group consisting of —N($R^2$)C(=O)O$R^6$, —OH, —O$R^6$, —NH$_2$, —NH$R^6$, —N$R^6R^6$, —OC(=O)O$R^6$, —OC(=O)N($R^2$)$R^6$, —N$R^7$C(=O)N($R^6$)($R^7$), —N($R^2$)C(=O)$R^6$, —N$R^2$S(=O)$_{1\text{-}2}R^6$, optionally substituted aryl, optionally substituted heteroaryl, —CH$_2$C(=O)OH, —CH$_2$C(=O)N$R^6R^6$, —N($R^2$)C(=O)(CH$_2$)$_{1\text{-}2}R^6$, N$R^2$S(=O)$_2$N($R^6$)($R^7$), and —N$R^2$C(=O)C(=O)N($R^6$)($R^7$);
$R^4$ is H or $C_1$-$C_6$ alkyl, or
$R^3$ and $R^4$ combine to form =O or —C(=O)N$R^{6a}$—C(=O)—N$R^{6a}$—;

$R^{5a}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;
$R^{5b}$ is selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;
$R^{5c}$ is independently selected from the group consisting of H, halo, $C_1$-$C_6$ alkyl, $C_1$-$C_6$ alkoxy, $C_1$-$C_6$ aminoalkyl, $C_1$-$C_6$ haloalkoxy, and $C_1$-$C_6$ haloalkyl;
each occurrence of $R^6$ is independently selected from the group consisting of optionally substituted $C_1$-$C_6$ alkyl, optionally substituted $C_3$-$C_8$ cycloalkyl, optionally substituted phenyl, and optionally substituted heteroaryl;
each occurrence of $R^{6a}$ is independently selected from the group consisting of H, optionally substituted $C_1$-$C_6$ alkyl, optionally substituted $C_3$-$C_8$ cycloalkyl, optionally substituted phenyl, and optionally substituted heteroaryl;
each occurrence of $R^7$ is independently selected from the group consisting of H and optionally substituted $C_1$-$C_6$ alkyl;
or, if $R^6$ and $R^7$ are bound to the same N atom, $R^6$ and $R^7$ optionally combine with the N atom to which both are bound to form optionally substituted 3-7 membered heterocyclyl; and
$R^8$ is selected from the group consisting of H and $C_1$-$C_6$ alkyl.

2. The compound of claim 1, wherein each occurrence of $R^6$ or $R^{6a}$ is independently selected from the group consisting of —(CH$_2$)$_{1\text{-}3}$-(optionally substituted heteroaryl), —(CH$_2$)$_{1\text{-}3}$-(optionally substituted heterocyclyl), and —(CH$_2$)$_{1\text{-}3}$-(optionally substituted aryl).

3. The compound of claim 1, wherein each occurrence of optionally substituted alkyl, optionally substituted heterocyclyl, or optionally substituted cycloalkyl is independently optionally substituted with at least one substituent selected from the group consisting of $C_1$-$C_6$ alkyl, halo, —O$R^a$, optionally substituted phenyl, optionally substituted heteroaryl, optionally substituted heterocyclyl, —N($R^a$)C(=O)$R^a$, —C(=O)N$R^aR^a$, and —N($R^a$)($R^a$), wherein each occurrence of $R^a$ is independently H, optionally substituted $C_1$-$C_6$ alkyl, optionally substituted $C_3$-$C_8$ cycloalkyl, optionally substituted aryl, or optionally substituted heteroaryl, or two $R^a$ groups combine with the N to which they are bound to form a heterocycle.

4. The compound of claim 1, wherein each occurrence of optionally substituted aryl or optionally substituted heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —O$R^b$, —N($R^b$)($R^b$), —NO$_2$, —S(=O)$_2$N($R^b$)($R^b$), acyl, and $C_1$-$C_6$ alkoxycarbonyl, wherein each occurrence of $R^b$ is independently H, $C_1$-$C_6$ alkyl, or $C_3$-$C_8$ cycloalkyl.

5. The compound of claim 1, wherein each occurrence of optionally substituted aryl or optionally substituted heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —O$R^c$, —N($R^c$)($R^c$), and $C_1$-$C_6$ alkoxycarbonyl, wherein each occurrence of $R^c$ is independently H, $C_1$-$C_6$ alkyl, or $C_3$-$C_8$ cycloalkyl.

6. The compound of claim 1, wherein $R^1$ is selected from the group consisting of optionally substituted phenyl and optionally substituted benzyl, wherein the phenyl or benzyl is optionally substituted with at least one selected from the group consisting of $C_1$-$C_6$ alkyl, halo, $C_1$-$C_3$ haloalkyl, and —CN.

7. The compound of claim 1, wherein $R^1$ is selected from the group consisting of 3,4-difluorophenyl, 3,5-difluorophenyl, 2,4,5-trifluorophenyl, 3,4,5-trifluorophenyl, 3,4-dichlorophenyl, 3-chloro-4-fluorophenyl, 4-chloro-3-fluorophenyl, 4-chloro-3-methylphenyl, 3-chloro-4-methylphenyl, 4-fluoro-3-methylphenyl, 3-fluoro-4-methylphenyl, 4-chloro-3-methoxyphenyl, 3-chloro-4-methoxyphenyl, 4-fluoro-3-methoxyphenyl, 3-fluoro-4-methoxyphenyl, phenyl, 3-chlorophenyl, 4-chlorophenyl, 3-fluorophenyl, 4-fluorophenyl, 3-trifluoromethylphenyl, 4-trifluoromethylphenyl, 3-trifluoromethyl-4-fluorophenyl, 4-trifluoromethyl-3-fluorophenyl, 3-cyanophenyl, 4-cyanophenyl, 3-cyano-4-fluorophenyl, 4-cyano-3-fluorophenyl, 3-difluoromethyl-4-fluorophenyl, 4-difluoromethyl-3-fluorophenyl, benzo[d][1,3]dioxol-5-yl, 2,3-dihydrobenzo[b][1,4]dioxin-6-yl, benzyl, 3-fluorobenzyl, 4-fluorobenzyl, 3-chlorobenzyl, 4-chlorobenzyl, 2-pyridyl, 4-methyl-2-pyridyl, 5-methyl-2-pyridyl, 6-methyl-2-pyridyl, 3-pyridyl, 2-methyl-3-pyridyl, 3-methyl-3-pyridyl, 4-pyridyl, 2-methyl-4-pyridyl, and 6-methyl-4-pyridyl.

8. The compound of claim 1, wherein each occurrence of $R^2$ is independently selected from the group consisting of H and methyl.

9. The compound of claim 1, wherein $R^3$ is selected from the group consisting of: —NH$_2$; —OH; —NH(pyridinyl); —NH(pyrimidinyl); —NH(piridinyl-pyrimidinyl); —NH(pyrrolo[2,3-d]pyrimidinyl); —NHS(=O)$_2$($C_1$-$C_6$ alkyl); —NHS(=O)$_2$($C_3$-$C_6$ cycloalkyl); —NHS(=O)$_2$(CH$_2$)$_{0-3}$pyridinyl; —NHS(=O)$_2$(benzyl); —NHS(=O)$_2$(pyrazolyl); —NHS(=O)$_2$(morpholinyl); —NHS(=O)$_2$NH($C_1$-$C_6$ alkyl); —NHS(=O)$_2$NH($C_3$-$C_6$ cycloalkyl); —NHS(=O)$_2$NH(CH$_2$)$_{0-3}$pyridinyl; —NHS(=O)$_2$NH(benzyl); —NHS(=O)$_2$NH(pyrazolyl); —NHS(=O)$_2$NH(morpholinyl); —NHC(=O)($C_1$-$C_6$ alkyl); —NHC(=O)($C_3$-$C_8$ cycloalkyl); —NHC(=O)($C_1$-$C_6$ haloalkyl); —NHC(=O)(pyrazolyl); —NHC(=O)(thiazolyl); —NHC(=O)(oxazolyl); —NHC(=O)(pyridinyl); —NHC(=O)(CH$_2$)$_{1-3}$(pyridinyl); —NHC(=O)(CH$_2$)$_{1-3}$(pyrazinyl); —NHC(=O)(CH$_2$)$_{1-3}$(pyrimidinyl); —NHC(=O)(CH$_2$)$_{1-3}$(quinolinyl); —NHC(=O)(CH$_2$)$_{1-3}$(isoxazolyl); —NHC(=O)(CH$_2$)$_{1-3}$(oxazolyl); —NHC(=O)(CH$_2$)$_{1-3}$(oxadiazolyl); —NHC(=O)(CH$_2$)$_{1-3}$(triazolyl); —NHC(=O)(CH$_2$)$_{1-3}$(thiazolyl); —NHC(=O)(CH$_2$)$_{1-3}$(imidazolyl); —NHC(=O)(CH$_2$)$_{1-3}$(pyrazolyl); —NHC(=O)(CH$_2$)$_{1-3}$(piperidinyl); —NHC(=O)(CH$_2$)$_{1-3}$(oxopiperidinyl); —NHC(=O)(CH$_2$)$_{1-3}$(pyrrolidinyl); —NHC(=O)(CH$_2$)$_{1-3}$(oxopyrrolidinyl); —NHC(=O)(CH$_2$)$_{1-3}$(tetrahydrofuryl); —NHC(=O)(CH$_2$)$_{1-3}$(tetrahydropyranyl); —NHC(=O)(CH$_2$)$_{1-3}$(2-oxooxazolidinyl); —NHC(=O)(CH$_2$)$_{1-3}$(morpholinyl); —NHC(=O)(CH$_2$)$_{1-3}$(thiomorpholinyl); —NHC(=O)(CH$_2$)$_{1-3}$(1-oxido-thiomorpholinyl); —NHC(=O)(CH$_2$)$_{1-3}$(1,1-dioxido-thiomorpholinyl); —NHC(=O)(CH$_2$)$_{1-3}$(oxoazetidinyl); —NHC(=O)(CH$_2$)$_{1-3}$(imidazo[1,2-a]pyridin-2-yl); —NHC(=O)(CH$_2$)$_{1-3}$C(=O)-(pyrrolidin-1-yl); —NHC(=O)O($C_1$-$C_6$ alkyl); —NHC(=O)O($C_3$-$C_8$ cycloalkyl); —NHC(=O)O($C_1$-$C_6$ haloalkyl); —NHC(=O)O(CH$_2$)$_{1-3}$(pyridinyl); —NHC(=O)O(CH$_2$)$_{1-3}$(pyrazinyl); —NHC(=O)O(CH$_2$)$_{1-3}$(pyrimidinyl); —NHC(=O)O(CH$_2$)$_{1-3}$(quinolinyl); —NHC(=O)O(CH$_2$)$_{1-3}$(isoxazolyl); —NHC(=O)O(CH$_2$)$_{1-3}$(oxazolyl); —NHC(=O)O(CH$_2$)$_{1-3}$(oxadiazolyl); —NHC(=O)O(CH$_2$)$_{1-3}$(triazolyl); —NHC(=O)O(CH$_2$)$_{1-3}$(thiazolyl); —NHC(=O)O(CH$_2$)$_{1-3}$(imidazolyl); —NHC(=O)O(CH$_2$)$_{1-3}$(pyrazolyl); —NHC(=O)O(CH$_2$)$_{1-3}$(piperidinyl); —NHC(=O)O(CH$_2$)$_{1-3}$(oxopiperidinyl); —NHC(=O)O(CH$_2$)$_{1-3}$(pyrrolidinyl); —NHC(=O)O(CH$_2$)$_{1-3}$(oxopyrrolidinyl); —NHC(=O)O(CH$_2$)$_{1-3}$(tetrahydrofuryl); —NHC(=O)O(CH$_2$)$_{1-3}$(tetrahydropyranyl); —NHC(=O)O(CH$_2$)$_{1-3}$(2-oxooxazolidinyl); —NHC(=O)O(CH$_2$)$_{1-3}$(morpholinyl); —NHC(=O)O(CH$_2$)$_{1-3}$(thiomorpholinyl); —NHC(=O)O(CH$_2$)$_{1-3}$(1-oxido-thiomorpholinyl); —NHC(=O)O(CH$_2$)$_{1-3}$(1,1-dioxido-thiomorpholinyl); —NHC(=O)O(CH$_2$)$_{1-3}$(oxoazetidinyl); —NHC(=O)O(CH$_2$)$_{1-3}$(imidazo[1,2-a]pyridin-2-yl); —NHC(=O)O(CH$_2$)$_{1-3}$C(=O)-(pyrrolidin-1-yl); —NHC(=O)NH($C_1$-$C_6$ alkyl); —NHC(=O)NH($C_3$-$C_8$ cycloalkyl); —NHC(=O)NH($C_1$-$C_6$ haloalkyl); —NHC(=O)NH(CH$_2$)$_{1-3}$(pyridinyl); —NHC(=O)NH(CH$_2$)$_{1-3}$(pyrazinyl); —NHC(=O)NH(CH$_2$)$_{1-3}$(pyrimidinyl); —NHC(=O)NH(CH$_2$)$_{1-3}$(quinolinyl); —NHC(=O)NH(CH$_2$)$_{1-3}$(isoxazolyl); —NHC(=O)NH(CH$_2$)$_{1-3}$(oxazolyl); —NHC(=O)NH(CH$_2$)$_{1-3}$(oxadiazolyl); —NHC(=O)NH(CH$_2$)$_{1-3}$(triazolyl); —NHC(=O)NH(CH$_2$)$_{1-3}$(thiazolyl); —NHC(=O)NH(CH$_2$)$_{1-3}$(imidazolyl); —NHC(=O)NH(CH$_2$)$_{1-3}$(pyrazolyl); —NHC(=O)NH(CH$_2$)$_{1-3}$(piperidinyl); —NHC(=O)NH(CH$_2$)$_{1-3}$(oxopiperidinyl); —NHC(=O)NH(CH$_2$)$_{1-3}$(pyrrolidinyl); —NHC(=O)NH(CH$_2$)$_{1-3}$(oxopyrrolidinyl); —NHC(=O)NH(CH$_2$)$_{1-3}$(tetrahydrofuryl); —NHC(=O)NH(CH$_2$)$_{1-3}$(tetrahydropyranyl); —NHC(=O)NH(CH$_2$)$_{1-3}$(2-oxooxazolidinyl); —NHC(=O)NH(CH$_2$)$_{1-3}$(morpholinyl); —NHC(=O)NH(CH$_2$)$_{1-3}$(thiomorpholinyl); —NHC(=O)NH(CH$_2$)$_{1-3}$(1-oxido-thiomorpholinyl); —NHC(=O)NH(CH$_2$)$_{1-3}$(1,1-dioxido-thiomorpholinyl); —NHC(=O)NH(CH$_2$)$_{1-3}$(oxoazetidinyl); —NHC(=O)NH(CH$_2$)$_{1-3}$(imidazo[1,2-a]pyridin-2-yl); —NHC(=O)NH(CH$_2$)$_{1-3}$C(=O)-(pyrrolidin-1-yl); —C(=O)NHC(=O)NH—; —C(=O)N($C_1$-$C_6$ alkyl)C(=O)NH—; —C(=O)N((CH$_2$)$_{1-3}$pyridinyl)CONH—; wherein the alkyl, cycloalkyl, heteroaryl, heterocyclyl, aryl, or benzyl group is optionally independently substituted with at least one group selected from the group consisting of $C_1$-$C_6$ alkyl; $C_1$-$C_6$ alkoxy; $C_1$-$C_6$ haloalkyl; $C_1$-$C_6$ haloalkoxy; —NH$_2$, —NH($C_1$-$C_6$ alkyl), —N($C_1$-$C_6$ alkyl)($C_1$-$C_6$ alkyl), halogen, —OH; —CN; phenoxy, —NHC(=O)H, —NHC(=O)$C_1$-$C_6$ alkyl, —C(=O)NH$_2$, —C(=O)NH$C_1$-$C_6$ alkyl, —C(=O)N($C_1$-$C_6$ alkyl)($C_1$-$C_6$ alkyl), tetrahydropyranyl, morpholinyl, —C(=O)CH$_3$, —C(=O)CH$_2$OH, —C(=O)NHCH$_3$, —C(=O)CH$_2$OMe, or an N-oxide thereof.

10. The compound of claim 1, wherein $R^4$ is H or CH$_3$.

11. The compound of claim 1, wherein $R^{5a}$, $R^{5b}$, and $R^{5c}$ are independently selected from the group consisting of H, F, and Cl.

12. The compound of claim 1, wherein one of $R^{5a}$, $R^{5b}$, and $R^{5c}$ is F, and the two remaining are H.

13. The compound of claim 1, which is selected from the group consisting of:

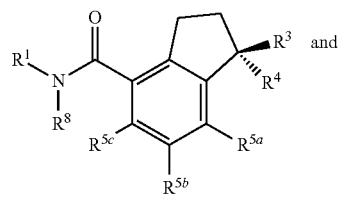

14. The compound of claim 1, which is selected from the group consisting of:

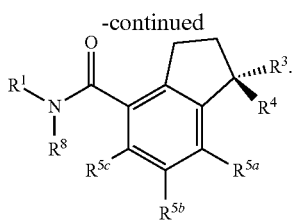

15. A compound selected from the group consisting of:

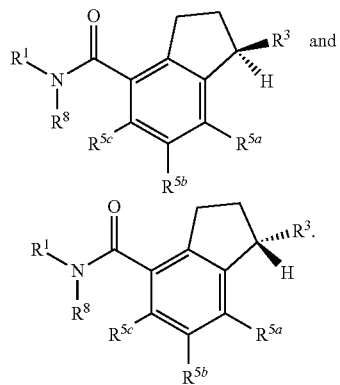

O-methyl, N—(S)-(4-((3,4-difluorophenyl)carbamoyl)-2,3-dihydro-1H-inden-1-yl) carbamate;
(S)—N-(3,4-difluorophenyl)-1-(3-methylureido)-2,3-dihydro-1H-indene-4-carboxamide;
O-pyridin-2-ylmethyl, N—(S)-(4-((3,4-difluorophenyl)carbamoyl)-2,3-dihydro-1H-inden-1-yl) carbamate;
O—((R)-5-oxopyrrolidin-2-yl)methyl, N—((S)-4-((3-chloro-4-fluorophenyl)carbamoyl)-7-fluoro-2,3-dihydro-1H-inden-1-yl) carbamate;
O-tert-butyl, N—(S)-(4-((3-chloro-4-fluorophenyl)carbamoyl)-7-fluoro-2,3-dihydro-1H-inden-1-yl) carbamate;
O-methyl, N—(S)-(7-fluoro-4-((4-fluoro-3-methylphenyl)carbamoyl)-2,3-dihydro-1H-inden-1-yl) carbamate;
(S)-7-fluoro-N-(4-fluoro-3-methylphenyl)-1-(3-methylureido)-2,3-dihydro-1H-indene-4-carboxamide;
(S)-1-amino-N-(3-chloro-4-fluorophenyl)-7-fluoro-2,3-dihydro-1H-indene-4-carboxamide;
O-2-(2-oxopyrrolidin-1-yl)ethyl, N—(S)-(4-((3-chloro-4-fluorophenyl)carbamoyl)-7-fluoro-2,3-dihydro-1H-inden-1-yl) carbamate;
O-pyridin-2-ylmethyl, N—(S)-(4-((3-chloro-4-fluorophenyl)carbamoyl)-2,3-dihydro-1H-inden-1-yl) carbamate;
O—((S)-5-oxopyrrolidin-2-yl)methyl, N—(S)-4-((3-chloro-4-fluorophenyl)carbamoyl)-7-fluoro-2,3-dihydro-1H-inden-1-yl) carbamate;
O-methyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-(3-methylureido)-2,3-dihydro-1H-indene-4-carboxamide;
O—((R)-5-oxopyrrolidin-2-yl)methyl, N—((S)-4-((3-chloro-4-fluorophenyl)carbamoyl)-2,3-dihydro-1H-inden-1-yl) carbamate;
O—((S)-5-oxopyrrolidin-2-yl)methyl, N—((S)-4-((3-chloro-4-fluorophenyl)carbamoyl)-2,3-dihydro-1H-inden-1-yl) carbamate;
O-pyridin-2-ylmethyl, N—(S)-(4-((4-fluoro-3-methylphenyl)carbamoyl)-2,3-dihydro-1H-inden-1-yl) carbamate;
O—((R)-5-oxopyrrolidin-2-yl)methyl, N—((S)-4-((4-fluoro-3-methylphenyl)carbamoyl)-2,3-dihydro-1H-inden-1-yl)carbamate;
O—((S)-5-oxopyrrolidin-2-yl)methyl, N—((S)-4-((4-fluoro-3-methylphenyl)carbamoyl)-2,3-dihydro-1H-inden-1-yl) carbamate;
O-2-oxo-2-(pyrrolidin-1-yl)ethyl, N—(S)-(4-((3-chloro-4-fluorophenyl)carbamoyl)-7-fluoro-2,3-dihydro-1H-inden-1-yl) carbamate;
O-pyridin-2-ylmethyl, N—(S)-(4-((3-chloro-4-fluorophenyl)carbamoyl)-7-fluoro-2,3-dihydro-1H-inden-1-yl) carbamate;
O—((S)-1-methyl-5-oxopyrrolidin-2-yl)methyl, N—(S)-4-((3-chloro-4-fluorophenyl)carbamoyl)-7-fluoro-2,3-dihydro-1H-inden-1-yl) carbamate;
O-pyridin-2-ylmethyl, N—(S)-(7-fluoro-4-((4-fluoro-3-methylphenyl)carbamoyl)-2,3-dihydro-1H-inden-1-yl) carbamate;
O-imidazo[1,2-a]pyridin-2-ylmethyl, N—(S)-(4-((3-chloro-4-fluorophenyl)carbamoyl)-7-fluoro-2,3-dihydro-1H-inden-1-yl) carbamate;
O-(6-morpholinopyridin-2-yl)methyl, N—(S)-(4-((3-chloro-4-fluorophenyl)carbamoyl)-7-fluoro-2,3-dihydro-1H-inden-1-yl) carbamate;
O—((R)-1-methyl-5-oxopyrrolidin-2-yl)methyl, N—((S)-4-((3-chloro-4-fluorophenyl)carbamoyl)-7-fluoro-2,3-dihydro-1H-inden-1-yl) carbamate;
O-(6-methoxypyridin-2-yl)methyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-(pyrimidin-2-ylamino)-2,3-dihydro-1H-indene-4-carboxamide;
O-(6-(dimethylamino) pyridin-2-yl)methyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-((5-methoxypyrimidin-2-yl)amino)-2,3-dihydro-1H-indene-4-carboxamide;
(S)—N-(3-chloro-4-fluorophenyl)-7-fluoro-1-((4-(pyridin-2-yl)pyrimidin-2-yl)amino)-2,3-dihydro-1H-indene-4-carboxamide;
tert-butyl 2-(((((S)-4-((3-chloro-4-fluorophenyl)carbamoyl)-7-fluoro-2,3-dihydro-1H-inden-1-yl)carbamoyl)oxy)methyl)-4,4-difluoropyrrolidine-1-carboxylate;
O-(4,4-difluoropyrrolidin-2-yl)methyl, N—(S)-4-((3-chloro-4-fluorophenyl)carbamoyl)-7-fluoro-2,3-dihydro-1H-inden-1-yl) carbamate;
O-(1-acetyl-4,4-difluoropyrrolidin-2-yl)methyl, N—(S)-4-((3-chloro-4-fluorophenyl)carbamoyl)-7-fluoro-2,3-dihydro-1H-inden-1-yl) carbamate;
O-(1-(2,2,2-trifluoroethyl)piperidin-4-yl)methyl, N—(S)-(4-((3-chloro-4-fluorophenyl)carbamoyl)-7-fluoro-2,3-dihydro-1H-inden-1-yl) carbamate;
(S)-2-((((4-((3-chloro-4-fluorophenyl)carbamoyl)-7-fluoro-2,3-dihydro-1H-inden-1-yl)carbamoyl)oxy)methyl)pyridine 1-oxide;
O—(S)-1-(pyridin-2-yl)ethyl, N—(S)-4-((3-chloro-4-fluorophenyl)carbamoyl)-7-fluoro-2,3-dihydro-1H-inden-1-yl) carbamate;

O—(S)-pyrrolidin-2-ylmethyl, N—((S)-4-((3-chloro-4-fluorophenyl)carbamoyl)-7-fluoro-2,3-dihydro-1H-inden-1-yl) carbamate;
O-3,3,3-trifluoropropyl, N—(S)-(4-((3-chloro-4-fluorophenyl)carbamoyl)-7-fluoro-2,3-dihydro-1H-inden-1-yl) carbamate;
O-(1-methyl-1H-pyrazol-3-yl)methyl, N—(S)-(4-((3-chloro-4-fluorophenyl)carbamoyl)-7-fluoro-2,3-dihydro-1H-inden-1-yl) carbamate;
O—(R)-5-oxopyrrolidin-3-yl, N—((S)-4-((3-chloro-4-fluorophenyl)carbamoyl)-7-fluoro-2,3-dihydro-1H-inden-1-yl) carbamate;
O-(6-methylpyridin-2-yl)methyl, N—(S)-(4-((3-chloro-4-fluorophenyl)carbamoyl)-7-fluoro-2,3-dihydro-1H-inden-1-yl) carbamate;
N—(S)-4-((3-chloro-4-fluorophenyl)carbamoyl)-7-fluoro-2,3-dihydro-1H-inden-1-yl, O-(pyridin-2-ylmethyl) carbamate;
(S)—N-(3-chloro-4-fluorophenyl)-7-fluoro-1-(2-methoxyacetamido)-2,3-dihydro-1H-indene-4-carboxamide;
(S)—N-(3-chloro-4-fluorophenyl)-7-fluoro-1-(3-fluoropropanamido)-2,3-dihydro-1H-indene-4-carboxamide;
(S)-1-acetamido-N-(3-chloro-4-fluorophenyl)-7-fluoro-2,3-dihydro-1H-indene-4-carboxamide;
O-pyrazin-2-ylmethyl, N—(S)-(4-((3-chloro-4-fluorophenyl)carbamoyl)-7-fluoro-2,3-dihydro-1H-inden-1-yl) carbamate;
O-pyrimidin-2-ylmethyl, N—(S)-(4-((3-chloro-4-fluorophenyl)carbamoyl)-7-fluoro-2,3-dihydro-1H-inden-1-yl) carbamate;
O-(4-chloropyridin-2-yl)methyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-hydroxy-2,3-dihydro-1H-indene-4-carboxamide;
O-isoxazol-3-ylmethyl, N—(S)-(4-((3-chloro-4-fluorophenyl)carbamoyl)-7-fluoro-2,3-dihydro-1H-inden-1-yl) carbamate;
O-2-(pyridin-2-yl)ethyl, N—(S)-(4-((3-chloro-4-fluorophenyl)carbamoyl)-7-fluoro-2,3-dihydro-1H-inden-1-yl) carbamate;
O-2,2-difluoroethyl, N—(S)-(4-((3-chloro-4-fluorophenyl)carbamoyl)-7-fluoro-2,3-dihydro-1H-inden-1-yl) carbamate;
O-pyrimidin-4-ylmethyl, N—(S)-(4-((3-chloro-4-fluorophenyl)carbamoyl)-7-fluoro-2,3-dihydro-1H-inden-1-yl) carbamate;
O-3-(2-oxopyrrolidin-1-yl)propyl, N—(S)-(4-((3-chloro-4-fluorophenyl)carbamoyl)-7-fluoro-2,3-dihydro-1H-inden-1-yl) carbamate;
O-(8-methylimidazo[1,2-a]pyridin-2-yl)methyl, N—(S)-(4-((3-chloro-4-fluorophenyl)carbamoyl)-7-fluoro-2,3-dihydro-1H-inden-1-yl) carbamate;
O-2,2,2-trifluoroethyl, N—(S)-(4-((3-chloro-4-fluorophenyl)carbamoyl)-7-fluoro-2,3-dihydro-1H-inden-1-yl) carbamate;
O—(S)-4-((3-chloro-4-fluorophenyl)carbamoyl)-7-fluoro-2,3-dihydro-1H-inden-1-yl, N-methylcarbamate;
N—(S)-4-((3-chloro-4-fluorophenyl)carbamoyl)-7-fluoro-2,3-dihydro-1H-inden-1-yl, O-(pyridin-2-ylmethyl) carbonate;
O-thiazol-5-ylmethyl, N—(S)-(4-((3-chloro-4-fluorophenyl)carbamoyl)-7-fluoro-2,3-dihydro-1H-inden-1-yl) carbamate;
O-thiazol-2-ylmethyl, N—(S)-(4-((3-chloro-4-fluorophenyl)carbamoyl)-7-fluoro-2,3-dihydro-1H-inden-1-yl) carbamate;
O-oxazol-4-ylmethyl, N—(S)-(4-((3-chloro-4-fluorophenyl)carbamoyl)-7-fluoro-2,3-dihydro-1H-inden-1-yl) carbamate;
O-oxazol-2-ylmethyl, N—(S)-(4-((3-chloro-4-fluorophenyl)carbamoyl)-7-fluoro-2,3-dihydro-1H-inden-1-yl) carbamate;
O-oxazol-5-ylmethyl, N—(S)-(4-((3-chloro-4-fluorophenyl)carbamoyl)-7-fluoro-2,3-dihydro-1H-inden-1-yl) carbamate;
O-2-(1H-imidazol-1-yl)ethyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-(pyridin-2-ylamino)-2,3-dihydro-1H-indene-4-carboxamide;
(S)—N-(4-((3-chloro-4-fluorophenyl)carbamoyl)-7-fluoro-2,3-dihydro-1H-inden-1-yl)-1-methyl-1H-pyrazole-3-carboxamide;
O-2-phenoxyethyl, N—(S)-(4-((3-chloro-4-fluorophenyl)carbamoyl)-7-fluoro-2,3-dihydro-1H-inden-1-yl) carbamate;
(S)—N-(4-((3-chloro-4-fluorophenyl)carbamoyl)-7-fluoro-2,3-dihydro-1H-inden-1-yl)-1-methyl-1H-pyrazole-5-carboxamide;
(S)—N-(3-chloro-4-fluorophenyl)-7-fluoro-1-((1-methyl-H-pyrazole)-3-sulfonamido)-2,3-dihydro-1H-indene-4-carboxamide;
O-(1-methyl-1H-1,2,4-triazol-3-yl)methyl, N—(S)-(4-((3-chloro-4-fluorophenyl)carbamoyl)-7-fluoro-2,3-dihydro-1H-inden-1-yl) carbamate;
O-(1-methyl-H-pyrazol-5-yl)methyl, N—(S)-(4-((3-chloro-4-fluorophenyl)carbamoyl)-7-fluoro-2,3-dihydro-1H-inden-1-yl) carbamate;
(S)-2-((4-((3-chloro-4-fluorophenyl)carbamoyl)-7-fluoro-2,3-dihydro-1H-inden-1-yl)amino)pyrimidine-4-carboxamide;
O-2-(4-methylthiazol-5-yl)ethyl, N—(S)-(4-((3-chloro-4-fluorophenyl)carbamoyl)-7-fluoro-2,3-dihydro-1H-inden-1-yl) carbamate;
O-(1-isopropyl-1H-pyrazol-3-yl)methyl, N—(S)-(4-((3-chloro-4-fluorophenyl)carbamoyl)-7-fluoro-2,3-dihydro-1H-inden-1-yl) carbamate;
O-(5-methoxypyridin-2-yl)methyl, N—(S)-(4-((3-chloro-4-fluorophenyl)carbamoyl)-7-fluoro-2,3-dihydro-1H-inden-1-yl) carbamate;
O—((S)-1-(2,2,2-trifluoroethyl)pyrrolidin-2-yl)methyl, N—((S)-4-((3-chloro-4-fluorophenyl)carbamoyl)-7-fluoro-2,3-dihydro-1H-inden-1-yl) carbamate;
O-(5-fluoropyridin-2-yl)methyl, N—(S)-(4-((3-chloro-4-fluorophenyl)carbamoyl)-7-fluoro-2,3-dihydro-1H-inden-1-yl) carbamate;
O-2-(1H-pyrazol-4-yl)ethyl, N—(S)-(4-((3-chloro-4-fluorophenyl)carbamoyl)-7-fluoro-2,3-dihydro-1H-inden-1-yl) carbamate;
O-2-methoxyethyl, N—(S)-(4-((3-chloro-4-fluorophenyl)carbamoyl)-7-fluoro-2,3-dihydro-1H-inden-1-yl) carbamate;
O—((R)-tetrahydrofuran-2-yl)methyl, N—((S)-4-((3-chloro-4-fluorophenyl)carbamoyl)-7-fluoro-2,3-dihydro-1H-inden-1-yl) carbamate;
O-tetrahydro-2H-pyran-4-yl, N—(S)-(4-((3-chloro-4-fluorophenyl)carbamoyl)-7-fluoro-2,3-dihydro-1H-inden-1-yl) carbamate;

O-3-methoxypropyl, N—(S)-(4-((3-chloro-4-fluorophenyl)carbamoyl)-7-fluoro-2,3-dihydro-1H-inden-1-yl) carbamate;
(S)—N-(4-((3-chloro-4-fluorophenyl)carbamoyl)-7-fluoro-2,3-dihydro-1H-inden-1-yl)picolinamide;
(S)—N-(4-((3-chloro-4-fluorophenyl)carbamoyl)-7-fluoro-2,3-dihydro-1H-inden-1-yl)thiazole-5-carboxamide;
(S)—N-(3-chloro-4-fluorophenyl)-7-fluoro-1-(methylsulfonamido)-2,3-dihydro-1H-indene-4-carboxamide;
(S)—N-(3-chloro-4-fluorophenyl)-7-fluoro-1-(2-morpholinoacetamido)-2,3-dihydro-1H-indene-4-carboxamide;
(S)—N-(4-((3-chloro-4-fluorophenyl)carbamoyl)-7-fluoro-2,3-dihydro-1H-inden-1-yl)nicotinamide;
(S)—N-(4-((3-chloro-4-fluorophenyl)carbamoyl)-7-fluoro-2,3-dihydro-1H-inden-1-yl)isonicotinamide;
(S)-4-((3-chloro-4-fluorophenyl)carbamoyl)-7-fluoro-2,3-dihydro-1H-inden-1-yl methyl carbonate;
O-thiazol-4-ylmethyl, N—(S)-(4-((3-chloro-4-fluorophenyl)carbamoyl)-7-fluoro-2,3-dihydro-1H-inden-1-yl) carbamate;
O-3-(1H-imidazol-1-yl)propyl, N—(S)-(4-((3-chloro-4-fluorophenyl)carbamoyl)-7-fluoro-2,3-dihydro-1H-inden-1-yl) carbamate;
O-pyridin-2-ylmethyl, N—(S)-(4-((3-cyano-4-fluorophenyl)carbamoyl)-7-fluoro-2,3-dihydro-1H-inden-1-yl) carbamate;
(S)—N-(4-((3-chloro-4-fluorophenyl)carbamoyl)-7-fluoro-2,3-dihydro-1H-inden-1-yl)thiazole-2-carboxamide;
(S)—N-(3-chloro-4-fluorophenyl)-1-(cyclopropanesulfonamido)-7-fluoro-2,3-dihydro-1H-indene-4-carboxamide;
(S)—N-(4-((3-chloro-4-fluorophenyl)carbamoyl)-7-fluoro-2,3-dihydro-1H-inden-1-yl)oxazole-5-carboxamide;
O-cyclopentyl, N—(S)-(4-((3-chloro-4-fluorophenyl)carbamoyl)-7-fluoro-2,3-dihydro-1H-inden-1-yl)carbamate;
O-(2-oxo-oxazolidin-5-yl)methyl, N—((S)-4-((3-chloro-4-fluorophenyl)carbamoyl)-7-fluoro-2,3-dihydro-1H-inden-1-yl) carbamate;
O-2-(1H-pyrazol-1-yl)ethyl, N—(S)-(4-((3-chloro-4-fluorophenyl)carbamoyl)-7-fluoro-2,3-dihydro-1H-inden-1-yl) carbamate;
O-(1-methyl-1H-imidazol-2-yl)methyl, N—(S)-(4-((3-chloro-4-fluorophenyl)carbamoyl)-7-fluoro-2,3-dihydro-1H-inden-1-yl) carbamate;
O-(3-fluoropyridin-2-yl)methyl, N—(S)-4-((3-chloro-4-fluorophenyl)carbamoyl)-7-fluoro-2,3-dihydro-1H-inden-1-yl) carbamate;
O—((R)-morpholin-3-yl)methyl, N—(S)-4-((3-chloro-4-fluorophenyl)carbamoyl)-7-fluoro-2,3-dihydro-1H-inden-1-yl) carbamate;
O-(4-methoxypyridin-2-yl)methyl, N—(S)-(4-((3-chloro-4-fluorophenyl)carbamoyl)-7-fluoro-2,3-dihydro-1H-inden-1-yl) carbamate;
O-2-hydroxyethyl, N—(S)-(4-((3-chloro-4-fluorophenyl)carbamoyl)-7-fluoro-2,3-dihydro-1H-inden-1-yl) carbamate;
O—((S)-tetrahydrofuran-2-yl)methyl, N—((S)-4-((3-chloro-4-fluorophenyl)carbamoyl)-7-fluoro-2,3-dihydro-1H-inden-1-yl)carbamate;
(S)—N-(3-chloro-4-fluorophenyl)-7-fluoro-1-(2-hydroxyacetamido)-2,3-dihydro-1H-indene-4-carboxamide;
(S)—N-(3-chloro-4-fluorophenyl)-7-fluoro-1-(3-(pyridin-3-yl)ureido)-2,3-dihydro-1H-indene-4-carboxamide;
(S)—N-(3-chloro-4-fluorophenyl)-7-fluoro-1-(3-(pyridin-4-yl)ureido)-2,3-dihydro-1H-indene-4-carboxamide;
(S)—N-(3-chloro-4-fluorophenyl)-7-fluoro-1-(thiazol-2-ylamino)-2,3-dihydro-1H-indene-4-carboxamide;
O-2-(piperidin-1-yl)ethyl, N—(S)-(4-((3-chloro-4-fluorophenyl)carbamoyl)-7-fluoro-2,3-dihydro-1H-inden-1-yl) carbamate;
O-pyridin-2-ylmethyl, N—(S)-(4-((3-(difluoromethyl)-4-fluorophenyl)carbamoyl)-7-fluoro-2,3-dihydro-1H-inden-1-yl) carbamate;
(S)—N-(3-chloro-4-fluorophenyl)-7-fluoro-1-(3-(pyridin-2-ylmethyl)ureido)-2,3-dihydro-1H-indene-4-carboxamide;
O-(6-cyanopyridin-2-yl)methyl, N—(S)-(4-((3-chloro-4-fluorophenyl)carbamoyl)-7-fluoro-2,3-dihydro-1H-inden-1-yl) carbamate;
O-quinolin-2-ylmethyl, N—(S)-(4-((3-chloro-4-fluorophenyl)carbamoyl)-7-fluoro-2,3-dihydro-1H-inden-1-yl) carbamate;
O-(5-methylpyrazin-2-yl)methyl, N—(S)-(4-((3-chloro-4-fluorophenyl)carbamoyl)-7-fluoro-2,3-dihydro-1H-inden-1-yl) carbamate;
O-2-morpholinoethyl-N—(S)-(4-((3-chloro-4-fluorophenyl)carbamoyl)-7-fluoro-2,3-dihydro-1H-inden-1-yl) carbamate;
O-[cis-4-hydroxycyclohexyl]-N—((S)-4-((3-chloro-4-fluorophenyl)carbamoyl)-7-fluoro-2,3-dihydro-1H-inden-1-yl)carbamate;
O-3-hydroxypropyl, N—(S)-(4-((3-chloro-4-fluorophenyl)carbamoyl)-7-fluoro-2,3-dihydro-1H-inden-1-yl) carbamate;
O-[trans-4-hydroxycyclohexyl]-N—((S)-4-((3-chloro-4-fluorophenyl)carbamoyl)-7-fluoro-2,3-dihydro-1H-inden-1-yl) carbamate;
O-2-acetamidoethyl, N—(S)-(4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-propionamido-2,3-dihydro-1H-indene-4-carboxamide;
(S)—N-(3-chloro-4-fluorophenyl)-7-fluoro-1-((4-methoxypyrimidin-2-yl)amino)-2,3-dihydro-1H-indene-4-carboxamide;
(S)—N-(3-chloro-4-fluorophenyl)-7-fluoro-1-((4-methylpyrimidin-2-yl)amino)-2,3-dihydro-1H-indene-4-carboxamide;
(S)—N-(3-chloro-4-fluorophenyl)-7-fluoro-1-((2-methoxypyrimidin-4-yl)amino)-2,3-dihydro-1H-indene-4-carboxamide;
(S)—N-(3-chloro-4-fluorophenyl)-7-fluoro-1-((5-methylpyrimidin-2-yl)amino)-2,3-dihydro-1H-indene-4-carboxamide;
(S)—N-(3-chloro-4-fluorophenyl)-7-fluoro-1-((6-methoxypyrimidin-4-yl)amino)-2,3-dihydro-1H-indene-4-carboxamide;
(S)—N-(3-chloro-4-fluorophenyl)-1-((4,6-dimethylpyrimidin-2-yl)amino)-7-fluoro-2,3-dihydro-1H-indene-4-carboxamide;
O—(S)-5-oxopyrrolidin-3-yl, N—((S)-4-((3-chloro-4-fluorophenyl)carbamoyl)-7-fluoro-2,3-dihydro-1H-inden-1-yl) carbamate;
(S)—N-(3-chloro-4-fluorophenyl)-7-fluoro-1-((2-(pyridin-2-yl)ethyl)sulfonamido)-2,3-dihydro-1H-indene-4-carboxamide;

O-(6-(trifluoromethyl)pyridin-2-yl)methyl, N—(S)-(4-((3-chloro-4-fluorophenyl)carbamoyl)-7-fluoro-2,3-dihydro-1H-inden-1-yl) carbamate;

O-(5-(trifluoromethyl) pyridin-2-yl)methyl, N—(S)-(4-((3-chloro-4-fluorophenyl)carbamoyl)-7-fluoro-2,3-dihydro-1H-inden-1-yl) carbamate;

O—(R)-tetrahydrofuran-3-yl, N—((S)-4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(3-(1-methyl-1H-pyrazol-3-yl)propanamido)-2,3-dihydro-1H-indene-4-carboxamide;

O-(5-cyanopyridin-2-yl)methyl, N—(S)-(4-((3-chloro-4-fluorophenyl)carbamoyl)-7-fluoro-2,3-dihydro-1H-inden-1-yl) carbamate;

O-(3-methylpyrazin-2-yl)methyl, N—(S)-(4-((3-chloro-4-fluorophenyl)carbamoyl)-7-fluoro-2,3-dihydro-1H-inden-1-yl) carbamate;

O-(1-acetylpiperidin-4-yl)methyl, N—(S)-(4-((3-chloro-4-fluorophenyl)carbamoyl)-7-fluoro-2,3-dihydro-1H-inden-1-yl) carbamate;

O-(1-(2-hydroxyacetyl)piperidin-4-yl)methyl, N—(S)-(4-((3-chloro-4-fluorophenyl)carbamoyl)-7-fluoro-2,3-dihydro-1H-inden-1-yl) carbamate;

O-(1-(methylcarbamoyl)piperidin-4-yl)methyl, N—(S)-(4-((3-chloro-4-fluorophenyl)carbamoyl)-7-fluoro-2,3-dihydro-1H-inden-1-yl) carbamate;

O-(1,1-dioxidothiomorpholin-3-yl)methyl-N—((S)-4-((3-chloro-4-fluorophenyl)carbamoyl)-7-fluoro-2,3-dihydro-1H-inden-1-yl) carbamate;

(S)—N-(3-chloro-4-fluorophenyl)-1-(cyclopropanecarboxamido)-7-fluoro-2,3-dihydro-1H-indene-4-carboxamide;

O—((S)-morpholin-3-yl)methyl, N—((S)-4-((3-chloro-4-fluorophenyl)carbamoyl)-7-fluoro-2,3-dihydro-1H-inden-1-yl) carbamate;

O—(S)-tetrahydrofuran-3-yl, N—((S)-4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-((2-methoxyethyl) sulfonamido)-2,3-dihydro-1H-indene-4-carboxamide;

(S)—N-(3-chloro-4-fluorophenyl)-7-fluoro-1-(phenylsulfonamido)-2,3-dihydro-1H-indene-4-carboxamide;

(S)—N-(3-chloro-4-fluorophenyl)-7-fluoro-1-(pyridine-2-sulfonamido)-2,3-dihydro-1H-indene-4-carboxamide;

O-(1-(2-methoxyacetyl) piperidin-4-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-((5-hydroxypyrimidin-2-yl)amino)-2,3-dihydro-1H-indene-4-carboxamide;

O-(1H-pyrazol-3-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(3-((1-methyl-H-pyrazol-3-yl)methyl)ureido)-2,3-dihydro-1H-indene-4-carboxamide;

O-(1H-1,2,4-triazol-3-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-7-fluoro-1-(pyrimidin-4-ylamino)-2,3-dihydro-1H-indene-4-carboxamide;

(S)—N-(3-chloro-4-fluorophenyl)-7-fluoro-1-((7-(4-methoxybenzyl)-7H-pyrrolo[2,3-d]pyrimidin-2-yl)amino)-2,3-dihydro-1H-indene-4-carboxamide;

O—((R)-6-oxopiperidin-2-yl)methyl, N—((S)-4-((3-chloro-4-fluorophenyl)carbamoyl)-7-fluoro-2,3-dihydro-1H-inden-1-yl) carbamate;

O—(R)-6-oxopiperidin-3-yl, N—((S)-4-((3-chloro-4-fluorophenyl)carbamoyl)-7-fluoro-2,3-dihydro-1H-inden-1-yl) carbamate;

O—(S)-6-oxopiperidin-3-yl, N—((S)-4-((3-chloro-4-fluorophenyl)carbamoyl)-7-fluoro-2,3-dihydro-1H-inden-1-yl) carbamate;

(S)—N-(3-chloro-4-fluorophenyl)-1-(3-cyclopropylureido)-7-fluoro-2,3-dihydro-1H-indene-4-carboxamide;

O—((S)-6-oxopiperidin-2-yl)methyl, N—((S)-4-((3-chloro-4-fluorophenyl)carbamoyl)-7-fluoro-2,3-dihydro-1H-inden-1-yl) carbamate;

O-(4-oxoazetidin-2-yl)methyl, N—((S)-4-((3-chloro-4-fluorophenyl)carbamoyl)-7-fluoro-2,3-dihydro-1H-inden-1-yl) carbamate;

O-methyl, N-(4-((3-chloro-4-fluorophenyl)carbamoyl)-7-fluoro-1-methyl-2,3-dihydro-1H-inden-1-yl) carbamate;

N-(3-chloro-4-fluorophenyl)-7-fluoro-1-methyl-1-(3-methylureido)-2,3-dihydro-1H-indene-4-carboxamide;

(S)—N-(3-chloro-4-fluorophenyl)-1-(cyclopropanesulfonamido)-2,3-dihydro-1H-indene-4-carboxamide;

O-pyridin-2-ylmethyl, N-(4-((3-chloro-4-fluorophenyl)carbamoyl)-7-fluoro-1-methyl-2,3-dihydro-1H-inden-1-yl) carbamate;

(S)—N-(3-chloro-4-fluorophenyl)-1-((cyclopropylmethyl)sulfonamido)-7-fluoro-2,3-dihydro-1H-indene-4-carboxamide;

(S)—N-(3-chloro-4-fluorophenyl)-7-fluoro-1-((phenylmethyl)sulfonamido)-2,3-dihydro-1H-indene-4-carboxamide;

O-cyclopropyl, N—(S)-(4-((3-chloro-4-fluorophenyl)carbamoyl)-7-fluoro-2,3-dihydro-1H-inden-1-yl)carbamate;

(S)—N-(3-chloro-4-fluorophenyl)-7-fluoro-1-((N-methylsulfamoyl)amino)-2,3-dihydro-1H-indene-4-carboxamide;

(S)—N-(3-chloro-4-fluorophenyl)-7-fluoro-1-(morpholine-4-sulfonamido)-2,3-dihydro-1H-indene-4-carboxamide;

O-cyclopropyl, N—(S)-(4-((3-chloro-4-fluorophenyl)carbamoyl)-2,3-dihydro-1H-inden-1-yl) carbamate;

(S)—N-(3-chloro-4-fluorophenyl)-1-((N-methylsulfamoyl)amino)-2,3-dihydro-1H-indene-4-carboxamide;

O-(1,3,4-oxadiazol-2-yl)methyl, N—(S)-(4-((3-chloro-4-fluorophenyl)carbamoyl)-7-fluoro-2,3-dihydro-1H-inden-1-yl) carbamate;

(S)—N-(3-chloro-4-fluorophenyl)-1-(ethylsulfonamido)-7-fluoro-2,3-dihydro-1H-indene-4-carboxamide;

(S)—N-(3-chloro-4-fluorophenyl)-7-fluoro-1-(propylsulfonamido)-2,3-dihydro-1H-indene-4-carboxamide;

(S)—N-(4-chloro-3-fluorophenyl)-7-fluoro-1-((2-methylpropyl)sulfonamido)-2,3-dihydro-1H-indene-4-carboxamide;

(S)—N-(3-chloro-4-fluorophenyl)-7-fluoro-1-((N-isopropylsulfamoyl)amino)-2,3-dihydro-1H-indene-4-carboxamide;

(S)—N-(3-chloro-4-fluorophenyl)-7-fluoro-1-((1-methylethyl)sulfonamido)-2,3-dihydro-1H-indene-4-carboxamide;

(S)—N-(3-chloro-4-fluorophenyl)-1-(cyclopentanesulfonamido)-7-fluoro-2,3-dihydro-1H-indene-4-carboxamide;
(S)—N-(3-chloro-4-fluorophenyl)-1-(cyclohexanesulfonamido)-7-fluoro-2,3-dihydro-1H-indene-4-carboxamide;
(S)—N-(3-chloro-4-fluorophenyl)-1-((N-cyclopropylsulfamoyl)amino)-2,3-dihydro-1H-indene-4-carboxamide;
(S)—N-(3-chloro-4-fluorophenyl)-1-((N-cyclopropylsulfamoyl)amino)-7-fluoro-2,3-dihydro-1H-indene-4-carboxamide;
O-(1-(tetrahydro-2H-pyran-2-yl)-1H-1,2,4-triazol-3-yl) methyl, N—((S)-4-((3-chloro-4-fluorophenyl)carbamoyl)-7-fluoro-2,3-dihydro-1H-inden-1-yl) carbamate;
N-(3-Chloro-4-fluorophenyl)-7-fluoro-1-oxo-2,3-dihydro-1H-indene-4-carboxamide;
((1-(methyl-d$_3$)-1H-1,2,4-triazol-3-yl)methyl-d$_2$ (S)-(4-((3-chloro-4-fluorophenyl)carbamoyl)-7-fluoro-2,3-dihydro-1H-inden-1-yl)carbamate;
(S)-(3-((((4-((3-chloro-4-fluorophenyl)carbamoyl)-7-fluoro-2,3-dihydro-1H-inden-1-yl)carbamoyl)oxy) methyl)-1H-1,2,4-triazol-1-yl)methyl phosphoric acid;
(S)-(3-((((4-((3-chloro-4-fluorophenyl)carbamoyl)-7-fluoro-2,3-dihydro-1H-inden-1-yl)carbamoyl)oxy) methyl)-1H-pyrazol-1-yl)methyl phosphoric acid;
O—(S)-2-cyanoethyl, N-4-(3-chloro-4-fluorophenylcarbamoyl)-7-fluoro-2,3-dihydro-1H-inden-1-yl carbamate;
O—(S)-3-cyanopropyl, N-4-(3-chloro-4-fluorophenylcarbamoyl)-7-fluoro-2,3-dihydro-1H-inden-1-yl carbamate;
N-(3-chloro-4-fluorophenyl)-7'-fluoro-2,5-dioxo-2',3'-dihydrospiro[imidazolidine-4,1'-indene]-4'-carboxamide;
N-(3-chloro-4-fluorophenyl)-7'-fluoro-2,5-dioxo-1-(pyridin-2-ylmethyl)-2',3'-dihydrospiro[imidazolidine-4,1'-indene]-4'-carboxamide;
N-(3-chloro-4-fluoro-phenyl)-7'-fluoro-1-methyl-2,5-dioxo-spiro[imidazolidine-4,1'-indane]-4'-carboxamide;
(S)-1-(((S)-tert-butylsulfinyl)amino)-N-(3-chloro-4-fluorophenyl)-7-fluoro-2,3-dihydro-1H-indene-4-carboxamide;
(S)-1-(((R)-tert-butylsulfinyl)amino)-N-(3-chloro-4-fluorophenyl)-7-fluoro-2,3-dihydro-1H-indene-4-carboxamide;
or a salt, solvate, prodrug, isotopically labelled derivative, stereoisomer, or tautomer thereof, or any mixtures thereof.

16. A pharmaceutical composition comprising at least one compound of claim 1 and at least one pharmaceutically acceptable carrier.

17. The pharmaceutical composition of claim 16, further comprising at least one additional agent useful for treating hepatitis B infection.

18. The pharmaceutical composition of claim 17, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator.

19. A method of treating or ameliorating hepatitis B virus infection in a subject, the method comprising administering to the subject in need thereof a therapeutically effective amount of at least one compound of claim 1.

20. The method of claim 19, wherein the at least one compound is administered to the subject in a pharmaceutically acceptable composition.

21. The method of claim 19, wherein the subject is further administered at least one additional agent useful for treating the hepatitis B infection.

22. The method of claim 21, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator.

23. The method of claim 21, wherein the subject is co-administered the at least one compound and the at least one additional agent.

24. The method of claim 21, wherein the at least one compound and the at least one additional agent are coformulated.

25. A method of inhibiting expression or function of a viral capsid protein directly or indirectly in a Hepatitis B virus-infected subject, the method comprising administering to the subject in need thereof a therapeutically effective amount of at least one compound of claim 1.

26. The method of claim 25, wherein the at least one compound is administered to the subject in a pharmaceutically acceptable composition.

27. The method of claim 25, wherein the subject is further administered at least one additional agent useful for treating the viral infection.

28. The method of claim 27, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator.

29. The method of claim 27, wherein the subject is co-administered the at least one compound and the at least one additional agent.

30. The method of claim 27, wherein the at least one compound and the at least one additional agent are coformulated.

31. The method of claim 19, wherein the subject is a mammal.

32. The method of claim 31, wherein the mammal is a human.

* * * * *